US012662453B2

(12) United States Patent
Kajita et al.

(10) Patent No.: US 12,662,453 B2
(45) Date of Patent: Jun. 23, 2026

(54) HETEROCYCLIC COMPOUND AND USE THEREOF

(71) Applicant: TAKEDA PHARMACEUTICAL COMPANY LIMITED, Osaka (JP)

(72) Inventors: Yuichi Kajita, Kanagawa (JP); Yuhei Miyanohana, Kanagawa (JP); Tatsuki Koike, Kanagawa (JP); Kohei Takeuchi, Kanagawa (JP); Yoshiteru Ito, Kanagawa (JP); Norihito Tokunaga, Kanagawa (JP); Takahiro Sugimoto, Kanagawa (JP); Tohru Miyazaki, Kanagawa (JP); Tsuneo Oda, Kanagawa (JP); Yasutaka Hoashi, Kanagawa (JP); Yasushi Hattori, Kanagawa (JP); Keisuke Imamura, Kanagawa (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 878 days.

(21) Appl. No.: 17/846,830

(22) Filed: Jun. 22, 2022

(65) Prior Publication Data

US 2023/0063805 A1 Mar. 2, 2023

Related U.S. Application Data

(60) Continuation of application No. 16/811,426, filed on Mar. 6, 2020, now Pat. No. 11,440,883, which is a continuation of application No. 16/577,449, filed on Sep. 20, 2019, now Pat. No. 10,584,097, which is a (Continued)

(30) Foreign Application Priority Data

Aug. 3, 2017 (JP) ................................ 2017-150685
Dec. 25, 2017 (JP) ................................ 2017-248495

(51) Int. Cl.

| | |
|---|---|
| *C07D 211/56* | (2006.01) |
| *A61P 25/00* | (2006.01) |
| *A61P 25/26* | (2006.01) |
| *C07D 205/04* | (2006.01) |
| *C07D 207/14* | (2006.01) |
| *C07D 211/36* | (2006.01) |
| *C07D 401/06* | (2006.01) |
| *C07D 401/10* | (2006.01) |
| *C07D 401/14* | (2006.01) |
| *C07D 403/06* | (2006.01) |
| *C07D 405/06* | (2006.01) |
| *C07D 405/10* | (2006.01) |
| *C07D 405/12* | (2006.01) |
| *C07D 409/10* | (2006.01) |
| *C07D 413/06* | (2006.01) |
| *C07D 417/06* | (2006.01) |
| *C07D 417/14* | (2006.01) |

(52) U.S. Cl.

CPC ............ *C07D 211/56* (2013.01); *A61P 25/00* (2018.01); *A61P 25/26* (2018.01); *C07D 205/04* (2013.01); *C07D 207/14* (2013.01); *C07D 211/36* (2013.01); *C07D 401/06* (2013.01); *C07D 401/10* (2013.01); *C07D 401/14* (2013.01); *C07D 403/06* (2013.01); *C07D 405/06* (2013.01); *C07D 405/10* (2013.01); *C07D 405/12* (2013.01); *C07D 409/10* (2013.01); *C07D 413/06* (2013.01); *C07D 417/06* (2013.01); *C07D 417/14* (2013.01)

(58) Field of Classification Search

CPC ............................... C07D 211/56; A61P 25/00
See application file for complete search history.

(56) References Cited

U.S. PATENT DOCUMENTS

| | | | |
|---|---|---|---|
| 6,166,193 | A | 12/2000 | Yanagisawa |
| 6,204,245 | B1 | 3/2001 | Siegel et al. |
| 6,506,774 | B1 | 1/2003 | Irving et al. |

(Continued)

FOREIGN PATENT DOCUMENTS

| | | | |
|---|---|---|---|
| CN | 103874695 | A | 6/2014 |
| EP | 0893498 | A2 | 1/1999 |

(Continued)

OTHER PUBLICATIONS

Boss, C., and Roch, C., "Orexin research: patent news from 2016," Expert Opin Ther Pat 27(10):1123-1133, Taylor & Francis, United Kingdom (Oct. 2017).

(Continued)

*Primary Examiner* — Golam M Shameem
(74) *Attorney, Agent, or Firm* — Sterne, Kessler, Goldstein & Fox P.L.L.C.

(57) ABSTRACT

The present invention provides a heterocyclic compound having an orexin type 2 receptor agonist activity.
A compound represented by the formula (I):

(I)

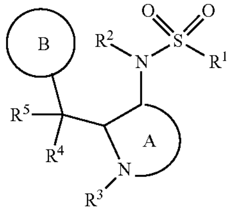

wherein each symbol is as described in the specification, or a salt thereof, is useful as an agent for the prophylaxis or treatment of narcolepsy.

8 Claims, No Drawings

Related U.S. Application Data division of application No. 16/052,967, filed on Aug. 2, 2018, now Pat. No. 10,428,023.

(56) References Cited

U.S. PATENT DOCUMENTS

| | | | | |
|---|---|---|---|---|
| 7,112,566 | B1 * | 9/2006 | Siegel | A61K 38/22 514/17.7 |
| 9,156,819 | B2 | 10/2015 | Kuduk et al. | |
| 10,428,023 | B2 * | 10/2019 | Kajita | C07D 211/36 |
| 10,584,097 | B2 * | 3/2020 | Kajita | A61P 25/00 |
| 11,028,048 | B2 * | 6/2021 | Hattori | C07D 407/06 |
| 11,440,883 | B2 * | 9/2022 | Kajita | A61P 25/26 |
| 2003/0083466 | A1 | 5/2003 | Yanagisawa | |
| 2005/0048538 | A1 | 3/2005 | Mignot et al. | |
| 2006/0035285 | A1 | 2/2006 | Sutton et al. | |
| 2006/0134109 | A1 | 6/2006 | Gaitanaris et al. | |
| 2007/0010445 | A1 | 1/2007 | Siegel et al. | |
| 2008/0260744 | A1 | 10/2008 | Gaitanaris et al. | |
| 2009/0178153 | A1 | 7/2009 | Gaitanaris et al. | |
| 2010/0150840 | A1 | 6/2010 | Yanagisawa | |
| 2011/0053859 | A1 | 3/2011 | Deadwyler et al. | |
| 2011/0185439 | A1 | 7/2011 | Gaitanaris et al. | |
| 2011/0214189 | A1 | 9/2011 | Gaitanaris et al. | |
| 2013/0102619 | A1 | 4/2013 | Kudok et al. | |
| 2013/0247233 | A1 | 9/2013 | Gaitanaris et al. | |
| 2014/0024650 | A1 | 1/2014 | Fukumoto et al. | |
| 2015/0140015 | A1 | 5/2015 | Voison | |
| 2016/0219845 | A1 | 8/2016 | Gaitanaris et al. | |
| 2016/0250224 | A1 | 9/2016 | Wan | |
| 2016/0271214 | A1 | 9/2016 | Ashley et al. | |
| 2016/0282365 | A1 | 9/2016 | Gaitanaris et al. | |
| 2016/0362376 | A1 | 12/2016 | Nagase et al. | |
| 2017/0188555 | A1 | 7/2017 | Gaitanaris et al. | |
| 2017/0226103 | A1 | 8/2017 | Kamenecka et al. | |
| 2017/0226137 | A1 | 8/2017 | Fujimoto et al. | |
| 2018/0064789 | A1 | 3/2018 | Voison et al. | |
| 2018/0179151 | A1 | 6/2018 | Nagase et al. | |
| 2018/0243245 | A1 | 8/2018 | England et al. | |

FOREIGN PATENT DOCUMENTS

| | | | |
|---|---|---|---|
| EP | 3029024 | A1 | 6/2016 |
| WO | WO-2001008720 | A2 | 2/2001 |
| WO | WO-2001074162 | A1 | 10/2001 |
| WO | WO-2004040000 | A2 | 5/2004 |
| WO | WO-2004054510 | A2 | 7/2004 |
| WO | WO-2009049215 | A1 | 4/2009 |
| WO | WO-2010060471 | A1 | 6/2010 |
| WO | WO-2010063663 | A1 | 6/2010 |
| WO | WO-2012137982 | A2 | 10/2012 |
| WO | WO-2014159591 | A1 | 10/2014 |
| WO | WO-2014170343 | A1 | 10/2014 |
| WO | WO-2014198880 | A1 | 12/2014 |
| WO | WO-2015048091 | A1 | 4/2015 |
| WO | WO-2015073707 | A1 | 5/2015 |
| WO | WO-2015088000 | A1 | 6/2015 |
| WO | WO-2015124932 | A1 | 8/2015 |
| WO | WO-2015124934 | A1 | 8/2015 |
| WO | WO-2015147240 | A1 | 10/2015 |
| WO | WO-2016025669 | A1 | 2/2016 |
| WO | WO-2016133160 | A1 | 8/2016 |
| WO | WO-2016199906 | A1 | 12/2016 |
| WO | WO-2017044889 | A1 | 3/2017 |
| WO | WO-2017135306 | A1 | 8/2017 |
| WO | WO-2018164191 | A1 | 9/2018 |
| WO | WO-2018164192 | A1 | 9/2018 |
| WO | WO-2019027003 | A1 | 2/2019 |
| WO | WO-2019112007 | A1 | 6/2019 |

OTHER PUBLICATIONS

Busquets, X., et al., "Decreased plasma levels of orexin-A in sleep apnea," Respiration 71(6):575-579, S. Karger AG, Switzerland (Nov.-Dec. 2004).

Chemelli, R.M., et al., "Narcolepsy in orexin knockout mice: molecular genetics of sleep regulation," Cell 98(4):437-451, Cell Press, United Kingdom (Aug. 1999).

Database Registry [Online] Chemical Abstracts Service, Feb. 28, 2013, "Methanesulfonamide, N-[(2R, 3S)-2-(phenylmethyl)-3-pyrrolidiny1]-rel-," XP002785179, retrieved from STN Database accession No. 1422063-50-5, examples 1422063-50-0.

Funato, H., et al., "Enhanced orexin receptor-2 signaling prevents diet-induced obesity and improves leptin sensitivity," Cell Metab 9(1):64-76, Cell Press, United Kingdom (Jan. 2009).

Jaeger, L.B., et al., "Effects of orexin-A on memory processing," Peptides 23(9):1683-1688, Elsevier, Netherlands (Sep. 2002).

Kushikata, T., et al., "Orexinergic neurons and barbiturate anesthesia," Neuroscience 121(4):855-863, Elsevier, Netherlands (2003).

Lin, L., et al., "The sleep disorder canine narcolepsy is caused by a mutation in the hypocretin (orexin) receptor 2 gene," Cell 98(3):365-376, Cell Press, United Kingdom (Aug. 1999).

Mieda, M., and Sakurai, T., "Orexin (hypocretin) receptor agonists and antagonists for treatment of sleep disorders. Rationale for development and current status," CNS Drugs 27(2):83-90, Aids International Ltd., United Kingdom (Feb. 2013).

Mieda, M., et al., "Orexin peptides prevent cataplexy and improve wakefulness in an orexin neuron-ablated model of narcolepsy in mice," Proceedings of the National Academy of Sciences of the United States of America 101(13):4649-4654, National Academy of Sciences, United States (Mar. 2004).

Nagahara, T., et al., "Design and Synthesis of Non-Peptide, Selective Orexin Receptor 2 Agonists," J Med Chem 58(20):7931-7937, American Chemical Society, United States (Oct. 2015).

Perez, M.V., et al., "Systems Genomics Identifies a Key Role for Hypocretin/Orexin Receptor-2 in Human Heart Failure," J Am Coll Cardiol 66(22):2522-2533, Elservier USA, United States (Dec. 2015).

Sakurai, T., et al., "Orexins and orexin receptors: a family of hypothalamic neuropeptides and G protein-coupled receptors that regulate feeding behavior," Cell 92(4):573-585, Cell Press, United Kingdom (Feb. 1998).

Shin, H.S., et al., "Orexin-A increases cell surface expression of AMPA receptors in the striatum," Biochem Biophys Res Commun 378(3):409-413, Academic Press, United States (Jan. 2009).

STN Search Results, 66 compounds, entered Mar. 6, 2018, 33 pages.

Thannickal, T.C., et al., "Hypocretin (orexin) cell loss in Parkinson's disease," Brain 130(Pt 6):1586-1595, Oxford University Press, United Kingdom (Jun. 2007).

Willie, J.T., et al., "Distinct narcolepsy syndromes in Orexin receptor-2 and Orexin null mice: molecular genetic dissection of Non-REM and REM sleep regulatory processes," Neuron 38(5):715-730, Cell Press, United Kingdom (Jun. 2003).

Desseilles, M., et al., "Neuroimaging insights into the pathophysiology of sleep disorders," Sleep 31(6):777-794, Oxford University Press, United Kingdom (Jun. 2008).

STN Registry entry for CASRN 2125419-42-1, Entry date Sep. 5, 2017, Accessed Jan. 30, 2021.

* cited by examiner

HETEROCYCLIC COMPOUND AND USE THEREOF

TECHNICAL FIELD

The present invention relates to a heterocyclic compound, particularly, a heterocyclic compound having an orexin type 2 receptor agonist activity.

BACKGROUND OF THE INVENTION

Orexin is a neuropeptide specifically produced in particular neurons located sparsely in the lateral hypothalamus and its surrounding area, and consists of two subtypes, orexin A and orexin B. Both orexin A and orexin B are endogenous ligands of the orexin receptors, which are G protein-coupled receptors mainly present in the brain, and two types of subtypes, type 1 and type 2, are known for the orexin receptors (non-patent document 1).

Since orexin-producing neurons (orexin neurons) are localized in the vicinity of the feeding center, and intraventricular administration of orexin peptide results in an increase in food intake, orexin initially attracted attention as a neuropeptide having a feeding behavioral regulation. Thereafter, however, it was reported that the cause of dog narcolepsy is genetic variation of orexin type 2 receptor (non-patent document 2), and the role of orexin in controlling sleep and wakefulness has been also attracted.

From the studies using a transgenic mouse having denatured orexin neurons and a double transgenic mouse obtained by crossing this mouse with orexin overexpressing transgenic mouse, it was clarified that narcolepsy-like symptoms that appear by degeneration of orexin neurons disappear due to sustained expression of orexin. Similarly, when orexin peptide was intraventricularly administered to a transgenic mouse having denatured orexin neuron, improvement of narcolepsy-like symptoms was also observed (non-patent document 3). Studies of orexin type 2 receptor knockout mice have suggested that orexin type 2 receptor is important for maintaining arousal (non-patent document 4, non-patent document 5). Such background suggests that orexin type 2 receptor agonists become therapeutic drugs for narcolepsy or therapeutic drugs for other sleep disorders exhibiting excessive sleepiness (non-patent document 6).

In addition, it is suggested that a peptidic agonist that selectively acts on the orexin type 2 receptor improves obesity due to high fat diet load in mice (non-patent document 7).

In addition, it is suggested that intraventricular administration of orexin peptide shortens the systemic anesthetic time of rat (non-patent document 8).

In addition, it is suggested that patients with sleep apnea syndrome show low orexin A concentration levels in plasma (non-patent document 9).

In addition, it is suggested that intraventricular administration of orexin peptide improves memory retention of senescence-accelerated model mouse (SAMP8) with cognitive dysfunction (non-patent document 10).

In addition, it is suggested that Orexin type 2 receptor agonist will be a therapeutic drug for cardiac failure (patent document 1, non-patent document 11).

In addition, it is suggested that the daytime sleepiness of Parkinson's disease patients is caused by orexin nerve fallout (non-patent document 12).

In addition, it is suggested that orexin regulates bone formation and bone loss, and orexin type 2 receptor agonist will be a therapeutic drug for diseases related to bone loss such as osteoporosis, rheumatoid arthritis and the like (patent document 2).

In addition, it is suggested that orexin receptor agonist is useful for the prophylaxis or treatment of sepsis, severe sepsis and septic shock, since the mortality was significantly improved by mere continuous administration of orexin from the periphery in septic shock model mouse (patent document 3).

Therefore, a compound having an orexin type 2 receptor agonist activity is expected to be useful as a novel therapeutic drug for narcolepsy, idiopathic hypersomnia, hypersomnia, sleep apnea syndrome, disturbance of consciousness such as coma and the like, narcolepsy syndrome accompanied by narcolepsy-like symptoms, hypersomnia syndrome accompanied by daytime hypersomnia (e.g., Parkinson's disease, Guillain-Barre syndrome and Kleine Levin syndrome), Alzheimer, obesity, insulin resistance syndrome, cardiac failure, diseases related to bone loss, sepsis and the like, further, anesthetic antagonist, a prophylactic or therapeutic drug for side effects As sulfonamide derivatives, a compound represented by the formula

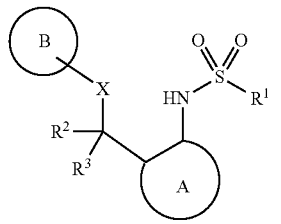

wherein each symbol is as described in the document (Patent Document 4), a compound represented by the formula

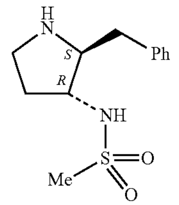

(RN 1422063-50-0) have been reported. The latter compound is an optically active form of "N-(2-benzylpyrrolidin-3-yl)methanesulfonamide" which is excluded from the compound (I) of the present invention. Additionally, compounds represented by the formula (RN 2184459-04-7)

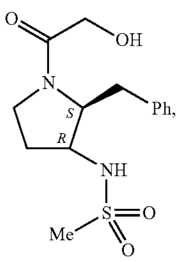

-continued
(RN 2183943-14-6)
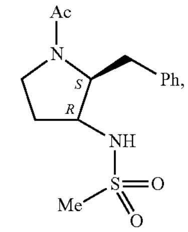
(RN 2183690-03-9)
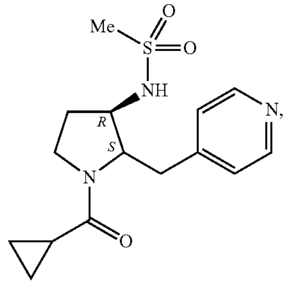
(RN 2181901-07-3)
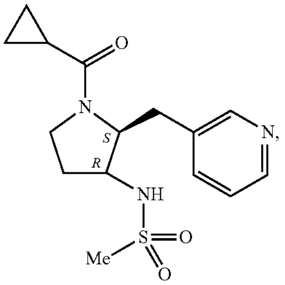
(RN 2181757-12-8)
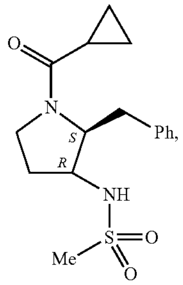
(RN 2127049-50-5)
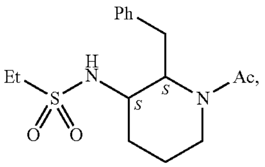
(RN 2125476-16-4)
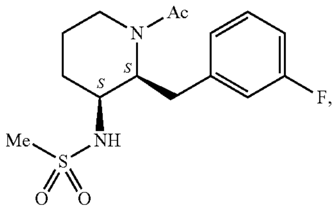
-continued
(RN 2125419-42-1)
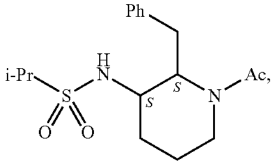
(RN 2185568-62-9)
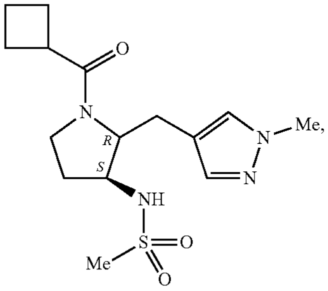
(RN 2185454-60-6)
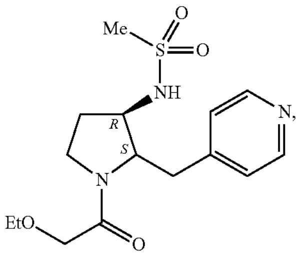
(RN 2185393-75-1)
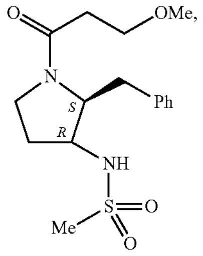
(RN 2185369-35-9)
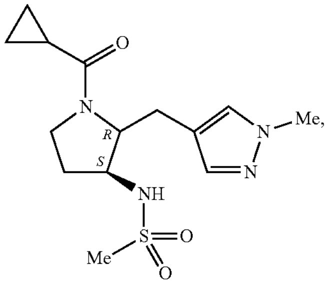
(RN 2185279-48-3)
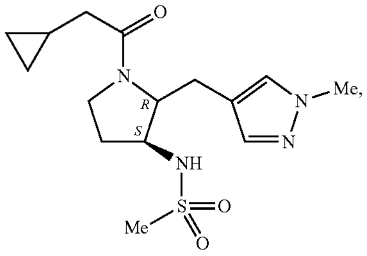

-continued (RN 2184868-49-1)

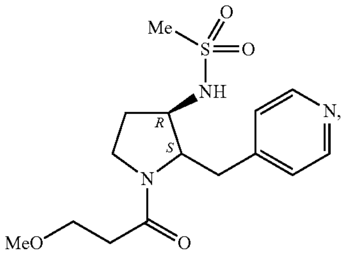

(RN 2183649-49-0)

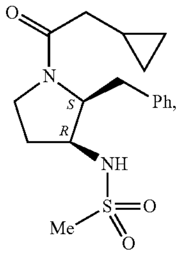

(RN 2183429-76-5)

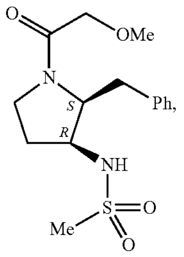

(RN 2182680-51-7)

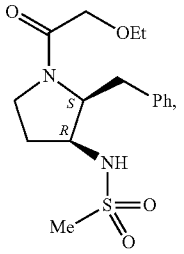

(RN 2180637-97-0)

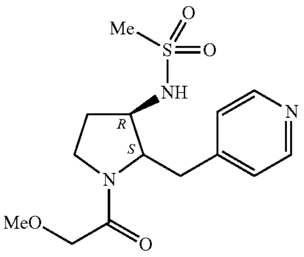

are reported.

In addition, as compounds having an orexin type 2 receptor agonist activity, the following compounds have been reported.

A compound represented by the formula

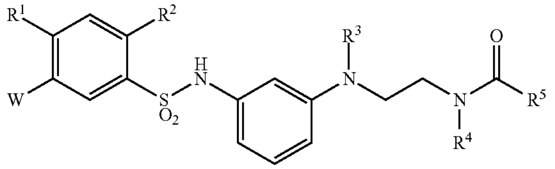

wherein each symbol is as described in the document (Patent Document 5).

A compound represented by the formula (I)

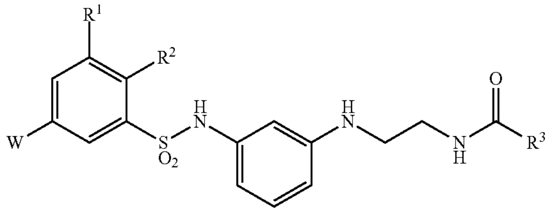

wherein each symbol is as described in the document (Patent Document 6).

A compound represented by the formula (I)

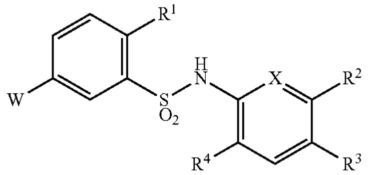

wherein each symbol is as described in the document (Patent Document 7).

A compound represented by the formula

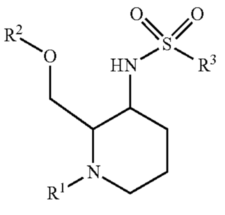

wherein each symbol is as described in the document (Patent Document 8).

However, it is considered that these compounds are not satisfactory in terms of activity, pharmacokinetics or safety, and the development of a compound having an orexin type 2 receptor agonist activity is still desired.

DOCUMENT LIST

Patent Document

[Patent Document 1] WO 2015/073707 A1
[Patent Document 2] WO 2015/048091 A1
[Patent Document 3] WO 2015/147240 A1

[Patent Document 4] WO 2012/137982 A9
[Patent Document 5] WO 2015/088000 A1
[Patent Document 6] WO 2016/133160 A1
[Patent Document 7] WO 2016/199906 A1
[Patent Document 8] WO 2017/135306 A1

Non-Patent Document

[Non-Patent Document 1] Cell, Vol. 92, 573-585, 1998
[Non-Patent Document 2] Cell, Vol. 98, 365-376, 1999
[Non-Patent Document 3] Proc. Natl. Acad. Sci. USA, Vol. 101, 4649-4654, 2004
[Non-Patent Document 4] Cell, Vol. 98, 437-451, 1999
[Non-Patent Document 5] Neuron, Vol. 38, 715-730, 2003
[Non-Patent Document 6] CNS Drugs, Vol. 27, 83-90, 2013
[Non-Patent Document 7] Cell Metabolism, Vol. 9, 64-76, 2009
[Non-Patent Document 8] Neuroscience, Vol. 121, 855-863, 2003
[Non-Patent Document 9] Respiration, Vol. 71, 575-579, 2004
[Non-Patent Document 10] Peptides, Vol. 23, 1683-1688, 2002
[Non-Patent Document 11] Journal of the American College of Cardiology. Vol. 66, 2015, Pages 2522-2533
[Non-Patent Document 12] Brain. Vol. 130, 2007, Pages 1586-1595

SUMMARY OF THE INVENTION

Problems to be Solved by the Invention

The present invention aims to provide a heterocyclic compound having an orexin type 2 receptor agonist activity.

Means of Solving the Problems

The present inventors have found that a compound represented by the following formula (I) or a salt thereof (sometimes to be referred to as compound (I) in the present specification) has an orexin type 2 receptor agonist activity. As a result of further studies, they have completed the present invention.

Accordingly, the present invention provides the following.

[1] A compound represented by the formula:

(I)

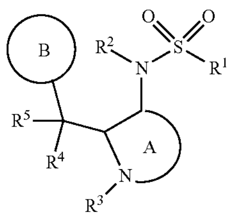

wherein $R^1$ is a substituent;

$R^2$, $R^3$, $R^4$ and $R^5$ are each independently a hydrogen atom, or a substituent;

Ring A is an optionally further substituted 4- to 7-membered nitrogen-containing monocyclic saturated heterocycle; and Ring B is an optionally further substituted ring, or a salt thereof, provided that N-(2-benzylpyrrolidin-3-yl)methanesulfonamide is excluded.

[2] The compound or salt of the above-mentioned [1], wherein Ring B is a ring further substituted by (a) an optionally substituted $C_{6-14}$ aryl group,
(b) an optionally substituted $C_{6-14}$ aryloxy group,
(c) an optionally substituted $C_{7-16}$ aralkyl group,
(d) an optionally substituted $C_{3-10}$ cycloalkyl group,
(e) an optionally substituted $C_{3-10}$ cycloalkenyl group,
(f) an optionally substituted $C_{3-10}$ cycloalkoxy group,
(g) an optionally substituted 5- to 14-membered aromatic heterocyclic group, or
(h) an optionally substituted 3- to 14-membered non-aromatic heterocyclic group, and optionally having additional substituent(s).

[3] The compound or salt of the above-mentioned [1], wherein $R^1$ is (1) a $C_{1-6}$ alkyl group optionally substituted by 1 to 3 substituents selected from
  (a) a halogen atom,
  (b) a cyano group,
  (c) a hydroxy group, and
  (d) a $C_{1-6}$ alkoxy group,
(2) a $C_{2-6}$ alkenyl group,
(3) a $C_{3-10}$ cycloalkyl group optionally substituted by 1 to 3 halogen atoms,
(4) a mono- or di-$C_{1-6}$ alkylamino group, or
(5) a 3- to 14-membered non-aromatic heterocyclic group;

$R^2$ is a hydrogen atom;

$R^3$ is (1) a hydrogen atom,
(2) a $C_{1-6}$ alkoxy-carbonyl group optionally substituted by 1 to 3 substituents selected from
  (a) a halogen atom,
  (b) a $C_{1-6}$ alkoxy group,
  (c) a $C_{3-10}$ cycloalkyl group optionally substituted by 1 to 3 substituents selected from
    (i) a halogen atom, and
    (ii) a $C_{1-6}$ alkyl group, and
  (d) a 3- to 14-membered non-aromatic heterocyclic group,
(3) a $C_{1-6}$ alkyl-carbonyl group optionally substituted by 1 to 3 substituents selected from
  (a) a halogen atom,
  (b) a $C_{3-10}$ cycloalkyl group,
  (c) a hydroxy group, and
  (d) a $C_{1-6}$ alkoxy group,
(4) a mono- or di-$C_{1-6}$ alkyl-carbamoyl group,
(5) a N—$C_{1-6}$ alkyl-N—$C_{1-6}$ alkoxy-carbamoyl group,
(6) a $C_{3-10}$ cycloalkyl-carbonyl group (the $C_{3-10}$ cycloalkyl in the $C_{3-10}$ cycloalkyl-carbonyl group may be a bridged ring group) optionally substituted by 1 to 3 substituents selected from
  (a) a halogen atom,
  (b) a $C_{1-6}$ alkyl group optionally substituted by 1 to 3 substituents selected from
    (i) a halogen atom, and
    (ii) a hydroxy group,
  (c) a hydroxy group,
  (d) a $C_{1-6}$ alkoxy group, and
  (e) a cyano group, (7) a $C_{3-10}$ cycloalkoxy-carbonyl group optionally substituted by 1 to 3 substituents selected from
(a) a halogen atom, and
(b) a $C_{1-6}$ alkyl group,
(8) a 3- to 14-membered non-aromatic heterocyclylcarbonyl group (the non-aromatic heterocycle in the non-aromatic heterocyclylcarbonyl group may be a spiro ring) optionally substituted by 1 to 3 substituents selected from
(a) a halogen atom, and
(b) a $C_{1-6}$ alkyl group,
(9) a 3- to 14-membered non-aromatic heterocyclyloxy-carbonyl group,
(10) a $C_{6-14}$ aryloxy-carbonyl group,
(11) a $C_{7-16}$ aralkyloxy-carbonyl group,
(12) a 5- to 14-membered aromatic heterocyclic group optionally substituted by 1 to 3 substituents selected from
(i) a halogen atom, and
(ii) a $C_{1-6}$ alkyl group,
(13) a 5- to 14-membered aromatic heterocyclylcarbonyl group optionally substituted by 1 to 3 $C_{1-6}$ alkyl groups, or
(14) a tri-$C_{1-6}$ alkylhydrazino-carbonyl group;
$R^4$ and $R^5$ are each independently a hydrogen atom or a halogen atom;
Ring A is
(1) a pyrrolidine ring,
(2) a piperidine ring, or
(3) an azetidine ring; and
Ring B is
(1) a $C_{6-14}$ aromatic hydrocarbon ring optionally further substituted by 1 to 3 substituents selected from
(a) a halogen atom,
(b) a $C_{1-6}$ alkyl group optionally substituted by 1 to 3 halogen atoms,
(c) a $C_{2-6}$ alkenyl group,
(d) a mono- or di-$C_{1-6}$ alkylamino group,
(e) a tri-$C_{1-6}$ alkylsilyloxy group,
(f) a $C_{6-14}$ aryl group optionally substituted by 1 to 4 substituents selected from
(i) a halogen atom,
(ii) a $C_{1-6}$ alkyl group optionally substituted by 1 to 3 halogen atoms, and
(iii) a $C_{1-6}$ alkoxy group,
(g) a $C_{6-14}$ aryloxy group,
(h) a $C_{7-16}$ aralkyl group optionally substituted by 1 to 3 $C_{1-6}$ alkyl groups,
(i) a $C_{3-10}$ cycloalkyl group,
(j) a $C_{3-10}$ cycloalkenyl group,
(k) a $C_{3-10}$ cycloalkoxy group,
(l) a 5- to 14-membered aromatic heterocyclic group optionally substituted by 1 to 3 $C_{1-6}$ alkyl groups, and
(m) a 3- to 14-membered non-aromatic heterocyclic group,
(2) a 5- to 14-membered aromatic heterocycle optionally further substituted by 1 to 3 substituents selected from
(a) a $C_{6-14}$ aryl group optionally substituted by 1 to 3 halogen atoms,
(b) a $C_{1-6}$ alkyl group, and
(c) a $C_{2-6}$ alkenyl group, or
(3) a 3- to 14-membered non-aromatic heterocycle optionally further substituted by 1 to 3 substituents selected from
(a) a $C_{6-14}$ aryl group, and
(b) a 5- to 14-membered aromatic heterocyclic group.

[4] The compound or salt of the above-mentioned [1], wherein $R^1$ is
(1) a $C_{1-6}$ alkyl group optionally substituted by 1 to 3 substituents selected from
(a) a halogen atom, and
(b) a $C_{1-6}$ alkoxy group,
(2) a $C_{3-6}$ cycloalkyl group optionally substituted by 1 to 3 halogen atoms, or
(3) a mono- or di-$C_{1-6}$ alkylamino group;
$R^2$ is a hydrogen atom;
$R^3$ is
(1) a $C_{1-6}$ alkoxy-carbonyl group,
(2) a $C_{1-6}$ alkyl-carbonyl group optionally substituted by 1 to 3 hydroxy groups,
(3) a mono- or di-$C_{1-6}$ alkyl-carbamoyl group,
(4) a N—$C_{1-6}$ alkyl-N—$C_{1-6}$ alkoxy-carbamoyl group,
(5) a $C_{3-6}$ cycloalkyl-carbonyl group (the $C_{3-6}$ cycloalkyl in the $C_{3-6}$ cycloalkyl-carbonyl group may be a bridged ring group) optionally substituted by 1 to 3 substituents selected from
(a) a halogen atom,
(b) a $C_{1-6}$ alkyl group optionally substituted by 1 to 3 halogen atoms,
(c) a hydroxy group,
(d) a $C_{1-6}$ alkoxy group, and
(e) a cyano group,
(6) an oxetanylcarbonyl group,
(7) an azetidinylcarbonyl group optionally substituted by 1 to 3 substituents selected from
(a) a halogen atom, and
(b) a $C_{1-6}$ alkyl group, or
(8) a 5-azaspiro[2.3]hexylcarbonyl group;
$R^4$ and $R^5$ are both hydrogen atoms;
Ring A is
(1) a pyrrolidine ring, or
(2) a piperidine ring; and
Ring B is
(1) a benzene ring
further substituted by one phenyl group optionally substituted by 1 to 3 substituents selected from
(i) a halogen atom, and
(ii) a $C_{1-6}$ alkyl group, and
optionally further substituted by one halogen atom,
(2) a pyridine ring further substituted by one phenyl group optionally substituted by 1 to 3 halogen atoms,
(3) a thiazole ring further substituted by one phenyl group optionally substituted by 1 to 3 halogen atoms, or
(4) a piperidine ring further substituted by one phenyl group.

[5] The compound or salt of the above-mentioned [1], wherein $R^1$ is
(1) a $C_{1-6}$ alkyl group,
(2) a $C_{3-6}$ cycloalkyl group optionally substituted by 1 to 3 halogen atoms, or
(3) a mono- or di-$C_{1-6}$ alkylamino group;
$R^2$ is a hydrogen atom;
$R^3$ is
(1) a $C_{1-6}$ alkyl-carbonyl group optionally substituted by 1 to 3 hydroxy groups,
(2) a mono- or di-$C_{1-6}$ alkyl-carbamoyl group,
(3) a N—$C_{1-6}$ alkyl-N—$C_{1-6}$ alkoxy-carbamoyl group, or
(4) an azetidinylcarbonyl group;
$R^4$ and $R^5$ are both hydrogen atoms;
Ring A is a pyrrolidine ring; and
Ring B is a benzene ring
further substituted by one phenyl group optionally substituted by 1 to 3 halogen atoms, and optionally further substituted by one halogen atom.

[6] N-((2S,3S)-2-((2,3'-difluorobiphenyl-3-yl)methyl)-1-(2-hydroxy-2-methylpropanoyl)pyrrolidin-3-yl)ethanesulfonamide or a salt thereof.

[7] N-((2S,3S)-1-(2-hydroxy-2-methylpropanoyl)-2-((2,3',5'-trifluorobiphenyl-3-yl)methyl)pyrrolidin-3-yl)methanesulfonamide or a salt thereof.

[8] N-((2S,3S)-1-(2-hydroxy-2-methylpropanoyl)-2-((2,3',5'-trifluorobiphenyl-3-yl)methyl)pyrrolidin-3-yl)ethanesulfonamide or a salt thereof.

[9] A compound selected from (1) N-((2S,3S)-1-(azetidin-1-ylcarbonyl)-2-((2,3'-difluorobiphenyl-3-yl)methyl)pyrrolidin-3-yl)methanesulfonamide, (2) N-((2S,3S)-1-(azetidin-1-ylcarbonyl)-2-((3',5'-difluorobiphenyl-3-yl)methyl)pyrrolidin-3-yl)ethanesulfonamide, (3) N-((2S,3S)-1-(azetidin-1-ylcarbonyl)-2-(biphenyl-3-ylmethyl)pyrrolidin-3-yl)ethanesulfonamide, (4) N-((2S,3S)-1-(azetidin-1-ylcarbonyl)-2-((2,3'-difluorobiphenyl-3-yl)methyl)pyrrolidin-3-yl)ethanesulfonamide, (5) (2S,3S)-2-((2,3'-difluorobiphenyl-3-yl)methyl)-3-((ethylsulfonyl)amino)-N,N-dimethylpyrrolidine-1-carboxamide, (6) (2S,3S)-2-((2,3'-difluorobiphenyl-3-yl)methyl)-3-((dimethylsulfamoyl)amino)-N,N-dimethylpyrrolidine-1-carboxamide, (7) (2S,3S)-3-((ethylsulfonyl)amino)-N,N-dimethyl-2-((2,3',5'-trifluorobiphenyl-3-yl)methyl)pyrrolidine-1-carboxamide, (8) (2S,3S)-2-(biphenyl-3-ylmethyl)-3-((ethylsulfonyl)amino)-N-methoxy-N-methylpyrrolidine-1-carboxamide, (9) N-[(2S,3S)-2-[(2,3'-difluoro[1,1'-biphenyl]-3-yl)methyl]-1-(2-hydroxy-2-methylpropanoyl)pyrrolidin-3-yl]-1-fluorocyclopropane-1-sulfonamide,

(10) N-{(2S,3S)-1-(azetidine-1-carbonyl)-2-[(2-fluoro[1,1'-biphenyl]-3-yl)methyl]pyrrolidin-3-yl}ethanesulfonamide,

(11) (2S,3S)-3-[(ethanesulfonyl)amino]-2-[(3'-fluoro[1,1'-biphenyl]-3-yl)methyl]-N-methoxy-N-methylpyrrolidine-1-carboxamide,

(12) (2S,3S)-3-[(dimethylsulfamoyl)amino]-2-[(2-fluoro[1,1'-biphenyl]-3-yl)methyl]-N,N-dimethylpyrrolidine-1-carboxamide,

(13) (2S,3S)-3-[(dimethylsulfamoyl)amino]-N,N-dimethyl-2-[(2,3',5'-trifluoro[1,1'-biphenyl]-3-yl)methyl]pyrrolidine-1-carboxamide, and

(14) (2S,3S)-2-[(3',5'-difluoro[1,1'-biphenyl]-3-yl)methyl]-3-[(ethanesulfonyl)amino]-N-methoxy-N-methylpyrrolidine-1-carboxamide or a salt thereof.

[10] A medicament comprising the compound or salt of the above-mentioned [1]-[9].

[11] The medicament of the above-mentioned [10], which is an orexin type 2 receptor agonist.

[12] The medicament of the above-mentioned [10], which is an agent for the prophylaxis or treatment of narcolepsy.

[13] The compound or salt of the above-mentioned [1]-[9] for use in the prophylaxis or treatment of narcolepsy.

[14] A method of activating an orexin type 2 receptor in a mammal, which comprises administering an effective amount of the compound or salt of the above-mentioned [1]-[9] to the mammal.

[15] A method for the prophylaxis or treatment of narcolepsy in a mammal, which comprises administering an effective amount of the compound or salt of the above-mentioned [1]-[9] to the mammal.

[16] Use of the compound or salt of the above-mentioned [1]-[9] for the manufacture of an agent for the prophylaxis or treatment of narcolepsy.

Effect of the Invention

The compound of the present invention has an orexin type 2 receptor agonist activity, and is useful as an agent for the prophylaxis or treatment of narcolepsy.

DETAILED DESCRIPTION OF THE INVENTION

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-4}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following Substituent group A.

[Substituent group A]

(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{7-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,

(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_1$-6 alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl) amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group, and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 heteroatoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 heteroatoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi- or tri-cyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, so phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 heteroatoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi- or tri-cyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-R-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the above-mentioned Substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_3$-10 cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkylphosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent group A".

Preferable examples of the optionally substituted amino group include an amino group, a mono- or di-(optionally halogenated $C_{1-6}$ alkyl) amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl) amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl) amino group (e.g., N-acetyl-N-methylamino) and a ($C_{1-6}$ alkyl) ($C_{6-14}$ aryl-carbonyl) amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxy group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from Substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from Substituent group A".

Preferable examples of the optionally substituted silyl group include a tri-$C_{1-6}$ alkylsilyl group (e.g., trimethylsilyl, tert-butyl(dimethyl)silyl).

In the present specification, examples of the "hydrocarbon ring" include a $C_{6-14}$ aromatic hydrocarbon ring, $C_{3-10}$ cycloalkane and $C_{3-10}$ cycloalkene.

In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocycle" include an aromatic heterocycle and a non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi- or tri-cyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiin, indole, isoindole, 1H-indazole, purine, isoquinoline, quinoline, phthalazine, naphthyridine, quinoxaline, quinazoline, cinnoline, carbazole, R-carboline, phenanthridine, acridine, phenazine, phenothiazine, phenoxazine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepane, diazepane, azepine, azocane, diazocane, oxepane and the like; and 9- to 14-membered fused polycyclic (preferably bi- or tri-cyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "nitrogen-containing heterocycle" include a heterocycle containing at least one nitrogen atom as a ring-constituting atom, from among the "heterocycle".

In the present specification, examples of the "4- to 7-so membered nitrogen-containing monocyclic saturated heterocycle" include a 4- to 7-membered saturated heterocycle containing at least one nitrogen atom as a ring-constituting atom, from among the "3- to 8-membered monocyclic non-aromatic heterocycle".

In the present specification, examples of the "ring" include a "hydrocarbon ring" and a "heterocycle".

The definition of each symbol in the formula (I) is explained in detail in the following.

$R^1$ is a substituent.

$R^1$ is preferably (1) an optionally substituted $C_{1-6}$ alkyl group (e.g., methyl, ethyl, propyl, isopropyl, butyl, isobutyl), (2) an optionally substituted $C_{2-6}$ alkenyl group (e.g., vinyl, allyl), (3) an optionally substituted $C_{3-10}$ cycloalkyl group (e.g., cyclopropyl), (4) an optionally substituted mono- or di-$C_{1-6}$ alkylamino group (e.g., dimethylamino), or (5) an optionally substituted 3- to 14-membered non-aromatic heterocyclic group (preferably a 3- to 8-membered monocyclic non-aromatic heterocyclic group (e.g., oxetanyl)).

Examples of the substituent of the above-mentioned "optionally substituted $C_{1-6}$ alkyl group", "optionally substituted $C_{2-6}$ alkenyl group", "optionally substituted $C_{3-10}$ cycloalkyl group", "optionally substituted mono- or di-$C_{1-6}$ alkylamino group" and "optionally substituted 3- to 14-membered non-aromatic heterocyclic group" include substituents selected from Substituent group A. The number of the substituents is preferably 1 to 3. When the number of the substituents is 2 or more, the respective substituents may be the same or different.

$R^1$ is more preferably (1) a $C_{1-6}$ alkyl group (e.g., methyl, ethyl, propyl, isopropyl, butyl, isobutyl) optionally substituted by 1 to 3 substituents selected from (a) a halogen atom (e.g., a fluorine atom, a chlorine atom), (b) a cyano group, (c) a hydroxy group, and (d) a $C_{1-6}$ alkoxy group (e.g., methoxy), (2) a $C_{2-6}$ alkenyl group (e.g., vinyl, allyl), (3) a $C_{3-10}$ cycloalkyl group (e.g., cyclopropyl), (4) a mono- or di-$C_{1-6}$ alkylamino group (e.g., dimethylamino), or
(5) a 3- to 14-membered non-aromatic heterocyclic group (preferably a 3- to 8-membered monocyclic non-aromatic heterocyclic group (e.g., oxetanyl)).

$R^1$ is further more preferably
(1) a $C_{1-6}$ alkyl group (e.g., methyl, ethyl, propyl, isopropyl, butyl, isobutyl) optionally substituted by 1 to 3 substituents selected from
(a) a halogen atom (e.g., a fluorine atom, a chlorine atom),
(b) a cyano group,
(c) a hydroxy group, and
(d) a $C_{1-6}$ alkoxy group (e.g., methoxy),
(2) a $C_{2-6}$ alkenyl group (e.g., vinyl, allyl),
(3) a $C_{3-6}$ cycloalkyl group (e.g., cyclopropyl),
(4) a mono- or di-$C_{1-6}$ alkylamino group (e.g., dimethylamino), or
(5) an oxetanyl group.

$R^1$ is still more preferably
(1) a $C_{1-6}$ alkyl group (e.g., methyl, ethyl, propyl) optionally substituted by 1 to 3 substituents selected from
(a) a halogen atom (e.g., a fluorine atom, a chlorine atom), and
(b) a $C_{1-6}$ alkoxy group (e.g., methoxy),
(2) a $C_{3-6}$ cycloalkyl group (e.g., cyclopropyl), or
(3) a mono- or di-$C_{1-6}$ alkylamino group (e.g., dimethylamino).

$R^1$ is particularly preferably
(1) a $C_{1-6}$ alkyl group (e.g., methyl, ethyl) optionally substituted by 1 to 3 substituents selected from
(a) a halogen atom (e.g., a fluorine atom), and
(b) a $C_{1-6}$ alkoxy group (e.g., methoxy), or
(2) a $C_{3-6}$ cycloalkyl group (e.g., cyclopropyl).

As another embodiment, $R^1$ is more preferably
(1) a $C_{1-6}$ alkyl group (e.g., methyl, ethyl, propyl, isopropyl, butyl, isobutyl) optionally substituted by 1 to 3 substituents selected from
(a) a halogen atom (e.g., a fluorine atom, a chlorine atom),
(b) a cyano group,
(c) a hydroxy group, and
(d) a $C_{1-6}$ alkoxy group (e.g., methoxy),
(2) a $C_{2-6}$ alkenyl group (e.g., vinyl, allyl),
(3) a $C_{3-10}$ cycloalkyl group (e.g., cyclopropyl) optionally substituted by 1 to 3 halogen atoms (e.g., a fluorine atom),
(4) a mono- or di-$C_{1-6}$ alkylamino group (e.g., dimethylamino), or
(5) a 3- to 14-membered non-aromatic heterocyclic group (preferably a 3- to 8-membered monocyclic non-aromatic heterocyclic group (e.g., oxetanyl)).

In this embodiment, $R^1$ is further more preferably
(1) a $C_{1-6}$ alkyl group (e.g., methyl, ethyl, propyl, isopropyl, butyl, isobutyl) optionally substituted by 1 to 3 substituents selected from
(a) a halogen atom (e.g., a fluorine atom, a chlorine atom),
(b) a cyano group,
(c) a hydroxy group, and
(d) a $C_{1-6}$ alkoxy group (e.g., methoxy),
(2) a $C_{2-6}$ alkenyl group (e.g., vinyl, allyl),
(3) a $C_{3-6}$ cycloalkyl group (e.g., cyclopropyl) optionally substituted by 1 to 3 halogen atoms (e.g., a fluorine atom),
(4) a mono- or di-$C_{1-6}$ alkylamino group (e.g., dimethylamino), or
(5) an oxetanyl group.

In this embodiment, $R^1$ is still more preferably
(1) a $C_{1-6}$ alkyl group (e.g., methyl, ethyl, propyl) optionally substituted by 1 to 3 substituents selected from
(a) a halogen atom (e.g., a fluorine atom, a chlorine atom), and
(b) a $C_{1-6}$ alkoxy group (e.g., methoxy),
(2) a $C_{3-6}$ cycloalkyl group (e.g., cyclopropyl) optionally substituted by 1 to 3 halogen atoms (e.g., a fluorine atom), or
(3) a mono- or di-$C_{1-6}$ alkylamino group (e.g., dimethylamino).

In this embodiment, $R^1$ is even more preferably
(1) a $C_{1-6}$ alkyl group (e.g., methyl, ethyl) optionally substituted by 1 to 3 substituents selected from
(a) a halogen atom (e.g., a fluorine atom), and
(b) a $C_{1-6}$ alkoxy group (e.g., methoxy),
(2) a $C_{3-6}$ cycloalkyl group (e.g., cyclopropyl) optionally substituted by 1 to 3 halogen atoms (e.g., a fluorine atom), or
(3) a mono- or di-$C_{1-6}$ alkylamino group (e.g., dimethylamino).

In this embodiment, $R^1$ is particularly preferably
(1) a $C_{1-6}$ alkyl group (e.g., methyl, ethyl),
(2) a $C_{3-6}$ cycloalkyl group (e.g., cyclopropyl) optionally substituted by 1 to 3 halogen atoms (e.g., a fluorine atom), or
(3) a mono- or di-$C_{1-6}$ alkylamino group (e.g., dimethylamino).

Or, $R^1$ is particularly preferably a $C_{1-6}$ alkyl group (e.g., methyl, ethyl).

$R^2$, $R^3$, $R^4$ and $R^5$ are each independently a hydrogen atom, or a substituent.

$R^2$ is preferably a hydrogen atom.

$R^3$ is preferably a hydrogen atom, or an acyl group.

$R^3$ is more preferably
(1) a hydrogen atom,
(2) an optionally substituted $C_{1-6}$ alkoxy-carbonyl group (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, 1,2-dimethylpropoxycarbonyl),
(3) an optionally substituted $C_{1-6}$ alkyl-carbonyl group (e.g., acetyl, propanoyl, 2-methylpropanoyl, butanoyl, 2-methylbutanoyl, 3-methylbutanoyl, pivaloyl),
(4) an optionally substituted mono- or di-$C_{1-6}$ alkyl-carbamoyl group (e.g., dimethylcarbamoyl, ethylcarbamoyl, N-ethyl-N-methylcarbamoyl),
(5) an optionally substituted $C_{3-10}$ cycloalkyl-carbonyl group (the $C_{3-10}$ cycloalkyl in the $C_{3-10}$ cycloalkyl-carbonyl group may be a bridged ring group, e.g., cyclopropylcarbonyl, cyclobutylcarbonyl, cyclopentylcarbonyl, bicyclo[1.1.1]pentylcarbonyl),
(6) an optionally substituted $C_{3-10}$ cycloalkoxy-carbonyl group (e.g., cyclopropoxycarbonyl, cyclobutyloxycarbonyl, cyclopentyloxycarbonyl, cyclohexyloxycarbonyl),
(7) an optionally substituted 3- to 14-membered non-aromatic heterocyclylcarbonyl group (preferably a 3- to 8-membered monocyclic non-aromatic heterocyclylcarbonyl group (the non-aromatic heterocycle in the non-aromatic heterocyclylcarbonyl group may be a spiro ring, e.g., oxetanylcarbonyl, azetidinylcarbonyl, 5-azaspiro[2.3]hexylcarbonyl)),
(8) an optionally substituted 3- to 14-membered non-aromatic heterocyclyloxycarbonyl group (preferably a 3- to 8-membered monocyclic non-aromatic heterocyclyloxycarbonyl group (e.g., oxetanyloxycarbonyl, tetrahydrofuryloxycarbonyl, tetrahydropyranyloxycarbonyl)), (9) an optionally substituted $C_{6-14}$ aryloxy-carbonyl group (e.g., phenoxycarbonyl), or

(10) an optionally substituted $C_{7-16}$ aralkyloxy-carbonyl group (e.g., benzyloxycarbonyl).

Examples of the substituent of the above-mentioned "optionally substituted $C_{1-6}$ alkoxy-carbonyl group", "optionally substituted $C_{1-6}$ alkyl-carbonyl group", "optionally substituted mono- or di-$C_{1-6}$ alkyl-carbamoyl group", "optionally substituted $C_{3-10}$ cycloalkyl-carbonyl group", "optionally substituted $C_{3-10}$ cycloalkoxy-carbonyl group", "optionally substituted 3- to 14-membered non-aromatic heterocyclylcarbonyl group", "optionally substituted 3- to 14-membered non-aromatic heterocyclyloxycarbonyl group", "optionally substituted $C_{6-14}$ aryloxy-carbonyl group" and "optionally substituted $C_{7-16}$ aralkyloxy-carbonyl group" each include the above-mentioned "substituent". The number of the substituents is preferably 1 to 3. When the number of the substituents is 2 or more, the respective substituents may be the same or different.

$R^3$ is further more preferably (1) a hydrogen atom, (2) a $C_{1-6}$ alkoxy-carbonyl group (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, 1,2-dimethylpropoxycarbonyl) optionally substituted by 1 to 3 substituents selected from
- (a) a halogen atom (e.g., a fluorine atom),
- (b) a $C_{1-6}$ alkoxy group (e.g., methoxy),
- (c) a $C_{3-10}$ cycloalkyl group (e.g., cyclopropyl, cyclobutyl, cyclopentyl) optionally substituted by 1 to 3 substituents selected from
  - (i) a halogen atom (e.g., a fluorine atom), and
  - (ii) a $C_{1-6}$ alkyl group (e.g., methyl), and
- (d) a 3- to 14-membered non-aromatic heterocyclic group (preferably a 3- to 8-membered monocyclic non-aromatic heterocyclic group (e.g., oxetanyl, tetrahydrofuryl)), (3) a $C_{1-6}$ alkyl-carbonyl group (e.g., acetyl, propanoyl, 2-methylpropanoyl, butanoyl, 2-methylbutanoyl, 3-methylbutanoyl, pivaloyl) optionally substituted by 1 to 3 substituents selected from
- (a) a halogen atom (e.g., a fluorine atom), and
- (b) a $C_{3-10}$ cycloalkyl group (e.g., cyclopropyl), (4) a mono- or di-$C_{1-6}$ alkyl-carbamoyl group (e.g., dimethylcarbamoyl, ethylcarbamoyl, N-ethyl-N-methylcarbamoyl), (5) a $C_{3-10}$ cycloalkyl-carbonyl group (the $C_{3-10}$ cycloalkyl in the $C_{3-10}$ cycloalkyl-carbonyl group may be a bridged ring group, e.g., cyclopropylcarbonyl, cyclobutylcarbonyl, cyclopentylcarbonyl, bicyclo[1.1.1]pentylcarbonyl) optionally substituted by 1 to 3 substituents selected from
- (a) a halogen atom (e.g., a fluorine atom),
- (b) a $C_{1-6}$ alkyl group (e.g., methyl) optionally substituted by 1 to 3 halogen atoms (e.g., a fluorine atom),
- (c) a hydroxy group,
- (d) a $C_{1-6}$ alkoxy group (e.g., methoxy), and
- (e) a cyano group, (6) a $C_{3-10}$ cycloalkoxy-carbonyl group (e.g., cyclopropoxycarbonyl, cyclobutyloxycarbonyl, cyclopentyloxycarbonyl, cyclohexyloxycarbonyl) optionally substituted by 1 to 3 substituents selected from
- (a) a halogen atom (e.g., a fluorine atom), and
- (b) a $C_{1-6}$ alkyl group (e.g., methyl), (7) a 3- to 14-membered non-aromatic heterocyclylcarbonyl group (preferably a 3- to 8-membered monocyclic non-aromatic heterocyclylcarbonyl group (the non-aromatic heterocycle in the non-aromatic heterocyclylcarbonyl group may be a spiro ring, e.g., oxetanylcarbonyl, azetidinylcarbonyl, 5-azaspiro[2.3]hexylcarbonyl)) optionally substituted by 1 to 3 substituents selected from
- (a) a halogen atom (e.g., a fluorine atom), and
- (b) a $C_{1-6}$ alkyl group (e.g., methyl), (8) a 3- to 14-membered non-aromatic heterocyclyloxycarbonyl group (preferably a 3- to 8-membered monocyclic non-aromatic heterocyclyloxycarbonyl group (e.g., oxetanyloxycarbonyl, tetrahydrofuryloxycarbonyl, tetrahydropyranyloxycarbonyl)), (9) a $C_{6-14}$ aryloxy-carbonyl group (e.g., phenoxycarbonyl), or

(10) a $C_{7-16}$ aralkyloxy-carbonyl group (e.g., benzyloxycarbonyl).

$R^3$ is still more preferably (1) a hydrogen atom, (2) a $C_{1-6}$ alkoxy-carbonyl group (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, 1,2-dimethylpropoxycarbonyl) optionally substituted by 1 to 3 substituents selected from
- (a) a halogen atom (e.g., a fluorine atom),
- (b) a $C_{1-6}$ alkoxy group (e.g., methoxy),
- (c) a $C_{3-6}$ cycloalkyl group (e.g., cyclopropyl, cyclobutyl, cyclopentyl) optionally substituted by 1 to 3 substituents selected from
  - (i) a halogen atom (e.g., a fluorine atom), and
  - (ii) a $C_{1-6}$ alkyl group (e.g., methyl),
- (d) an oxetanyl group, and
- (e) a tetrahydrofuryl group, (3) a $C_{1-6}$ alkyl-carbonyl group (e.g., acetyl, propanoyl, 2-methylpropanoyl, butanoyl, 2-methylbutanoyl, 3-methylbutanoyl, pivaloyl) optionally substituted by 1 to 3 substituents selected from
- (a) a halogen atom (e.g., a fluorine atom), and
- (b) a $C_{3-6}$ cycloalkyl group (e.g., cyclopropyl), (4) a mono- or di-$C_{1-6}$ alkyl-carbamoyl group (e.g., dimethylcarbamoyl, ethylcarbamoyl, N-ethyl-N-methylcarbamoyl), (5) a $C_{3-6}$ cycloalkyl-carbonyl group (the $C_{3-6}$ cycloalkyl in the $C_{3-6}$ cycloalkyl-carbonyl group may be a bridged ring group, e.g., cyclopropylcarbonyl, cyclobutylcarbonyl, cyclopentylcarbonyl, bicyclo[1.1.1]pentylcarbonyl) optionally substituted by 1 to 3 substituents selected from
- (a) a halogen atom (e.g., a fluorine atom),
- (b) a $C_{1-6}$ alkyl group (e.g., methyl) optionally substituted by 1 to 3 halogen atoms (e.g., a fluorine atom),
- (c) a hydroxy group,
- (d) a $C_{1-6}$ alkoxy group (e.g., methoxy), and
- (e) a cyano group, (6) a $C_{3-6}$ cycloalkoxy-carbonyl group (e.g., cyclopropoxycarbonyl, cyclobutyloxycarbonyl, cyclopentyloxycarbonyl, cyclohexyloxycarbonyl) optionally substituted by 1 to 3 substituents selected from
- (a) a halogen atom (e.g., a fluorine atom), and
- (b) a $C_{1-6}$ alkyl group (e.g., methyl), (7) an oxetanylcarbonyl group, (8) an azetidinylcarbonyl group optionally substituted by 1 to 3 substituents selected from (a) a halogen atom (e.g., a fluorine atom), and
(b) a $C_{1-6}$ alkyl group (e.g., methyl),
(9) a 5-azaspiro[2.3]hexylcarbonyl group,
(10) an oxetanyloxycarbonyl group,
(11) a tetrahydrofuryloxycarbonyl group,
(12) a tetrahydropyranyloxycarbonyl group,
(13) a phenoxycarbonyl group, or
(14) a benzyloxycarbonyl group.

$R^3$ is even more preferably
(1) a $C_{1-6}$ alkoxy-carbonyl group (e.g., methoxycarbonyl, ethoxycarbonyl, isopropoxycarbonyl),
(2) a $C_{1-6}$ alkyl-carbonyl group (e.g., acetyl, 2-methylpropanoyl, pivaloyl),
(3) a mono- or di-$C_{1-6}$ alkyl-carbamoyl group (e.g., dimethylcarbamoyl, ethylcarbamoyl),
(4) a $C_{3-6}$ cycloalkyl-carbonyl group (the $C_{3-6}$ cycloalkyl in the $C_{3-6}$ cycloalkyl-carbonyl group may be a bridged ring group, e.g., cyclopropylcarbonyl, cyclobutylcarbonyl, bicyclo[1.1.1]pentylcarbonyl) optionally substituted by 1 to 3 substituents selected from
(a) a halogen atom (e.g., a fluorine atom),
(b) a $C_{1-6}$ alkyl group (e.g., methyl) optionally substituted by 1 to 3 halogen atoms (e.g., a fluorine atom),
(c) a hydroxy group,
(d) a $C_{1-6}$ alkoxy group (e.g., methoxy), and
(e) a cyano group,
(5) a $C_{3-6}$ cycloalkoxy-carbonyl group (e.g., cyclopropoxycarbonyl),
(6) a phenoxycarbonyl group,
(7) an oxetanylcarbonyl group,
(8) an azetidinylcarbonyl group optionally substituted by 1 to 3 substituents selected from
(a) a halogen atom (e.g., a fluorine atom), and
(b) a $C_{1-6}$ alkyl group (e.g., methyl), or
(9) a 5-azaspiro[2.3]hexylcarbonyl group.

$R^3$ is particularly preferably
(1) a $C_{1-6}$ alkoxy-carbonyl group (e.g., ethoxycarbonyl, isopropoxycarbonyl),
(2) a $C_{1-6}$ alkyl-carbonyl group (e.g., 2-methylpropanoyl, pivaloyl),
(3) a $C_{3-6}$ cycloalkyl-carbonyl group (the $C_{3-6}$ cycloalkyl in the $C_{3-6}$ cycloalkyl-carbonyl group may be a bridged ring group, e.g., cyclopropylcarbonyl, cyclobutylcarbonyl, bicyclo[1.1.1]pentylcarbonyl) optionally substituted by 1 to 3 substituents selected from
(a) a halogen atom (e.g., a fluorine atom),
(b) a $C_{1-6}$ alkyl group (e.g., methyl) optionally substituted by 1 to 3 halogen atoms (e.g., a fluorine atom),
(c) a hydroxy group,
(d) a $C_{1-6}$ alkoxy group (e.g., methoxy), and
(e) a cyano group,
(4) an oxetanylcarbonyl group,
(5) an azetidinylcarbonyl group optionally substituted by 1 to 3 substituents selected from
(a) a halogen atom (e.g., a fluorine atom), and
(b) a $C_{1-6}$ alkyl group (e.g., methyl), or
(6) a 5-azaspiro[2.3]hexylcarbonyl group.

As another embodiment, $R^3$ is more preferably
(1) a hydrogen atom,
(2) an optionally substituted $C_{1-6}$ alkoxy-carbonyl group (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, 1,2-dimethylpropoxycarbonyl),
(3) an optionally substituted $C_{1-6}$ alkyl-carbonyl group (e.g., acetyl, propanoyl, 2-methylpropanoyl, butanoyl, 2-methylbutanoyl, 3-methylbutanoyl, pivaloyl),
(4) an optionally substituted mono- or di-$C_{1-6}$ alkyl-carbamoyl group (e.g., dimethylcarbamoyl, ethylcarbamoyl, N-ethyl-N-methylcarbamoyl, N-isopropyl-N-methylcarbamoyl),
(5) an optionally substituted N—$C_{1-6}$ alkyl-N—$C_{1-6}$ alkoxy-carbamoyl group (e.g., N-methoxy-N-methylcarbamoyl),
(6) an optionally substituted $C_{3-10}$ cycloalkyl-carbonyl group (the $C_{3-10}$ cycloalkyl in the $C_{3-10}$ cycloalkyl-carbonyl group may be a bridged ring group, e.g., cyclopropylcarbonyl, cyclobutylcarbonyl, cyclopentylcarbonyl, bicyclo[1.1.1]pentylcarbonyl),
(7) an optionally substituted $C_{3-10}$ cycloalkoxy-carbonyl group (e.g., cyclopropoxycarbonyl, cyclobutyloxycarbonyl, cyclopentyloxycarbonyl, cyclohexyloxycarbonyl),
(8) an optionally substituted 3- to 14-membered non-aromatic heterocyclylcarbonyl group (preferably a 3- to 8-membered monocyclic non-aromatic heterocyclylcarbonyl group (the non-aromatic heterocycle in the non-aromatic heterocyclylcarbonyl group may be a spiro ring, e.g., oxetanylcarbonyl, azetidinylcarbonyl, 5-azaspiro[2.3]hexylcarbonyl)),
(9) an optionally substituted 3- to 14-membered non-aromatic heterocyclyloxycarbonyl group (preferably a 3- to 8-membered monocyclic non-aromatic heterocyclyloxycarbonyl group (e.g., oxetanyloxycarbonyl, tetrahydrofuryloxycarbonyl, tetrahydropyranyloxycarbonyl)),
(10) an optionally substituted $C_{6-14}$ aryloxy-carbonyl group (e.g., phenoxycarbonyl), or
(11) an optionally substituted $C_{7-16}$ aralkyloxy-carbonyl group (e.g., benzyloxycarbonyl).

Examples of the substituent of the above-mentioned "optionally substituted $C_{1-6}$ alkoxy-carbonyl group", "optionally substituted $C_{1-6}$ alkyl-carbonyl group", "optionally substituted mono- or di-$C_{1-6}$ alkyl-carbamoyl group", "optionally substituted N—$C_{1-6}$ alkyl-N—$C_{1-6}$ alkoxy-carbamoyl group", "optionally substituted $C_{3-10}$ cycloalkyl-carbonyl group", "optionally substituted $C_{3-10}$ cycloalkoxy-carbonyl group", "optionally substituted 3- to 14-membered non-aromatic heterocyclylcarbonyl group", "optionally substituted 3- to 14-membered non-aromatic heterocyclyloxy-carbonyl group", "optionally substituted $C_{6-14}$ aryloxy-carbonyl group" and "optionally substituted $C_{7-16}$ aralkyloxy-carbonyl group" each include the above-mentioned "substituent". The number of the substituents is preferably 1 to 3. When the number of the substituents is 2 or more, the respective substituents may be the same or different.

In this embodiment, $R^3$ is further more preferably
(1) a hydrogen atom,
(2) a $C_{1-6}$ alkoxy-carbonyl group (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, 1,2-dimethylpropoxycarbonyl) optionally substituted by 1 to 3 substituents selected from
(a) a halogen atom (e.g., a fluorine atom),
(b) a $C_{1-6}$ alkoxy group (e.g., methoxy),
(c) a $C_{3-10}$ cycloalkyl group (e.g., cyclopropyl, cyclobutyl, cyclopentyl) optionally substituted by 1 to 3 substituents selected from
(i) a halogen atom (e.g., a fluorine atom), and
(ii) a $C_{1-6}$ alkyl group (e.g., methyl), and (d) a 3- to 14-membered non-aromatic heterocyclic group (preferably a 3- to 8-membered monocyclic non-aromatic heterocyclic group (e.g., oxetanyl, tetrahydrofuryl)), (3) a $C_{1-6}$ alkyl-carbonyl group (e.g., acetyl, propanoyl, 2-methylpropanoyl, butanoyl, 2-methylbutanoyl, 3-methylbutanoyl, pivaloyl) optionally substituted by 1 to 3 substituents selected from (a) a halogen atom (e.g., a fluorine atom), (b) a $C_{3-10}$ cycloalkyl group (e.g., cyclopropyl), (c) a hydroxy group, and (d) a $C_{1-6}$ alkoxy group (e.g., methoxy), (4) a mono- or di-$C_{1-6}$ alkyl-carbamoyl group (e.g., dimethylcarbamoyl, ethylcarbamoyl, N-ethyl-N-methylcarbamoyl, N-isopropyl-N-methylcarbamoyl), (5) a N—$C_{1-6}$ alkyl-N—$C_{1-6}$ alkoxy-carbamoyl group (e.g., N-methoxy-N-methylcarbamoyl), (6) a $C_{3-10}$ cycloalkyl-carbonyl group (the $C_{3-10}$ cycloalkyl in the $C_{3-10}$ cycloalkyl-carbonyl group may be a bridged ring group, e.g., cyclopropylcarbonyl, cyclobutylcarbonyl, cyclopentylcarbonyl, bicyclo[1.1.1]pentylcarbonyl) optionally substituted by 1 to 3 substituents selected from (a) a halogen atom (e.g., a fluorine atom), (b) a $C_{1-6}$ alkyl group (e.g., methyl) optionally substituted by 1 to 3 halogen atoms (e.g., a fluorine atom), (c) a hydroxy group, (d) a $C_{1-6}$ alkoxy group (e.g., methoxy), and (e) a cyano group, (7) a $C_{3-10}$ cycloalkoxy-carbonyl group (e.g., cyclopropoxycarbonyl, cyclobutyloxycarbonyl, cyclopentyloxycarbonyl, cyclohexyloxycarbonyl) optionally substituted by 1 to 3 substituents selected from (a) a halogen atom (e.g., a fluorine atom), and (b) a $C_{1-6}$ alkyl group (e.g., methyl), (8) a 3- to 14-membered non-aromatic heterocyclylcarbonyl group (preferably a 3- to 8-membered monocyclic non-aromatic heterocyclylcarbonyl group (the non-aromatic heterocycle in the non-aromatic heterocyclylcarbonyl group may be a spiro ring, e.g., oxetanylcarbonyl, azetidinylcarbonyl, 5-azaspiro[2.3]hexylcarbonyl)) optionally substituted by 1 to 3 substituents selected from (a) a halogen atom (e.g., a fluorine atom), and (b) a $C_{1-6}$ alkyl group (e.g., methyl), (9) a 3- to 14-membered non-aromatic heterocyclyloxycarbonyl group (preferably a 3- to 8-membered monocyclic non-aromatic heterocyclyloxycarbonyl group (e.g., oxetanyloxycarbonyl, tetrahydrofuryloxycarbonyl, tetrahydropyranyloxycarbonyl)),

(10) a $C_{6-4}$ aryloxy-carbonyl group (e.g., phenoxycarbonyl), or

(11) a $C_{7-16}$ aralkyloxy-carbonyl group (e.g., benzyloxycarbonyl).

In this embodiment, $R^3$ is still more preferably (1) a hydrogen atom, (2) a $C_{1-6}$ alkoxy-carbonyl group (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, 1,2-dimethylpropoxycarbonyl) optionally substituted by 1 to 3 substituents selected from (a) a halogen atom (e.g., a fluorine atom), (b) a $C_{1-6}$ alkoxy group (e.g., methoxy), (c) a $C_{3-6}$ cycloalkyl group (e.g., cyclopropyl, cyclobutyl, cyclopentyl) optionally substituted by 1 to 3 substituents selected from (i) a halogen atom (e.g., a fluorine atom), and (ii) a $C_{1-6}$ alkyl group (e.g., methyl), (d) an oxetanyl group, and (e) a tetrahydrofuryl group, (3) a $C_{1-6}$ alkyl-carbonyl group (e.g., acetyl, propanoyl, 2-methylpropanoyl, butanoyl, 2-methylbutanoyl, 3-methylbutanoyl, pivaloyl) optionally substituted by 1 to 3 substituents selected from (a) a halogen atom (e.g., a fluorine atom), (b) a $C_{3-6}$ cycloalkyl group (e.g., cyclopropyl), (c) a hydroxy group, and (d) a $C_{1-6}$ alkoxy group (e.g., methoxy), (4) a mono- or di-$C_{1-6}$ alkyl-carbamoyl group (e.g., dimethylcarbamoyl, ethylcarbamoyl, N-ethyl-N-methylcarbamoyl, N-isopropyl-N-methylcarbamoyl), (5) a N—$C_{1-6}$ alkyl-N—$C_{1-6}$ alkoxy-carbamoyl group (e.g., N-methoxy-N-methylcarbamoyl), (6) a $C_{3-6}$ cycloalkyl-carbonyl group (the $C_{3-6}$ cycloalkyl in the $C_{3-6}$ cycloalkyl-carbonyl group may be a bridged ring group, e.g., cyclopropylcarbonyl, cyclobutylcarbonyl, cyclopentylcarbonyl, bicyclo[1.1.1]pentylcarbonyl) optionally substituted by 1 to 3 substituents selected from (a) a halogen atom (e.g., a fluorine atom), (b) a $C_{1-6}$ alkyl group (e.g., methyl) optionally substituted by 1 to 3 halogen atoms (e.g., a fluorine atom), (c) a hydroxy group, (d) a $C_{1-6}$ alkoxy group (e.g., methoxy), and (e) a cyano group, (7) a $C_{3-6}$ cycloalkoxy-carbonyl group (e.g., cyclopropoxycarbonyl, cyclobutyloxycarbonyl, cyclopentyloxycarbonyl, cyclohexyloxycarbonyl) optionally substituted by 1 to 3 substituents selected from (a) a halogen atom (e.g., a fluorine atom), and (b) a $C_{1-6}$ alkyl group (e.g., methyl), (8) an oxetanylcarbonyl group, (9) an azetidinylcarbonyl group optionally substituted by 1 to 3 substituents selected from (a) a halogen atom (e.g., a fluorine atom), and (b) a $C_{1-6}$ alkyl group (e.g., methyl),

(10) a 5-azaspiro[2.3]hexylcarbonyl group,

(11) an oxetanyloxycarbonyl group,

(12) a tetrahydrofuryloxycarbonyl group,

(13) a tetrahydropyranyloxycarbonyl group,

(14) a phenoxycarbonyl group, or

(15) a benzyloxycarbonyl group.

In this embodiment, $R^3$ is even more preferably (1) a $C_{1-6}$ alkoxy-carbonyl group (e.g., methoxycarbonyl, ethoxycarbonyl, isopropoxycarbonyl), (2) a $C_{1-6}$ alkyl-carbonyl group (e.g., acetyl, 2-methylpropanoyl, pivaloyl) optionally substituted by 1 to 3 hydroxy groups, (3) a mono- or di-$C_{1-6}$ alkyl-carbamoyl group (e.g., dimethylcarbamoyl, ethylcarbamoyl), (4) a $C_{3-6}$ cycloalkyl-carbonyl group (the $C_{3-6}$ cycloalkyl in the $C_{3-6}$ cycloalkyl-carbonyl group may be a bridged ring group, e.g., cyclopropylcarbonyl, cyclobutylcarbonyl, bicyclo[1.1.1]pentylcarbonyl) optionally substituted by 1 to 3 substituents selected from (a) a halogen atom (e.g., a fluorine atom), (b) a $C_{1-6}$ alkyl group (e.g., methyl) optionally substituted by 1 to 3 halogen atoms (e.g., a fluorine atom), (c) a hydroxy group, (d) a $C_{1-6}$ alkoxy group (e.g., methoxy), and (e) a cyano group, (5) a $C_{3-6}$ cycloalkoxy-carbonyl group (e.g., cyclopropoxycarbonyl), (6) a phenoxycarbonyl group,
(7) an oxetanylcarbonyl group,
(8) an azetidinylcarbonyl group optionally substituted by 1 to 3 substituents selected from
(a) a halogen atom (e.g., a fluorine atom), and
(b) a $C_{1-6}$ alkyl group (e.g., methyl), or
(9) a 5-azaspiro[2.3]hexylcarbonyl group.

In this embodiment, $R^3$ is particularly preferably
(1) a $C_{1-6}$ alkoxy-carbonyl group (e.g., ethoxycarbonyl, isopropoxycarbonyl),
(2) a $C_{1-6}$ alkyl-carbonyl group (e.g., 2-methylpropanoyl, pivaloyl) optionally substituted by 1 to 3 hydroxy groups,
(3) a mono- or di-$C_{1-6}$ alkyl-carbamoyl group (e.g., dimethylcarbamoyl),
(4) a $C_{3-6}$ cycloalkyl-carbonyl group (the $C_{3-6}$ cycloalkyl in the $C_{3-6}$ cycloalkyl-carbonyl group may be a bridged ring group, e.g., cyclopropylcarbonyl, cyclobutylcarbonyl, bicyclo[1.1.1]pentylcarbonyl) optionally substituted by 1 to 3 substituents selected from
(a) a halogen atom (e.g., a fluorine atom),
(b) a $C_{1-6}$ alkyl group (e.g., methyl) optionally substituted by 1 to 3 halogen atoms (e.g., a fluorine atom),
(c) a hydroxy group,
(d) a $C_{1-6}$ alkoxy group (e.g., methoxy), and
(e) a cyano group,
(5) an oxetanylcarbonyl group,
(6) an azetidinylcarbonyl group optionally substituted by 1 to 3 substituents selected from
(a) a halogen atom (e.g., a fluorine atom), and
(b) a $C_{1-6}$ alkyl group (e.g., methyl), or
(7) a 5-azaspiro[2.3]hexylcarbonyl group.

As another embodiment, $R^3$ is more preferably
(1) a hydrogen atom,
(2) an optionally substituted $C_{1-6}$ alkoxy-carbonyl group (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, 1,2-dimethylpropoxycarbonyl),
(3) an optionally substituted $C_{1-6}$ alkyl-carbonyl group (e.g., acetyl, propanoyl, 2-methylpropanoyl, butanoyl, 2-methylbutanoyl, 3-methylbutanoyl, pivaloyl),
(4) an optionally substituted mono- or di-$C_{1-6}$ alkyl-carbamoyl group (e.g., dimethylcarbamoyl, ethylcarbamoyl, N-ethyl-N-methylcarbamoyl, N-isopropyl-N-methylcarbamoyl),
(5) an optionally substituted N—$C_{1-6}$ alkyl-N—$C_{1-6}$ alkoxy-carbamoyl group (e.g., N-methoxy-N-methylcarbamoyl),
(6) an optionally substituted $C_{3-10}$ cycloalkyl-carbonyl group (the $C_{3-10}$ cycloalkyl in the $C_{3-10}$ cycloalkyl-carbonyl group may be a bridged ring group, e.g., cyclopropylcarbonyl, cyclobutylcarbonyl, cyclopentylcarbonyl, bicyclo[1.1.1]pentylcarbonyl),
(7) an optionally substituted $C_{3-10}$ cycloalkoxy-carbonyl group (e.g., cyclopropoxycarbonyl, cyclobutyloxycarbonyl, cyclopentyloxycarbonyl, cyclohexyloxycarbonyl),
(8) an optionally substituted 3- to 14-membered non-aromatic heterocyclylcarbonyl group (preferably a 3- to 8-membered monocyclic non-aromatic heterocyclylcarbonyl group (the non-aromatic heterocycle in the non-aromatic heterocyclylcarbonyl group may be a spiro ring, e.g., oxetanylcarbonyl, azetidinylcarbonyl, 5-azaspiro[2.3]hexylcarbonyl, isoxazolidinylcarbonyl)),
(9) an optionally substituted 3- to 14-membered non-aromatic heterocyclyloxycarbonyl group (preferably a 3- to 8-membered monocyclic non-aromatic heterocyclyloxycarbonyl group (e.g., oxetanyloxycarbonyl, tetrahydrofuryloxycarbonyl, tetrahydropyranyloxycarbonyl)),
(10) an optionally substituted $C_{6-14}$ aryloxy-carbonyl group (e.g., phenoxycarbonyl),
(11) an optionally substituted $C_{7-16}$ aralkyloxy-carbonyl group (e.g., benzyloxycarbonyl),
(12) an optionally substituted 5- to 14-membered aromatic heterocyclic group (preferably a 5- to 6-membered monocyclic aromatic heterocyclic group (e.g., imidazolyl, pyridazinyl)),
(13) an optionally substituted 5- to 14-membered aromatic heterocyclylcarbonyl group (preferably a 5- to 6-membered monocyclic aromatic heterocyclylcarbonyl group (e.g., pyrazolylcarbonyl, furylcarbonyl)), or
(14) an optionally substituted tri-$C_{1-6}$ alkylhydrazino-carbonyl group (e.g., trimethylhydrazinocarbonyl).

Examples of the substituent of the above-mentioned "optionally substituted $C_{1-6}$ alkoxy-carbonyl group", "optionally substituted $C_{1-6}$ alkyl-carbonyl group", "optionally substituted mono- or di-$C_{1-6}$ alkyl-carbamoyl group", "optionally substituted N—$C_{1-6}$ alkyl-N—$C_{1-6}$ alkoxy-carbamoyl group", "optionally substituted $C_{3-10}$ cycloalkyl-carbonyl group", "optionally substituted $C_{3-10}$ cycloalkoxy-carbonyl group", "optionally substituted 3- to 14-membered non-aromatic heterocyclylcarbonyl group", "optionally substituted 3- to 14-membered non-aromatic heterocyclyloxy-carbonyl group", "optionally substituted $C_{6-14}$ aryloxy-carbonyl group", "optionally substituted $C_{7-16}$ aralkyloxy-carbonyl group", "optionally substituted 5- to 14-membered aromatic heterocyclic group", "optionally substituted 5- to 14-membered aromatic heterocyclylcarbonyl group" and "tri-$C_{1-6}$ alkylhydrazino-carbonyl group" each include the above-mentioned "substituent". The number of the substituents is preferably 1 to 3. When the number of the substituents is 2 or more, the respective substituents may be the same or different.

In this embodiment, $R^3$ is further more preferably
(1) a hydrogen atom,
(2) a $C_{1-6}$ alkoxy-carbonyl group (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, 1,2-dimethylpropoxycarbonyl) optionally substituted by 1 to 3 substituents selected from
(a) a halogen atom (e.g., a fluorine atom),
(b) a $C_{1-6}$ alkoxy group (e.g., methoxy),
(c) a $C_{3-10}$ cycloalkyl group (e.g., cyclopropyl, cyclobutyl, cyclopentyl) optionally substituted by 1 to 3 substituents selected from
(i) a halogen atom (e.g., a fluorine atom), and
(ii) a $C_{1-6}$ alkyl group (e.g., methyl), and
(d) a 3- to 14-membered non-aromatic heterocyclic group (preferably a 3- to 8-membered monocyclic non-aromatic heterocyclic group (e.g., oxetanyl, tetrahydrofuryl)),
(3) a $C_{1-6}$ alkyl-carbonyl group (e.g., acetyl, propanoyl, 2-methylpropanoyl, butanoyl, 2-methylbutanoyl, 3-methylbutanoyl, pivaloyl) optionally substituted by 1 to 3 substituents selected from
(a) a halogen atom (e.g., a fluorine atom),
(b) a $C_{3-10}$ cycloalkyl group (e.g., cyclopropyl),
(c) a hydroxy group, and
(d) a $C_{1-6}$ alkoxy group (e.g., methoxy), (4) a mono- or di-$C_{1-6}$ alkyl-carbamoyl group (e.g., dimethylcarbamoyl, ethylcarbamoyl, N-ethyl-N-methylcarbamoyl, N-isopropyl-N-methylcarbamoyl),
(5) a N—$C_{1-6}$ alkyl-N—$C_{1-6}$ alkoxy-carbamoyl group (e.g., N-methoxy-N-methylcarbamoyl),
(6) a $C_{3-10}$ cycloalkyl-carbonyl group (the $C_{3-10}$ cycloalkyl in the $C_{3-10}$ cycloalkyl-carbonyl group may be a bridged ring group, e.g., cyclopropylcarbonyl, cyclobutylcarbonyl, cyclopentylcarbonyl, bicyclo[1.1.1]pentylcarbonyl) optionally substituted by 1 to 3 substituents selected from
(a) a halogen atom (e.g., a fluorine atom),
(b) a $C_{1-6}$ alkyl group (e.g., methyl) optionally substituted by 1 to 3 substituents selected from
(i) a halogen atom (e.g., a fluorine atom), and
(ii) a hydroxy group,
(c) a hydroxy group,
(d) a $C_{1-6}$ alkoxy group (e.g., methoxy), and
(e) a cyano group,
(7) a $C_{3-10}$ cycloalkoxy-carbonyl group (e.g., cyclopropoxycarbonyl, cyclobutyloxycarbonyl, cyclopentyloxycarbonyl, cyclohexyloxycarbonyl) optionally substituted by 1 to 3 substituents selected from
(a) a halogen atom (e.g., a fluorine atom), and
(b) a $C_{1-6}$ alkyl group (e.g., methyl),
(8) a 3- to 14-membered non-aromatic heterocyclylcarbonyl group (preferably a 3- to 8-membered monocyclic non-aromatic heterocyclylcarbonyl group (the non-aromatic heterocycle in the non-aromatic heterocyclylcarbonyl group may be a spiro ring, e.g., oxetanylcarbonyl, azetidinylcarbonyl, 5-azaspiro[2.3]hexylcarbonyl, isoxazolidinylcarbonyl)) optionally substituted by 1 to 3 substituents selected from
(a) a halogen atom (e.g., a fluorine atom), and
(b) a $C_{1-6}$ alkyl group (e.g., methyl),
(9) a 3- to 14-membered non-aromatic heterocyclyloxycarbonyl group (preferably a 3- to 8-membered monocyclic non-aromatic heterocyclyloxycarbonyl group (e.g., oxetanyloxycarbonyl, tetrahydrofuryloxycarbonyl, tetrahydropyranyloxycarbonyl)),
(10) a $C_{6-14}$ aryloxy-carbonyl group (e.g., phenoxycarbonyl),
(11) a $C_{7-16}$ aralkyloxy-carbonyl group (e.g., benzyloxycarbonyl),
(12) a 5- to 14-membered aromatic heterocyclic group (preferably a 5- to 6-membered monocyclic aromatic heterocyclic group (e.g., imidazolyl, pyridazinyl)) optionally substituted by 1 to 3 substituents selected from
(i) a halogen atom (e.g., a chlorine atom), and
(ii) a $C_{1-6}$ alkyl group (e.g., methyl, ethyl),
(13) a 5- to 14-membered aromatic heterocyclylcarbonyl group (preferably a 5- to 6-membered monocyclic aromatic heterocyclylcarbonyl group (e.g., pyrazolylcarbonyl, furylcarbonyl)) optionally substituted by 1 to 3 $C_{1-6}$ alkyl groups (e.g., methyl), or
(14) a tri-$C_{1-6}$ alkylhydrazino-carbonyl group (e.g., trimethylhydrazinocarbonyl).

In this embodiment, $R^3$ is still more preferably
(1) a hydrogen atom,
(2) a $C_{1-6}$ alkoxy-carbonyl group (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, 1,2-dimethylpropoxycarbonyl) optionally substituted by 1 to 3 substituents selected from
(a) a halogen atom (e.g., a fluorine atom),
(b) a $C_{1-6}$ alkoxy group (e.g., methoxy),
(c) a $C_{3-6}$ cycloalkyl group (e.g., cyclopropyl, cyclobutyl, cyclopentyl) optionally substituted by 1 to 3 substituents selected from
(i) a halogen atom (e.g., a fluorine atom), and
(ii) a $C_{1-6}$ alkyl group (e.g., methyl),
(d) an oxetanyl group, and
(e) a tetrahydrofuryl group,
(3) a $C_1$-6 alkyl-carbonyl group (e.g., acetyl, propanoyl, 2-methylpropanoyl, butanoyl, 2-methylbutanoyl, 3-methylbutanoyl, pivaloyl) optionally substituted by 1 to 3 substituents selected from
(a) a halogen atom (e.g., a fluorine atom),
(b) a $C_{3-6}$ cycloalkyl group (e.g., cyclopropyl),
(c) a hydroxy group, and
(d) a $C_{1-6}$ alkoxy group (e.g., methoxy),
(4) a mono- or di-$C_{1-6}$ alkyl-carbamoyl group (e.g., dimethylcarbamoyl, ethylcarbamoyl, N-ethyl-N-methylcarbamoyl, N-isopropyl-N-methylcarbamoyl),
(5) a N—$C_{1-6}$ alkyl-N—$C_{1-6}$ alkoxy-carbamoyl group (e.g., N-methoxy-N-methylcarbamoyl),
(6) a $C_{3-6}$ cycloalkyl-carbonyl group (the $C_{3-6}$ cycloalkyl in the $C_{3-6}$ cycloalkyl-carbonyl group may be a bridged ring group, e.g., cyclopropylcarbonyl, cyclobutylcarbonyl, cyclopentylcarbonyl, bicyclo[1.1.1]pentylcarbonyl) optionally substituted by 1 to 3 substituents selected from
(a) a halogen atom (e.g., a fluorine atom),
(b) a $C_{1-6}$ alkyl group (e.g., methyl) optionally substituted by 1 to 3 substituents selected from
(i) a halogen atom (e.g., a fluorine atom), and
(ii) a hydroxy group,
(c) a hydroxy group,
(d) a $C_{1-6}$ alkoxy group (e.g., methoxy), and
(e) a cyano group,
(7) a $C_{3-6}$ cycloalkoxy-carbonyl group (e.g., cyclopropoxycarbonyl, cyclobutyloxycarbonyl, cyclopentyloxycarbonyl, cyclohexyloxycarbonyl) optionally substituted by 1 to 3 substituents selected from
(a) a halogen atom (e.g., a fluorine atom), and
(b) a $C_{1-6}$ alkyl group (e.g., methyl),
(8) an oxetanylcarbonyl group,
(9) an azetidinylcarbonyl group optionally substituted by 1 to 3 substituents selected from
(a) a halogen atom (e.g., a fluorine atom), and
(b) a $C_{1-6}$ alkyl group (e.g., methyl),
(10) a 5-azaspiro[2.3]hexylcarbonyl group,
(11) an oxetanyloxycarbonyl group,
(12) a tetrahydrofuryloxycarbonyl group,
(13) a tetrahydropyranyloxycarbonyl group,
(14) a phenoxycarbonyl group,
(15) a benzyloxycarbonyl group,
(16) an isoxazolidinylcarbonyl group,
(17) a pyrazolylcarbonyl group optionally substituted by 1 to 3 $C_1$-6 alkyl groups (e.g., methyl),
(18) a furylcarbonyl group,
(19) an imidazolyl group optionally substituted by 1 to 3 $C_{1-6}$ alkyl groups (e.g., methyl, ethyl),
(20) a pyridazinyl group optionally substituted by 1 to 3 substituents selected from
(i) a halogen atom (e.g., a chlorine atom), and
(ii) a $C_{1-6}$ alkyl group (e.g., methyl), or
(21) a tri-$C_{1-6}$ alkylhydrazino-carbonyl group (e.g., trimethylhydrazinocarbonyl).

In this embodiment, $R^3$ is even more preferably
(1) a $C_{1-6}$ alkoxy-carbonyl group (e.g., methoxycarbonyl, ethoxycarbonyl, isopropoxycarbonyl), (2) a $C_{1-6}$ alkyl-carbonyl group (e.g., acetyl, 2-methylpropanoyl, pivaloyl) optionally substituted by 1 to 3 hydroxy groups, (3) a mono- or di-$C_{1-6}$ alkyl-carbamoyl group (e.g., dimethylcarbamoyl, ethylcarbamoyl), (4) a N—$C_{1-6}$ alkyl-N—$C_{1-6}$ alkoxy-carbamoyl group (e.g., N-methoxy-N-methylcarbamoyl), (5) a $C_{3-6}$ cycloalkyl-carbonyl group (the $C_{3-6}$ cycloalkyl in the $C_{3-6}$ cycloalkyl-carbonyl group may be a bridged ring group, e.g., cyclopropylcarbonyl, cyclobutylcarbonyl, bicyclo[1.1.1]pentylcarbonyl) optionally substituted by 1 to 3 substituents selected from (a) a halogen atom (e.g., a fluorine atom), (b) a $C_{1-6}$ alkyl group (e.g., methyl) optionally substituted by 1 to 3 halogen atoms (e.g., a fluorine atom), (c) a hydroxy group, (d) a $C_{1-6}$ alkoxy group (e.g., methoxy), and (e) a cyano group, (6) a $C_{3-6}$ cycloalkoxy-carbonyl group (e.g., cyclopropoxycarbonyl), (7) a phenoxycarbonyl group, (8) an oxetanylcarbonyl group, (9) an azetidinylcarbonyl group optionally substituted by 1 to 3 substituents selected from (a) a halogen atom (e.g., a fluorine atom), and (b) a $C_{1-6}$ alkyl group (e.g., methyl), or

(10) a 5-azaspiro[2.3]hexylcarbonyl group.

In this embodiment, $R^3$ is even more preferably (1) a $C_{1-6}$ alkoxy-carbonyl group (e.g., ethoxycarbonyl, isopropoxycarbonyl), (2) a $C_{1-6}$ alkyl-carbonyl group (e.g., 2-methylpropanoyl, pivaloyl) optionally substituted by 1 to 3 hydroxy groups, (3) a mono- or di-$C_{1-6}$ alkyl-carbamoyl group (e.g., dimethylcarbamoyl), (4) a N—$C_{1-6}$ alkyl-N—$C_{1-6}$ alkoxy-carbamoyl group (e.g., N-methoxy-N-methylcarbamoyl), (5) a $C_{3-6}$ cycloalkyl-carbonyl group (the $C_{3-6}$ cycloalkyl in the $C_{3-6}$ cycloalkyl-carbonyl group may be a bridged ring group, e.g., cyclopropylcarbonyl, cyclobutylcarbonyl, bicyclo[1.1.1]pentylcarbonyl) optionally substituted by 1 to 3 substituents selected from (a) a halogen atom (e.g., a fluorine atom), (b) a $C_{1-6}$ alkyl group (e.g., methyl) optionally substituted by 1 to 3 halogen atoms (e.g., a fluorine atom), (c) a hydroxy group, (d) a $C_{1-6}$ alkoxy group (e.g., methoxy), and (e) a cyano group, (6) an oxetanylcarbonyl group, (7) an azetidinylcarbonyl group optionally substituted by 1 to 3 substituents selected from (a) a halogen atom (e.g., a fluorine atom), and (b) a $C_{1-6}$ alkyl group (e.g., methyl), or (8) a 5-azaspiro[2.3]hexylcarbonyl group.

In this embodiment, $R^3$ is particularly preferably (1) a $C_{1-6}$ alkyl-carbonyl group (e.g., 2-methylpropanoyl) optionally substituted by 1 to 3 hydroxy groups, (2) a mono- or di-$C_{1-6}$ alkyl-carbamoyl group (e.g., dimethylcarbamoyl), (3) a N—$C_{1-6}$ alkyl-N—$C_{1-6}$ alkoxy-carbamoyl group (e.g., N-methoxy-N-methylcarbamoyl), or (4) an azetidinylcarbonyl group.

Or, $R^3$ is particularly preferably a $C_{1-6}$ alkyl-carbonyl group (e.g., 2-methylpropanoyl) optionally substituted by 1 to 3 hydroxy groups.

$R^4$ and $R^5$ are preferably each independently a hydrogen atom or a halogen atom (e.g., a fluorine atom).

$R^4$ and $R^5$ are particularly preferably both hydrogen atoms.

Ring A is an optionally further substituted 4- to 7-membered nitrogen-containing monocyclic saturated heterocycle.

Ring A optionally has substituent(s), in addition to $R^3$, $—NR^2SO_2R^1$ and $—CR^4R^5$-Ring B in the formula (I). Examples of the substituent include the above-mentioned "substituent". The number of the substituents is preferably 1 to 3. When the number of the substituents is 2 or more, the respective substituents may be the same or different.

Ring A is preferably (1) an optionally further substituted pyrrolidine ring, (2) an optionally further substituted piperidine ring, or (3) an optionally further substituted azetidine ring.

Ring A is more preferably (1) a pyrrolidine ring, (2) a piperidine ring, or (3) an azetidine ring.

Ring A is still more preferably (1) a pyrrolidine ring, or (2) a piperidine ring.

Ring B is an optionally further substituted ring.

Ring B optionally has substituent(s), in addition to $—CR^4R^5$-Ring A in the formula (I). Examples of the substituent include the above-mentioned "substituent". The number of the substituents is preferably 1 to 3. When the number of the substituents is 2 or more, the respective substituents may be the same or different.

Ring B is preferably (1) an optionally further substituted $C_{6-14}$ aromatic hydrocarbon ring (e.g., benzene, naphthalene), (2) an optionally further substituted 5- to 14-membered aromatic heterocycle (preferably a 5- to 6-membered monocyclic aromatic heterocycle (e.g., pyridine, pyrazole, thiazole, oxazole)), or (3) an optionally further substituted 3- to 14-membered non-aromatic heterocycle (preferably a 3- to 8-membered monocyclic non-aromatic heterocycle (e.g., pyrrolidine, piperidine), a 9- to 14-membered fused polycyclic (preferably bi- or tri-cyclic) non-aromatic heterocycle (e.g., dibenzofuran)).

Ring B is more preferably (1) a $C_{6-14}$ aromatic hydrocarbon ring (e.g., benzene, naphthalene) optionally further substituted by 1 to 3 substituents selected from (a) a halogen atom (e.g., a fluorine atom, a chlorine atom, a bromine atom, an iodine atom), (b) a $C_{1-6}$ alkyl group (e.g., methyl, isopropyl) optionally substituted by 1 to 3 halogen atoms (e.g., a fluorine atom), (c) a $C_{2-6}$ alkenyl group (e.g., vinyl, propen-2-yl), (d) a mono- or di-$C_{1-6}$ alkylamino group (e.g., dimethylamino), (e) a tri-$C_{1-6}$ alkylsilyloxy group (e.g., triisopropylsilyloxy), (f) a $C_{6-14}$ aryl group (e.g., phenyl) optionally substituted by 1 to 4 substituents selected from (i) a halogen atom (e.g., a fluorine atom, a chlorine atom), (ii) a $C_{1-6}$ alkyl group (e.g., methyl) optionally substituted by 1 to 3 halogen atoms (e.g., a fluorine atom), and (iii) a $C_{1-6}$ alkoxy group (e.g., methoxy), (g) a $C_{6-14}$ aryloxy group (e.g., phenoxy), (h) a $C_{7-16}$ aralkyl group (e.g., benzyl) optionally substituted by 1 to 3 $C_{1-6}$ alkyl groups (e.g., methyl), (i) a $C_{3-10}$ cycloalkyl group (e.g., cyclopropyl, cyclobutyl),
(j) a $C_{3-10}$ cycloalkenyl group (e.g., cyclopenten-1-yl, cyclohexen-1-yl),
(k) a $C_{3-10}$ cycloalkoxy group (e.g., cyclohexyloxy),
(l) a 5- to 14-membered aromatic heterocyclic group (preferably a 5- to 6-membered monocyclic aromatic heterocyclic group (e.g., pyridyl, thienyl, pyrazolyl, pyrimidinyl), a 8- to 14-membered fused polycyclic (preferably bi- or tri-cyclic) aromatic heterocyclic group (e.g., indazolyl)) optionally substituted by 1 to 3 $C_{1-6}$ alkyl groups (e.g., methyl), and
(m) a 3- to 14-membered non-aromatic heterocyclic group (preferably a 3- to 8-membered monocyclic non-aromatic heterocyclic group (e.g., pyrrolidinyl), a 9- to 14-membered fused polycyclic (preferably bi- or tri-cyclic) non-aromatic heterocyclic group (e.g., dihydroindolyl)),
(2) a 5- to 14-membered aromatic heterocycle (preferably a 5- to 6-membered monocyclic aromatic heterocycle (e.g., pyridine, pyrazole, thiazole, oxazole)) optionally further substituted by 1 to 3 substituents selected from
(a) a $C_{6-14}$ aryl group (e.g., phenyl) optionally substituted by 1 to 3 halogen atoms (e.g., a fluorine atom),
(b) a $C_{1-6}$ alkyl group (e.g., methyl, isopropyl), and
(c) a $C_{2-6}$ alkenyl group (e.g., propen-2-yl), or
(3) a 3- to 14-membered non-aromatic heterocycle (preferably a 3- to 8-membered monocyclic non-aromatic heterocycle (e.g., pyrrolidine, piperidine), a 9- to 14-membered fused polycyclic (preferably bi- or tricyclic) non-aromatic heterocycle (e.g., dibenzofuran)) optionally further substituted by 1 to 3 substituents selected from
(a) a $C_{6-14}$ aryl group (e.g., phenyl), and
(b) a 5- to 14-membered aromatic heterocyclic group (preferably a 5- to 6-membered monocyclic aromatic heterocyclic group (e.g., pyrimidinyl)).

Ring B is further more preferably
(1) a benzene ring optionally further substituted by 1 to 3 substituents selected from
(a) a halogen atom (e.g., a fluorine atom, a chlorine atom, a bromine atom, an iodine atom),
(b) a $C_{1-6}$ alkyl group (e.g., methyl, isopropyl) optionally substituted by 1 to 3 halogen atoms (e.g., a fluorine atom),
(c) a $C_{2-6}$ alkenyl group (e.g., vinyl, propen-2-yl),
(d) a mono- or di-$C_{1-6}$ alkylamino group (e.g., dimethylamino),
(e) a tri-$C_{1-6}$ alkylsilyloxy group (e.g., triisopropylsilyloxy),
(f) a $C_{6-14}$ aryl group (e.g., phenyl) optionally substituted by 1 to 4 substituents selected from
(i) a halogen atom (e.g., a fluorine atom, a chlorine atom),
(ii) a $C_{1-6}$ alkyl group (e.g., methyl) optionally substituted by 1 to 3 halogen atoms (e.g., a fluorine atom), and
(iii) a $C_{1-6}$ alkoxy group (e.g., methoxy),
(g) a $C_{6-14}$ aryloxy group (e.g., phenoxy),
(h) a $C_{7-16}$ aralkyl group (e.g., benzyl) optionally substituted by 1 to 3 $C_{1-6}$ alkyl groups (e.g., methyl),
(i) a $C_{3-10}$ cycloalkyl group (e.g., cyclopropyl, cyclobutyl),
(j) a $C_{3-10}$ cycloalkenyl group (e.g., cyclopenten-1-yl, cyclohexen-1-yl),
(k) a $C_{3-10}$ cycloalkoxy group (e.g., cyclohexyloxy),
(l) a 5- to 14-membered aromatic heterocyclic group (preferably a 5- to 6-membered monocyclic aromatic heterocyclic group (e.g., pyridyl, thienyl, pyrazolyl, pyrimidinyl), a 8- to 14-membered fused polycyclic (preferably bi- or tri-cyclic) aromatic heterocyclic group (e.g., indazolyl)) optionally substituted by 1 to 3 $C_{1-6}$ alkyl groups (e.g., methyl), and
(m) a 3- to 14-membered non-aromatic heterocyclic group (preferably a 3- to 8-membered monocyclic non-aromatic heterocyclic group (e.g., pyrrolidinyl), a 9- to 14-membered fused polycyclic (preferably bi- or tri-cyclic) non-aromatic heterocyclic group (e.g., dihydroindolyl)),
(2) a naphthalene ring,
(3) a pyridine ring optionally further substituted by 1 to 3 substituents selected from
(a) a $C_{6-14}$ aryl group (e.g., phenyl) optionally substituted by 1 to 3 halogen atoms (e.g., a fluorine atom),
(b) a $C_{1-6}$ alkyl group (e.g., isopropyl), and
(c) a $C_{2-6}$ alkenyl group (e.g., propen-2-yl),
(4) a pyrazole ring optionally further substituted by 1 or 2 $C_{6-14}$ aryl groups (e.g., phenyl),
(5) a thiazole ring optionally further substituted by 1 or 2 substituents selected from
(a) a $C_{6-14}$ aryl group (e.g., phenyl) optionally substituted by 1 to 3 halogen atoms (e.g., a fluorine atom), and
(b) a $C_{1-6}$ alkyl group (e.g., methyl),
(6) an oxazole ring optionally further substituted by 1 or 2 $C_{6-14}$ aryl groups (e.g., phenyl),
(7) a pyrrolidine ring optionally further substituted by 1 to 3 $C_{6-14}$ aryl groups (e.g., phenyl),
(8) a piperidine ring optionally further substituted by 1 to 3 substituents selected from
(a) a $C_{6-14}$ aryl group (e.g., phenyl), and
(b) a 5- to 14-membered aromatic heterocyclic group (preferably a 5- to 6-membered monocyclic aromatic heterocyclic group (e.g., pyrimidinyl)), or
(9) a dibenzofuran ring.

Ring B is still more preferably
(1) a benzene ring optionally further substituted by 1 to 3 substituents selected from
(a) a halogen atom (e.g., a fluorine atom, a chlorine atom, a bromine atom, an iodine atom),
(b) a $C_{1-6}$ alkyl group (e.g., methyl, isopropyl) optionally substituted by 1 to 3 halogen atoms (e.g., a fluorine atom),
(c) a $C_{2-6}$ alkenyl group (e.g., vinyl, propen-2-yl),
(d) a mono- or di-$C_{1-6}$ alkylamino group (e.g., dimethylamino),
(e) a tri-$C_{1-6}$ alkylsilyloxy group (e.g., triisopropylsilyloxy),
(f) a phenyl group optionally substituted by 1 to 4 substituents selected from
(i) a halogen atom (e.g., a fluorine atom, a chlorine atom),
(ii) a $C_{1-6}$ alkyl group (e.g., methyl) optionally substituted by 1 to 3 halogen atoms (e.g., a fluorine atom), and
(iii) a $C_{1-6}$ alkoxy group (e.g., methoxy),
(g) a phenoxy group,
(h) a benzyl group optionally substituted by 1 to 3 $C_{1-6}$ alkyl groups (e.g., methyl),
(i) a $C_{3-6}$ cycloalkyl group (e.g., cyclopropyl, cyclobutyl),
(j) a $C_{3-6}$ cycloalkenyl group (e.g., cyclopenten-1-yl, cyclohexen-1-yl), (k) a $C_{3-6}$ cycloalkoxy group (e.g., cyclohexyloxy),
(l) a pyridyl group,
(m) a thienyl group,
(n) a pyrimidinyl group,
(o) a pyrazolyl group optionally substituted by 1 to 3 $C_{1-6}$ alkyl groups (e.g., methyl),
(p) an indazolyl group optionally substituted by 1 to 3 $C_{1-6}$ alkyl groups (e.g., methyl),
(q) a pyrrolidinyl group, and
(r) a dihydroindolyl group, (2) a naphthalene ring,
(3) a pyridine ring optionally further substituted by 1 to 3 substituents selected from
(a) a phenyl group optionally substituted by 1 to 3 halogen atoms (e.g., a fluorine atom),
(b) a $C_{1-6}$ alkyl group (e.g., isopropyl), and
(c) a $C_{2-6}$ alkenyl group (e.g., propen-2-yl), (4) a pyrazole ring optionally further substituted by 1 or 2 phenyl groups,
(5) a thiazole ring optionally further substituted by 1 or 2 substituents selected from
(a) a phenyl group optionally substituted by 1 to 3 halogen atoms (e.g., a fluorine atom), and
(b) a $C_{1-6}$ alkyl group (e.g., methyl), (6) an oxazole ring optionally further substituted by 1 or 2 phenyl groups,
(7) a pyrrolidine ring optionally further substituted by 1 to 3 phenyl groups,
(8) a piperidine ring optionally further substituted by 1 to 3 substituents selected from
(a) a phenyl group, and
(b) a pyrimidinyl group, or (9) a dibenzofuran ring.

Ring B is even more preferably
(1) a benzene ring further substituted by 1 or 2 substituents selected from
(a) a halogen atom (e.g., a fluorine atom),
(b) a $C_{2-6}$ alkenyl group (e.g., propen-2-yl),
(c) a tri-$C_{1-6}$ alkylsilyloxy group (e.g., triisopropylsilyloxy),
(d) a phenyl group optionally substituted by 1 to 3 substituents selected from
(i) a halogen atom (e.g., a fluorine atom, a chlorine atom), and
(ii) a $C_{1-6}$ alkyl group (e.g., methyl) optionally substituted by 1 to 3 halogen atoms (e.g., a fluorine atom),
(e) a phenoxy group,
(f) a benzyl group optionally substituted by 1 to 3 $C_{1-6}$ alkyl groups (e.g., methyl),
(g) a $C_{3-6}$ cycloalkyl group (e.g., cyclobutyl),
(h) a $C_{3-6}$ cycloalkoxy group (e.g., cyclohexyloxy),
(i) a thienyl group,
(j) an indazolyl group optionally substituted by 1 to 3 $C_{1-6}$ alkyl groups (e.g., methyl), and
(k) a pyrrolidinyl group, (2) a pyridine ring further substituted by one substituent selected from
(a) a phenyl group optionally substituted by 1 to 3 halogen atoms (e.g., a fluorine atom), and
(b) a $C_{2-6}$ alkenyl group (e.g., propen-2-yl), (3) a pyrazole ring further substituted by one phenyl group,
(4) a thiazole ring further substituted by one phenyl group optionally substituted by 1 to 3 halogen atoms (e.g., a fluorine atom),
(5) a piperidine ring further substituted by one phenyl group, or
(6) a dibenzofuran ring.

Ring B is particularly preferably
(1) a benzene ring further substituted by 1 or 2 substituents selected from
(a) a halogen atom (e.g., a fluorine atom), and
(b) a phenyl group optionally substituted by 1 to 3 substituents selected from
(i) a halogen atom (e.g., a fluorine atom, a chlorine atom), and
(ii) a $C_{1-6}$ alkyl group (e.g., methyl), (2) a pyridine ring further substituted by one phenyl group optionally substituted by 1 to 3 halogen atoms (e.g., a fluorine atom),
(3) a thiazole ring further substituted by one phenyl group optionally substituted by 1 to 3 halogen atoms (e.g., a fluorine atom), or
(4) a piperidine ring further substituted by one phenyl group.

As another embodiment, Ring B is preferably
(1) an optionally further substituted $C_{6-14}$ aromatic hydrocarbon ring (e.g., benzene, naphthalene),
(2) an optionally further substituted 5- to 14-membered aromatic heterocycle (preferably a 5- to 6-membered monocyclic aromatic heterocycle (e.g., pyridine, pyrazole, thiazole, oxazole), a 8- to 14-membered fused polycyclic (preferably bi- or tri-cyclic) aromatic heterocycle (e.g., benzofuran)), or
(3) an optionally further substituted 3- to 14-membered non-aromatic heterocycle (preferably a 3- to 8-membered monocyclic non-aromatic heterocycle (e.g., pyrrolidine, piperidine), a 9- to 14-membered fused polycyclic (preferably bi- or tri-cyclic) non-aromatic heterocycle (e.g., dibenzofuran)).

In this embodiment, Ring B is more preferably
(1) a $C_{6-14}$ aromatic hydrocarbon ring (e.g., benzene, naphthalene) optionally further substituted by 1 to 3 substituents selected from
(a) a halogen atom (e.g., a fluorine atom, a chlorine atom, a bromine atom, an iodine atom),
(b) a $C_{1-6}$ alkyl group (e.g., methyl, isopropyl) optionally substituted by 1 to 3 halogen atoms (e.g., a fluorine atom),
(c) a $C_{2-6}$ alkenyl group (e.g., vinyl, propen-2-yl),
(d) a mono- or di-$C_{1-6}$ alkylamino group (e.g., dimethylamino),
(e) a tri-$C_{1-6}$ alkylsilyloxy group (e.g., triisopropylsilyloxy),
(f) a $C_{6-14}$ aryl group (e.g., phenyl) optionally substituted by 1 to 4 substituents selected from
(i) a halogen atom (e.g., a fluorine atom, a chlorine atom),
(ii) a $C_{1-6}$ alkyl group (e.g., methyl) optionally substituted by 1 to 3 halogen atoms (e.g., a fluorine atom), and
(iii) a $C_{1-6}$ alkoxy group (e.g., methoxy),
(g) a $C_{6-14}$ aryloxy group (e.g., phenoxy),
(h) a $C_{7-16}$ aralkyl group (e.g., benzyl) optionally substituted by 1 to 3 $C_{1-6}$ alkyl groups (e.g., methyl),
(i) a $C_{3-10}$ cycloalkyl group (e.g., cyclopropyl, cyclobutyl),
(j) a $C_{3-10}$ cycloalkenyl group (e.g., cyclopenten-1-yl, cyclohexen-1-yl),
(k) a $C_{3-10}$ cycloalkoxy group (e.g., cyclohexyloxy),
(l) a 5- to 14-membered aromatic heterocyclic group (preferably a 5- to 6-membered monocyclic aromatic heterocyclic group (e.g., pyridyl, thienyl, pyrazolyl, pyrimidinyl), a 8- to 14-membered fused polycyclic (preferably bi- or tri-cyclic) aromatic heterocyclic group (e.g., indazolyl)) optionally substituted by 1 to 3 $C_{1-6}$ alkyl groups (e.g., methyl), and
(m) a 3- to 14-membered non-aromatic heterocyclic group (preferably a 3- to 8-membered monocyclic non-aromatic heterocyclic group (e.g., pyrrolidinyl), a 9- to 14-membered fused polycyclic (preferably bi- or tri-cyclic) non-aromatic heterocyclic group (e.g., dihydroindolyl)),
(2) a 5- to 14-membered aromatic heterocycle (preferably a 5- to 6-membered monocyclic aromatic heterocycle (e.g., pyridine, pyrazole, thiazole, oxazole), a 8- to 14-membered fused polycyclic (preferably bi- or tri-cyclic) aromatic heterocycle (e.g., benzofuran)) optionally further substituted by 1 to 3 substituents selected from
(a) a $C_{6-14}$ aryl group (e.g., phenyl) optionally substituted by 1 to 3 halogen atoms (e.g., a fluorine atom),
(b) a $C_{1-6}$ alkyl group (e.g., methyl, isopropyl), and
(c) a $C_{2-6}$ alkenyl group (e.g., propen-2-yl), or
(3) a 3- to 14-membered non-aromatic heterocycle (preferably a 3- to 8-membered monocyclic non-aromatic heterocycle (e.g., pyrrolidine, piperidine), a 9- to 14-membered fused polycyclic (preferably bi- or tri-cyclic) non-aromatic heterocycle (e.g., dibenzofuran)) optionally further substituted by 1 to 3 substituents selected from
(a) a $C_{6-14}$ aryl group (e.g., phenyl), and
(b) a 5- to 14-membered aromatic heterocyclic group (preferably a 5- to 6-membered monocyclic aromatic heterocyclic group (e.g., pyrimidinyl)).

In this embodiment, Ring B is further more preferably
(1) a benzene ring optionally further substituted by 1 to 3 substituents selected from
(a) a halogen atom (e.g., a fluorine atom, a chlorine atom, a bromine atom, an iodine atom),
(b) a $C_{1-6}$ alkyl group (e.g., methyl, isopropyl) optionally substituted by 1 to 3 halogen atoms (e.g., a fluorine atom),
(c) a $C_{2-6}$ alkenyl group (e.g., vinyl, propen-2-yl),
(d) a mono- or di-$C_{1-6}$ alkylamino group (e.g., dimethylamino),
(e) a tri-$C_{1-6}$ alkylsilyloxy group (e.g., triisopropylsilyloxy),
(f) a $C_{6-14}$ aryl group (e.g., phenyl) optionally substituted by 1 to 4 substituents selected from
(i) a halogen atom (e.g., a fluorine atom, a chlorine atom),
(ii) a $C_{1-6}$ alkyl group (e.g., methyl) optionally substituted by 1 to 3 halogen atoms (e.g., a fluorine atom), and
(iii) a $C_{1-6}$ alkoxy group (e.g., methoxy),
(g) a $C_{6-14}$ aryloxy group (e.g., phenoxy),
(h) a $C_{7-16}$ aralkyl group (e.g., benzyl) optionally substituted by 1 to 3 $C_{1-6}$ alkyl groups (e.g., methyl),
(i) a $C_{3-10}$ cycloalkyl group (e.g., cyclopropyl, cyclobutyl),
(j) a $C_{3-10}$ cycloalkenyl group (e.g., cyclopenten-1-yl, cyclohexen-1-yl),
(k) a $C_{3-10}$ cycloalkoxy group (e.g., cyclohexyloxy),
(l) a 5- to 14-membered aromatic heterocyclic group (preferably a 5- to 6-membered monocyclic aromatic heterocyclic group (e.g., pyridyl, thienyl, pyrazolyl, pyrimidinyl), a 8- to 14-membered fused polycyclic (preferably bi- or tri-cyclic) aromatic heterocyclic group (e.g., indazolyl)) optionally substituted by 1 to 3 $C_{1-6}$ alkyl groups (e.g., methyl), and
(m) a 3- to 14-membered non-aromatic heterocyclic group (preferably a 3- to 8-membered monocyclic non-aromatic heterocyclic group (e.g., pyrrolidinyl), a 9- to 14-membered fused polycyclic (preferably bi- or tri-cyclic) non-aromatic heterocyclic group (e.g., dihydroindolyl)),
(2) a naphthalene ring,
(3) a pyridine ring optionally further substituted by 1 to 3 substituents selected from
(a) a $C_{6-14}$ aryl group (e.g., phenyl) optionally substituted by 1 to 3 halogen atoms (e.g., a fluorine atom),
(b) a $C_{1-6}$ alkyl group (e.g., isopropyl), and
(c) a $C_{2-6}$ alkenyl group (e.g., propen-2-yl),
(4) a pyrazole ring optionally further substituted by 1 or 2 $C_{6-14}$ aryl groups (e.g., phenyl),
(5) a thiazole ring optionally further substituted by 1 or 2 substituents selected from
(a) a $C_{6-14}$ aryl group (e.g., phenyl) optionally substituted by 1 to 3 halogen atoms (e.g., a fluorine atom), and
(b) a $C_{1-6}$ alkyl group (e.g., methyl),
(6) an oxazole ring optionally further substituted by 1 or 2 $C_{6-14}$ aryl groups (e.g., phenyl),
(7) a pyrrolidine ring optionally further substituted by 1 to 3 $C_{6-14}$ aryl groups (e.g., phenyl),
(8) a piperidine ring optionally further substituted by 1 to 3 substituents selected from
(a) a $C_{6-14}$ aryl group (e.g., phenyl), and
(b) a 5- to 14-membered aromatic heterocyclic group (preferably a 5- to 6-membered monocyclic aromatic heterocyclic group (e.g., pyrimidinyl)),
(9) a dibenzofuran ring, or
(10) a benzofuran ring optionally further substituted by 1 to 3 $C_{1-6}$ alkyl groups (e.g., isopropyl).

In this embodiment, Ring B is still more preferably
(1) a benzene ring optionally further substituted by 1 to 3 substituents selected from
(a) a halogen atom (e.g., a fluorine atom, a chlorine atom, a bromine atom, an iodine atom),
(b) a $C_{1-6}$ alkyl group (e.g., methyl, isopropyl) optionally substituted by 1 to 3 halogen atoms (e.g., a fluorine atom),
(c) a $C_{2-6}$ alkenyl group (e.g., vinyl, propen-2-yl),
(d) a mono- or di-$C_{1-6}$ alkylamino group (e.g., dimethylamino),
(e) a tri-$C_{1-6}$ alkylsilyloxy group (e.g., triisopropylsilyloxy),
(f) a phenyl group optionally substituted by 1 to 4 substituents selected from
(i) a halogen atom (e.g., a fluorine atom, a chlorine atom),
(ii) a $C_{1-6}$ alkyl group (e.g., methyl) optionally substituted by 1 to 3 halogen atoms (e.g., a fluorine atom), and
(iii) a $C_{1-6}$ alkoxy group (e.g., methoxy),
(g) a phenoxy group,
(h) a benzyl group optionally substituted by 1 to 3 $C_{1-6}$ alkyl groups (e.g., methyl),
(i) a $C_{3-6}$ cycloalkyl group (e.g., cyclopropyl, cyclobutyl),
(j) a $C_{3-6}$ cycloalkenyl group (e.g., cyclopenten-1-yl, cyclohexen-1-yl),
(k) a $C_{3-6}$ cycloalkoxy group (e.g., cyclohexyloxy),
(l) a pyridyl group,
(m) a thienyl group, (n) a pyrimidinyl group,
(o) a pyrazolyl group optionally substituted by 1 to 3 $C_{1-6}$ alkyl groups (e.g., methyl),
(p) an indazolyl group optionally substituted by 1 to 3 $C_{1-6}$ alkyl groups (e.g., methyl),
(q) a pyrrolidinyl group, and
(r) a dihydroindolyl group,
(2) a naphthalene ring,
(3) a pyridine ring optionally further substituted by 1 to 3 substituents selected from
(a) a phenyl group optionally substituted by 1 to 3 halogen atoms (e.g., a fluorine atom),
(b) a $C_{1-6}$ alkyl group (e.g., isopropyl), and
(c) a $C_{2-6}$ alkenyl group (e.g., propen-2-yl),
(4) a pyrazole ring optionally further substituted by 1 or 2 phenyl groups,
(5) a thiazole ring optionally further substituted by 1 or 2 substituents selected from
(a) a phenyl group optionally substituted by 1 to 3 halogen atoms (e.g., a fluorine atom), and
(b) a $C_{1-6}$ alkyl group (e.g., methyl),
(6) an oxazole ring optionally further substituted by 1 or 2 phenyl groups,
(7) a pyrrolidine ring optionally further substituted by 1 to 3 phenyl groups,
(8) a piperidine ring optionally further substituted by 1 to 3 substituents selected from
(a) a phenyl group, and
(b) a pyrimidinyl group,
(9) a dibenzofuran ring, or
(10) a benzofuran ring optionally further substituted by 1 to 3 $C_1$-6 alkyl groups (e.g., isopropyl).

In this embodiment, Ring B is even more preferably
(1) a benzene ring further substituted by 1 or 2 substituents selected from
(a) a halogen atom (e.g., a fluorine atom),
(b) a $C_{2-6}$ alkenyl group (e.g., propen-2-yl),
(c) a tri-$C_{1-6}$ alkylsilyloxy group (e.g., triisopropylsilyloxy),
(d) a phenyl group optionally substituted by 1 to 3 substituents selected from
(i) a halogen atom (e.g., a fluorine atom, a chlorine atom), and
(ii) a $C_{1-6}$ alkyl group (e.g., methyl) optionally substituted by 1 to 3 halogen atoms (e.g., a fluorine atom),
(e) a phenoxy group,
(f) a benzyl group optionally substituted by 1 to 3 $C_{1-6}$ alkyl groups (e.g., methyl),
(g) a $C_{3-6}$ cycloalkyl group (e.g., cyclobutyl),
(h) a $C_{3-6}$ cycloalkoxy group (e.g., cyclohexyloxy),
(i) a thienyl group,
(j) an indazolyl group optionally substituted by 1 to 3 $C_{1-6}$ alkyl groups (e.g., methyl), and
(k) a pyrrolidinyl group,
(2) a pyridine ring further substituted by one substituent selected from
(a) a phenyl group optionally substituted by 1 to 3 halogen atoms (e.g., a fluorine atom), and
(b) a $C_{2-6}$ alkenyl group (e.g., propen-2-yl),
(3) a pyrazole ring further substituted by one phenyl group,
(4) a thiazole ring further substituted by one phenyl group optionally substituted by 1 to 3 halogen atoms (e.g., a fluorine atom),
(5) a piperidine ring further substituted by one phenyl group, or
(6) a dibenzofuran ring.

As another embodiment, Ring B is preferably a ring further substituted by
(a) an optionally substituted $C_{6-14}$ aryl group,
(b) an optionally substituted $C_{6-14}$ aryloxy group,
(c) an optionally substituted $C_{7-16}$ aralkyl group,
(d) an optionally substituted $C_{3-10}$ cycloalkyl group,
(e) an optionally substituted $C_{3-10}$ cycloalkenyl group,
(f) an optionally substituted $C_{3-10}$ cycloalkoxy group,
(g) an optionally substituted 5- to 14-membered aromatic heterocyclic group, or
(h) an optionally substituted 3- to 14-membered non-aromatic heterocyclic group, and
optionally having additional substituent(s).

In this embodiment, Ring B is more preferably
(1) a $C_{6-14}$ aromatic hydrocarbon ring (e.g., benzene) further substituted by
(a) an optionally substituted $C_{6-14}$ aryl group (e.g., phenyl),
(b) an optionally substituted $C_{6-14}$ aryloxy group (e.g., phenoxy),
(c) an optionally substituted $C_{7-16}$ aralkyl group (e.g., benzyl),
(d) an optionally substituted $C_{3-10}$ cycloalkyl group (e.g., cyclopropyl, cyclobutyl),
(e) an optionally substituted $C_{3-10}$ cycloalkenyl group (e.g., cyclopenten-1-yl, cyclohexen-1-yl),
(f) an optionally substituted $C_{3-10}$ cycloalkoxy group (e.g., cyclohexyloxy),
(g) an optionally substituted 5- to 14-membered aromatic heterocyclic group (preferably a 5- to 6-membered monocyclic aromatic heterocyclic group (e.g., pyridyl, thienyl, pyrazolyl, pyrimidinyl), a 8- to 14-membered fused polycyclic (preferably bi- or tri-cyclic) aromatic heterocyclic group (e.g., indazolyl)), or
(h) an optionally substituted 3- to 14-membered non-aromatic heterocyclic group (preferably a 3- to 8-membered monocyclic non-aromatic heterocyclic group (e.g., pyrrolidinyl), a 9- to 14-membered fused polycyclic (preferably bi- or tri-cyclic) non-aromatic heterocyclic group (e.g., dihydroindolyl)), and
optionally having additional substituent(s),
(2) a 5- to 14-membered aromatic heterocycle (preferably a 5- to 6-membered monocyclic aromatic heterocycle (e.g., pyridine, pyrazole, thiazole, oxazole)) further substituted by an optionally substituted $C_{6-14}$ aryl group (e.g., phenyl), and
optionally having additional substituent(s), or
(3) a 3- to 14-membered non-aromatic heterocycle (preferably a 3- to 8-membered monocyclic non-aromatic heterocycle (e.g., pyrrolidine, piperidine)) further substituted by
(a) an optionally substituted $C_{6-14}$ aryl group (e.g., phenyl), or
(b) an optionally substituted 5- to 14-membered aromatic heterocyclic group (preferably a 5- to 6-membered monocyclic aromatic heterocyclic group (e.g., pyrimidinyl)).

In this embodiment, Ring B is further more preferably
(1) a $C_{6-14}$ aromatic hydrocarbon ring (e.g., benzene) further substituted by
(a) a $C_{6-14}$ aryl group (e.g., phenyl) optionally substituted by 1 to 4 substituents selected from
(i) a halogen atom (e.g., a fluorine atom, a chlorine atom), (ii) a $C_{1-6}$ alkyl group (e.g., methyl) optionally substituted by 1 to 3 halogen atoms (e.g., a fluorine atom), and (iii) a $C_{1-6}$ alkoxy group (e.g., methoxy), (b) a $C_{6-14}$ aryloxy group (e.g., phenoxy), (c) a $C_{7-16}$ aralkyl group (e.g., benzyl) optionally substituted by 1 to 3 $C_{1-6}$ alkyl groups (e.g., methyl), (d) a $C_{3-10}$ cycloalkyl group (e.g., cyclopropyl, cyclobutyl), (e) a $C_{3-10}$ cycloalkenyl group (e.g., cyclopenten-1-yl, cyclohexen-1-yl), (f) a $C_{3-10}$ cycloalkoxy group (e.g., cyclohexyloxy), (g) a 5- to 14-membered aromatic heterocyclic group (preferably a 5- to 6-membered monocyclic aromatic heterocyclic group (e.g., pyridyl, thienyl, pyrazolyl, pyrimidinyl), a 8- to 14-membered fused polycyclic (preferably bi- or tri-cyclic) aromatic heterocyclic group (e.g., indazolyl)) optionally substituted by 1 to 3 $C_{1-6}$ alkyl groups (e.g., methyl), or (h) a 3- to 14-membered non-aromatic heterocyclic group (preferably a 3- to 8-membered monocyclic non-aromatic heterocyclic group (e.g., pyrrolidinyl), a 9- to 14-membered fused polycyclic (preferably bi- or tri-cyclic) non-aromatic heterocyclic group (e.g., dihydroindolyl)), and optionally further substituted by 1 or 2 substituents selected from (i) a halogen atom (e.g., a fluorine atom), and (j) a $C_{1-6}$ alkyl group (e.g., methyl), (2) a 5- to 14-membered aromatic heterocycle (preferably a 5- to 6-membered monocyclic aromatic heterocycle (e.g., pyridine, pyrazole, thiazole, oxazole))

further substituted by a $C_{6-14}$ aryl group (e.g., phenyl) optionally substituted by 1 to 3 halogen atoms (e.g., a fluorine atom), and optionally further substituted by 1 or 2 $C_{1-6}$ alkyl groups (e.g., methyl), or (3) a 3- to 14-membered non-aromatic heterocycle (preferably a 3- to 8-membered monocyclic non-aromatic heterocycle (e.g., pyrrolidine, piperidine)) further substituted by (a) a $C_{6-14}$ aryl group (e.g., phenyl), or (b) a 5- to 14-membered aromatic heterocyclic group (preferably a 5- to 6-membered monocyclic aromatic heterocyclic group (e.g., pyrimidinyl)).

In this embodiment, Ring B is still more preferably (1) a benzene ring further substituted by (a) a $C_{6-14}$ aryl group (e.g., phenyl) optionally substituted by 1 to 4 substituents selected from (i) a halogen atom (e.g., a fluorine atom, a chlorine atom), (ii) a $C_{1-6}$ alkyl group (e.g., methyl) optionally substituted by 1 to 3 halogen atoms (e.g., a fluorine atom), and (iii) a $C_{1-6}$ alkoxy group (e.g., methoxy), (b) a $C_{6-14}$ aryloxy group (e.g., phenoxy), (c) a $C_{7-16}$ aralkyl group (e.g., benzyl) optionally substituted by 1 to 3 $C_{1-6}$ alkyl groups (e.g., methyl), (d) a $C_{3-10}$ cycloalkyl group (e.g., cyclopropyl, cyclobutyl), (e) a $C_{3-10}$ cycloalkenyl group (e.g., cyclopenten-1-yl, cyclohexen-1-yl), (f) a $C_{3-10}$ cycloalkoxy group (e.g., cyclohexyloxy), (g) a 5- to 14-membered aromatic heterocyclic group (preferably a 5- to 6-membered monocyclic aromatic heterocyclic group (e.g., pyridyl, thienyl, pyrazolyl, pyrimidinyl), a 8- to 14-membered fused polycyclic (preferably bi- or tri-cyclic) aromatic heterocyclic group (e.g., indazolyl)) optionally substituted by 1 to 3 $C_{1-6}$ alkyl groups (e.g., methyl), or (h) a 3- to 14-membered non-aromatic heterocyclic group (preferably a 3- to 8-membered monocyclic non-aromatic heterocyclic group (e.g., pyrrolidinyl), a 9- to 14-membered fused polycyclic (preferably bi- or tri-cyclic) non-aromatic heterocyclic group (e.g., dihydroindolyl)), and optionally further substituted by 1 or 2 substituents selected from (i) a halogen atom (e.g., a fluorine atom), and (j) a $C_{1-6}$ alkyl group (e.g., methyl), (2) a pyridine ring further substituted by a $C_{6-14}$ aryl group (e.g., phenyl) optionally substituted by 1 to 3 halogen atoms (e.g., a fluorine atom), (3) a pyrazole ring further substituted by a $C_{6-14}$ aryl group (e.g., phenyl), (4) a thiazole ring further substituted by a $C_{6-14}$ aryl group (e.g., phenyl) optionally substituted by 1 to 3 halogen atoms (e.g., a fluorine atom), and optionally further substituted by one $C_{1-6}$ alkyl group (e.g., methyl), (5) an oxazole ring further substituted by a $C_{6-14}$ aryl group (e.g., phenyl), (6) a pyrrolidine ring further substituted by a $C_{6-14}$ aryl group (e.g., phenyl), or (7) a piperidine ring further substituted by (a) a $C_{6-14}$ aryl group (e.g., phenyl), and (b) a 5- to 14-membered aromatic heterocyclic group (preferably a 5- to 6-membered monocyclic aromatic heterocyclic group (e.g., pyrimidinyl)).

In this embodiment, Ring B is still more preferably (1) a benzene ring further substituted by (a) a phenyl group optionally substituted by 1 to 4 substituents selected from (i) a halogen atom (e.g., a fluorine atom, a chlorine atom), (ii) a $C_{1-6}$ alkyl group (e.g., methyl) optionally substituted by 1 to 3 halogen atoms (e.g., a fluorine atom), and (iii) a $C_{1-6}$ alkoxy group (e.g., methoxy), (b) a phenoxy group, (c) a benzyl group optionally substituted by 1 to 3 $C_{1-6}$ alkyl groups (e.g., methyl), (d) a $C_{3-6}$ cycloalkyl group (e.g., cyclopropyl, cyclobutyl), (e) a $C_{3-6}$ cycloalkenyl group (e.g., cyclopenten-1-yl, cyclohexen-1-yl), (f) a $C_{3-6}$ cycloalkoxy group (e.g., cyclohexyloxy), (g) a pyridyl group, (h) a thienyl group, (i) a pyrimidinyl group, (j) a pyrazolyl group optionally substituted by 1 to 3 $C_{1-6}$ alkyl groups (e.g., methyl), (k) an indazolyl group optionally substituted by 1 to 3 $C_{1-6}$ alkyl groups (e.g., methyl), (l) a pyrrolidinyl group, or (m) a dihydroindolyl group, and optionally further substituted by 1 or 2 substituents selected from (o) a halogen atom (e.g., a fluorine atom), and (p) a $C_{1-6}$ alkyl group (e.g., methyl), (2) a pyridine ring further substituted by a phenyl group optionally substituted by 1 to 3 halogen atoms (e.g., a fluorine atom),
(3) a pyrazole ring further substituted by a phenyl group,
(4) a thiazole ring further substituted by a phenyl group optionally substituted by 1 to 3 halogen atoms (e.g., a fluorine atom), and optionally further substituted by one $C_{1-6}$ alkyl group (e.g., methyl),
(5) an oxazole ring further substituted by a phenyl group,
(6) a pyrrolidine ring further substituted by a phenyl group, or
(7) a piperidine ring further substituted by
(a) a phenyl group, or
(b) a pyrimidinyl group.

In this embodiment, Ring B is even more preferably
(1) a benzene ring
further substituted by
(a) a phenyl group optionally substituted by 1 to 3 substituents selected from
(i) a halogen atom (e.g., a fluorine atom, a chlorine atom), and
(ii) a $C_{1-6}$ alkyl group (e.g., methyl) optionally substituted by 1 to 3 halogen atoms (e.g., a fluorine atom),
(b) a phenoxy group,
(c) a benzyl group optionally substituted by 1 to 3 $C_{1-6}$ alkyl groups (e.g., methyl),
(d) a $C_{3-6}$ cycloalkyl group (e.g., cyclobutyl),
(e) a $C_{3-6}$ cycloalkoxy group (e.g., cyclohexyloxy),
(f) a thienyl group,
(g) an indazolyl group optionally substituted by 1 to 3 $C_{1-6}$ alkyl groups (e.g., methyl), or
(h) a pyrrolidinyl group, and optionally further substituted by one halogen atom (e.g., a fluorine atom),
(2) a pyridine ring further substituted by one phenyl group optionally substituted by 1 to 3 halogen atoms (e.g., a fluorine atom),
(3) a pyrazole ring further substituted by one phenyl group,
(4) a thiazole ring further substituted by one phenyl group optionally substituted by 1 to 3 halogen atoms (e.g., a fluorine atom), or
(5) a piperidine ring further substituted by one phenyl group.

In this embodiment, Ring B is particularly preferably
(1) a benzene ring
further substituted by one phenyl group optionally substituted by 1 to 3 substituents selected from
(i) a halogen atom (e.g., a fluorine atom, a chlorine atom), and
(ii) a $C_{1-6}$ alkyl group (e.g., methyl), and
optionally further substituted by one halogen atom (e.g., a fluorine atom),
(2) a pyridine ring further substituted by one phenyl group optionally substituted by 1 to 3 halogen atoms (e.g., a fluorine atom),
(3) a thiazole ring further substituted by one phenyl group optionally substituted by 1 to 3 halogen atoms (e.g., a fluorine atom), or
(4) a piperidine ring further substituted by one phenyl group.

In this embodiment, Ring B is most preferably a benzene ring
further substituted by one phenyl group optionally substituted by 1 to 3 halogen atoms (e.g., a fluorine atoms), and optionally further substituted by one halogen atom (e.g., a fluorine atoms).

Regarding Ring A of compound (I), the configuration based on the carbon atom that —$NR^2SO_2R^1$ is bonded to and the carbon atom that —$CR^4R^5$-Ring B is bonded to (for example, when Ring A is a pyrrolidine ring or a piperidine ring, the configuration based on 2- and 3-positions) is preferably cis-form. That is, compound (I) is preferably represented by the formula (IA) or (IB):

(IA)

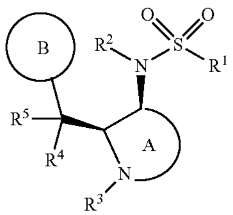

(IB)

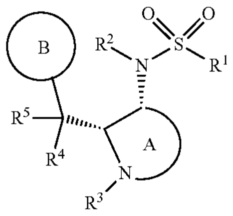

wherein each symbol is as defined above,
more preferably represented by the formula (IA):

(IA)

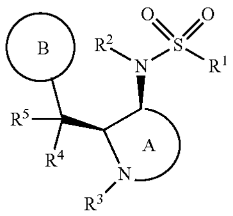

wherein each symbol is as defined above.

Preferable examples of compound (I) include the following compounds. These compounds are preferably represented by the above formula (IA) or (IB), more preferably represented by the formula (IA).

[Compound A-1]

Compound (I) wherein
$R^1$ is
(1) an optionally substituted $C_{1-6}$ alkyl group (e.g., methyl, ethyl, propyl, isopropyl, butyl, isobutyl),
(2) an optionally substituted $C_{2-6}$ alkenyl group (e.g., vinyl, allyl),
(3) an optionally substituted $C_{3-10}$ cycloalkyl group (e.g., cyclopropyl),
(4) an optionally substituted mono- or di-$C_{1-6}$ alkylamino group (e.g., dimethylamino), or
(5) an optionally substituted 3- to 14-membered non-aromatic heterocyclic group (preferably a 3- to 8-membered monocyclic non-aromatic heterocyclic group (e.g., oxetanyl));
$R^2$ is a hydrogen atom;
$R^3$ is
(1) a hydrogen atom,
(2) an optionally substituted $C_{1-6}$ alkoxy-carbonyl group (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, 1,2-dimethylpropoxycarbonyl),
(3) an optionally substituted $C_{1-6}$ alkyl-carbonyl group (e.g., acetyl, propanoyl, 2-methylpropanoyl, butanoyl, 2-methylbutanoyl, 3-methylbutanoyl, pivaloyl),
(4) an optionally substituted mono- or di-$C_{1-6}$ alkyl-carbamoyl group (e.g., dimethylcarbamoyl, ethylcarbamoyl, N-ethyl-N-methylcarbamoyl),
(5) an optionally substituted $C_{3-10}$ cycloalkyl-carbonyl group (the $C_{3-10}$ cycloalkyl in the $C_{3-10}$ cycloalkyl-carbonyl group may be a bridged ring group, e.g., cyclopropylcarbonyl, cyclobutylcarbonyl, cyclopentylcarbonyl, bicyclo[1.1.1]pentylcarbonyl),
(6) an optionally substituted $C_{3-10}$ cycloalkoxy-carbonyl group (e.g., cyclopropoxycarbonyl, cyclobutyloxycarbonyl, cyclopentyloxycarbonyl, cyclohexyloxycarbonyl),
(7) an optionally substituted 3- to 14-membered non-aromatic heterocyclylcarbonyl group (preferably a 3- to 8-membered monocyclic non-aromatic heterocyclylcarbonyl group (the non-aromatic heterocycle in the non-aromatic heterocyclylcarbonyl group may be a spiro ring, e.g., oxetanylcarbonyl, azetidinylcarbonyl, 5-azaspiro[2.3]hexylcarbonyl)),
(8) an optionally substituted 3- to 14-membered non-aromatic heterocyclyloxycarbonyl group (preferably a 3- to 8-membered monocyclic non-aromatic heterocyclyloxycarbonyl group (e.g., oxetanyloxycarbonyl, tetrahydrofuryloxycarbonyl, tetrahydropyranyloxycarbonyl)),
(9) an optionally substituted $C_{6-14}$ aryloxy-carbonyl group (e.g., phenoxycarbonyl), or
(10) an optionally substituted $C_{7-16}$ aralkyloxy-carbonyl group (e.g., benzyloxycarbonyl);
$R^4$ and $R^5$ are each independently a hydrogen atom or a halogen atom (e.g., a fluorine atom);
Ring A is
(1) an optionally further substituted pyrrolidine ring,
(2) an optionally further substituted piperidine ring, or
(3) an optionally further substituted azetidine ring; and
Ring B is
(1) an optionally further substituted $C_{6-14}$ aromatic hydrocarbon ring (e.g., benzene, naphthalene),
(2) an optionally further substituted 5- to 14-membered aromatic heterocycle (preferably a 5- to 6-membered monocyclic aromatic heterocycle (e.g., pyridine, pyrazole, thiazole, oxazole)), or
(3) an optionally further substituted 3- to 14-membered non-aromatic heterocycle (preferably a 3- to 8-membered monocyclic non-aromatic heterocycle (e.g., pyrrolidine, piperidine), a 9- to 14-membered fused polycyclic (preferably bi- or tri-cyclic) non-aromatic heterocycle (e.g., dibenzofuran)).

[Compound B-1]

Compound (I) wherein
$R^1$ is
(1) a $C_{1-6}$ alkyl group (e.g., methyl, ethyl, propyl, isopropyl, butyl, isobutyl) optionally substituted by 1 to 3 substituents selected from
(a) a halogen atom (e.g., a fluorine atom, a chlorine atom),
(b) a cyano group,
(c) a hydroxy group, and
(d) a $C_{1-6}$ alkoxy group (e.g., methoxy),
(2) a $C_{2-6}$ alkenyl group (e.g., vinyl, allyl),
(3) a $C_{3-10}$ cycloalkyl group (e.g., cyclopropyl),
(4) a mono- or di-$C_{1-6}$ alkylamino group (e.g., dimethylamino), or
(5) a 3- to 14-membered non-aromatic heterocyclic group (preferably a 3- to 8-membered monocyclic non-aromatic heterocyclic group (e.g., oxetanyl));
$R^2$ is a hydrogen atom;
$R^3$ is
(1) a hydrogen atom,
(2) a $C_{1-6}$ alkoxy-carbonyl group (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, 1,2-dimethylpropoxycarbonyl) optionally substituted by 1 to 3 substituents selected from
(a) a halogen atom (e.g., a fluorine atom),
(b) a $C_{1-6}$ alkoxy group (e.g., methoxy),
(c) a $C_{3-10}$ cycloalkyl group (e.g., cyclopropyl, cyclobutyl, cyclopentyl) optionally substituted by 1 to 3 substituents selected from
(i) a halogen atom (e.g., a fluorine atom), and
(ii) a $C_{1-6}$ alkyl group (e.g., methyl), and
(d) a 3- to 14-membered non-aromatic heterocyclic group (preferably a 3- to 8-membered monocyclic non-aromatic heterocyclic group (e.g., oxetanyl, tetrahydrofuryl)),
(3) a $C_{1-6}$ alkyl-carbonyl group (e.g., acetyl, propanoyl, 2-methylpropanoyl, butanoyl, 2-methylbutanoyl, 3-methylbutanoyl, pivaloyl) optionally substituted by 1 to 3 substituents selected from
(a) a halogen atom (e.g., a fluorine atom), and
(b) a $C_{3-10}$ cycloalkyl group (e.g., cyclopropyl),
(4) a mono- or di-$C_{1-6}$ alkyl-carbamoyl group (e.g., dimethylcarbamoyl, ethylcarbamoyl, N-ethyl-N-methylcarbamoyl),
(5) a $C_{3-10}$ cycloalkyl-carbonyl group (the $C_{3-10}$ cycloalkyl in the $C_{3-10}$ cycloalkyl-carbonyl group may be a bridged ring group, e.g., cyclopropylcarbonyl, cyclobutylcarbonyl, cyclopentylcarbonyl, bicyclo[1.1.1]pentylcarbonyl) optionally substituted by 1 to 3 substituents selected from
(a) a halogen atom (e.g., a fluorine atom),
(b) a $C_{1-6}$ alkyl group (e.g., methyl) optionally substituted by 1 to 3 halogen atoms (e.g., a fluorine atom),
(c) a hydroxy group,
(d) a $C_{1-6}$ alkoxy group (e.g., methoxy), and
(e) a cyano group,
(6) a $C_{3-10}$ cycloalkoxy-carbonyl group (e.g., cyclopropoxycarbonyl, cyclobutyloxycarbonyl, cyclopentyloxycarbonyl, cyclohexyloxycarbonyl) optionally substituted by 1 to 3 substituents selected from
(a) a halogen atom (e.g., a fluorine atom), and
(b) a $C_{1-6}$ alkyl group (e.g., methyl),
(7) a 3- to 14-membered non-aromatic heterocyclylcarbonyl group (preferably a 3- to 8-membered monocyclic non-aromatic heterocyclylcarbonyl group (the non-aromatic heterocycle in the non-aromatic heterocyclylcarbonyl group may be a spiro ring, e.g., oxetanylcarbonyl, azetidinylcarbonyl, 5-azaspiro[2.3]hexylcarbonyl)) optionally substituted by 1 to 3 substituents selected from
(a) a halogen atom (e.g., a fluorine atom), and
(b) a $C_{1-6}$ alkyl group (e.g., methyl),
(8) a 3- to 14-membered non-aromatic heterocyclyloxycarbonyl group (preferably a 3- to 8-membered monocyclic non-aromatic heterocyclyloxycarbonyl group (e.g., oxetanyloxycarbonyl, tetrahydrofuryloxycarbonyl, tetrahydropyranyloxycarbonyl)), (9) a $C_{6-14}$ aryloxy-carbonyl group (e.g., phenoxycarbonyl), or

(10) a $C_{7-16}$ aralkyloxy-carbonyl group (e.g., benzyloxycarbonyl);

$R^4$ and $R^5$ are each independently a hydrogen atom or a halogen atom (e.g., a fluorine atom);

Ring A is (1) a pyrrolidine ring, (2) a piperidine ring, or (3) an azetidine ring; and Ring B is (1) a $C_{6-14}$ aromatic hydrocarbon ring (e.g., benzene, naphthalene) optionally further substituted by 1 to 3 substituents selected from (a) a halogen atom (e.g., a fluorine atom, a chlorine atom, a bromine atom, an iodine atom), (b) a $C_{1-6}$ alkyl group (e.g., methyl, isopropyl) optionally substituted by 1 to 3 halogen atoms (e.g., a fluorine atom), (c) a $C_{2-6}$ alkenyl group (e.g., vinyl, propen-2-yl), (d) a mono- or di-$C_{1-6}$ alkylamino group (e.g., dimethylamino), (e) a tri-$C_{1-6}$ alkylsilyloxy group (e.g., triisopropylsilyloxy), (f) a $C_{6-14}$ aryl group (e.g., phenyl) optionally substituted by 1 to 4 substituents selected from (i) a halogen atom (e.g., a fluorine atom, a chlorine atom), (ii) a $C_{1-6}$ alkyl group (e.g., methyl) optionally substituted by 1 to 3 halogen atoms (e.g., a fluorine atom), and (iii) a $C_{1-6}$ alkoxy group (e.g., methoxy), (g) a $C_{6-14}$ aryloxy group (e.g., phenoxy), (h) a $C_{7-16}$ aralkyl group (e.g., benzyl) optionally substituted by 1 to 3 $C_{1-6}$ alkyl groups (e.g., methyl), (i) a $C_{3-10}$ cycloalkyl group (e.g., cyclopropyl, cyclobutyl), (j) a $C_{3-10}$ cycloalkenyl group (e.g., cyclopenten-1-yl, cyclohexen-1-yl), (k) a $C_{3-10}$ cycloalkoxy group (e.g., cyclohexyloxy), (l) a 5- to 14-membered aromatic heterocyclic group (preferably a 5- to 6-membered monocyclic aromatic heterocyclic group (e.g., pyridyl, thienyl, pyrazolyl, pyrimidinyl), a 8- to 14-membered fused polycyclic (preferably bi- or tri-cyclic) aromatic heterocyclic group (e.g., indazolyl)) optionally substituted by 1 to 3 $C_{1-6}$ alkyl groups (e.g., methyl), and (m) a 3- to 14-membered non-aromatic heterocyclic group (preferably a 3- to 8-membered monocyclic non-aromatic heterocyclic group (e.g., pyrrolidinyl), a 9- to 14-membered fused polycyclic (preferably bi- or tri-cyclic) non-aromatic heterocyclic group (e.g., dihydroindolyl)), (2) a 5- to 14-membered aromatic heterocycle (preferably a 5- to 6-membered monocyclic aromatic heterocycle (e.g., pyridine, pyrazole, thiazole, oxazole)) optionally further substituted by 1 to 3 substituents selected from (a) a $C_{6-14}$ aryl group (e.g., phenyl) optionally substituted by 1 to 3 halogen atoms (e.g., a fluorine atom), (b) a $C_{1-6}$ alkyl group (e.g., methyl, isopropyl), and (c) a $C_{2-6}$ alkenyl group (e.g., propen-2-yl), or (3) a 3- to 14-membered non-aromatic heterocycle (preferably a 3- to 8-membered monocyclic non-aromatic heterocycle (e.g., pyrrolidine, piperidine), a 9- to 14-membered fused polycyclic (preferably bi- or tri-cyclic) non-aromatic heterocycle (e.g., dibenzofuran)) optionally further substituted by 1 to 3 substituents selected from (a) a $C_{6-14}$ aryl group (e.g., phenyl), and (b) a 5- to 14-membered aromatic heterocyclic group (preferably a 5- to 6-membered monocyclic aromatic heterocyclic group (e.g., pyrimidinyl)).

[Compound C-1]

The above-mentioned Compound B-1 wherein

Ring B is (1) a benzene ring optionally further substituted by 1 to 3 substituents selected from (a) a halogen atom (e.g., a fluorine atom, a chlorine atom, a bromine atom, an iodine atom), (b) a $C_{1-6}$ alkyl group (e.g., methyl, isopropyl) optionally substituted by 1 to 3 halogen atoms (e.g., a fluorine atom), (c) a $C_{2-6}$ alkenyl group (e.g., vinyl, propen-2-yl), (d) a mono- or di-$C_{1-6}$ alkylamino group (e.g., dimethylamino), (e) a tri-$C_{1-6}$ alkylsilyloxy group (e.g., triisopropylsilyloxy), (f) a $C_{6-14}$ aryl group (e.g., phenyl) optionally substituted by 1 to 4 substituents selected from (i) a halogen atom (e.g., a fluorine atom, a chlorine atom), (ii) a $C_{1-6}$ alkyl group (e.g., methyl) optionally substituted by 1 to 3 halogen atoms (e.g., a fluorine atom), and (iii) a $C_{1-6}$ alkoxy group (e.g., methoxy), (g) a $C_{6-14}$ aryloxy group (e.g., phenoxy), (h) a $C_{7-16}$ aralkyl group (e.g., benzyl) optionally substituted by 1 to 3 $C_{1-6}$ alkyl groups (e.g., methyl), (i) a $C_{3-10}$ cycloalkyl group (e.g., cyclopropyl, cyclobutyl), (j) a $C_{3-10}$ cycloalkenyl group (e.g., cyclopenten-1-yl, cyclohexen-1-yl), (k) a $C_{3-10}$ cycloalkoxy group (e.g., cyclohexyloxy), (l) a 5- to 14-membered aromatic heterocyclic group (preferably a 5- to 6-membered monocyclic aromatic heterocyclic group (e.g., pyridyl, thienyl, pyrazolyl, pyrimidinyl), a 8- to 14-membered fused polycyclic (preferably bi- or tri-cyclic) aromatic heterocyclic group (e.g., indazolyl)) optionally substituted by 1 to 3 $C_{1-6}$ alkyl groups (e.g., methyl), and (m) a 3- to 14-membered non-aromatic heterocyclic group (preferably a 3- to 8-membered monocyclic non-aromatic heterocyclic group (e.g., pyrrolidinyl), a 9- to 14-membered fused polycyclic (preferably bi- or tri-cyclic) non-aromatic heterocyclic group (e.g., dihydroindolyl)), (2) a naphthalene ring, (3) a pyridine ring optionally further substituted by 1 to 3 substituents selected from (a) a $C_{6-14}$ aryl group (e.g., phenyl) optionally substituted by 1 to 3 halogen atoms (e.g., a fluorine atom), (b) a $C_{1-6}$ alkyl group (e.g., isopropyl), and (c) a $C_{2-6}$ alkenyl group (e.g., propen-2-yl), (4) a pyrazole ring optionally further substituted by 1 or 2 $C_{6-14}$ aryl groups (e.g., phenyl), (5) a thiazole ring optionally further substituted by 1 or 2 substituents selected from (a) a $C_{6-14}$ aryl group (e.g., phenyl) optionally substituted by 1 to 3 halogen atoms (e.g., a fluorine atom), and (b) a $C_{1-6}$ alkyl group (e.g., methyl), (6) an oxazole ring optionally further substituted by 1 or 2 $C_{6-14}$ aryl groups (e.g., phenyl),
(7) a pyrrolidine ring optionally further substituted by 1 to 3 $C_{6-14}$ aryl groups (e.g., phenyl),
(8) a piperidine ring optionally further substituted by 1 to 3 substituents selected from
(a) a $C_{6-14}$ aryl group (e.g., phenyl), and
(b) a 5- to 14-membered aromatic heterocyclic group (preferably a 5- to 6-membered monocyclic aromatic heterocyclic group (e.g., pyrimidinyl)), or
(9) a dibenzofuran ring.

[Compound D-1]

Compound (I) wherein
$R^1$ is
(1) a $C_{1-6}$ alkyl group (e.g., methyl, ethyl, propyl, isopropyl, butyl, isobutyl) optionally substituted by 1 to 3 substituents selected from
(a) a halogen atom (e.g., a fluorine atom, a chlorine atom),
(b) a cyano group,
(c) a hydroxy group, and
(d) a $C_{1-6}$ alkoxy group (e.g., methoxy),
(2) a $C_{2-6}$ alkenyl group (e.g., vinyl, allyl),
(3) a $C_{3-6}$ cycloalkyl group (e.g., cyclopropyl),
(4) a mono- or di-$C_{1-6}$ alkylamino group (e.g., dimethylamino),
or
(5) an oxetanyl group;
$R^2$ is a hydrogen atom;
$R^3$ is
(1) a hydrogen atom,
(2) a $C_{1-6}$ alkoxy-carbonyl group (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, 1,2-dimethylpropoxycarbonyl) optionally substituted by 1 to 3 substituents selected from
(a) a halogen atom (e.g., a fluorine atom),
(b) a $C_{1-6}$ alkoxy group (e.g., methoxy),
(c) a $C_{3-6}$ cycloalkyl group (e.g., cyclopropyl, cyclobutyl, cyclopentyl) optionally substituted by 1 to 3 substituents selected from
(i) a halogen atom (e.g., a fluorine atom), and
(ii) a $C_{1-6}$ alkyl group (e.g., methyl),
(d) an oxetanyl group, and
(e) a tetrahydrofuryl group,
(3) a $C_{1-6}$ alkyl-carbonyl group (e.g., acetyl, propanoyl, 2-methylpropanoyl, butanoyl, 2-methylbutanoyl, 3-methylbutanoyl, pivaloyl) optionally substituted by 1 to 3 substituents selected from
(a) a halogen atom (e.g., a fluorine atom), and
(b) a $C_{3-6}$ cycloalkyl group (e.g., cyclopropyl),
(4) a mono- or di-$C_{1-6}$ alkyl-carbamoyl group (e.g., dimethylcarbamoyl, ethylcarbamoyl, N-ethyl-N-methylcarbamoyl),
(5) a $C_{3-6}$ cycloalkyl-carbonyl group (the $C_{3-6}$ cycloalkyl in the $C_{3-6}$ cycloalkyl-carbonyl group may be a bridged ring group, e.g., cyclopropylcarbonyl, cyclobutylcarbonyl, cyclopentylcarbonyl, bicyclo[1.1.1]pentylcarbonyl) optionally substituted by 1 to 3 substituents selected from
(a) a halogen atom (e.g., a fluorine atom),
(b) a $C_{1-6}$ alkyl group (e.g., methyl) optionally substituted by 1 to 3 halogen atoms (e.g., a fluorine atom),
(c) a hydroxy group,
(d) a $C_{1-6}$ alkoxy group (e.g., methoxy), and
(e) a cyano group,
(6) a $C_{3-6}$ cycloalkoxy-carbonyl group (e.g., cyclopropoxycarbonyl, cyclobutyloxycarbonyl, cyclopentyloxycarbonyl, cyclohexyloxycarbonyl) optionally substituted by 1 to 3 substituents selected from
(a) a halogen atom (e.g., a fluorine atom), and
(b) a $C_{1-6}$ alkyl group (e.g., methyl),
(7) an oxetanylcarbonyl group,
(8) an azetidinylcarbonyl group optionally substituted by 1 to 3 substituents selected from
(a) a halogen atom (e.g., a fluorine atom), and
(b) a $C_{1-6}$ alkyl group (e.g., methyl),
(9) a 5-azaspiro[2.3]hexylcarbonyl group,
(10) an oxetanyloxycarbonyl group,
(11) a tetrahydrofuryloxycarbonyl group,
(12) a tetrahydropyranyloxycarbonyl group,
(13) a phenoxycarbonyl group, or
(14) a benzyloxycarbonyl group;
$R^4$ and $R^5$ are each independently a hydrogen atom or a halogen atom (e.g., a fluorine atom);
Ring A is
(1) a pyrrolidine ring,
(2) a piperidine ring, or
(3) an azetidine ring; and
Ring B is
(1) a benzene ring optionally further substituted by 1 to 3 substituents selected from
(a) a halogen atom (e.g., a fluorine atom, a chlorine atom, a bromine atom, an iodine atom),
(b) a $C_{1-6}$ alkyl group (e.g., methyl, isopropyl) optionally substituted by 1 to 3 halogen atoms (e.g., a fluorine atom),
(c) a $C_{2-6}$ alkenyl group (e.g., vinyl, propen-2-yl),
(d) a mono- or di-$C_{1-6}$ alkylamino group (e.g., dimethylamino),
(e) a tri-$C_{1-6}$ alkylsilyloxy group (e.g., triisopropylsilyloxy),
(f) a phenyl group optionally substituted by 1 to 4 substituents selected from
(i) a halogen atom (e.g., a fluorine atom, a chlorine atom),
(ii) a $C_{1-6}$ alkyl group (e.g., methyl) optionally substituted by 1 to 3 halogen atoms (e.g., a fluorine atom), and
(iii) a $C_{1-6}$ alkoxy group (e.g., methoxy),
(g) a phenoxy group,
(h) a benzyl group optionally substituted by 1 to 3 $C_{1-6}$ alkyl groups (e.g., methyl),
(i) a $C_{3-6}$ cycloalkyl group (e.g., cyclopropyl, cyclobutyl),
(j) a $C_{3-6}$ cycloalkenyl group (e.g., cyclopenten-1-yl, cyclohexen-1-yl),
(k) a $C_{3-6}$ cycloalkoxy group (e.g., cyclohexyloxy),
(l) a pyridyl group,
(m) a thienyl group,
(n) a pyrimidinyl group,
(o) a pyrazolyl group optionally substituted by 1 to 3 $C_{1-6}$ alkyl groups (e.g., methyl),
(p) an indazolyl group optionally substituted by 1 to 3 $C_{1-6}$ alkyl groups (e.g., methyl),
(q) a pyrrolidinyl group, and
(r) a dihydroindolyl group,
(2) a naphthalene ring,
(3) a pyridine ring optionally further substituted by 1 to 3 substituents selected from
(a) a phenyl group optionally substituted by 1 to 3 halogen atoms (e.g., a fluorine atom),
(b) a $C_{1-6}$ alkyl group (e.g., isopropyl), and (c) a $C_{2-6}$ alkenyl group (e.g., propen-2-yl),
(4) a pyrazole ring optionally further substituted by 1 or 2 phenyl groups,
(5) a thiazole ring optionally further substituted by 1 or 2 substituents selected from
(a) a phenyl group optionally substituted by 1 to 3 halogen atoms (e.g., a fluorine atom), and
(b) a $C_{1-6}$ alkyl group (e.g., methyl),
(6) an oxazole ring optionally further substituted by 1 or 2 phenyl groups,
(7) a pyrrolidine ring optionally further substituted by 1 to 3 phenyl groups,
(8) a piperidine ring optionally further substituted by 1 to 3 substituents selected from
(a) a phenyl group, and
(b) a pyrimidinyl group, or
(9) a dibenzofuran ring.

[Compound E-1]

Compound (I) wherein
$R^1$ is
(1) a $C_{1-6}$ alkyl group (e.g., methyl, ethyl, propyl) optionally substituted by 1 to 3 substituents selected from
(a) a halogen atom (e.g., a fluorine atom, a chlorine atom), and
(b) a $C_{1-6}$ alkoxy group (e.g., methoxy),
(2) a $C_{3-6}$ cycloalkyl group (e.g., cyclopropyl), or
(3) a mono- or di-$C_{1-6}$ alkylamino group (e.g., dimethylamino);
$R^2$ is a hydrogen atom;
$R^3$ is
(1) a $C_{1-6}$ alkoxy-carbonyl group (e.g., methoxycarbonyl, ethoxycarbonyl, isopropoxycarbonyl),
(2) a $C_{1-6}$ alkyl-carbonyl group (e.g., acetyl, 2-methylpropanoyl, pivaloyl),
(3) a mono- or di-$C_{1-6}$ alkyl-carbamoyl group (e.g., dimethylcarbamoyl, ethylcarbamoyl),
(4) a $C_{3-6}$ cycloalkyl-carbonyl group (the $C_{3-6}$ cycloalkyl in the $C_{3-6}$ cycloalkyl-carbonyl group may be a bridged ring group, e.g., cyclopropylcarbonyl, cyclobutylcarbonyl, bicyclo[1.1.1]pentylcarbonyl) optionally substituted by 1 to 3 substituents selected from
(a) a halogen atom (e.g., a fluorine atom),
(b) a $C_{1-6}$ alkyl group (e.g., methyl) optionally substituted by 1 to 3 halogen atoms (e.g., a fluorine atom),
(c) a hydroxy group,
(d) a $C_{1-6}$ alkoxy group (e.g., methoxy), and
(e) a cyano group,
(5) a $C_{3-6}$ cycloalkoxy-carbonyl group (e.g., cyclopropoxycarbonyl),
(6) a phenoxycarbonyl group,
(7) an oxetanylcarbonyl group,
(8) an azetidinylcarbonyl group optionally substituted by 1 to 3 substituents selected from
(a) a halogen atom (e.g., a fluorine atom), and
(b) a $C_{1-6}$ alkyl group (e.g., methyl), or
(9) a 5-azaspiro[2.3]hexylcarbonyl group;
$R^4$ and $R^5$ are both hydrogen atoms;
Ring A is
(1) a pyrrolidine ring, or
(2) a piperidine ring; and
Ring B is
(1) a benzene ring further substituted by 1 or 2 substituents selected from
(a) a halogen atom (e.g., a fluorine atom),
(b) a $C_{2-6}$ alkenyl group (e.g., propen-2-yl),
(c) a tri-$C_{1-6}$ alkylsilyloxy group (e.g., triisopropylsilyloxy),
(d) a phenyl group optionally substituted by 1 to 3 substituents selected from
(i) a halogen atom (e.g., a fluorine atom), and
(ii) a $C_{1-6}$ alkyl group (e.g., methyl) optionally substituted by 1 to 3 halogen atoms (e.g., a fluorine atom),
(e) a phenoxy group,
(f) a benzyl group optionally substituted by 1 to 3 $C_{1-6}$ alkyl groups (e.g., methyl),
(g) a $C_{3-6}$ cycloalkyl group (e.g., cyclobutyl),
(h) a $C_{3-6}$ cycloalkoxy group (e.g., cyclohexyloxy),
(i) a thienyl group,
(j) an indazolyl group optionally substituted by 1 to 3 $C_{1-6}$ alkyl groups (e.g., methyl), and
(k) a pyrrolidinyl group,
(2) a pyridine ring further substituted by one substituent selected from
(a) a phenyl group optionally substituted by 1 to 3 halogen atoms (e.g., a fluorine atom), and
(b) a $C_{2-6}$ alkenyl group (e.g., propen-2-yl),
(3) a pyrazole ring further substituted by one phenyl group,
(4) a thiazole ring further substituted by one phenyl group optionally substituted by 1 to 3 halogen atoms (e.g., a fluorine atom),
(5) a piperidine ring further substituted by one phenyl group, or
(6) a dibenzofuran ring.

[Compound F-1]

Compound (I) wherein
$R^1$ is
(1) a $C_{1-6}$ alkyl group (e.g., methyl, ethyl) optionally substituted by 1 to 3 substituents selected from
(a) a halogen atom (e.g., a fluorine atom), and
(b) a $C_{1-6}$ alkoxy group (e.g., methoxy), or
(2) a $C_{3-6}$ cycloalkyl group (e.g., cyclopropyl);
$R^2$ is a hydrogen atom;
$R^3$ is
(1) a $C_{1-6}$ alkoxy-carbonyl group (e.g., ethoxycarbonyl, isopropoxycarbonyl),
(2) a $C_{1-6}$ alkyl-carbonyl group (e.g., 2-methylpropanoyl, pivaloyl),
(3) a $C_{3-6}$ cycloalkyl-carbonyl group (the $C_{3-6}$ cycloalkyl in the $C_{3-6}$ cycloalkyl-carbonyl group may be a bridged ring group, e.g., cyclopropylcarbonyl, cyclobutylcarbonyl, bicyclo[1.1.1]pentylcarbonyl) optionally substituted by 1 to 3 substituents selected from
(a) a halogen atom (e.g., a fluorine atom),
(b) a $C_{1-6}$ alkyl group (e.g., methyl) optionally substituted by 1 to 3 halogen atoms (e.g., a fluorine atom),
(c) a hydroxy group,
(d) a $C_{1-6}$ alkoxy group (e.g., methoxy), and
(e) a cyano group,
(4) an oxetanylcarbonyl group,
(5) an azetidinylcarbonyl group optionally substituted by 1 to 3 substituents selected from
(a) a halogen atom (e.g., a fluorine atom), and
(b) a $C_{1-6}$ alkyl group (e.g., methyl), or
(6) a 5-azaspiro[2.3]hexylcarbonyl group;
$R^4$ and $R^5$ are both hydrogen atoms;
Ring A is
(1) a pyrrolidine ring, or
(2) a piperidine ring; and
Ring B is
(1) a benzene ring further substituted by 1 or 2 substituents selected from
(a) a halogen atom (e.g., a fluorine atom), and (b) a phenyl group optionally substituted by 1 to 3 substituents selected from (i) a halogen atom (e.g., a fluorine atom), and (ii) a $C_{1-6}$ alkyl group (e.g., methyl), (2) a pyridine ring further substituted by one phenyl group optionally substituted by 1 to 3 halogen atoms (e.g., a fluorine atom), (3) a thiazole ring further substituted by one phenyl group optionally substituted by 1 to 3 halogen atoms (e.g., a fluorine atom), or (4) a piperidine ring further substituted by one phenyl group.

[Compound A-2]

Compound (I) wherein $R^1$ is (1) an optionally substituted $C_{1-6}$ alkyl group (e.g., methyl, ethyl, propyl, isopropyl, butyl, isobutyl), (2) an optionally substituted $C_{2-6}$ alkenyl group (e.g., vinyl, allyl), (3) an optionally substituted $C_{3-10}$ cycloalkyl group (e.g., cyclopropyl), (4) an optionally substituted mono- or di-$C_{1-6}$ alkylamino group (e.g., dimethylamino), or (5) an optionally substituted 3- to 14-membered non-aromatic heterocyclic group (preferably a 3- to 8-membered monocyclic non-aromatic heterocyclic group (e.g., oxetanyl));

$R^2$ is a hydrogen atom;

$R^3$ is (1) a hydrogen atom, (2) an optionally substituted $C_{1-6}$ alkoxy-carbonyl group (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, 1,2-dimethylpropoxycarbonyl), (3) an optionally substituted $C_{1-6}$ alkyl-carbonyl group (e.g., acetyl, propanoyl, 2-methylpropanoyl, butanoyl, 2-methylbutanoyl, 3-methylbutanoyl, pivaloyl), (4) an optionally substituted mono- or di-$C_{1-6}$ alkyl-carbamoyl group (e.g., dimethylcarbamoyl, ethylcarbamoyl, N-ethyl-N-methylcarbamoyl, N-isopropyl-N-methylcarbamoyl), (5) an optionally substituted N—$C_{1-6}$ alkyl-N—$C_{1-6}$ alkoxy-carbamoyl group (e.g., N-methoxy-N-methylcarbamoyl), (6) an optionally substituted $C_{3-10}$ cycloalkyl-carbonyl group (the $C_{3-10}$ cycloalkyl in the $C_{3-10}$ cycloalkyl-carbonyl group may be a bridged ring group, e.g., cyclopropylcarbonyl, cyclobutylcarbonyl, cyclopentylcarbonyl, bicyclo[1.1.1]pentylcarbonyl), (7) an optionally substituted $C_{3-10}$ cycloalkoxy-carbonyl group (e.g., cyclopropoxycarbonyl, cyclobutyloxycarbonyl, cyclopentyloxycarbonyl, cyclohexyloxycarbonyl), (8) an optionally substituted 3- to 14-membered non-aromatic heterocyclylcarbonyl group (preferably a 3- to 8-membered monocyclic non-aromatic heterocyclylcarbonyl group (the non-aromatic heterocycle in the non-aromatic heterocyclylcarbonyl group may be a spiro ring, e.g., oxetanylcarbonyl, azetidinylcarbonyl, 5-azaspiro[2.3]hexylcarbonyl)), (9) an optionally substituted 3- to 14-membered non-aromatic heterocyclyloxycarbonyl group (preferably a 3- to 8-membered monocyclic non-aromatic heterocyclyloxycarbonyl group (e.g., oxetanyloxycarbonyl, tetrahydrofuryloxycarbonyl, tetrahydropyranyloxycarbonyl)),

(10) an optionally substituted $C_{6-14}$ aryloxy-carbonyl group (e.g., phenoxycarbonyl), or

(11) an optionally substituted $C_{7-16}$ aralkyloxy-carbonyl group (e.g., benzyloxycarbonyl);

$R^4$ and $R^5$ are each independently a hydrogen atom or a halogen atom (e.g., a fluorine atom);

Ring A is (1) an optionally further substituted pyrrolidine ring, (2) an optionally further substituted piperidine ring, or (3) an optionally further substituted azetidine ring; and Ring B is (1) an optionally further substituted $C_{6-14}$ aromatic hydrocarbon ring (e.g., benzene, naphthalene), (2) an optionally further substituted 5- to 14-membered aromatic heterocycle (preferably a 5- to 6-membered monocyclic aromatic heterocycle (e.g., pyridine, pyrazole, thiazole, oxazole)), or (3) an optionally further substituted 3- to 14-membered non-aromatic heterocycle (preferably a 3- to 8-membered monocyclic non-aromatic heterocycle (e.g., pyrrolidine, piperidine), a 9- to 14-membered fused polycyclic (preferably bi- or tri-cyclic) non-aromatic heterocycle (e.g., dibenzofuran)).

[Compound B-2]

Compound (I) wherein $R^1$ is (1) a $C_{1-6}$ alkyl group (e.g., methyl, ethyl, propyl, isopropyl, butyl, isobutyl) optionally substituted by 1 to 3 substituents selected from (a) a halogen atom (e.g., a fluorine atom, a chlorine atom), (b) a cyano group, (c) a hydroxy group, and (d) a $C_{1-6}$ alkoxy group (e.g., methoxy), (2) a $C_{2-6}$ alkenyl group (e.g., vinyl, allyl), (3) a $C_{3-10}$ cycloalkyl group (e.g., cyclopropyl), (4) a mono- or di-$C_{1-6}$ alkylamino group (e.g., dimethylamino), or (5) a 3- to 14-membered non-aromatic heterocyclic group (preferably a 3- to 8-membered monocyclic non-aromatic heterocyclic group (e.g., oxetanyl));

$R^2$ is a hydrogen atom;

$R^3$ is (1) a hydrogen atom, (2) a $C_{1-6}$ alkoxy-carbonyl group (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, 1,2-dimethylpropoxycarbonyl) optionally substituted by 1 to 3 substituents selected from (a) a halogen atom (e.g., a fluorine atom), (b) a $C_{1-6}$ alkoxy group (e.g., methoxy), (c) a $C_{3-10}$ cycloalkyl group (e.g., cyclopropyl, cyclobutyl, cyclopentyl) optionally substituted by 1 to 3 substituents selected from (i) a halogen atom (e.g., a fluorine atom), and (ii) a $C_{1-6}$ alkyl group (e.g., methyl), and (d) a 3- to 14-membered non-aromatic heterocyclic group (preferably a 3- to 8-membered monocyclic non-aromatic heterocyclic group (e.g., oxetanyl, tetrahydrofuryl)), (3) a $C_{1-6}$ alkyl-carbonyl group (e.g., acetyl, propanoyl, 2-methylpropanoyl, butanoyl, 2-methylbutanoyl, 3-methylbutanoyl, pivaloyl) optionally substituted by 1 to 3 substituents selected from (a) a halogen atom (e.g., a fluorine atom), (b) a $C_{3-10}$ cycloalkyl group (e.g., cyclopropyl), (c) a hydroxy group, and
(d) a $C_{1-6}$ alkoxy group (e.g., methoxy),
(4) a mono- or di-$C_{1-6}$ alkyl-carbamoyl group (e.g., dimethylcarbamoyl, ethylcarbamoyl, N-ethyl-N-methylcarbamoyl, N-isopropyl-N-methylcarbamoyl),
(5) a N—$C_{1-6}$ alkyl-N—$C_{1-6}$ alkoxy-carbamoyl group (e.g., N-methoxy-N-methylcarbamoyl),
(6) a $C_{3-10}$ cycloalkyl-carbonyl group (the $C_{3-10}$ cycloalkyl in the $C_{3-10}$ cycloalkyl-carbonyl group may be a bridged ring group, e.g., cyclopropylcarbonyl, cyclobutylcarbonyl, cyclopentylcarbonyl, bicyclo[1.1.1]pentylcarbonyl) optionally substituted by 1 to 3 substituents selected from
(a) a halogen atom (e.g., a fluorine atom),
(b) a $C_{1-6}$ alkyl group (e.g., methyl) optionally substituted by 1 to 3 halogen atoms (e.g., a fluorine atom),
(c) a hydroxy group,
(d) a $C_{1-6}$ alkoxy group (e.g., methoxy), and
(e) a cyano group,
(7) a $C_3$-10 cycloalkoxy-carbonyl group (e.g., cyclopropoxycarbonyl, cyclobutyloxycarbonyl, cyclopentyloxycarbonyl, cyclohexyloxycarbonyl) optionally substituted by 1 to 3 substituents selected from
(a) a halogen atom (e.g., a fluorine atom), and
(b) a $C_{1-6}$ alkyl group (e.g., methyl),
(8) a 3- to 14-membered non-aromatic heterocyclylcarbonyl group (preferably a 3- to 8-membered monocyclic non-aromatic heterocyclylcarbonyl group (the non-aromatic heterocycle in the non-aromatic heterocyclylcarbonyl group may be a spiro ring, e.g., oxetanylcarbonyl, azetidinylcarbonyl, 5-azaspiro[2.3]hexylcarbonyl)) optionally substituted by 1 to 3 substituents selected from
(a) a halogen atom (e.g., a fluorine atom), and
(b) a $C_{1-6}$ alkyl group (e.g., methyl),
(9) a 3- to 14-membered non-aromatic heterocyclyloxycarbonyl group (preferably a 3- to 8-membered monocyclic non-aromatic heterocyclyloxycarbonyl group (e.g., oxetanyloxycarbonyl, tetrahydrofuryloxycarbonyl, tetrahydropyranyloxycarbonyl)),
(10) a $C_{6-14}$ aryloxy-carbonyl group (e.g., phenoxycarbonyl), or
(11) a $C_{7-16}$ aralkyloxy-carbonyl group (e.g., benzyloxycarbonyl);
$R^4$ and $R^5$ are each independently a hydrogen atom or a halogen atom (e.g., a fluorine atom);
Ring A is
(1) a pyrrolidine ring,
(2) a piperidine ring, or
(3) an azetidine ring; and
Ring B is
(1) a $C_{6-14}$ aromatic hydrocarbon ring (e.g., benzene, naphthalene) optionally further substituted by 1 to 3 substituents selected from
(a) a halogen atom (e.g., a fluorine atom, a chlorine atom, a bromine atom, an iodine atom),
(b) a $C_{1-6}$ alkyl group (e.g., methyl, isopropyl) optionally substituted by 1 to 3 halogen atoms (e.g., a fluorine atom),
(c) a $C_{2-6}$ alkenyl group (e.g., vinyl, propen-2-yl),
(d) a mono- or di-$C_{1-6}$ alkylamino group (e.g., dimethylamino),
(e) a tri-$C_{1-6}$ alkylsilyloxy group (e.g., triisopropylsilyloxy),
(f) a $C_{6-14}$ aryl group (e.g., phenyl) optionally substituted by 1 to 4 substituents selected from
(i) a halogen atom (e.g., a fluorine atom, a chlorine atom),
(ii) a $C_{1-6}$ alkyl group (e.g., methyl) optionally substituted by 1 to 3 halogen atoms (e.g., a fluorine atom), and
(iii) a $C_{1-6}$ alkoxy group (e.g., methoxy),
(g) a $C_{6-14}$ aryloxy group (e.g., phenoxy),
(h) a $C_{7-16}$ aralkyl group (e.g., benzyl) optionally substituted by 1 to 3 $C_{1-6}$ alkyl groups (e.g., methyl),
(i) a $C_{3-10}$ cycloalkyl group (e.g., cyclopropyl, cyclobutyl),
(j) a $C_{3-10}$ cycloalkenyl group (e.g., cyclopenten-1-yl, cyclohexen-1-yl),
(k) a $C_{3-10}$ cycloalkoxy group (e.g., cyclohexyloxy),
(l) a 5- to 14-membered aromatic heterocyclic group (preferably a 5- to 6-membered monocyclic aromatic heterocyclic group (e.g., pyridyl, thienyl, pyrazolyl, pyrimidinyl), a 8- to 14-membered fused polycyclic (preferably bi- or tri-cyclic) aromatic heterocyclic group (e.g., indazolyl)) optionally substituted by 1 to 3 $C_{1-6}$ alkyl groups (e.g., methyl), and
(m) a 3- to 14-membered non-aromatic heterocyclic group (preferably a 3- to 8-membered monocyclic non-aromatic heterocyclic group (e.g., pyrrolidinyl), a 9- to 14-membered fused polycyclic (preferably bi- or tri-cyclic) non-aromatic heterocyclic group (e.g., dihydroindolyl)),
(2) a 5- to 14-membered aromatic heterocycle (preferably a 5- to 6-membered monocyclic aromatic heterocycle (e.g., pyridine, pyrazole, thiazole, oxazole)) optionally further substituted by 1 to 3 substituents selected from
(a) a $C_{6-14}$ aryl group (e.g., phenyl) optionally substituted by 1 to 3 halogen atoms (e.g., a fluorine atom),
(b) a $C_{1-6}$ alkyl group (e.g., methyl, isopropyl), and
(c) a $C_{2-6}$ alkenyl group (e.g., propen-2-yl), or
(3) a 3- to 14-membered non-aromatic heterocycle (preferably a 3- to 8-membered monocyclic non-aromatic heterocycle (e.g., pyrrolidine, piperidine), a 9- to 14-membered fused polycyclic (preferably bi- or tri-cyclic) non-aromatic heterocycle (e.g., dibenzofuran)) optionally further substituted by 1 to 3 substituents selected from
(a) a $C_{6-14}$ aryl group (e.g., phenyl), and
(b) a 5- to 14-membered aromatic heterocyclic group (preferably a 5- to 6-membered monocyclic aromatic heterocyclic group (e.g., pyrimidinyl)).

[Compound C-2]

The above-mentioned Compound B-2 wherein
Ring B is
(1) a benzene ring optionally further substituted by 1 to 3 substituents selected from
(a) a halogen atom (e.g., a fluorine atom, a chlorine atom, a bromine atom, an iodine atom),
(b) a $C_{1-6}$ alkyl group (e.g., methyl, isopropyl) optionally substituted by 1 to 3 halogen atoms (e.g., a fluorine atom),
(c) a $C_{2-6}$ alkenyl group (e.g., vinyl, propen-2-yl),
(d) a mono- or di-$C_{1-6}$ alkylamino group (e.g., dimethylamino),
(e) a tri-$C_{1-6}$ alkylsilyloxy group (e.g., triisopropylsilyloxy),
(f) a $C_{6-14}$ aryl group (e.g., phenyl) optionally substituted by 1 to 4 substituents selected from
(i) a halogen atom (e.g., a fluorine atom, a chlorine atom), (ii) a $C_{1-6}$ alkyl group (e.g., methyl) optionally substituted by 1 to 3 halogen atoms (e.g., a fluorine atom), and
(iii) a $C_{1-6}$ alkoxy group (e.g., methoxy),
(g) a $C_{6-14}$ aryloxy group (e.g., phenoxy),
(h) a $C_{7-16}$ aralkyl group (e.g., benzyl) optionally substituted by 1 to 3 $C_{1-6}$ alkyl groups (e.g., methyl),
(i) a $C_{3-10}$ cycloalkyl group (e.g., cyclopropyl, cyclobutyl),
(j) a $C_{3-10}$ cycloalkenyl group (e.g., cyclopenten-1-yl, cyclohexen-1-yl),
(k) a $C_{3-10}$ cycloalkoxy group (e.g., cyclohexyloxy),
(l) a 5- to 14-membered aromatic heterocyclic group (preferably a 5- to 6-membered monocyclic aromatic heterocyclic group (e.g., pyridyl, thienyl, pyrazolyl, pyrimidinyl), a 8- to 14-membered fused polycyclic (preferably bi- or tri-cyclic) aromatic heterocyclic group (e.g., indazolyl)) optionally substituted by 1 to 3 $C_{1-6}$ alkyl groups (e.g., methyl), and
(m) a 3- to 14-membered non-aromatic heterocyclic group (preferably a 3- to 8-membered monocyclic non-aromatic heterocyclic group (e.g., pyrrolidinyl), a 9- to 14-membered fused polycyclic (preferably bi- or tri-cyclic) non-aromatic heterocyclic group (e.g., dihydroindolyl)),
(2) a naphthalene ring,
(3) a pyridine ring optionally further substituted by 1 to 3 substituents selected from
(a) a $C_{6-14}$ aryl group (e.g., phenyl) optionally substituted by 1 to 3 halogen atoms (e.g., a fluorine atom),
(b) a $C_{1-6}$ alkyl group (e.g., isopropyl), and
(c) a $C_{2-6}$ alkenyl group (e.g., propen-2-yl),
(4) a pyrazole ring optionally further substituted by 1 or 2 $C_{6-14}$ aryl groups (e.g., phenyl),
(5) a thiazole ring optionally further substituted by 1 or 2 substituents selected from
(a) a $C_{6-14}$ aryl group (e.g., phenyl) optionally substituted by 1 to 3 halogen atoms (e.g., a fluorine atom), and
(b) a $C_{1-6}$ alkyl group (e.g., methyl),
(6) an oxazole ring optionally further substituted by 1 or 2 $C_{6-14}$ aryl groups (e.g., phenyl),
(7) a pyrrolidine ring optionally further substituted by 1 to 3 $C_{6-14}$ aryl groups (e.g., phenyl),
(8) a piperidine ring optionally further substituted by 1 to 3 substituents selected from
(a) a $C_{6-14}$ aryl group (e.g., phenyl), and
(b) a 5- to 14-membered aromatic heterocyclic group (preferably a 5- to 6-membered monocyclic aromatic heterocyclic group (e.g., pyrimidinyl)), or
(9) a dibenzofuran ring.

[Compound D-2]

Compound (I) wherein
$R^1$ is
(1) a $C_{1-6}$ alkyl group (e.g., methyl, ethyl, propyl, isopropyl, butyl, isobutyl) optionally substituted by 1 to 3 substituents selected from
(a) a halogen atom (e.g., a fluorine atom, a chlorine atom),
(b) a cyano group,
(c) a hydroxy group, and
(d) a $C_{1-6}$ alkoxy group (e.g., methoxy),
(2) a $C_{2-6}$ alkenyl group (e.g., vinyl, allyl),
(3) a $C_{3-6}$ cycloalkyl group (e.g., cyclopropyl),
(4) a mono- or di-$C_{1-6}$ alkylamino group (e.g., dimethylamino),
or
(5) an oxetanyl group;
$R^2$ is a hydrogen atom;
$R^3$ is
(1) a hydrogen atom,
(2) a $C_{1-6}$ alkoxy-carbonyl group (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, 1,2-dimethylpropoxycarbonyl) optionally substituted by 1 to 3 substituents selected from
(a) a halogen atom (e.g., a fluorine atom),
(b) a $C_{1-6}$ alkoxy group (e.g., methoxy),
(c) a $C_{3-6}$ cycloalkyl group (e.g., cyclopropyl, cyclobutyl, cyclopentyl) optionally substituted by 1 to 3 substituents selected from
(i) a halogen atom (e.g., a fluorine atom), and
(ii) a $C_{1-6}$ alkyl group (e.g., methyl),
(d) an oxetanyl group, and
(e) a tetrahydrofuryl group,
(3) a $C_{1-6}$ alkyl-carbonyl group (e.g., acetyl, propanoyl, 2-methylpropanoyl, butanoyl, 2-methylbutanoyl, 3-methylbutanoyl, pivaloyl) optionally substituted by 1 to 3 substituents selected from
(a) a halogen atom (e.g., a fluorine atom),
(b) a $C_{3-6}$ cycloalkyl group (e.g., cyclopropyl),
(c) a hydroxy group, and
(d) a $C_{1-6}$ alkoxy group (e.g., methoxy),
(4) a mono- or di-$C_{1-6}$ alkyl-carbamoyl group (e.g., dimethylcarbamoyl, ethylcarbamoyl, N-ethyl-N-methylcarbamoyl, N-isopropyl-N-methylcarbamoyl),
(5) a N—$C_{1-6}$ alkyl-N—$C_{1-6}$ alkoxy-carbamoyl group (e.g., N-methoxy-N-methylcarbamoyl),
(6) a $C_{3-6}$ cycloalkyl-carbonyl group (the $C_{3-6}$ cycloalkyl in the $C_{3-6}$ cycloalkyl-carbonyl group may be a bridged ring group, e.g., cyclopropylcarbonyl, cyclobutylcarbonyl, cyclopentylcarbonyl, bicyclo[1.1.1]pentylcarbonyl) optionally substituted by 1 to 3 substituents selected from
(a) a halogen atom (e.g., a fluorine atom),
(b) a $C_{1-6}$ alkyl group (e.g., methyl) optionally substituted by 1 to 3 halogen atoms (e.g., a fluorine atom),
(c) a hydroxy group,
(d) a $C_{1-6}$ alkoxy group (e.g., methoxy), and
(e) a cyano group,
(7) a $C_{3-6}$ cycloalkoxy-carbonyl group (e.g., cyclopropoxycarbonyl, cyclobutyloxycarbonyl, cyclopentyloxycarbonyl, cyclohexyloxycarbonyl) optionally substituted by 1 to 3 substituents selected from
(a) a halogen atom (e.g., a fluorine atom), and
(b) a $C_{1-6}$ alkyl group (e.g., methyl),
(8) an oxetanylcarbonyl group,
(9) an azetidinylcarbonyl group optionally substituted by 1 to 3 substituents selected from
(a) a halogen atom (e.g., a fluorine atom), and
(b) a $C_{1-6}$ alkyl group (e.g., methyl),
(10) a 5-azaspiro[2.3]hexylcarbonyl group,
(11) an oxetanyloxycarbonyl group,
(12) a tetrahydrofuryloxycarbonyl group,
(13) a tetrahydropyranyloxycarbonyl group,
(14) a phenoxycarbonyl group, or
(15) a benzyloxycarbonyl group;
$R^4$ and $R^5$ are each independently a hydrogen atom or a halogen atom (e.g., a fluorine atom);
Ring A is
(1) a pyrrolidine ring,
(2) a piperidine ring, or
(3) an azetidine ring; and Ring B is (1) a benzene ring optionally further substituted by 1 to 3 substituents selected from (a) a halogen atom (e.g., a fluorine atom, a chlorine atom, a bromine atom, an iodine atom), (b) a $C_{1-6}$ alkyl group (e.g., methyl, isopropyl) optionally substituted by 1 to 3 halogen atoms (e.g., a fluorine atom), (c) a $C_{2-6}$ alkenyl group (e.g., vinyl, propen-2-yl), (d) a mono- or di-$C_{1-6}$ alkylamino group (e.g., dimethylamino), (e) a tri-$C_{1-6}$ alkylsilyloxy group (e.g., triisopropylsilyloxy), (f) a phenyl group optionally substituted by 1 to 4 substituents selected from (i) a halogen atom (e.g., a fluorine atom, a chlorine atom), (ii) a $C_{1-6}$ alkyl group (e.g., methyl) optionally substituted by 1 to 3 halogen atoms (e.g., a fluorine atom), and (iii) a $C_{1-6}$ alkoxy group (e.g., methoxy), (g) a phenoxy group, (h) a benzyl group optionally substituted by 1 to 3 $C_{1-6}$ alkyl groups (e.g., methyl), (i) a $C_{3-6}$ cycloalkyl group (e.g., cyclopropyl, cyclobutyl), (j) a $C_{3-6}$ cycloalkenyl group (e.g., cyclopenten-1-yl, cyclohexen-1-yl), (k) a $C_{3-6}$ cycloalkoxy group (e.g., cyclohexyloxy), (l) a pyridyl group, (m) a thienyl group, (n) a pyrimidinyl group, (o) a pyrazolyl group optionally substituted by 1 to 3 $C_{1-6}$ alkyl groups (e.g., methyl), (p) an indazolyl group optionally substituted by 1 to 3 $C_{1-6}$ alkyl groups (e.g., methyl), (q) a pyrrolidinyl group, and (r) a dihydroindolyl group, (2) a naphthalene ring, (3) a pyridine ring optionally further substituted by 1 to 3 substituents selected from (a) a phenyl group optionally substituted by 1 to 3 halogen atoms (e.g., a fluorine atom), (b) a $C_{1-6}$ alkyl group (e.g., isopropyl), and (c) a $C_{2-6}$ alkenyl group (e.g., propen-2-yl), (4) a pyrazole ring optionally further substituted by 1 or 2 phenyl groups, (5) a thiazole ring optionally further substituted by 1 or 2 substituents selected from (a) a phenyl group optionally substituted by 1 to 3 halogen atoms (e.g., a fluorine atom), and (b) a $C_{1-6}$ alkyl group (e.g., methyl), (6) an oxazole ring optionally further substituted by 1 or 2 phenyl groups, (7) a pyrrolidine ring optionally further substituted by 1 to 3 phenyl groups, (8) a piperidine ring optionally further substituted by 1 to 3 substituents selected from (a) a phenyl group, and (b) a pyrimidinyl group, or (9) a dibenzofuran ring.

[Compound E-2]

Compound (I) wherein $R^1$ is (1) a $C_{1-6}$ alkyl group (e.g., methyl, ethyl, propyl) optionally substituted by 1 to 3 substituents selected from (a) a halogen atom (e.g., a fluorine atom, a chlorine atom), and (b) a $C_{1-6}$ alkoxy group (e.g., methoxy), (2) a $C_{3-6}$ cycloalkyl group (e.g., cyclopropyl), or (3) a mono- or di-$C_{1-6}$ alkylamino group (e.g., dimethylamino);

$R^2$ is a hydrogen atom;

$R^3$ is (1) a $C_{1-6}$ alkoxy-carbonyl group (e.g., methoxycarbonyl, ethoxycarbonyl, isopropoxycarbonyl), (2) a $C_{1-6}$ alkyl-carbonyl group (e.g., acetyl, 2-methylpropanoyl, pivaloyl) optionally substituted by 1 to 3 hydroxy groups, (3) a mono- or di-$C_{1-6}$ alkyl-carbamoyl group (e.g., dimethylcarbamoyl, ethylcarbamoyl), (4) a $C_{3-6}$ cycloalkyl-carbonyl group (the $C_{3-6}$ cycloalkyl in the $C_{3-6}$ cycloalkyl-carbonyl group may be a bridged ring group, e.g., cyclopropylcarbonyl, cyclobutylcarbonyl, bicyclo[1.1.1]pentylcarbonyl) optionally substituted by 1 to 3 substituents selected from (a) a halogen atom (e.g., a fluorine atom), (b) a $C_{1-6}$ alkyl group (e.g., methyl) optionally substituted by 1 to 3 halogen atoms (e.g., a fluorine atom), (c) a hydroxy group, (d) a $C_{1-6}$ alkoxy group (e.g., methoxy), and (e) a cyano group, (5) a $C_{3-6}$ cycloalkoxy-carbonyl group (e.g., cyclopropoxycarbonyl), (6) a phenoxycarbonyl group, (7) an oxetanylcarbonyl group, (8) an azetidinylcarbonyl group optionally substituted by 1 to 3 substituents selected from (a) a halogen atom (e.g., a fluorine atom), and (b) a $C_{1-6}$ alkyl group (e.g., methyl), or (9) a 5-azaspiro[2.3]hexylcarbonyl group;

$R^4$ and $R^5$ are both hydrogen atoms;

Ring A is (1) a pyrrolidine ring, or (2) a piperidine ring; and

Ring B is (1) a benzene ring further substituted by 1 or 2 substituents selected from (a) a halogen atom (e.g., a fluorine atom), (b) a $C_{2-6}$ alkenyl group (e.g., propen-2-yl), (c) a tri-$C_{1-6}$ alkylsilyloxy group (e.g., triisopropylsilyloxy), (d) a phenyl group optionally substituted by 1 to 3 substituents selected from (i) a halogen atom (e.g., a fluorine atom, a chlorine atom), and (ii) a $C_{1-6}$ alkyl group (e.g., methyl) optionally substituted by 1 to 3 halogen atoms (e.g., a fluorine atom), (e) a phenoxy group, (f) a benzyl group optionally substituted by 1 to 3 $C_{1-6}$ alkyl groups (e.g., methyl), (g) a $C_{3-6}$ cycloalkyl group (e.g., cyclobutyl), (h) a $C_{3-6}$ cycloalkoxy group (e.g., cyclohexyloxy), (i) a thienyl group, (j) an indazolyl group optionally substituted by 1 to 3 $C_{1-6}$ alkyl groups (e.g., methyl), and (k) a pyrrolidinyl group, (2) a pyridine ring further substituted by one substituent selected from (a) a phenyl group optionally substituted by 1 to 3 halogen atoms (e.g., a fluorine atom), and (b) a $C_{2-6}$ alkenyl group (e.g., propen-2-yl), (3) a pyrazole ring further substituted by one phenyl group, (4) a thiazole ring further substituted by one phenyl group optionally substituted by 1 to 3 halogen atoms (e.g., a fluorine atom), (5) a piperidine ring further substituted by one phenyl group, or (6) a dibenzofuran ring.

[Compound F-2]

Compound (I) wherein $R^1$ is (1) a $C_{1-6}$ alkyl group (e.g., methyl, ethyl) optionally substituted by 1 to 3 substituents selected from (a) a halogen atom (e.g., a fluorine atom), and (b) a $C_{1-6}$ alkoxy group (e.g., methoxy), or (2) a $C_{3-6}$ cycloalkyl group (e.g., cyclopropyl);

$R^2$ is a hydrogen atom;

$R^3$ is (1) a $C_{1-6}$ alkoxy-carbonyl group (e.g., ethoxycarbonyl, isopropoxycarbonyl), (2) a $C_{1-6}$ alkyl-carbonyl group (e.g., 2-methylpropanoyl, pivaloyl) optionally substituted by 1 to 3 hydroxy groups, (3) a mono- or di-$C_{1-6}$ alkyl-carbamoyl group (e.g., dimethylcarbamoyl), (4) a $C_{3-6}$ cycloalkyl-carbonyl group (the $C_{3-6}$ cycloalkyl in the $C_{3-6}$ cycloalkyl-carbonyl group may be a bridged ring group, e.g., cyclopropylcarbonyl, cyclobutylcarbonyl, bicyclo[1.1.1]pentylcarbonyl) optionally substituted by 1 to 3 substituents selected from (a) a halogen atom (e.g., a fluorine atom), (b) a $C_{1-6}$ alkyl group (e.g., methyl) optionally substituted by 1 to 3 halogen atoms (e.g., a fluorine atom), (c) a hydroxy group, (d) a $C_{1-6}$ alkoxy group (e.g., methoxy), and (e) a cyano group, (5) an oxetanylcarbonyl group, (6) an azetidinylcarbonyl group optionally substituted by 1 to 3 substituents selected from (a) a halogen atom (e.g., a fluorine atom), and (b) a $C_{1-6}$ alkyl group (e.g., methyl), or (7) a 5-azaspiro[2.3]hexylcarbonyl group;

$R^4$ and $R^5$ are both hydrogen atoms;

Ring A is (1) a pyrrolidine ring, or (2) a piperidine ring; and

Ring B is (1) a benzene ring further substituted by 1 or 2 substituents selected from (a) a halogen atom (e.g., a fluorine atom), and (b) a phenyl group optionally substituted by 1 to 3 substituents selected from (i) a halogen atom (e.g., a fluorine atom, a chlorine atom), and (ii) a $C_{1-6}$ alkyl group (e.g., methyl), (2) a pyridine ring further substituted by one phenyl group optionally substituted by 1 to 3 halogen atoms (e.g., a fluorine atom), (3) a thiazole ring further substituted by one phenyl group optionally substituted by 1 to 3 halogen atoms (e.g., a fluorine atom), or (4) a piperidine ring further substituted by one phenyl group.

[Compound A-3]

Compound (I) wherein $R^1$ is (1) an optionally substituted $C_{1-6}$ alkyl group (e.g., methyl, ethyl, propyl, isopropyl, butyl, isobutyl), (2) an optionally substituted $C_{2-6}$ alkenyl group (e.g., vinyl, allyl), (3) an optionally substituted $C_{3-10}$ cycloalkyl group (e.g., cyclopropyl), (4) an optionally substituted mono- or di-$C_{1-6}$ alkylamino group (e.g., dimethylamino), or (5) an optionally substituted 3- to 14-membered non-aromatic heterocyclic group (preferably a 3- to 8-membered monocyclic non-aromatic heterocyclic group (e.g., oxetanyl));

$R^2$ is a hydrogen atom;

$R^3$ is (1) a hydrogen atom, (2) an optionally substituted $C_{1-6}$ alkoxy-carbonyl group (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, 1,2-dimethylpropoxycarbonyl), (3) an optionally substituted $C_{1-6}$ alkyl-carbonyl group (e.g., acetyl, propanoyl, 2-methylpropanoyl, butanoyl, 2-methylbutanoyl, 3-methylbutanoyl, pivaloyl), (4) an optionally substituted mono- or di-$C_{1-6}$ alkyl-carbamoyl group (e.g., dimethylcarbamoyl, ethylcarbamoyl, N-ethyl-N-methylcarbamoyl, N-isopropyl-N-methylcarbamoyl), (5) an optionally substituted N—$C_{1-6}$ alkyl-N—$C_{1-6}$ alkoxy-carbamoyl group (e.g., N-methoxy-N-methylcarbamoyl), (6) an optionally substituted $C_{3-10}$ cycloalkyl-carbonyl group (the $C_{3-10}$ cycloalkyl in the $C_{3-10}$ cycloalkyl-carbonyl group may be a bridged ring group, e.g., cyclopropylcarbonyl, cyclobutylcarbonyl, cyclopentylcarbonyl, bicyclo[1.1.1]pentylcarbonyl), (7) an optionally substituted $C_{3-10}$ cycloalkoxy-carbonyl group (e.g., cyclopropoxycarbonyl, cyclobutyloxycarbonyl, cyclopentyloxycarbonyl, cyclohexyloxycarbonyl), (8) an optionally substituted 3- to 14-membered non-aromatic heterocyclylcarbonyl group (preferably a 3- to 8-membered monocyclic non-aromatic heterocyclylcarbonyl group (the non-aromatic heterocycle in the non-aromatic heterocyclylcarbonyl group may be a spiro ring, e.g., oxetanylcarbonyl, azetidinylcarbonyl, 5-azaspiro[2.3]hexylcarbonyl, isoxazolidinylcarbonyl)), (9) an optionally substituted 3- to 14-membered non-aromatic heterocyclyloxycarbonyl group (preferably a 3- to 8-membered monocyclic non-aromatic heterocyclyloxycarbonyl group (e.g., oxetanyloxycarbonyl, tetrahydrofuryloxycarbonyl, tetrahydropyranyloxycarbonyl)),

(10) an optionally substituted $C_{6-14}$ aryloxy-carbonyl group (e.g., phenoxycarbonyl),

(11) an optionally substituted $C_{7-16}$ aralkyloxy-carbonyl group (e.g., benzyloxycarbonyl),

(12) an optionally substituted 5- to 14-membered aromatic heterocyclic group (preferably a 5- to 6-membered monocyclic aromatic heterocyclic group (e.g., imidazolyl, pyridazinyl)),

(13) an optionally substituted 5- to 14-membered aromatic heterocyclylcarbonyl group (preferably a 5- to 6-membered monocyclic aromatic heterocyclylcarbonyl group (e.g., pyrazolylcarbonyl, furylcarbonyl)), or

(14) an optionally substituted tri-$C_{1-6}$ alkylhydrazinocarbonyl group (e.g., trimethylhydrazinocarbonyl);

$R^4$ and $R^5$ are each independently a hydrogen atom or a halogen atom (e.g., a fluorine atom);
Ring A is
(1) an optionally further substituted pyrrolidine ring,
(2) an optionally further substituted piperidine ring, or
(3) an optionally further substituted azetidine ring; and
Ring B is
(1) an optionally further substituted $C_{6-14}$ aromatic hydrocarbon ring (e.g., benzene, naphthalene),
(2) an optionally further substituted 5- to 14-membered aromatic heterocycle (preferably a 5- to 6-membered monocyclic aromatic heterocycle (e.g., pyridine, pyrazole, thiazole, oxazole), a 8- to 14-membered fused polycyclic (preferably bi- or tri-cyclic) aromatic heterocycle (e.g., benzofuran)), or
(3) an optionally further substituted 3- to 14-membered non-aromatic heterocycle (preferably a 3- to 8-membered monocyclic non-aromatic heterocycle (e.g., pyrrolidine, piperidine), a 9- to 14-membered fused polycyclic (preferably bi- or tri-cyclic) non-aromatic heterocycle (e.g., dibenzofuran)).

[Compound Aa-3]
The above-mentioned Compound A-3 wherein
Ring B is
(1) a $C_{6-14}$ aromatic hydrocarbon ring (e.g., benzene) further substituted by
(a) an optionally substituted $C_{6-14}$ aryl group (e.g., phenyl),
(b) an optionally substituted $C_{6-14}$ aryloxy group (e.g., phenoxy),
(c) an optionally substituted $C_{7-16}$ aralkyl group (e.g., benzyl),
(d) an optionally substituted $C_{3-10}$ cycloalkyl group (e.g., cyclopropyl, cyclobutyl),
(e) an optionally substituted $C_{3-10}$ cycloalkenyl group (e.g., cyclopenten-1-yl, cyclohexen-1-yl),
(f) an optionally substituted $C_{3-10}$ cycloalkoxy group (e.g., cyclohexyloxy),
(g) an optionally substituted 5- to 14-membered aromatic heterocyclic group (preferably a 5- to 6-membered monocyclic aromatic heterocyclic group (e.g., pyridyl, thienyl, pyrazolyl, pyrimidinyl), a 8- to 14-membered fused polycyclic (preferably bi- or tri-cyclic) aromatic heterocyclic group (e.g., indazolyl)), or
(h) an optionally substituted 3- to 14-membered non-aromatic heterocyclic group (preferably a 3- to 8-membered monocyclic non-aromatic heterocyclic group (e.g., pyrrolidinyl), a 9- to 14-membered fused polycyclic (preferably bi- or tri-cyclic) non-aromatic heterocyclic group (e.g., dihydroindolyl)), and
optionally having additional substituent(s),
(2) a 5- to 14-membered aromatic heterocycle (preferably a 5- to 6-membered monocyclic aromatic heterocycle (e.g., pyridine, pyrazole, thiazole, oxazole))
further substituted by an optionally substituted $C_{6-14}$ aryl group (e.g., phenyl), and
optionally having additional substituent(s), or
(3) a 3- to 14-membered non-aromatic heterocycle (preferably a 3- to 8-membered monocyclic non-aromatic heterocycle (e.g., pyrrolidine, piperidine)) further substituted by
(a) an optionally substituted $C_{6-14}$ aryl group (e.g., phenyl), or
(b) an optionally substituted 5- to 14-membered aromatic heterocyclic group (preferably a 5- to 6-membered monocyclic aromatic heterocyclic group (e.g., pyrimidinyl))

[Compound B-3]
Compound (I) wherein
$R^1$ is
(1) a $C_{1-6}$ alkyl group (e.g., methyl, ethyl, propyl, isopropyl, butyl, isobutyl) optionally substituted by 1 to 3 substituents selected from
(a) a halogen atom (e.g., a fluorine atom, a chlorine atom),
(b) a cyano group,
(c) a hydroxy group, and
(d) a $C_{1-6}$ alkoxy group (e.g., methoxy),
(2) a $C_{2-6}$ alkenyl group (e.g., vinyl, allyl),
(3) a $C_{3-10}$ cycloalkyl group (e.g., cyclopropyl) optionally substituted by 1 to 3 halogen atoms (e.g., a fluorine atom),
(4) a mono- or di-$C_{1-6}$ alkylamino group (e.g., dimethylamino), or
(5) a 3- to 14-membered non-aromatic heterocyclic group (preferably a 3- to 8-membered monocyclic non-aromatic heterocyclic group (e.g., oxetanyl));
$R^2$ is a hydrogen atom;
$R^3$ is
(1) a hydrogen atom,
(2) a $C_{1-6}$ alkoxy-carbonyl group (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, 1,2-dimethylpropoxycarbonyl) optionally substituted by 1 to 3 substituents selected from
(a) a halogen atom (e.g., a fluorine atom),
(b) a $C_{1-6}$ alkoxy group (e.g., methoxy),
(c) a $C_{3-10}$ cycloalkyl group (e.g., cyclopropyl, cyclobutyl, cyclopentyl) optionally substituted by 1 to 3 substituents selected from
(i) a halogen atom (e.g., a fluorine atom), and
(ii) a $C_{1-6}$ alkyl group (e.g., methyl), and
(d) a 3- to 14-membered non-aromatic heterocyclic group (preferably a 3- to 8-membered monocyclic non-aromatic heterocyclic group (e.g., oxetanyl, tetrahydrofuryl)),
(3) a $C_{1-6}$ alkyl-carbonyl group (e.g., acetyl, propanoyl, 2-methylpropanoyl, butanoyl, 2-methylbutanoyl, 3-methylbutanoyl, pivaloyl) optionally substituted by 1 to 3 substituents selected from
(a) a halogen atom (e.g., a fluorine atom),
(b) a $C_{3-10}$ cycloalkyl group (e.g., cyclopropyl),
(c) a hydroxy group, and
(d) a $C_{1-6}$ alkoxy group (e.g., methoxy),
(4) a mono- or di-$C_{1-6}$ alkyl-carbamoyl group (e.g., dimethylcarbamoyl, ethylcarbamoyl, N-ethyl-N-methylcarbamoyl, N-isopropyl-N-methylcarbamoyl),
(5) a N—$C_{1-6}$ alkyl-N—$C_{1-6}$ alkoxy-carbamoyl group (e.g., N-methoxy-N-methylcarbamoyl),
(6) a $C_{3-10}$ cycloalkyl-carbonyl group (the $C_{3-10}$ cycloalkyl in the $C_{3-10}$ cycloalkyl-carbonyl group may be a bridged ring group, e.g., cyclopropylcarbonyl, cyclobutylcarbonyl, cyclopentylcarbonyl, bicyclo[1.1.1]pentylcarbonyl) optionally substituted by 1 to 3 substituents selected from
(a) a halogen atom (e.g., a fluorine atom),
(b) a $C_{1-6}$ alkyl group (e.g., methyl) optionally substituted by 1 to 3 substituents selected from (i) a halogen atom (e.g., a fluorine atom), and
(ii) a hydroxy group,
(c) a hydroxy group,
(d) a $C_{1-6}$ alkoxy group (e.g., methoxy), and
(e) a cyano group,
(7) a $C_{3-10}$ cycloalkoxy-carbonyl group (e.g., cyclopropoxycarbonyl, cyclobutyloxycarbonyl, cyclopentyloxycarbonyl, cyclohexyloxycarbonyl) optionally substituted by 1 to 3 substituents selected from
(a) a halogen atom (e.g., a fluorine atom), and
(b) a $C_{1-6}$ alkyl group (e.g., methyl),
(8) a 3- to 14-membered non-aromatic heterocyclylcarbonyl group (preferably a 3- to 8-membered monocyclic non-aromatic heterocyclylcarbonyl group (the non-aromatic heterocycle in the non-aromatic heterocyclylcarbonyl group may be a spiro ring, e.g., oxetanylcarbonyl, azetidinylcarbonyl, 5-azaspiro[2.3]hexylcarbonyl, isoxazolidinylcarbonyl)) optionally substituted by 1 to 3 substituents selected from
(a) a halogen atom (e.g., a fluorine atom), and
(b) a $C_{1-6}$ alkyl group (e.g., methyl),
(9) a 3- to 14-membered non-aromatic heterocyclyloxycarbonyl group (preferably a 3- to 8-membered monocyclic non-aromatic heterocyclyloxycarbonyl group (e.g., oxetanyloxycarbonyl, tetrahydrofuryloxycarbonyl, tetrahydropyranyloxycarbonyl)),
(10) a $C_{6-14}$ aryloxy-carbonyl group (e.g., phenoxycarbonyl),
(11) a $C_{7-16}$ aralkyloxy-carbonyl group (e.g., benzyloxycarbonyl),
(12) a 5- to 14-membered aromatic heterocyclic group (preferably a 5- to 6-membered monocyclic aromatic heterocyclic group (e.g., imidazolyl, pyridazinyl)) optionally substituted by 1 to 3 substituents selected from
(i) a halogen atom (e.g., a chlorine atom), and
(ii) a $C_{1-6}$ alkyl group (e.g., methyl, ethyl),
(13) a 5- to 14-membered aromatic heterocyclylcarbonyl group (preferably a 5- to 6-membered monocyclic aromatic heterocyclylcarbonyl group (e.g., pyrazolylcarbonyl, furylcarbonyl)) optionally substituted by 1 to 3 $C_{1-6}$ alkyl groups (e.g., methyl), or
(14) a tri-$C_{1-6}$ alkylhydrazino-carbonyl group (e.g., trimethylhydrazinocarbonyl);
$R^4$ and $R^5$ are each independently a hydrogen atom or a halogen atom (e.g., a fluorine atom);
Ring A is
(1) a pyrrolidine ring,
(2) a piperidine ring, or
(3) an azetidine ring; and
Ring B is
(1) a $C_{6-14}$ aromatic hydrocarbon ring (e.g., benzene, naphthalene) optionally further substituted by 1 to 3 substituents selected from
(a) a halogen atom (e.g., a fluorine atom, a chlorine atom, a bromine atom, an iodine atom),
(b) a $C_{1-6}$ alkyl group (e.g., methyl, isopropyl) optionally substituted by 1 to 3 halogen atoms (e.g., a fluorine atom),
(c) a $C_{2-6}$ alkenyl group (e.g., vinyl, propen-2-yl),
(d) a mono- or di-$C_{1-6}$ alkylamino group (e.g., dimethylamino),
(e) a tri-$C_{1-6}$ alkylsilyloxy group (e.g., triisopropylsilyloxy),
(f) a $C_{6-14}$ aryl group (e.g., phenyl) optionally substituted by 1 to 4 substituents selected from (i) a halogen atom (e.g., a fluorine atom, a chlorine atom),
(ii) a $C_{1-6}$ alkyl group (e.g., methyl) optionally substituted by 1 to 3 halogen atoms (e.g., a fluorine atom), and
(iii) a $C_{1-6}$ alkoxy group (e.g., methoxy),
(g) a $C_{6-14}$ aryloxy group (e.g., phenoxy),
(h) a $C_{7-16}$ aralkyl group (e.g., benzyl) optionally substituted by 1 to 3 $C_{1-6}$ alkyl groups (e.g., methyl),
(i) a $C_{3-10}$ cycloalkyl group (e.g., cyclopropyl, cyclobutyl),
(j) a $C_{3-10}$ cycloalkenyl group (e.g., cyclopenten-1-yl, cyclohexen-1-yl),
(k) a $C_{3-10}$ cycloalkoxy group (e.g., cyclohexyloxy),
(l) a 5- to 14-membered aromatic heterocyclic group (preferably a 5- to 6-membered monocyclic aromatic heterocyclic group (e.g., pyridyl, thienyl, pyrazolyl, pyrimidinyl), a 8- to 14-membered fused polycyclic (preferably bi- or tri-cyclic) aromatic heterocyclic group (e.g., indazolyl)) optionally substituted by 1 to 3 $C_{1-6}$ alkyl groups (e.g., methyl), and
(m) a 3- to 14-membered non-aromatic heterocyclic group (preferably a 3- to 8-membered monocyclic non-aromatic heterocyclic group (e.g., pyrrolidinyl), a 9- to 14-membered fused polycyclic (preferably bi- or tri-cyclic) non-aromatic heterocyclic group (e.g., dihydroindolyl)),
(2) a 5- to 14-membered aromatic heterocycle (preferably a 5- to 6-membered monocyclic aromatic heterocycle (e.g., pyridine, pyrazole, thiazole, oxazole), a 8- to 14-membered fused polycyclic (preferably bi- or tri-cyclic) aromatic heterocycle (e.g., benzofuran)) optionally further substituted by 1 to 3 substituents selected from
(a) a $C_{6-14}$ aryl group (e.g., phenyl) optionally substituted by 1 to 3 halogen atoms (e.g., a fluorine atom),
(b) a $C_{1-6}$ alkyl group (e.g., methyl, isopropyl), and
(c) a $C_{2-6}$ alkenyl group (e.g., propen-2-yl), or
(3) a 3- to 14-membered non-aromatic heterocycle (preferably a 3- to 8-membered monocyclic non-aromatic heterocycle (e.g., pyrrolidine, piperidine), a 9- to 14-membered fused polycyclic (preferably bi- or tri-cyclic) non-aromatic heterocycle (e.g., dibenzofuran)) optionally further substituted by 1 to 3 substituents selected from
(a) a $C_{6-14}$ aryl group (e.g., phenyl), and
(b) a 5- to 14-membered aromatic heterocyclic group (preferably a 5- to 6-membered monocyclic aromatic heterocyclic group (e.g., pyrimidinyl)).

[Compound Ba-3]

The above-mentioned Compound B-3 wherein
Ring B is
(1) a $C_{6-14}$ aromatic hydrocarbon ring (e.g., benzene) further substituted by
(a) a $C_{6-14}$ aryl group (e.g., phenyl) optionally substituted by 1 to 4 substituents selected from
(i) a halogen atom (e.g., a fluorine atom, a chlorine atom),
(ii) a $C_{1-6}$ alkyl group (e.g., methyl) optionally substituted by 1 to 3 halogen atoms (e.g., a fluorine atom), and
(iii) a $C_{1-6}$ alkoxy group (e.g., methoxy),
(b) a $C_{6-14}$ aryloxy group (e.g., phenoxy),
(c) a $C_{7-16}$ aralkyl group (e.g., benzyl) optionally substituted by 1 to 3 $C_{1-6}$ alkyl groups (e.g., methyl),
(d) a $C_{3-10}$ cycloalkyl group (e.g., cyclopropyl, cyclobutyl), (e) a $C_{3-10}$ cycloalkenyl group (e.g., cyclopenten-1-yl, cyclohexen-1-yl),
(f) a $C_{3-10}$ cycloalkoxy group (e.g., cyclohexyloxy),
(g) a 5- to 14-membered aromatic heterocyclic group (preferably a 5- to 6-membered monocyclic aromatic heterocyclic group (e.g., pyridyl, thienyl, pyrazolyl, pyrimidinyl), a 8- to 14-membered fused polycyclic (preferably bi- or tri-cyclic) aromatic heterocyclic group (e.g., indazolyl)) optionally substituted by 1 to 3 $C_{1-6}$ alkyl groups (e.g., methyl), or
(h) a 3- to 14-membered non-aromatic heterocyclic group (preferably a 3- to 8-membered monocyclic non-aromatic heterocyclic group (e.g., pyrrolidinyl), a 9- to 14-membered fused polycyclic (preferably bi- or tri-cyclic) non-aromatic heterocyclic group (e.g., dihydroindolyl)), and
optionally further substituted by 1 or 2 substituents selected from
(i) a halogen atom (e.g., a fluorine atom), and
(j) a $C_{1-6}$ alkyl group (e.g., methyl),
(2) a 5- to 14-membered aromatic heterocycle (preferably a 5- to 6-membered monocyclic aromatic heterocycle (e.g., pyridine, pyrazole, thiazole, oxazole))
further substituted by a $C_{6-14}$ aryl group (e.g., phenyl) optionally substituted by 1 to 3 halogen atoms (e.g., a fluorine atom), and
optionally further substituted by 1 or 2 $C_{1-6}$ alkyl groups (e.g., methyl), or
(3) a 3- to 14-membered non-aromatic heterocycle (preferably a 3- to 8-membered monocyclic non-aromatic heterocycle (e.g., pyrrolidine, piperidine)) further substituted by
(a) a $C_{6-14}$ aryl group (e.g., phenyl), or
(b) a 5- to 14-membered aromatic heterocyclic group (preferably a 5- to 6-membered monocyclic aromatic heterocyclic group (e.g., pyrimidinyl)).

[Compound C-3]

The above-mentioned Compound B-3 wherein
Ring B is
(1) a benzene ring optionally further substituted by 1 to 3 substituents selected from
(a) a halogen atom (e.g., a fluorine atom, a chlorine atom, a bromine atom, an iodine atom),
(b) a $C_{1-6}$ alkyl group (e.g., methyl, isopropyl) optionally substituted by 1 to 3 halogen atoms (e.g., a fluorine atom),
(c) a $C_{2-6}$ alkenyl group (e.g., vinyl, propen-2-yl),
(d) a mono- or di-$C_{1-6}$ alkylamino group (e.g., dimethylamino),
(e) a tri-$C_{1-6}$ alkylsilyloxy group (e.g., triisopropylsilyloxy),
(f) a $C_{6-14}$ aryl group (e.g., phenyl) optionally substituted by 1 to 4 substituents selected from
(i) a halogen atom (e.g., a fluorine atom, a chlorine atom),
(ii) a $C_{1-6}$ alkyl group (e.g., methyl) optionally substituted by 1 to 3 halogen atoms (e.g., a fluorine atom), and
(iii) a $C_{1-6}$ alkoxy group (e.g., methoxy),
(g) a $C_{6-14}$ aryloxy group (e.g., phenoxy),
(h) a $C_{7-16}$ aralkyl group (e.g., benzyl) optionally substituted by 1 to 3 $C_{1-6}$ alkyl groups (e.g., methyl),
(i) a $C_{3-10}$ cycloalkyl group (e.g., cyclopropyl, cyclobutyl),
(j) a $C_{3-10}$ cycloalkenyl group (e.g., cyclopenten-1-yl, cyclohexen-1-yl),
(k) a $C_3$-10 cycloalkoxy group (e.g., cyclohexyloxy),
(l) a 5- to 14-membered aromatic heterocyclic group (preferably a 5- to 6-membered monocyclic aromatic heterocyclic group (e.g., pyridyl, thienyl, pyrazolyl, pyrimidinyl), a 8- to 14-membered fused polycyclic (preferably bi- or tri-cyclic) aromatic heterocyclic group (e.g., indazolyl)) optionally substituted by 1 to 3 $C_{1-6}$ alkyl groups (e.g., methyl), and
(m) a 3- to 14-membered non-aromatic heterocyclic group (preferably a 3- to 8-membered monocyclic non-aromatic heterocyclic group (e.g., pyrrolidinyl), a 9- to 14-membered fused polycyclic (preferably bi- or tri-cyclic) non-aromatic heterocyclic group (e.g., dihydroindolyl)),
(2) a naphthalene ring,
(3) a pyridine ring optionally further substituted by 1 to 3 substituents selected from
(a) a $C_{6-14}$ aryl group (e.g., phenyl) optionally substituted by 1 to 3 halogen atoms (e.g., a fluorine atom),
(b) a $C_{1-6}$ alkyl group (e.g., isopropyl), and
(c) a $C_{2-6}$ alkenyl group (e.g., propen-2-yl),
(4) a pyrazole ring optionally further substituted by 1 or 2 $C_{6-14}$ aryl groups (e.g., phenyl),
(5) a thiazole ring optionally further substituted by 1 or 2 substituents selected from
(a) a $C_{6-14}$ aryl group (e.g., phenyl) optionally substituted by 1 to 3 halogen atoms (e.g., a fluorine atom), and
(b) a $C_{1-6}$ alkyl group (e.g., methyl),
(6) an oxazole ring optionally further substituted by 1 or 2 $C_{6-14}$ aryl groups (e.g., phenyl),
(7) a pyrrolidine ring optionally further substituted by 1 to 3 $C_{6-14}$ aryl groups (e.g., phenyl),
(8) a piperidine ring optionally further substituted by 1 to 3 substituents selected from
(a) a $C_{6-14}$ aryl group (e.g., phenyl), and
(b) a 5- to 14-membered aromatic heterocyclic group (preferably a 5- to 6-membered monocyclic aromatic heterocyclic group (e.g., pyrimidinyl)),
(9) a dibenzofuran ring, or
(10) a benzofuran ring optionally further substituted by 1 to 3 $C_{1-6}$ alkyl groups (e.g., isopropyl).

[Compound Ca-3]

The above-mentioned Compound B-3 wherein
Ring B is
(1) a benzene ring
further substituted by
(a) a $C_{6-14}$ aryl group (e.g., phenyl) optionally substituted by 1 to 4 substituents selected from
(i) a halogen atom (e.g., a fluorine atom, a chlorine atom),
(ii) a $C_{1-6}$ alkyl group (e.g., methyl) optionally substituted by 1 to 3 halogen atoms (e.g., a fluorine atom), and
(iii) a $C_{1-6}$ alkoxy group (e.g., methoxy),
(b) a $C_{6-14}$ aryloxy group (e.g., phenoxy),
(c) a $C_{7-16}$ aralkyl group (e.g., benzyl) optionally substituted by 1 to 3 $C_{1-6}$ alkyl groups (e.g., methyl),
(d) a $C_{3-10}$ cycloalkyl group (e.g., cyclopropyl, cyclobutyl),
(e) a $C_{3-10}$ cycloalkenyl group (e.g., cyclopenten-1-yl, cyclohexen-1-yl),
(f) a $C_{3-10}$ cycloalkoxy group (e.g., cyclohexyloxy),
(g) a 5- to 14-membered aromatic heterocyclic group (preferably a 5- to 6-membered monocyclic aromatic heterocyclic group (e.g., pyridyl, thienyl, pyrazolyl, pyrimidinyl), a 8- to 14-membered fused polycyclic (preferably bi- or tri-cyclic) aromatic heterocyclic group (e.g., indazolyl)) optionally substituted by 1 to 3 $C_{1-6}$ alkyl groups (e.g., methyl), or
(h) a 3- to 14-membered non-aromatic heterocyclic group (preferably a 3- to 8-membered monocyclic non-aromatic heterocyclic group (e.g., pyrrolidinyl), a 9- to 14-membered fused polycyclic (preferably bi- or tri-cyclic) non-aromatic heterocyclic group (e.g., dihydroindolyl)), and
optionally further substituted by 1 or 2 substituents selected from
(i) a halogen atom (e.g., a fluorine atom), and
(j) a $C_{1-6}$ alkyl group (e.g., methyl),
(2) a pyridine ring further substituted by a $C_{6-14}$ aryl group (e.g., phenyl) optionally substituted by 1 to 3 halogen atoms (e.g., a fluorine atom),
(3) a pyrazole ring further substituted by a $C_{6-14}$ aryl group (e.g., phenyl),
(4) a thiazole ring
further substituted by a $C_{6-14}$ aryl group (e.g., phenyl) optionally substituted by 1 to 3 halogen atoms (e.g., a fluorine atom), and
optionally further substituted by one $C_{1-6}$ alkyl group (e.g., methyl),
(5) an oxazole ring further substituted by a $C_{6-14}$ aryl group (e.g., phenyl),
(6) a pyrrolidine ring further substituted by a $C_{6-14}$ aryl group (e.g., phenyl), or
(7) a piperidine ring further substituted by
(a) a $C_{6-14}$ aryl group (e.g., phenyl), and
(b) a 5- to 14-membered aromatic heterocyclic group (preferably a 5- to 6-membered monocyclic aromatic heterocyclic group (e.g., pyrimidinyl)).

[Compound D-3]

Compound (I) wherein
$R^1$ is
(1) a $C_{1-6}$ alkyl group (e.g., methyl, ethyl, propyl, isopropyl, butyl, isobutyl) optionally substituted by 1 to 3 substituents selected from
(a) a halogen atom (e.g., a fluorine atom, a chlorine atom),
(b) a cyano group,
(c) a hydroxy group, and
(d) a $C_{1-6}$ alkoxy group (e.g., methoxy),
(2) a $C_{2-6}$ alkenyl group (e.g., vinyl, allyl),
(3) a $C_{3-6}$ cycloalkyl group (e.g., cyclopropyl) optionally substituted by 1 to 3 halogen atoms (e.g., a fluorine atom),
(4) a mono- or di-$C_{1-6}$ alkylamino group (e.g., dimethylamino),
or
(5) an oxetanyl group;
$R^2$ is a hydrogen atom;
$R^3$ is
(1) a hydrogen atom,
(2) a $C_{1-6}$ alkoxy-carbonyl group (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, 1,2-dimethylpropoxycarbonyl) optionally substituted by 1 to 3 substituents selected from
(a) a halogen atom (e.g., a fluorine atom),
(b) a $C_{1-6}$ alkoxy group (e.g., methoxy),
(c) a $C_{3-6}$ cycloalkyl group (e.g., cyclopropyl, cyclobutyl, cyclopentyl) optionally substituted by 1 to 3 substituents selected from
(i) a halogen atom (e.g., a fluorine atom), and
(ii) a $C_{1-6}$ alkyl group (e.g., methyl),
(d) an oxetanyl group, and
(e) a tetrahydrofuryl group,
(3) a $C_{1-6}$ alkyl-carbonyl group (e.g., acetyl, propanoyl, 2-methylpropanoyl, butanoyl, 2-methylbutanoyl, 3-methylbutanoyl, pivaloyl) optionally substituted by 1 to 3 substituents selected from
(a) a halogen atom (e.g., a fluorine atom),
(b) a $C_{3-6}$ cycloalkyl group (e.g., cyclopropyl),
(c) a hydroxy group, and
(d) a $C_{1-6}$ alkoxy group (e.g., methoxy),
(4) a mono- or di-$C_{1-6}$ alkyl-carhamoyl group (e.g., dimethylcarbamoyl, ethylcarbamoyl, N-ethyl-N-methylcarbamoyl, N-isopropyl-N-methylcarbamoyl),
(5) a N—$C_{1-6}$ alkyl-N—$C_{1-6}$ alkoxy-carbamoyl group (e.g., N-methoxy-N-methylcarbamoyl),
(6) a $C_{3-6}$ cycloalkyl-carbonyl group (the $C_{3-6}$ cycloalkyl in the $C_{3-6}$ cycloalkyl-carbonyl group may be a bridged ring group, e.g., cyclopropylcarbonyl, cyclobutylcarbonyl, cyclopentylcarbonyl, bicyclo[1.1.1]pentylcarbonyl) optionally substituted by 1 to 3 substituents selected from
(a) a halogen atom (e.g., a fluorine atom),
(b) a $C_{1-6}$ alkyl group (e.g., methyl) optionally substituted by 1 to 3 substituents selected from
(i) a halogen atom (e.g., a fluorine atom), and
(ii) a hydroxy group,
(c) a hydroxy group,
(d) a $C_{1-6}$ alkoxy group (e.g., methoxy), and
(e) a cyano group,
(7) a $C_{3-6}$ cycloalkoxy-carbonyl group (e.g., cyclopropoxycarbonyl, cyclobutyloxycarbonyl, cyclopentyloxycarbonyl, cyclohexyloxycarbonyl) optionally substituted by 1 to 3 substituents selected from
(a) a halogen atom (e.g., a fluorine atom), and
(b) a $C_{1-6}$ alkyl group (e.g., methyl),
(8) an oxetanylcarbonyl group,
(9) an azetidinylcarbonyl group optionally substituted by 1 to 3 substituents selected from
(a) a halogen atom (e.g., a fluorine atom), and
(b) a $C_{1-6}$ alkyl group (e.g., methyl),
(10) a 5-azaspiro[2.3]hexylcarbonyl group,
(11) an oxetanyloxycarbonyl group,
(12) a tetrahydrofuryloxycarbonyl group,
(13) a tetrahydropyranyloxycarbonyl group,
(14) a phenoxycarbonyl group,
(15) a benzyloxycarbonyl group,
(16) an isoxazolidinylcarbonyl group,
(17) a pyrazolylcarbonyl group optionally substituted by 1 to 3 $C_{1-6}$ alkyl groups (e.g., methyl),
(18) a furylcarbonyl group,
(19) an imidazolyl group optionally substituted by 1 to 3 $C_{1-6}$ alkyl groups (e.g., methyl, ethyl),
(20) a pyridazinyl group optionally substituted by 1 to 3 substituents selected from
(i) a halogen atom (e.g., a chlorine atom), and
(ii) a $C_{1-6}$ alkyl group (e.g., methyl), or
(21) a tri-$C_{1-6}$ alkylhydrazino-carbonyl group (e.g., trimethylhydrazinocarbonyl);
$R^4$ and $R^5$ are each independently a hydrogen atom or a halogen atom (e.g., a fluorine atom);
Ring A is
(1) a pyrrolidine ring,
(2) a piperidine ring, or
(3) an azetidine ring; and Ring B is
(1) a benzene ring optionally further substituted by 1 to 3 substituents selected from (a) a halogen atom (e.g., a fluorine atom, a chlorine atom, a bromine atom, an iodine atom),
(b) a $C_{1-6}$ alkyl group (e.g., methyl, isopropyl) optionally substituted by 1 to 3 halogen atoms (e.g., a fluorine atom),
(c) a $C_{2-6}$ alkenyl group (e.g., vinyl, propen-2-yl),
(d) a mono- or di-$C_{1-6}$ alkylamino group (e.g., dimethylamino),
(e) a tri-$C_{1-6}$ alkylsilyloxy group (e.g., triisopropylsilyloxy),
(f) a phenyl group optionally substituted by 1 to 4 substituents selected from
(i) a halogen atom (e.g., a fluorine atom, a chlorine atom),
(ii) a $C_{1-6}$ alkyl group (e.g., methyl) optionally substituted by 1 to 3 halogen atoms (e.g., a fluorine atom), and
(iii) a $C_{1-6}$ alkoxy group (e.g., methoxy),
(g) a phenoxy group,
(h) a benzyl group optionally substituted by 1 to 3 $C_{1-6}$ alkyl groups (e.g., methyl),
(i) a $C_{3-6}$ cycloalkyl group (e.g., cyclopropyl, cyclobutyl),
(j) a $C_{3-6}$ cycloalkenyl group (e.g., cyclopenten-1-yl, cyclohexen-1-yl),
(k) a $C_{3-6}$ cycloalkoxy group (e.g., cyclohexyloxy),
(l) a pyridyl group,
(m) a thienyl group,
(n) a pyrimidinyl group,
(o) a pyrazolyl group optionally substituted by 1 to 3 $C_{1-6}$ alkyl groups (e.g., methyl),
(p) an indazolyl group optionally substituted by 1 to 3 $C_{1-6}$ alkyl groups (e.g., methyl),
(q) a pyrrolidinyl group, and
(r) a dihydroindolyl group,
(2) a naphthalene ring,
(3) a pyridine ring optionally further substituted by 1 to 3 substituents selected from
(a) a phenyl group optionally substituted by 1 to 3 halogen atoms (e.g., a fluorine atom),
(b) a $C_{1-6}$ alkyl group (e.g., isopropyl), and
(c) a $C_{2-6}$ alkenyl group (e.g., propen-2-yl),
(4) a pyrazole ring optionally further substituted by 1 or 2 phenyl groups,
(5) a thiazole ring optionally further substituted by 1 or 2 substituents selected from
(a) a phenyl group optionally substituted by 1 to 3 halogen atoms (e.g., a fluorine atom), and
(b) a $C_{1-6}$ alkyl group (e.g., methyl),
(6) an oxazole ring optionally further substituted by 1 or 2 phenyl groups,
(7) a pyrrolidine ring optionally further substituted by 1 to 3 phenyl groups,
(8) a piperidine ring optionally further substituted by 1 to 3 substituents selected from
(a) a phenyl group, and
(b) a pyrimidinyl group,
(9) a dibenzofuran ring, or
(10) a benzofuran ring optionally further substituted by 1 to 3 $C_{1-6}$ alkyl groups (e.g., isopropyl).

[Compound Da-3]

The above-mentioned Compound D-3 wherein
Ring B is
(1) a benzene ring
further substituted by
(a) a phenyl group optionally substituted by 1 to 4 substituents selected from
(i) a halogen atom (e.g., a fluorine atom, a chlorine atom),
(ii) a $C_{1-6}$ alkyl group (e.g., methyl) optionally substituted by 1 to 3 halogen atoms (e.g., a fluorine atom), and
(iii) a $C_{1-6}$ alkoxy group (e.g., methoxy),
(b) a phenoxy group,
(c) a benzyl group optionally substituted by 1 to 3 $C_{1-6}$ alkyl groups (e.g., methyl),
(d) a $C_{3-6}$ cycloalkyl group (e.g., cyclopropyl, cyclobutyl),
(e) a $C_{3-6}$ cycloalkenyl group (e.g., cyclopenten-1-yl, cyclohexen-1-yl),
(f) a $C_{3-6}$ cycloalkoxy group (e.g., cyclohexyloxy),
(g) a pyridyl group,
(h) a thienyl group,
(i) a pyrimidinyl group,
(j) a pyrazolyl group optionally substituted by 1 to 3 $C_{1-6}$ alkyl groups (e.g., methyl),
(k) an indazolyl group optionally substituted by 1 to 3 $C_{1-6}$ alkyl groups (e.g., methyl),
(l) a pyrrolidinyl group, or
(m) a dihydroindolyl group, and optionally further substituted by 1 or 2 substituents selected from
(o) a halogen atom (e.g., a fluorine atom), and
(p) a $C_{1-6}$ alkyl group (e.g., methyl),
(2) a pyridine ring further substituted by a phenyl group optionally substituted by 1 to 3 halogen atoms (e.g., a fluorine atom),
(3) a pyrazole ring further substituted by a phenyl group,
(4) a thiazole ring
further substituted by a phenyl group optionally substituted by 1 to 3 halogen atoms (e.g., a fluorine atom), and optionally further substituted by one $C_{1-6}$ alkyl group (e.g., methyl),
(5) an oxazole ring further substituted by a phenyl group,
(6) a pyrrolidine ring further substituted by a phenyl group,
or
(7) a piperidine ring further substituted by
(a) a phenyl group, or
(b) a pyrimidinyl group.

[Compound E-3]

Compound (I) wherein
$R^1$ is
(1) a $C_{1-6}$ alkyl group (e.g., methyl, ethyl, propyl) optionally substituted by 1 to 3 substituents selected from
(a) a halogen atom (e.g., a fluorine atom, a chlorine atom), and
(b) a $C_{1-6}$ alkoxy group (e.g., methoxy),
(2) a $C_{3-6}$ cycloalkyl group (e.g., cyclopropyl) optionally substituted by 1 to 3 halogen atoms (e.g., a fluorine atom), or
(3) a mono- or di-$C_{1-6}$ alkylamino group (e.g., dimethylamino);
$R^2$ is a hydrogen atom;
$R^3$ is
(1) a $C_{1-6}$ alkoxy-carbonyl group (e.g., methoxycarbonyl, ethoxycarbonyl, isopropoxycarbonyl),
(2) a $C_{1-6}$ alkyl-carbonyl group (e.g., acetyl, 2-methylpropanoyl, pivaloyl) optionally substituted by 1 to 3 hydroxy groups,
(3) a mono- or di-$C_{1-6}$ alkyl-carbamoyl group (e.g., dimethylcarbamoyl, ethylcarbamoyl),
(4) a N—$C_{1-6}$ alkyl-N—$C_{1-6}$ alkoxy-carbamoyl group (e.g., N-methoxy-N-methylcarbamoyl), (5) a $C_{3-6}$ cycloalkyl-carbonyl group (the $C_{3-6}$ cycloalkyl in the $C_{3-6}$ cycloalkyl-carbonyl group may be a bridged ring group, e.g., cyclopropylcarbonyl, cyclobutylcarbonyl, bicyclo[1.1.1]pentylcarbonyl) optionally substituted by 1 to 3 substituents selected from
(a) a halogen atom (e.g., a fluorine atom),
(b) a $C_{1-6}$ alkyl group (e.g., methyl) optionally substituted by 1 to 3 halogen atoms (e.g., a fluorine atom),
(c) a hydroxy group,
(d) a $C_{1-6}$ alkoxy group (e.g., methoxy), and
(e) a cyano group,
(6) a $C_{3-6}$ cycloalkoxy-carbonyl group (e.g., cyclopropoxycarbonyl),
(7) a phenoxycarbonyl group,
(8) an oxetanylcarbonyl group,
(9) an azetidinylcarbonyl group optionally substituted by 1 to 3 substituents selected from
(a) a halogen atom (e.g., a fluorine atom), and
(b) a $C_{1-6}$ alkyl group (e.g., methyl), or
(10) a 5-azaspiro[2.3]hexylcarbonyl group;
$R^4$ and $R^5$ are both hydrogen atoms;
Ring A is
(1) a pyrrolidine ring, or
(2) a piperidine ring; and
Ring B is
(1) a benzene ring further substituted by 1 or 2 substituents selected from
(a) a halogen atom (e.g., a fluorine atom),
(b) a $C_{2-6}$ alkenyl group (e.g., propen-2-yl),
(c) a tri-$C_{1-6}$ alkylsilyloxy group (e.g., triisopropylsilyloxy),
(d) a phenyl group optionally substituted by 1 to 3 substituents selected from
(i) a halogen atom (e.g., a fluorine atom, a chlorine atom), and
(ii) a $C_{1-6}$ alkyl group (e.g., methyl) optionally substituted by 1 to 3 halogen atoms (e.g., a fluorine atom),
(e) a phenoxy group,
(f) a benzyl group optionally substituted by 1 to 3 $C_{1-6}$ alkyl groups (e.g., methyl),
(g) a $C_{3-6}$ cycloalkyl group (e.g., cyclobutyl),
(h) a $C_{3-6}$ cycloalkoxy group (e.g., cyclohexyloxy),
(i) a thienyl group,
(j) an indazolyl group optionally substituted by 1 to 3 $C_{1-6}$ alkyl groups (e.g., methyl), and
(k) a pyrrolidinyl group,
(2) a pyridine ring further substituted by one substituent selected from
(a) a phenyl group optionally substituted by 1 to 3 halogen atoms (e.g., a fluorine atom), and
(b) a $C_{2-6}$ alkenyl group (e.g., propen-2-yl),
(3) a pyrazole ring further substituted by one phenyl group,
(4) a thiazole ring further substituted by one phenyl group optionally substituted by 1 to 3 halogen atoms (e.g., a fluorine atom),
(5) a piperidine ring further substituted by one phenyl group, or
(6) a dibenzofuran ring.

[Compound Ea-3]

The above-mentioned Compound E-3 wherein
Ring B is
(1) a benzene ring
further substituted by
(a) a phenyl group optionally substituted by 1 to 3 substituents selected from
(i) a halogen atom (e.g., a fluorine atom, a chlorine atom), and
(ii) a $C_{1-6}$ alkyl group (e.g., methyl) optionally substituted by 1 to 3 halogen atoms (e.g., a fluorine atom),
(b) a phenoxy group,
(c) a benzyl group optionally substituted by 1 to 3 $C_{1-6}$ alkyl groups (e.g., methyl),
(d) a $C_{3-6}$ cycloalkyl group (e.g., cyclobutyl),
(e) a $C_{3-6}$ cycloalkoxy group (e.g., cyclohexyloxy),
(f) a thienyl group,
(g) an indazolyl group optionally substituted by 1 to 3 $C_{1-6}$ alkyl groups (e.g., methyl), or
(h) a pyrrolidinyl group, and
optionally further substituted by one halogen atom (e.g., a fluorine atom),
(2) a pyridine ring further substituted by one phenyl group optionally substituted by 1 to 3 halogen atoms (e.g., a fluorine atom),
(3) a pyrazole ring further substituted by one phenyl group,
(4) a thiazole ring further substituted by one phenyl group optionally substituted by 1 to 3 halogen atoms (e.g., a fluorine atom), or
(5) a piperidine ring further substituted by one phenyl group.

[Compound F-3]

Compound (I) wherein
$R^1$ is
(1) a $C_{1-6}$ alkyl group (e.g., methyl, ethyl) optionally substituted by 1 to 3 substituents selected from
(a) a halogen atom (e.g., a fluorine atom), and
(b) a $C_{1-6}$ alkoxy group (e.g., methoxy),
(2) a $C_{3-6}$ cycloalkyl group (e.g., cyclopropyl) optionally substituted by 1 to 3 halogen atoms (e.g., a fluorine atom), or
(3) a mono- or di-$C_{1-6}$ alkylamino group (e.g., dimethylamino);
$R^2$ is a hydrogen atom;
$R^3$ is
(1) a $C_{1-6}$ alkoxy-carbonyl group (e.g., ethoxycarbonyl, isopropoxycarbonyl),
(2) a $C_{1-6}$ alkyl-carbonyl group (e.g., 2-methylpropanoyl, pivaloyl) optionally substituted by 1 to 3 hydroxy groups,
(3) a mono- or di-$C_{1-6}$ alkyl-carbamoyl group (e.g., dimethylcarbamoyl),
(4) a N—$C_{1-6}$ alkyl-N—$C_{1-6}$ alkoxy-carbamoyl group (e.g., N-methoxy-N-methylcarbamoyl),
(5) a $C_{3-6}$ cycloalkyl-carbonyl group (the $C_{3-6}$ cycloalkyl in the $C_{3-6}$ cycloalkyl-carbonyl group may be a bridged ring group, e.g., cyclopropylcarbonyl, cyclobutylcarbonyl, bicyclo[1.1.1]pentylcarbonyl) optionally substituted by 1 to 3 substituents selected from
(a) a halogen atom (e.g., a fluorine atom),
(b) a $C_{1-6}$ alkyl group (e.g., methyl) optionally substituted by 1 to 3 halogen atoms (e.g., a fluorine atom),
(c) a hydroxy group,
(d) a $C_{1-6}$ alkoxy group (e.g., methoxy), and
(e) a cyano group,
(6) an oxetanylcarbonyl group,
(7) an azetidinylcarbonyl group optionally substituted by 1 to 3 substituents selected from
(a) a halogen atom (e.g., a fluorine atom), and
(b) a $C_{1-6}$ alkyl group (e.g., methyl), or (8) a 5-azaspiro[2.3]hexylcarbonyl group;

$R^4$ and $R^5$ are both hydrogen atoms;

Ring A is (1) a pyrrolidine ring, or (2) a piperidine ring; and

Ring B is (1) a benzene ring further substituted by one phenyl group optionally substituted by 1 to 3 substituents selected from (i) a halogen atom (e.g., a fluorine atom, a chlorine atom), and (ii) a $C_{1-6}$ alkyl group (e.g., methyl), and optionally further substituted by one halogen atom (e.g., a fluorine atom), (2) a pyridine ring further substituted by one phenyl group optionally substituted by 1 to 3 halogen atoms (e.g., a fluorine atom), (3) a thiazole ring further substituted by one phenyl group optionally substituted by 1 to 3 halogen atoms (e.g., a fluorine atom), or (4) a piperidine ring further substituted by one phenyl group.

[Compound G-1]

Compound (I) wherein $R^1$ is (1) a $C_{1-6}$ alkyl group (e.g., methyl, ethyl), (2) a $C_{3-6}$ cycloalkyl group (e.g., cyclopropyl) optionally substituted by 1 to 3 halogen atoms (e.g., a fluorine atom), or (3) a mono- or di-$C_{1-6}$ alkylamino group (e.g., dimethylamino);

$R^2$ is a hydrogen atom;

$R^3$ is (1) a $C_{1-6}$ alkyl-carbonyl group (e.g., 2-methylpropanoyl) optionally substituted by 1 to 3 hydroxy groups, (2) a mono- or di-$C_{1-6}$ alkyl-carbamoyl group (e.g., dimethylcarbamoyl), (3) a N—$C_{1-6}$ alkyl-N—$C_{1-6}$ alkoxy-carbamoyl group (e.g., N-methoxy-N-methylcarbamoyl), or (4) an azetidinylcarbonyl group;

$R^4$ and $R^5$ are both hydrogen atoms;

Ring A is a pyrrolidine ring; and

Ring B is a benzene ring further substituted by one phenyl group optionally substituted by 1 to 3 halogen atoms (e.g., a fluorine atoms), and optionally further substituted by one halogen atom (e.g., a fluorine atoms).

[Compound G-2]

Compound (I) wherein $R^1$ is a $C_{1-6}$ alkyl group (e.g., methyl, ethyl);

$R^2$ is a hydrogen atom;

$R^3$ is a $C_{1-6}$ alkyl-carbonyl group (e.g., 2-methylpropanoyl) optionally substituted by 1 to 3 hydroxy groups;

$R^4$ and $R^5$ are both hydrogen atoms;

Ring A is a pyrrolidine ring; and

Ring B is a benzene ring further substituted by one phenyl group optionally substituted by 1 to 3 halogen atoms (e.g., a fluorine atoms), and optionally further substituted by one halogen atom (e.g., a fluorine atoms).

[Compound H]

N-((2S,3S)-2-((2,3'-difluorobiphenyl-3-yl)methyl)-1-(2-hydroxy-2-methylpropanoyl)pyrrolidin-3-yl)ethanesulfonamide or a salt thereof.

[Compound I]

N-((2S,3S)-1-(2-hydroxy-2-methylpropanoyl)-2-((2,3',5'-trifluorobiphenyl-3-yl)methyl)pyrrolidin-3-yl)methanesulfonamide or a salt thereof.

[Compound J]

N-((2S,3S)-1-(2-hydroxy-2-methylpropanoyl)-2-((2,3',5'-trifluorobiphenyl-3-yl)methyl)pyrrolidin-3-yl)ethanesulfonamide or a salt thereof.

[Compound K]

A compound selected from (1) N-((2S,3S)-1-(azetidin-1-ylcarbonyl)-2-((2,3'-difluorobiphenyl-3-yl)methyl)pyrrolidin-3-yl)methanesulfonamide, (2) N-((2S,3S)-1-(azetidin-1-ylcarbonyl)-2-((3',5'-difluorobiphenyl-3-yl)methyl)pyrrolidin-3-yl)ethanesulfonamide, (3) N-((2S,3S)-1-(azetidin-1-ylcarbonyl)-2-(biphenyl-3-ylmethyl)pyrrolidin-3-yl)ethanesulfonamide, (4) N-((2S,3S)-1-(azetidin-1-ylcarbonyl)-2-((2,3'-difluorobiphenyl-3-yl)methyl)pyrrolidin-3-yl)ethanesulfonamide, (5) (2S,3S)-2-((2,3'-difluorobiphenyl-3-yl)methyl)-3-((ethylsulfonyl)amino)-N,N-dimethylpyrrolidine-1-carboxamide, (6) (2S,3S)-2-((2,3'-difluorobiphenyl-3-yl)methyl)-3-((dimethylsulfamoyl)amino)-N,N-dimethylpyrrolidine-1-carboxamide, (7) (2S,3S)-3-((ethylsulfonyl)amino)-N,N-dimethyl-2-((2,3',5'-trifluorobiphenyl-3-yl)methyl)pyrrolidine-1-carboxamide, (8) (2S,3S)-2-(biphenyl-3-ylmethyl)-3-((ethylsulfonyl)amino)-N-methoxy-N-methylpyrrolidine-1-carboxamide, (9) N-[(2S,3S)-2-[(2,3'-difluoro[1,1'-biphenyl]-3-yl)methyl]-1-(2-hydroxy-2-methylpropanoyl)pyrrolidin-3-yl]-1-fluorocyclopropane-1-sulfonamide,

(10) N-{(2S,3S)-1-(azetidine-1-carbonyl)-2-[(2-fluoro[1,1'-biphenyl]-3-yl)methyl]pyrrolidin-3-yl}ethanesulfonamide,

(11) (2S,3S)-3-[(ethanesulfonyl)amino]-2-[(3'-fluoro[1,1'-biphenyl]-3-yl)methyl]-N-methoxy-N-methylpyrrolidine-1-carboxamide,

(12) (2S,3S)-3-[(dimethylsulfamoyl)amino]-2-[(2-fluoro[1,1'-biphenyl]-3-yl)methyl]-N,N-dimethylpyrrolidine-1-carboxamide,

(13) (2S,3S)-3-[(dimethylsulfamoyl)amino]-N,N-dimethyl-2-[(2,3',5'-trifluoro[1,1'-biphenyl]-3-yl)methyl]pyrrolidine-1-carboxamide, and

(14) (2S,3S)-2-[(3',5'-difluoro[1,1'-biphenyl]-3-yl)methyl]-3-[(ethanesulfonyl)amino]-N-methoxy-N-methylpyrrolidine-1-carboxamide or a salt thereof.

[Compound L]

A compound selected from (1) (2S,3S)-2-((2,3'-difluorobiphenyl-3-yl)methyl)-3-((ethylsulfonyl)amino)-N,N-dimethylpyrrolidine-1-carboxamide, (2) (2S,3S)-3-((ethylsulfonyl)amino)-N,N-dimethyl-2-((2,3',5'-trifluorobiphenyl-3-yl)methyl)pyrrolidine-1-carboxamide, (3) N-[(2S,3S)-2-[(2,3'-difluoro[1,1'-biphenyl]-3-yl)methyl]-1-(2-hydroxy-2-methylpropanoyl)pyrrolidin-3-yl]-1-fluorocyclopropane-1-sulfonamide, (4) N-{(2S,3S)-1-(azetidine-1-carbonyl)-2-[(2-fluoro[1,1'-biphenyl]-3-yl)methyl]pyrrolidin-3-yl}ethanesulfonamide, (5) (2S,3S)-3-[(ethanesulfonyl)amino]-2-[(3'-fluoro[1,1'-biphenyl]-3-yl)methyl]-N-methoxy-N-methylpyrrolidine-1-carboxamide, and (6) (2S,3S)-3-[(dimethylsulfamoyl)amino]-2-[(2-fluoro[1,1'-biphenyl]-3-yl)methyl]-N,N-dimethylpyrrolidine-1-carboxamide or a salt thereof.

Specific examples of compound (I) include the compounds of the below-mentioned Examples 1 to 488.

As a salt of a compound represented by the formula (I), a pharmacologically acceptable salt is preferable, and examples of such salt include a salt with inorganic base, a salt with organic base, a salt with inorganic acid, a salt with organic acid, a salt with basic or acidic amino acid and the like.

Preferable examples of the salt with inorganic base include alkali metal salts such as sodium salt, potassium salt and the like, alkaline earth metal salts such as calcium salt, magnesium salt and the like, aluminum salt, ammonium salt and the like.

Preferable examples of the salt with organic base include salts with trimethylamine, triethylamine, pyridine, picoline, ethanolamine, diethanolamine, triethanolamine, tromethamine[tris(hydroxymethyl)methylamine], tert-butylamine, cyclohexylamine, benzylamine, dicyclohexylamine, N,N-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like.

Preferable examples of the salt with acidic amino acid include salts with aspartic acid, glutamic acid and the like.

The production method of the compound of the present invention is explained below.

The raw material compound and reagent used and the compound obtained in each step in the following production method may be each in a form of a salt, and examples of such salt include those similar to the salts of the compound represented by the formula (I), and the like.

When the compound obtained in each step is a free form, it can be converted to the objective salt according to a method known per se. When the compound obtained in each step is a salt, it can be converted to the objective free form or the other salt according to a method known per se.

The compound obtained in each step can be used directly as the reaction mixture or as a crude product for the next reaction. Alternatively, the compound obtained in each step can be isolated and purified from a reaction mixture according to a method known per se, for example, a separation means such as concentration, crystallization, recrystallization, distillation, solvent extraction, fractional distillation, column chromatography and the like.

When the raw material compound and reagent used in each step are commercially available, the commercially available product can also be used directly.

In the reaction in each step, while the reaction time varies depending on the kind of the reagent and solvent to be used, it is generally 1 min-48 hr, preferably 10 min-8 hr, unless otherwise specified.

In the reaction in each step, while the reaction temperature varies depending on the kind of the reagent and solvent to be used, it is generally −78° C.-300° C., preferably −78° C.-150° C., unless otherwise specified.

In the reaction in each step, while the pressure varies depending on the kind of the reagent and solvent to be used, it is generally 1 atm-20 atm, preferably 1 atm-3 atm, unless otherwise specified.

Microwave synthesizer such as Initiator manufactured by Biotage and the like may be used for the reaction in each step. While the reaction temperature varies depending on the kind of the reagent and solvent to be used, it is generally room temperature −300° C., preferably 50° C.-250° C., unless otherwise specified. While the reaction time varies depending on the kind of the reagent and solvent to be used, it is generally 1 min-48 hr, preferably 1 min-8 hr, unless otherwise specified.

In the reaction in each step, the reagent is used in an amount of 0.5 equivalents −20 equivalents, preferably 0.8 equivalents −5 equivalents, relative to the substrate, unless otherwise specified. When the reagent is used as a catalyst, the reagent is used in an amount of 0.001 equivalent −1 equivalent, preferably 0.01 equivalent −0.2 equivalent, relative to the substrate. When the reagent is used as a reaction solvent, the reagent is used in a solvent amount.

Unless otherwise specified, the reaction in each step is carried out without solvent, or by dissolving or suspending the raw material compound in a suitable solvent. Examples of the solvent include those described in Examples and the following solvents.

- alcohols: methanol, ethanol, tert-butyl alcohol, 2-methoxyethanol and the like;
- ethers: diethyl ether, diphenyl ether, tetrahydrofuran, 1,2-dimethoxyethane and the like;
- aromatic hydrocarbons: chlorobenzene, toluene, xylene and the like;
- saturated hydrocarbons: cyclohexane, hexane and the like; amides: N,N-dimethylformamide, N-methylpyrrolidone and the like;
- halogenated hydrocarbons: dichloromethane, carbon tetrachloride and the like;
- nitriles: acetonitrile and the like;
- sulfoxides: dimethyl sulfoxide and the like;
- aromatic organic bases: pyridine and the like;
- anhydrides: acetic anhydride and the like;
- organic acids: formic acid, acetic acid, trifluoroacetic acid and the like;
- inorganic acids: hydrochloric acid, sulfuric acid and the like;
- esters: ethyl acetate and the like;
- ketones: acetone, methyl ethyl ketone and the like; water.

The above-mentioned solvent can be used in a mixture of two or more kinds thereof in an appropriate ratio.

When a base is used for the reaction in each step, examples thereof include those described in Examples and the following bases.

- inorganic bases: sodium hydroxide, magnesium hydroxide, sodium carbonate, calcium carbonate, sodium hydrogen carbonate and the like;
- organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;
- metal alkoxides: sodium ethoxide, potassium tert-butoxide and the like;
- alkali metal hydrides: sodium hydride and the like; metal amides: sodium amide, lithium diisopropylamide, lithium hexamethyldisilazide and the like;
- organic lithiums: n-butyllithium and the like.

When an acid or an acid catalyst is used for the reaction in each step, examples thereof include those described in Examples and the following acids and acid catalysts. inorganic acids: hydrochloric acid, sulfuric acid, nitric acid, hydrobromic acid, phosphoric acid and the like;

organic acids: acetic acid, trifluoroacetic acid, citric acid, p-toluenesulfonic acid, 10-camphorsulfonic acid and the like; Lewis acid: boron trifluoride diethyl ether complex, zinc iodide, anhydrous aluminum chloride, anhydrous zinc chloride, anhydrous iron chloride and the like.

Unless otherwise specified, the reaction in each step is so carried out according to a method known per se, for example, the method described in Jikken Kagaku Kouza, 5th Edition, vol. 13-19 (the Chemical Society of Japan ed.); Shin Jikken Kagaku Kouza, vol. 14-15 (the Chemical Society of Japan ed.); Fine Organic Chemistry, Revised 2nd Edition (L. F. Tietze, Th. Eicher, Nankodo); Organic Name Reactions, the Reaction Mechanism and Essence, Revised Edition (Hideo Togo, Kodansha); ORGANIC SYNTHESES Collective Volume I-VII (John Wiley & Sons Inc.); Modern Organic Synthesis in the Laboratory A Collection of Standard Experimental Procedures (Jie Jack Li, OXFORD UNIVERSITY); Comprehensive Heterocyclic Chemistry III, Vol. 1-Vol. 14 (Elsevier Japan); Strategic Applications of Named Reactions in Organic Synthesis (translated by Kiyoshi Tomioka, Kagakudojin); Comprehensive Organic Transformations (VCH Publishers Inc.), 1989, or the like, or the method described in Examples.

In each step, the protection or deprotection reaction of an functional group is carried out according to a method known per se, for example, the method described in “Protective Groups in Organic Synthesis, 4th Ed”, Wiley-Interscience, Inc., 2007 (Theodora W. Greene, Peter G. M. Wuts); “Protecting Groups 3rd Ed.” Thieme, 2004 (P. J. Kocienski), or the like, or the method described in Examples.

Examples of the protecting group for a hydroxy group of an alcohol and the like and a phenolic hydroxy group include ether-type protecting groups such as methoxymethyl ether, benzyl ether, tert-butyldimethylsilyl ether, tetrahydropyranyl ether and the like; carboxylate ester-type protecting groups such as acetate ester and the like; sulfonate ester-type protecting groups such as methanesulfonate ester and the like; carbonate ester-type protecting groups such as tert-butylcarbonate and the like, and the like.

Examples of the protecting group for a carbonyl group of an aldehyde include acetal-type protecting groups such as dimethylacetal and the like; cyclic acetal-type protecting groups such as 1,3-dioxane and the like, and the like.

Examples of the protecting group for a carbonyl group of a ketone include ketal-type protecting groups such as dimethylketal and the like; cyclic ketal-type protecting groups such as 1,3-dioxane and the like; oxime-type protecting groups such as O-methyloxime and the like; hydrazone-type protecting groups such as N,N-dimethylhydrazone and the like, and the like.

Examples of the protecting group for a carboxyl group include ester-type protecting groups such as methyl ester and the like; amide-type protecting groups such as N,N-dimethylamide and the like, and the like.

Examples of the protecting group for a thiol include ether-type protecting groups such as benzyl thioether and the like; ester-type protecting groups such as thioacetate ester, thiocarbonate, thiocarbamate and the like, and the like.

Examples of the protecting group for an amino group and an aromatic heterocycle such as imidazole, pyrrole, indole and the like include carbamate-type protecting groups such as benzyl carbamate and the like; amide-type protecting groups such as acetamide and the like; alkyl amine-type protecting groups such as N-triphenylmethylamine and the like; sulfonamide-type protecting groups such as methanesulfonamide and the like, and the like.

The protecting groups can be removed according to a method known per se, for example, by employing a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method, and the like.

When reduction reaction is carried out in each step, examples of the reducing agent to be used include metal hydrides such as lithium aluminum hydride, sodium triacetoxyborohydride, sodium cyanoborohydride, diisobutylaluminum hydride (DIBAL-H), sodium borohydride, tetramethylammonium triacetoxyborohydride and the like; boranes such as borane tetrahydrofuran complex and the like; Raney nickel; Raney cobalt; hydrogen; formic acid; triethylsilane and the like. When carbon-carbon double bond or triple bond is reduced, a method using a catalyst such as palladium-carbon, Lindlar’s catalyst and the like may be employed.

When oxidation reaction is carried out in each step, examples of the oxidizing agent to be used include peroxides such as m-chloroperbenzoic acid (mCPBA), hydrogen peroxide, tert-butylhydroperoxide and the like; perchlorates such as tetrabutylammonium perchlorate and the like; chlorates such as sodium chlorate and the like; chlorites such as sodium chlorite and the like; periodates such as sodium periodate and the like; hypervalent iodine reagents such as iodosylbenzene and the like; reagents containing manganese such as manganese dioxide, potassium permanganate and the like; leads such as lead tetraacetate and the like; reagents containing chromium such as pyridinium chlorochromate (PCC), pyridinium dichromate (PDC), Jones reagent and the like; halogen compounds such as N-bromosuccinimide (NBS) and the like; oxygen; ozone; sulfur trioxide-pyridine complex; osmium tetroxide; selenium dioxide; 2,3-dichloro-5,6-dicyano-1,4-benzoquinone (DDQ) and the like.

When radical cyclization reaction is carried out in each step, examples of the radical initiator to be used include azo compounds such as azobisisobutyronitrile (AIBN) and the like; water-soluble radical initiators such as 4-4'-azobis-4-cyanopentanoic acid (ACPA) and the like; triethylboron in the presence of air or oxygen; benzoyl peroxide and the like. Examples of the radical reagent to be used include tributylstannane, tristrimethylsilylsilane, 1,1,2,2-tetraphenyldisilane, diphenylsilane, samarium iodide and the like.

When Wittig reaction is carried out in each step, examples of the Wittig reagent to be used include alkylidene phosphoranes and the like. The alkylidene phosphoranes can be prepared according to a method known per se, for example, by reacting a phosphonium salt with a strong base.

When Horner-Emmons reaction is carried out in each step, examples of the reagent to be used include phosphonoacetates such as methyl dimethylphosphonoacetate, ethyl diethylphosphonoacetate and the like; and bases such as alkali metal hydrides, organic lithiums and the like.

When Friedel-Crafts reaction is carried out in each step, a combination of a Lewis acid and an acid chloride or a combination of a Lewis acid and an alkylating agent (e.g., an alkyl halide, an alcohol, an olefin etc.) is used as a reagent. Alternatively, an organic acid or an inorganic acid can also be used instead of a Lewis acid, and an anhydride such as acetic anhydride and the like can also be used instead of an acid chloride.

When aromatic nucleophilic substitution reaction is carried out in each step, a nucleophile (e.g., an amine, imidazole etc.) and a base (e.g., an organic base etc.) are used as a reagent.

When nucleophilic addition reaction by a carbo anion, nucleophilic 1,4-addition reaction (Michael addition reaction) by a carbo anion or nucleophilic substitution reaction by a carbo anion is carried out in each step, and examples of the base to be used for generation of the carbo anion include organic lithiums, metal alkoxides, inorganic bases, organic bases and the like.

When Grignard reaction is carried out in each step, examples of the Grignard reagent to be used include arylmagnesium halides such as phenylmagnesium bromide and the like; and alkylmagnesium halides such as methylmagnesium bromide and the like. The Grignard reagent can be prepared according to a method known per se, for example, by reacting an alkyl halide or an aryl halide with a metal magnesium in an ether or tetrahydrofuran as a solvent.

When Knoevenagel condensation reaction is carried out in each step, a compound having an activated methylene group with two electron withdrawing groups (e.g., malonic acid, diethyl malonate, malononitrile etc.) and a base (e.g., an organic base, a metal alkoxide, an inorganic base) are used as a reagent.

When Vilsmeier-Haack reaction is carried out in each step, phosphoryl chloride and an amide derivative (e.g., N,N-dimethylformamide etc.) are used as a reagent.

When azidation reaction of an alcohol, an alkyl halide or a sulfonate is carried out in each step, examples of the azidating agent to be used include diphenylphosphorylazide (DPPA), trimethylsilylazide, sodium azide and the like. For example, for the azidation reaction of an alcohol, a method using diphenylphosphorylazide and 1,8-diazabicyclo[5.4.0]undec-7-ene (DBU), a method using trimethylsilylazide and a Lewis acid, and the like are employed.

When reductive amination reaction is carried out in each step, examples of the reducing agent to be used include sodium triacetoxyborohydride, sodium cyanoborohydride, hydrogen, formic acid and the like. When the substrate is an amine compound, examples of the carbonyl compound to be used include paraformaldehyde, aldehydes such as acetaldehyde and the like, and ketones such as cyclohexanone and the like. When the substrate is a carbonyl compound, examples of the amine to be used include ammonia, primary amines such as methylamine and the like; secondary amines such as dimethylamine and the like, and the like.

When Mitsunobu reaction is carried out in each step, an azodicarboxylate (e.g., diethyl azodicarboxylate (DEAD), diisopropyl azodicarboxylate (DIAD) etc.) and triphenylphosphine are used as a reagent.

When esterification reaction, amidation reaction or urea formation reaction is carried out in each step, examples of the reagent to be used include acyl halides such as acid chlorides, acid bromides and the like; activated carboxylic acids such as acid anhydrides, activated esters, sulfates and the like. Examples of the activating agent of the carboxylic acid include carbodiimide condensing agents such as 1-ethyl-3-(3-dimethylaminopropyl)carbodiimide hydrochloride (WSCD) and the like; triazine condensing agents such as 4-(4,6-dimethoxy-1,3,5-triazin-2-yl)-4-methylmorpholinium chloride n-hydrate (DMT-MM) and the like; carbonate condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformates such as ethyl chloroformate and the like; O-(7-azabenzotriazol-1-yl)-N,N,N',N'-tetramethyluronium hexafluorophosphorate (HATU); sulfuric acid; combinations thereof and the like. When carbodiimide condensing agent is used, an additive such as 1-hydroxybenzotriazole (HOBt), N-hydroxysuccinimide (HOSu), dimethylaminopyridine (DMAP) and the like may be added to the reaction system.

When coupling reaction is carried out in each step, examples of the metal catalyst to be used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride and the like; nickel compounds such as tetrakis(triphenylphosphine)nickel(0) and the like; rhodium compounds such as tris(triphenylphosphine)rhodium(III) chloride and the like; cobalt compounds; copper compounds such as copper oxide, copper(I) iodide and the like; platinum compounds and the like. In addition, a base can be added to the reaction system, and examples thereof include inorganic bases and the like.

When thiocarbonylation reaction is carried out in each step, phosphorus pentasulfide is typically used as the thiocarbonylating agent. Alternatively, a reagent having a 1,3,2,4-dithiadiphosphetane-2,4-disulfide structure (e.g., 2,4-bis(4-methoxyphenyl)-1,3,2,4-dithiadiphosphetane-2,4-disulfide (Lawesson reagent) etc.) can also be used instead of phosphorus pentasulfide.

When Wohl-Ziegler reaction is carried out in each step, examples of the halogenating agent to be used include N-iodosuccinimide, N-bromosuccinimide (NBS), N-chlorosuccinimide (NCS), bromine, sulfuryl chloride and the like. In addition, the reaction can be accelerated by subjecting a radical initiator such as heat, light, benzoyl peroxide, azobisisobutyronitrile and the like to the reaction system reaction.

When halogenation reaction of a hydroxy group is carried cut in each step, examples of the halogenating agent to be used include hydrohalic acids and acid halides of inorganic acids, specifically, hydrochloric acid, thionyl chloride, phosphorus oxychloride and the like for chlorination, 48% hydrobromic acid and the like for bromination. In addition, a method of producing an alkyl halide by reacting an alcohol with triphenylphosphine and carbon tetrachloride or carbon tetrabromide or the like can be employed. Alternatively, a method of producing an alkyl halide via two step comprising converting an alcohol to the corresponding sulfonate, and then reacting the sulfonate with lithium bromide, lithium chloride or sodium iodide can also be employed.

When Arbuzov reaction is carried out in each step, examples of the reagent to be used include alkyl halides such as ethyl bromoacetate and the like; and phosphites such as triethyl phosphite, tri(isopropyl) phosphite and the like.

When sulfonate esterification reaction is carried out in each step, examples of the sulfonating agent to be used include methanesulfonyl chloride, p-toluenesulfonyl chloride, methanesulfonic anhydride, p-toluenesulfonic anhydride and the like.

When hydrolysis reaction is carried out in each step, an acid or a base is used as a reagent. For acid hydrolysis reaction of tert-butyl ester, formic acid, triethylsilane and the like may be added to reductively-trap tert-butyl cation which is by-produced.

When dehydration reaction is carried out in each step, examples of the dehydrating agent to be used include sulfuric acid, diphosphorus pentaoxide, phosphorus oxychloride, N,N'-dicyclohexylcarbodiimide, alumina, polyphosphoric acid and the like.

Compound (7) used in the below-mentioned Reaction Scheme 3 can be produced from compound (1) according to the method shown in the following Reaction Scheme 1. As used herein, M is a magnesium halide, or an alkali metal such as lithium and the like, and the other symbols are as defined above.

Reaction Scheme 1

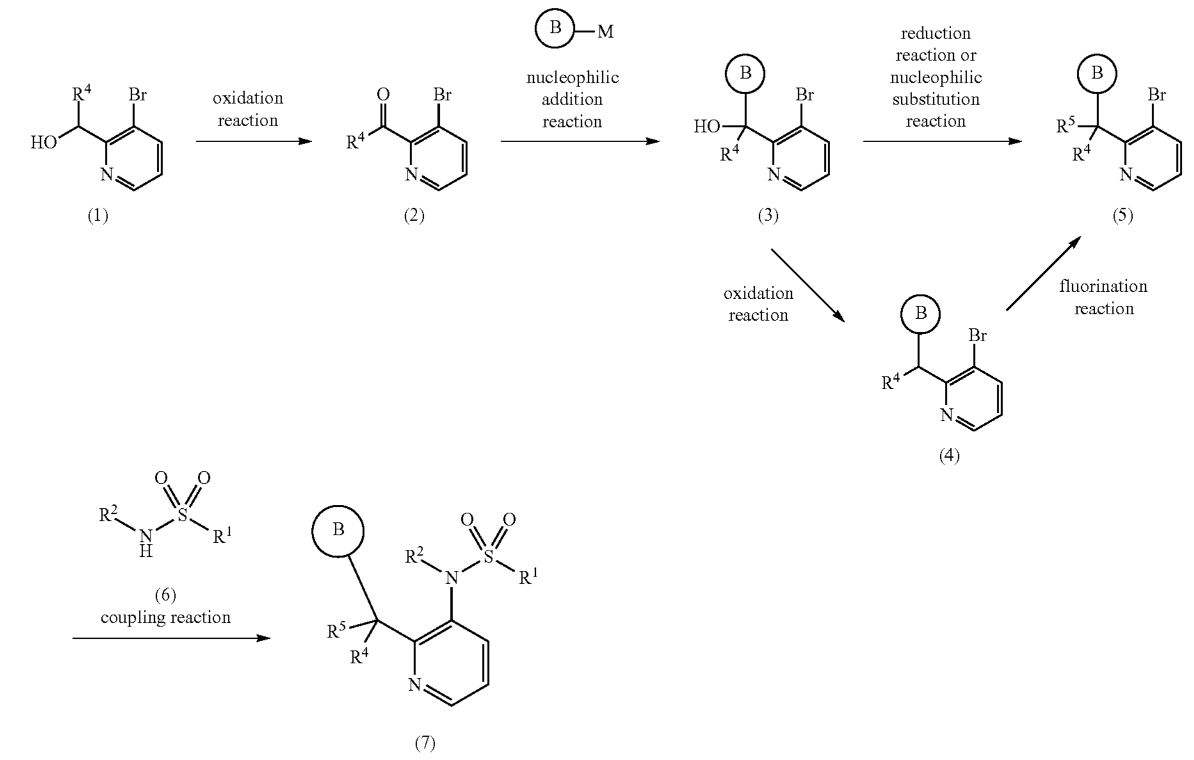

Compound (1) may be commercially available, or can be produced according to a method known per se or a method analogous thereto.

Compound (3) can be produced by subjecting compound (2) to a nucleophilic addition reaction with an organometallic reagent. Examples of the organometallic reagent to be used include organic magnesium halides, organic lithiums and the like. The organometallic reagent can be prepared according to a method known per se.

Compound (4) can be produced, for example, by subjecting compound (3) wherein $R^4$ is a hydrogen atom to an oxidation reaction.

Compound (5) wherein $R^5$ is a hydrogen atom can be produced, for example, by subjecting compound (3) to a reduction reaction.

Compound (5) wherein $R^5$ is a $C_{1-6}$ alkoxy group can be produced, for example, by subjecting compound (3) to a nucleophilic substitution reaction with an electrophile in the presence of a base. Examples of the electrophile to be used include alkyl halides and the like. Examples of the base to be used include alkali metal hydrides and the like.

Compound (5) wherein $R^4$ and $R^5$ are both fluorine atoms can be produced, for example, by subjecting compound (4) to a fluorination reaction. Examples of the reagent to be used include fluorinating agents such as diethylaminosulfur trifluoride (DAST), bis(2-methoxyethyl)aminosulfur trifluoride (BAST), 1,1,2,2-tetrafluoroethyl-N,N-dimethylamine (TFEDMA) and the like.

Compound (7) can be produced by subjecting compound (5) and compound (6) to a coupling reaction. Compound (6) may be commercially available, or can be produced according to a method known per se or a method analogous thereto.

Compound (7) can also be produced from compound (8) according to the method shown in the following Reaction Scheme 2. As used herein, Hal is a halogen atom, $LG^1$ and $LG^2$ are each independently a leaving group, and the other symbols are as defined above.

Reaction Scheme 2

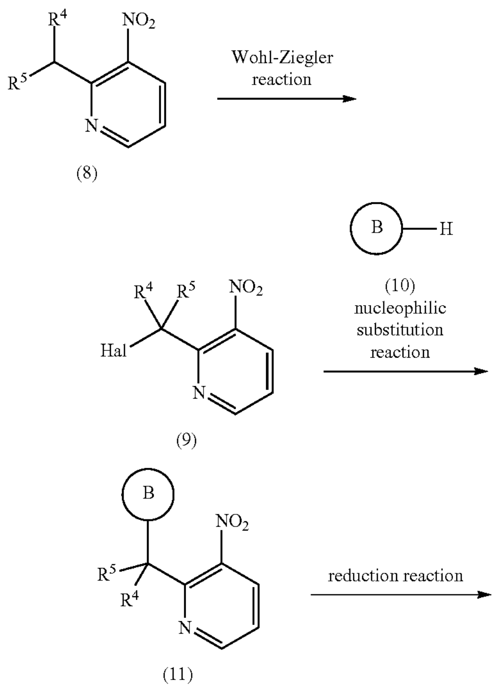

-continued

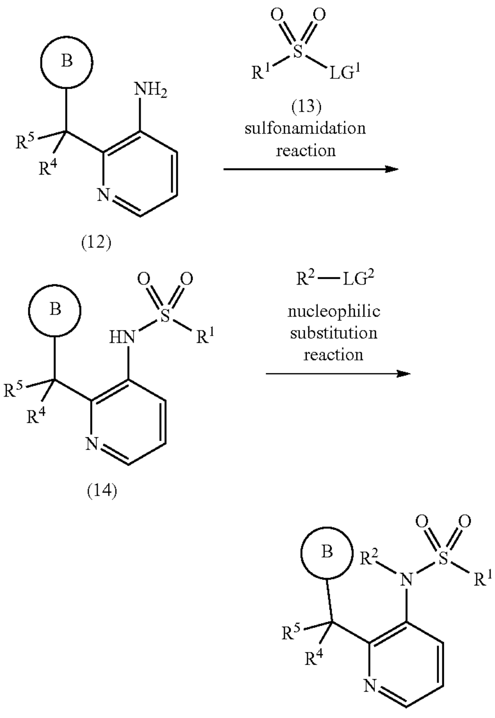

(12)

(14)

(7)

Reaction Scheme 3

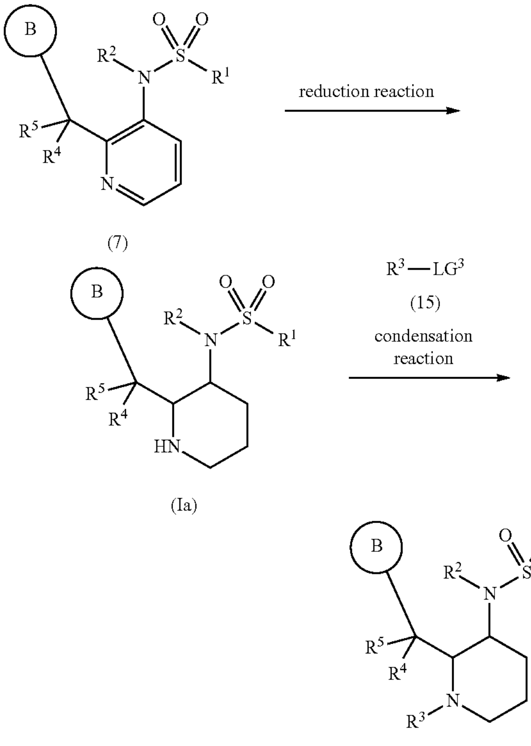

(7)

(Ia)

(Ib)

Examples of the "leaving group" represented by $LG^1$ or $LG^2$ include halogen atoms, optionally halogenated $C_{1-6}$ alkylsulfonyloxy groups (e.g., methanesulfonyloxy, ethanesulfonyloxy, trifluoromethanesulfonyloxy), $C_{6-14}$ arylsulfonyloxy groups optionally substituted by $C_{1-6}$ alkyl (e.g., benzenesulfonyloxy, toluenesulfonyloxy) and the like.

Compound (8) may be commercially available, or can be produced according to a method known per se or a method analogous thereto.

Compound (11) can be produced by subjecting compound (9) to a nucleophilic substitution reaction with compound (10). Examples of the compound (10) to be used include cyclic amines (e.g., pyrrolidine, piperidine), pyrazole and the like. In addition, a base may be added to the reaction system. Examples of the base include inorganic bases, organic bases, alkali metal hydrides and the like.

Compound (14) can be produced by subjecting compound (12) to a sulfonamidation reaction with compound (13) in the presence of a base. Examples of the base to be used include organic bases and the like. Compound (13) may be commercially available, or can be produced according to a method known per se.

Compound (7) can be produced by subjecting compound (14) to a nucleophilic substitution reaction with an electrophile in the presence of a base. Examples of the electrophile to be used include alkyl halides and the like. Examples of the base to be used include alkali metal hydrides and the like.

Compound (Ia) and compound (Ib), which are compound (I) wherein Ring A is a piperidine ring, can be produced from compound (7) according to the method shown in the following Reaction Scheme 3. As used herein, $LG^3$ is a leaving group, and the other symbols are as defined above.

Examples of the "leaving group" represented by $LG^3$ include those exemplified as the "leaving group" represented by $LG^1$ or $LG^2$.

Compound (Ia) can be produced by subjecting compound (7) to a reduction reaction. Examples of the reducing agent to be used include catalysts such as palladium carbon, rhodium carbon, platinum carbon and the like.

Compound (Ib) can be produced by subjecting compound (Ia) and compound (15) to a condensation reaction. Examples of the compound (15) to be used include acyl halides such as acid chlorides, acid bromides, alkyl chloroformates, carbamoyl chlorides and the like; activated carboxylic acids such as acid anhydrides, activated esters, sulfate esters and the like. Examples of the activating agent for carboxylic acid include carbodiimide condensing agents such as 1-ethyl-3-(3-dimethylaminopropyl)carbodiimide hydrochloride (WSCD) and the like; triazine condensing agents such as 4-(4,6-dimethoxy-1,3,5-triazin-2-yl)-4-methylmorpholinium chloride-n-hydrate (DMT-MM) and the like; carbonate ester condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformates such as ethyl chloroformate and the like; O-(7-azabenzotriazol-1-yl)-N,N,N',N'-tetramethyluronium hexafluorophosphorate (HATU); sulfuric acid; combinations thereof, and the like. In addition, a base may be added to the reaction system. Examples of the base include inorganic bases, organic bases and the like. When a carbodiimide condensing agent is used, an additive such as 1-hydroxybenzotriazole (HOBt), N-hydroxysuccinimide (HOSu), dimethylaminopyridine (DMAP) and the like may be further added to the reaction system.

Compound (Ic) and compound (Id), which are compound (I) wherein $R^2$ is a hydrogen atom, and compound (I) can be produced from compound (16) according to the method shown in the following Reaction Scheme 4. As used herein, $P^1$ is a protecting group, $LG^4$ is a leaving group, and other symbols are as defined above.

Reaction Scheme 4

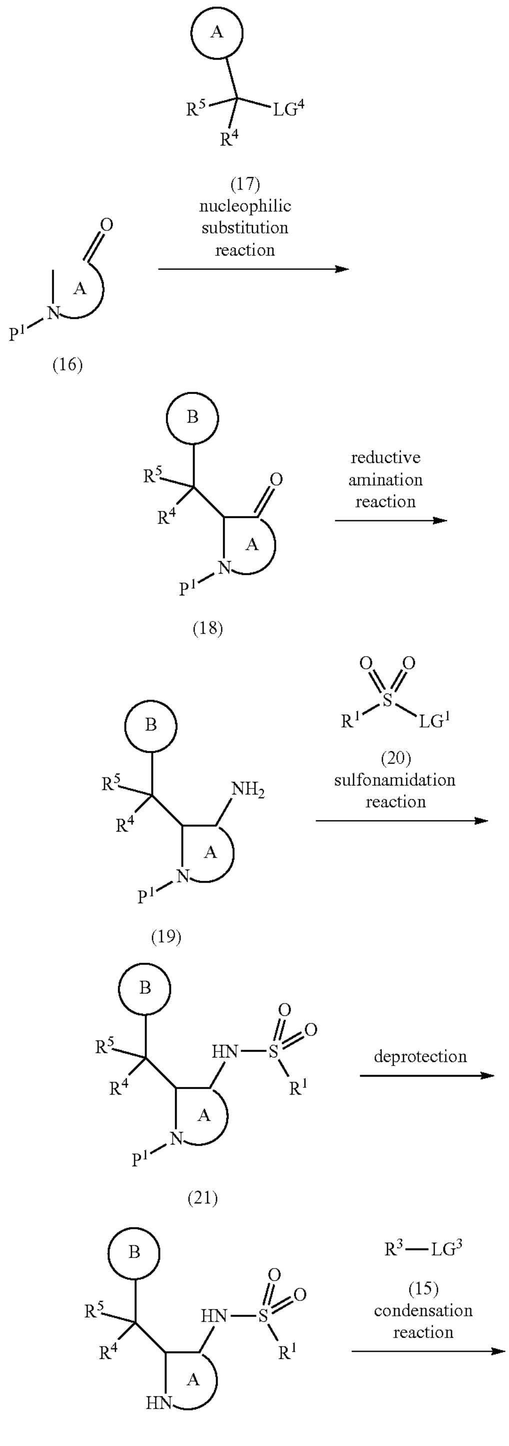

(Ic)

-continued

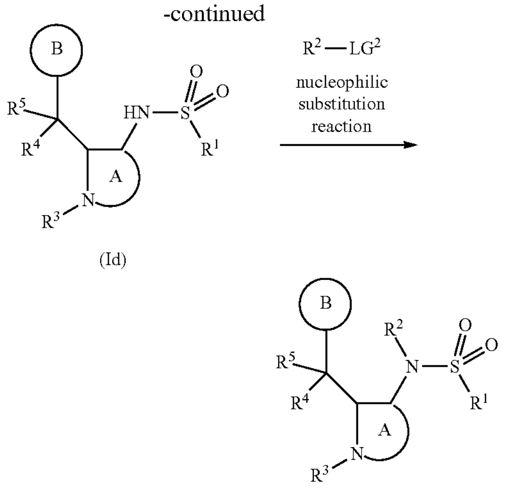

(Id)

(I)

Examples of the "protecting group" represented by $P^1$ include those exemplified as the above-mentioned "protecting group for an amino group and an aromatic heterocycle such as imidazole, pyrrole, indole and the like".

Examples of the "leaving group" represented by $LG^4$ include those exemplified as the "leaving group" represented by $LG^1$ or $LG^2$.

Compound (16) and compound (17) may be commercially available, or can be produced according to a method known per se or a method analogous thereto.

Compound (18) can be produced by subjecting compound (16) to a nucleophilic substitution reaction with compound (17) in the presence of a base. Examples of the base to be used include alkali metal hydrides, organic lithiums and the like. Alternatively, compound (18) can also be produced by two step reaction, i.e., by converting compound (16) to the corresponding enamine, and then reacting the enamine with compound (17).

Examples of the amine to be used for the enamine formation include pyrrolidine, morpholine, N,N-dimethylhydrazine and the like. A base may be added to the reaction system of the enamine and compound (17). Examples of the base include alkali metal hydrides, organic lithiums and the like. In addition, a catalyst may be added to the reaction system in order to promote the reaction. Examples of the catalyst to be used include tetrabutylammonium iodide and the like.

Compound (19) can be produced by subjecting compound (18) to a reductive amination reaction. Examples of the reducing agent to be used include sodium triacetoxyborohydride, sodium cyanoborohydride, hydrogen, formic acid and the like. Examples of the amine to be used include ammonia and the like. In addition, a metal catalyst may be added to the reaction system. Examples of the catalyst to be used include iridium catalysts and the like. Alternatively, Compound (19) can also be produced by two step reaction, i.e., by converting compound (18) to the corresponding oxime, and then subjecting the oxime to a reduction reaction. Examples of the amines to be used for the oxime formation include hydroxylamine, O-methylhydroxylamine and the like. Examples of the reducing agent to be used include boranes such as borane tetrahydrofuran complex and the like, sodium borohydride and the like. In addition, a metal catalyst may be added to the reaction system. Examples of the catalyst to be used include molybdenum trioxide and the like.

Compound (21) can be produced by subjecting compound (19) to a sulfonamidation reaction with compound (20) in the presence of a base. Examples of the base to be used include organic bases and the like. Compound (20) may be commercially available, or can be produced according to a method known per se.

Compound (Id) can be produced by subjecting compound (Ic) and compound (15) to a condensation reaction. Examples of the compound (15) to be used include acyl halides such as acid chlorides, acid bromides, alkyl chloroformates, carbamoyl chlorides and the like; activated carboxylic acids such as acid anhydrides, activated esters, sulfate esters and the like. Examples of the activating agent for carboxylic acid include carbodiimide condensing agents such as 1-ethyl-3-(3-dimethylaminopropyl)carbodiimide hydrochloride (WSCD) and the like; triazine condensing agents such as 4-(4,6-dimethoxy-1,3,5-triazin-2-yl)-4-methylmorpholinium chloride-n-hydrate (DMT-MM) and the like; carbonate ester condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformates such as ethyl chloroformate and the like; O-(7-azabenzotriazol-1-yl)-N,N,N',N'-tetramethyluronium hexafluorophosphorate (HATU); sulfuric acid; combinations thereof, and the like. In addition, a base may be added to the reaction system. Examples of the base include inorganic bases, organic bases and the like. When a carbodiimide condensing agent is used, an additive such as 1-hydroxybenzotriazole (HOBt), N-hydroxysuccinimide (HOSu), dimethylaminopyridine (DMAP) and the like may be further added to the reaction system.

Compound (I) can be produced by subjecting compound (Id) to a nucleophilic substitution reaction with an electrophile in the presence of a base. Examples of the electrophile to be used include alkyl halide and the like. Examples of the base to be used include alkali metal hydrides and the like.

In the thus-obtained compound (I), an intramolecular functional group can also be converted to an object functional group by a combination of chemical reactions known per se. Examples of the chemical reaction include oxidation reaction, reduction reaction, alkylation reaction, acylation reaction, ureation reaction, hydrolysis reaction, amination reaction, esterification reaction, aryl coupling reaction, deprotection reaction and the like.

In the above-mentioned production method, when a starting compound has an amino group, a carboxyl group, a hydroxy group, a carbonyl group or a mercapto group as a substituent, a protecting group generally used in the peptide chemistry may be introduced into these groups, and the object compound can be obtained by removing the protecting group as necessary after the reaction.

Compound (I) obtained by the above-mentioned production method can be isolated and purified by a known means, such as solvent extraction, liquid conversion, phase transfer, crystallization, recrystallization, chromatography and the like.

When compound (I) contains optical isomer, stereoisomer, regio isomer and rotamer, these compounds are also included in compound (I), and each can be obtained as a single product by a synthesis method or a separation method known per se. For example, when an optical isomer exists in compound (I), an optical isomer resolved from the compound is also encompassed in compound (I).

Here, an optical isomer can be produced by a method known per se.

Compound (I) May be a Crystal.

A crystal of compound (I) (hereinafter sometimes to be abbreviated as the crystal of the present invention) can be produced by crystallizing compound (I), by applying a crystallization method known per se.

In the present specification, the melting point means a melting point measured, for example, by micro melting point apparatus (Yanako, MP-500D or Buchi, B-545), DSC (differential scanning calorimetry analysis) apparatus (METTLER TOLEDO, DSC1) and the like.

Generally, the melting point sometimes varies depending on the measurement device, measurement condition and the like. The crystal in the present specification may be a crystal showing a melting point different from the values described in the present specification as long as the difference is within a general error range.

The crystal of the present invention is superior in the physicochemical properties (e.g., melting point, solubility, stability) and biological properties (e.g., pharmacokinetics (absorbability, distribution, metabolism, excretion), efficacy expression), and is extremely useful as a medicament.

Compound (I) may be used as a prodrug. A prodrug of the compound (I) means a compound which is converted to the compound (I) of the present invention with a reaction due to an enzyme, an gastric acid, etc. under the physiological condition in the living body, that is, a compound which is converted to the compound (I) of the present invention with oxidation, reduction, hydrolysis, etc. according to an enzyme; a compound which is converted to the compound (I) of the present invention by hydrolysis etc. due to gastric acid, etc.

A prodrug of compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, etc.);

a compound obtained by subjecting a hydroxy group in compound (I) to an acylation, alkylation, phosphorylation or boration (e.g., a compound obtained by subjecting an hydroxy group in compound (I) to an acetylation, palmitoylation, propanoylation, pivaloylation, succinylation, fumarylation, alanylation, dimethylaminomethylcarbonylation, etc.);

a compound obtained by subjecting a carboxyl group in compound (I) to an esterification or amidation (e.g., a compound obtained by subjecting a carboxyl group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl) methyl esterification, cyclohexyloxycarbonylethyl esterification and methylamidation, etc.)

and the like. Any of these compounds can be produced from compound (I) by a method known per se.

A prodrug for compound (I) may also be one which is converted into compound (I) under a physiological condition, such as those described in IYAKUHIN no KAIHATSU (Development of Pharmaceuticals), Vol. 7, Design of Molecules, p.163-198, Published by HIROKAWA SHOTEN (1990).

In the present specification, a prodrug may form a salt, and as such salt, those exemplified as a salt of the compound represented by the above-mentioned formula (I) can be mentioned.

Compound (I) may be labeled with an isotope (e.g., $^3H$, $^{13}C$, $^{14}C$, $^{18}F$, $^{35}S$, $^{125}I$) and the like.

Compound (I) labeled with or substituted by an isotope can be used, for example, as a tracer used for Positron Emission Tomography (PET) (PET tracer), and is useful in the field of medical diagnosis and the like.

Furthermore, compound (I) may be a hydrate or a non-hydrate, or a non-solvate (e.g., anhydride), or a solvate (e.g., hydrate).

Compound (I) also encompasses a deuterium conversion form wherein $^1H$ is converted to $^2H$ (D).

Furthermore, compound (I) may be a pharmaceutically acceptable cocrystal or cocrystal salt. The cocrystal or cocrystal salt means a crystalline substance constituted with two or more special solids at room temperature, each having different physical properties (e.g., structure, melting point, melting heat, hygroscopicity, solubility and stability). The cocrystal or cocrystal salt can be produced by a cocrystallization method known per se.

Compound (I) or a prodrug thereof (hereinafter sometimes to be simply abbreviated as the compound of the present invention) can be used as it is or in the form of a pharmaceutical composition (also referred to as a medicament) by mixing with a pharmacologically acceptable carrier etc. to mammals (e.g., human, mouse, rat, rabbit, dog, cat, bovine, horse, swine, monkey) as an agent for the prophylaxis or treatment of various diseases mentioned below.

As pharmacologically acceptable carriers, various organic or inorganic carrier substances conventionally used as preparation materials can be used. These are incorporated as excipient, lubricant, binder and disintegrant for solid preparations; or solvent, solubilizing agent, suspending agent, isotonicity agent, buffer and soothing agent for liquid preparations; and the like; and preparation additives such as preservative, antioxidant, colorant, sweetening agent and the like can be added as necessary.

Preferable examples of the excipient include lactose, sucrose, D-mannitol, D-sorbitol, starch, gelatinated starch, dextrin, crystalline cellulose, low-substituted hydroxypropylcellulose, sodium carboxymethylcellulose, gum arabic, pullulan, light anhydrous silicic acid, synthetic aluminum silicate and magnesium alumino metasilicate.

Preferable examples of the lubricant include magnesium stearate, calcium stearate, talc and colloidal silica.

Preferable examples of the binder include gelatinated starch, sucrose, gelatin, gum arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose and polyvinylpyrrolidone.

Preferable examples of the disintegrant include lactose, sucrose, starch, carboxymethylcellulose, calcium carboxymethylcellulose, croscarmellose sodium, sodium carboxymethyl starch, light anhydrous silicic acid and low-substituted hydroxypropylcellulose.

Preferable examples of the solvent include water for injection, physiological brine, Ringer's solution, alcohol, propylene glycol, polyethylene glycol, sesame oil, corn oil, olive oil and cottonseed oil.

Preferable examples of the solubilizing agent include polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate.

Preferable examples of the suspending agent include surfactants such as stearyltriethanolamine, sodium lauryl sulfate, lauryl aminopropionate, lecithin, benzalkonium chloride, benzethonium chloride, glycerol monostearate and the like; hydrophilic polymers such as poly(vinyl alcohol), polyvinylpyrrolidone, carboxymethylcellulose sodium, methylcellulose, hydroxymethylcellulose, hydroxyethylcellulose, hydroxypropylcellulose and the like, polysorbates; and polyoxyethylene hydrogenated castor oil.

Preferable examples of the isotonicity agent include sodium chloride, glycerol, D-mannitol, D-sorbitol and glucose.

Preferable examples of the buffer include buffers of phosphate, acetate, carbonate, citrate etc.

Preferable examples of the soothing agent include benzyl alcohol.

Preferable examples of the preservative include p-oxybenzoate esters, chlorobutanol, benzyl alcohol, phenethyl alcohol, dehydroacetic acid and sorbic acid.

Preferable examples of the antioxidant include sulfite salts and ascorbate salts.

Preferable examples of the colorant include aqueous food tar colors (e.g., food colors such as Food Color Red Nos. 2 and 3, Food Color Yellow Nos. 4 and 5, Food Color Blue Nos. 1 and 2 and the like food colors), water insoluble lake dyes (e.g., aluminum salt of the above-mentioned aqueous food tar color), natural dyes (e.g., β-carotene, chlorophyll, red iron oxide) and the like.

Preferable examples of the sweetening agent include saccharin sodium, dipotassium glycyrrhizinate, aspartame and stevia.

Examples of the dosage form of the above-mentioned pharmaceutical composition include oral preparations such as tablet (including sugar-coated tablet, film-coated tablet, sublingual tablet, orally disintegrating tablet, buccal tablet), capsule (including soft capsule, microcapsule), pill, granule, powder, troche, syrup, liquid, emulsion, suspension, aerosol, films (e.g., orally disintegrable films, oral mucosa-adhesive film) and the like; and parenteral agents such as injection (e.g., subcutaneous injection, intravenous injection, intramuscular injection, intraperitoneal injection, drip infusion), external preparation (e.g., transdermal absorption type preparation, ointment, lotion, adhesive preparation), suppository (e.g., rectal suppository, vaginal suppository), pellet, nasal preparation, pulmonary preparation (inhalant), eye drop and the like. The compound and medicament of the present invention can be respectively safely administered orally or parenterally (e.g., intrarectal, intravenous, intraarterial, intramuscular, subcutaneous, intraorgan, intranasal, intradermal, instillation, intracerebral, intravaginal, intraperitoneal, intratumoral, proximal tumor administrations, and administration to the lesion).

These preparations may be a release control preparation (e.g., sustained-release microcapsule) such as an immediate-release preparation, a sustained-release preparation and the like.

The pharmaceutical composition can be produced according to a method conventionally used in the field of pharmaceutical formulation, for example, the method described in the Japanese Pharmacopoeia, and the like.

While the content of the compound of the present invention in the pharmaceutical composition of the present invention varies depending on the dosage form, dose of the compound of the present invention and the like, it is, for example, about 0.1 to 100 wt %.

When an oral preparation is produced, coating may be applied where necessary for the purpose of taste masking, enteric solubility or sustainability.

Examples of the coating base used for coating include sugar coating base, water-soluble film coating base, enteric film coating base, and sustained-release film coating base.

As the sugar coating base, sucrose is used, and one or more kinds selected from talc, and the precipitated calcium carbonate, gelatin, gum arabic, pullulan, carnauba wax and the like may be further used in combination.

Examples of the water-soluble film coating base include cellulose polymers such as hydroxypropylcellulose, hydroxypropylmethylcellulose, hydroxyethylcellulose, methylhydroxyethylcellulose and the like; synthetic polymers such as polyvinyl acetal diethylaminoacetate, aminoalkylmethacrylate copolymer E [Eudragit E (trade name)], polyvinylpyrrolidone and the like; and polysaccharides such as pullulan and the like.

Examples of the enteric film coating base include cellulose polymers such as hydroxypropylmethylcellulose phthalate, hydroxypropylmethylcellulose acetate succinate, carboxymethylethylcellulose, cellulose acetate phthalate and the like; acrylic acid polymers such as methacrylic acid copolymer L [Eudragit L (trade name)], methacrylic acid copolymer LD [Eudragit L-30D-55 (trade name)], methacrylic acid copolymer S [Eudragit S (trade name)] and the like; and naturally-occurring substances such as shellac and the like.

Examples of the sustained-release film coating base include cellulose polymers such as ethylcellulose and the like; and acrylic acid polymers such as aminoalkylmethacrylate copolymer RS [Eudragit RS (trade name)], ethyl acrylate-methyl methacrylate copolymer suspension [Eudragit NE (trade name)] and the like.

Two or more kinds of the above-mentioned coating bases may be used in a mixture at an appropriate ratio. In addition, for example, light shielding agents such as titanium oxide, red ferric oxide and the like may also be used during coating.

Since the compound of the present invention shows low toxicity (e.g., acute toxicity, chronic toxicity, genetic toxicity, reproductive toxicity, cardiotoxicity, carcinogenicity) and less side effects, it can be used as a prophylactic or therapeutic agent, or diagnostic agent for various diseases in mammals (e.g., human, bovine, horse, dog, cat, monkey, mouse, rat).

The compound of the present invention has an excellent an orexin type 2 receptor agonist activity, and may treat, prevent or ameliorate the risk of various neurological and psychiatric diseases associated with an orexin type 2 receptor. The compound of the present invention is useful as an agent for the prophylaxis or treatment of various diseases such as narcolepsy, idiopathic hypersomnia, hypersomnia, sleep apnea syndrome, narcolepsy syndrome accompanied by narcolepsy-like symptoms, hypersomnia syndrome accompanied by daytime hypersomnia (e.g., Kleine Levin syndrome, major depression with hypersomnia, Lewy body dementia, Parkinson's disease, progressive supranuclear paralysis, Prader-Willi syndrome, Mobius syndrome, hypoventilation syndrome, Niemann-Pick disease type C, brain contusion, cerebral infarction, brain tumor, muscular dystrophy, multiple sclerosis, acute disseminated encephalomyelitis, Guillain-Barre syndrome, Rasmussen's encephalitis, Wernicke's encephalitis, limbic encephalitis, Hashimoto's encephalopathy), coma, loss of consciousness, obesity (e.g., malignant mastocytosis, exogenous obesity, hyperinsulinar obesity, hyperplasmic obesity, hypop hyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity), insulin resistance syndrome, Alzheimer's disease, disturbance of consciousness such as coma and the like, side effects and complications due to anesthesia, sleep disturbance, sleep problem, insomnia, Intermittent sleep, nocturnal myoclonus, REM sleep interruption, jet lag, jet lag syndrome, sleep disorder of alternating worker, sleep disorder, night terror, depression, major depression, sleepwalking disease, enuresis, sleep disorder, Alzheimer's dusk, diseases associated with circadian rhythm, fibromyalgia, condition arising from decline in the quality of sleep, overeating, obsessive compulsive eating disorder, obesity-related disease, hypertension, diabetes, elevated plasma insulin concentration and insulin resistance, hyperlipidemia, hyperlipemia, endometrial cancer, breast cancer, prostate cancer, colorectal cancer, cancer, osteoarthritis, obstructive sleep apnea, cholelithiasis, gallstones, cardiac disease, abnormal heartbeat, arrhythmia, myocardial infarction, congestive cardiac failure, cardiac failure, coronary heart disease, cardiovascular disorder, sudden death, polycysticovarian disease, craniopharingioma, Froelich's syndrome, growth hormone deficient, normal mutant short stature, Turner's syndrome, children suffering from acute lymphoblastic leukemia, syndrome X, reproductive hormone abnormality, declining fertility, infertility, male gonadal function decline, sexual and reproductive dysfunction such as female male hirsutism, fetal defects associated with pregnant women obesity, gastrointestinal motility disorders such as obesity-related gastroesophageal reflux, obesity hypoventilation syndrome (Pickwick syndrome), respiratory diseases such as dyspnea, inflammation such as systemic inflammation of the vascular system, arteriosclerosis, hypercholesterolemia, hyperuricemia, lower back pain, gall bladder disease, gout, kidney cancer, risk of secondary outcomes of obesity, such as lowering the risk of left ventricular hypertrophy, migraine pain, headache, neuropathic pain, Parkinson's disease, psychosis, schizophrenia, facial flushing, night sweats, diseases of the genital/urinary system, diseases related to sexual function or fertility, dysthymic disorder, bipolar disorder, bipolar I disorder, bipolar II disorder, cyclothymic disorder, acute stress disorder, agoraphobia, generalized anxiety disorder, obsessive disorder, panic attack, panic disorder, posttraumatic stress disorder, separation anxiety disorder, social phobia, anxiety disorder, acute neurological and psychiatric disorders such as cardiac bypass surgery and post-transplant cerebral deficit, stroke, ischemic stroke, cerebral ischemia, spinal cord trauma, head trauma, perinatal hypoxia, cardiac arrest, hypoglycemic nerve injury, Huntington's chorea, amyotrophic lateral sclerosis, multiple sclerosis, eye damage, retinopathy, cognitive impairment, muscle spasm, tremor, epilepsy, disorders associated with muscle spasticity, delirium, amnestic disorder, age-related cognitive decline, schizoaffective disorder, delusional disorder, drug addiction, dyskinesia, chronic fatigue syndrome, fatigue, medication-induced Parkinsonism syndrome, Jill-do La Tourette's syndrome, chorea, myoclonus, tic, restless legs syndrome, dystonia, dyskinesia, attention deficit hyperactivity disorder (ADHD), behavior disorder, urinary incontinence, withdrawal symptoms, trigeminal neuralgia, hearing loss, tinnitus, nerve damage, retinopathy, macular degeneration, vomiting, cerebral edema, pain, bone pain, arthralgia, toothache, cataplexy, and traumatic brain injury (TBI).

Particularly, the compound of the present invention is useful as an agent for the prophylaxis or treatment of narcolepsy, idiopathic hypersomnia, hypersomnia, sleep apnea syndrome, narcolepsy syndrome accompanied by narcolepsy-like symptoms, hypersomnia syndrome accompanied by daytime hypersomnia (e.g., Parkinson's disease, Guillain-Barre syndrome and Kleine Levin syndrome), Alzheimer's disease, obesity, insulin resistance syndrome, cardiac failure, diseases related to bone loss, sepsis, disturbance of consciousness such as coma and the like, side effects and complications due to anesthesia, and the like, or anesthetic antagonist.

While the dose of the compound of the present invention varies depending on the subject of administration, administration route, target disease, symptom and the like, for example, when the compound of the present invention is administered orally or parenterally to an adult patient, its dose is for example, about 0.01 to 100 mg/kg body weight per dose, preferably 0.1 to 50 mg/kg body weight per dose and more preferably 0.5 to 20 mg/kg body weight per dose. This amount is desirably administered in one to 3 portions daily.

The compound of the present invention can be used in combination with other drugs (hereinafter to be abbreviated as concomitant drug).

By combining the compound of the present invention and a concomitant drug, a superior effect, for example, (1) the dose can be reduced as compared to single administration of the compound of the present invention or a concomitant drug,
(2) the drug to be combined with the compound of the present invention can be selected according to the condition of patients (mild case, severe case and the like),
(3) the period of treatment can be set longer by selecting a concomitant drug having different action and mechanism from the compound of the present invention,
(4) a sustained treatment effect can be designed by selecting a concomitant drug having different action and mechanism from the compound of the present invention,
(5) a synergistic effect can be afforded by a combined use of the compound of the present invention and a concomitant drug, and the like, can be achieved.

In the present specification, the compound of the present invention and a concomitant drug used in combination are referred to as the "combination agent of the present invention".

When using the combination agent of the present invention, the administration time of the compound of the present invention and the concomitant drug is not restricted, and the compound of the present invention or a pharmaceutical composition thereof, or the concomitant drug or a pharmaceutical composition thereof can be administered to an administration subject simultaneously, or may be administered at different times. The dosage of the concomitant drug may be determined according to the dose clinically used, and can be appropriately selected depending on an administration subject, administration route, disease, combination and the like.

The administration mode of the combination agent of the present invention and the concomitant drug is not particularly limited, and the compound of the present invention and the concomitant drug only need to be combined on administration. Examples of such administration mode include the following: (1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The dose of the concomitant drug can be appropriately determined based on the dose employed in clinical situations. The mixing ratio of the compound of the present invention and a concomitant drug can be appropriately determined depending on the administration subject, administration route, target disease, symptom, combination and the like.

For example, the content of the compound of the present invention in the combination agent of the present invention differs depending on the form of a preparation, and usually from about 0.01 to about 100 wt %, preferably from about 0.1 to about 50 wt %, further preferably from about 0.5 to about 20 wt %, based on the whole preparation.

The content of the concomitant drug in the combination agent of the present invention differs depending on the form of a preparation, and usually from about 0.01 to about 100 wt %, preferably from about 0.1 to about 50 wt %, further preferably from about 0.5 to about 20 wt %, based on the whole preparation.

The content of additives such as a carrier and the like in the combination agent of the present invention differs depending on the form of a preparation, and usually from about 1 to about 99.99 wt %, preferably from about 10 to about 90 wt %, based on the preparation.

Similar contents may be employed even when the compound of the present invention and a concomitant drug are separately formulated into preparations.

Examples of the concomitant drug include the followings. A therapeutic drug for narcolepsy (e.g., methylphenidate, amphetamine, pemoline, phenelzine, protriptyline, sodium oxybate, modafinil, caffeine), antiobesity drug (amphetamine, benzfetamine, bromocriptine, bupropion, diethylpropion, exenatide, fenfluramine, liothyronine, liraglutide, mazindol, methamphetamine, octreotide, octreotide, orlistat, phendimetrazine, phendimetrazine, phenmetrazine, phentermine, Qnexa (registered trade mark), phenylpropanolamine, pramlintide, propylhexedrine, recombinant leptin, sibutramine, topiramate, zimelidine, zonisamide, Lorcaserin, metformin), acetylcholine esterase inhibitor (e.g., donepezil, rivastigmine, galanthamine, zanapezil, idebenone, tacrine), antidementia agent (e.g., memantine), inhibitor of β amyloid protein production, secretion, accumulation, aggregation and/or deposition, (3 secretase inhibitor (e.g., 6-(4-biphenylyl)methoxy-2-[2-(N,N-dimethylamino)ethyl]tetralin, 6-(4-biphenylyl)methoxy-2-(N,N-dimethylamino)methyltetralin, 6-(4-biphenylyl)methoxy-2-(N,N-dipropylamino)methyltetralin, 2-(N,N-dimethylamino)methyl-6-(4'-methoxybiphenyl-4-yl)methoxytetralin, 6-(4-biphenylyl)methoxy-2-[2-(N,N-diethylamino)ethyl]tetralin, 2-[2-(N,N-dimethylamino)ethyl]-6-(4'-methylbiphenyl-4-yl)methoxytetralin, 2-[2-(N,N-dimethylamino)ethyl]-6-(4'-methoxybiphenyl-4-yl)

methoxytetralin, 6-(2',4'-dimethoxybiphenyl-4-yl)methoxy-2-[2-(N,N-dimethylamino)ethyl]tetralin, 6-[4-(1,3-benzodioxol-5-yl)phenyl]methoxy-2-[2-(N,N-dimethylamino)ethyl]tetralin, 6-(3',4'-dimethoxybiphenyl-4-yl)methoxy-2-[2-(N,N-dimethylamino)ethyl]tetralin, an optically active form thereof, a salt thereof and a hydrate thereof, OM99-2 (WO01/00663)), γ secretase inhibitor, β amyloid protein aggregation inhibitor (e.g., PTI-00703, ALZHEMED (NC-531), PPI-368 (National Publication of International Patent Application No. 11-514333), PPI-558 (National Publication of International Patent Application No. 2001-500852), SKF-74652 (Biochem. J. (1999), 340(1), 283-289)), β amyloid vaccine, β amyloid-degrading enzyme and the like, brain function enhancer (e.g., aniracetam, nicergoline), therapeutic drug for Parkinson's disease [(e.g., dopamine receptor agonist (e.g., L-DOPA, bromocriptine, pergolide, talipexole, pramipexole, cabergoline, amantadine), monoamine oxidase enzyme (MAO) inhibitor (e.g., deprenyl, selegiline, remacemide, riluzole), anticholinergic agent (e.g., trihexyphenidyl, biperiden), COMT inhibitor (e.g., entacapone)], therapeutic drug for amyotrophic lateral sclerosis (e.g., riluzole etc., neurotrophic factor), therapeutic drug for abnormal behavior accompanying progress of dementia, wandering and the like (e.g., sedative, anti-anxiety drug), apoptosis inhibitor (e.g., CPI-1189, IDN-6556, CEP-1347), neuronal differentiation. regenerate promoter (e.g., leteprinim, xaliproden; SR-57746-A), SB-216763, Y-128, VX-853, prosaptide, 5,6-dimethoxy-2-[2,2,4,6,7-pentamethyl-3-(4-methylphenyl)-2,3-dihydro-1-benzofuran-5-yl]isoindoline, 5,6-dimethoxy-2-[3-(4-isopropylphenyl)-2,2,4,6,7-pentamethyl-2,3-dihydro-1-benzofuran-5-yl]isoindoline, 6-[3-(4-isopropylphenyl)-2,2,4,6,7-pentamethyl-2,3-dihydro-1-benzofuran-5-yl]-6,7-dihydro-5H-[1,3]dioxolo[4,5-f]isoindole and an optically active form, salt or hydrate thereof), non-steroidal antiinflammatory agents (meloxicam, tenoxicam, indomethacin, ibuprofen, celecoxib, rofecoxib, aspirin, indomethacin etc.), steroid drug (dexamethasone, hexestrol, cortisone acetate etc.), disease-modifying anti-rheumatic drug (DMARDs), anticytokine drug (e.g., TNF inhibitor, MAP kinase inhibitor), therapeutic agent for incontinence, frequent urination (e.g., flavoxate hydrochloride, oxybutynin hydrochloride, propiverine hydrochloride), phosphodiesterase inhibitor (e.g., sildenafil(citrate)), dopamine agonist (e.g., apomorphine), antiarrhythmic drugs (e.g., mexiletine), sex hormone or a derivative thereof (e.g., progesterone, estradiol, estradiol benzoate), therapeutic agent for osteoporosis (e.g., alfacalcidol, calcitriol, elcatonin, calcitonin salmon, estriol, ipriflavone, pamidronate disodium, alendronate sodium hydrate, incadronate disodium), parathyroid hormone (PTH), calcium receptor antagonists, therapeutic drug for insomnia (e.g., benzodiazepines medicament, non-benzodiazepines medicament, melatonin agonist, orexin receptor antagonists), therapeutic drug for schizophrenia (e.g., typical antipsychotic agents such as haloperidol and the like; atypical antipsychotic agents such as clozapine, olanzapine, risperidone, aripiprazole and the like; medicament acting on metabotropic glutamate receptor or ion channel conjugated-type glutamate receptor; phosphodiesterase inhibitor), benzodiazepines medicament (chlordiazepoxide, diazepam, potassium clorazepate, lorazepam, clonazepam, alprazolam etc.), L-type calcium channel inhibitor (pregabalin etc.), tricyclic or tetracyclic antidepressant (imipramine hydrochloride, amitriptyline hydrochloride, desipramine hydrochloride, clomipramine hydrochloride etc.), selective serotonin reuptake inhibitor (fluvoxamine maleate, fluoxetine hydrochloride, citalopram hydrobromide, sertraline hydrochloride, paroxetine hydrochloride, escitalopram oxalate etc.), serotonin-noradrenaline reuptake inhibitor (venlafaxine hydrochloride, duloxetine hydrochloride, desvenlafaxine hydrochloride etc.), noradrenaline reuptake inhibitor (reboxetine mesylate etc.), mirtazapine, trazodone hydrochloride, nefazodone hydrochloride, bupropion hydrochloride, setiptiline maleate, 5-$HT_{1A}$ agonist, (buspirone hydrochloride, tandospirone citrate, osemozotan hydrochloride etc.), 5-$HT_{2A}$ antagonist, 5-$HT_{2A}$ inverse agonist, 5-$HT_3$ antagonist (cyamemazine etc.), heart non-selective 3 inhibitor (propranolol hydrochloride, oxprenolol hydrochloride etc.), histamine $H_1$ antagonist (hydroxyzine hydrochloride etc.), CRF antagonist, other antianxiety drug (meprobamate etc.), tachykinin antagonist (MK-869, saredutant etc.), medicament that acts on metabotropic glutamate receptor, CCK antagonist, β3 adrenaline antagonist (amibegron hydrochloride etc.), GAT-1 inhibitor (tiagabine hydrochloride etc.), N-type calcium channel inhibitor, carbonic anhydrase II inhibitor, NMDA glycine moiety agonist, NMDA antagonist (memantine etc.), peripheral benzodiazepine receptor agonist, vasopressin antagonist, vasopressin V1b antagonist, vasopressin V1a antagonist, phosphodiesterase inhibitor, opioid antagonist, opioid agonist, uridine, nicotinic acid receptor agonist, thyroid hormone (T3, T4), TSH, TRH, MAO inhibitor (phenelzine sulfate, tranylcypromine sulfate, moclobemide etc.), therapeutic drug for bipolar disorder (lithium carbonate, sodium valproate, lamotrigine, riluzole, felbamate etc.), cannabinoid CB1 antagonist (rimonabant etc.), FAAH inhibitor, sodium channel inhibitor, anti-ADHD drug (methylphenidate hydrochloride, methamphetamine hydrochloride etc.), therapeutic drug for alcoholism, therapeutic drug for autism, therapeutic drug for chronic fatigue syndrome, therapeutic drug for spasm, therapeutic drug for fibromyalgia syndrome, therapeutic drug for headache, therapeutic drug for quitting smoking, therapeutic drug for myasthenia gravis, therapeutic drug for cerebral infarction, therapeutic drug for mania, therapeutic drug for hypersomnia, therapeutic drug for pain, therapeutic drug for dysthymia, therapeutic drug for autonomic ataxia, therapeutic drug for male and female sexual dysfunction, therapeutic drug for migraine, therapeutic drug for pathological gambler, therapeutic drug for restless legs syndrome, therapeutic drug for substance addiction, therapeutic drug for alcohol-related syndrome, therapeutic drug for irritable bowel syndrome, therapeutic drug for lipid abnormality such as cholesterol-lowering drug (statin series (pravastatin sodium, atorvastatin, simvastatin, rosuvastatin etc.), fibrate (clofibrate etc.), squalene synthetase inhibitor), therapeutic drug for abnormal behavior or suppressant of dromomania due to dementia (sedatives, antianxiety drug etc.), therapeutic drug for diabetes, therapeutic agent for diabetic complications, therapeutic drug for hypertension, therapeutic drug for hypotension, diuretic, chemotherapeutic agent, immunotherapeutic agent, antithrombotic agent, anti-cancer agent and the like.

Two or more kinds of the above-mentioned concomitant drug may be used in a mixture at an appropriate ratio.

When the compound of the present invention is applied to each of the above-mentioned diseases, it can also be used in combination with biologics (e.g., antibody drug, nucleic acid or nucleic acid derivative, aptamer drug, vaccine preparation), or can be used in combination with a gene therapy method and the like, or can also be used in combination with a treatment in psychiatric field without using drugs.

Examples of the antibody drug and vaccine preparation include vaccine preparation against angiotensin II, vaccine preparation against CETP, CETP antibody, antibody against TNFα antibody and other cytokines, amyloid β vaccine preparation, vaccine for type 1 diabetes (e.g., DIAPEP-277 of Peptor), anti-HIV antibody and HIV vaccine preparation, as well as antibodies or vaccine preparations against cytokines, renin-angiotensin type enzymes and products thereof, antibodies or vaccine preparations against enzymes or proteins involved in blood lipid metabolism, antibodies or vaccines relating to enzymes and proteins involved in blood coagulation or fibrinolysis system, antibodies or vaccine preparations against proteins involved in sugar metabolism and insulin resistance, and the like. In addition, it can be used in combination with biologics relating to growth factors such as GH, IGF and the like.

Examples of the gene therapy method include a treatment method using gene relating to cytokine, renin-angiotensin type enzyme and product thereof, G protein, G protein conjugated receptor and phosphorylating enzyme thereof, a treatment method using a DNA decoy such as NFκB decoy and the like, a treatment method using antisense, a treatment method using a gene relating to a enzyme or protein involved in blood lipid metabolism (e.g., a gene relating to metabolism, excretion and absorption of cholesterol or triglyceride or HDL-cholesterol or blood phospholipid), a treatment method using a gene relating to a enzyme or protein involved in angiogenesis therapy for peripheral vascular obstruction and the like (e.g., growth factors such as HGF, VEGF etc.), a treatment method using a gene relating to a protein involved in glucose metabolism and insulin resistance, antisense against cytokines such as TNF etc., and the like.

Examples of the treatment method in the psychiatric field without using drug include modified electroconvulsive therapy, deep brain stimulation therapy, repetitive transcranial magnetic stimulation therapy, psychotherapy including cognitive behavioral therapy and the like.

The compound of the present invention can also be used in combination with various organ regeneration methods such as cardiac regeneration, renal regeneration, pancreatic regeneration, revascularization and the like, cell transplantation therapy utilizing bone marrow cells (bone marrow-derived mononuclear cell, myelogenic stem cell), or artificial organ utilizing tissue engineering (e.g., artificial blood vessel, cardiomyocyte sheet).

EXAMPLES

The present invention is explained in detail in the following by referring to Examples, Experimental Examples and Formulation Examples. However, the examples do not limit the present invention and the examples can be modified within the scope of the present invention.

The "room temperature" in the following Examples is generally about 10° C. to about 35° C. The ratio for mixed solvent is, unless otherwise specified, a volume mixing ratio and % means wt % unless otherwise specified.

The elution by column chromatography in the Examples was performed under the observation by TLC (Thin Layer Chromatography) unless otherwise specified. In the observation by TLC, 60 $F_{254}$ manufactured by Merck was used as a TLC plate, the solvent used as an elution solvent in column chromatography was used as an eluent, and UV detector was used for the detection. In silica gel column chromatography, the indication of NH means use of aminopropylsilane-bonded silica gel and the indication of Diol means use of 3-(2,3-dihydroxypropoxy)propylsilane-bonded silica gel. In preparative HPLC (high performance liquid chromatography), the indication of C18 means use of octadecyl-bonded silica gel. The ratio for elution solvent is, unless otherwise specified, a volume mixing ratio.

$^1$H NMR was measured by Fourier transform NMR. For the analysis of $^1$H NMR, ACD/SpecManager (trade name) software and the like were used. Peaks of a hydroxyl group, an amino group and the like, having very mild proton peak, are not sometimes described.

MS was measured by LC/MS. As the ionization method, ESI method, or APCI method was used. The data indicates actual measured value (found). While molecular ion peak is generally observed, a fragment ion is sometimes observed. In the case of a salt, a molecular ion peak or fragment ion peak of free form is generally observed.

The unit of sample concentration (c) for optical rotation ($[\alpha]_D$) is g/100 mL.

Elemental analysis value (Anal.) is described as calculated value (Calcd) and actual measured value (Found).

In Example, the cis/trans expression contained in compound name basically means a cis or trans mixture of two kinds of optical isomers when the corresponding partial structure contains two asymmetric centers. Exceptionally, the cis/trans expression means a single optical isomer when indicated as "optional active".

Peaks by powder X-ray diffraction in the Examples mean peaks measured at room temperature by using Ultima IV (Rigaku Corporation, Japan) using Cu Kα radiation as a radiation source. The measurement conditions are as follows.

Electric pressure/Electric current: 40 kV/50 mA
Scan speed: 6 degrees/min
Scan range of 2 Theta: 2-35 degrees
The crystallinity by powder X-ray diffraction in the Examples was calculated by the Hermans method.

In the following Examples, the following abbreviations are used.

mp: melting point
MS: mass spectrum
M: mol concentration
N: normality
$CDCl_3$: deuterochloroform
DMSO-$d_6$: deuterodimethyl sulfoxide
$^1$H NMR: proton nuclear magnetic resonance
LC/MS: liquid chromatograph mass spectrometer
ESI: electrospray ionization, Electron Spray Ionization
APCI: atomospheric pressure chemical ionization, atmospheric pressure chemical ionization
$Pd_2(dba)_3$: tris(dibenzylideneacetone)dipalladium(0)
TFA: trifluoroacetic acid
DIPEA: N-ethyl-N-isopropylpropan-2-amine
DMF: N,N-dimethylformamide
THF: tetrahydrofuran
$CH_3CN$: acetonitrile
DME: 1,2-dimethoxyethane
MeOH: methanol
EtOH: ethanol
t-AmOH: 2-methyl-2-butanol
$Pd(PPh_3)_4$: palladium-triphenylphosphine (1:4)
tBuXphos: 2-di-tert-butylphosphino-2',4',6'-triisopropylbiphenyl
XPhos Pd G3: (2-dicyclohexylphosphino-2',4',6'-triisopropyl-1,1'-biphenyl) [2-(2'-amino-1,1'-biphenyl)]palladium(II) methanesulfonate
$PPh_3$: triphenylphosphine
AcOH: acetic acid
TBAI: tetrabutylammonium iodide
TEA: triethylamine ($A-taPhos)_2PdCl_2$: 4-(di-tert-butylphosphino)-N,N-dimethylaniline-dichloropalladium (2:1)

T3P: 2,4,6-tripropyl-1,3,5,2,4,6-trioxatriphosphinane 2,4,6-trioxide

HATU: O-(7-azabenzotriazol-1-yl)-N,N,N',N'-tetramethyluronium hexafluorophosphate DMAP: N,N-dimethyl-4-aminopyridine CPME: methoxycyclopentane tBu: tert-butyl Boc: tert-butoxycarbonyl Example 1 cis-2-(3-benzylbenzyl)-N-ethyl-3-((methylsulfonyl)amino)piperidine-1-carboxamide A) 1-benzyl-3-bromobenzene A mixture of (chloromethyl)benzene (3.78 g), (3-bromophenyl)boronic acid (6.00 g), $Pd(PPh_3)_4$ (1.73 g), sodium carbonate (3.16 g), DME (60 mL) and water (30 mL) was stirred at 100° C. for 15 hr. The reaction mixture was added to water, and the mixture was extracted with ethyl acetate. The organic layer was separated, washed with saturated brine, dried over anhydrous sodium sulfate, and concentrated under reduced pressure. The residue was purified by silica gel column chromatography (petroleum ether) to give the title compound (4.50 g).

$^1H$ NMR (400 MHz, $CDCl_3$) δ3.94 (2H, s), 7.10-7.25 (5H, m), 7.28-7.40 (4H, m).

B) (3-benzylphenyl) (3-bromopyridin-2-yl)methanol

To a mixture of magnesium (147 mg) and THF (10 mL) were added iodine (catalytic amount) and 1-benzyl-3-bromobenzene (1.49 g). The mixture was heated under reflux for 1 hr, and cooled to 20° C. To the mixture was added 3-bromopyridine-2-carbaldehyde (750 mg), and the mixture was stirred under nitrogen atmosphere at 20° C. for 15 hr. The reaction mixture was added to saturated aqueous ammonium chloride solution, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/petroleum ether) to give the title compound (900 mg).

1H NMR (400 MHz, $CDCl_3$) δ 3.97 (2H, s), 5.23 (1H, d, J=6.8 Hz), 5.94 (1H, d, J=5.2 Hz), 7.03-7.08 (1H, m), 7.10-7.31 (9H, m), 7.83-7.90 (1H, m), 8.59 (1H, dd, J=4.4, 1.2 Hz).

C) 2-(3-benzylbenzyl)-3-bromopyridine

To a mixture of (3-benzylphenyl) (3-bromopyridin-2-yl)methanol (900 mg) and TFA (5 mL) was added triethylsilane (10 mL). The mixture was stirred at 60° C. for 40 hr, and the reaction mixture was concentrated under reduced pressure. The obtained residue was basified to pH7 to 8 with saturated aqueous sodium hydrogencarbonate solution, and the mixture was extracted with ethyl acetate. The organic layer was washed with saturated brine, dried over anhydrous sodium sulfate, and concentrated under reduced pressure. The residue was purified by silica gel column chromatography (ethyl acetate/petroleum ether) to give the title compound (1.10 g).

$^1H$ NMR (400 MHz, $CDCl_3$) δ3.95 (2H, s), 4.32 (2H, s), 7.00-7.08 (2H, m), 7.10-7.23 (6H, m), 7.25-7.30 (2H, m), 8.83 (1H, dd, J=8.0, 1.6 Hz), 8.50 (1H, dd, J=4.8, 1.6 Hz).

D) N-(2-(3-benzylbenzyl)pyridin-3-yl)methanesulfonamide

A mixture of 2-(3-benzylbenzyl)-3-bromopyridine (1.10 g), methanesulfonamide (464 mg), tBuXphos (166 mg), $Pd_2(dba)_3$ (149 mg), cesium carbonate (1.59 g) and DME (20 mL) was stirred under nitrogen atmosphere at 85° C. for 15 hr. The reaction mixture was added to water, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/petroleum ether) to give the title compound (260 mg).

$^1H$ NMR (400 MHz, $CDCl_3$) δ2.39 (3H, s), 3.93 (2H, s), 4.22 (2H, s), 6.21 (1H, brs), 7.00-7.35 (10H, m), 8.87 (1H, d, J=7.2 Hz), 8.44 (1H, d, J=3.6 Hz).

E) N-(cis-2-(3-benzylbenzyl)piperidin-3-yl)methanesulfonamide

A mixture of N-(2-(3-benzylbenzyl)pyridin-3-yl)methanesulfonamide (200 mg), 5% rhodium on carbon (350 mg), THF (9 mL) and AcOH (1 mL) was stirred under hydrogen atmosphere of 35 psi at 20° C. for 15 hr. The reaction mixture was filtered, and the filtrate was added to water. The mixture was neutralized with saturated aqueous sodium hydrogencarbonate solution, and extracted with ethyl acetate. The organic layer was separated, washed with saturated brine, dried over anhydrous sodium sulfate, and concentrated under reduced pressure. The residue was purified by silica gel column chromatography (dichloromethane/methanol) and preparative thin layer chromatography to give the title compound (30 mg).

MS: $[M+H]^+$ 359.0.

F) cis-2-(3-benzylbenzyl)-N-ethyl-3-((methylsulfonyl)amino)piperidine-1-carboxamide A mixture of N-(cis-2-(3-benzylbenzyl)piperidin-3-yl)methanesulfonamide (30 mg), TEA (25 mg) and isocyanatoethane (8 mg) in THE (5 mL) was stirred at 20° C. for 15 hr. The reaction mixture was added to water, and the mixture was extracted with ethyl acetate. The organic layer was washed with saturated brine, dried over anhydrous sodium sulfate, and concentrated under reduced pressure. The residue was purified by preparative HPLC (Fuji C18 (300×25), YMC 250×20, mobile phase: water/acetonitrile (0.1% aqueous ammonia solution)). The obtained fraction was concentrated under reduced pressure, and freeze-dried to give the title compound (6 mg).

$^1H$ NMR (400 MHz, $CDCl_3$) δ 0.72 (3H, t, J=7.2 Hz), 1.60-1.90 (4H, m), 2.75-3.00 (8H, m), 3.50-3.60 (2H, m), 3.93 (2H, s), 4.05-4.15 (1H, m), 4.22-4.32 (1H, m), 4.59 (1H, d, J=7.2 Hz), 7.03-7.08 (3H, m), 7.15-7.35 (6H, m).

Example 19 tert-butyl cis-2-(biphenyl-3-ylmethyl)-3-((methylsulfonyl)amino)piperidine-1-carboxylate A) tert-butyl 2-(biphenyl-3-ylmethyl)-3-oxopiperidine-1-carboxylate To a mixture of tert-butyl 3-oxopiperidine-1-carboxylate (3.49 g) and toluene (38 mL) was added pyrrolidine (1.87 g) at room temperature. The mixture was stirred at room temperature for 30 min, heated under reflux for 1 hr using Dean-Stark apparatus, and concentrated under reduced pressure. The obtained residue was mixed with $CH_3CN$ (38 mL), and 3-(bromomethyl)biphenyl (5.19 g) was added thereto at room temperature. The mixture was heated under reflux for 1 hr, and the reaction mixture was poured into water, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (3.42 g).

MS: $[M+H-(tBu)]^+$310.2.

B) tert-butyl cis-3-amino-2-(biphenyl-3-ylmethyl) piperidine-1-carboxylate

To a mixture of tert-butyl 2-(biphenyl-3-ylmethyl)-3-oxopiperidine-1-carboxylate (3.41 g), THF (25 mL) and MeOH (25 mL) was added ammonium acetate (7.19 g) at room temperature. The mixture was stirred at room temperature for 1 hr, and sodium triacetoxyborohydride (3.56 g) was added thereto. The mixture was stirred at room temperature for 18 hr. The reaction mixture was poured into saturated aqueous sodium hydrogencarbonate solution at 0° C., and the mixture was extracted with ethyl acetate. The organic layer was separated, washed with water and saturated brine, dried over anhydrous magnesium sulfate, and concentrated under reduced pressure. The residue was purified by silica gel column chromatography (methanol/ethyl acetate) to give the title compound (1.67 g).

MS: $[M+H]^+$ 367.2.

C) tert-butyl cis-2-(biphenyl-3-ylmethyl)-3-((methylsulfonyl)amino)piperidine-1-carboxylate To a mixture of tert-butyl cis-3-amino-2-(biphenyl-3-ylmethyl)piperidine-1-carboxylate (1.66 g), THF (15 mL) and TEA (0.917 g) was added methanesulfonyl chloride (0.623 g) at 0° C. The mixture was stirred at room temperature for 1 hr, poured into ice water, and extracted with ethyl acetate. The organic layer was separated, washed with aqueous sodium hydrogencarbonate solution and saturated brine, dried over anhydrous magnesium sulfate, and concentrated under reduced pressure. The residue was purified by silica gel column chromatography (ethyl acetate/hexane) to give the title compound (1.75 g).

$^1H$ NMR (300 MHz, $CDCl_3$) δ 1.11 (9H, s), 1.61-1.74 (2H, m), 1.75-1.84 (1H, m), 1.88-1.97 (1H, m), 2.83-2.98 (3H, m), 3.00 (3H, s), 3.57-3.68 (1H, m), 4.04-4.12 (1H, m), 4.41 (1H, d, J=7.9 Hz), 4.73-4.83 (1H, m), 7.17 (1H, d, J=7.2 Hz), 7.30-7.39 (3H, m), 7.39-7.46 (3H, m), 7.52-7.58 (2H, m).

Example 24 methyl cis-2-(3-iodobenzyl)-3-((methylsulfonyl) amino)piperidine-1-carboxylate

A) tert-butyl 2-(3-iodobenzyl)-3-oxopiperidine-1-carboxylate

To a mixture of tert-butyl 3-oxopiperidine-1-carboxylate (10 g) and toluene (100 mL) was added pyrrolidine (4.28 g) at room temperature. The mixture was stirred at room temperature for 30 min, and concentrated under reduced pressure. The residue was mixed with $CH_3CN$ (100 mL), and 1-(bromomethyl)-3-iodobenzene (17.9 g) was added to the mixture. The mixture was stirred overnight at 80° C., and the reaction mixture was concentrated under reduced pressure. The residue was dissolved in ethyl acetate and 1M hydrochloric acid, and the solution was stirred for 30 min, and extracted with ethyl acetate. The separated organic layer was washed with saturated brine, dried over anhydrous magnesium sulfate, and concentrated under reduced pressure. The residue was purified by silica gel column chromatography (ethyl acetate/hexane) to give the title compound (14.7 g).

MS: $[M+H-Boc]^+$ 316.0.

B) tert-butyl cis-3-amino-2-(3-iodobenzyl)piperidine-1-carboxylate

To a mixture of tert-butyl 2-(3-iodobenzyl)-3-oxopiperidine-1-carboxylate (3.9 g), MeOH (40 mL) and THE (40 mL) was added ammonium acetate (7.24 g) at room temperature. The mixture was stirred at room temperature for 1 hr, sodium triacetaxyborohydride (3.58 g) was added thereto, and the mixture was stirred at room temperature for 18 hr. The reaction mixture was added to saturated aqueous sodium hydrogencarbonate solution under ice-cooling, and the mixture was extracted with ethyl acetate. The separated organic layer washed with water and saturated brine, dried over anhydrous magnesium sulfate, and concentrated under reduced pressure. The residue was purified by silica gel column chromatography (NH, ethyl acetate/hexane) to give the title compound (2.14 g).

MS: $[M+H]^+$ 417.1.

C) tert-butyl cis-2-(3-iodobenzyl)-3-((methylsulfonyl)amino)piperidine-1-carboxylate To a mixture of tert-butyl cis-3-amino-2-(3-iodobenzyl) piperidine-1-carboxylate (2.00 g) and THE (20 mL) were added TEA (0.972 g) and methanesulfonyl chloride (0.660 g) at 0° C. The mixture was stirred at room temperature for 1 hr. To the mixture was added saturated aqueous sodium hydrogencarbonate solution, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (1.66 g).

MS: $[M-H]^-$ 493.1.

D) N-(cis-2-(3-iodobenzyl)piperidin-3-yl)methanesulfonamide hydrochloride

To a mixture of tert-butyl cis-2-(3-iodobenzyl)-3-((methylsulfonyl)amino)piperidine-1-carboxylate (1.66 g) and THE (8 mL) was added 4M hydrogen chloride/ethyl acetate solution (8.39 mL) at room temperature. The mixture was stirred overnight at room temperature, and concentrated under reduced pressure. The residue was suspended in ethyl acetate, and the solid was collected by filtration. The obtained solid was washed with ethyl acetate to give the title compound (1.29 g).

MS: $[M+H]^+$ 395.0.

E) methyl cis-2-(3-iodobenzyl)-3-((methylsulfonyl) amino)piperidine-1-carboxylate To a mixture of N-(cis-2-(3-iodobenzyl)piperidin-3-yl) methanesulfonamide hydrochloride (1.3 g), TEA (1.22 g)

and THF (20 mL) was added methyl carbonochloridate (0.570 g) at room temperature. The mixture was stirred at room temperature for 10 min, and concentrated under reduced pressure. The residue was purified by silica gel column chromatography (ethyl acetate/hexane) to give the title compound (1.30 g).

$^1$H NMR (300 MHz, DMSO-$d_6$) δ 1.35-1.56 (1H, m), 1.59-1.76 (3H, m), 2.78-2.87 (2H, m), 2.89-3.04 (4H, m), 3.05-3.23 (2H, m), 3.33-3.52 (2H, m), 3.67-3.87 (1H, m), 4.37-4.65 (1H, m), 7.00-7.10 (1H, m), 7.12-7.21 (1H, m), 7.34 (1H, s), 7.48-7.56 (2H, m).

Example 27 methyl cis-3-((methylsulfonyl)amino)-2-(3-(pyrrolidin-1-yl)benzyl)piperidine-1-carboxylate A mixture of methyl cis-2-(3-iodobenzyl)-3-((methylsulfonyl)amino)piperidine-1-carboxylate (40 mg), pyrrolidine (12.6 mg), $Pd_2(dba)_3$ (8.10 mg), dicyclohexyl(2',6'-diisopropoxybiphenyl-2-yl)phosphine (12.4 mg), cesium carbonate (86 mg) and t-AmOH (1 mL) was subjected to microwave irradiation at 100° C. for 1 hr. The mixture was poured into water, and extracted with ethyl acetate. The organic layer was separated, washed with saturated brine, dried over anhydrous magnesium sulfate, and concentrated under reduced pressure. The residue was purified by silica gel column chromatography (NH, ethyl acetate/hexane) to give the title compound (19.0 mg).

$^1$H NMR (300 MHz, DMSO-$d_6$) δ 1.32-1.57 (1H, m), 1.61-1.76 (3H, m), 1.86-1.99 (4H, m), 2.68-2.84 (2H, m), 2.90-3.03 (4H, m), 3.08-3.23 (5H, m), 3.34-3.52 (2H, m), 3.61-3.89 (1H, m), 4.39-4.71 (1H, m), 6.23-6.47 (3H, m), 6.92-7.06 (1H, m), 7.28-7.40 (1H, m).

Example 64 isopropyl cis-3-((methylsulfonyl)amino)-2-((6-phenylpyridin-2-yl)methyl)piperidine-1-carboxylate

A) (6-phenylpyridin-2-yl)methanol

A mixture of (6-bromopyridin-2-yl)methanol (5.10 g), phenylboronic acid (4.96 g), $Pd(PPh_3)_4$ (1.25 g), 2M aqueous sodium carbonate solution (33.9 mL) and DME (55 mL) was heated under reflux for 15 hr under argon atmosphere. The reaction mixture was poured into water, and the mixture was extracted with ethyl acetate-THF. The insoluble substance was removed by filtration, and the organic layer was separated, washed with water and saturated brine, dried over anhydrous magnesium sulfate, and concentrated under reduced pressure. The residue was purified by silica gel column chromatography (ethyl acetate/hexane) and silica gel column chromatography (NH, ethyl acetate/hexane) to give the title compound (3.76 g).

MS: $[M+H]^+$ 186.1.

B) 2-(bromomethyl)-6-phenylpyridine

To a mixture of (6-phenylpyridin-2-yl)methanol (3.74 g), $PPh_3$ (6.36 g) and benzotrifluoride (150 mL) was added tetrabromomethane (8.04 g) at 0° C. The mixture was stirred at 0° C. for 3 hr, and the insoluble substance was removed by filtration, and washed with ethyl acetate. The filtrate was concentrated under reduced pressure. The residue was purified by silica gel column chromatography (ethyl acetate/hexane) to give the title compound (4.03 g).

MS: $[M+H]^+$ 248.0.

C) tert-butyl 3-oxo-2-((6-phenylpyridin-2-yl)methyl)piperidine-1-carboxylate To a mixture of tert-butyl 3-oxopiperidine-1-carboxylate (2.69 g) and toluene (29 mL) was added pyrrolidine (1.44 g) at room temperature. The mixture was stirred at room temperature for 30 min, heated under reflux for 1 hr using Dean-Stark apparatus, and concentrated under reduced pressure. The residue was mixed with $CH_3CN$ (29 mL), and 2-(bromomethyl)-6-phenylpyridine (4.02 g) was added to the mixture at room temperature. The mixture was stirred at room temperature for 15 hr, and the reaction mixture was poured into water, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (2.56 g).

MS: $[M+H]^+$ 367.2.

D) tert-butyl cis-3-amino-2-((6-phenylpyridin-2-yl)methyl)piperidine-1-carboxylate To a mixture of tert-butyl 3-oxo-2-((6-phenylpyridin-2-yl)methyl)piperidine-1-carboxylate (2.55 g), MeOH (19 mL) and THF (19 mL) was added ammonium acetate (5.36 g) at room temperature. The mixture was stirred at room temperature for 1 hr, and sodium triacetoxyborohydride (2.65 g) was added thereto. The mixture was stirred at room temperature for 3 hr. The reaction mixture was poured into saturated aqueous sodium hydrogencarbonate solution under ice-cooling, and the mixture was extracted with ethyl acetate. The organic layer was separated, washed with water and saturated brine, dried over anhydrous magnesium sulfate, and concentrated under reduced pressure. The residue was purified by silica gel column chromatography (methanol/ethyl acetate) to give the title compound (977 mg).

MS: $[M+H]^+$ 368.2.

E) tert-butyl cis-3-((methylsulfonyl)amino)-2-((6-phenylpyridin-2-yl)methyl)piperidine-1-carboxylate To a mixture of tert-butyl cis-3-amino-2-((6-phenylpyridin-2-yl)methyl)piperidine-1-carboxylate (973 mg), TEA (536 mg) and THE (9 mL) was added methanesulfonyl chloride (364 mg) at 0° C. The mixture was stirred at room temperature for 1 hr, and the reaction mixture was poured into ice water, and the mixture was extracted with ethyl acetate. The organic layer was separated, washed with aqueous sodium hydrogencarbonate solution and saturated brine, dried over anhydrous magnesium sulfate, and concentrated under reduced pressure. The residue was purified by silica gel column chromatography (ethyl acetate/hexane) to give the title compound (1.05 g).

MS: $[M+H]^+$ 446.2.

F) N-(cis-2-((6-phenylpyridin-2-yl)methyl)piperidin-3-yl)methanesulfonamide To a mixture of tert-butyl cis-3-((methylsulfonyl)amino)-2-((6-phenylpyridin-2-yl)methyl)piperidine-1-carboxylate (991 mg) and toluene (11 mL) was added TFA (11 mL) at room temperature. The mixture was stirred at room temperature for 1 hr, and the reaction mixture was poured into saturated aqueous sodium hydrogencarbonate solution under ice-cooling. The mixture was basified to pH=8 with potassium carbonate, and extracted with ethyl acetate/THF. The organic layer was separated, washed with water and saturated brine, dried over anhydrous magnesium sulfate, and concentrated under reduced pressure. The obtained solid was collected by filtration, and washed with diisopropyl ether to give the title compound (671 mg).

MS: $[M+H]^+$ 346.1.

G) isopropyl cis-3-((methylsulfonyl)amino)-2-((6-phenylpyridin-2-yl)methyl)piperidine-1-carboxylate To a mixture of N-(cis-2-((6-phenylpyridin-2-yl)methyl)piperidin-3-yl)methanesulfonamide (150 mg) and THF (2.17 mL) were added TEA (132 mg) and isopropyl carbonochloridate (0.326 mL) at room temperature. The mixture was stirred at room temperature for 1 hr, and the reaction mixture was poured into water, and the mixture was extracted with ethyl acetate. The organic layer was separated, dried over anhydrous sodium sulfate, and concentrated under reduced pressure. The residue was purified by silica gel column chromatography (ethyl acetate/hexane) to give the title compound (157 mg).

$^1$H NMR (300 MHz, $CDCl_3$) δ 1.12 (6H, d, J=6.4 Hz), 1.75 (4H, brs), 2.05-2.19 (1H, m), 2.67-2.90 (3H, m), 2.88-3.06 (2H, m), 3.35 (1H, dd, J=13.9, 5.7 Hz), 3.53-3.68 (1H, m), 3.96-4.14 (1H, m), 4.84 (2H, d, J=5.7 Hz), 7.14-7.22 (1H, m), 7.38-7.52 (3H, m), 7.55-7.59 (1H, m), 7.66-7.74 (1H, m), 7.90-7.98 (2H, m).

Example 75 ethyl cis-2-(biphenyl-3-ylmethyl)-3-((methylsulfonyl)amino)pyrrolidine-1-carboxylate A) tert-butyl 2-(biphenyl-3-ylmethyl)-3-oxopyrrolidine-1-carboxylate To a mixture of tert-butyl 3-oxopyrrolidine-1-carboxylate (3.5 g) and toluene (30 mL) was added pyrrolidine (1.61 g) at room temperature. The mixture was stirred at 100° C. for 3 hr, and concentrated. $CH_3CN$ (30 mL) and 3-(bromomethyl)biphenyl (4.67 g) were added thereto at room temperature. The mixture was stirred overnight under nitrogen atmosphere at 80° C., and concentrated. The obtained residue was diluted with water, and the mixture was extracted with ethyl acetate. The organic layer was dried over anhydrous magnesium sulfate, and concentrated under reduced pressure. The residue was purified by silica gel column chromatography (ethyl acetate/hexane) to give the title compound (2.92 g).

MS: $[M+H-Boc]^+$ 252.2.

B) tert-butyl cis-2-(biphenyl-3-ylmethyl)-3-((1-phenylethyl)amino)pyrrolidine-1-carboxylate A mixture of tert-butyl 2-(biphenyl-3-ylmethyl)-3-oxopyrrolidine-1-carboxylate (2.38 g), 1-phenylethanamine (0.903 g), ytterbium(3+) tris(trifluoromethanesulfonate) (0.420 g) and toluene (20 mL) was stirred at 100° C. for 4 hr. The reaction mixture was partitioned between ethyl acetate-water, and the organic layer was washed with saturated brine, and concentrated under reduced pressure. To a mixture of the obtained residue (3.08 g), $CH_3CN$ (30 mL) and AcOH (5 mL) was added sodium triacetoxyborohydride (4.30 g) at 0° C. The mixture was stirred at room temperature for 1 hr, and neutralized with 4M aqueous sodium hydroxide solution. The obtained mixture was partitioned between ethyl acetate-aqueous sodium hydrogencarbonate solution, and the organic layer was washed with saturated brine, and concentrated under reduced pressure. The residue was purified by silica gel column chromatography (NH, ethyl acetate/hexane) to give the title compound (2.29 g).

MS: $[M+H]^+$ 457.3.

C) tert-butyl cis-3-amino-2-(biphenyl-3-ylmethyl)pyrrolidine-1-carboxylate

A mixture of tert-butyl cis-2-(biphenyl-3-ylmethyl)-3-((1-phenylethyl)amino)pyrrolidine-1-carboxylate (2.29 g), 20% palladium hydroxide on carbon (3.52 g), 1M hydrochloric acid (10.0 mL) and MeOH (50 mL) was stirred overnight under normal hydrogen atmosphere at room temperature. The catalyst was removed by filtration, and the filtrate was concentrated under reduced pressure. The residue was purified by silica gel column chromatography (NH, ethyl acetate/hexane) to give the title compound (865 mg).

MS, found: 297.2.

D) tert-butyl cis-2-(biphenyl-3-ylmethyl)-3-((methylsulfonyl)amino)pyrrolidine-1-carboxylate To a mixture of tert-butyl cis-3-amino-2-(biphenyl-3-ylmethyl)pyrrolidine-1-carboxylate (865 mg), TEA (497 mg) and THF (50 mL) was added methanesulfonyl chloride (337 mg) at 0° C. The mixture was stirred at room temperature for 1 hr, poured into ice water, and extracted with ethyl acetate. The organic layer was separated, washed with saturated aqueous sodium hydrogencarbonate solution and saturated brine, dried over anhydrous magnesium sulfate, and concentrated under reduced pressure. The residue was purified by silica gel column chromatography (ethyl acetate/hexane) to give the title compound (750 mg).

MS: $[M-H]^-$ 429.2.

E) N-(cis-2-(biphenyl-3-ylmethyl)pyrrolidin-3-yl)methanesulfonamide hydrochloride A mixture of tert-butyl cis-2-(biphenyl-3-ylmethyl)-3-((methylsulfonyl)amino)pyrrolidine-1-carboxylate (750 mg) and 4M hydrogen chloride/ethyl acetate solution (20 mL) was stirred at room temperature for 3 days. The precipitate was collected by filtration to give the title compound (500 mg).

MS: $[M+H]^+$ 331.1.

F) ethyl cis-2-(biphenyl-3-ylmethyl)-3-((methylsulfonyl)amino)pyrrolidine-1-carboxylate To a mixture of N-(cis-2-(biphenyl-3-ylmethyl)pyrrolidin-3-yl)methanesulfonamide hydrochloride (40 mg), TEA (33.1 mg) and THE (3 mL) was added ethyl carbonochloridate (23.7 mg) at room temperature. The mixture was stirred at room temperature for 30 min, the reaction solution was poured into saturated aqueous sodium hydrogencarbonate solution at room temperature, and the mixture was extracted with ethyl acetate. The organic layer was separated, washed with saturated brine, dried over anhydrous magnesium sulfate, and concentrated under reduced pressure. The obtained solid was crystallized from ethyl acetate-heptane to give the title compound (32.0 mg).

$^1$H NMR (300 MHz, DMSO-$d_6$) δ 0.64-1.23 (3H, m), 1.72-2.25 (2H, m), 2.60-3.48 (8H, m), 3.54-4.25 (3H, m), 7.11-7.69 (10H, m).

Example 76

Optically active isopropyl cis-3-((methylsulfonyl) amino)-2-((6-phenylpyridin-2-yl)methyl)piperidine-1-carboxylate A racemate (120 mg) of isopropyl cis-3-((methylsulfonyl) amino)-2-((6-phenylpyridin-2-yl)methyl)piperidine-1-carboxylate was resolved by HPLC (column: CHIRALPAK AD-H(UG065), 4.6 mmID×250 mmL, Manufactured by Daicel Chemical Industries, mobile phase: hexane/2-propanol=700/300) to give the title compound (49.4 mg) having a shorter retention time. The title compound was purified by HPLC (C18, mobile phase: water/acetonitrile (containing 0.1% TFA)), and to the obtained fraction was added saturated aqueous sodium hydrogencarbonate solution, and the mixture was extracted with ethyl acetate. The extract was dried over anhydrous magnesium sulfate, and concentrated under reduced pressure to give the title compound (43.0 mg).

$^1$H NMR (300 MHz, DMSO-$d_6$) δ0.47 (2H, brs), 0.64-1.12 (4H, m)), 1.48 (1H, brs), 1.74 (3H, brs), 2.93-3.24 (6H, m), 3.43 (1H, d, J=6.1 Hz), 3.86 (1H, brs), 4.31 (1H, brs), 4.76 (1H, brs), 7.11-7.22 (1H, m), 7.34-7.54 (4H, m), 7.73 (2H, brs), 8.00-8.11 (2H, m).

Example 81

N-(cis-2-(biphenyl-3-ylmethyl)pyrrolidin-3-yl)methanesulfonamide

A mixture of tert-butyl cis-2-(biphenyl-3-ylmethyl)-3-((methylsulfonyl)amino)pyrrolidine-1-carboxylate (0.950 g), TFA (3.08 g) and dichloromethane (10 mL) was stirred under nitrogen atmosphere at 15° C. for 2 hr. The reaction solution was neutralized (pH=7) with saturated aqueous sodium hydrogencarbonate solution. The aqueous layer was extracted with dichloromethane, and the combined organic layers were washed with saturated brine, dried over anhydrous sodium sulfate, and concentrated under reduced pressure. The residue was purified by silica gel column chromatography (EtOH/ethyl acetate) to give the title compound (0.378 g).

$^1$H NMR (400 MHz, $CDCl_3$) δ 1.85-1.96 (1H, m), 2.22-2.34 (1H, m), 2.74-2.86 (2H, m), 2.94 (3H, s), 3.00-3.15 (2H, m), 3.25-3.33 (1H, m), 3.90-3.96 (1H, m), 7.18-7.25 (1H, m), 7.30-7.48 (6H, m), 7.54-7.63 (2H, m).

Example 88 tert-butyl cis-3-((methylsulfonyl)amino)-2-((2-phenyl-1,3-thiazol-4-yl)methyl)piperidine-1-carboxylate A) 4-(chloromethyl)-2-phenyl-1,3-thiazole A mixture of benzenecarbothioamide (6.86 g), 1,3-dichloroacetone (6.35 g) and toluene (50 mL) was heated under reflux for 3 hr. The reaction mixture was cooled, and water was added thereto. The mixture was extracted with ethyl acetate, and the extract was washed with water and saturated brine, dried over anhydrous sodium sulfate, and concentrated under reduced pressure. The residue was purified by silica gel column chromatography (ethyl acetate/hexane) to give the title compound (9.77 g).

MS: $[M+H]^-$ 210.1.

B) tert-butyl 3-oxo-2-((2-phenyl-1,3-thiazol-4-yl) methyl)piperidine-1-carboxylate To a mixture of tert-butyl 3-oxopiperidine-1-carboxylate (0.950 g) and toluene (10 mL) was added pyrrolidine (0.509 g) at room temperature. The mixture was stirred at room temperature for 30 min, and concentrated. The residue was mixed with $CH_3CN$ (10 mL), and 4-(chloromethyl)-2-phenyl-1,3-thiazole (1 g) and TBAI (0.352 g) were added to the mixture at room temperature. The mixture was stirred overnight at 80° C., and the reaction mixture was concentrated. The obtained residue was partitioned between ethyl acetate-water, and extracted with ethyl acetate. The organic layer was washed with saturated brine, dried over anhydrous magnesium sulfate, and concentrated under reduced pressure. The residue was purified by silica gel column chromatography (ethyl acetate/hexane) to give the title compound (0.580 g).

MS: $[M+H]^+$ 373.1.

C) tert-butyl cis-3-amino-2-((2-phenyl-1,3-thiazol-4-yl)methyl)piperidine-1-carboxylate To a mixture of tert-butyl 3-oxo-2-((2-phenyl-1,3-thiazol-4-yl)methyl)piperidine-1-carboxylate (580 mg), ammonium acetate (1200 mg), MeOH (5 mL) and THF (5 mL) was added sodium triacetoxyborohydride (495 mg) at room temperature. The mixture was stirred overnight at room temperature, and concentrated. The obtained residue was mixed with saturated aqueous sodium hydrogencarbonate solution, and the mixture was extracted with ethyl acetate. The organic layer was washed with saturated brine, dried over anhydrous magnesium sulfate, and concentrated under reduced pressure. The residue was purified by silica gel column chromatography (methanol/ethyl acetate) to give the title compound (213 mg).

MS: $[M+H]^+$ 374.2.

D) tert-butyl cis-3-((methylsulfonyl)amino)-2-((2-phenyl-1,3-thiazol-4-yl)methyl)piperidine-1-carboxylate To a mixture of tert-butyl cis-3-amino-2-((2-phenyl-1,3-thiazol-4-yl)methyl)piperidine-1-carboxylate (212 mg), TEA (86 mg) and THE (5 mL) was added methanesulfonic anhydride (119 mg) at room temperature. The mixture was stirred at room temperature for 10 min, and the reaction mixture was concentrated. The residue was purified by silica gel column chromatography (ethyl acetate/hexane) to give the title compound (212 mg).

$^1$H NMR (300 MHz, $CDCl_3$) δ 1.33 (9H, s), 1.58-1.83 (3H, m), 2.00-2.11 (1H, m), 2.75-3.07 (5H, m), 3.27 (1H, dd, J=14.4, 6.1 Hz), 3.54-3.69 (1H, m), 4.01 (1H, d, J=11.4 Hz), 4.75 (1H, q, J=5.8 Hz), 6.14 (1H, brs), 7.01 (1H, s), 7.39-7.49 (3H, m), 7.86-8.01 (2H, m).

Example 89 isopropyl cis-3-((methylsulfonyl)amino)-2-((2-phenyl-1,3-thiazol-4-yl)methyl)piperidine-1-carboxylate A) N-(cis-2-((2-phenyl-1,3-thiazol-4-yl)methyl)piperidin-3-yl)methanesulfonamide dihydrochloride To a mixture of tert-butyl cis-3-((methylsulfonyl)amino)-2-((2-phenyl-1,3-thiazol-4-yl)methyl)piperidine-1-carboxylate (207 mg) and ethyl acetate (5 mL) was added 4M hydrogen chloride/ethyl acetate solution (2 mL) at room temperature. The mixture was stirred overnight at room temperature, and the reaction mixture was concentrated to give the title compound (200 mg).

MS: $[M+H]^+$ 352.1.

B) isopropyl cis-3-((methylsulfonyl)amino)-2-((2-phenyl-1,3-thiazol-4-yl)methyl)piperidine-1-carboxylate To a mixture of N-(cis-2-((2-phenyl-1,3-thiazol-4-yl)methyl)piperidin-3-yl)methanesulfonamide dihydrochloride (60 mg), TEA (71.5 mg) and THE (2 mL) was added 2M isopropyl carbonochloridate/toluene solution (0.106 mL) at room temperature. The mixture was stirred at room temperature for 3 hr, and the reaction mixture was directly purified by silica gel column chromatography (ethyl acetate/hexane) to give the title compound (43.0 mg).

$^1$H NMR (300 MHz, $CDCl_3$) δ1.04-1.21 (6H, m), 1.59-1.83 (3H, m), 2.03-2.15 (1H, m), 2.81-3.05 (5H, m), 3.30 (1H, dd, J=14.8, 6.4 Hz), 3.53-3.71 (1H, m), 3.98-4.09 (1H, m), 4.69-4.91 (2H, m), 6.38 (1H, brs), 7.02 (1H, s), 7.38-7.53 (3H, m), 7.90-8.02 (2H, m).

Example 93

N-(cis-2-(biphenyl-3-ylmethyl)-1-(cyclopropylcarbonyl)piperidin-3-yl)methanesulfonamide To a mixture of N-(cis-2-(biphenyl-3-ylmethyl)piperidin-3-yl)methanesulfonamide (100 mg), TEA (58.8 mg) and dichloromethane (1 mL) was added cyclopropanecarbonyl chloride (45.5 mg) under nitrogen atmosphere at 0° C. The mixture was stirred at 0° C. for 1 hr. To the mixture was added saturated aqueous sodium hydrogencarbonate solution, and the mixture was extracted with dichloromethane. The organic layer was separated, washed with saturated brine, dried over anhydrous sodium sulfate, and concentrated under reduced pressure. The residue was purified by HPLC (column: Phenomenex Gemini, mobile phase: water/$CH_3CN$ (containing 0.05% $NH_3$—$H_2O$)) to give the title compound (56.0 mg).

$^1$H NMR (400 MHz, DMSO-$d_6$) δ 0.53-0.40 (4H, m), 1.26-1.76 (5H, m), 2.90-3.05 (6H, m), 3.23-3.52 (1H, m), 4.28-4.66 (1H, m), 4.88-5.18 (1H, m), 7.16 (1H, d, J=7.6 Hz), 7.27-7.47 (7H, m), 7.57-7.62 (2H, m).

Example 100 isopropyl cis-2-((6-(2,5-difluorophenyl)pyridin-2-yl)methyl)-3-((methylsulfonyl)amino)piperidine-1-carboxylate A) isopropyl 3-oxopiperidine-1-carboxylate To a mixture of 1-benzyl piperidin-3-one hydrochloride (15.0 g), TEA (7.40 g) and $CH_3CN$ (100 mL) was added dropwise 2M isopropyl carbonochloridate/toluene solution (59.8 mL) at 0° C. The mixture was stirred at room temperature for 2 hr, and the insoluble substance was removed by filtration, and washed with $CH_3CN$. The filtrate was concentrated under reduced pressure. The residue was diluted with saturated aqueous sodium hydrogencarbonate solution, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (11.0 g).

$^1$H NMR (300 MHz, $CDCl_3$) δ 1.25 (6H, d, J=6.4 Hz), 1.95-2.04 (2H, m), 2.48 (2H, t, J=6.6 Hz), 3.60-3.66 (2H, m), 4.04 (2H, s), 4.94 (1H, spt, J=6.2 Hz).

B) 2-bromo-6-(bromomethyl)pyridine

To a mixture of (6-bromopyridin-2-yl)methanol (5.22 g), $PPh_3$ (8.74 g) and benzotrifluoride (210 mL) was added tetrabromomethane (11.1 g) at 0° C. The mixture was stirred at 0° C. for 2 hr, and the insoluble substance was removed by filtration, and washed with ethyl acetate/diethyl ether. The filtrate was concentrated under reduced pressure. The residue was purified by silica gel column chromatography (ethyl acetate/hexane) to give the title compound (7.33 g).

$^1$H NMR (300 MHz, $CDCl_3$) δ 4.50 (2H, s), 7.39-7.45 (2H, m), 7.52-7.60 (1H, m).

C) isopropyl 2-((6-bromopyridin-2-yl)methyl)-3-oxopiperidine-1-carboxylate

To a mixture of isopropyl 3-oxopiperidine-1-carboxylate (4.50 g) and toluene (52 mL) was added pyrrolidine (2.59 g) at room temperature. The mixture was stirred at room temperature for 30 min, and concentrated. Toluene and $CH_3CN$ were added thereto, and the mixture was concentrated. The residue was mixed with $CH_3CN$ (52 mL), and 2-bromo-6-(bromomethyl)pyridine (7.32 g) was added thereto at room temperature. The mixture was heated under reflux for 15 hr, and the reaction mixture was poured into water, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (2.72 g).

MS: $[M+H]^+$ 355.0.

D) isopropyl cis-3-amino-2-((6-bromopyridin-2-yl)methyl)piperidine-1-carboxylate To a mixture of isopropyl 2-((6-bromopyridin-2-yl)methyl)-3-oxopiperidine-1-carboxylate (2.71 g), MeOH (23 mL) and THF (23 mL) was added ammonium acetate (5.88 g) at room temperature. The mixture was stirred at room temperature for 1 hr, and sodium triacetoxyborohydride (3.23 g) was added thereto. The mixture was stirred at room temperature for 15 hr. The mixture was poured into saturated aqueous sodium hydrogencarbonate solution under ice-cooling, and the mixture was extracted with ethyl acetate. The organic layer was separated, washed with water and saturated brine, dried over anhydrous magnesium sulfate, and concentrated under reduced pressure. The residue was purified by silica gel column chromatography (methanol/ethyl acetate) to give the title compound (373 mg).

MS: $[M+H]^+$ 356.0.

E) isopropyl cis-2-((6-bromopyridin-2-yl)methyl)-3-((methylsulfonyl)amino)piperidine-1-carboxylate To a mixture of isopropyl cis-3-amino-2-((6-bromopyridin-2-yl)methyl)piperidine-1-carboxylate (369 mg), TEA (210 mg) and THF (3.5 mL) was added methanesulfonyl chloride (142 mg) at room temperature. The mixture was stirred at room temperature for 1 hr, and the reaction solution was poured into water, and the mixture was extracted with ethyl acetate. The organic layer was separated, washed with aqueous sodium hydrogencarbonate solution and saturated brine, dried over anhydrous magnesium sulfate, and concentrated under reduced pressure. The residue was purified by silica gel column chromatography (ethyl acetate/hexane) to give the title compound (340 mg).

MS: $[M+H]^+$ 434.0.

F) isopropyl cis-2-((6-(2,5-difluorophenyl)pyridin-2-yl)methyl)-3-((methylsulfonyl)amino)piperidine-1-carboxylate A mixture of isopropyl cis-2-((6-bromopyridin-2-yl)methyl)-3-((methylsulfonyl)amino)piperidine-1-carboxylate (73 mg), (2,5-difluorophenyl)boronic acid (39.8 mg), 2M aqueous sodium carbonate solution (0.210 mL) and DME (1.1 mL) was heated under reflux under argon atmosphere for 9 hr. The mixture was poured into water, and extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (58.6 mg).

$^1$H NMR (300 MHz, $CDCl_3$) δ 0.92-1.12 (6H, m), 1.60-1.83 (3H, m), 2.02-2.07 (1H, m), 2.91 (3H, s), 2.94-3.06 (2H, m), 3.30 (1H, dd, J=14.0, 5.7 Hz), 3.57-3.68 (1H, m), 3.99-4.13 (1H, m), 4.73 (1H, spt, J=6.2 Hz), 4.84-4.92 (1H, m), 5.64 (1H, brs), 7.01-7.16 (2H, m), 7.22-7.26 (1H, m), 7.62-7.74 (3H, m).

Example 101 ethyl (2S,3S)-2-(biphenyl-3-ylmethyl)-3-((methylsulfonyl)amino)pyrrolidine-1-carboxylate A racemate (146 mg) of ethyl cis-2-(biphenyl-3-ylmethyl)-3-((methylsulfonyl)amino)pyrrolidine-1-carboxylate was resolved by HPLC (column: CHIRALCEL OD(IK001), 50 mmID×500 mmL, Manufactured by Daicel Chemical Industries, mobile phase: hexane/2-propanol=450/550) to give the title compound (47 mg) having a shorter retention time.

$^1$H NMR (300 MHz, DMSO-$d_6$) δ 0.62-1.16 (3H, m), 1.71-2.23 (2H, m), 2.67-3.50 (8H, m), 3.55-4.26 (3H, m), 7.10-7.68 (10H, m).

Example 116 isopropyl cis-2-((2',3'-difluorobiphenyl-3-yl)methyl)-3-((methylsulfonyl)amino)piperidine-1-carboxylate A mixture of isopropyl cis-2-(3-iodobenzyl)-3-((methylsulfonyl)amino)piperidine-1-carboxylate (96 mg), (2,3-difluorophenyl)boronic acid (95 mg), XPhos Pd G3 (8.46 mg), 1M aqueous tripotassium phosphate solution (0.6 mL) and THF (1 mL) was heated under reflux for 1 hr. The mixture was diluted with ethyl acetate, washed with water and saturated brine, dried over anhydrous sodium sulfate, and concentrated under reduced pressure. The residue was purified by silica gel column chromatography (ethyl acetate/hexane) to give the title compound (71.0 mg).

$^1$H NMR (300 MHz, $CDCl_3$) δ 0.82 (3H, brs), 1.03 (3H, d, J=6.4 Hz), 1.59-1.99 (4H, m), 2.98 (6H, s), 3.56-3.73 (1H, m), 4.01-4.13 (1H, m), 4.38 (1H, d, J=7.6 Hz), 4.54-4.69 (1H, m), 4.74-4.89 (1H, m), 7.07-7.25 (4H, m), 7.30-7.42 (3H, m)

Example 117 isopropyl cis-2-(3-iodobenzyl)-3-((methylsulfonyl)amino)piperidine-1-carboxylate To a mixture of N-(cis-2-(3-iodobenzyl)piperidin-3-yl)methanesulfonamide hydrochloride (1.29 g), TEA (0.909 g) and THF (15 mL) was added 2M isopropyl carbonochloridate/toluene solution (1.80 mL) at room temperature. To the mixture was added saturated aqueous sodium hydrogencarbonate solution at room temperature, and the mixture was purified by silica gel column chromatography (ethyl acetate/hexane) to give the title compound (1.16 g).

$^1$H NMR (300 MHz, $CDCl_3$) δ 0.83-1.00 (3H, m), 1.10 (3H, d, J=6.1 Hz), 1.58-1.98 (4H, m), 2.70-2.92 (3H, m), 3.00 (3H, s), 3.51-3.68 (1H, m), 4.03-4.14 (1H, m), 4.22-4.38 (1H, m), 4.58-4.82 (2H, m), 6.92-7.07 (1H, m), 7.15 (1H, d, J=7.6 Hz), 7.48-7.58 (2H, m)

Example 122 isopropyl cis-3-((methylsulfonyl)amino)-2-((3-phenyl-1H-pyrazol-1-yl)methyl)piperidine-1-carboxylate A) 3-nitro-2-((3-phenyl-1H-pyrazol-1-yl)methyl)pyridine A mixture of 2-(bromomethyl)-3-nitropyridine (100 mg), 3-phenyl-1H-pyrazole (69.8 mg) and DMF (2 mL) was stirred at 60° C. for 17 hr. The mixture was partitioned between ethyl acetate-water, and the organic layer was washed with saturated brine, and concentrated under reduced pressure. The residue was purified by silica gel column chromatography (NH, ethyl acetate/hexane) to give the title compound (87 mg).

MS: $[M+H]^+$ 281.0.

B) 2-((3-phenyl-1H-pyrazol-1-yl)methyl)pyridin-3-amine

A mixture of 3-nitro-2-((3-phenyl-1H-pyrazol-1-yl)methyl)pyridine (793 mg), 10% palladium on carbon (301 mg) and EtOH (35 mL) was stirred under normal hydrogen atmosphere at room temperature for 1 hr. The catalyst was removed by filtration, and the filtrate was concentrated under reduced pressure. The residue was purified by silica gel column chromatography (ethyl acetate/hexane) to give the title compound (509 mg).

MS: $[M+H]^+$ 251.0.

C) N-(2-((3-phenyl-1H-pyrazol-1-yl)methyl)pyridin-3-yl)methanesulfonamide

A mixture of 2-((3-phenyl-1H-pyrazol-1-yl)methyl)pyridin-3-amine (550 mg), TEA (667 mg), methanesulfonyl chloride (629 mg) and THE (10 mL) was stirred at room temperature for 1 hr. To the mixture were added MeOH (5 mL) and 2M aqueous sodium hydroxide solution (2.20 mL). The mixture was stirred at 50° C. for 3 hr. The reaction solution was partitioned between ethyl acetate-water, and the organic layer was washed with saturated brine, and concentrated under reduced pressure. The residue was purified by silica gel column chromatography (ethyl acetate/hexane) to give the title compound (650 mg).

MS: $[M+H]^+$ 329.0.

D) N-(cis-2-((3-phenyl-1H-pyrazol-1-yl)methyl)piperidin-3-yl)methanesulfonamide

A mixture of N-(2-((3-phenyl-1H-pyrazol-1-yl)methyl)pyridin-3-yl)methanesulfonamide (648 mg), 5% platinum on carbon (150 mg), 35% hydrochloric acid (411 mg), MeOH (23 mL) and water (7 mL) was stirred under hydrogen atmosphere of 3 MPa at 50° C. for 2 hr. To the mixture was added 5% platinum on carbon (75 mg), and the mixture was stirred under hydrogen atmosphere of 3 MPa at 50° C. for 2 hr. The catalyst was removed by filtration, and the filtrate was concentrated under reduced pressure. The obtained residue was partitioned between THF-aqueous sodium hydrogencarbonate solution, and the organic layer was washed with saturated brine, and concentrated under reduced pressure. The residue was purified by silica gel column chromatography (NH, ethyl acetate/hexane), and crystallized from ethyl acetate to give the title compound (110 mg).

MS: $[M+H]^+$ 335.1.

E) isopropyl cis-3-((methylsulfonyl)amino)-2-((3-phenyl-1H-pyrazol-1-yl)methyl)piperidine-1-carboxylate A mixture of N-(cis-2-((3-phenyl-1H-pyrazol-1-yl)methyl)piperidin-3-yl)methanesulfonamide (110 mg), TEA (66.6 mg), 2 M isopropyl carbonochloridate/toluene solution (0.247 mL) and THF (3 mL) was stirred at room temperature for 30 min. The mixture was partitioned between ethyl acetate-aqueous sodium hydrogencarbonate solution, and the organic layer was washed with saturated brine, and concentrated under reduced pressure. The residue was purified by silica gel column chromatography (ethyl acetate/hexane) to give the title compound (93 mg).

$^1$H NMR (300 MHz, DMSO-$d_6$) δ 0.62 (6H, d, J=5.3 Hz, minor), 0.81-1.12 (6H, m, major), 1.41-1.83 (4H, m), 3.03 (3H, s), 3.06-3.21 (1H, m), 3.41-3.54 (1H, m), 3.74-3.96 (1H, m), 4.26-4.59 (3H, m), 4.60-4.80 (1H, m), 6.62 (1H, d, J=1.5 Hz), 7.21-7.30 (1H, m), 7.32-7.41 (2H, m), 7.47 (1H, brs), 7.60 (1H, d, J=2.3 Hz), 7.76 (2H, d, J=7.6 Hz).

Example 178 isopropyl cis-3-((cyclopropylsulfonyl)amino)-2-((6-phenylpyridin-2-yl)methyl)piperidine-1-carboxylate A) tert-butyl cis-3-(((benzyloxy)carbonyl)amino)-2-((6-phenylpyridin-2-yl)methyl)piperidine-1-carboxylate To a mixture of tert-butyl cis-3-amino-2-((6-phenylpyridin-2-yl)methyl)piperidine-1-carboxylate (1.05 g), sodium hydrogencarbonate (0.360 g), THE (7 mL) and water (7 mL) was added 1-(((benzyloxy)carbonyl)oxy)pyrrolidine-2,5-dione (0.748 g) at room temperature. The mixture was vigorously stirred at room temperature for 2 hr, poured into water, and extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (1.37 g).

MS: $[M+H]^+$ 502.2.

B) benzyl (cis-2-((6-phenylpyridin-2-yl)methyl)piperidin-3-yl) carbamate

To a mixture of tert-butyl cis-3-(((benzyloxy)carbonyl)amino)-2-((6-phenylpyridin-2-yl)methyl)piperidine-1-carboxylate (1.37 g) and toluene (15 mL) was added TFA (15 mL) at room temperature. The mixture was stirred at room temperature for 1 hr, and added to saturated aqueous sodium hydrogencarbonate solution under ice-cooling. The mixture was basified to pH=8 with potassium carbonate, and extracted with ethyl acetate. The organic layer was separated, washed with water and saturated brine, dried over anhydrous magnesium sulfate, and concentrated under reduced pressure. The residue was purified by silica gel column chromatography (NH, ethyl acetate/hexane) to give the title compound (966 mg).

MS: $[M+H]^+$ 402.1.

C) isopropyl cis-3-(((benzyloxy)carbonyl)amino)-2-((6-phenylpyridin-2-yl)methyl)piperidine-1-carboxylate To a mixture of benzyl (cis-2-((6-phenylpyridin-2-yl)methyl)piperidin-3-yl)carbamate (960 mg), TEA (726 mg) and THE (20 mL) was added 2M isopropyl carbonochloridate/toluene solution (2.39 mL) at room temperature. The mixture was stirred at room temperature for 1 hr, added to aqueous sodium hydrogencarbonate solution, and extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (1.11 g).

MS: $[M+H]^+$ 488.2.

D) isopropyl cis-3-amino-2-((6-phenylpyridin-2-yl)methyl)piperidine-1-carboxylate A mixture of isopropyl cis-3-(((benzyloxy)carbonyl)amino)-2-((6-phenylpyridin-2-yl)methyl)piperidine-1-carboxylate (1.09 g), 10% palladium hydroxide on carbon (0.36 g) and MeOH (22 mL) was stirred under normal hydrogen atmosphere at room temperature for 1.5 hr. The catalyst was removed by filtration, and the filtrate was concentrated under reduced pressure. The residue was purified by silica gel column chromatography (methanol/ethyl acetate) to give the title compound (703 mg).

MS: $[M+H]^+$ 354.1.

E) isopropyl cis-3-((cyclopropylsulfonyl)amino)-2-((6-phenylpyridin-2-yl)methyl)piperidine-1-carboxylate To a mixture of isopropyl cis-3-amino-2-((6-phenylpyridin-2-yl)methyl)piperidine-1-carboxylate (28 mg), TEA (0.00971 mg) and THF (1.0 mL) was added cyclopropanesulfonyl chloride (13.5 mg). The mixture was stirred at room temperature for 3 hr, and the reaction mixture was poured into water, and the mixture was extracted with ethyl acetate. The organic layer was filtered using Top-Phase Separation Filter Tube, and the filtrate was concentrated by blowing of air at 60° C. The residue was purified by HPLC (YMCTriartC18, mobile phase: water/MeCN (10 mM ammonium bicarbonate)). The obtained fraction was concentrated by blowing of air at 60° C. to give the title compound (12.7 mg).

MS: $[M+H]^+$ 458.1.

Example 206

N-(cis-2-(biphenyl-3-ylmethyl)-1-(cyclopropylcarbonyl)pyrrolidin-3-yl)methanesulfonamide To a mixture of N-(cis-2-(biphenyl-3-ylmethyl)pyrrolidin-3-yl)methanesulfonamide (52.0 mg), TEA (47.8 mg) and THF (1.2 mL) was added cyclopropanecarbonyl chloride (32.9 mg) at room temperature. The mixture was stirred at room temperature for 50 min, and poured into aqueous sodium hydrogencarbonate solution, and extracted with ethyl acetate. The organic layer was separated, washed with saturated brine, dried over anhydrous magnesium sulfate, and concentrated under reduced pressure. The residue was purified by silica gel column chromatography (methanol/ethyl acetate) to give a solid. The solid was collected by filtration, and washed with isopropyl ether/hexane to give the title compound (38.0 mg).

$^1$H NMR (300 MHz, $CDCl_3$) δ0.07-0.62 (2H, m), 0.72-1.08 (3H, m), 1.71-1.91 (1H, m), 2.23-2.36 (1H, m), 2.49-2.74 (2H, m), 2.92-3.06 (2H, m), 3.22 (1H, td, J=13.1, 3.0 Hz), 3.47-3.76 (2H, m), 3.96-4.10 (1H, m), 4.52-4.80 (2H, m), 7.17 (1H, d, J=7.6 Hz), 7.30-7.49 (6H, m), 7.52-7.58 (2H, m).

Example 209

N-(cis-2-(biphenyl-3-ylmethyl)-1-isobutyryl pyrrolidin-3-yl)methanesulfonamide

To a mixture of N-(cis-2-(biphenyl-3-ylmethyl)pyrrolidin-3-yl)methanesulfonamide (51.2 mg), TEA (47.0 mg) and THF (2 mL) was added 2-methylpropanoyl chloride (24.8 mg) at 0° C. The mixture was stirred at 0° C. for 30 min, and to the mixture was added water at 0° C., and the mixture was extracted with ethyl acetate. The organic layer was separated, washed with saturated brine, dried over anhydrous magnesium sulfate, and concentrated under reduced pressure. The residue was purified by silica gel column chromatography (methanol/ethyl acetate). The obtained solid was recrystallized from ethyl acetate/hexane to give the title compound (29.0 mg).

$^1$H NMR (300 MHz, $CDCl_3$) δ 0.50-1.19 (6H, m), 1.71-2.51 (4H, m), 2.54-2.74 (1H, m), 2.87-3.09 (2H, m), 3.11-3.27 (1H, m), 3.38-3.84 (2H, m), 3.91-4.09 (1H, m), 4.23-4.55 (1H, m), 4.57-4.74 (1H, m), 7.09-7.62 (9H, m).

Example 210 optically active isopropyl cis-3-((methylsulfonyl)amino)-2-((2-phenyl-1,3-thiazol-4-yl)methyl)piperidine-1-carboxylate A racemate (82 mg) of isopropyl cis-3-((methylsulfonyl)amino)-2-((2-phenyl-1,3-thiazol-4-yl)methyl)piperidine-1-carboxylate was resolved by SFC (column: CHIRALCEL ODH (TB001), 4.6 mmID×150 mmL, Manufactured by Daicel Chemical Industries, mobile phase: carbon dioxide/methanol=770/230) to give the title compound (381 mg) having a longer retention time.

$^1$H NMR (300 MHz, $CDCl_3$) δ 0.96-1.24 (6H, m), 1.60-1.87 (3H, m), 2.08 (1H, d, J=9.5 Hz), 2.78-3.07 (5H, m), 3.30 (1H, dd, J=14.6, 6.2 Hz), 3.52-3.76 (1H, m), 4.05 (1H, d, J=14.8 Hz), 4.67-4.90 (2H, m), 6.31 (1H, brs), 7.02 (1H, s), 7.38-7.52 (3H, m), 7.89-8.04 (2H, m).

Example 213 isopropyl cis-3-((methylsulfonyl)amino)-2-(pyridin-3-ylmethyl)piperidine-1-carboxylate A) tert-butyl 2-((6-chloropyridin-3-yl)methyl)-3-oxopiperidine-1-carboxylate To a mixture of tert-butyl 3-oxopiperidine-1-carboxylate (2.00 g) and toluene (20 mL) was added pyrrolidine (0.857 g) at room temperature. The mixture was stirred for 15 min, and concentrated under reduced pressure. The residue was dissolved in $CH_3CN$ (20 mL), and 2-chloro-5-(chloromethyl)pyridine (1.63 g) and TBAI (0.742 g) were added thereto. The mixture was heated under reflux for 1 hr, and the reaction mixture was diluted with water. The mixture was extracted with ethyl acetate, and the extract was concentrated under reduced pressure. The residue was purified by silica gel column chromatography (ethyl acetate/hexane) to give the title compound (1.61 g).

MS: $[M+H]^+$ 325.3.

B) tert-butyl cis-3-amino-2-((6-chloropyridin-3-yl)methyl)piperidine-1-carboxylate To a mixture of tert-butyl 2-((6-chloropyridin-3-yl)methyl)-3-oxopiperidine-1-carboxylate (1.61 g), THF (15 mL) and MeOH (15 mL) was added ammonium acetate (3.82 g) at room temperature. The mixture was stirred at room temperature for 1 hr, and sodium triacetoxyborohydride (2.10 g) was added thereto. The mixture was stirred overnight at room temperature, poured into saturated aqueous sodium hydrogencarbonate solution under ice-cooling, and extracted with ethyl acetate. The organic layer was separated, washed with water and saturated brine, dried over anhydrous magnesium sulfate, and concentrated under reduced pressure. The residue was purified by silica gel column chromatography (NH, methanol/ethyl acetate) to give the title compound (567 mg).

MS: $[M+H]^+$ 326.2.

C) tert-butyl cis-2-((6-chloropyridin-3-yl)methyl)-3-((methylsulfonyl)amino)piperidine-1-carboxylate To a mixture of tert-butyl cis-3-amino-2-((6-chloropyridin-3-yl)methyl)piperidine-1-carboxylate (567 mg), TEA (264 mg) and THF (8 mL) was added methanesulfonic anhydride (364 mg) at room temperature. The mixture was stirred at room temperature for 2 hr, and the reaction solution was concentrated. The residue was purified by silica gel column chromatography (ethyl acetate/hexane) to give the title compound (650 mg).

MS: $[M+H]^+$ 404.2.

D) N-(cis-2-((6-chloropyridin-3-yl)methyl)piperidin-3-yl)methanesulfonamide dihydrochloride A mixture of tert-butyl cis-2-((6-chloropyridin-3-yl)methyl)-3-((methylsulfonyl)amino)piperidine-1-carboxylate (645 mg) and hydrogen chloride/methanol solution (776 mg) was stirred overnight at room temperature. The mixture was concentrated under reduced pressure to give the title compound (557 mg).

MS: $[M+H]^+$ 304.1.

E) isopropyl cis-2-((6-chloropyridin-3-yl)methyl)-3-((methylsulfonyl)amino)piperidine-1-carboxylate To a mixture of N-(cis-2-((6-chloropyridin-3-yl)methyl) piperidin-3-yl)methanesulfonamide dihydrochloride (200 mg), TEA (215 mg) and THF (5 mL) was added 2M isopropyl carbonochloridate/toluene solution (0.319 mL) at room temperature. The mixture was stirred overnight at room temperature. To the mixture was added saturated aqueous sodium hydrogencarbonate solution, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (222 mg).

MS: $[M+H]^+$ 390.2.

F) isopropyl cis-3-((methylsulfonyl)amino)-2-(pyridin-3-ylmethyl)piperidine-1-carboxylate A mixture of isopropyl cis-2-((6-chloropyridin-3-yl) methyl)-3-((methylsulfonyl)amino)piperidine-1-carboxylate (91.0 mg), 5.5% palladium on carbon (30 mg) and EtOH (5 mL) was stirred under normal hydrogen atmosphere at room temperature for 2 days. The catalyst was removed by filtration, and the filtrate was concentrated under reduced pressure. The similar reaction was carried out using isopropyl cis-2-((6-chloropyridin-3-yl)methyl)-3-((methylsulfonyl)amino)piperidine-1-carboxylate (117 mg) and 5.5% palladium on carbon (40 mg) and EtOH (5 mL). The combined residues were purified by silica gel column chromatography (NH, ethyl acetate/hexane) to give the title compound (144 mg).

$^1$H NMR (300 MHz, DMSO-$d_6$) δ0.49-1.13 (6H, m), 1.49 (1H, brs), 1.60-1.82 (3H, m), 2.81-2.91 (2H, m), 2.92-3.07 (4H, m), 3.35-3.50 (1H, m), 3.85 (1H, d, J=14.4 Hz), 4.26-4.67 (2H, m), 7.27 (1H, brs), 7.39 (1H, brs), 7.54 (1H, dt, J=7.8, 2.0 Hz), 8.36 (2H, d, J=2.3 Hz).

Example 214 isopropyl cis-3-((methylsulfonyl)amino)-2-((1-phenylpiperidin-3-yl)methyl)piperidine-1-carboxylate A) isopropyl cis-3-((methylsulfonyl)amino)-2-(piperidin-3-ylmethyl)piperidine-1-carboxylate A mixture of isopropyl cis-3-((methylsulfonyl)amino)-2-(pyridin-3-ylmethyl)piperidine-1-carboxylate (142 mg), 5% rhodium on carbon(50% wet, 30 mg), MeOH (25 mL) and AcOH (5 mL) was stirred under hydrogen atmosphere of 3 MPa at 50° C. for 3 hr. The catalyst was removed by filtration, and the filtrate was concentrated under reduced pressure. The residue was purified by silica gel column chromatography (NH, ethyl acetate/hexane) to give the title compound (140 mg).

MS: $[M+H]^+$ 362.2.

B) isopropyl cis-3-((methylsulfonyl)amino)-2-((1-phenylpiperidin-3-yl)methyl)piperidine-1-carboxylate To a mixture of isopropyl cis-3-((methylsulfonyl)amino)-2-(piperidin-3-ylmethyl)piperidine-1-carboxylate (28.6 mg), bromobenzene (24.8 mg), cesium carbonate (103 mg) and t-AmOH (1 mL) were added $Pd_2(dba)_3$ (7.24 mg) and dicyclohexyl(2',6'-diisopropoxybiphenyl-2-yl)phosphine (7.38 mg) at room temperature. The mixture was heated under reflux under nitrogen atmosphere for 4 hr. To the mixture was added water, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (23.6 mg).

$^1$H NMR (300 MHz, DMSO-$d_6$) δ0.92-2.04 (18H, m), 2.22-2.45 (1H, m), 2.55-2.87 (2H, m), 2.92 (3H, s), 3.20-3.64 (2H, m), 3.79 (1H, brs), 4.43 (1H, brs), 4.76 (1H, quin, J=6.2 Hz), 6.72 (1H, t, J=7.2 Hz), 6.90 (2H, dd, J=8.5, 3.2 Hz), 7.09-7.27 (3H, m).

Example 227

N-(cis-2-(biphenyl-3-ylmethyl)-1-(2,2-dimethylpropanoyl)pyrrolidin-3-yl)methanesulfonamide To a mixture of N-(cis-2-(biphenyl-3-ylmethyl)pyrrolidin-3-yl)methanesulfonamide hydrochloride (40 mg), pivalic acid (13.4 mg), HATU (49.7 mg) and DMF (0.5 ml) was added TEA (33.1 mg) at 0° C. The mixture was stirred at room temperature for 30 min, and to the mixture was added saturated aqueous sodium hydrogencarbonate solution, and the mixture was extracted with ethyl acetate. The organic layer was separated, washed with water and saturated brine, dried over anhydrous sodium sulfate, and concentrated under reduced pressure. The residue was purified by silica gel column chromatography (methanol/ethyl acetate) to give the title compound (39 mg).

$^1$H NMR (300 MHz, $CDCl_3$) δ 1.26 (9H, s), 1.89-2.05 (1H, m), 2.20-2.34 (1H, m), 2.45 (3H, s), 2.78-2.93 (1H, m), 3.19-3.29 (1H, m), 3.62-3.77 (2H, m), 3.89-4.04 (1H, m), 4.45 (1H, d, J=8.3 Hz), 4.70-4.80 (1H, m), 7.30-7.49 (6H, m), 7.52-7.62 (3H, m).

Example 254

N-(cis-1-(cyclobutylcarbonyl)-2-((2-(3-fluorophenyl)-1,3-thiazol-4-yl)methyl)pyrrolidin-3-yl)methanesulfonamide A) 2-bromo-4-(bromomethyl)-1,3-thiazole To a mixture of (2-bromo-1,3-thiazol-4-yl)methanol (5.0 g) and THF (50 ml) was added phosphorous tribromide (6.97 g) at 0° C. The mixture was stirred overnight under nitrogen atmosphere at room temperature. The mixture was poured into ice water at room temperature, and extracted with ethyl acetate. The organic layer was separated, washed with saturated aqueous sodium hydrogencarbonate solution and water, dried over anhydrous magnesium sulfate, and concentrated under reduced pressure. The residue was purified by silica gel column chromatography (ethyl acetate/hexane) to give the title compound (3.90 g).

MS: $[M+H]^+$ 255.7.

B) tert-butyl 2-((2-bromo-1,3-thiazol-4-yl)methyl)-3-oxopyrrolidine-1-carboxylate To a mixture of tert-butyl 3-oxopyrrolidine-1-carboxylate (20.2 g) and toluene (200 mL) was added pyrrolidine (8.53 g) at room temperature. The mixture was heated under reflux overnight, and the reaction solution was concentrated. The residue was mixed with $CH_3CN$ (200 mL), and a mixture of 2-bromo-4-(bromomethyl)-1,3-thiazole (14.0 g), TBAI (4.03 g) and $CH_3CN$ (200 mL) was added thereto at 80° C. The mixture was stirred under nitrogen atmosphere at 80° C. for 3 hr, and concentrated under reduced pressure. The mixture was poured into water, and extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (13.5 g).

MS: $[M-H]^-$ 358.8.

C) tert-butyl cis-3-amino-2-((2-bromo-1,3-thiazol-4-yl)methyl)pyrrolidine-1-carboxylate To a mixture of tert-butyl 2-((2-bromo-1,3-thiazol-4-yl)methyl)-3-oxopyrrolidine-1-carboxylate (13.6 g), ammonium formate (25.0 g) and MeOH (40 ml) was added chloro[N-[4-(dimethylamino)phenyl]-2-pyridinecarboxamidato](pentamethylcyclopentadienyl) iridium(III) (0.454 g) at room temperature. The mixture was heated under reflux for 2 hr. The reaction solution was concentrated. The obtained residue was diluted with ethyl acetate, and the mixture was washed with a mixture of saturated brine and saturated aqueous sodium hydrogencarbonate solution, dried over anhydrous sodium sulfate, and concentrated under reduced pressure to give the title compound (6.18 g).

MS: $[M+H]^+$ 362.1.

D) tert-butyl cis-2-((2-bromo-1,3-thiazol-4-yl)methyl)-3-((methylsulfonyl)amino)pyrrolidine-1-carboxylate A mixture of tert-butyl cis-3-amino-2-((2-bromo-1,3-thiazol-4-yl)methyl)pyrrolidine-1-carboxylate (145 mg), TEA (81 mg) and THF (2 ml) was stirred at 0° C., and methanesulfonic anhydride (91 mg) was added thereto at 0° C. The reaction mixture was concentrated under reduced pressure, and the residue was purified by silica gel column chromatography (ethyl acetate/hexane) to give the title compound (53 mg).

MS: $[M+H]^+$ 440.0.

E) N-(cis-2-((2-bromo-1,3-thiazol-4-yl)methyl)-1-(cyclobutylcarbonyl)pyrrolidin-3-yl)methanesulfonamide tert-Butyl cis-2-((2-bromo-1,3-thiazol-4-yl)methyl)-3-((methylsulfonyl)amino)pyrrolidine-1-carboxylate (650 mg) and 4M hydrogen chloride/ethyl acetate solution (7.38 ml) were mixed at room temperature. After 30 min, and the reaction solution was concentrated. The obtained residue was mixed with THF (7.5 ml), and TEA (747 mg) and cyclobutanecarbonyl chloride (262 mg) at 0° C. were added thereto. The mixture was stirred at room temperature for 1 hr, to the reaction solution was added saturated brine, and the mixture was concentrated under reduced pressure. The residue was purified by silica gel column chromatography (ethyl acetate/hexane) to give the title compound (422 mg).

MS: $[M+H]^+$ 422.1.

F) N-(cis-1-(cyclobutylcarbonyl)-2-((2-(3-fluorophenyl)-1,3-thiazol-4-yl)methyl)pyrrolidin-3-yl)methanesulfonamide To a mixture of N-(cis-2-((2-bromo-1,3-thiazol-4-yl)methyl)-1-(cyclobutylcarbonyl)pyrrolidin-3-yl)methanesulfonamide (60.0 mg), (3-fluorophenyl)boronic acid (29.8 mg), potassium carbonate (40.2 mg), water (0.40 ml) and DME (1.2 ml) was added $(A\text{-}taPhos)_2PdCl_2$ (5.7 mg) at room temperature. The mixture was stirred under nitrogen atmosphere at 80° C. for 3 hr. The reaction mixture was purified by silica gel column chromatography (NH, ethyl acetate/hexane) and silica gel column chromatography (ethyl acetate/hexane), and the obtained compound was triturated in diethyl ether/hexane to give the title compound (35.2 mg).

$^1H$ NMR (300 MHz, $CDCl_3$) δ 1.33-1.52 (1H, m), 1.81-2.58 (7H, m), 2.94-3.45 (7H, m), 3.61 (1H, dd, J=14.8, 6.1 Hz), 4.00-4.21 (1H, m), 4.30-4.59 (1H, m), 6.94-7.04 (1H, m), 7.10-7.20 (1H, m), 7.39-7.51 (1H, m), 7.59-7.68 (1H, m), 7.69-7.79 (1H, m), 8.12 (1H, d, J=9.1 Hz).

Example 255

N-(cis-1-(cyclobutylcarbonyl)-2-((2-(2-fluorophenyl)-1,3-thiazol-4-yl)methyl)pyrrolidin-3-yl)methanesulfonamide To a mixture of N-(cis-2-((2-bromo-1,3-thiazol-4-yl)methyl)-1-(cyclobutylcarbonyl)pyrrolidin-3-yl)methanesulfonamide (60.0 mg), (2-fluorophenyl)boronic acid (30.0 mg), potassium carbonate (40.1 mg), water (0.40 ml) and DME (1.2 ml) was added $(A\text{-}taPhos)_2PdCl_2$ (6.0 mg) at room temperature. The mixture was stirred under nitrogen atmosphere at 80° C. for 3 hr. The reaction mixture was purified by silica gel column chromatography (NH, ethyl acetate/hexane) and silica gel column chromatography (ethyl acetate/hexane), and the obtained compound was triturated in diethyl ether/hexane to give the title compound (38.2 mg).

$^1H$ NMR (300 MHz, $CDCl_3$) δ 1.23-1.43 (1H, m), 1.82-2.59 (7H, m), 2.94-3.46 (7H, m), 3.66 (1H, dd, J=14.8, 5.7 Hz), 4.01-4.19 (1H, m), 4.30-4.62 (1H, m), 7.02-7.12 (1H, m), 7.16-7.25 (1H, m), 7.28-7.36 (1H, m), 7.38-7.49 (1H, m), 8.14-8.29 (2H, m).

Example 256

N-(cis-1-(cyclobutylcarbonyl)-2-((2-(2,3-difluorophenyl)-1,3-thiazol-4-yl)methyl)pyrrolidin-3-yl)methanesulfonamide To a mixture of N-(cis-2-((2-bromo-1,3-thiazol-4-yl)methyl)-1-(cyclobutylcarbonyl)pyrrolidin-3-yl)methanesulfonamide (60.0 mg), (2,3-difluorophenyl)boronic acid (35.0 mg), potassium carbonate (40.1 mg), water (0.40 ml) and DME (1.2 ml) was added $(A\text{-}taPhos)_2PdCl_2$ (6.0 mg) at room temperature. The mixture was stirred under nitrogen atmosphere at 80° C. for 3 hr. The reaction mixture was purified by silica gel column chromatography (NH, ethyl acetate/hexane) and silica gel column chromatography (ethyl acetate/hexane), and the obtained compound was triturated in diethyl ether/hexane to give the title compound (38.4 mg).

$^1H$ NMR (300 MHz, $CDCl_3$) δ 1.20-1.44 (1H, m), 1.81-2.03 (2H, m), 2.06-2.61 (5H, m), 2.94-3.44 (7H, m), 3.67 (1H, dd, J=14.6, 5.9 Hz), 4.00-4.19 (1H, m), 4.30-4.60 (1H, m), 7.05-7.51 (3H, m), 7.89-8.12 (2H, m).

Example 258

N-(cis-1-(cyclobutylcarbonyl)-2-((2-(3,5-difluorophenyl)-1,3-thiazol-4-yl)methyl)pyrrolidin-3-yl)methanesulfonamide To a mixture of N-(cis-2-((2-bromo-1,3-thiazol-4-yl)methyl)-1-(cyclobutylcarbonyl)pyrrolidin-3-yl)methanesulfonamide (51.1 mg), (3,5-difluorophenyl)boronic acid (25.3 mg), potassium carbonate (35.1 mg), water (0.40 ml) and DME (1.2 ml) was added (A-taPhos)$_2$PdCl$_2$ (3.7 mg) at room temperature. The mixture was stirred overnight under nitrogen atmosphere at 80° C. The reaction mixture was purified by silica gel column chromatography (NH, ethyl acetate/hexane) and silica gel column chromatography (ethyl acetate/hexane), and the obtained compound was triturated in diethyl ether/hexane to give the title compound (30.2 mg).

$^1$H NMR (300 MHz, CDCl$_3$) δ 1.33-1.52 (1H, m), 1.80-2.03 (2H, m), 2.06-2.58 (5H, m), 2.96-3.05 (3H, m), 3.07-3.45 (4H, m), 3.60 (1H, dd, J=14.8, 6.4 Hz), 3.98-4.20 (1H, m), 4.30-4.57 (1H, m), 6.84-6.95 (1H, m), 6.99-7.10 (1H, m), 7.42-7.53 (2H, m), 7.94 (1H, d, J=8.7 Hz).

Example 259

N-(cis-1-(cyclobutylcarbonyl)-2-((2-phenyl-1,3-thiazol-4-yl)methyl)pyrrolidin-3-yl)cyclopropane-sulfonamide A) tert-butyl 3-oxo-2-((2-phenyl-1,3-thiazol-4-yl)methyl)pyrrolidine-1-carboxylate To a mixture of tert-butyl 3-oxopyrrolidine-1-carboxylate (185 mg) and toluene (2.00 ml) was added pyrrolidine (85 mg) at room temperature. The mixture was stirred at room temperature for 15 min, and concentrated under reduced pressure. The residue was mixed with CH$_3$CN (2 ml), and 4-(chloromethyl)-2-phenyl-1,3-thiazole (105 mg) and TBAI (36.9 mg) were added thereto. The mixture was heated under reflux for 1.5 hr, and the reaction mixture was diluted with water. The mixture was extracted with ethyl acetate, and the extract was concentrated under reduced pressure. The residue was purified by silica gel column chromatography (ethyl acetate/hexane) to give the title compound (45.3 mg).

MS: [M+H]$^+$ 359.1.

B) tert-butyl cis-3-amino-2-((2-phenyl-1,3-thiazol-4-yl)methyl)pyrrolidine-1-carboxylate To a mixture of tert-butyl 3-oxo-2-((2-phenyl-1,3-thiazol-4-yl)methyl)pyrrolidine-1-carboxylate (3.66 g), ammonium formate (6.44 g) and MeOH (30 ml) was added chloro[N-[4-(dimethylamino)phenyl]-2-pyridinecarboxamidato](pentamethylcyclopentadienyl)iridium(III) (123 mg) at room temperature. The mixture was stirred under argon atmosphere at 70° C. for 2 hr. The mixture was concentrated under reduced pressure, and the residue was diluted with ethyl acetate, and the mixture was washed with saturated aqueous sodium hydrogencarbonate solution and saturated brine, and concentrated under reduced pressure to give the title compound (3.42 g).

MS: [M+H]$^+$ 360.1.

C) tert-butyl cis-3-((cyclopropylsulfonyl)amino)-2-((2-phenyl-1,3-thiazol-4-yl)methyl)pyrrolidine-1-carboxylate To a mixture of tert-butyl cis-3-amino-2-((2-phenyl-1,3-thiazol-4-yl)methyl)pyrrolidine-1-carboxylate (810 mg), TEA (0.81 ml), DMAP (91.0 mg), THF (5.0 ml) and DMF (6.0 ml) was added cyclopropanesulfonyl chloride (0.57 ml) at room temperature. The mixture was stirred at room temperature for 2 hr. To the reaction mixture was added 5% aqueous acetic acid solution, and the mixture was extracted with ethyl acetate. The organic layer was separated, washed with water and saturated brine, dried over anhydrous sodium sulfate, and concentrated under reduced pressure. The residue was purified by silica gel column chromatography (ethyl acetate/hexane) to give the title compound (317 mg).

MS: [M+H]$^+$ 464.3.

D) N-(cis-1-(cyclobutylcarbonyl)-2-((2-phenyl-1,3-thiazol-4-yl)methyl)pyrrolidin-3-yl)cyclopropane-sulfonamide To a mixture of tert-butyl cis-3-((cyclopropylsulfonyl)amino)-2-((2-phenyl-1,3-thiazol-4-yl)methyl)pyrrolidine-1-carboxylate (72.0 mg), cyclopentyl methyl ether (2.0 mL) and MeOH (2.0 mL) was added 4M hydrogen chloride/cyclopentyl methyl ether solution (2.0 mL) at room temperature. The mixture was stirred at room temperature for 2 hr, and concentrated under reduced pressure. To the residue were added DMF (2.0 mL), THF (2.0 mL), TEA (0.088 mL) and cyclobutanecarbonyl chloride (0.050 mL), and the mixture was stirred overnight at room temperature. To the reaction mixture was added water, and the mixture was extracted with ethyl acetate. The organic layer was separated, washed with water and saturated brine, dried over sodium sulfate, and concentrated under reduced pressure. The residue was purified by silica gel column chromatography (NH, ethyl acetate/hexane) and silica gel column chromatography (ethyl acetate/hexane). The obtained compound was purified by HPLC (C18, mobile phase: water/acetonitrile (containing 0.1% TFA)), and to the obtained fraction was added saturated aqueous sodium hydrogencarbonate solution, and the mixture was extracted with ethyl acetate. The extract was dried over sodium sulfate, and concentrated under reduced pressure, and the obtained compound was triturated in diethyl ether/hexane to give the title compound (15.5 mg).

$^1$H NMR (300 MHz, CDCl$_3$) δ 0.81-1.44 (6H, m), 1.80-2.53 (7H, m), 3.03-3.53 (4H, m), 3.65 (1H, dd, J=14.8, 5.7 Hz), 4.03-4.21 (1H, m), 4.45-4.58 (1H, m), 6.88-6.98 (1H, m), 7.41-7.52 (3H, m), 7.88-8.00 (2H, m), 8.11 (1H, d, J=9.5 Hz).

Example 261

N-((2S,3S)-2-(biphenyl-3-ylmethyl)-1-(cyclobutyl-carbonyl)pyrrolidin-3-yl)methanesulfonamide A) tert-butyl 2-(3-bromobenzyl)-3-oxopyrrolidine-1-carboxylate To a mixture of tert-butyl 3-oxopyrrolidine-1-carboxylate (5.4 g) and toluene (50.0 ml) was added pyrrolidine (2.49 g) at room temperature. The mixture was stirred for 15 min, and concentrated. The residue was mixed with CH$_3$CN (50 ml), and 1-bromo-3-(bromomethyl)benzene (7.29 g) and TBAI (2.15 g) were added thereto. The mixture was heated under reflux for 1 hr, and the reaction mixture was diluted with water. The mixture was extracted with ethyl acetate, and the extract was concentrated under reduced pressure. The residue was purified by silica gel column chromatography (ethyl acetate/hexane) to give the title compound (4.00 g).

MS, found: 254.2.

B) tert-butyl cis-3-amino-2-(3-bromobenzyl)pyrrolidine-1-carboxylate

To a mixture of tert-butyl 2-(3-bromobenzyl)-3-oxopyrrolidine-1-carboxylate (1.54 g), ammonium formate (1.37 g)

and MeOH (25 ml) was added chloro[N-[4-(dimethylamino) phenyl]-2-pyridinecarboxamidato] (pentamethylcyclopentadienyl)iridium(III) (0.026 g) at room temperature. The mixture was stirred under nitrogen atmosphere at 70° C. for 2 hr. The mixture was neutralized with saturated aqueous sodium hydrogencarbonate solution at 0° C., and concentrated under reduced pressure. The mixture was extracted with ethyl acetate. The organic layer was separated, washed with saturated brine, dried over anhydrous magnesium sulfate, and concentrated under reduced pressure. The residue was purified by silica gel column chromatography (methanol/ethyl acetate) to give the title compound (565 mg).

MS, found: 299.2.

C) tert-butyl (2S,3S)-3-amino-2-(3-bromobenzyl) pyrrolidine-1-carboxylate

A racemate (1.5 g) of tert-butyl cis-3-amino-2-(3-bromobenzyl)pyrrolidine-1-carboxylate was resolved by HPLC (column: CHIRALPAK AD(AK001), 50 mmID×500 mmL, Manufactured by Daicel Chemical Industries, mobile phase: hexane/ethanol/diethylamine=850/150/1) to give the title compound (650 mg) having a shorter retention time.

MS, found: 299.0.

D) tert-butyl (2S,3S)-2-(3-bromobenzyl)-3-((methylsulfonyl)amino)pyrrolidine-1-carboxylate A mixture of tert-butyl (2S,3S)-3-amino-2-(3-bromobenzyl)pyrrolidine-1-carboxylate (920 mg), TEA (786 mg) and THE (10 ml) was stirred, and methanesulfonic anhydride (541 mg) was added thereto at room temperature. After 0.5 hr, the reaction mixture was concentrated under reduced pressure. The residue was purified by silica gel column chromatography (ethyl acetate/hexane) to give the title compound (1.05 g).

MS, found: 333.1.

E) N-((2S,3S)-2-(3-bromobenzyl)pyrrolidin-3-yl) methanesulfonamide hydrochloride To 4M hydrogen chloride/ethyl acetate solution (5.42 mL) was added tert-butyl (2S,3S)-2-(3-bromobenzyl)-3-((methylsulfonyl)amino)pyrrolidine-1-carboxylate (470 mg) at room temperature. The mixture was stirred for 1 hr, and the reaction solution was concentrated to give the title compound (370 mg).

MS: $[M+H]^+$ 333.1.

F) N-((2S,3S)-2-(3-bromobenzyl)-1-(cyclobutylcarbonyl)pyrrolidin-3-yl)methanesulfonamide To a mixture of N-((2S,3S)-2-(3-bromobenzyl)pyrrolidin-3-yl)methanesulfonamide hydrochloride (200 mg), TEA (274 mg) and THF (5 ml) was added cyclobutanecarbonyl chloride (96 mg) at room temperature. The mixture was stirred at room temperature for 2 hr. To the mixture was added saturated aqueous sodium hydrogencarbonate solution, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane) to give the title compound (220 mg).

MS: $[M+H]^+$ 415.2.

G) N-((2S,3S)-2-(biphenyl-3-ylmethyl)-1-(cyclobutylcarbonyl)pyrrolidin-3-yl)methanesulfonamide A mixture of N-((2S,3S)-2-(3-bromobenzyl)-1-(cyclobutylcarbonyl)pyrrolidin-3-yl)methanesulfonamide (55 mg), phenylboronic acid (48.4 mg), XPhos Pd G3 (5.60 mg), 1M aqueous tripotassium phosphate solution (0.397 ml) and THF (1 ml) was heated under reflux for 1 hr. The reaction mixture was concentrated under reduced pressure, and the residue was diluted with ethyl acetate. The mixture was washed with saturated aqueous sodium hydrogencarbonate solution, and purified by silica gel column chromatography (methanol/ethyl acetate). The obtained solid was crystallized from ethyl acetate-diisopropyl ether-hexane to give the title compound (31 mg).

$^1$H NMR (300 MHz, $CDCl_3$) δ 1.31-3.01 (11H, m), 3.04-3.79 (4H, m), 3.89-4.74 (3H, m), 7.07-7.63 (10H, m).

Example 262

N-((2S,3S)-1-(cyclobutylcarbonyl)-2-((3'-fluorobiphenyl-3-yl)methyl)pyrrolidin-3-yl)methanesulfonamide A) tert-butyl (2S,3S)-2-((3'-fluorobiphenyl-3-yl) methyl)-3-((methylsulfonyl)amino)pyrrolidine-1-carboxylate A mixture of tert-butyl (2S,3S)-2-(3-bromobenzyl)-3-((methylsulfonyl)amino)pyrrolidine-1-carboxylate (2.38 g), (3-fluorophenyl)boronic acid (1.15 g), XPhos Pd G3 (0.139 g), 1M aqueous tripotassium phosphate solution (16.5 ml) and THE (50 ml) was stirred at 70° C. for 2 hr. The mixture was concentrated under reduced pressure, and the residue was diluted with saturated aqueous sodium hydrogencarbonate solution, and the mixture was extracted with ethyl acetate. The organic layer was washed with saturated brine, dried over anhydrous magnesium sulfate, and concentrated under reduced pressure. The residue was purified by silica gel column chromatography (NH, ethyl acetate/hexane) to give the title compound (2.37 g).

MS: $[M+H-Boc]^+$ 349.3.

B) N-((2S,3S)-2-((3'-fluorobiphenyl-3-yl)methyl) pyrrolidin-3-yl)methanesulfonamide hydrochloride To a mixture of tert-butyl (2S,3S)-2-((3'-fluorobiphenyl-3-yl)methyl)-3-((methylsulfonyl)amino)pyrrolidine-1-carboxylate (2.37 g) and ethyl acetate (10 ml) was added 4M hydrogen chloride/ethyl acetate solution (26.4 ml) at room temperature. The mixture was stirred at room temperature for 2 hr. The mixture was concentrated under reduced pressure, and the obtained solid was collected by filtration with ethyl acetate. The obtained solid was washed with ethyl acetate, and dried to give the title compound (1.88 g).

MS: $[M+H]^+$ 349.3.

C) N-((2S,3S)-1-(cyclobutylcarbonyl)-2-((3'-fluorobiphenyl-3-yl)methyl)pyrrolidin-3-yl)methanesulfonamide To a mixture of N-((2S,3S)-2-((3'-fluorobiphenyl-3-yl) methyl)pyrrolidin-3-yl)methanesulfonamide hydrochloride (1.10 g), TEA (1.45 g) and THF (20 ml) was added dropwise cyclobutanecarbonyl chloride (0.508 g) at 0° C. The mixture was stirred at room temperature for 1 hr. To the mixture was added saturated aqueous sodium hydrogencarbonate solution, and the mixture was concentrated under reduced pressure to remove THF. The remaining aqueous layer was extracted with ethyl acetate. The organic layer was separated, washed with saturated brine, dried over anhydrous magnesium sulfate, and concentrated under reduced pressure. The residue was purified by silica gel column chromatography (ethyl acetate/hexane). The residue was crystallized from ethyl acetate-hexane to give the title compound (1.10 g).

$^1$H NMR (300 MHz, DMSO-$d_6$) δ 0.91-2.41 (9H, m), 2.53-3.05 (5H, m), 3.09-3.58 (2H, m), 3.75-3.96 (1H, m), 4.04-4.46 (1H, m), 7.03-7.77 (9H, m).

Example 266

N-((2S,3S)-2-((3'-fluorobiphenyl-3-yl)methyl)-1-((1-fluorocyclobutyl)carbonyl)pyrrolidin-3-yl)methanesulfonamide A) N-((2S,3S)-2-(3-bromobenzyl)-1-((1-fluorocyclobutyl)carbonyl)pyrrolidin-3-yl)methanesulfonamide To a mixture of N-((2S,3S)-2-(3-bromobenzyl)pyrrolidin-3-yl)methanesulfonamide hydrochloride (100 mg), 1-fluorocyclobutanecarboxylic acid (50 mg) and DME (2 ml) were added HATU (154 mg) and DIPEA (105 mg) at room temperature. The mixture was stirred at room temperature for 2 hr. To the mixture was added saturated aqueous sodium hydrogencarbonate solution, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (109 mg).

MS: $[M+H]^+$ 433.1.

B) N-((2S,3S)-2-((3'-fluorobiphenyl-3-yl)methyl)-1-((1-fluorocyclobutyl)carbonyl)pyrrolidin-3-yl)methanesulfonamide A mixture of N-((2S,3S)-2-(3-bromobenzyl)-1-((1-fluorocyclobutyl)carbonyl)pyrrolidin-3-yl)methanesulfonamide (54.4 mg), (3-fluorophenyl)boronic acid (52.7 mg), XPhos Pd G3 (5.31 mg), 1M tripotassium phosphate (0.377 ml) and THF (1 ml) was stirred at 70° C. for 2 hr. To the mixture was added saturated aqueous sodium hydrogencarbonate solution, and the mixture was extracted with ethyl acetate. The organic layer was separated, washed with saturated brine, dried over anhydrous magnesium sulfate, and concentrated under reduced pressure. The residue was purified by silica gel column chromatography (NH, ethyl acetate/hexane). The residue was crystallized from ethyl acetate-hexane to give the title compound (42.4 mg).

$^1$H NMR (300 MHz, DMSO-$d_6$) δ 1.28-2.41 (7H, m), 2.52-2.64 (1H, m), 2.70-2.86 (4H, m), 3.00 (1H, dd, J=13.8, 6.6 Hz), 3.38-3.63 (2H, m), 3.81-4.00 (1H, m, J=10.2 Hz), 4.37-4.58 (1H, m), 7.12-7.23 (1H, m), 7.24-7.41 (2H, m), 7.43-7.63 (6H, m).

Example 269

N-(cis-1-(cyclobutylcarbonyl)-2-((2-phenyl-1,3-thiazol-4-yl)methyl)pyrrolidin-3-yl)-1-fluoromethanesulfonamide A) tert-butyl cis-3-(((fluoromethyl)sulfonyl)amino)-2-((2-phenyl-1,3-thiazol-4-yl)methyl)pyrrolidine-1-carboxylate To a mixture of tert-butyl cis-3-amino-2-((2-phenyl-1,3-thiazol-4-yl)methyl)pyrrolidine-1-carboxylate (108 mg), DIPEA (58.2 mg) and THF (1 ml) was added fluoromethanesulfonyl chloride (31.8 mg) at 0° C. To the reaction mixture was added water, and the mixture was concentrated under reduced pressure. The residue was diluted with ethyl acetate, and the mixture was washed with saturated brine, dried over anhydrous sodium sulfate, and concentrated under reduced pressure. The residue was purified by silica gel column chromatography (ethyl acetate/hexane) to give the title compound (62.5 mg).

MS: $[M+H]^+$ 456.1.

B) N-(cis-1-(cyclobutylcarbonyl)-2-((2-phenyl-1,3-thiazol-4-yl)methyl)pyrrolidin-3-yl)-1-fluoromethanesulfonamide To a mixture of tert-butyl cis-3-(((fluoromethyl)sulfonyl)amino)-2-((2-phenyl-1,3-thiazol-4-yl)methyl)pyrrolidine-1-carboxylate (31.2 mg) and MeOH (0.200 ml) was added 4M hydrogen chloride/cyclopentyl methyl ether solution (0.342 ml) at room temperature. The mixture was stirred at room temperature for 1 hr, and the reaction solution was concentrated. The residue was mixed with THE (0.7 ml), and TEA (34.7 mg) and cyclobutanecarbonyl chloride (12.2 mg) were added thereto at 0° C. The mixture was stirred at room temperature for 1 hr, and to the mixture was added saturated brine, and the mixture was concentrated under reduced pressure. The residue was purified by silica gel column chromatography (ethyl acetate/hexane) to give the title compound (22.2 mg).

$^1$H NMR (300 MHz, $CDCl_3$) δ ppm 1.35-1.53 (1H, m), 1.81-2.02 (2H, m), 2.14 (5H, br. s.), 3.03-3.39 (4H, m), 3.67 (1H, dd, J=14.8, 5.7 Hz), 4.13-4.28 (1H, m), 4.42-4.59 (1H, m), 4.92-5.32 (2H, m), 6.98 (1H, s), 7.41-7.51 (3H, m), 7.90-8.03 (2H, m), 8.96 (1H, d, J=8.7 Hz)

Example 293

N-(cis-2-((2-fluorobiphenyl-3-yl)methyl)-1-isobutyryl pyrrolidin-3-yl)methanesulfonamide A) 1-bromo-3-(bromomethyl)-2-fluorobenzene To a mixture of (3-bromo-2-fluorophenyl)methanol (5.13 g), $PPh_3$ (7.88 g) and trifluoromethylbenzene (180 ml) was added tetrabromomethane (9.96 g) at 0° C. The mixture was stirred at 0° C. for 2 hr, and the insoluble substance was removed by filtration, and washed with diethyl ether. The filtrate was concentrated under reduced pressure. The residue was purified by silica gel column chromatography (ethyl acetate/hexane) to give the title compound (6.70 g).

$^1$H NMR (300 MHz, $CDCl_3$) δ 4.51 (2H, d, J=1.1 Hz), 7.02 (1H, td, J=8.0, 1.4 Hz), 7.30-7.37 (1H, m), 7.51 (1H, ddd, J=8.1, 6.4, 1.7 Hz).

B) tert-butyl 2-(3-bromo-2-fluorobenzyl)-3-oxopyrrolidine-1-carboxylate

To a mixture of tert-butyl 3-oxopyrrolidine-1-carboxylate (3.30 g) and toluene (28 ml) was added pyrrolidine (1.52 g) at room temperature. The mixture was stirred at room temperature for 30 min, heated under reflux using Dean-Stark apparatus for 30 min, and concentrated under reduced pressure. The residue was mixed with $CH_3CN$ (28 ml), and 1-bromo-3-(bromomethyl)-2-fluorobenzene (4.77 g) and TBAI (1.32 g) were added to the mixture at room temperature. The mixture was heated under reflux for 4.5 hr, and the reaction mixture was poured into water, and the mixture was extracted with ethyl acetate. The organic layer was washed with water and saturated brine, dried over anhydrous magnesium sulfate, and concentrated under reduced pressure. The residue was purified by silica gel column chromatography (ethyl acetate/hexane) to give the title compound (1.71 g).

$^1$H NMR (300 MHz, $CDCl_3$) δ 1.45 (9H, s), 2.12-2.30 (1H, m), 2.44-2.59 (1H, m), 2.97-3.40 (3H, m), 3.74-4.02 (1H, m), 4.21 (1H, t, J=5.1 Hz), 6.89-6.96 (1H, m), 7.05 (1H, t, J=6.7 Hz), 7.43 (1H, ddd, J=8.0, 6.4, 1.9 Hz).

C) tert-butyl cis-3-amino-2-(3-bromo-2-fluorobenzyl)pyrrolidine-1-carboxylate

A mixture of tert-butyl 2-(3-bromo-2-fluorobenzyl)-3-oxopyrrolidine-1-carboxylate (941 mg), ammonium formate (1.28 g), chloro[N-[4-(dimethylamino)phenyl]-2-pyridinecarboxamidato] (pentamethylcyclopentadienyl)iridium(III) (30.5 mg) and MeOH (20 ml) was stirred under argon atmosphere at 70° C. for 2.5 hr. The reaction mixture was poured into saturated aqueous sodium hydrogencarbonate solution under ice-cooling, and the mixture was extracted with ethyl acetate. The organic layer was washed with water and saturated brine, dried over anhydrous magnesium sulfate, and concentrated under reduced pressure. The residue was purified by silica gel column chromatography (methanol/ethyl acetate) to give the title compound (427 mg).

MS: $[M+H-(tBu)]^+$ 316.9.

D) tert-butyl cis-2-(3-bromo-2-fluorobenzyl)-3-((methylsulfonyl)amino)pyrrolidine-1-carboxylate To a mixture of tert-butyl cis-3-amino-2-(3-bromo-2-fluorobenzyl)pyrrolidine-1-carboxylate (421 mg), TEA (228 mg) and THF (4 ml) was added methanesulfonyl chloride (155 mg) at room temperature. The mixture was stirred at room temperature for 1 hr, and the reaction mixture was poured into water, and the mixture was extracted with ethyl acetate. The organic layer was washed with aqueous sodium hydrogencarbonate solution and saturated brine, dried over anhydrous magnesium sulfate, and concentrated under reduced pressure to give crystals. The crystals were collected by filtration, and washed with diisopropyl ether-hexane to give the title compound (437 mg).

MS: $[M-H]^-$ 448.9.

E) N-(cis-2-(3-bromo-2-fluorobenzyl)pyrrolidin-3-yl)methanesulfonamide

To a mixture of tert-butyl cis-2-(3-bromo-2-fluorobenzyl)-3-((methylsulfonyl)amino)pyrrolidine-1-carboxylate (434 mg) and toluene (4.8 ml) was added TFA (4.8 ml) at room temperature. The mixture was stirred at room temperature for 1 hr, and the reaction mixture was poured into saturated aqueous sodium hydrogencarbonate solution under ice-cooling. The mixture was basified to pH=8 with potassium carbonate, and extracted with ethyl acetate. The organic layer was washed with water and saturated brine, dried over anhydrous magnesium sulfate, and concentrated under reduced pressure to give crystals. The crystals were collected by filtration, and washed with diisopropyl ether-hexane to give the title compound (245 mg).

MS: $[M+H]^+$ 350.9.

F) N-(cis-2-(3-bromo-2-fluorobenzyl)-1-isobutyryl pyrrolidin-3-yl)methanesulfonamide To a mixture of N-(cis-2-(3-bromo-2-fluorobenzyl)pyrrolidin-3-yl)methanesulfonamide (120 mg), TEA (104 mg) and THE (3 ml) was added 2-methylpropanoyl chloride (72.8 mg) at room temperature. The mixture was stirred at room temperature for 1 hr, added to aqueous sodium hydrogencarbonate solution, and extracted with THE-ethyl acetate. The organic layer was washed with water and saturated brine, dried over anhydrous magnesium sulfate, and concentrated under reduced pressure to give crystals. The crystals were collected by filtration, and washed with diisopropyl ether-hexane to give the title compound (132 mg).

MS: $[M+H]^+$ 421.0.

G) N-(cis-2-((2-fluorobiphenyl-3-yl)methyl)-1-isobutyryl pyrrolidin-3-yl)methanesulfonamide A mixture of N-(cis-2-(3-bromo-2-fluorobenzyl)-1-isobutyryl pyrrolidin-3-yl)methanesulfonamide (63 mg), phenylboronic acid (36.5 mg), XPhos Pd G3 (6.33 mg), 1 M aqueous tripotassium phosphate solution (0.449 ml) and THF (1.5 ml) was stirred under argon atmosphere at 70° C. for 1 hr. The mixture was poured into aqueous sodium hydrogencarbonate solution, and extracted with THF-ethyl acetate. The organic layer was washed with water and saturated brine, dried over anhydrous magnesium sulfate, and concentrated under reduced pressure. The residue was purified by silica gel column chromatography (methanol/ethyl acetate) to give the title compound (52.8 mg).

$^1$H NMR (300 MHz, $CDCl_3$) δ 0.57-1.14 (6H, m), 1.83-2.13 (1H, m), 2.27-2.41 (1H, m), 2.53-3.20 (6H, m), 3.40-3.55 (2H, m), 3.65-4.11 (1H, m), 4.35-4.67 (1H, m), 4.81-4.89 (1H, m), 7.10-7.20 (1H, m), 7.28-7.54 (7H, m).

Example 294

N-(cis-2-((2,3'-difluorobiphenyl-3-yl)methyl)-1-isobutyryl pyrrolidin-3-yl)methanesulfonamide A mixture of N-(cis-2-(3-bromo-2-fluorobenzyl)-1-isobutyryl pyrrolidin-3-yl)methanesulfonamide (62 mg), (3-fluorophenyl)boronic acid (41.2 mg), Xphos Pd G3 (6.23 mg), 1 M aqueous tripotassium phosphate solution (0.441 ml) and THE (1.5 ml) was stirred under argon atmosphere at 70° C. for 1 hr. The mixture was poured into aqueous sodium hydrogencarbonate solution, and extracted with THE-ethyl acetate. The organic layer was washed with water and saturated brine, dried over anhydrous magnesium sulfate, and concentrated under reduced pressure. The residue was purified by silica gel column chromatography (methanol/ethyl acetate) to give the title compound (53.2 mg).

$^1$H NMR (300 MHz, $CDCl_3$) δ 0.56-1.13 (6H, m), 1.86-2.08 (1H, m), 2.29-2.43 (1H, m), 2.55-3.21 (6H, m), 3.41-

3.78 (2H, m), 3.97-4.11 (1H, m), 4.36-4.67 (1H, m), 4.77-4.86 (1H, m), 7.03-7.11 (1H, m), 7.14-7.23 (2H, m), 7.27-7.51 (4H, m).

Example 299

N-(cis-1-(cyclobutylcarbonyl)-2-((5-fluorobiphenyl-3-yl)methyl)pyrrolidin-3-yl)methanesulfonamide A) tert-butyl 2-(3-bromo-5-fluorobenzyl)-3-oxopyrrolidine-1-carboxylate To a mixture of tert-butyl 3-oxopyrrolidine-1-carboxylate (3.44 g) and toluene (30 ml) was added pyrrolidine (1.59 g) at room temperature. The mixture was stirred at room temperature for 20 min, heated under reflux for 20 min using Dean-Stark apparatus, and concentrated under reduced pressure. The residue was mixed with $CH_3CN$ (30 ml), and 1-bromo-3-(bromomethyl)-5-fluorobenzene (4.98 g) and TBAI (1.37 g) were added to the mixture at room temperature. The mixture was heated under reflux for 4.5 hr, and the reaction mixture was poured into water, and the mixture was extracted with ethyl acetate. The organic layer was washed with water and saturated brine, dried over anhydrous magnesium sulfate, and concentrated under reduced pressure. The residue was purified by silica gel column chromatography (ethyl acetate/hexane) to give the title compound (2.83 g).

MS: $[M+H\text{-}Boc]^+$271.9.

B) tert-butyl cis-3-amino-2-(3-bromo-5-fluorobenzyl)pyrrolidine-1-carboxylate

A mixture of tert-butyl 2-(3-bromo-5-fluorobenzyl)-3-oxopyrrolidine-1-carboxylate (2.82 g), ammonium formate (3.82 g), chloro[N-[4-(dimethylamino)phenyl]-2-pyridinecarboxamidato](pentamethylcyclopentadienyl)iridium(III) (0.069 g) and MeOH (60 ml) was stirred under argon atmosphere at 70° C. for 2.5 hr. The reaction mixture was poured into saturated aqueous sodium hydrogencarbonate solution under ice-cooling, and the mixture was extracted with ethyl acetate. The organic layer was washed with water and saturated brine, dried over anhydrous magnesium sulfate, and concentrated under reduced pressure. The residue was purified by silica gel column chromatography (methanol/ethyl acetate) to give the title compound (1.07 g).

MS: $[M+H-(tBu)]^+$316.9.

C) tert-butyl cis-2-(3-bromo-5-fluorobenzyl)-3-((methylsulfonyl)amino)pyrrolidine-1-carboxylate To a mixture of tert-butyl cis-3-amino-2-(3-bromo-5-fluorobenzyl)pyrrolidine-1-carboxylate (1.06 g), TEA (0.575 g) and THF (10 ml) was added methanesulfonyl chloride (0.390 g) at room temperature. The mixture was stirred at room temperature for 1 hr, and the reaction mixture was poured into water, and the mixture was extracted with ethyl acetate. The organic layer was washed with aqueous sodium hydrogencarbonate solution and saturated brine, dried over anhydrous magnesium sulfate, and concentrated under reduced pressure to give crystals. The crystals were collected by filtration, and washed with diisopropyl ether-hexane to give the title compound (1.09 g).

MS: $[M-H]^-$ 448.8.

D) N-(cis-2-(3-bromo-5-fluorobenzyl)pyrrolidin-3-yl)methanesulfonamide

To a mixture of tert-butyl cis-2-(3-bromo-5-fluorobenzyl)-3-((methylsulfonyl)amino)pyrrolidine-1-carboxylate (1.09 g) and toluene (12 ml) was added TFA (12 ml) at room temperature. The mixture was stirred at room temperature for 1 hr, and poured into saturated aqueous sodium hydrogencarbonate solution under ice-cooling. The mixture was basified to pH=8 with potassium carbonate, and extracted with ethyl acetate. The organic layer was washed with water and saturated brine, dried over anhydrous magnesium sulfate, and concentrated under reduced pressure to give crystals. The crystals were collected by filtration, and washed with diisopropyl ether-hexane to give the title compound (245 mg).

MS: $[M+H]^+$ 350.9.

E) N-(cis-2-(3-bromo-5-fluorobenzyl)-1-(cyclobutylcarbonyl)pyrrolidin-3-yl)methanesulfonamide To a mixture of N-(cis-2-(3-bromo-5-fluorobenzyl)pyrrolidin-3-yl)methanesulfonamide (229 mg), TEA (198 mg) and THE (5.6 ml) was added cyclobutanecarbonyl chloride (155 mg) at room temperature. The mixture was stirred at room temperature for 1 hr, added to aqueous sodium hydrogencarbonate solution, and extracted with THE-ethyl acetate. The organic layer was washed with water and saturated brine, dried over anhydrous magnesium sulfate, and concentrated under reduced pressure to give crystals. The crystals were collected by filtration, and washed with diiscpropyl ether-hexane to give the title compound (261 mg).

MS: $[M+H]^+$ 433.0.

F) N-(cis-1-(cyclobutylcarbonyl)-2-((5-fluorobiphenyl-3-yl)methyl)pyrrolidin-3-yl)methanesulfonamide A mixture of N-(cis-2-(3-bromo-5-fluorobenzyl)-1-(cyclobutylcarbonyl)pyrrolidin-3-yl)methanesulfonamide (128 mg), phenylboronic acid (72.0 mg), XPhos Pd G3 (12.5 mg), 1 M aqueous tripotassium phosphate solution (0.886 ml) and THF (3 ml) was stirred under argon atmosphere at 70° C. for 1 hr. The mixture was poured into aqueous sodium hydrogencarbonate solution, and extracted with THF-ethyl acetate. The organic layer was washed with water and saturated brine, dried over anhydrous magnesium sulfate, and concentrated under reduced pressure. The residue was purified by silica gel column chromatography (methanol/ethyl acetate) to give the title compound (107 mg).

$^1H$ NMR (300 MHz, $CDCl_3$) δ 1.66-2.39 (8H, m), 2.47-3.22 (6H, m), 3.28-3.78 (2H, m), 3.89-4.04 (1H, m), 4.23-4.81 (2H, m), 6.84-7.10 (1H, m), 7.11-7.19 (1H, m), 7.31-7.48 (4H, m), 7.50-7.57 (2H, m).

Example 300

N-(cis-1-(cyclobutylcarbonyl)-2-((3',5-difluorobiphenyl-3-yl)methyl)pyrrolidin-3-yl)methanesulfonamide A mixture of N-(cis-2-(3-bromo-5-fluorobenzyl)-1-(cyclobutylcarbonyl)pyrrolidin-3-yl)methanesulfonamide (126 mg), (3-fluorophenyl)boronic acid (81 mg), XPhos Pd G3 (12.3 mg), 1 M aqueous tripotassium phosphate solution (0.872 ml) and THF (2.9 ml) was stirred under argon atmosphere at 70° C. for 1 hr. The mixture was poured into aqueous sodium hydrogencarbonate solution, and extracted with THF-ethyl acetate. The organic layer was washed with water and saturated brine, dried over anhydrous magnesium sulfate, and concentrated under reduced pressure. The residue was purified by silica gel column chromatography (methanol/ethyl acetate) to give the title compound (118 mg).

$^1$H NMR (300 MHz, $CDCl_3$) δ 1.67-2.38 (8H, m), 2.43-3.22 (6H, m), 3.28-3.82 (2H, m), 3.89-4.06 (1H, m), 4.22-4.66 (1H, m), 4.68-4.84 (1H, m), 6.88-7.24 (4H, m), 7.27-7.45 (3H, m).

Example 303

N-(cis-1-(cyclobutylcarbonyl)-2-((6-fluorobiphenyl-3-yl)methyl)pyrrolidin-3-yl)methanesulfonamide A) tert-butyl 2-(3-bromo-4-fluorobenzyl)-3-oxopyrrolidine-1-carboxylate To a mixture of tert-butyl 3-oxopyrrolidine-1-carboxylate (3.46 g) and toluene (30 ml) was added pyrrolidine (1.59 g) at room temperature. The mixture was stirred at room temperature for 30 min, heated under reflux for 30 min using Dean-Stark apparatus, and concentrated under reduced pressure. The residue was mixed with $CH_3CN$ (30 ml), and 2-bromo-4-(bromomethyl)-1-fluorobenzene (5.00 g) and TBAI (1.38 g) were added to the mixture at room temperature. The mixture was heated under reflux for 4 hr, and the reaction mixture was poured into water, and the mixture was extracted with ethyl acetate. The organic layer was washed with water and saturated brine, dried over anhydrous magnesium sulfate, and concentrated under reduced pressure. The residue was purified by silica gel column chromatography (ethyl acetate/hexane) to give the title compound (1.59 g).

MS: $[M+H-Boc]^+$ 271.9.

B) tert-butyl cis-3-amino-2-(3-bromo-4-fluorobenzyl)pyrrolidine-1-carboxylate

A mixture of tert-butyl 2-(3-bromo-4-fluorobenzyl)-3-oxopyrrolidine-1-carboxylate (1.59 g), ammonium formate (1.35 g), chloro[N-[4-(dimethylamino)phenyl]-2-pyridinecarboxamidato] (pentamethylcyclopentadienyl)iridium(III) (0.026 g) and MeOH (25 ml) was stirred under argon atmosphere at 70° C. for 2.5 hr. The reaction mixture was poured into saturated aqueous sodium hydrogencarbonate solution under ice-cooling, and the mixture was extracted with ethyl acetate. The organic layer was washed with water and saturated brine, dried over anhydrous magnesium sulfate, and concentrated under reduced pressure. The residue was purified by silica gel column chromatography (methanol/ethyl acetate) to give the title compound (548 mg).

MS: $[M+H-(tBu)]^+$ 317.0.

C) tert-butyl cis-2-(3-bromo-4-fluorobenzyl)-3-((methylsulfonyl)amino)pyrrolidine-1-carboxylate To a mixture of tert-butyl cis-3-amino-2-(3-bromo-4-fluorobenzyl)pyrrolidine-1-carboxylate (542 mg), TEA (294 mg) and THF (5.1 ml) was added methanesulfonyl chloride (200 mg) at room temperature. The mixture was stirred at room temperature for 1 hr, and the reaction mixture was poured into water, and the mixture was extracted with ethyl acetate. The organic layer was washed with aqueous sodium hydrogencarbonate solution and saturated brine, dried over anhydrous magnesium sulfate, and concentrated under reduced pressure. The residue was purified by silica gel column chromatography (ethyl acetate/hexane) to give the title compound (482 mg).

MS: $[M-H]^-$ 448.8.

D) N-(cis-2-(3-bromo-4-fluorobenzyl)pyrrolidin-3-yl)methanesulfonamide

To a mixture of tert-butyl cis-2-(3-bromo-4-fluorobenzyl)-3-((methylsulfonyl)amino)pyrrolidine-1-carboxylate (477 mg) and toluene (5.3 ml) was added TFA (5.3 ml) at room temperature. The mixture was stirred at room temperature for 1 hr, and poured into saturated aqueous sodium hydrogencarbonate solution under ice-cooling. The mixture was basified to pH=8 with potassium carbonate, and extracted with ethyl acetate. The organic layer was washed with water and saturated brine, dried over anhydrous magnesium sulfate, and concentrated under reduced pressure to give crystals. The crystals were collected by filtration, and washed with diisopropyl ether-hexane to give the title compound (323 mg).

MS: $[M+H]^+$ 350.9.

E) N-(cis-2-(3-bromo-4-fluorobenzyl)-1-(cyclobutylcarbonyl)pyrrolidin-3-yl)methanesulfonamide To a mixture of N-(cis-2-(3-bromo-4-fluorobenzyl)pyrrolidin-3-yl)methanesulfonamide (160 mg), TEA (138 mg) and THE (3.9 ml) was added cyclobutanecarbonyl chloride (108 mg) at room temperature. The mixture was stirred at room temperature for 1 hr, added to aqueous sodium hydrogencarbonate solution, and extracted with THF-ethyl acetate. The organic layer was washed with water and saturated brine, dried over anhydrous magnesium sulfate, and concentrated under reduced pressure to give crystals. The crystals were collected by filtration, and washed with diisopropyl ether-hexane to give the title compound (149 mg).

MS: $[M+H]^+$ 433.0.

F) N-(cis-1-(cyclobutylcarbonyl)-2-((6-fluorobiphenyl-3-yl)methyl)pyrrolidin-3-yl)methanesulfonamide A mixture of N-(cis-2-(3-bromo-4-fluorobenzyl)-1-(cyclobutylcarbonyl)pyrrolidin-3-yl)methanesulfonamide (72 mg), phenylboronic acid (40.5 mg), XPhos Pd G3 (7.03 mg), 1 M aqueous tripotassium phosphate solution (0.498 ml) and THF (1.7 ml) was stirred under argon atmosphere at 70° C. for 1 hr. The mixture was poured into aqueous sodium hydrogencarbonate solution, and extracted with THF-ethyl acetate. The organic layer was washed with water and saturated brine, dried over anhydrous magnesium sulfate, and concentrated under reduced pressure. The residue was purified by silica gel column chromatography (methanol/ethyl acetate) to give the title compound (61.3 mg).

$^1$H NMR (300 MHz, $CDCl_3$) δ 1.65-2.58 (9H, m), 2.60-3.20 (5H, m), 3.30-3.80 (2H, m), 3.88-4.04 (1H, m), 4.18-4.76 (2H, m), 7.06-7.21 (2H, m), 7.28-7.54 (6H, m).

Example 304

N-(cis-1-(cyclobutylcarbonyl)-2-((3',6-difluorobiphenyl-3-yl)methyl)pyrrolidin-3-yl)methanesulfonamide A mixture of N-(cis-2-(3-bromo-4-fluorobenzyl)-1-(cyclobutylcarbonyl)pyrrolidin-3-yl)methanesulfonamide (71 mg), (3-fluorophenyl)boronic acid (45.9 mg), XPhos Pd G3 (6.93 mg), 1 M aqueous tripotassium phosphate solution (0.492 ml) and THF (1.7 ml) was stirred under argon atmosphere at 70° C. for 1 hr. The mixture was poured into aqueous sodium hydrogencarbonate solution, and extracted with THF-ethyl acetate. The organic layer was washed with water and saturated brine, dried over anhydrous magnesium sulfate, and concentrated under reduced pressure. The residue was purified by silica gel column chromatography (methanol/ethyl acetate) to give crystals. The crystals were collected by filtration, and washed with diisopropyl ether-hexane to give the title compound (59.6 mg).

$^1$H NMR (300 MHz, $CDCl_3$) δ 1.68-2.57 (9H, m), 2.65-3.20 (5H, m), 3.28-3.81 (2H, m), 3.88-4.05 (1H, m), 4.19-4.74 (2H, m), 7.02-7.26 (4H, m), 7.28-7.45 (3H, m).

Example 305

N-((2S,3S)-2-((3'-fluorobiphenyl-3-yl)methyl)-1-((1-methylcyclobutyl)carbonyl)pyrrolidin-3-yl)methanesulfonamide To a mixture of N-((2S,3S)-2-((3'-fluorobiphenyl-3-yl)methyl)pyrrolidin-3-yl)methanesulfonamide hydrochloride (50 mg), 1-methylcyclobutanecarboxylic acid (17.8 mg), TEA (65.7 mg) and DMF (2 mL) was added HATU (59.3 mg) at room temperature, and the mixture was stirred at room temperature for 30 min. To the mixture was added saturated aqueous sodium hydrogencarbonate solution, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane), and crystallized from ethanol and water to give the title compound (50 mg).

$^1$H NMR (300 MHz, $CDCl_3$) δ 1.41 (3H, s), 1.60-2.06 (5H, m), 2.19-2.32 (1H, m), 2.33-2.49 (2H, m), 2.55 (3H, s), 2.85-3.02 (1H, m), 3.09-3.25 (1H, m), 3.26-3.49 (2H, m), 3.86-4.04 (1H, m), 4.35-4.49 (1H, m), 4.60-4.74 (1H, m), 6.92-7.13 (1H, m), 7.27-7.58 (7H, m).

Example 306

N-((2S,3S)-1-(bicyclo[1.1.1]pent-1-ylcarbonyl)-2-((3'-fluorobiphenyl-3-yl)methyl)pyrrolidin-3-yl)methanesulfonamide To a mixture of N-((2S,3S)-2-((3'-fluorobiphenyl-3-yl)methyl)pyrrolidin-3-yl)methanesulfonamide hydrochloride (50 mg), bicyclo[1.1.1]pentane-1-carboxylic acid (17.5 mg), TEA (65.7 mg) and DMF (2 mL) was added HATU (59.3 mg) at room temperature, and the mixture was stirred at room temperature for 30 min. To the mixture was added saturated aqueous sodium hydrogencarbonate solution, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane), and crystallized from ethyl acetate and hexane to give the title compound (10 mg).

$^1$H NMR (300 MHz, $CDCl_3$) δ 1.66-1.94 (2H, m), 2.07-2.34 (6H, m), 2.46-2.60 (3H, m), 2.90-3.23 (2H, m), 3.32-3.82 (3H, m), 3.89-4.07 (1H, m), 4.30-4.47 (1H, m), 4.57-4.70 (1H, m), 6.98-7.10 (1H, m), 7.27-7.55 (7H, m).

Example 307

N-((2S,3S)-1-(bicyclo[1.1.1]pent-1-ylcarbonyl)-2-((3',5'-difluorobiphenyl-3-yl)methyl)pyrrolidin-3-yl)methanesulfonamide

A) N-((2S,3S)-1-(bicyclo[1.1.1]pent-1-ylcarbonyl)-2-(3-bromobenzyl)pyrrolidin-3-yl)methanesulfonamide To a mixture of N-((2S,3S)-2-(3-bromobenzyl)pyrrolidin-3-yl)methanesulfonamide hydrochloride (240 mg), bicyclo[1.1.1]pentane-1-carboxylic acid (80 mg), TEA (328 mg) and DMF (2 mL) was added HATU (296 mg) at room temperature, and the mixture was stirred at room temperature for 30 min. To the mixture was added saturated aqueous sodium hydrogencarbonate solution, and the mixture was extracted with ethyl acetate. The organic layer was separated, washed with saturated brine, dried over anhydrous magnesium sulfate, and concentrated under reduced pressure. The residue was purified by silica gel column chromatography (methanol/ethyl acetate) to give the title compound (270 mg).

MS: $[M+H]^+$ 427.2.

B) N-((2S,3S)-1-(bicyclo[1.1.1]pent-1-ylcarbonyl)-2-((3',5'-difluorobiphenyl-3-yl)methyl)pyrrolidin-3-yl)methanesulfonamide A mixture of N-((2S,3S)-1-(bicyclo[1.1.1]pent-1-ylcarbonyl)-2-(3-bromobenzyl)pyrrolidin-3-yl)methanesulfonamide (55 mg), (3,5-difluorophenyl)boronic acid (61.0 mg), XPhos Pd G3 (5.45 mg), 1M aqueous tripotassium phosphate solution (0.356 mL) and THE (1 mL) was heated under reflux for 1 hr. The mixture was concentrated under reduced pressure, and the residue was diluted with ethyl acetate. The mixture was washed with water and saturated brine, and purified by silica gel column chromatography (ethyl acetate/hexane), and the obtained product was crystallized from ethyl acetate and hexane to give the title compound (25 mg).

$^1$H NMR (300 MHz, $CDCl_3$) δ 1.68-1.87 (2H, m), 2.08-2.35 (6H, m), 2.44-2.65 (3H, m), 2.67-3.87 (5H, m), 3.88-4.05 (1H, m), 4.36-4.51 (1H, m), 4.57-4.67 (1H, m), 6.73-6.86 (1H, m), 7.02-7.12 (2H, m), 7.28-7.50 (4H, m).

Example 308

N-((2S,3S)-2-((3'-fluorobiphenyl-3-yl)methyl)-1-((1-hydroxycyclobutyl)carbonyl)pyrrolidin-3-yl)methanesulfonamide To a mixture of N-((2S,3S)-2-((3'-fluorobiphenyl-3-yl)methyl)pyrrolidin-3-yl)methanesulfonamide hydrochloride (49.6 mg), 1-hydroxycyclobutanecarboxylic acid (18.0 mg) and DMF (1 ml) were added HATU (73.5 mg) and DIPEA (50.0 mg) at room temperature. The mixture was stirred overnight at room temperature. To the mixture was added saturated aqueous sodium hydrogencarbonate solution, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (45.5 mg).

$^1$H NMR (300 MHz, DMSO-$d_6$) δ 1.28 (1H, dd, J=19.1, 8.5 Hz), 1.55-2.14 (5H, m), 2.36-2.46 (2H, m), 2.62-2.74 (3H, m), 2.80 (1H, dd, J=13.6, 4.9 Hz), 2.91-3.06 (1H, m), 3.48-3.68 (2H, m), 3.84 (1H, brs), 4.36-4.72 (1H, m), 5.63-6.07 (1H, m), 7.12-7.23 (1H, m), 7.31-7.42 (2H, m), 7.45-7.57 (5H, m), 7.64 (1H, s).

Example 309

N-((2S,3S)-2-((3'-fluorobiphenyl-3-yl)methyl)-1-((1-(trifluoromethyl)cyclobutyl)carbonyl)pyrrolidin-3-yl)methanesulfonamide To a mixture of N-((2S,3S)-2-((3'-fluorobiphenyl-3-yl) methyl)pyrrolidin-3-yl)methanesulfonamide hydrochloride (51.0 mg), 1-(trifluoromethyl)cyclobutanecarboxylic acid (26.7 mg) and DMF (1 ml) were added HATU (76 mg) and DIPEA (51.4 mg) at room temperature. The mixture was stirred overnight at room temperature. To the mixture was added saturated aqueous sodium hydrogencarbonate solution, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (54.5 mg).

$^1$H NMR (300 MHz, DMSO-$d_6$) δ 1.40 (1H, d, J=10.6 Hz), 1.74-2.08 (2H, m), 2.11-2.37 (4H, m), 2.53-2.66 (1H, m), 2.68-2.83 (4H, m), 2.98 (1H, dd, J=13.8, 6.6 Hz), 3.32-3.41 (1H, m), 3.45-3.61 (1H, m), 3.86 (1H, d, J=9.8 Hz), 4.53 (1H, q, J=7.3 Hz), 7.12-7.24 (1H, m), 7.30-7.41 (2H, m), 7.43-7.56 (4H, m), 7.59 (1H, s), 7.63 (1H, s).

Example 310

N-((2S,3S)-1-(cyclobutylcarbonyl)-2-((3',5'-difluorobiphenyl-3-yl)methyl)pyrrolidin-3-yl)methanesulfonamide A mixture of N-((2S,3S)-2-(3-bromobenzyl)-1-(cyclobutylcarbonyl)pyrrolidin-3-yl)methanesulfonamide (49.5 mg), (3,5-difluorophenyl)boronic acid (28.2 mg), 1M aqueous tripotassium phosphate solution (0.358 ml), XPhos Pd G3 (3.03 mg) and THF (2 ml) was stirred under nitrogen atmosphere at 70° C. for 1 hr. To the mixture was added saturated aqueous sodium hydrogencarbonate solution, and the mixture was extracted with ethyl acetate. The organic layer was separated, washed with saturated brine, dried over anhydrous magnesium sulfate, and concentrated under reduced pressure. The residue was purified by silica gel column chromatography (NH, ethyl acetate/hexane). The obtained solid was crystallized from ethyl acetate/hexane to give the title compound (32.7 mg).

$^1$H NMR (300 MHz, DMSO-$d_6$) δ 0.86-2.40 (9H, m), 2.64-3.30 (6H, m), 3.33-3.58 (1H, m), 3.75-3.98 (1H, m), 4.02-4.46 (1H, m), 7.13-7.69 (8H, m).

Example 311

N-((2S,3S)-1-(cyclobutylcarbonyl)-2-((3'-methylbiphenyl-3-yl)methyl)pyrrolidin-3-yl)methanesulfonamide A mixture of N-((2S,3S)-2-(3-bromobenzyl)-1-(cyclobutylcarbonyl)pyrrolidin-3-yl)methanesulfonamide (51.4 mg), (3-methylphenyl)boronic acid (25.2 mg), 1M aqueous tripotassium phosphate solution (0.371 ml), XPhos Pd G3 (3.14 mg) and THF (2 ml) was stirred under nitrogen atmosphere at 70° C. for 1 hr. To the mixture was added saturated aqueous sodium hydrogencarbonate solution, and the mixture was extracted with ethyl acetate. The organic layer was separated, washed with saturated brine, dried over anhydrous magnesium sulfate, and concentrated under reduced pressure. The residue was purified by silica gel column chromatography (NH, ethyl acetate/hexane) to give the title compound (52.0 mg).

$^1$H NMR (300 MHz, DMSO-$d_6$) δ 0.91-2.36 (8H, m), 2.37 (3H, s), 2.64-3.07 (5H, m), 3.11-3.60 (3H, m), 3.73-3.97 (1H, m), 4.01-4.45 (1H, m), 7.09-7.69 (9H, m).

Example 312

N-((2S,3S)-1-(cyclobutylcarbonyl)-2-((3'-fluorobiphenyl-3-yl)methyl)pyrrolidin-3-yl)-1-methoxymethanesulfonamide A) tert-butyl (2S,3S)-2-(3-bromobenzyl)-3-(((bromomethyl)sulfonyl)amino)pyrrolidine-1-carboxylate To a mixture of tert-butyl (2S,3S)-3-amino-2-(3-bromobenzyl)pyrrolidine-1-carboxylate (900 mg) and THE (3 ml) were added DIPEA (1.33 mL) and bromomethanesulfonyl chloride (0.392 mL) at 0° C. The mixture was stirred for 30 min, and to the mixture was added saturated aqueous sodium hydrogencarbonate solution, and the mixture was extracted with ethyl acetate. The organic layer was separated, dried over anhydrous sodium sulfate, and concentrated under reduced pressure to give the title compound (1.35 g).

MS: $[M-H]^+$ 510.8

B) tert-butyl (2S,3S)-2-(3-bromobenzyl)-3-(((methoxymethyl)sulfonyl)amino)pyrrolidine-1-carboxylate A mixture of tert-butyl (2S,3S)-2-(3-bromobenzyl)-3-(((bromomethyl)sulfonyl)amino)pyrrolidine-1-carboxylate (1.20 g), silver(I) carbonate (3.23 g) and MeOH (3 ml) was heated in a sealed tube to 100° C. The mixture was stirred for 3 hr, and filtered, saturated aqueous sodium hydrogencarbonate solution was added thereto, and the mixture was extracted with ethyl acetate. The organic layer was separated, dried over anhydrous sodium sulfate, and concentrated under reduced pressure. The residue was purified by silica gel column chromatography (ethyl acetate/hexane) to give the title compound (640 mg).

MS: $[M-H]^+$ 460.9

C) tert-butyl (2S,3S)-2-((3'-fluorobiphenyl-3-yl) methyl)-3-(((methoxymethyl)sulfonyl)amino)pyrrolidine-1-carboxylate A mixture of tert-butyl (2S,3S)-2-(3-bromobenzyl)-3-(((methoxymethyl)sulfonyl)amino)pyrrolidine-1-carboxylate (342 mg), (3-fluorophenyl)boronic acid (155 mg), XPhos Pd G3 (125 mg), 1M aqueous tripotassium phosphate solution (1 ml) and THE (1 ml) was stirred at 60° C. for 1 hr. To the mixture was added saturated aqueous sodium hydrogencarbonate solution, and the mixture was extracted with ethyl acetate. The organic layer was separated, dried over anhydrous sodium sulfate, and concentrated under reduced pressure. The residue was purified by silica gel column chromatography (ethyl acetate/hexane) to give the title compound (286 mg).

MS: $[M-H]^+$477.0.

D) N-((2S,3S)-1-(cyclobutylcarbonyl)-2-((3'-fluorobiphenyl-3-yl)methyl)pyrrolidin-3-yl)-1-methoxymethanesulfonamide To tert-butyl (2S,3S)-2-((3'-fluorobiphenyl-3-yl)methyl)-3-(((methoxymethyl)sulfonyl)amino)pyrrolidine-1-carboxylate (58 mg) was added 4M hydrogen chloride/ethyl acetate solution (1 ml), and the mixture was stirred for 1 hr. The reaction solution was concentrated, and to a mixture of the residue and THF (1 ml) were added TEA (0.084 mL) and cyclobutanecarbonyl chloride (17.2 mg) at room temperature. The mixture was stirred for 30 min, and to the mixture was added saturated aqueous sodium hydrogencarbonate solution, and the mixture was extracted with ethyl acetate. The organic layer was separated, dried over anhydrous sodium sulfate, and concentrated under reduced pressure. The residue was purified by silica gel column chromatography (ethyl acetate/hexane) to give the title compound (28 mg).

$^1$H NMR (300 MHz, $CDCl_3$) δ 1.63-2.01 (4H, m), 2.07-2.67 (5H, m), 3.00-3.23 (2H, m), 3.26-3.53 (2H, m), 3.55-3.71 (3H, m), 3.92-4.27 (3H, m), 4.50 (2H, s), 6.93-7.24 (2H, m), 7.29-7.55 (6H, m).

Example 313

N-((2S,3S)-1-(azetidin-1-ylcarbonyl)-2-((3'-fluorobiphenyl-3-yl)methyl)pyrrolidin-3-yl)methanesulfonamide To a mixture of N-((2S,3S)-2-((3'-fluorobiphenyl-3-yl)methyl)pyrrolidin-3-yl)methanesulfonamide hydrochloride (50.2 mg) and THE (2 ml) were added bis(trichloromethyl) carbonate (31.0 mg) and DIPEA (33.7 mg) at 0° C. The mixture was stirred at 0° C. for 10 min, and the reaction solution was concentrated. To the obtained residue were added THF (2 ml) and azetidine (22.3 mg). The mixture was stirred at room temperature for 2 hr. To the mixture was added saturated aqueous sodium hydrogencarbonate solution, and the mixture was extracted with ethyl acetate. The organic layer was separated, washed with water and saturated brine, dried over anhydrous magnesium sulfate, and concentrated under reduced pressure. The residue was purified by silica gel column chromatography (NH, ethyl acetate/hexane). The obtained solid was crystallized from ethyl acetate/hexane to give the title compound (44.7 mg).

$^1$H NMR (300 MHz, DMSO-$d_6$) δ 1.79-2.02 (3H, m), 2.08 (1H, dt, J=7.5, 4.0 Hz), 2.68-2.79 (1H, m), 2.83 (3H, s), 2.86-2.97 (1H, m), 3.09-3.22 (1H, m), 3.26-3.38 (1H, m), 3.60 (2H, q, J=7.6 Hz), 3.79 (3H, q, J=7.6 Hz), 4.28 (1H, q, J=6.7 Hz), 7.12-7.23 (1H, m), 7.26-7.32 (1H, m), 7.32-7.41 (1H, m), 7.44-7.55 (5H, m), 7.57 (1H, s).

Example 314

N-((2S,3S)-2-((3'-fluorobiphenyl-3-yl)methyl)-1-((1-methoxycyclobutyl)carbonyl)pyrrolidin-3-yl)methanesulfonamide To a mixture of N-((2S,3S)-2-((3'-fluorobiphenyl-3-yl)methyl)pyrrolidin-3-yl)methanesulfonamide hydrochloride (50 mg), 1-methoxycyclobutanecarboxylic acid (20.3 mg), TEA (65.7 mg) and DMF (2 mL) was added HATU (59.3 mg) at room temperature, and the mixture was stirred at room temperature for 30 min. To the mixture was added saturated aqueous sodium hydrogencarbonate solution, and the mixture was extracted with so ethyl acetate. The organic layer was separated, washed with saturated brine, dried over anhydrous magnesium sulfate, and concentrated under reduced pressure. The residue was purified by silica gel column chromatography (ethyl acetate/hexane), and crystallized from ethyl acetate, diisopropyl ether and hexane to give the title compound (53 mg).

$^1$H NMR (300 MHz, $CDCl_3$) δ 1.60-2.03 (3H, m), 2.03-2.20 (2H, m), 2.20-2.37 (1H, m), 2.42-2.61 (5H, m), 2.85-2.98 (1H, m), 3.08 (3H, s), 3.19-3.30 (1H, m), 3.52-3.66 (2H, m), 3.91-4.09 (1H, m), 4.36-4.48 (1H, m), 4.68-4.80 (1H, m), 6.98-7.09 (1H, m), 7.26-7.48 (6H, m), 7.53-7.58 (1H, m).

Example 315

N-(cis-1-(cyclobutylcarbonyl)-2-((2-(3,5-difluorophenyl)-1,3-thiazol-4-yl)methyl)pyrrolidin-3-yl)ethanesulfonamide A) tert-butyl cis-2-((2-bromo-1,3-thiazol-4-yl)methyl)-3-((ethylsulfonyl)amino)pyrrolidine-1-carboxylate To a mixture of tert-butyl cis-3-amino-2-((2-bromo-1,3-thiazol-4-yl)methyl)pyrrolidine-1-carboxylate (500 mg), TEA (209 mg) and THF (5 mL) was added ethanesulfonyl chloride (213 mg) at room temperature. The mixture was stirred at room temperature for 1 hr, and diluted with ethyl acetate. The insoluble substance was removed by filtration, and the filtrate was concentrated under reduced pressure. The residue was purified by silica gel column chromatography (ethyl acetate/hexane) to give the title compound (610 mg).

MS: $[M+H]^+$ 454.1.

B) tert-butyl cis-2-((2-(3,5-difluorophenyl)-1,3-thiazol-4-yl)methyl)-3-((ethylsulfonyl)amino)pyrrolidine-1-carboxylate A mixture of tert-butyl cis-2-((2-bromo-1,3-thiazol-4-yl)methyl)-3-((ethylsulfonyl)amino)pyrrolidine-1-carboxylate (610 mg), (3,5-difluorophenyl)boronic acid (318 mg), $(A\text{-}taPhos)_2PdCl_2$ (90 mg), potassium carbonate (371 mg), DME (4.8 mL) and water (1.6 mL) was stirred under nitrogen atmosphere at 90° C. for 30 min. The mixture was purified by silica gel column chromatography (NH, ethyl acetate/hexane) to give the title compound (595 mg).

MS: $[M+H]^+$ 488.3.

C) N-(cis-2-((2-(3,5-difluorophenyl)-1,3-thiazol-4-yl)methyl)pyrrolidin-3-yl)ethanesulfonamide dihydrochloride To a mixture of tert-butyl cis-2-((2-(3,5-difluorophenyl)-1,3-thiazol-4-yl)methyl)-3-((ethylsulfonyl)amino)pyrrolidine-1-carboxylate (595 mg) and MeOH (2 mL) was added 4M hydrogen chloride/cyclopentyl methyl ether solution (8 mL) at room temperature. The mixture was stirred at room temperature for 30 min, and the reaction mixture was concentrated to give the title compound (560 mg).

MS: $[M+H]^+$ 388.2.

D) N-(cis-1-(cyclobutylcarbonyl)-2-((2-(3,5-difluorophenyl)-1,3-thiazol-4-yl)methyl)pyrrolidin-3-yl)ethanesulfonamide To a mixture of N-(cis-2-((2-(3,5-difluorophenyl)-1,3-thiazol-4-yl)methyl)pyrrolidin-3-yl)ethanesulfonamide dihydrochloride (100 mg), TEA (110 mg) and THE (2 mL) was added cyclobutanecarbonyl chloride (38.6 mg) at room temperature. The mixture was stirred at room temperature for 1 hr, and the reaction mixture was diluted with ethyl acetate. The insoluble substance was removed by filtration, and the filtrate was concentrated under reduced pressure. The residue was purified by silica gel column chromatography (ethyl acetate/hexane) to give the title compound (73 mg).

$^1$H NMR (300 MHz, DMSO-$d_6$) δ 1.16 (3H, s), 1.28-2.23 (8H, m), 2.65-3.47 (7H, m), 3.77-3.96 (1H, m), 4.15-4.49 (1H, m), 7.31-7.74 (5H, m).

Example 316

N-(cis-2-((2-(3,5-difluorophenyl)-1,3-thiazol-4-yl)methyl)-1-((1-methylcyclobutyl)carbonyl)pyrrolidin-3-yl)ethanesulfonamide To a mixture of N-(cis-2-((2-(3,5-difluorophenyl)-1,3-thiazol-4-yl)methyl)pyrrolidin-3-yl)ethanesulfonamide dihydrochloride (100 mg), 1-methylcyclobutanecarboxylic acid (29.8 mg), TEA (110 mg) and DMF (2 mL) was added HATU (99 mg) at room temperature, and the mixture was stirred at room temperature for 30 min. To the mixture was added saturated aqueous sodium hydrogencarbonate solution, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane), and crystallized from ethyl acetate, diisopropyl ether and hexane to give the title compound (68 mg).

$^1$H NMR (300 MHz, DMSO-$d_6$) δ 1.08-1.30 (6H, m), 1.35-1.51 (1H, m), 1.55-1.69 (2H, m), 1.70-1.93 (2H, m), 2.04-2.21 (2H, m), 2.24-2.39 (1H, m), 2.82-3.30 (6H, m), 3.75-3.94 (1H, m), 4.39-4.53 (1H, m), 7.31-7.44 (1H, m), 7.48 (1H, s), 7.52-7.69 (3H, m).

Example 317

N-(cis-2-((2-(3,5-difluorophenyl)-1,3-thiazol-4-yl)methyl)-1-((1-hydroxycyclobutyl)carbonyl)pyrrolidin-3-yl)ethanesulfonamide To a mixture of N-(cis-2-((2-(3,5-difluorophenyl)-1,3-thiazol-4-yl)methyl)pyrrolidin-3-yl)ethanesulfonamide dihydrochloride (100 mg), 1-hydroxycyclobutanecarboxylic acid (30.3 mg), TEA (110 mg) and DMF (2 mL) was added HATU (99 mg) at room temperature, and the mixture was stirred at room temperature for 30 min. To the mixture was added saturated aqueous sodium hydrogencarbonate solution, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane), and crystallized from ethyl acetate, diisopropyl ether and hexane to give the title compound (56 mg).

$^1$H NMR (300 MHz, DMSO-$d_6$) δ 1.16 (3H, t, J=7.4 Hz), 1.22-1.49 (1H, m), 1.55-1.82 (2H, m), 1.83-2.17 (3H, m), 2.31-2.47 (2H, m), 2.87-3.28 (4H, m), 3.37-3.52 (1H, m), 3.54-3.71 (1H, m), 3.73-3.94 (1H, m), 4.39-4.57 (1H, m), 5.73 (1H, s), 7.31-7.43 (1H, m), 7.47 (1H, s), 7.51-7.58 (1H, m), 7.59-7.68 (2H, m).

Example 318

N-(cis-1-(bicyclo[1.1.1]pent-1-ylcarbonyl)-2-((2-(3,5-difluorophenyl)-1,3-thiazol-4-yl)methyl)pyrrolidin-3-yl)ethanesulfonamide To a mixture of N-(cis-2-((2-(3,5-difluorophenyl)-1,3-thiazol-4-yl)methyl)pyrrolidin-3-yl)ethanesulfonamide dihydrochloride (100 mg), bicyclo[1.1.1]pentane-1-carboxylic acid (29.2 mg), TEA (110 mg) and DMF (2 mL) was added HATU (99 mg) at room temperature, and the mixture was stirred at room temperature for 30 min. To the mixture was added saturated aqueous sodium hydrogencarbonate solution, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane), and crystallized from ethyl acetate, diisopropyl ether and hexane to give the title compound (41 mg)

$^1$H NMR (300 MHz, DMSO-$d_6$) b 1.11-1.21 (3H, m), 1.63-2.03 (7H, m), 2.05-2.19 (1H, m), 2.22-2.42 (1H, m), 2.75-3.55 (6H, m), 3.75-3.96 (1H, m), 4.34-4.60 (1H, m), 7.27-7.69 (5H, m).

Example 319

N-(cis-1-(cyclobutylcarbonyl)-2-((2-phenyl-1,3-thiazol-4-yl)methyl)pyrrolidin-3-yl)methanesulfonamide A) tert-butyl cis-3-((methylsulfonyl)amino)-2-((2-phenyl-1,3-thiazol-4-yl)methyl)pyrrolidine-1-carboxylate To a mixture of tert-butyl cis-3-amino-2-((2-phenyl-1,3-thiazol-4-yl)methyl)pyrrolidine-1-carboxylate (45.3 mg), TEA (25.5 mg) and THE (1 mL) was added methanesulfonic anhydride (28.5 mg) at 0° C., and the reaction solution was concentrated under reduced pressure. The residue was purified by silica gel column chromatography (ethyl acetate/hexane) to give the title compound (44.3 mg).

MS: $[M+H]^+$ 438.2.

B) N-(cis-1-(cyclobutylcarbonyl)-2-((2-phenyl-1,3-thiazol-4-yl)methyl)pyrrolidin-3-yl)methanesulfonamide A mixture of tert-butyl cis-3-((methylsulfonyl)amino)-2-((2-phenyl-1,3-thiazol-4-yl)methyl)pyrrolidine-1-carboxylate (44.3 mg), 4M hydrogen chloride/cyclopentyl methyl ether solution (0.506 mL) and MeOH (0.25 mL) was stirred at room temperature for 30 min, and the reaction solution was concentrated under reduced pressure. The residue was suspended in THF (0.8 mL), and TEA (51.2 mg) and cyclobutanecarbonyl chloride (18.0 mg) were added thereto at 0° C. The mixture was stirred at room temperature for 1 hr, saturated brine was added thereto, and the mixture was concentrated under reduced pressure. The residue was purified by silica gel column chromatography (methanol/ethyl acetate) to give the title compound (32.9 mg).

$^1H$ NMR (400 MHz, $CDCl_3$) δ 1.32-1.51 (1H, m), 1.82-2.03 (2H, m), 2.07-2.59 (5H, m), 2.96-3.03 (3H, m), 3.07-3.41 (4H, m), 3.55-3.67 (1H, m), 4.02-4.09 (1H, m), 4.29-4.58 (1H, m), 6.84-7.04 (1H, m), 7.39-7.53 (3H, m), 7.88-8.00 (2H, m), 8.29 (1H, d, J=9.5 Hz).

Example 320

N-((2S,3S)-1-(cyclobutylcarbonyl)-2-((2-(3-fluorophenyl)-1,3-thiazol-4-yl)methyl)pyrrolidin-3-yl) methanesulfonamide A racemate (123 mg) of N-(cis-1-(cyclobutylcarbonyl)-2-((2-(3-fluorophenyl)-1,3-thiazol-4-yl)methyl)pyrrolidin-3-yl)methanesulfonamide was resolved by HPLC (column: CHIRALPAK OD (IK001), 50 mmID×500 mmL, Manufactured by Daicel Chemical Industries, mobile phase: hexane/ethanol=600/400) to give a compound having a shorter retention time. The obtained compound was triturated in diethyl ether/hexane to give the title compound (43.2 mg).

$^1H$ NMR (300 MHz, $CDCl_3$) δ 1.35-1.50 (1H, m), 1.82-2.47 (7H, m), 2.95-3.40 (7H, m), 3.61 (1H, dd, J=14.7, 6.0 Hz), 3.88-4.19 (1H, m), 4.30-4.57 (1H, m), 6.89-7.05 (1H, m), 7.10-7.20 (1H, m), 7.40-7.50 (1H, m), 7.59-7.68 (1H, m), 7.70-7.78 (1H, m), 8.12 (1H, d, J=9.1 Hz).

Example 321

N-((2S,3S)-1-(cyclobutylcarbonyl)-2-((2-phenyl-1,3-thiazol-4-yl)methyl)pyrrolidin-3-yl)cyclopropanesulfonamide A racemate (234 mg) of N-(cis-1-(cyclobutylcarbonyl)-2-((2-phenyl-1,3-thiazol-4-yl)methyl)pyrrolidin-3-yl)cyclopropanesulfonamide was resolved by HPLC (column: CHIRALPAK AS (CC001), 50 mmID×500 mmL, Manufactured by Daicel Chemical Industries, mobile phase: hexane/ethanol=700/300) to give a compound having a longer retention time. The obtained compound was triturated in diethyl ether/hexane to give the title compound (42.6 mg).

$^1H$ NMR (300 MHz, $CDCl_3$) δ 0.80-1.44 (5H, m), 1.81-2.50 (8H, m), 3.02-3.39 (4H, m), 3.65 (1H, dd, J=14.8, 5.7 Hz), 4.03-4.21 (1H, m), 4.43-4.57 (1H, m), 6.89-6.97 (1H, m), 7.41-7.57 (3H, m), 7.90-7.96 (2H, m), 8.11 (1H, d, J=9.8 Hz).

Example 322

N-(cis-2-((2-(3,5-difluorophenyl)-1,3-thiazol-4-yl) methyl)-1-((1-methylcyclobutyl)carbonyl)pyrrolidin-3-yl)methanesulfonamide A) tert-butyl cis-2-((2-(3,5-difluorophenyl)-1,3-thiazol-4-yl)methyl)-3-((methylsulfonyl)amino)pyrrolidine-1-carboxylate A mixture of tert-butyl cis-2-((2-bromo-1,3-thiazol-4-yl) methyl)-3-((methylsulfonyl)amino)pyrrolidine-1-carboxylate (430 mg), (3,5-difluorophenyl)boronic acid (231 mg), $(A\text{-}taPhos)_2PdCl_2$ (32.8 mg), potassium carbonate (270 mg), DME (4 mL) and water (1 mL) was stirred under nitrogen atmosphere at 80° C. for 30 min. The reaction solution was concentrated under reduced pressure, and the residue was purified by silica gel column chromatography (ethyl acetate/hexane) to give the title compound (379 mg).

MS: $[M+H]^+$ 474.1.

B) N-(cis-2-((2-(3,5-difluorophenyl)-1,3-thiazol-4-yl)methyl)pyrrolidin-3-yl)methanesulfonamide dihydrochloride A mixture of tert-butyl cis-2-((2-(3,5-difluorophenyl)-1,3-thiazol-4-yl)methyl)-3-((methylsulfonyl)amino)pyrrolidine-1-carboxylate (379 mg), 4M hydrogen chloride/cyclopentyl methyl ether solution (4 mL) and MeOH (2 mL) was stirred at room temperature for 1 hr, and the reaction solution was concentrated under reduced pressure to give the title compound (420 mg).

MS: $[M+H]^+$ 374.0.

C) N-(cis-2-((2-(3,5-difluorophenyl)-1,3-thiazol-4-yl)methyl)-1-((1-methylcyclobutyl)carbonyl)pyrrolidin-3-yl)methanesulfonamide To a mixture of N-(cis-2-((2-(3,5-difluorophenyl)-1,3-thiazol-4-yl)methyl)pyrrolidin-3-yl)methanesulfonamide dihydrochloride (80 mg) and DMF (1 mL) were added TEA (0.106 mL), 1-methylcyclobutanecarboxylic acid (20.9 mg) and HATU (69.5 mg) at room temperature. The mixture was stirred for 1 hr, and to the mixture was added saturated aqueous sodium hydrogencarbonate solution, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane) to give the title compound (60.7 mg).

$^1H$ NMR (300 MHz, $CDCl_3$) δ 1.33 (3H, s), 1.64-1.85 (4H, m), 1.88-2.00 (1H, m), 2.06-2.20 (1H, m), 2.22-2.55 (2H, m), 2.98-3.31 (6H, m), 3.68 (1H, dd, J=14.7, 6.4 Hz), 4.01-4.24 (1H, m), 4.51 (1H, t, J=6.6 Hz), 6.76-7.00 (1H, m), 7.08 (1H, s), 7.38-7.63 (2H, m), 8.21 (1H, d, J=8.7 Hz).

Example 323

N-(cis-2-((2-(3,5-difluorophenyl)-1,3-thiazol-4-yl) methyl)-1-((1-hydroxycyclobutyl)carbonyl)pyrrolidin-3-yl)methanesulfonamide To a mixture of N-(cis-2-((2-(3,5-difluorophenyl)-1,3-thiazol-4-yl)methyl)pyrrolidin-3-yl)methanesulfonamide dihydrochloride (80 mg) and DMF (1 mL) were added TEA (0.106 mL), 1-hydroxycyclobutanecarboxylic acid (21.2 mg) and HATU (69.5 mg) at room temperature. The mixture was stirred for 1 hr, and to the mixture was added saturated aqueous sodium hydrogencarbonate solution, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane) to give the title compound (65 mg).

$^1H$ NMR (300 MHz, $CDCl_3$) δ 1.41-1.56 (1H, m), 1.63-1.74 (1H, m), 1.88-2.23 (4H, m), 2.35-2.40 (1H, m), 2.42-2.58 (1H, m), 2.58-2.78 (1H, m), 3.02 (3H, s), 3.19 (1H, d, J=14.7 Hz), 3.29-3.43 (1H, m), 3.45-3.74 (2H, m), 3.98-4.27

(1H, m), 4.53 (1H, t, J=6.6 Hz), 6.79-6.95 (1H, m), 7.10 (1H, s), 7.41-7.54 (2H, m), 8.02 (1H, d, J=9.0 Hz).

Example 324

N-((2S,3S)-2-(biphenyl-3-ylmethyl)-1-(cyclobutylcarbonyl)pyrrolidin-3-yl)-1-methoxymethanesulfonamide A) tert-butyl (2S,3S)-2-(biphenyl-3-ylmethyl)-3-(((methoxymethyl)sulfonyl)amino)pyrrolidine-1-carboxylate A mixture of tert-butyl (2S,3S)-2-(3-bromobenzyl)-3-(((methoxymethyl)sulfonyl)amino)pyrrolidine-1-carboxylate (200 mg), phenylboronic acid (79 mg), XPhos Pd G3 (73.2 mg), 1M aqueous tripotassium phosphate solution (1 ml) and THF (1 ml) was stirred at 60° C. for 30 min. To the mixture was added saturated aqueous sodium hydrogencarbonate solution, and the mixture was extracted with ethyl acetate. The organic layer was separated, dried over anhydrous sodium sulfate, and concentrated under reduced pressure. The residue was purified by silica gel column chromatography (ethyl acetate/hexane) to give the title compound (188 mg).

MS: $[M-H]^+$459.0.

B) N-((2S,3S)-2-(biphenyl-3-ylmethyl)-1-(cyclobutylcarbonyl)pyrrolidin-3-yl)-1-methoxymethanesulfonamide To tert-butyl (2S,3S)-2-(biphenyl-3-ylmethyl)-3-(((methoxymethyl)sulfonyl)amino)pyrrolidine-1-carboxylate (70.2 mg) was added 4M hydrogen chloride/ethyl acetate solution (1 mL) at room temperature. The mixture was stirred for 1.5 hr, and the reaction solution was concentrated under reduced pressure. To the obtained residue were added THE (1 mL), TEA (0.106 mL) and cyclobutanecarbonyl chloride (21.7 mg). The mixture was stirred at room temperature for 1 hr. To the mixture was added saturated aqueous sodium hydrogencarbonate solution, and the mixture was extracted with ethyl acetate. The organic layer was separated, dried over anhydrous sodium sulfate, and concentrated under reduced pressure. The residue was purified by silica gel column chromatography (ethyl acetate/hexane) to give the title compound (12.3 mg).

$^1H$ NMR (300 MHz, $CDCl_3$) δ 1.62-2.03 (4H, m), 2.15 (4H, dd, J=8.1, 4.7 Hz), 3.13 (2H, s), 3.27-3.38 (1H, m), 3.41-3.51 (1H, m), 3.52-3.72 (4H, m), 4.08 (2H, s), 4.19 (1H, s), 4.37-4.71 (2H, m), 7.32-7.67 (9H, m).

Example 328

N-((2S,3S)-2-((3'-fluorobiphenyl-3-yl)methyl)-1-(oxetan-2-ylcarbonyl)pyrrolidin-3-yl)methanesulfonamide To a mixture of N-((2S,3S)-2-((3'-fluorobiphenyl-3-yl)methyl)pyrrolidin-3-yl)methanesulfonamide hydrochloride (50 mg), oxetane-2-carboxylic acid (15.9 mg), TEA (65.7 mg) and DMF (1 mL) was added HATU (59.3 mg) at room temperature, and the mixture was stirred at room temperature for 30 min. To the mixture was added saturated aqueous sodium hydrogencarbonate solution, and the mixture was extracted with ethyl acetate. The organic layer was separated, washed with saturated brine, dried over anhydrous magnesium sulfate, and concentrated under reduced pressure. The residue was purified by silica gel column chromatography (methanol/ethyl acetate), and crystallized from ethyl acetate, diisopropyl ether and hexane to give the title compound (40 mg).

$^1H$ NMR (300 MHz, DMSO-$d_6$) δ 1.75-2.44 (4H, m), 2.54-3.10 (6H, m), 3.15-4.04 (3H, m), 4.15-4.57 (3H, m), 7.11-7.69 (9H, m).

Example 333

N-(cis-1-(azetidin-1-ylcarbonyl)-2-((6-(3-fluorophenyl)pyridin-2-yl)methyl)pyrrolidin-3-yl)methanesulfonamide A) (6-(3-fluorophenyl)pyridin-2-yl)methanol A mixture of (6-bromopyridin-2-yl)methanol (10.0 g), (3-fluorophenyl)boronic acid (12.0 g), $(A\text{-}taPhos)_2PdCl_2$ (2.10 g), 2M aqueous sodium carbonate solution (100 mL) and DME (300 mL) was stirred under nitrogen atmosphere at 70° C. for 5 hr. The reaction mixture was poured into water, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (10.8 g).

MS: $[M+H]^+$ 204.2.

B) 2-(bromomethyl)-6-(3-fluorophenyl)pyridine

To a mixture of (6-(3-fluorophenyl)pyridin-2-yl)methanol (10.8 g) and THF (300 mL) was added phosphorous tribromide (43.2 g) at 0° C. The mixture was stirred under nitrogen atmosphere overnight at room temperature. The reaction mixture was poured into ice water, and the mixture was extracted with ethyl acetate. The organic layer was separated, washed with saturated aqueous sodium hydrogencarbonate solution and water, dried over anhydrous magnesium sulfate, and concentrated under reduced pressure. The residue was purified by silica gel column chromatography (ethyl acetate/hexane) to give the title compound (13.5 g).

MS: $[M+H]^+$ 265.9.

C) tert-butyl 2-((6-(3-fluorophenyl)pyridin-2-yl)methyl)-3-oxopyrrolidine-1-carboxylate A mixture of pyrrolidine (7.74 g), tert-butyl 3-oxopyrrolidine-1-carboxylate (17.5 g) and toluene (200 mL) was refluxed overnight. The mixture was concentrated under reduced pressure. To a mixture of the obtained residue, TBAI (3.75 g) and $CH_3CN$ (200 mL) was added a solution of 2-(bromomethyl)-6-(3-fluorophenyl)pyridine (13.5 g) in $CH_3CN$ (200 mL) at 80° C. The mixture was stirred under nitrogen atmosphere at 80° C. for 3 hr. The reaction mixture was poured into water at room temperature, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (16.0 g).

MS: $[M+H]^+$ 371.1.

D) tert-butyl cis-3-amino-2-((6-(3-fluorophenyl)pyridin-2-yl)methyl)pyrrolidine-1-carboxylate A mixture of ammonium formate (40 g), chloro[N-[4-(dimethylamino)phenyl]-2-pyridinecarboxamidato] (pentamethylcyclopentadienyl)iridium(III) (0.521 g), tert-butyl 2-((6-(3-fluorophenyl)pyridin-2-yl)methyl)-3-oxopyrrolidine-1-carboxylate (16.0 g) and MeOH (500 mL) was refluxed for 5 hr. The reaction mixture was concentrated, and the residue was poured into saturated brine at room temperature, and the mixture was extracted with ethyl acetate. The organic layer was washed with saturated aqueous sodium hydrogencarbonate solution, dried over anhydrous magnesium sulfate, and concentrated under reduced pressure. The residue was purified by silica gel column chromatography (methanol/ethyl acetate) to give the title compound (9.00 g).

MS: $[M+H]^+$ 372.1.

E) tert-butyl cis-2-((6-(3-fluorophenyl)pyridin-2-yl)methyl)-3-((methylsulfonyl)amino)pyrrolidine-1-carboxylate To a mixture of tert-butyl cis-3-amino-2-((6-(3-fluorophenyl)pyridin-2-yl)methyl)pyrrolidine-1-carboxylate (1.10 g), TEA (653 mg) and THE (30 mL) was added methanesulfonic anhydride (690 mg) at 0° C. The mixture was stirred at room temperature for 30 min, and the reaction mixture was concentrated under reduced pressure. The residue was purified by silica gel column chromatography (ethyl acetate/hexane) to give the title compound (1.14 g).

MS: $[M+H]^+$ 450.1.

F) N-(cis-2-((6-(3-fluorophenyl)pyridin-2-yl)methyl)pyrrolidin-3-yl)methanesulfonamide dihydrochloride To a mixture of tert-butyl cis-2-((6-(3-fluorophenyl)pyridin-2-yl)methyl)-3-((methylsulfonyl)amino)pyrrolidine-1-carboxylate (1.10 g) and cyclopentyl methyl ether (10 mL) was added 4M hydrogen chloride/cyclopentyl methyl ether solution (10 mL) at 0° C. The mixture was stirred overnight under nitrogen atmosphere at room temperature, and the reaction mixture was concentrated to give the title compound (1.00 g).

MS: $[M+H]^+$ 350.0.

G) N-(cis-1-(azetidin-1-ylcarbonyl)-2-((6-(3-fluorophenyl)pyridin-2-yl)methyl)pyrrolidin-3-yl)methanesulfonamide To a mixture of bis(trichloromethyl) carbonate (69.5 mg) and THF (7 mL) was added a mixture of N-(cis-2-((6-(3-fluorophenyl)pyridin-2-yl)methyl)pyrrolidin-3-yl)methanesulfonamide dihydrochloride (120 mg), DIPEA (148 mg) and THF (7 mL) at 0° C. The mixture was stirred at 0° C. for 20 min, and concentrated under reduced pressure to give an intermediate. To a mixture of the obtained intermediate and THF (7 mL) was added azetidine (85 mg) at 0° C. The mixture was stirred under nitrogen atmosphere at room temperature for 1 hr, and concentrated under reduced pressure. The residue was purified by silica gel column chromatography (methanol/ethyl acetate) to give the title compound (85 mg).

$^1H$ NMR (300 MHz, $CDCl_3$) δ 1.24-1.46 (1H, m), 1.94-2.09 (1H, m), 2.11-2.30 (2H, m), 2.85 (3H, s), 2.97-3.19 (2H, m), 3.23-3.37 (1H, m), 3.43-3.60 (1H, m), 3.69-3.84 (2H, m), 3.91-4.15 (3H, m), 4.44-4.62 (1H, m), 7.05-7.25 (2H, m), 7.41-7.86 (5H, m), 8.47-8.67 (1H, m).

Example 338

N-(cis-2-((6-(3-fluorophenyl)pyridin-2-yl)methyl)-1-((1-hydroxycyclobutyl)carbonyl)pyrrolidin-3-yl)methanesulfonamide To a mixture of N-(cis-2-((6-(3-fluorophenyl)pyridin-2-yl)methyl)pyrrolidin-3-yl)methanesulfonamide dihydrochloride (51.1 mg), 1-hydroxycyclobutanecarboxylic acid (24.3 mg), TEA (72.6 mg) and DMF (1.0 mL) was added HATU (54.2 mg) at room temperature. The mixture was stirred at room temperature for 1 hr, to the reaction mixture was added saturated aqueous sodium hydrogencarbonate solution, and the mixture was extracted with ethyl acetate. The organic layer was separated, washed with water and saturated brine, dried over sodium sulfate, and concentrated under reduced pressure. The residue was purified by silica gel column chromatography (ethyl acetate/hexane), triturated in diethyl ether and hexane to give the title compound (27.3 mg).

$^1H$ NMR (300 MHz, $CDCl_3$) δ 1.29-1.43 (1H, m), 1.58-1.74 (1H, m), 1.86-2.21 (5H, m), 2.38-2.53 (1H, m), 2.61-2.95 (4H, m), 3.21-3.37 (2H, m), 3.41-3.58 (1H, m), 3.72 (1H, dd, J=14.0, 6.4 Hz), 4.05-4.21 (1H, m), 4.62 (1H, t, J=6.6 Hz), 7.10-7.21 (2H, m), 7.43-7.83 (5H, m), 8.73 (1H, d, J=8.7 Hz).

Example 339

N-((2S,3S)-2-((2-(3,5-difluorophenyl)-1,3-thiazol-4-yl)methyl)-1-((1-hydroxycyclobutyl)carbonyl)pyrrolidin-3-yl)methanesulfonamide A) tert-butyl (2S,3S)-3-amino-2-((2-bromo-1,3-thiazol-4-yl)methyl)pyrrolidine-1-carboxylate A racemate (550 mg) of tert-butyl cis-3-amino-2-((2-bromo-1,3-thiazol-4-yl)methyl)pyrrolidine-1-carboxylate was resolved by HPLC (column: CHIRALPAK AD (NF001), 50 mmID×500 mmL, Manufactured by Daicel Chemical Industries, mobile phase: hexane/ethanol=850/150) to give the title compound (207 mg) having a shorter retention time.

MS: $[M+H]^+$ 362.1.

B) tert-butyl (2S,3S)-2-((2-bromo-1,3-thiazol-4-yl)methyl)-3-((methylsulfonyl)amino)pyrrolidine-1-carboxylate To a mixture of tert-butyl (2S,3S)-3-amino-2-((2-bromo-1,3-thiazol-4-yl)methyl)pyrrolidine-1-carboxylate (150 mg) and THE (1 mL) were added TEA (126 mg) and methanesulfonic anhydride (87 mg) at room temperature. The mixture was stirred for 30 min, and to the mixture was added saturated aqueous sodium hydrogencarbonate solution, and the mixture was extracted with ethyl acetate. The organic layer was separated, dried over anhydrous sodium sulfate, and concentrated under reduced pressure to give the title compound (184 mg).

MS: $[M-H]^+$437.8.

C) tert-butyl (2S,3S)-2-((2-(3,5-difluorophenyl)-1,3-thiazol-4-yl)methyl)-3-((methylsulfonyl)amino)pyrrolidine-1-carboxylate A mixture of tert-butyl (2S,3S)-2-((2-bromo-1,3-thiazol-4-yl)methyl)-3-((methylsulfonyl)amino)pyrrolidine-1-carboxylate (182 mg), (3,5-difluorophenyl)boronic acid (131 mg), potassium carbonate (114 mg), (A-taPhos)$_2$PdCl$_2$ (13.9 mg), DME (4 mL) and water (1 mL) was stirred at 60° C. for 30 min. To the mixture was added water, and the mixture was extracted with ethyl acetate. The organic layer was separated, dried over anhydrous sodium sulfate, and concentrated under reduced pressure. The residue was purified by silica gel column chromatography (ethyl acetate/hexane) to give the title compound (172 mg).

MS: [M−H]-471.9.

D) N-((2S,3S)-2-((2-(3,5-difluorophenyl)-1,3-thiazol-4-yl)methyl)pyrrolidin-3-yl)methanesulfonamide dihydrochloride To a mixture of tert-butyl (2S,3S)-2-((2-(3,5-difluorophenyl)-1,3-thiazol-4-yl)methyl)-3-((methylsulfonyl)amino) pyrrolidine-1-carboxylate (172 mg) and MeOH (2 mL) was added 4M hydrogen chloride/cyclopentyl methyl ether (1 mL) at room temperature. The mixture was stirred for 2 hr, and concentrated under reduced pressure to give the title compound (173 mg).

MS: $[M+H]^+$ 374.0.

E) N-((2S,3S)-2-((2-(3,5-difluorophenyl)-1,3-thiazol-4-yl)methyl)-1-((1-hydroxycyclobutyl)carbonyl)pyrrolidin-3-yl)methanesulfonamide To a mixture of N-((2S,3S)-2-((2-(3,5-difluorophenyl)-1,3-thiazol-4-yl)methyl)pyrrolidin-3-yl)methanesulfonamide dihydrochloride (72.6 mg) and DMF (1 mL) were added TEA (82 mg), 1-hydroxycyclobutanecarboxylic acid (22.7 mg) and HATU (74.2 mg) at room temperature. The mixture was stirred for 1 hr, and to the mixture was added saturated aqueous sodium hydrogencarbonate solution, and the mixture was extracted with ethyl acetate. The organic layer was separated, washed with saturated brine, dried over anhydrous sodium sulfate, and concentrated under reduced pressure. The residue was purified by silica gel column chromatography (ethyl acetate/hexane) to give the title compound (68.5 mg).

$^1$H NMR (300 MHz, CDCl$_3$) δ 1.43-1.54 (1H, m), 1.62-1.73 (1H, m), 1.88-2.22 (5H, m), 2.40-2.57 (1H, m), 2.59-2.75 (1H, m), 3.02 (3H, s), 3.21 (1H, s), 3.30-3.45 (1H, m), 3.47-3.60 (1H, m), 3.66 (1H, dd, J=14.9, 6.6 Hz), 4.00-4.21 (1H, m), 4.53 (1H, t, J=6.6 Hz), 6.84-6.95 (1H, m), 7.10 (1H, s), 7.44-7.50 (2H, m), 8.02 (1H, d, J=9.0 Hz).

Example 340

N-((2S,3S)-1-(azetidin-1-ylcarbonyl)-2-((2-(3,5-difluorophenyl)-1,3-thiazol-4-yl)methyl)pyrrolidin-3-yl)methanesulfonamide To a mixture of N-((2S,3S)-2-((2-(3,5-difluorophenyl)-1,3-thiazol-4-yl)methyl)pyrrolidin-3-yl)methanesulfonamide dihydrochloride (92.6 mg) and THE (1 mL) were added bis(trichloromethyl) carbonate (30.8 mg) and DIPEA (53.6 mg) at 0° C. The mixture was stirred for 30 min, and to the mixture was added water, and the mixture was extracted with ethyl acetate. The organic layer was separated, dried over anhydrous sodium sulfate, and concentrated under reduced pressure. To the obtained residue were added THF (1 mL) and azetidine (35.5 mg). The mixture was stirred at room temperature for 1 hr. The reaction mixture was concentrated under reduced pressure, and the residue was purified by silica gel column chromatography (ethyl acetate/hexane), and crystallized from ethyl acetate/hexane to give the title compound (56 mg).

$^1$H NMR (300 MHz, CDCl$_3$) δ 1.26 (1H, t, J=7.2 Hz), 2.06-2.27 (3H, m), 3.00 (3H, s), 3.10-3.24 (3H, m), 3.47 (1H, dd, J=14.7, 6.8 Hz), 3.75 (2H, q, J=7.8 Hz), 3.95-4.15 (3H, m), 4.28-4.52 (1H, m), 6.79-6.97 (1H, m), 7.13 (1H, s), 7.49 (2H, m), 8.02 (1H, d, J=7.9 Hz).

Example 341

N-((2S,3S)-1-((3-fluoroazetidin-1-yl)carbonyl)-2-((3'-fluorobiphenyl-3-yl)methyl)pyrrolidin-3-yl) methanesulfonamide A) (2S,3S)-2-((3'-fluorobiphenyl-3-yl)methyl)-3-((methylsulfonyl)amino)pyrrolidine-1-carbonyl chloride To a mixture of N-((2S,3S)-2-((3'-fluorobiphenyl-3-yl) methyl)pyrrolidin-3-yl)methanesulfonamide hydrochloride (101 mg) and THE (2 mL) were added bis(trichloromethyl) carbonate (62.3 mg) and DIPEA (67.8 mg) at 0° C. The mixture was stirred at 0° C. for 15 min, and the reaction solution was concentrated under reduced pressure to give the title compound (152 mg).

MS: $[M+H]^+$ 411.2.

B) N-((2S,3S)-1-((3-fluoroazetidin-1-yl)carbonyl)-2-((3'-fluorobiphenyl-3-yl)methyl)pyrrolidin-3-yl) methanesulfonamide To a mixture of (2S,3S)-2-((3'-fluorobiphenyl-3-yl) methyl)-3-((methylsulfonyl)amino)pyrrolidine-1-carbonyl chloride (50 mg) and THE (1 mL) were added 3-fluoroazetidine hydrochloride (19.3 mg) and DIPEA (33.5 mg) at room temperature. The mixture was stirred at room temperature for 1 hr. To the mixture was added saturated aqueous sodium hydrogencarbonate solution, and the mixture was extracted with ethyl acetate. The organic layer was separated, washed with saturated brine, dried over anhydrous magnesium sulfate, and concentrated under reduced pressure. The residue was purified by silica gel column chromatography (NH, ethyl acetate/hexane), and the obtained solid was crystallized from ethyl acetate/hexane to give the title compound (37.8 mg).

$^1$H NMR (300 MHz, DMSO-d$_6$) δ 1.80-1.98 (1H, m), 2.02-2.19 (1H, m), 2.70-2.79 (1H, m), 2.82 (3H, s), 2.92 (1H, dd, J=13.8, 6.2 Hz), 3.12-3.25 (1H, m), 3.32-3.39 (1H, m), 3.55-3.74 (1H, m), 3.75-4.01 (3H, m), 4.03-4.19 (1H, m), 4.28 (1H, q, J=6.4 Hz), 5.00-5.37 (1H, m), 7.11-7.23 (1H, m), 7.25-7.32 (1H, m), 7.32-7.39 (1H, m), 7.43-7.55 (5H, m), 7.58 (1H, s).

Example 342

N-((2S,3S)-1-((3,3-difluoroazetidin-1-yl)carbonyl)-2-((3'-fluorobiphenyl-3-yl)methyl)pyrrolidin-3-yl) methanesulfonamide To a mixture of 3,3-difluoroazetidine hydrochloride (22.4 mg), DIPEA (33.5 mg) and THF (0.5 mL) was added a mixture of (2S,3S)-2-((3'-fluorobiphenyl-3-yl)methyl)-3-((methylsulfonyl)amino)pyrrolidine-1-carbonyl chloride (50 mg) and THF (0.5 mL) at room temperature. The mixture was stirred at room temperature for 2 hr. To the mixture was added saturated aqueous sodium hydrogencarbonate solution, and the mixture was extracted with ethyl acetate. The organic layer was separated, washed with saturated brine, dried over anhydrous magnesium sulfate, and concentrated under reduced pressure. The residue was purified by silica gel column chromatography (NH, ethyl acetate/hexane), and the obtained solid was crystallized from ethyl acetate/hexane to give the title compound (28.4 mg).

$^1$H NMR (300 MHz, DMSO-$d_6$) δ 1.84-2.02 (1H, m), 2.07-2.20 (1H, m), 2.74 (1H, dd, J=13.4, 7.4 Hz), 2.84 (3H, s), 2.87-2.99 (1H, m), 3.16-3.27 (1H, m), 3.32-3.42 (1H, m), 3.76-3.90 (1H, m), 3.99 (2H, td, J=13.1, 10.6 Hz), 4.20 (2H, td, J=13.3, 10.6 Hz), 4.31 (1H, q, J=6.6 Hz), 7.12-7.23 (1H, m), 7.24-7.31 (1H, m), 7.31-7.38 (1H, m), 7.43-7.55 (5H, m), 7.58 (1H, s).

Example 343

N-((2S,3S)-2-((3'-fluorobiphenyl-3-yl)methyl)-1-((2-methylazetidin-1-yl)carbonyl)pyrrolidin-3-yl)methanesulfonamide To a mixture of 2-methylazetidine hydrochloride (46.5 mg), DIPEA (112 mg) and THE (0.5 mL) was added a mixture of (2S,3S)-2-((3'-fluorobiphenyl-3-yl)methyl)-3-((methylsulfonyl)amino)pyrrolidine-1-carbonyl chloride (50 mg) and THE (0.5 mL) at room temperature. The mixture was stirred at room temperature for 5 hr. To the mixture was added saturated aqueous sodium hydrogencarbonate solution, and the mixture was extracted with ethyl acetate. The organic layer was separated, washed with saturated brine, dried over anhydrous magnesium sulfate, and concentrated under reduced pressure. The residue was purified by silica gel column chromatography (NH, ethyl acetate/hexane) to give the title compound (31.1 mg).

$^1$H NMR (300 MHz, DMSO-$d_6$) δ 1.03-1.24 (3H, m), 1.55-1.94 (2H, m), 1.97-2.23 (2H, m), 2.68-2.89 (4H, m), 2.90-3.05 (1H, m), 3.14 (1H, t, J=8.9 Hz), 3.23-3.39 (1H, m), 3.40-3.75 (1H, m), 3.75-3.91 (2H, m), 3.97-4.40 (2H, m), 7.13-7.23 (1H, m), 7.23-7.41 (2H, m), 7.44-7.63 (6H, m).

Example 344

N-((2S,3S)-2-((3',5'-difluorobiphenyl-3-yl)methyl)-1-((1-hydroxycyclobutyl)carbonyl)pyrrolidin-3-yl)methanesulfonamide

A) N-((2S,3S)-2-(3-bromobenzyl)-1-((1-hydroxycyclobutyl)carbonyl)pyrrolidin-3-yl)methanesulfonamide To a mixture of N-((2S,3S)-2-(3-bromobenzyl)pyrrolidin-3-yl)methanesulfonamide hydrochloride (101 mg), 1-hydroxycyclobutanecarboxylic acid (38.1 mg) and DMF (1 mL) were added HATU (156 mg) and DIPEA (106 mg) at room temperature. The mixture was stirred at room temperature for 2 hr. To the mixture was added saturated aqueous sodium hydrogencarbonate solution, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (105 mg).

MS: $[M+H]^+$ 431.1.

B) N-((2S,3S)-2-((3',5'-difluorobiphenyl-3-yl)methyl)-1-((1-hydroxycyclobutyl)carbonyl)pyrrolidin-3-yl)methanesulfonamide A mixture of N-((2S,3S)-2-(3-bromobenzyl)-1-((1-hydroxycyclobutyl)carbonyl)pyrrolidin-3-yl)methanesulfonamide (49.5 mg), (3,5-difluorophenyl)boronic acid (27.2 mg), XPhos Pd G3 (2.91 mg), 1M aqueous tripotassium phosphate solution (0.344 mL) and THF (2 mL) was stirred at 70° C. for 1 hr. To the mixture was added saturated aqueous sodium hydrogencarbonate solution, and the mixture was extracted with ethyl acetate. The organic layer was separated, washed with saturated brine, dried over anhydrous magnesium sulfate, and concentrated under reduced pressure. The residue was purified by silica gel column chromatography (NH, ethyl acetate/hexane), and the obtained solid was collected by filtration with hexane to give the title compound (33.2 mg).

$^1$H NMR (300 MHz, DMSO-$d_6$) δ 1.16-1.37 (2H, m), 1.57-1.72 (1H, m), 1.82-1.97 (2H, m), 2.08 (1H, brs), 2.35-2.47 (2H, m), 2.63-2.75 (3H, m), 2.75-2.86 (1H, m), 2.91-3.04 (1H, m), 3.45-3.67 (2H, m), 3.75-3.93 (1H, m), 4.33-4.72 (1H, m), 5.71-6.02 (1H, m), 7.20 (1H, tt, J=9.2, 2.3 Hz), 7.37 (1H, d, J=7.2 Hz), 7.39-7.47 (3H, m), 7.48-7.57 (2H, m), 7.65 (1H, s).

Example 345

N-((2S,3S)-1-(azetidin-1-ylcarbonyl)-2-((3',5'-difluorobiphenyl-3-yl)methyl)pyrrolidin-3-yl)methanesulfonamide

A) N-((2S,3S)-1-(azetidin-1-ylcarbonyl)-2-(3-bromobenzyl)pyrrolidin-3-yl)methanesulfonamide To a mixture of N-((2S,3S)-2-(3-bromobenzyl)pyrrolidin-3-yl)methanesulfonamide hydrochloride (101 mg) and THF (2 mL) were added bis(trichloromethyl) carbonate (64.9 mg) and DIPEA (70.6 mg) at 0° C. The mixture was stirred at 0° C. for 15 min, and the reaction solution was concentrated under reduced pressure. To the residue were added THF (2 mL) and azetidine (46.8 mg), and the mixture was stirred at room temperature for 2 hr. To the mixture was added saturated aqueous sodium hydrogencarbonate solution, and the mixture was extracted with ethyl acetate. The organic layer was separated, washed with water and saturated brine, dried over anhydrous magnesium sulfate, and concentrated under reduced pressure. The residue was purified by silica gel column chromatography (methanol/ethyl acetate) to give the title compound (78.4 mg).

MS: $[M+H]^+$ 416.2.

B) N-((2S,3S)-1-(azetidin-1-ylcarbonyl)-2-((3',5'-difluorobiphenyl-3-yl)methyl)pyrrolidin-3-yl)methanesulfonamide A mixture of N-((2S,3S)-1-(azetidin-1-ylcarbonyl)-2-(3-bromobenzyl)pyrrolidin-3-yl)methanesulfonamide (46.8 mg), (3,5-difluorophenyl)boronic acid (26.6 mg), XPhos Pd G3 (2.85 mg), 1M aqueous tripotassium phosphate solution (0.337 mL) and THE (2 mL) was stirred at 70° C. for 1 hr. To the mixture was added saturated aqueous sodium hydrogencarbonate solution, and the mixture was extracted with ethyl acetate. The organic layer was separated, washed with saturated brine, dried over anhydrous magnesium sulfate, and concentrated under reduced pressure. The residue was purified by silica gel column chromatography (NH, ethyl acetate/hexane), and the obtained solid was crystallized from ethyl acetate/hexane to give the title compound (35.8 mg).

$^1$H NMR (300 MHz, DMSO-$d_6$) δ 1.83-2.14 (4H, m), 2.69-2.80 (1H, m), 2.83 (3H, s), 2.86-2.97 (1H, m), 3.09-3.21 (1H, m, J=9.5 Hz), 3.34 (1H, brs), 3.61 (2H, q, J=7.6 Hz), 3.79 (3H, q, J=8.0 Hz), 4.28 (1H, d, J=6.4 Hz), 7.15-7.26 (1H, m), 7.29-7.34 (1H, m), 7.34-7.40 (1H, m), 7.44 (2H, dd, J=9.5, 2.3 Hz), 7.48 (1H, brs), 7.53 (1H, d, J=7.6 Hz), 7.60 (1H, s).

Example 346

N-((2S,3S)-1-((1-cyanocyclobutyl)carbonyl)-2-((3'-fluorobiphenyl-3-yl)methyl)pyrrolidin-3-yl)methanesulfonamide To a mixture of N-((2S,3S)-2-((3'-fluorobiphenyl-3-yl)methyl)pyrrolidin-3-yl)methanesulfonamide hydrochloride (30 mg), 1-cyanocyclobutanecarboxylic acid (11.7 mg) and DMF (1 mL) were added HATU (44.5 mg) and DIPEA (30.2 mg) at room temperature. The mixture was stirred overnight at room temperature. To the mixture was added saturated aqueous sodium hydrogencarbonate solution, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane), and the obtained solid was crystallized from ethyl acetate/hexane to give the title compound (28.7 mg).

$^1$H NMR (300 MHz, DMSO-$d_6$) δ 1.58-1.75 (1H, m), 1.94-2.11 (2H, m), 2.14-2.25 (1H, m), 2.37-2.48 (3H, m), 2.52-2.59 (1H, m), 2.71-2.83 (4H, m), 3.01 (1H, dd, J=13.6, 6.4 Hz), 3.37-3.45 (1H, m), 3.48-3.61 (1H, m), 3.85-4.05 (1H, m), 4.46 (1H, q, J=6.4 Hz), 7.09-7.23 (1H, m), 7.26-7.38 (2H, m), 7.42-7.56 (4H, m), 7.58-7.67 (2H, m).

Example 347

N-((2S,3S)-1-(5-azaspiro[2.3]hex-5-ylcarbonyl)-2-((3'-fluorobiphenyl-3-yl)methyl)pyrrolidin-3-yl)methanesulfonamide To a mixture of N-((2S,3S)-2-((3'-fluorobiphenyl-3-yl)methyl)pyrrolidin-3-yl)methanesulfonamide hydrochloride (30.3 mg) and THE (2 mL) were added bis(trichloromethyl) carbonate (18.7 mg) and DIPEA (20.4 mg) at 0° C. The mixture was stirred at 0° C. for 20 min, and concentrated under reduced pressure. To the residue were added THE (2 mL), 5-azaspiro[2.3]hexane hydrochloride (37.7 mg) and DIPEA (81 mg), and the mixture was stirred overnight at room temperature. To the mixture was added saturated aqueous sodium hydrogencarbonate solution, and the mixture was extracted with ethyl acetate. The organic layer was separated, washed with saturated brine, dried over anhydrous magnesium sulfate, and concentrated under reduced pressure. The residue was purified by silica gel column chromatography (ethyl acetate/hexane), and the obtained solid was crystallized from ethyl acetate/hexane to give the title compound (27.2 mg).

$^1$H NMR (300 MHz, DMSO-$d_6$) δ 0.38-0.52 (4H, m), 1.80-1.97 (1H, m), 2.03-2.20 (1H, m), 2.68-2.79 (1H, m), 2.85 (3H, s), 2.88-2.98 (1H, m), 3.13-3.25 (1H, m), 3.26-3.38 (1H, m), 3.64 (2H, d, J=8.0 Hz), 3.80 (1H, brs), 3.86 (2H, d, J=8.0 Hz), 4.23-4.41 (1H, m), 7.11-7.24 (1H, m), 7.25-7.31 (1H, m), 7.32-7.39 (1H, m), 7.43-7.55 (5H, m), 7.55-7.60 (1H, m).

Example 348

N-((2S,3S)-1-(azetidin-1-ylcarbonyl)-2-((2-(3,5-difluorophenyl)-1,3-thiazol-4-yl)methyl)pyrrolidin-3-yl)ethanesulfonamide A) tert-butyl (2S,3S)-2-((2-bromo-1,3-thiazol-4-yl)methyl)-3-((ethylsulfonyl)amino)pyrrolidine-1-carboxylate To a mixture of tert-butyl (2S,3S)-3-amino-2-((2-bromo-1,3-thiazol-4-yl)methyl)pyrrolidine-1-carboxylate (300 mg), TEA (126 mg) and THF (3 mL) was added ethanesulfonyl chloride (128 mg) at room temperature. The mixture was stirred at room temperature for 1 hr, and diluted with ethyl acetate. The insoluble substance was removed by filtration, and the filtrate was concentrated under reduced pressure. The residue was purified by silica gel column chromatography (ethyl acetate/hexane) to give the title compound (240 mg).

MS: $[M+H]^+$ 454.2.

B) tert-butyl (2S,3S)-2-((2-(3,5-difluorophenyl)-1,3-thiazol-4-yl)methyl)-3-((ethylsulfonyl)amino)pyrrolidine-1-carboxylate A mixture of tert-butyl (2S,3S)-2-((2-bromo-1,3-thiazol-4-yl)methyl)-3-((ethylsulfonyl)amino)pyrrolidine-1-carboxylate (240 mg), (3,5-difluorophenyl)boronic acid (125 mg), $(A\text{-}taPhos)_2PdCl_2$ (35.5 mg), potassium carbonate (146 mg), DME (2.4 mL) and water (0.8 mL) was stirred under nitrogen atmosphere at 90° C. for 30 min. The mixture was purified by silica gel column chromatography (NH, ethyl acetate/hexane) to give the title compound (240 mg).

MS: $[M+H]^+$ 488.2.

C) N-((2S,3S)-2-((2-(3,5-difluorophenyl)-1,3-thiazol-4-yl)methyl)pyrrolidin-3-yl)ethanesulfonamide dihydrochloride To a mixture of tert-butyl (2S,3S)-2-((2-(3,5-difluorophenyl)-1,3-thiazol-4-yl)methyl)-3-((ethylsulfonyl)amino)pyrrolidine-1-carboxylate (240 mg) and MeOH (1 mL) was added 4M hydrogen chloride/cyclopentyl methyl ether solution (4 mL) at room temperature. The mixture was stirred at room temperature for 30 min, and the reaction mixture was concentrated to give the title compound (226 mg).

MS: $[M+H]^+$ 388.2.

D) N-((2S,3S)-1-(azetidin-1-ylcarbonyl)-2-((2-(3,5-difluorophenyl)-1,3-thiazol-4-yl)methyl)pyrrolidin-3-yl)ethanesulfonamide A mixture of N-((2S,3S)-2-((2-(3,5-difluorophenyl)-1,3-thiazol-4-yl)methyl)pyrrolidin-3-yl)ethanesulfonamide dihydrochloride (70 mg), DIPEA (79 mg) and THE (5 mL) was added a solution of bis(trichloromethyl) carbonate (36.1 mg) in THE (5 mL) at 0° C. The mixture was stirred at 0° C. for 20 min, and the reaction solution was concentrated. To the obtained residue were added THE (5 mL) and azetidine (43.4 mg). The mixture was stirred at room temperature for 1 hr. The reaction mixture was concentrated under reduced pressure, and the residue was purified by silica gel column chromatography (methanol/ethyl acetate) to give the title compound (52 mg).

$^1$H NMR (300 MHz, DMSO-$d_6$) δ 1.10-1.22 (3H, m), 1.70-1.89 (1H, m), 1.93-2.16 (3H, m), 2.83-3.21 (5H, m), 3.23-3.30 (1H, m), 3.56-3.70 (2H, m), 3.76-3.93 (3H, m), 4.27-4.40 (1H, m), 7.33-7.44 (1H, m), 7.47-7.55 (2H, m), 7.57-7.70 (2H, m).

Example 349

N-((2S,3S)-2-((2,3'-difluorobiphenyl-3-yl)methyl)-1-(2,2-dimethylpropanoyl)pyrrolidin-3-yl)methanesulfonamide A) tert-butyl (2S,3S)-3-amino-2-(3-bromo-2-fluorobenzyl)pyrrolidine-1-carboxylate A racemate (848 mg) of tert-butyl cis-3-amino-2-(3-bromo-2-fluorobenzyl)pyrrolidine-1-carboxylate was resolved by HPLC (column: CHIRALPAK AD (AK001), 50 mmID×500 mmL, Manufactured by Daicel Chemical Industries, mobile phase: hexane/ethanol=850/150) to give the title compound (352 mg) having a shorter retention time.

MS: $[M+H-tBu]^+$316.9.

B) tert-butyl (2S,3S)-2-(3-bromo-2-fluorobenzyl)-3-((methylsulfonyl)amino)pyrrolidine-1-carboxylate To a mixture of tert-butyl (2S,3S)-3-amino-2-(3-bromo-2-fluorobenzyl)pyrrolidine-1-carboxylate (349 mg), TEA (189 mg) and THF (3.3 mL) was added methanesulfonyl chloride (129 mg) at room temperature. The mixture was stirred at room temperature for 1 hr, and the reaction mixture was poured into water, and the mixture was extracted with ethyl acetate. The organic layer was washed with aqueous sodium hydrogencarbonate solution and saturated brine, dried over anhydrous magnesium sulfate, and concentrated under reduced pressure. The residue was purified by silica gel column chromatography (ethyl acetate/hexane) to give the title compound (386 mg).

MS: $[M+H-Boc]^+$350.9.

C) tert-butyl (2S,3S)-2-((2,3'-difluorobiphenyl-3-yl)methyl)-3-((methylsulfonyl)amino)pyrrolidine-1-carboxylate A mixture of tert-butyl (2S,3S)-2-(3-bromo-2-fluorobenzyl)-3-((methylsulfonyl)amino)pyrrolidine-1-carboxylate (380 mg), (3-fluorophenyl)boronic acid (236 mg), XPhos Pd G3 (35.6 mg), 1 M aqueous tripotassium phosphate solution (2.53 mL) and THF (9 mL) was stirred under argon atmosphere at 70° C. for 1 hr. The mixture was poured into aqueous sodium hydrogencarbonate solution, and extracted with ethyl acetate. The organic layer was washed with water and saturated brine, dried over anhydrous magnesium sulfate, and concentrated under reduced pressure. The residue was purified by silica gel column chromatography (ethyl acetate/hexane) to give crystals. The crystals were collected by filtration, and washed with diisopropyl ether-hexane to give the title compound (353 mg).

MS: $[M-H]^-$ 465.0.

D) N-((2S,3S)-2-((2,3'-difluorobiphenyl-3-yl)methyl)pyrrolidin-3-yl)methanesulfonamide To a mixture of tert-butyl (2S,3S)-2-((2,3'-difluorobiphenyl-3-yl)methyl)-3-((methylsulfonyl)amino)pyrrolidine-1-carboxylate (349 mg) and toluene (3.8 mL) was added TFA (3.8 mL) at room temperature. The mixture was stirred at room temperature for 1 hr, and poured into saturated aqueous sodium hydrogencarbonate solution under ice-cooling. The mixture was basified to pH=8 with potassium carbonate, and extracted with ethyl acetate-THF. The organic layer was washed with water and saturated brine, dried over anhydrous magnesium sulfate, and concentrated under reduced pressure. The residue was purified by silica gel column chromatography (NH, methanol/ethyl acetate) to give the title compound (283 mg).

MS: $[M+H]^+$ 367.2.

E) N-((2S,3S)-2-((2,3'-difluorobiphenyl-3-yl)methyl)-1-(2,2-dimethylpropanoyl)pyrrolidin-3-yl)methanesulfonamide To a mixture of N-((2S,3S)-2-((2,3'-difluorobiphenyl-3-yl)methyl)pyrrolidin-3-yl)methanesulfonamide (68 mg), TEA (75 mg) and THE (1.6 mL) was added 2,2-dimethylpropanoyl chloride (67.1 mg) at room temperature. The mixture was stirred at room temperature for 3 hr, added to aqueous sodium hydrogencarbonate solution, and extracted with ethyl acetate-THF. The organic layer was washed with water and saturated brine, dried over anhydrous magnesium sulfate, and concentrated under reduced pressure. The residue was purified by silica gel column chromatography (ethyl acetate/hexane) to give the title compound (68.9 mg).

$^1$H NMR (300 MHz, $CDCl_3$) δ 1.25 (9H, s), 1.95-2.04 (1H, m), 2.28-2.39 (1H, m), 2.53 (3H, s), 2.92-3.08 (2H, m), 3.64-3.71 (2H, m), 3.92-4.05 (1H, m), 4.65-4.75 (2H, m), 7.03-7.11 (1H, m), 7.15-7.26 (2H, m), 7.27-7.32 (2H, m), 7.36-7.45 (1H, m), 7.53 (1H, td, J=7.1, 1.7 Hz).

Example 350

N-((2S,3S)-1-(cyclobutylcarbonyl)-2-((2,3'-difluorobiphenyl-3-yl)methyl)pyrrolidin-3-yl)methanesulfonamide To a mixture of N-((2S,3S)-2-((2,3'-difluorobiphenyl-3-yl)methyl)pyrrolidin-3-yl)methanesulfonamide (66 mg), TEA (54.7 mg) and THF (1.6 mL) was added cyclobutanecarbonyl chloride (42.7 mg) at room temperature. The mixture was stirred at room temperature for 2 hr, added to aqueous sodium hydrogencarbonate solution, and extracted with ethyl acetate-THF. The organic layer was washed with water and saturated brine, dried over anhydrous magnesium sulfate, and concentrated under reduced pressure. The residue was purified by silica gel column chromatography (methanol/ethyl acetate) to give crystals. The crystals were collected by filtration, and washed with diisopropyl ether-hexane to give the title compound (49.9 mg).

$^1$H NMR (300 MHz, $CDCl_3$) δ 1.67-2.40 (8H, m), 2.57-3.22 (6H, m), 3.27-3.77 (2H, m), 3.94-4.08 (1H, m), 4.26-4.64 (1H, m), 4.75-4.83 (1H, m), 7.03-7.12 (1H, m), 7.14-7.24 (2H, m), 7.27-7.34 (2H, m), 7.36-7.50 (2H, m).

Example 351

N-((2S,3S)-2-((2,3'-difluorobiphenyl-3-yl)methyl)-1-((1-methylcyclopropyl)carbonyl)pyrrolidin-3-yl)methanesulfonamide To a solution of N-((2S,3S)-2-((2,3'-difluorobiphenyl-3-yl)methyl)pyrrolidin-3-yl)methanesulfonamide (66 mg), 1-methylcyclopropanecarboxylic acid (23.4 mg), DIPEA (46.6 mg) and DMF (1 mL) was added HATU (103 mg) at room temperature. The mixture was stirred at room temperature for 3 hr, added to aqueous sodium hydrogencarbonate solution, and extracted with ethyl acetate-THF. The organic layer was washed with water and saturated brine, dried over anhydrous magnesium sulfate, and concentrated under reduced pressure. The residue was purified by silica gel column chromatography (ethyl acetate/hexane) to give the title compound (54.5 mg).

$^1$H NMR (300 MHz, $CDCl_3$) δ 0.46-0.61 (2H, m), 0.71-0.80 (1H, m), 0.94-1.03 (1H, m), 1.25 (3H, s), 1.88-2.02 (1H, m), 2.27-2.39 (1H, m), 2.70 (3H, s), 2.91-2.99 (1H, m), 3.05 (1H, dd, J=14.2, 7.4 Hz), 3.58-3.76 (2H, m), 3.94-4.06 (1H, m), 4.66 (1H, q, J=6.5 Hz), 4.77 (1H, dd, J=9.3, 4.4 Hz), 7.03-7.11 (1H, m), 7.17 (1H, t, J=7.8 Hz), 7.20-7.25 (1H, m), 7.27-7.44 (4H, m).

Example 352

N-((2S,3S)-1-(azetidin-1-ylcarbonyl)-2-((2,3'-difluorobiphenyl-3-yl)methyl)pyrrolidin-3-yl)methanesulfonamide To a mixture of N-((2S,3S)-2-((2,3'-difluorobiphenyl-3-yl)methyl)pyrrolidin-3-yl)methanesulfonamide (68 mg), DIPEA (48.0 mg) and THF (1.6 mL) was added bis(trichloromethyl) carbonate (44.1 mg) at 0° C. The mixture was stirred at 0° C. for 20 min, and the reaction mixture was concentrated under reduced pressure. The residue was diluted with THF (1.6 mL), and azetidine (63.6 mg) was added thereto at room temperature. The mixture was stirred at 70° C. for 20 min, added to aqueous sodium hydrogencarbonate solution, and extracted with ethyl acetate-THF. The organic layer was washed with water and saturated brine, dried over anhydrous magnesium sulfate, and concentrated under reduced pressure. The residue was purified by silica gel column chromatography (methanol/ethyl acetate) to give the title compound (40.0 mg).

$^1$H NMR (300 MHz, $CDCl_3$) δ 1.89-2.01 (1H, m), 2.13-2.26 (3H, m), 2.68 (3H, s), 2.90-2.99 (1H, m), 3.02-3.11 (1H, m), 3.24-3.41 (2H, m), 3.80-4.06 (5H, m), 4.53 (1H, q, J=6.8 Hz), 4.64 (1H, dd, J=9.1, 3.4 Hz), 7.03-7.11 (1H, m), 7.16-7.25 (2H, m), 7.27-7.33 (2H, m), 7.36-7.44 (2H, m).

Example 364

N-((2S,3S)-1-(azetidin-1-ylcarbonyl)-2-(biphenyl-3-ylmethyl)pyrrolidin-3-yl)ethanesulfonamide A) tert-butyl (2S,3S)-2-(3-bromobenzyl)-3-((ethylsulfonyl)amino)pyrrolidine-1-carboxylate To a mixture of tert-butyl (2S,3S)-3-amino-2-(3-bromobenzyl)pyrrolidine-1-carboxylate (3.2 g), TEA (1.37 g) and THF (50 mL) was added ethanesulfonyl chloride (1.39 g) at room temperature. The mixture was stirred at room temperature for 1 hr. The insoluble substance was removed by filtration, and washed with ethyl acetate. The filtrate was concentrated under reduced pressure. The residue was purified by silica gel column chromatography (ethyl acetate/hexane). The obtained oil was crystallized from ethyl acetate, and diluted with hexane. The precipitate was collected by filtration to give the title compound (3.46 g).

MS: $[M+H-Boc]^+$ 347.2.

B) tert-butyl (2S,3S)-2-(biphenyl-3-ylmethyl)-3-((ethylsulfonyl)amino)pyrrolidine-1-carboxylate A mixture of tert-butyl (2S,3S)-2-(3-bromobenzyl)-3-((ethylsulfonyl)amino)pyrrolidine-1-carboxylate (1.0 g), phenylboronic acid (0.409 g), XPhos Pd G3 (0.057 g), 1 M aqueous tripotassium phosphate solution (6.71 mL) and THF (20 mL) was stirred at 70° C. for 1.5 hr. The mixture was concentrated. The residue was partitioned between ethyl acetate and water, and the mixture was extracted with ethyl acetate. The extract was washed with 1 M aqueous sodium hydroxide solution and saturated brine, dried over anhydrous magnesium sulfate, and concentrated under reduced pressure. The residue was crystallized from ethyl acetate/hexane, and the precipitate was collected by filtration to give the title compound (714 mg).

MS: $[M+H-Boc]^+$ 345.3.

C) N-((2S,3S)-2-(biphenyl-3-ylmethyl)pyrrolidin-3-yl)ethanesulfonamide hydrochloride A mixture of tert-butyl (2S,3S)-2-(biphenyl-3-ylmethyl)-3-((ethylsulfonyl)amino)pyrrolidine-1-carboxylate (714 mg), 4M hydrogen chloride/ethyl acetate solution (5 mL) and ethyl acetate (10 mL) was stirred overnight at room temperature. The mixture was diluted with ethyl acetate, and the precipitate was collected by filtration to give the title compound (576 mg).

MS: $[M+H]^+$ 345.3.

D) N-((2S,3S)-1-(azetidin-1-ylcarbonyl)-2-(biphenyl-3-ylmethyl)pyrrolidin-3-yl)ethanesulfonamide A mixture of N-((2S,3S)-2-(biphenyl-3-ylmethyl)pyrrolidin-3-yl)ethanesulfonamide hydrochloride (576 mg), DIPEA (391 mg) and THF (10 mL) was added dropwise to a mixture of bis(trichloromethyl) carbonate (359 mg) and THF (10 mL), and the mixture was stirred at room temperature for 30 min, and concentrated. The residue was partitioned between ethyl acetate and saturated aqueous sodium hydrogencarbonate solution, and the mixture was extracted with ethyl acetate. The organic layer was washed with saturated brine, dried over anhydrous magnesium sulfate, and concentrated under reduced pressure. The residue was mixed with THF (10 mL), and to the mixture was added azetidine (432 mg) at room temperature. The mixture was stirred at room temperature for 4 hr. Azetidine (432 mg) was added to the mixture, and the mixture was stirred at room temperature for 15 min, and concentrated. The obtained residue was partitioned between ethyl acetate and 1 M hydrochloric acid, and the mixture was extracted with ethyl acetate. The organic layer was washed with saturated brine, dried over anhydrous magnesium sulfate, and concentrated under reduced pressure. The obtained crystals were recrystallized from ethyl acetate/hexane to give the title compound (453 mg).

$^1$H NMR (300 MHz, $CDCl_3$) δ 1.18 (3H, t, J=7.4 Hz), 1.75-1.92 (1H, m), 2.08-2.24 (3H, m), 2.73-2.97 (3H, m), 3.16-3.42 (3H, m), 3.80-3.97 (3H, m), 4.02 (2H, q, J=8.0 Hz), 4.32 (1H, d, J=8.3 Hz), 4.46-4.55 (1H, m), 7.27-7.49 (6H, m), 7.51 (1H, s), 7.55-7.62 (2H, m).

Example 366

(2S,3S)-2-((3',5'-difluorobiphenyl-3-yl)methyl)-N,N-dimethyl-3-((methylsulfonyl)amino)pyrrolidine-1-carboxamide A) tert-butyl (2S,3S)-2-((3',5'-difluorobiphenyl-3-yl)methyl)-3-((methylsulfonyl)amino)pyrrolidine-1-carboxylate A mixture of tert-butyl (2S,3S)-2-(3-bromobenzyl)-3-((methylsulfonyl)amino)pyrrolidine-1-carboxylate (1.73 g), (3,5-difluorophenyl)boronic acid (0.947 g), potassium carbonate (1.11 g), (A-taPhos)$_2$PdCl$_2$ (0.135 g), DME (20 mL) and water (4 mL) was stirred at 70° C. for 2 hr. The mixture was concentrated under reduced pressure, and the residue was purified by silica gel column chromatography (NH, ethyl acetate/hexane) to give the title compound (1.74 g).

MS:[M+Na]$^+$ 489.3.

B) N-((2S,3S)-2-((3',5'-difluorobiphenyl-3-yl)methyl)pyrrolidin-3-yl)methanesulfonamide hydrochloride A mixture of tert-butyl (2S,3S)-2-((3',5'-difluorobiphenyl-3-yl)methyl)-3-((methylsulfonyl)amino)pyrrolidine-1-carboxylate (1.74 g), 4M hydrogen chloride/CPME solution (18.7 mL) and methanol (10 mL) was stirred at room temperature for 2 hr. The reaction mixture was concentrated under reduced pressure. The obtained solid was washed with ethyl acetate to give the title compound (1.47 g).

MS: [M+H]$^+$ 367.2.

C) (2S,3S)-2-((3',5'-difluorobiphenyl-3-yl)methyl)-N,N-dimethyl-3-((methylsulfonyl)amino)pyrrolidine-1-carboxamide To a mixture of N-((2S,3S)-2-((3',5'-difluorobiphenyl-3-yl)methyl)pyrrolidin-3-yl)methanesulfonamide hydrochloride (1.47 g) and THF (20 mL) were added TEA (1.29 g) and dimethylcarbamoyl chloride (0.589 g) at room temperature. The mixture was stirred at room temperature for 1 hr, and to the mixture was added saturated brine, and the mixture was concentrated under reduced pressure. The residue was purified by silica gel column chromatography (NH, ethyl acetate/hexane) to give the title compound (1.49 g).

$^1$H NMR (400 MHz, CDCl$_3$) δ 2.03-2.11 (2H, m), 2.63-2.72 (1H, m), 2.73 (3H, s), 2.85 (6H, s), 3.23-3.38 (2H, m), 3.56-3.65 (1H, m), 3.85-3.93 (1H, m), 4.41-4.50 (1H, m), 4.69 (1H, d, J=8.6 Hz), 6.73-6.81 (1H, m), 7.06-7.15 (2H, m), 7.32-7.41 (3H, m), 7.49 (1H, s).

Example 373

(2S,3S)-2-((2,3'-difluorobiphenyl-3-yl)methyl)-3-((ethylsulfonyl)amino)-N,N-dimethylpyrrolidine-1-carboxamide A) tert-butyl (2S,3S)-2-(3-bromo-2-fluorobenzyl)-3-((ethylsulfonyl)amino)pyrrolidine-1-carboxylate To a mixture of tert-butyl (2S,3S)-3-amino-2-(3-bromo-2-fluorobenzyl)pyrrolidine-1-carboxylate (1.20 g), TEA (0.651 g), DMAP (0.118 g) and THF (11.5 mL) was added ethanesulfonyl chloride (0.620 g) at room temperature. The mixture was stirred at room temperature for 2 hr, poured into water, and extracted with ethyl acetate. The organic layer was washed with 10% aqueous citric acid solution, aqueous sodium hydrogencarbonate solution and saturated brine, dried over anhydrous magnesium sulfate, and concentrated under reduced pressure. The residue was purified by silica gel column chromatography (ethyl acetate/hexane) to give the title compound (1.43 g).

MS: [M−H]$^-$ 463.1.

B) tert-butyl (2S,3S)-2-((2,3'-difluorobiphenyl-3-yl)methyl)-3-((ethylsulfonyl)amino)pyrrolidine-1-carboxylate A mixture of tert-butyl (2S,3S)-2-(3-bromo-2-fluorobenzyl)-3-((ethylsulfonyl)amino)pyrrolidine-1-carboxylate (465 mg), (3-fluorophenyl)boronic acid (280 mg), XPhos Pd G3 (42.3 mg), 1 M aqueous tripotassium phosphate solution (3.00 mL) and THF (11 mL) was stirred under argon atmosphere at 70° C. for 1 hr. The reaction mixture was poured into aqueous sodium hydrogencarbonate solution, and the mixture was extracted with ethyl acetate. The organic layer was washed with water and saturated brine, dried over anhydrous magnesium sulfate, and concentrated under reduced pressure. The residue was purified by silica gel column chromatography (ethyl acetate/hexane) to give the title compound (449 mg).

MS: [M−H]$^-$ 479.2.

C) N-((2S,3S)-2-((2,3'-difluorobiphenyl-3-yl)methyl)pyrrolidin-3-yl)ethanesulfonamide To a mixture of tert-butyl (2S,3S)-2-((2,3'-difluorobiphenyl-3-yl)methyl)-3-((ethylsulfonyl)amino)pyrrolidine-1-carboxylate (444 mg) and toluene (4.8 mL) was added TFA (4.8 mL) at room temperature. The mixture was stirred at room temperature for 1 hr, and the reaction solution was poured into saturated aqueous sodium hydrogencarbonate solution under ice-cooling. The mixture was basified to pH=8 with potassium carbonate, and extracted with ethyl acetate/THF. The organic layer was washed with water and saturated brine, dried over anhydrous magnesium sulfate, and concentrated under reduced pressure. The residue was purified by silica gel column chromatography (NH, methanol/ethyl acetate) to give the title compound (341 mg).

MS: [M+H]$^+$ 381.2.

D) (2S,3S)-2-((2,3'-difluorobiphenyl-3-yl)methyl)-3-((ethylsulfonyl)amino)pyrrolidine-1-carbonyl chloride To a mixture of N-((2S,3S)-2-((2,3'-difluorobiphenyl-3-yl)methyl)pyrrolidin-3-yl)ethanesulfonamide (215 mg), DIPEA (146 mg) and THF (4.8 mL) was added bis(trichloromethyl) carbonate (134 mg) at 0° C. The mixture was stirred at 0° C. for 10 min, and then at room temperature for 10 min. The mixture was poured into water, and extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane), and the obtained crystals were collected by filtration, and washed with diisopropyl ether/hexane to give the title compound (223 mg).

MS: [M−H]$^-$ 441.1.

E) (2S,3S)-2-((2,3'-difluorobiphenyl-3-yl)methyl)-3-((ethylsulfonyl)amino)-N,N-dimethylpyrrolidine-1-carboxamide To a mixture of (2S,3S)-2-((2,3'-difluorobiphenyl-3-yl)methyl)-3-((ethylsulfonyl)amino)pyrrolidine-1-carbonyl chloride (110 mg) and THF (1.9 mL) was added 2M dimethylamine/THF solution (0.373 mL) at room temperature. The mixture was stirred at room temperature for 30 min, and then at 70° C. for 10 min. The mixture was poured into aqueous sodium hydrogencarbonate solution, and extracted with ethyl acetate/THF. The organic layer was separated, washed with water and saturated brine, dried over anhydrous magnesium sulfate, and concentrated under reduced pressure. The residue was purified by silica gel column chromatography (methanol/ethyl acetate) to give the title compound (97.0 mg).

$^1$H NMR (300 MHz, $CDCl_3$) δ 1.27 (3H, t, J=7.4 Hz), 2.06-2.20 (2H, m), 2.79 (6H, s), 2.81-2.95 (3H, m), 3.00-3.10 (1H, m), 3.28 (1H, ddd, J=10.3, 8.4, 4.4 Hz), 3.62 (1H, dt, J=10.3, 7.9 Hz), 3.88-3.98 (1H, m), 4.48-4.59 (2H, m), 7.02-7.10 (1H, m), 7.16 (1H, t, J=7.6 Hz), 7.20-7.25 (1H, m), 7.26-7.31 (2H, m), 7.32-7.43 (2H, m).

Example 387

N-((2S,3S)-2-((2,3'-difluorobiphenyl-3-yl)methyl)-1-(2-hydroxy-2-methylpropanoyl)pyrrolidin-3-yl) methanesulfonamide To a mixture of N-((2S,3S)-2-((2,3'-difluorobiphenyl-3-yl)methyl)pyrrolidin-3-yl)methanesulfonamide (60 mg), 2-hydroxy-2-methylpropanoic acid (22.2 mg), DIPEA (42.3 mg) and DMF (1 mL) was added HATU (93 mg) at room temperature. The mixture was stirred at room temperature for 3 hr, and the reaction mixture was poured into aqueous sodium hydrogencarbonate solution, and the mixture was extracted with ethyl acetate/THF. The organic layer was separated, washed with water and saturated brine, dried over anhydrous magnesium sulfate, and concentrated under reduced pressure. The residue was purified by silica gel column chromatography (methanol/ethyl acetate) to give the title compound (63.8 mg).

$^1$H NMR (300 MHz, $CDCl_3$) δ1.41 (3H, s), 1.43 (3H, s), 1.89-2.01 (1H, m), 2.29-2.41 (1H, m), 2.66 (3H, s), 2.91-3.00 (1H, m), 3.06-3.16 (1H, m), 3.68 (2H, brs), 3.84 (1H, brs), 3.97-4.10 (1H, m), 4.74 (2H, brs), 7.07 (1H, tdd, J=8.4, 2.6, 1.0 Hz), 7.16-7.25 (2H, m), 7.26-7.33 (2H, m), 7.36-7.45 (2H, m).

Example 389

N-((2S,3S)-2-((2,3'-difluorobiphenyl-3-yl)methyl)-1-(2-hydroxy-2-methylpropanoyl)pyrrolidin-3-yl)ethanesulfonamide To a mixture of N-((2S,3S)-2-((2,3'-difluorobiphenyl-3-yl)methyl)pyrrolidin-3-yl)ethanesulfonamide (59 mg), 2-hydroxy-2-methylpropanoic acid (21.0 mg), DIPEA (40.1 mg) and DMF (1 mL) was added HATU (88 mg) at room temperature. The mixture was stirred at room temperature for 3 hr, and the reaction mixture was poured into aqueous sodium hydrogencarbonate solution, and the mixture was extracted with ethyl acetate/THF. The organic layer was separated, washed with water and saturated brine, dried over anhydrous magnesium sulfate, and concentrated under reduced pressure. The residue was purified by silica gel column chromatography (methanol/ethyl acetate) to give the title compound (62.4 mg).

$^1$H NMR (300 MHz, $CDCl_3$) δ 1.22 (3H, t, J=7.4 Hz), 1.40 (3H, s), 1.42 (3H, s), 1.85-1.99 (1H, m), 2.28-2.41 (1H, m), 2.86 (2H, q, J=7.4 Hz), 2.95 (1H, dd, J=15.0, 3.9 Hz), 3.08-3.19 (1H, m), 3.67 (2H, brs), 3.83-4.06 (2H, m), 4.56 (1H, brs), 4.73 (1H, brs), 7.07 (1H, tdd, J=8.4, 2.6, 1.0 Hz), 7.15-7.25 (2H, m), 7.27-7.32 (2H, m), 7.36-7.44 (2H, m).

Example 395

N-((2S,3S)-1-(2-hydroxy-2-methylpropanoyl)-2-((2,3',5'-trifluorobiphenyl-3-yl)methyl)pyrrolidin-3-yl) methanesulfonamide A) tert-butyl (2S,3S)-3-((methylsulfonyl)amino)-2-((2,3',5'-trifluorobiphenyl-3-yl)methyl)pyrrolidine-1-carboxylate A mixture of tert-butyl (2S,3S)-2-(3-bromo-2-fluorobenzyl)-3-((methylsulfonyl)amino)pyrrolidine-1-carboxylate (450 mg), (3,5-difluorophenyl)boronic acid (315 mg), XPhos Pd G3 (42.2 mg), 1 M aqueous tripotassium phosphate solution (2.99 mL) and THF (11 mL) was stirred under argon atmosphere at 70° C. for 1 hr. The reaction mixture was poured into aqueous sodium hydrogencarbonate solution, and the mixture was extracted with ethyl acetate. The organic layer was washed with water and saturated brine, dried over anhydrous magnesium sulfate, and concentrated under reduced pressure. The residue was purified by silica gel column chromatography (ethyl acetate/hexane) to give the title compound (482 mg).

MS: $[M-H]^-$ 483.2.

B) N-((2S,3S)-2-((2,3',5'-trifluorobiphenyl-3-yl) methyl)pyrrolidin-3-yl)methanesulfonamide To a mixture of tert-butyl (2S,3S)-3-((methylsulfonyl) amino)-2-((2,3',5'-trifluorobiphenyl-3-yl)methyl)pyrrolidine-1-carboxylate (477 mg) and toluene (5.2 mL) was added TFA (5.2 mL) at room temperature. The mixture was stirred at room temperature for 1 hr, and the reaction mixture was poured into saturated aqueous sodium hydrogencarbonate solution under ice-cooling. The mixture was basified to pH=8 with potassium carbonate, and extracted with ethyl acetate/THF. The organic layer was washed with water and saturated brine, dried over anhydrous magnesium sulfate, and concentrated under reduced pressure. The residue was purified by silica gel column chromatography (NH, methanol/ethyl acetate) to give the title compound (339 mg).

MS: $[M+H]^+$ 385.2.

C) N-((2S,3S)-1-(2-hydroxy-2-methylpropanoyl)-2-((2,3',5'-trifluorobiphenyl-3-yl)methyl)pyrrolidin-3-yl)methanesulfonamide To a mixture of N-((2S,3S)-2-((2,3',5'-trifluorobiphenyl-3-yl)methyl)pyrrolidin-3-yl)methanesulfonamide (60 mg), 2-hydroxy-2-methylpropanoic acid (21.1 mg), DIPEA (40.3 mg) and DMF (1 mL) was added HATU (89 mg) at room temperature. The mixture was stirred at room temperature for 3 hr, and the reaction mixture was poured into aqueous sodium hydrogencarbonate solution, and the mixture was extracted with ethyl acetate/THF. The organic layer was separated, washed with water and saturated brine, dried over anhydrous magnesium sulfate, and concentrated under reduced pressure. The residue was purified by silica gel column chromatography (methanol/ethyl acetate) to give the title compound (63.1 mg).

$^1$H NMR (300 MHz, $CDCl_3$) δ 1.40 (3H, s), 1.42 (3H, s), 1.91-2.03 (1H, m), 2.30-2.42 (1H, m), 2.70 (3H, s), 2.89-2.97 (1H, m), 3.10 (1H, dd, J=14.0, 8.0 Hz), 3.63-3.84 (3H, m), 3.96-4.07 (1H, m), 4.68-4.84 (2H, m), 6.82 (1H, tt, J=8.9, 2.3 Hz), 7.02-7.10 (2H, m), 7.19 (1H, t, J=7.6 Hz), 7.26-7.31 (1H, m), 7.44 (1H, t, J=6.7 Hz).

Example 399

(2S,3S)-3-((ethylsulfonyl)amino)-N,N-dimethyl-2-((2,3',5'-trifluorobiphenyl-3-yl)methyl)pyrrolidine-1-carboxamide A) (2S,3S)-2-(3-bromo-2-fluorobenzyl)-3-((ethylsulfonyl)amino)-N,N-dimethylpyrrolidine-1-carboxamide To a mixture of tert-butyl (2S,3S)-2-(3-bromo-2-fluorobenzyl)-3-((ethylsulfonyl)amino)pyrrolidine-1-carboxylate (340 mg) and MeOH (1 mL) was added 4M hydrogen chloride/CPME solution (3.65 mL) at room temperature. The mixture was stirred for 1 hr, and the reaction solution was concentrated under reduced pressure. The obtained residue was mixed with THE (4 mL). To the mixture were added TEA (739 mg) and dimethylcarbamoyl chloride (393 mg) at room temperature. The mixture was stirred at 70° C. for 1 hr. To the reaction mixture was added saturated brine, and the mixture was extracted with ethyl acetate. The extract was dried over anhydrous sodium sulfate, and concentrated under reduced pressure. The obtained solid was washed with ethyl acetate to give the title compound (327 mg).

MS: $[M+H]^+$ 436.2.

B) (2S,3S)-3-((ethylsulfonyl)amino)-N,N-dimethyl-2-((2,3',5'-trifluorobiphenyl-3-yl)methyl)pyrrolidine-1-carboxamide A mixture of (2S,3S)-2-(3-bromo-2-fluorobenzyl)-3-((ethylsulfonyl)amino)-N,N-dimethylpyrrolidine-1-carboxamide (70.4 mg), (3,5-difluorophenyl)boronic acid (38.2 mg), XPhos Pd G3 (4.10 mg), 1 M aqueous tripotassium phosphate solution (0.484 mL) and THF (2 mL) was stirred at 70° C. for 1.5 hr. To the mixture was added saturated aqueous sodium hydrogencarbonate solution, and the mixture was extracted with ethyl acetate. The organic layer was separated, washed with saturated brine, dried over anhydrous magnesium sulfate, and concentrated under reduced pressure. The residue was purified by silica gel column chromatography (NH, ethyl acetate/hexane) to give the title compound (62.0 mg).

$^1$H NMR (400 MHz, DMSO-$d_6$) δ 1.20 (3H, t, J=7.3 Hz), 1.82-1.98 (1H, m), 2.02-2.19 (1H, m), 2.58 (6H, s), 2.68 (1H, dd, J=14.1, 9.2 Hz), 2.91 (1H, dd, J=13.4, 5.7 Hz), 2.96-3.06 (2H, m), 3.07-3.18 (1H, m), 3.54-3.65 (1H, m), 3.76 (1H, t, J=6.1 Hz), 4.35-4.47 (1H, m), 7.13-7.21 (1H, m), 7.23-7.32 (3H, m), 7.33-7.41 (2H, m), 7.51 (1H, d, J=6.8 Hz).

Example 402

N-((2S,3S)-1-isobutyryl-2-((2,3',5'-trifluorobiphenyl-3-yl)methyl)pyrrolidin-3-yl)methanesulfonamide To a mixture of N-((2S,3S)-2-((2,3',5'-trifluorobiphenyl-3-yl)methyl)pyrrolidin-3-yl)methanesulfonamide (60 mg), TEA (47.4 mg) and THF (1.4 mL) was added 2-methylpropanoyl chloride (33.3 mg) at room temperature. The mixture was stirred at room temperature for 1 hr, poured into aqueous sodium hydrogencarbonate solution, and extracted with ethyl acetate/THF. The organic layer was washed with water and saturated brine, dried over anhydrous magnesium sulfate, and concentrated under reduced pressure. The residue was purified by silica gel column chromatography (methanol/ethyl acetate), and the obtained solid was collected by filtration, and washed with diisopropyl ether/hexane to give the title compound (56.7 mg).

$^1$H NMR (300 MHz, $CDCl_3$) δ 0.56-1.12 (6H, m), 1.86-2.05 (1H, m), 2.31-2.43 (1H, m), 2.54-3.21 (6H, m), 3.42-3.79 (2H, m), 3.96-4.10 (1H, m), 4.36-4.68 (1H, m), 4.72-4.80 (1H, m), 6.77-6.86 (1H, m), 6.98-7.53 (5H, m).

Example 404

N-((2S,3S)-2-((3',5'-difluorobiphenyl-3-yl)methyl)-1-(2-hydroxy-2-methylpropanoyl)pyrrolidin-3-yl)ethanesulfonamide A) tert-butyl (2S,3S)-2-((3',5'-difluorobiphenyl-3-yl)methyl)-3-((ethylsulfonyl)amino)pyrrolidine-1-carboxylate A mixture of tert-butyl (2S,3S)-2-(3-bromobenzyl)-3-((ethylsulfonyl)amino)pyrrolidine-1-carboxylate (1.00 g), (3,5-difluorophenyl)boronic acid (0.529 g), XPhos Pd G3 (0.057 g), 1 M aqueous tripotassium phosphate solution (6.71 mL) and THE (20 mL) was stirred at 70° C. for 2 hr. The reaction mixture was concentrated under reduced pressure, the residue was diluted with saturated aqueous sodium hydrogencarbonate solution, and the mixture was extracted with ethyl acetate. The organic layer was washed with saturated brine, dried over anhydrous magnesium sulfate, and concentrated under reduced pressure. The residue was purified by silica gel column chromatography (NH, ethyl acetate/hexane) to give the title compound (1.08 g).

MS: $[M+H-Boc]^+$ 381.3.

B) N-((2S,3S)-2-((3',5'-difluorobiphenyl-3-yl)methyl)pyrrolidin-3-yl)ethanesulfonamide hydrochloride To a mixture of tert-butyl (2S,3S)-2-((3',5'-difluorobiphenyl-3-yl)methyl)-3-((ethylsulfonyl)amino)pyrrolidine-1-carboxylate (1.10 g) and ethyl acetate (5 mL) was added 4M hydrogen chloride/ethyl acetate solution (11.2 mL) at room temperature. The mixture was stirred at room temperature for 2 hr, and concentrated under reduced pressure. The obtained solid was collected by filtration with ethyl acetate, and dried to give the title compound (875 mg).

MS: $[M+H]^+$ 381.3.

C) N-((2S,3S)-2-((3',5'-difluorobiphenyl-3-yl)methyl)-1-(2-hydroxy-2-methylpropanoyl)pyrrolidin-3-yl)ethanesulfonamide To a mixture of N-((2S,3S)-2-((3',5'-difluorobiphenyl-3-yl)methyl)pyrrolidin-3-yl)ethanesulfonamide hydrochloride (100 mg), 2-hydroxy-2-methylpropanoic acid (32.5 mg), DIPEA (62.0 mg) and DMF (1 mL) was added HATU (137 mg) at room temperature. The mixture was stirred at room temperature for 3 hr, to the reaction mixture was added water, and the mixture was extracted with ethyl acetate. The organic layer was washed with water and saturated brine, dried over anhydrous magnesium sulfate, and concentrated under reduced pressure. The residue was purified by silica gel column chromatography (methanol/ethyl acetate), and recrystallized from ethyl acetate/hexane to give the title compound (60.0 mg).

$^1$H NMR (300 MHz, DMSO-$d_6$) δ 0.99-1.33 (9H, m), 1.80-2.24 (2H, m), 2.61-3.21 (4H, m), 3.38-3.93 (3H, m), 4.31-4.52 (1H, m), 4.95-5.37 (1H, m), 7.20 (1H, tt, J=9.3, 2.3 Hz), 7.30-7.54 (6H, m), 7.65 (1H, s).

Example 417

N-((2S,3S)-2-((2,3'-difluorobiphenyl-3-yl)methyl)-1-(2-hydroxy-2-methylpropanoyl)pyrrolidin-3-yl)-1-fluoromethanesulfonamide A) tert-butyl (2S,3S)-2-(3-bromo-2-fluorobenzyl)-3-(((fluoromethyl)sulfonyl)amino)pyrrolidine-1-carboxylate To a mixture of tert-butyl (2S,3S)-3-amino-2-(3-bromo-2-fluorobenzyl)pyrrolidine-1-carboxylate (1.24 g), DIPEA (0.859 g) and THE (11 mL) was added fluoromethanesulfonyl chloride (0.484 g) at 0° C. The mixture was stirred at room temperature for 1 hr, poured into water, and extracted with ethyl acetate. The organic layer was washed with aqueous sodium hydrogencarbonate solution and saturated brine, dried over anhydrous magnesium sulfate, and concentrated under reduced pressure. The residue was purified by silica gel column chromatography (ethyl acetate/hexane) to give the title compound (1.49 g).

MS: $[M-H]^-$ 466.9.

B) N-((2S,3S)-2-(3-bromo-2-fluorobenzyl)pyrrolidin-3-yl)-1-fluoromethanesulfonamide To a mixture of tert-butyl (2S,3S)-2-(3-bromo-2-fluorobenzyl)-3-(((fluoromethyl)sulfonyl)amino)pyrrolidine-1-carboxylate (1.48 g) and toluene (16 mL) was added TFA (16 mL) at room temperature. The mixture was stirred at room temperature for 1 hr, and the reaction solution was poured into saturated aqueous sodium hydrogencarbonate solution under ice-cooling. The mixture was basified to pH=8 with potassium carbonate, and extracted with ethyl acetate/THF(3:1). The organic layer was washed with water and saturated brine, dried over anhydrous magnesium sulfate, and concentrated under reduced pressure. The residue was purified by silica gel column chromatography (NH, methanol/ethyl acetate) to give the title compound (1.09 g).

MS: $[M+H]^+$ 368.9.

C) N-((2S,3S)-2-(3-bromo-2-fluorobenzyl)-1-(2-hydroxy-2-methylpropanoyl)pyrrolidin-3-yl)-1-fluoromethanesulfonamide To a mixture of N-((2S,3S)-2-(3-bromo-2-fluorobenzyl)pyrrolidin-3-yl)-1-fluoromethanesulfonamide (556 mg), 2-hydroxy-2-methylpropanoic acid (204 mg), DIPEA (389 mg) and DMF (10 ml) was added HATU (859 mg) at room temperature. The mixture was stirred at room temperature for 3.5 hr, and the reaction mixture was poured into aqueous sodium hydrogencarbonate solution, and the mixture was extracted with ethyl acetate/THF. The organic layer was washed with water and saturated brine, dried over anhydrous magnesium sulfate, and concentrated under reduced pressure. The obtained solid was collected by filtration, and washed with diisopropyl ether to give the title compound (627 mg).

MS: $[M+H]^+$ 455.0.

D) N-((2S,3S)-2-((2,3'-difluorobiphenyl-3-yl)methyl)-1-(2-hydroxy-2-methylpropanoyl)pyrrolidin-3-yl)-1-fluoromethanesulfonamide A mixture of N-((2S,3S)-2-(3-bromo-2-fluorobenzyl)-1-(2-hydroxy-2-methylpropanoyl)pyrrolidin-3-yl)-1-fluoromethanesulfonamide (73 mg), (3-fluorophenyl)boronic acid (44.9 mg), XPhos Pd G3 (6.79 mg), 1 M aqueous tripotassium phosphate solution (0.481 mL) and THF (1.6 mL) was stirred under argon atmosphere at 70° C. for 1 hr. The reaction mixture was poured into aqueous sodium hydrogencarbonate solution, and the mixture was extracted with ethyl acetate. The organic layer was washed with water and saturated brine, dried over anhydrous magnesium sulfate, and concentrated under reduced pressure. The residue was purified by silica gel column chromatography (ethyl acetate/hexane) to give the title compound (57.0 mg).

$^1$H NMR (300 MHz, $CDCl_3$) δ 1.42 (3H, s), 1.43 (3H, s), 1.85-2.02 (1H, m), 2.29-2.40 (1H, m), 2.95-3.04 (1H, m), 3.13 (1H, dd, J=14.0, 8.0 Hz), 3.62-3.88 (3H, m), 4.03-4.12 (1H, m), 4.59-4.82 (2H, m), 4.85-5.06 (2H, m), 7.04-7.12 (1H, m), 7.17-7.25 (2H, m), 7.27-7.34 (2H, m), 7.36-7.45 (2H, m).

Example 421

N-((2S,3S)-2-((3',5'-difluorobiphenyl-3-yl)methyl)-1-(2-hydroxy-2-methylpropanoyl)pyrrolidin-3-yl)-1-fluoromethanesulfonamide A) tert-butyl (2S,3S)-2-(3-bromobenzyl)-3-(((fluoromethyl)sulfonyl)amino)pyrrolidine-1-carboxylate To a mixture of tert-butyl (2S,3S)-3-amino-2-(3-bromobenzyl)pyrrolidine-1-carboxylate (1.22 g), DIPEA (0.888 g) and THF (12 mL) was added fluoromethanesulfonyl chloride (0.501 g) at 0° C. The mixture was stirred at room temperature for 1.5 hr, poured into water, and extracted with ethyl acetate. The organic layer was washed with aqueous sodium hydrogencarbonate solution and saturated brine, dried over anhydrous magnesium sulfate, and concentrated under reduced pressure. The residue was purified by silica gel column chromatography (ethyl acetate/hexane) to give the title compound (1.46 g).

MS: $[M+H-Boc]^+$350.9.

B) N-((2S,3S)-2-(3-bromobenzyl)pyrrolidin-3-yl)-1-fluoromethanesulfonamide

To a mixture of tert-butyl (2S,3S)-2-(3-bromobenzyl)-3-(((fluoromethyl)sulfonyl)amino)pyrrolidine-1-carboxylate (1.45 g) and toluene (15.5 mL) was added TFA (15.5 mL) at room temperature. The mixture was stirred at room temperature for 1 hr, and the reaction solution was poured into saturated aqueous sodium hydrogencarbonate solution under ice-cooling. The mixture was basified to pH=8 with potassium carbonate, and extracted with ethyl acetate/THF. The organic layer was washed with water and saturated brine, dried over anhydrous magnesium sulfate, and concentrated under reduced pressure. The residue was purified by silica gel column chromatography (NH, methanol/ethyl acetate) to give the title compound (693 mg).

MS: $[M+H]^+$ 350.9.

C) N-((2S,3S)-2-(3-bromobenzyl)-1-(2-hydroxy-2-methylpropanoyl)pyrrolidin-3-yl)-1-fluoromethanesulfonamide To a mixture of N-((2S,3S)-2-(3-bromobenzyl)pyrrolidin-3-yl)-1-fluoromethanesulfonamide (692 mg), 2-hydroxy-2-methylpropanoic acid (267 mg), DIPEA (509 mg) and DMF (13 mL) was added HATU (1.12 g) at room temperature. The mixture was stirred at room temperature for 3.5 hr, and the reaction mixture was poured into aqueous sodium hydrogencarbonate solution, and the mixture was extracted with ethyl acetate/THF. The organic layer was washed with water and saturated brine, dried over anhydrous magnesium sulfate, and concentrated under reduced pressure. The residue was purified by silica gel column chromatography (ethyl acetate/hexane) to give the title compound (788 mg).

MS: $[M+H]^+$ 437.0.

D) N-((2S,3S)-2-((3',5'-difluorobiphenyl-3-yl)methyl)-1-(2-hydroxy-2-methylpropanoyl)pyrrolidin-3-yl)-1-fluoromethanesulfonamide A mixture of N-((2S,3S)-2-(3-bromobenzyl)-1-(2-hydroxy-2-methylpropanoyl)pyrrolidin-3-yl)-1-fluoromethanesulfonamide (71 mg), (3,5-difluorophenyl)boronic acid (51.3 mg), XPhos Pd G3 (6.87 mg), 1 M aqueous tripotassium phosphate solution (0.487 mL) and THF (1.6 mL) was stirred under argon atmosphere at 70° C. for 1 hr. The reaction mixture was poured into aqueous sodium hydrogencarbonate solution, and the mixture was extracted with ethyl acetate. The organic layer was washed with water and saturated brine, dried over anhydrous magnesium sulfate, and concentrated under reduced pressure. The residue was purified by silica gel column chromatography (ethyl acetate/hexane) to give the title compound (41.4 mg).

$^1H$ NMR (300 MHz, $CDCl_3$) δ 1.43 (6H, brs), 1.83-1.99 (1H, m), 2.26-2.39 (1H, m), 2.98-3.19 (2H, m), 3.73 (3H, brs), 4.03-4.13 (1H, m), 4.55-5.04 (4H, m), 6.79 (1H, tt, J=8.9, 2.3 Hz), 7.05-7.14 (2H, m), 7.31-7.51 (4H, m).

Example 423

1-fluoro-N-((2S,3S)-1-(2-hydroxy-2-methylpropanoyl)-2-((2,3',5'-trifluorobiphenyl-3-yl)methyl)pyrrolidin-3-yl)methanesulfonamide A mixture of N-((2S,3S)-2-(3-bromo-2-fluorobenzyl)-1-(2-hydroxy-2-methylpropanoyl)pyrrolidin-3-yl)-1-fluoromethanesulfonamide (73 mg), (3,5-difluorophenyl)boronic acid (50.6 mg), XPhos Pd G3 (6.79 mg), 1 M aqueous tripotassium phosphate solution (0.481 mL) and THF (1.6 mL) was stirred under argon atmosphere at 70° C. for 1 hr. The reaction mixture was poured into aqueous sodium hydrogencarbonate solution, and the mixture was extracted with ethyl acetate. The organic layer was washed with water and saturated brine, dried over anhydrous magnesium sulfate, and concentrated under reduced pressure. The residue was purified by silica gel column chromatography (ethyl acetate/hexane) to give the title compound (44.4 mg).

$^1H$ NMR (300 MHz, $CDCl_3$) δ 1.41 (3H, s), 1.43 (3H, s), 1.89-2.03 (1H, m), 2.30-2.41 (1H, m), 2.93-3.01 (1H, m), 3.12 (1H, dd, J=14.0, 7.6 Hz), 3.63-3.83 (3H, m), 4.02-4.13 (1H, m), 4.65-4.86 (2H, m), 4.87-5.08 (2H, m), 6.82 (1H, tt, J=8.9, 2.5 Hz), 7.01-7.10 (2H, m), 7.21 (1H, t, J=7.6 Hz), 7.27-7.32 (1H, m), 7.41-7.48 (1H, m).

Example 424

1,1-difluoro-N-((2S,3S)-1-(2-hydroxy-2-methylpropanoyl)-2-((2,3',5'-trifluorobiphenyl-3-yl)methyl)pyrrolidin-3-yl)methanesulfonamide A) tert-butyl (2S,3S)-2-(3-bromo-2-fluorobenzyl)-3-(((difluoromethyl)sulfonyl)amino)pyrrolidine-1-carboxylate To a mixture of tert-butyl (2S,3S)-3-amino-2-(3-bromo-2-fluorobenzyl)pyrrolidine-1-carboxylate (1.33 g), 2,6-ditert-butylpyridine (1.50 g) and THF (11 mL) was added difluoromethanesulfonyl chloride (1.07 g) at −78° C. The mixture was stirred at 0° C. for 1 hr, poured into water, and extracted with ethyl acetate. The organic layer was washed with aqueous sodium hydrogencarbonate solution and saturated brine, dried over anhydrous magnesium sulfate, and concentrated under reduced pressure. The residue was purified by silica gel column chromatography (ethyl acetate/hexane) to give the title compound (955 mg).

MS: $[M-H]^-$ 484.9.

B) N-((2S,3S)-2-(3-bromo-2-fluorobenzyl)pyrrolidin-3-yl)-1,1-difluoromethanesulfonamide To a mixture of tert-butyl (2S,3S)-2-(3-bromo-2-fluorobenzyl)-3-(((difluoromethyl)sulfonyl)amino)pyrrolidine-1-carboxylate (949 mg) and toluene (10.2 mL) was added TFA (10.2 mL) at room temperature. The mixture was stirred at room temperature for 1 hr, and the reaction solution was poured into saturated aqueous sodium hydrogencarbonate solution under ice-cooling. The mixture was basified to pH=8 with potassium carbonate, and extracted with ethyl acetate/THF. The organic layer was washed with water and saturated brine, dried over anhydrous magnesium sulfate, and concentrated under reduced pressure. The residue was purified by silica gel column chromatography (NH, methanol/ethyl acetate) to give the title compound (643 mg).

MS: $[M+H]^+$ 386.9.

C) N-((2S,3S)-2-(3-bromo-2-fluorobenzyl)-1-(2-hydroxy-2-methylpropanoyl)pyrrolidin-3-yl)-1,1-difluoromethanesulfonamide To a mixture of N-((2S,3S)-2-(3-bromo-2-fluorobenzyl)pyrrolidin-3-yl)-1,1-difluoromethanesulfonamide (639 mg), 2-hydroxy-2-methylpropanoic acid (223 mg), DIPEA (427 mg) and DMF (11 mL) was added HATU (941 mg) at room temperature. The mixture was stirred at room temperature for 3.5 hr, and the reaction mixture was poured into aqueous sodium hydrogencarbonate solution, and the mixture was extracted with ethyl acetate/THF. The organic layer was washed with water and saturated brine, dried over anhydrous magnesium sulfate, and concentrated under reduced pressure. The residue was purified by silica gel column chromatography (ethyl acetate/hexane) to give the title compound (702 mg).

MS: $[M+H]^+$ 473.0.

D) 1,1-difluoro-N-((2S,3S)-1-(2-hydroxy-2-methylpropanoyl)-2-((2,3',5'-trifluorobiphenyl-3-yl)methyl)pyrrolidin-3-yl)methanesulfonamide A mixture of N-((2S,3S)-2-(3-bromo-2-fluorobenzyl)-1-(2-hydroxy-2-methylpropanoyl)pyrrolidin-3-yl)-1,1-difluoromethanesulfonamide (76 mg), (3,5-difluorophenyl)boronic acid (50.7 mg), XPhos Pd G3 (6.80 mg), 1 M aqueous tripotassium phosphate solution (0.482 mL) and THF (1.6 mL) was stirred under argon atmosphere at 70° C. for 1 hr. The reaction mixture was poured into aqueous sodium hydrogencarbonate solution, and the mixture was extracted with ethyl acetate. The organic layer was washed with water and saturated brine, dried over anhydrous magnesium sulfate, and concentrated under reduced pressure. The residue was purified by silica gel column chromatography (ethyl acetate/hexane) to give the title compound (63.6 mg).

$^1H$ NMR (300 MHz, $CDCl_3$) δ 1.42 (3H, s), 1.43 (3H, s), 1.88-2.03 (1H, m), 2.36-2.42 (1H, m), 2.94-3.02 (1H, m), 3.13 (1H, dd, J=14.0, 7.8 Hz), 3.64-3.80 (3H, m), 4.11-4.22 (1H, m), 4.75 (1H, brs), 5.10 (1H, brs), 6.04 (1H, t, J=54.0 Hz), 6.83 (1H, tt, J=8.9, 2.3 Hz), 7.01-7.09 (2H, m), 7.21 (1H, t, J=7.6 Hz), 7.26-7.32 (1H, m), 7.43 (1H, t, J=6.4 Hz).

Example 428

N-((2S,3S)-2-((3'-chloro-2,5'-difluorobiphenyl-3-yl) methyl)-1-(2-hydroxy-2-methylpropanoyl)pyrrolidin-3-yl)methanesulfonamide A) N-((2S,3S)-2-(3-bromo-2-fluorobenzyl)pyrrolidin-3-yl)methanesulfonamide hydrochloride To tert-butyl (2S,3S)-2-(3-bromo-2-fluorobenzyl)-3-((methylsulfonyl)amino)pyrrolidine-1-carboxylate (5 g) was added 4M hydrogen chloride/ethyl acetate solution (22.2 mL) at room temperature. The mixture was stirred at room temperature for 10 hr, and the reaction solution was concentrated under reduced pressure. The obtained solid was washed with diisopropyl ether to give the title compound (4.11 g).

MS: $[M+H]^+$ 351.1.

B) N-((2S,3S)-2-(3-bromo-2-fluorobenzyl)-1-(2-hydroxy-2-methylpropanoyl)pyrrolidin-3-yl)methanesulfonamide To a mixture of N-((2S,3S)-2-(3-bromo-2-fluorobenzyl) pyrrolidin-3-yl)methanesulfonamide hydrochloride (4.11 g), 2-hydroxy-2-methylpropanoic acid (1.32 g) and DMF (40 mL) were added HATU (4.84 g) and TEA (4.29 g) at room temperature. The mixture was stirred overnight at room temperature, to the reaction mixture was added saturated aqueous sodium hydrogencarbonate solution, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (3.30 g).

MS: $[M+H]^+$ 437.2.

C) N-((2S,3S)-2-((3'-chloro-2,5'-difluorobiphenyl-3-yl)methyl)-1-(2-hydroxy-2-methylpropanoyl)pyrrolidin-3-yl)methanesulfonamide A mixture of N-((2S,3S)-2-(3-bromo-2-fluorobenzyl)-1-(2-hydroxy-2-methylpropanoyl)pyrrolidin-3-yl)methanesulfonamide (70 mg), (3-chloro-5-fluorophenyl)boronic acid (41.9 mg), XPhos Pd G3 (4.06 mg), 1 M aqueous tripotassium phosphate solution (0.480 mL) and THF (2 mL) was stirred at 70° C. for 1 hr. The reaction mixture was purified by silica gel column chromatography (NH, ethyl acetate/hexane), and then purified by HPLC (C18, mobile phase: water/acetonitrile (containing 0.1% TFA)). To the obtained fraction was added saturated aqueous sodium hydrogencarbonate solution, and the mixture was extracted with ethyl acetate. The organic layer was washed with saturated brine, dried over anhydrous magnesium sulfate, and concentrated under reduced pressure to give the title compound (19 mg).

$^1H$ NMR (400 MHz, DMSO-$d_6$) δ 1.01-1.27 (6H, m), 1.96-2.06 (1H, m), 2.08-2.25 (1H, m), 2.55-2.73 (1H, m), 2.91 (3H, s), 2.95-3.12 (1H, m), 3.42-3.98 (3H, m), 4.56-4.71 (1H, m), 4.92-5.39 (1H, m), 7.05-7.20 (1H, m), 7.29-7.53 (6H, m).

Example 431

N-((2S,3S)-2-((3'-chloro-2-fluorobiphenyl-3-yl) methyl)-1-(2-hydroxy-2-methylpropanoyl)pyrrolidin-3-yl)ethanesulfonamide A) N-((2S,3S)-2-(3-bromo-2-fluorobenzyl)pyrrolidin-3-yl)ethanesulfonamide hydrochloride To tert-butyl (2S,3S)-2-(3-bromo-2-fluorobenzyl)-3-((ethylsulfonyl)amino)pyrrolidine-1-carboxylate (847 mg) was added 4M hydrogen chloride/ethyl acetate solution (8 mL) at room temperature. The mixture was stirred at room temperature for 1 hr, and the reaction mixture was concentrated under reduced pressure. The obtained solid was washed with ethyl acetate to give the title compound (527 mg).

MS: $[M+H]^+$ 364.9.

B) N-((2S,3S)-2-(3-bromo-2-fluorobenzyl)-1-(2-hydroxy-2-methylpropanoyl)pyrrolidin-3-yl)ethanesulfonamide To a mixture of N-((2S,3S)-2-(3-bromo-2-fluorobenzyl) pyrrolidin-3-yl)ethanesulfonamide hydrochloride (727 mg), 2-hydroxy-2-methylpropanoic acid (227 mg) and DMF (5 mL) were added HATU (1.03 g) and TEA (549 mg) at room temperature. The mixture was stirred at room temperature for 2 hr, to the reaction mixture was added saturated aqueous sodium hydrogencarbonate solution, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (569 mg).

MS: $[M+H]^+$ 451.0.

C) N-((2S,3S)-2-((3'-chloro-2-fluorobiphenyl-3-yl) methyl)-1-(2-hydroxy-2-methylpropanoyl)pyrrolidin-3-yl)ethanesulfonamide A mixture of N-((2S,3S)-2-(3-bromo-2-fluorobenzyl)-1-(2-hydroxy-2-methylpropanoyl)pyrrolidin-3-yl)ethanesulfonamide (60 mg), (3-chlorophenyl)boronic acid (31.2 mg), XPhos Pd G3 (3.38 mg), 1 M aqueous tripotassium phosphate solution (0.399 mL) and THE (2 mL) was stirred at 70° C. for 1 hr. The reaction mixture was purified by silica gel column chromatography (NH, ethyl acetate/hexane), and then purified by HPLC (C18, mobile phase: water/acetonitrile (containing 0.1% TFA)). To the obtained fraction was added saturated aqueous sodium hydrogencarbonate solution, and the mixture was extracted with ethyl acetate. The organic layer was washed with saturated brine, dried over anhydrous magnesium sulfate, and concentrated under reduced pressure to give the title compound (38 mg).

$^1H$ NMR (400 MHz, DMSO-$d_6$) δ 1.03-1.17 (6H, m), 1.18-1.23 (3H, m), 1.99-2.23 (2H, m), 2.54-2.67 (1H, m), 2.95-3.11 (3H, m), 3.62-3.83 (2H, m), 3.84-3.98 (1H, m), 4.53-4.73 (1H, m), 4.89-5.04 (1H, m), 7.07-7.17 (1H, m), 7.26-7.39 (2H, m), 7.41-7.52 (4H, m), 7.54-7.62 (1H, m).

Example 435

N-((2S,3S)-1-(2-hydroxy-2-methylpropanoyl)-2-((2,3',5'-trifluorobiphenyl-3-yl)methyl)pyrrolidin-3-yl) ethanesulfonamide A mixture of N-((2S,3S)-2-(3-bromo-2-fluorobenzyl)-1-(2-hydroxy-2-methylpropanoyl)pyrrolidin-3-yl)ethanesulfonamide (70 mg), (3,5-difluorophenyl)boronic acid (36.7 mg), XPhos Pd G3 (3.94 mg), 1 M aqueous tripotassium phosphate solution (0.465 mL) and THE (3 mL) was stirred at 70° C. for 1.5 hr. The reaction mixture was partitioned between ethyl acetate and water, and the mixture was extracted with ethyl acetate. The organic layer was washed with aqueous sodium hydrogencarbonate solution and saturated brine, dried over anhydrous magnesium sulfate, and concentrated under reduced pressure. The residue was purified by silica gel column chromatography (NH, methanol/ethyl acetate). The obtained solid was recrystallized from ethyl acetate/hexane/water to give the title compound (65.9 mg).

$^1H$ NMR (400 MHz, $CDCl_3$) δ 1.24 (3H, t, J=7.3 Hz), 1.39 (3H, s), 1.41 (3H, s), 1.87-2.01 (1H, m), 2.28-2.43 (1H, m), 2.79-2.98 (3H, m), 3.05-3.18 (1H, m), 3.68 (2H, brs), 3.83 (1H, brs), 3.90-4.05 (1H, m), 4.50-4.63 (1H, m), 4.75 (1H, brs), 6.74-6.90 (1H, m), 6.98-7.11 (2H, m), 7.14-7.22 (1H, m), 7.24-7.32 (1H, m), 7.36-7.47 (1H, m).

Example 437

N-((2S,3S)-2-((3'-chloro-2,5'-difluorobiphenyl-3-yl)methyl)-1-(2-hydroxy-2-methylpropanoyl)pyrrolidin-3-yl)ethanesulfonamide A mixture of N-((2S,3S)-2-(3-bromo-2-fluorobenzyl)-1-(2-hydroxy-2-methylpropanoyl)pyrrolidin-3-yl)ethanesulfonamide (70 mg), (3-chloro-5-fluorophenyl)boronic acid (40.6 mg), XPhos Pd G3 (3.94 mg), 1 M aqueous tripotassium phosphate solution (0.465 mL) and THE (3 mL) was stirred at 70° C. for 2.5 hr. The reaction mixture was partitioned between ethyl acetate and water, and the mixture was extracted with ethyl acetate. The organic layer was washed with aqueous sodium hydrogencarbonate solution and saturated brine, dried over anhydrous magnesium sulfate, and concentrated under reduced pressure. The residue was purified by silica gel column chromatography (NH, methanol/ethyl acetate). The obtained solid was recrystallized from ethyl acetate/hexane/water to give the title compound (10 mg).

$^1H$ NMR (400 MHz, $CDCl_3$) δ1.24 (3H, t, J=6.8 Hz), 1.40 (3H, s), 1.41 (3H, brs), 1.82-2.04 (1H, m), 2.25-2.44 (1H, m), 2.77-3.01 (3H, m), 3.05-3.23 (1H, m), 3.68 (2H, brs), 3.81 (1H, brs), 3.90-4.08 (1H, m), 4.39-4.58 (1H, m), 4.75 (1H, brs), 7.04-7.22 (3H, m), 7.23-7.35 (2H, m), 7.37-7.47 (1H, m).

Example 439

N-((2S,3S)-1-(2-hydroxy-2-methylpropanoyl)-2-((2,3',5'-trifluorobiphenyl-3-yl)methyl)pyrrolidin-3-yl)cyclopropanesulfonamide

A) tert-butyl (2S,3S)-2-(3-bromo-2-fluorobenzyl)-3-((cyclopropylsulfonyl)amino)pyrrolidine-1-carboxylate To a mixture of tert-butyl (2S,3S)-3-amino-2-(3-bromo-2-fluorobenzyl)pyrrolidine-1-carboxylate (1 g), TEA (0.542 g), DMAP (0.327 g) and THE (10 mL) was added cyclopropanesulfonyl chloride (0.753 g) at room temperature. The mixture was stirred at 50° C. for 3.5 hr, and to the reaction mixture was added ethyl acetate. The insoluble substance was removed by filtration, and the filtrate was concentrated under reduced pressure. The residue was purified by silica gel column chromatography (ethyl acetate/hexane) to give the title compound (1.2 g).

MS: [M+H-Boc]$^+$ 377.1.

B) N-((2S,3S)-2-(3-bromo-2-fluorobenzyl)pyrrolidin-3-yl)cyclopropanesulfonamide hydrochloride To tert-butyl (2S,3S)-2-(3-bromo-2-fluorobenzyl)-3-((cyclopropylsulfonyl)amino)pyrrolidine-1-carboxylate (722 mg) was added 4M hydrogen chloride/ethyl acetate solution (7.56 mL) at room temperature. The mixture was stirred at room temperature for 2 hr, and concentrated under reduced pressure. The residue was washed with diisopropyl ether to give the title compound (617 mg).

MS: [M+H]$^+$ 377.1.

C) N-((2S,3S)-2-(3-bromo-2-fluorobenzyl)-1-(2-hydroxy-2-methylpropanoyl)pyrrolidin-3-yl)cyclopropanesulfonamide To a mixture of N-((2S,3S)-2-(3-bromo-2-fluorobenzyl)pyrrolidin-3-yl)cyclopropanesulfonamide hydrochloride (607 mg), 2-hydroxy-2-methylpropanoic acid (183 mg) and DMF (10 mL) were added HATU (837 mg) and TEA (445 mg) at room temperature. The mixture was stirred at room temperature for 2 hr, to the reaction mixture was added saturated aqueous sodium hydrogencarbonate solution, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (527 mg).

MS: [M+H]$^+$ 463.1.

D) N-((2S,3S)-1-(2-hydroxy-2-methylpropanoyl)-2-((2,3',5'-trifluorobiphenyl-3-yl)methyl)pyrrolidin-3-yl)cyclopropanesulfonamide A mixture of N-((2S,3S)-2-(3-bromo-2-fluorobenzyl)-1-(2-hydroxy-2-methylpropanoyl)pyrrolidin-3-yl)cyclopropanesulfonamide (73.3 mg), (3,5-difluorophenyl)boronic acid (37.5 mg), XPhos Pd G3 (4.02 mg), 1 M aqueous tripotassium phosphate solution (0.475 mL) and THE (3 mL) was stirred at 70° C. for 1.5 hr. The reaction mixture was partitioned between ethyl acetate and water, and the mixture was extracted with ethyl acetate. The organic layer was washed with aqueous sodium hydrogencarbonate solution and saturated brine, dried over anhydrous magnesium sulfate, and concentrated under reduced pressure. The residue was purified by silica gel column chromatography (NH, ethyl acetate/hexane) to give the title compound (35.8 mg).

$^1H$ NMR (400 MHz, $CDCl_3$) δ0.83-0.98 (2H, m), 1.10 (2H, brs), 1.38 (3H, brs), 1.40 (3H, brs), 1.93-2.14 (2H, m), 2.25-2.45 (1H, m), 2.80-2.99 (1H, m), 3.05-3.23 (1H, m), 3.71 (2H, brs), 3.86 (1H, brs), 3.95-4.06 (1H, m), 4.78 (1H, brs), 4.96 (1H, d, J=7.1 Hz), 6.81 (1H, t, J=8.4 Hz), 6.99-7.11 (2H, m), 7.12-7.20 (1H, m), 7.22-7.31 (1H, m), 7.40 (1H, brs).

Example 362

N-((2S,3S)-1-(azetidin-1-ylcarbonyl)-2-((3',5'-difluorobiphenyl-3-yl)methyl)pyrrolidin-3-yl)ethanesulfonamide A) (2S,3S)-2-((3',5'-difluoro[biphenyl]-3-yl)methyl)-3-((ethylsulfonyl)amino)pyrrolidine-1-carbonyl chloride To a mixture of N-((2S,3S)-2-((3',5'-difluorobiphenyl-3-yl)methyl)pyrrolidin-3-yl)ethanesulfonamide hydrochloride (1.0 g), DIPEA (0.620 g) and THF (30 mL) was added bis(trichloromethyl) carbonate (0.569 g) in THF (5 mL) at 0° C. After being stirred at 0° C. for 10 min, the mixture was warmed up to room temperature and stirred for 3 hr. The mixture was concentrated in vacuo. The residue was triturated with ethyl acetate and the insoluble substance was removed by filtration. The filtrate was concentrated in vacuo. The residue was purified by silica gel column chromatography (ethyl acetate/hexane) to give the title compound (1.06 g).

MS: $[M-H]^-$ 441.2.

B) N-((2S,3S)-1-(azetidin-1-ylcarbonyl)-2-((3',5'-difluorobiphenyl-3-yl)methyl)pyrrolidin-3-yl)ethanesulfonamide To a mixture of (2S,3S)-2-((3',5'-difluoro[biphenyl]-3-yl)methyl)-3-((ethylsulfonyl)amino)pyrrolidine-1-carbonyl chloride (500 mg), azetidine (129 mg) and THF (10 mL) was added TEA (343 mg) at room temperature. The mixture was stirred at room temperature for 3 hr, then diluted with THF and the insoluble substance was removed by filtration. The filtrate was concentrated in vacuo. The residue was purified by silica gel column chromatography (methanol/ethyl acetate) and recrystallized from ethyl acetate/hexane to give the title compound (380 mg).

$^1H$ NMR (300 MHz, $CDCl_3$) δ 1.18-1.28 (3H, m), 1.75-1.90 (1H, m), 2.08-2.25 (3H, m), 2.81-2.99 (3H, m), 3.16 (1H, dd, J=14.0, 4.9 Hz), 3.26-3.43 (2H, m), 3.80-4.08 (5H, m), 4.36 (1H, d, J=8.7 Hz), 4.43-4.53 (1H, m), 6.78 (1H, tt, J=8.9, 2.3 Hz), 7.07-7.17 (2H, m), 7.31-7.43 (3H, m), 7.46-7.50 (1H, m).

Example 372

N-((2S,3S)-1-(azetidin-1-ylcarbonyl)-2-((2,3'-difluorobiphenyl-3-yl)methyl)pyrrolidin-3-yl)ethanesulfonamide Azetidine (244 mg) was added to a stirred mixture of (2S,3S)-2-((2,3'-difluorobiphenyl-3-yl)methyl)-3-((ethylsulfonyl)amino)pyrrolidine-1-carbonyl chloride (632 mg) and THF (6 mL) at room temperature. After being stirred for 30 min, the reaction mixture was concentrated in vacuo. The residue was diluted with ethyl acetate, washed with saturated brine, dried over anhydrous sodium sulfate, filtrated and concentrated in vacuo. The obtained solid was crystallized from ethyl acetate/ethanol to give the title compound (416 mg).

$^1H$ NMR (400 MHz, $CDCl_3$) δ 1.23 (3H, t, J=7.4 Hz), 1.82-1.97 (1H, m), 2.08-2.30 (3H, m), 2.78-2.91 (2H, m), 2.92-3.06 (2H, m), 3.22-3.40 (2H, m), 3.74-4.02 (5H, m), 4.46-4.61 (2H, m), 7.03-7.11 (1H, m), 7.14-7.25 (2H, m), 7.26-7.44 (4H, m).

Example 377

(2S,3S)-2-((2,3'-difluorobiphenyl-3-yl)methyl)-3-((dimethylsulfamoyl)amino)-N,N-dimethylpyrrolidine-1-carboxamide A) tert-butyl (2S,3S)-2-(3-bromo-2-fluorobenzyl)-3-((dimethylsulfamoyl)amino)pyrrolidine-1-carboxylate Dimethylsulfamoyl chloride (2.31 g) was added to a mixture of tert-butyl (2S,3S)-3-amino-2-(3-bromo-2-fluorobenzyl)pyrrolidine-1-carboxylate (2.5 g), TEA (1.36 g), DMAP (0.982 g) and THE (25 mL) at room temperature. After being stirred at 50° C. for 4 hr, the reaction mixture was poured into water and extracted with ethyl acetate. The organic layer was washed with saturated brine, dried over anhydrous magnesium sulfate and concentrated in vacuo. The residue was purified by silica gel column chromatography (ethyl acetate/hexane) to give the title compound (2.4 g).

MS: $[M+H-Boc]^+$ 380.0.

B) N'-((2S,3S)-2-(3-bromo-2-fluorobenzyl)pyrrolidin-3-yl)-N,N-dimethylsulfuric diamide hydrochloride A mixture of tert-butyl (2S,3S)-2-(3-bromo-2-fluorobenzyl)-3-((dimethylsulfamoyl)amino)pyrrolidine-1-carboxylate (2.4 g) and 4M hydrogen chloride/ethyl acetate solution (12.5 mL) was stirred at room temperature under a dry atmosphere ($CaCl_2$ tube) overnight. The mixture was concentrated in vacuo. The residue was washed with diisopropyl ether to give the title compound (1.78 g).

MS: $[M+H]^+$ 379.9.

C) (2S,3S)-2-(3-bromo-2-fluorobenzyl)-3-((dimethylsulfamoyl)amino)-N,N-dimethylpyrrolidine-1-carboxamide To a mixture of N'-((2S,3S)-2-(3-bromo-2-fluorobenzyl)pyrrolidin-3-yl)-N,N-dimethylsulfuric diamide hydrochloride (1.78 g), TEA (4.32 g) and THF (20 mL) was added dimethylcarbamoyl chloride (2.30 g) at room temperature. The mixture was refluxed for 3 hr. The mixture was quenched with saturated aqueous sodium hydrogencarbonate solution and extracted with ethyl acetate. The organic layer was separated, washed with saturated brine, dried over anhydrous magnesium sulfate and concentrated in vacuo. The residue was purified by silica gel column chromatography (NH, ethyl acetate/hexane) to give the title compound (1.9 g).

MS: $[M+H]^+$ 451.0.

D) (2S,3S)-2-((2,3'-difluorobiphenyl-3-yl)methyl)-3-((dimethylsulfamoyl)amino)-N,N-dimethylpyrrolidine-1-carboxamide A mixture of (2S,3S)-2-(3-bromo-2-fluorobenzyl)-3-((dimethylsulfamoyl)amino)-N,N-dimethylpyrrolidine-1-carboxamide (600 mg), (3-fluorophenyl)boronic acid (242 mg), XPhos Pd G3 (16.9 mg), 1M aqueous tripotassium phosphate solution (3.99 mL) and THE (6 mL) was stirred at 70° C. for 1 hr. The aqueous phase was removed and the organic layer was concentrated in vacuo. The residue was purified by silica gel column chromatography (NH, ethyl acetate/ hexane) and the resulting solid was crystallized from ethyl acetate/hexane to give the title compound (562 mg).

$^1$H NMR (400 MHz, $CDCl_3$) δ 2.03-2.23 (2H, m), 2.73 (6H, s), 2.76 (6H, s), 2.85-2.93 (1H, m), 2.94-3.03 (1H, m), 3.20-3.32 (1H, m), 3.53-3.67 (1H, m), 3.81-3.92 (1H, m), 4.48 (1H, d, J=8.1 Hz), 4.54-4.62 (1H, m), 7.01-7.08 (1H, m), 7.12-7.18 (1H, m), 7.20-7.26 (2H, m), 7.27-7.43 (3H, m).

Example 407

(2S,3S)-2-(biphenyl-3-ylmethyl)-3-((ethylsulfonyl)amino)-N-methoxy-N-methylpyrrolidine-1-carboxamide To a stirred mixture of N-((2S,3S)-2-(biphenyl-3-ylmethyl)pyrrolidin-3-yl)ethanesulfonamide hydrochloride (293 mg), DIPEA (298 mg) and THF (3 mL) was added methoxy(methyl)carbamoyl chloride (143 mg) at room temperature. After 15 min, the reaction mixture was concentrated in vacuo. The residue was diluted with ethyl acetate, washed with saturated brine, and purified by silica gel column chromatography (ethyl acetate/hexane) and recrystallized from ethyl acetate/hexane to give the title compound (302 mg).

$^1$H NMR (400 MHz, $CDCl_3$) δ 1.19 (3H, t, J=7.4 Hz), 1.83-1.94 (1H, m), 2.06-2.23 (1H, m), 2.72-2.94 (3H, m), 2.98 (3H, s), 3.17-3.27 (1H, m), 3.42-3.52 (1H, m), 3.55 (3H, s), 3.60-3.70 (1H, m), 3.86-4.02 (1H, m), 4.40 (1H, d, J=8.8 Hz), 4.52-4.68 (1H, m), 7.27-7.62 (9H, m).

Example 441

N-{(2S,3S)-1-(oxetane-2-carbonyl)-2-[(2,3',5'-trifluoro[1,1'-biphenyl]-3-yl)methyl]pyrrolidin-3-yl}methanesulfonamide A) N-((2S,3S)-2-(3-bromo-2-fluorobenzyl)-1-(oxetan-2-ylcarbonyl)pyrrolidin-3-yl)methanesulfonamide HATU (374 mg) was added to a mixture of N-((2S,3S)-2-(3-bromo-2-fluorobenzyl)pyrrolidin-3-yl)methanesulfonamide hydrochloride (318 mg), oxetane-2-carboxylic acid (100 mg), TEA (415 mg) and DMF (6 mL) at room temperature. The mixture was stirred at room temperature for 30 min. The mixture was quenched with saturated aqueous sodium hydrogencarbonate solution and extracted with ethyl acetate. The organic layer was separated, washed with saturated brine, dried over anhydrous magnesium sulfate and concentrated in vacuo. The residue was purified by silica gel column chromatography (methanol/ethyl acetate). The solid was crystallized from ethyl acetate/diisopropyl ether/hexane to give the title compound (244 mg)

MS: $[M+H]^+$ 435.2.

B) N-{(2S,3S)-1-(oxetane-2-carbonyl)-2-[(2,3',5'-trifluoro[1,1'-biphenyl]-3-yl)methyl]pyrrolidin-3-yl}methanesulfonamide A mixture of N-((2S,3S)-2-(3-bromo-2-fluorobenzyl)-1-(oxetan-2-ylcarbonyl)pyrrolidin-3-yl)methanesulfonamide (76.5 mg), (3,5-difluorophenyl)boronic acid (41.6 mg), Xphos Pd G3 (4.46 mg), 1M aqueous tripotassium phosphate solution (0.527 mL) and THF (3 mL) was stirred at 70° C. for 1.5 hr. The mixture was partitioned between ethyl acetate and water and extracted with ethyl acetate. The extract was washed with aqueous sodium hydrogencarbonate solution and saturated brine, dried over anhydrous magnesium sulfate, filtered and concentrated in vacuo to give a solid. The residue was purified by silica gel column chromatography (NH, methanol/ethyl acetate) to give the title compound (42.4 mg).

$^1$H NMR (400 MHz, $CDCl_3$) δ 1.82-1.98 (1H, m), 2.25-2.63 (2H, m), 2.69-3.03 (5H, m), 3.06-3.16 (1H, m), 3.25-3.81 (2H, m), 3.93-4.58 (3H, m), 4.62-5.25 (3H, m), 6.76-7.55 (6H, m).

Example 450

N-[(2S,3S)-2-[(2,3'-difluoro[1,1'-biphenyl]-3-yl)methyl]-1-(2-hydroxy-2-methylpropanoyl)pyrrolidin-3-yl]-1-fluorocyclopropane-1-sulfonamide A) tert-butyl (2S,3S)-3-((cyclopropylsulfonyl)amino)-2-((2,3'-difluoro[biphenyl]-3-yl)methyl)pyrrolidine-1-carboxylate A mixture of tert-butyl (2S,3S)-2-(3-bromo-2-fluorobenzyl)-3-((cyclopropylsulfonyl)amino)pyrrolidine-1-carboxylate (1.17 g), (3-fluorophenyl)boronic acid (0.514 g), XPhos Pd G3 (0.207 g), 1M aqueous tripotassium phosphate solution (7.35 mL) and THF (10 mL) was stirred at 70° C. for 1 hr. The mixture was poured into water at room temperature and extracted with ethyl acetate. The organic layer was separated, washed with saturated brine, dried over anhydrous magnesium sulfate and concentrated in vacuo. The residue was purified by silica gel column chromatography (NH, ethyl acetate/Hexane) to give title compound (1.02 g).

MS: $[M+H-Boc]^+$393.1.

B) tert-butyl (2S,3S)-2-((2,3'-difluoro[biphenyl]-3-yl)methyl)-3-(((1-fluorocyclopropyl)sulfonyl)amino)pyrrolidine-1-carboxylate To a mixture of tert-butyl (2S,3S)-3-((cyclopropylsulfonyl)amino)-2-((2,3'-difluoro[biphenyl]-3-yl)methyl)pyrrolidine-1-carboxylate (156 mg) and THF (3 mL) was added 2.6M n-butyllithium/hexane solution (0.268 mL) dropwise at −78° C. After being stirred at −78° C. for 1 hr, a solution of N-fluoro-N-(phenylsulfonyl)benzenesulfonamide (120 mg) in THF (1 mL) was added dropwise to the reaction mixture. The mixture was stirred at 0° C. under nitrogen atmosphere for 1 hr and then at room temperature for 2 hr. The mixture was quenched with saturated aqueous ammonium chloride solution and extracted with ethyl acetate. The organic layer was separated, washed with water and saturated brine, dried over anhydrous magnesium sulfate and concentrated in vacuo. The residue was purified by silica gel column chromatography (ethyl acetate/hexane) to give title compound (81.9 mg).

MS: $[M+H-Boc]^+$411.3.

C) N-((2S,3S)-2-((2,3'-difluoro[biphenyl]-3-yl)methyl)pyrrolidin-3-yl)-1-fluorocyclopropanesulfonamide hydrochloride To a mixture of tert-butyl (2S,3S)-2-((2,3'-difluoro[biphenyl]-3-yl)methyl)-3-(((1-fluorocyclopropyl)sulfonyl)amino)pyrrolidine-1-carboxylate (81.9 mg) and ethyl acetate (0.5 mL) was added 4M hydrogen chloride/ethyl acetate solution (0.802 mL) at room temperature. The mixture was stirred at room temperature overnight. The mixture was concentrated in vacuo to give the title compound (57.0 mg).

MS: $[M+H]^+$ 411.3.

D) N-[(2S,3S)-2-[(2,3'-difluoro[1,1'-biphenyl]-3-yl) methyl]-1-(2-hydroxy-2-methylpropanoyl)pyrrolidin-3-yl]-1-fluorocyclopropane-1-sulfonamide A mixture of N-((2S,3S)-2-((2,3'-difluoro[biphenyl]-3-yl) methyl)pyrrolidin-3-yl)-1-fluorocyclopropanesulfonamide hydrochloride (447 mg), DIPEA (1.29 g) and THF (5 mL) was stirred at room temperature for 30 min. To the suspension was added dropwise 1-chloro-2-methyl-1-oxopropan-2-yl acetate (198 mg) at 0° C., and the mixture was stirred at same temperature for 1 hr. To the mixture were added water (2 mL) and 4M aqueous lithium hydroxide solution (2.00 mL) and the mixture was stirred at room temperature overnight. The mixture was diluted with saturated brine and extracted with ethyl acetate. The organic layer was separated, dried over anhydrous magnesium sulfate and concentrated in vacuo. The residue was purified by silica gel column chromatography (NH, ethyl acetate/hexane) and then preparative HPLC (C18, mobile phase: water/acetonitrile (containing 0.1% TFA)). The desired fraction was neutralized with saturated aqueous sodium hydrogencarbonate solution and extracted with ethyl acetate. The organic layer was separated, washed with water and saturated brine, dried over anhydrous magnesium sulfate and concentrated in vacuo. The solid was crystallized from ethanol/water to give the title compound (140 mg).

$^1$H NMR (400 MHz, $CDCl_3$) δ 1.14-1.52 (10H, m), 1.79-2.03 (1H, m), 2.28-2.42 (1H, m), 2.91-3.04 (1H, m), 3.11-3.26 (1H, m), 3.52-3.95 (3H, m), 4.07-4.24 (1H, m), 4.69-5.06 (2H, m), 7.03-7.10 (1H, m), 7.15-7.25 (2H, m), 7.27-7.44 (4H, m).

Example 456

N-{(2S,3S)-1-(azetidine-1-carbonyl)-2-[(2-fluoro[1,1'-biphenyl]-3-yl)methyl]pyrrolidin-3-yl}ethanesulfonamide A) N-((2S,3S)-2-((2-fluoro[biphenyl]-3-yl)methyl) pyrrolidin-3-yl)ethanesulfonamide hydrochloride A mixture of tert-butyl (2S,3S)-2-(3-bromo-2-fluorobenzyl)-3-((ethylsulfonyl)amino)pyrrolidine-1-carboxylate (0.698 g), phenylboronic acid (0.238 g), XPhos Pd G3 (0.019 g), 2M aqueous tripotassium phosphate solution (2.25 mL) and THF (3 mL) was stirred at 70° C. for 1 hr. The aqueous phase was removed and the organic layer was concentrated in vacuo. The residue was purified by silica gel column chromatography (NH, ethyl acetate/hexane) to give a solid. 4M hydrogen chloride/ethyl acetate solution (7.50 mL) was added to a stirred mixture of the solid (694 mg) and ethyl acetate (2 mL) at room temperature. After 18 hr, the reaction mixture was concentrated in vacuo, and the resulting solid was collected by filtration to give the title compound (568 mg).

MS: $[M+H]^+$ 363.3.

B) N-{(2S,3S)-1-(azetidine-1-carbonyl)-2-[(2-fluoro [1,1'-biphenyl]-3-yl)methyl]pyrrolidin-3-yl}ethanesulfonamide To a stirred mixture of N-((2S,3S)-2-((2-fluoro[biphenyl]-3-yl)methyl)pyrrolidin-3-yl)ethanesulfonamide hydrochloride (568 mg), bis(trichloromethyl) carbonate (254 mg) and THF (6 mL) was added DIPEA (368 mg) at 0° C. After being stirred at room temperature for 30 min, the reaction mixture was concentrated in vacuo. The residue was diluted with ethyl acetate, washed with saturated brine, and purified by silica gel column chromatography (ethyl acetate/hexane) to give an oil. Azetidine (243 mg) was added to a stirred mixture of the oil (603 mg) and THE (7 mL) at room temperature. After being stirred for 30 min, the reaction mixture was concentrated in vacuo. The residue was diluted with ethyl acetate, washed with saturated brine, dried over anhydrous sodium sulfate, filtrated and concentrated in vacuo. The obtained solid was crystallized from hexane/ethanol to give the title compound (516 mg).

$^1$H NMR (400 MHz, $CDCl_3$) δ 1.21 (3H, t, J=7.4 Hz), 1.82-1.96 (1H, m), 2.06-2.28 (3H, m), 2.76-2.90 (2H, m), 2.93-3.08 (2H, m), 3.20-3.40 (2H, m), 3.82 (2H, q, J=7.8 Hz), 3.88-4.06 (3H, m), 4.52 (1H, q, J=6.6 Hz), 4.58-4.65 (1H, m), 7.13-7.20 (1H, m), 7.27-7.33 (1H, m), 7.33-7.39 (2H, m), 7.41-7.48 (2H, m), 7.49-7.56 (2H, m).

Example 457

N-{(2S,3S)-1-(3-hydroxy-2,2-dimethylpropanoyl)-2-[(2,3',5'-trifluoro[1,1'-biphenyl]-3-yl)methyl]pyrrolidin-3-yl}methanesulfonamide A) N-((2S,3S)-2-((2,3',5'-trifluorobiphenyl-3-yl) methyl)pyrrolidin-3-yl)methanesulfonamide hydrochloride A mixture of tert-butyl (2S,3S)-3-((methylsulfonyl) amino)-2-((2,3',5'-trifluorobiphenyl-3-yl)methyl)pyrrolidine-1-carboxylate (1.67 g), 4M hydrogen chloride/ethyl acetate solution (20 mL) and ethyl acetate (20 mL) was stirred at room temperature overnight. The mixture was diluted with ethyl acetate and the precipitate was collected by filtration to give the title compound (1.37 g).

MS: $[M+H]^+$ 385.2.

B) N-{(2S,3S)-1-(3-hydroxy-2,2-dimethylpropanoyl)-2-[(2,3',5'-trifluoro[1,1'-biphenyl]-3-yl) methyl]pyrrolidin-3-yl}methanesulfonamide HATU (67.8 mg) was added to a mixture of N-((2S,3S)-2-((2,3',5'-trifluorobiphenyl-3-yl)methyl)pyrrolidin-3-yl) methanesulfonamide hydrochloride (50 mg), 3-hydroxy-2,2-dimethylpropanoic acid (18.2 mg), DIPEA (77 mg) and DMF (1 mL) at room temperature. After being stirred at room temperature for 7 hr, the reaction mixture was diluted with water and extracted with ethyl acetate. The extract was washed with saturated aqueous sodium hydrogencarbonate solution, water and saturated brine, dried over anhydrous magnesium sulfate and concentrated in vacuo. The residue was purified by silica gel column chromatography (ethyl acetate) to give an oil. The oil was crystallized from ethyl acetate/hexane to give the title compound (24.7 mg).

$^1$H NMR (300 MHz, $CDCl_3$) δ 1.18 (3H, s), 1.19 (3H, s), 1.86-2.11 (1H, m), 2.31-2.47 (1H, m), 2.31-2.47 (1H, m), 2.72 (3H, s), 2.86 (1H, dd, J=13.8, 5.5 Hz), 3.06 (1H, dd, J=13.4, 7.4 Hz), 3.15-3.25 (1H, m), 3.28-3.39 (1H, m), 3.53 (1H, dd, J=10.8, 6.2 Hz), 3.64-3.73 (2H, m), 3.89-4.08 (1H, m), 4.56-4.68 (1H, m), 4.75-4.84 (1H, m), 6.77-6.87 (1H, m), 7.01-7.13 (2H, m), 7.15-7.26 (2H, m), 7.38-7.47 (1H, m).

Example 459

N-{(2S,3S)-1-(azetidine-1-carbonyl)-2-[(3'-fluoro[1,1'-biphenyl]-3-yl)methyl]pyrrolidin-3-yl}-1-fluoromethanesulfonamide A) benzyl ((2S,3S)-2-(3-bromobenzyl)pyrrolidin-3-yl)carbamate hydrochloride To a mixture of tert-butyl (2S,3S)-3-amino-2-(3-bromobenzyl)pyrrolidine-1-carboxylate (10.7 g), 2M aqueous sodium hydroxide solution (19 mL) and THF (100 mL) was added benzyl carbonochloridate (5.98 g) at 0° C. The mixture was stirred at room temperature for 30 min. To the mixture was added saturated aqueous sodium hydrogencarbonate solution and extracted with ethyl acetate. The organic layer was separated, washed with water and saturated brine, dried over anhydrous sodium sulfate and concentrated in vacuo. To a mixture of obtained residue and ethyl acetate (20 mL) was added 4M hydrogen chloride/ethyl acetate solution (75 mL) at room temperature. The mixture was stirred at room temperature overnight. The mixture was concentrated in vacuo. The residue was triturated with ethyl acetate and the precipitate was collected by filtration to give the title compound (12.8 g).

MS: $[M+H]^+$ 389.0.

B) benzyl ((2S,3S)-1-(azetidin-1-ylcarbonyl)-2-(3-bromobenzyl)pyrrolidin-3-yl)carbamate To a mixture of benzyl ((2S,3S)-2-(3-bromobenzyl)pyrrolidin-3-yl)carbamate hydrochloride (5 g) and THF (100 mL) were added bis(trichloromethyl) carbonate (2.79 g) and DIPEA (3.04 g) at 0° C. After being stirred at 0° C. for 20 min, the mixture was concentrated in vacuo. To the residue were added THF (100 mL) and azetidine (5.36 g). The mixture was stirred at room temperature overnight. The mixture was quenched with saturated aqueous sodium hydrogencarbonate solution at room temperature and extracted with ethyl acetate. The organic layer was separated, washed with saturated brine, dried over anhydrous magnesium sulfate and concentrated in vacuo. The solid was crystallized from ethyl acetate/diisopropyl ether to give the title compound (4.74 g).

MS: $[M+H]^+$ 472.1.

C) benzyl ((2S,3S)-1-(azetidin-1-ylcarbonyl)-2-((3'-fluoro[biphenyl]-3-yl)methyl)pyrrolidin-3-yl)carbamate A mixture of benzyl ((2S,3S)-1-(azetidin-1-ylcarbonyl)-2-(3-bromobenzyl)pyrrolidin-3-yl)carbamate (1.4 g), (3-fluorophenyl)boronic acid (0.539 g), XPhos Pd G3 (0.038 g), 1M aqueous tripotassium phosphate solution (8.89 mL) and THF (20 mL) was stirred at 70° C. for 5 hr. After cooling, the insoluble substance was removed by filtration, and the filtrate was concentrated in vacuo. The residue was extracted with ethyl acetate/THF. The organic layer was separated, washed with saturated brine, passed through NH silica gel and concentrated in vacuo. The obtained solid was washed with ethyl acetate and diisopropyl ether to give the title compound (1.25 g).

MS: $[M+H]^+$ 488.2.

D) ((2S,3S)-3-amino-2-((3'-fluoro[biphenyl]-3-yl)methyl)pyrrolidin-1-yl) (azetidin-1-yl)methanone A mixture of benzyl ((2S,3S)-1-(azetidin-1-ylcarbonyl)-2-((3'-fluoro[biphenyl]-3-yl)methyl)pyrrolidin-3-yl)carbamate (1.25 g), 10% palladium on carbon (0.12 g), EtOH (20 mL) and THF (20 mL) was hydrogenated under balloon pressure at room temperature for 1 hr. The catalyst was removed by filtration and the filtrate was concentrated in vacuo. The residue was purified by silica gel column chromatography (NH, methanol/ethyl acetate) to give the title compound (900 mg).

MS: $[M+H]^+$ 354.0.

E) N-{(2S,3S)-1-(azetidine-1-carbonyl)-2-[(3'-fluoro[1,1'-biphenyl]-3-yl)methyl]pyrrolidin-3-yl}-1-fluoromethanesulfonamide To a mixture of ((2S,3S)-3-amino-2-((3'-fluoro[biphenyl]-3-yl)methyl)pyrrolidin-1-yl) (azetidin-1-yl)methanone (100 mg) and THF (2 mL) were added DIPEA (47.5 mg) and fluoromethanesulfonyl chloride (41.3 mg) at room temperature. After being stirred for 30 min, the mixture was concentrated in vacuo. The residue was purified by silica gel column chromatography (ethyl acetate/hexane). The solid was crystallized from ethyl acetate/hexane to give the title compound (58 mg).

$^1H$ NMR (400 MHz, DMSO-$d_6$) δ 1.86-2.00 (3H, m), 2.02-2.16 (1H, m), 2.70-2.82 (1H, m), 2.85-2.95 (1H, m), 3.10-3.21 (1H, m), 3.32-3.38 (1H, m), 3.52-3.64 (2H, m), 3.72-3.88 (3H, m), 4.20-4.31 (1H, m), 5.17-5.50 (2H, m), 7.14-7.22 (1H, m), 7.26-7.30 (1H, m), 7.33-7.39 (1H, m), 7.46-7.58 (5H, m), 8.22 (1H, brs).

Example 460

N-{(2S,3S)-1-(azetidine-1-carbonyl)-2-[([1,1'-biphenyl]-3-yl)methyl]pyrrolidin-3-yl}-1-fluoromethanesulfonamide A) benzyl ((2S,3S)-1-(azetidin-1-ylcarbonyl)-2-([biphenyl]-3-ylmethyl)pyrrolidin-3-yl)carbamate A mixture of benzyl ((2S,3S)-1-(azetidin-1-ylcarbonyl)-2-(3-bromobenzyl)pyrrolidin-3-yl)carbamate (1.4 g), phenylboronic acid (0.470 g), XPhos Pd G3 (0.038 g), 1M aqueous tripotassium phosphate solution (8.89 mL) and THE (20 mL) was stirred at 70° C. for 5 hr. After cooling, the insoluble substance was removed by filtration, and the filtrate was concentrated in vacuo. The residue was extracted with ethyl acetate/THF. The organic layer was separated, washed with saturated brine, passed through NH silica gel and concentrated in vacuo. The obtained solid was washed with ethyl acetate and diisopropyl ether to give the title compound (1.08 g).

MS: $[M+H]^+$ 470.2.

B) ((2S,3S)-3-amino-2-([biphenyl]-3-ylmethyl)pyrrolidin-1-yl) (azetidin-1-yl)methanone A mixture of benzyl ((2S,3S)-1-(azetidin-1-ylcarbonyl)-2-([biphenyl]-3-ylmethyl)pyrrolidin-3-yl)carbamate (1.08 g), 10% palladium on carbon (0.10 g), EtOH (20 mL) and THE (20 mL) was hydrogenated under balloon pressure at room temperature for 1 hr. The catalyst was removed by filtration and the filtrate was concentrated in vacuo. The residue was purified by silica gel column chromatography (NH, methanol/ethyl acetate) to give the title compound (700 mg).

MS: $[M+H]^+$ 336.1.

C) N-{(2S,3S)-1-(azetidine-1-carbonyl)-2-[([1,1'-biphenyl]-3-yl)methyl]pyrrolidin-3-yl}-1-fluoromethanesulfonamide To a mixture of ((2S,3S)-3-amino-2-([biphenyl]-3-ylmethyl)pyrrolidin-1-yl) (azetidin-1-yl)methanone (100 mg) in THF (2 mL) were added DIPEA (50.1 mg) and fluoromethanesulfonyl chloride (43.5 mg) at 0° C. After being stirred for 30 min, the mixture was concentrated in vacuo. The residue was purified by silica gel column chromatography (ethyl acetate/hexane). The solid was crystallized from ethyl acetate/hexane to give the title compound (98 mg).

$^1$H NMR (400 MHz, DMSO-$d_6$) δ 1.85-1.99 (3H, m), 2.03-2.14 (1H, m), 2.69-2.79 (1H, m), 2.85-2.95 (1H, m), 3.12-3.20 (1H, m), 3.31-3.39 (1H, m), 3.52-3.67 (2H, m), 3.71-3.87 (3H, m), 4.19-4.29 (1H, m), 5.18-5.46 (2H, m), 7.21-7.29 (1H, m), 7.31-7.38 (2H, m), 7.42-7.50 (3H, m), 7.51-7.55 (1H, m), 7.64-7.72 (2H, m), 8.22 (1H, brs).

Example 462

N-{(2S,3S)-1-(azetidine-1-carbonyl)-2-[(3'-fluoro[1,1'-biphenyl]-3-yl)methyl]pyrrolidin-3-yl}cyclopropanesulfonamide To a mixture of ((2S,3S)-3-amino-2-((3'-fluoro[biphenyl]-3-yl)methyl)pyrrolidin-1-yl) (azetidin-1-yl)methanone (200 mg) and THF (4 mL) were added DIPEA (95 mg), DMAP (69.1 mg) and cyclopropanesulfonyl chloride (88 mg) at room temperature. After being stirred for 10 hr, the mixture was quenched with saturated aqueous sodium hydrogencarbonate solution and extracted with ethyl acetate. The organic layer was separated, dried over anhydrous sodium sulfate and concentrated in vacuo. The residue was purified by silica gel column chromatography (methanol/ethyl acetate). The solid was crystallized from ethyl acetate/diisopropyl ether to give the title compound (221 mg).

$^1$H NMR (400 MHz, DMSO-$d_6$) δ 0.77-1.00 (4H, m), 1.88-2.03 (3H, m), 2.03-2.16 (1H, m), 2.37-2.48 (1H, m), 2.70-2.81 (1H, m), 2.88-2.97 (1H, m), 3.13-3.23 (1H, m), 3.33-3.39 (1H, m), 3.53-3.65 (2H, m), 3.72-3.86 (3H, m), 4.21-4.30 (1H, m), 7.13-7.23 (1H, m), 7.26-7.39 (2H, m), 7.45-7.61 (6H, m).

Example 463

N-{(2S,3S)-1-(azetidine-1-carbonyl)-2-[([1,1'-biphenyl]-3-yl)methyl]pyrrolidin-3-yl}cyclopropanesulfonamide To a mixture of ((2S,3S)-3-amino-2-([biphenyl]-3-ylmethyl)pyrrolidin-1-yl) (azetidin-1-yl)methanone (200 mg) and THF (4 mL) were added DIPEA (100 mg), DMAP (14.6 mg) and cyclopropanesulfonyl chloride (92 mg) at room temperature. After being stirred overnight, the mixture was quenched with saturated aqueous sodium hydrogencarbonate solution and extracted with ethyl acetate. The organic layer was separated, dried over anhydrous sodium sulfate and concentrated in vacuo. The residue was purified by silica gel column chromatography (methanol/ethyl acetate). The solid was crystallized from ethyl acetate/diisopropyl ether to give the title compound (228 mg).

$^1$H NMR (400 MHz, DMSO-$d_6$) δ 0.79-0.99 (4H, m), 1.87-2.01 (3H, m), 2.02-2.15 (1H, m), 2.38-2.47 (1H, m), 2.69-2.79 (1H, m), 2.87-2.98 (1H, m), 3.12-3.22 (1H, m), 3.32-3.39 (1H, m), 3.51-3.67 (2H, m), 3.72-3.84 (3H, m), 4.20-4.30 (1H, m), 7.22-7.29 (1H, m), 7.30-7.39 (2H, m), 7.41-7.49 (3H, m), 7.50-7.57 (2H, m), 7.62-7.71 (2H, m).

Example 466

N-{(2S,3S)-1-(azetidine-1-carbonyl)-2-[(2-fluoro[1,1'-biphenyl]-3-yl)methyl]pyrrolidin-3-yl}-1-fluoromethanesulfonamide A) tert-butyl (2S,3S)-3-(((benzyloxy)carbonyl)amino)-2-(3-bromo-2-fluorobenzyl)pyrrolidine-1-carboxylate To a mixture of tert-butyl (2S,3S)-3-amino-2-(3-bromo-2-fluorobenzyl)pyrrolidine-1-carboxylate (1.43 g), 2M aqueous sodium hydroxide solution (2.30 mL) and THF (20 mL) was added benzyl carbonochloridate (0.719 g) at 0° C. The mixture was stirred at room temperature for 30 min. To the mixture was added saturated aqueous sodium hydrogencarbonate solution and extracted with ethyl acetate. The organic layer was separated, washed with water and saturated brine, dried over anhydrous sodium sulfate and concentrated in vacuo to give the title compound (2.03 g).

MS: $[M+H-Boc]^+$ 407.0.

B) benzyl ((2S,3S)-2-(3-bromo-2-fluorobenzyl)pyrrolidin-3-yl)carbamate hydrochloride A mixture of tert-butyl (2S,3S)-3-(((benzyloxy)carbonyl)amino)-2-(3-bromo-2-fluorobenzyl)pyrrolidine-1-carboxylate (1.94 g) and 4M hydrogen chloride/ethyl acetate solution (9.58 mL) was stirred at room temperature overnight. The mixture was concentrated in vacuo. The residue was triturated with ethyl acetate and the precipitate was collected by filtration to give the title compound (1.54 g).

MS: $[M+H]^+$ 407.0.

C) benzyl ((2S,3S)-1-(azetidin-1-ylcarbonyl)-2-(3-bromo-2-fluorobenzyl)pyrrolidin-3-yl)carbamate To a mixture of benzyl ((2S,3S)-2-(3-bromo-2-fluorobenzyl)pyrrolidin-3-yl)carbamate hydrochloride (1.54 g) and THE (30 mL) were added bis(trichloromethyl) carbonate (0.824 g) and DIPEA (0.897 g) at 0° C. After being stirred at 0° C. for 20 min, the mixture was concentrated in vacuo. To the residue were added THE (30 mL) and azetidine (0.991 g). The mixture was stirred at room temperature overnight. The mixture was quenched with saturated aqueous sodium hydrogencarbonate solution at room temperature and extracted with ethyl acetate. The organic layer was separated, washed with saturated brine, dried over anhydrous magnesium sulfate and concentrated in vacuo. The solid was crystallized from ethyl acetate/diisopropyl ether to give the title compound (1.64 g).

MS: $[M+H]^+$ 490.1.

D) benzyl ((2S,3S)-1-(azetidin-1-ylcarbonyl)-2-((2-fluoro[biphenyl]-3-yl)methyl)pyrrolidin-3-yl)carbamate A mixture of benzyl ((2S,3S)-1-(azetidin-1-ylcarbonyl)-2-(3-bromo-2-fluorobenzyl)pyrrolidin-3-yl)carbamate (600 mg), phenylboronic acid (194 mg), XPhos Pd G3 (15.5 mg), 1M aqueous tripotassium phosphate solution (3.67 mL) and THE (20 mL) was stirred at 70° C. for 5 hr. After cooling, the insoluble substance was removed by filtration, and the filtrate was concentrated in vacuo. The residue was extracted with ethyl acetate/THF. The organic layer was separated, washed with saturated brine, passed through NH silica gel and concentrated in vacuo. The obtained solid was washed with ethyl acetate and diisopropyl ether to give the title compound (500 mg).

MS: $[M+H]^+$ 488.2.

E) ((2S,3S)-3-amino-2-((2-fluoro[biphenyl]-3-yl) methyl)pyrrolidin-1-yl) (azetidin-1-yl)methanone A mixture of benzyl ((2S,3S)-1-(azetidin-1-ylcarbonyl)-2-((2-fluoro[biphenyl]-3-yl)methyl)pyrrolidin-3-yl)carbamate (500 mg), 10% palladium on carbon (50 mg), EtOH (20 mL) and THE (20 mL) was hydrogenated under balloon pressure at room temperature for 1 hr. The catalyst was removed by filtration and the filtrate was concentrated in vacuo. The residue was purified by silica gel column chromatography (NH, methanol/ethyl acetate) to give the title compound (360 mg).

MS: $[M+H]^+$ 354.0.

F) N-{(2S,3S)-1-(azetidine-1-carbonyl)-2-[(2-fluoro [1,1'-biphenyl]-3-yl)methyl]pyrrolidin-3-yl}-1-fluoromethanesulfonamide To a mixture of ((2S,3S)-3-amino-2-((2-fluoro[biphenyl]-3-yl)methyl)pyrrolidin-1-yl) (azetidin-1-yl)methanone (100 mg) and THF (2 mL) were added DIPEA (47.5 mg) and fluoromethanesulfonyl chloride (41.3 mg) at 0° C. After being stirred for 30 min, the mixture was concentrated in vacuo. The residue was purified by silica gel column chromatography (ethyl acetate/hexane). The solid was crystallized from ethyl acetate/hexane to give the title compound (98 mg).

$^1$H NMR (400 MHz, DMSO-$d_6$) δ 1.90-2.19 (4H, m), 2.60-2.71 (1H, m), 2.86-2.97 (1H, m), 3.09-3.20 (1H, m), 3.32-3.39 (1H, m), 3.43-3.53 (2H, m), 3.66-3.77 (2H, m), 3.80-3.89 (1H, m), 4.34-4.46 (1H, m), 5.22-5.55 (2H, m), 7.13-7.20 (1H, m), 7.25-7.34 (2H, m), 7.35-7.42 (1H, m), 7.44-7.51 (2H, m), 7.52-7.57 (2H, m), 8.15-8.34 (1H, m).

Example 467

N-{(2S,3S)-1-(azetidine-1-carbonyl)-2-[(2,3'-difluoro[1,1'-biphenyl]-3-yl)methyl]pyrrolidin-3-yl}-1-fluoromethanesulfonamide A) benzyl ((2S,3S)-1-(azetidin-1-ylcarbonyl)-2-((2,3'-difluoro[biphenyl]-3-yl)methyl)pyrrolidin-3-yl) carbamate A mixture of benzyl ((2S,3S)-1-(azetidin-1-ylcarbonyl)-2-(3-bromo-2-fluorobenzyl)pyrrolidin-3-yl)carbamate (600 mg), (3-fluorophenyl)boronic acid (223 mg), XPhos Pd G3 (15.5 mg), 1M aqueous tripotassium phosphate solution (3.67 mL) and THF (20 mL) was stirred at 70° C. for 5 hr. After cooling, the insoluble substance was removed by filtration, and the filtrate was concentrated in vacuo. The residue was extracted with ethyl acetate/THF. The organic layer was separated, washed with saturated brine, passed through NH silica gel and concentrated in vacuo. The obtained solid was washed with ethyl acetate and diisopropyl ether to give the title compound (475 mg).

MS: $[M+H]^+$ 506.2.

B) ((2S,3S)-3-amino-2-((2,3'-difluoro[biphenyl]-3-yl)methyl)pyrrolidin-1-yl) (azetidin-1-yl)methanone A mixture of benzyl ((2S,3S)-1-(azetidin-1-ylcarbonyl)-2-((2,3'-difluoro[biphenyl]-3-yl)methyl)pyrrolidin-3-yl)carbamate (475 mg), 10% palladium on carbon (0.47 g), EtOH (20 mL) and THE (20 mL) was hydrogenated under balloon pressure at room temperature for 1 hr. The catalyst was removed by filtration and the filtrate was concentrated in vacuo. The residue was purified by silica gel column chromatography (NH, methanol/ethyl acetate) to give the title compound (330 mg).

MS: $[M+H]^+$ 372.1.

C) N-{(2S,3S)-1-(azetidine-1-carbonyl)-2-[(2,3'-difluoro[1,1'-biphenyl]-3-yl)methyl]pyrrolidin-3-yl}-1-fluoromethanesulfonamide To a mixture of ((2S,3S)-3-amino-2-((2,3'-difluoro[biphenyl]-3-yl)methyl)pyrrolidin-1-yl) (azetidin-1-yl)methanone (100 mg) and THE (2 mL) were added DIPEA (45.2 mg) and fluoromethanesulfonyl chloride (39.3 mg) at 0° C. After being stirred for 30 min, the mixture was concentrated in vacuo. The residue was purified by silica gel column chromatography (ethyl acetate/hexane). The solid was crystallized from ethyl acetate/hexane to give the title compound (80 mg).

$^1$H NMR (400 MHz, DMSO-$d_6$) δ 1.85-2.21 (4H, m), 2.60-2.70 (1H, m), 2.88-2.99 (1H, m), 3.08-3.18 (1H, m), 3.32-3.39 (1H, m), 3.42-3.52 (2H, m), 3.65-3.76 (2H, m), 3.78-3.91 (1H, m), 4.34-4.45 (1H, m), 5.22-5.56 (2H, m), 7.15-7.28 (2H, m), 7.29-7.42 (4H, m), 7.48-7.57 (1H, m), 8.15-8.36 (1H, m).

Example 471

N-[(2S,3S)-2-[([1,1'-biphenyl]-3-yl)methyl]-1-(cyclobutanecarbonyl)pyrrolidin-3-yl]ethanesulfonamide To a mixture of N-((2S,3S)-2-(biphenyl-3-ylmethyl)pyrrolidin-3-yl)ethanesulfonamide hydrochloride (100 mg), cyclobutanecarboxylic acid (31.5 mg), HATU (120 mg) and DMF (1 mL) was added TEA (80 mg) at 0° C. The mixture was stirred at room temperature for 30 min. To the mixture was added saturated aqueous sodium hydrogencarbonate solution and extracted with ethyl acetate. The organic layer was separated, washed with water and saturated brine, dried over anhydrous sodium sulfate and concentrated in vacuo. The residue was purified by silica gel column chromatography (methanol/ethyl acetate). The residue was crystallized from ethyl acetate/diisopropyl ether to give the title compound (75 mg).

$^1$H NMR (400 MHz, DMSO-$d_6$) δ 0.91-1.30 (5H, m), 1.38-2.36 (8H, m), 2.63-3.31 (5H, m), 3.38-3.88 (2H, m), 3.99-4.39 (1H, m), 7.12-7.68 (9H, m).

Example 474

(2S,3S)-3-[(ethanesulfonyl)amino]-2-[(3'-fluoro[1,1'-biphenyl]-3-yl)methyl]-N-methoxy-N-methylpyrrolidine-1-carboxamide A) tert-butyl (2S,3S)-3-((ethylsulfonyl)amino)-2-((3'-fluoro[biphenyl]-3-yl)methyl)pyrrolidine-1-carboxylate A mixture of tert-butyl (2S,3S)-2-(3-bromobenzyl)-3-((ethylsulfonyl)amino)pyrrolidine-1-carboxylate (671 mg), (3-fluorophenyl)boronic acid (273 mg), XPhos Pd G3 (38.1 mg), 1M aqueous tripotassium phosphate solution (4.50 mL) and THE (7.5 mL) was stirred at 70° C. for 1 hr. The mixture was concentrated in vacuo to remove THF, and the residue was extracted with ethyl acetate. The organic layer was concentrated in vacuo. The residue was purified by silica gel column chromatography (NH, ethyl acetate/hexane) to give the title compound (690 mg).

MS: $[M-H]^-$ 461.3.

B) N-((2S,3S)-2-((3'-fluoro[biphenyl]-3-yl)methyl) pyrrolidin-3-yl)ethanesulfonamide hydrochloride 4M Hydrogen chloride/ethyl acetate solution (7.46 mL) was added to a stirred mixture of tert-butyl (2S,3S)-3-((ethylsulfonyl)amino)-2-((3'-fluoro[biphenyl]-3-yl)methyl) pyrrolidine-1-carboxylate (0.690 g) and ethyl acetate (3 mL) at room temperature. After 1 hr, the resulting solid was collected by filtration to give the title compound (508 mg).

MS: $[M+H]^+$ 363.2.

C) (2S,3S)-3-((ethylsulfonyl)amino)-2-((3'-fluoro [biphenyl]-3-yl)methyl)pyrrolidine-1-carbonyl chloride To a mixture of N-((2S,3S)-2-((3'-fluoro[biphenyl]-3-yl) methyl)pyrrolidin-3-yl)ethanesulfonamide hydrochloride (508 mg), bis(trichloromethyl) carbonate (302 mg) and THF (6 mL) was added DIPEA (329 mg) at 0° C. After being stirred at room temperature for 30 min, the reaction mixture was concentrated in vacuo. The residue was diluted with ethyl acetate, washed with saturated brine, and purified by silica gel column chromatography (ethyl acetate/hexane) to give the title compound (542 mg).

MS: $[M-H]^-$ 423.2.

D) (2S,3S)-3-[(ethanesulfonyl)amino]-2-[(3'-fluoro [1,1'-biphenyl]-3-yl)methyl]-N-methoxy-N-methylpyrrolidine-1-carboxamide DIPEA (330 mg) was added to a stirred mixture of (2S,3S)-3-((ethylsulfonyl)amino)-2-((3'-fluoro[biphenyl]-3-yl)methyl)pyrrolidine-1-carbonyl chloride (271 mg), N-methoxymethanamine hydrochloride (124 mg) and THF (3 mL) at room temperature. After being stirred at 60° C. for 2 hr, the reaction mixture was cooled down to room temperature, quenched with saturated brine and concentrated in vacuo. The residue was purified by silica gel column chromatography (ethyl acetate/hexane) to give a solid. The solid was crystallized from ethyl acetate/hexane to give the title compound (248 mg).

$^1H$ NMR (400 MHz, $CDCl_3$) δ 1.23 (3H, t, J=7.4 Hz), 1.80-1.92 (1H, m), 2.09-2.23 (1H, m), 2.86 (2H, q, J=7.3 Hz), 2.90-2.97 (1H, m), 2.98 (3H, s), 3.14-3.22 (1H, m), 3.42-3.52 (1H, m), 3.56 (3H, s), 3.60-3.70 (1H, m), 3.89-4.01 (1H, m), 4.35 (1H, d, J=8.8 Hz), 4.53-4.66 (1H, m), 6.98-7.07 (1H, m), 7.27-7.45 (6H, m), 7.50 (1H, s).

Example 475

(2S,3S)-3-[(dimethylsulfamoyl)amino]-2-[(2-fluoro [1,1'-biphenyl]-3-yl)methyl]-N,N-dimethylpyrrolidine-1-carboxamide A mixture of (2S,3S)-2-(3-bromo-2-fluorobenzyl)-3-((dimethylsulfamoyl)amino)-N,N-dimethylpyrrolidine-1-carboxamide (650 mg), phenylboronic acid (228 mg), XPhos Pd G3 (18.3 mg), 1M aqueous tripotassium phosphate solution (4.32 mL) and THE (3.6 mL) was stirred at 70° C. for 1 hr. The mixture was diluted with saturated aqueous sodium hydrogencarbonate solution and extracted with ethyl acetate. The organic layer was separated, washed with saturated brine, dried over anhydrous magnesium sulfate and concentrated in vacuo. The residue was purified by column chromatography (NH, ethyl acetate/hexane). The solid was crystallized from ethyl acetate/hexane to give the title compound (560 mg).

$^1H$ NMR (400 MHz, $CDCl_3$) δ 2.05-2.22 (2H, m), 2.71 (6H, s), 2.77 (6H, s), 2.84-2.92 (1H, m), 2.96-3.07 (1H, m), 3.20-3.30 (1H, m), 3.55-3.66 (1H, m), 3.82-3.91 (1H, m), 4.31-4.42 (1H, m), 4.54-4.63 (1H, m), 7.11-7.19 (1H, m), 7.26-7.39 (3H, m), 7.40-7.47 (2H, m), 7.48-7.56 (2H, m).

Example 476

(2S,3S)-3-[(dimethylsulfamoyl)amino]-N,N-dimethyl-2-[(2,3',5'-trifluoro[1,1'-biphenyl]-3-yl)methyl] pyrrolidine-1-carboxamide A mixture of (2S,3S)-2-(3-bromo-2-fluorobenzyl)-3-((dimethylsulfamoyl)amino)-N,N-dimethylpyrrolidine-1-carboxamide (650 mg), (3,5-difluorophenyl)boronic acid (296 mg), XPhos Pd G3 (18.3 mg), 1M aqueous tripotassium phosphate solution (4.32 mL) and THE (3.6 mL) was stirred at 70° C. for 1 hr. The mixture was diluted with saturated aqueous sodium hydrogencarbonate solution and extracted with ethyl acetate. The organic layer was separated, washed with saturated brine, dried over anhydrous magnesium sulfate and concentrated in vacuo. The residue was purified by silica gel column chromatography (NH, ethyl acetate/hexane). The solid was crystallized from ethyl acetate/hexane to give the title compound (600 mg).

$^1H$ NMR (400 MHz, $CDCl_3$) δ 2.03-2.21 (2H, m), 2.75 (6H, s), 2.77 (6H, s), 2.83-2.93 (1H, m), 2.94-3.04 (1H, m), 3.20-3.32 (1H, m), 3.54-3.65 (1H, m), 3.81-3.92 (1H, m), 4.30-4.40 (1H, m), 4.52-4.63 (1H, m), 6.76-6.84 (1H, m), 7.02-7.10 (2H, m), 7.13-7.20 (1H, m), 7.21-7.25 (1H, m), 7.34-7.41 (1H, m).

Example 477

(2S,3S)-2-[(3',5'-difluoro[1,1'-biphenyl]-3-yl) methyl]-3-[(ethanesulfonyl)amino]-N-methoxy-N-methylpyrrolidine-1-carboxamide To a mixture of N-((2S,3S)-2-((3',5'-difluorobiphenyl-3-yl)methyl)pyrrolidin-3-yl)ethanesulfonamide hydrochloride (500 mg), TEA (607 mg) and THF (10 mL) was added N-methoxy-N-methylcarbamoyl chloride (310 mg) at room temperature. The mixture was refluxed for 15 min. The mixture was diluted with THF and the precipitate was removed by filtration. The filtrate was concentrated in vacuo. The residue was purified by silica gel column chromatography (ethyl acetate/hexane) and recrystallized from ethyl acetate/hexane to give the title compound (467 mg).

$^1H$ NMR (300 MHz, $CDCl_3$) δ 1.27 (3H, t, J=7.4 Hz), 1.78-1.93 (1H, m), 2.11-2.27 (1H, m), 2.85-3.00 (6H, m), 3.07-3.18 (1H, m), 3.41-3.53 (1H, m), 3.57 (3H, s), 3.59-3.72 (1H, m), 3.90-4.03 (1H, m), 4.39 (1H, d, J=9.1 Hz), 4.55-4.65 (1H, m), 6.77 (1H, tt, J=8.9, 2.3 Hz), 7.07-7.18 (2H, m), 7.31-7.43 (3H, m), 7.45-7.52 (1H, m).

Example 479

1-fluoro-N-[(2S,3S)-2-[(2-fluoro[1,1'-biphenyl]-3-yl)methyl]-1-(2-hydroxy-2-methylpropanoyl)pyrrolidin-3-yl]cyclopropane-1-sulfonamide A) tert-butyl (2S,3S)-3-((cyclopropylsulfonyl)amino)-2-((2-fluoro[biphenyl]-3-yl)methyl)pyrrolidine-1-carboxylate A mixture of tert-butyl (2S,3S)-2-(3-bromo-2-fluorobenzyl)-3-((cyclopropylsulfonyl)amino)pyrrolidine-1-carboxylate (500 mg), phenylboronic acid (153 mg), XPhos Pd G3 (8.87 mg), 1M aqueous tripotassium phosphate solution (3.14 mL) and THF (2 mL) was stirred at 70° C. for 1 hr. The mixture was poured into water at room temperature and extracted with ethyl acetate. The organic layer was separated, washed with saturated brine, dried over anhydrous magnesium sulfate and concentrated in vacuo. The residue was purified by silica gel column chromatography (NH, ethyl acetate/hexane) to give the title compound (490 mg).

MS: $[M+H-Boc]^+$ 375.1.

B) 1-fluoro-N-[(2S,3S)-2-[(2-fluoro[1,1'-biphenyl]-3-yl)methyl]-1-(2-hydroxy-2-methylpropanoyl)pyrrolidin-3-yl]cyclopropane-1-sulfonamide To a mixture of tert-butyl (2S,3S)-3-((cyclopropylsulfonyl)amino)-2-((2-fluoro[biphenyl]-3-yl)methyl)pyrrolidine-1-carboxylate (490 mg) and THF (4 mL) was added 2.6M n-butyllithium/hexane solution (1.39 mL) dropwise at −78° C. After being stirred at −78° C. for 30 min, a mixture of N-fluoro-N-(phenylsulfonyl)benzenesulfonamide (488 mg) and THE (4 mL) was added dropwise to the reaction mixture. The mixture was stirred at 0° C. under nitrogen atmosphere for 1 hr. The mixture was quenched with saturated aqueous ammonium chloride solution and extracted with ethyl acetate. The organic layer was separated, washed with water and saturated brine, dried over anhydrous magnesium sulfate and concentrated in vacuo. The residue was purified by silica gel column chromatography (ethyl acetate/hexane). The mixture of the residue (280 mg) and 4M hydrogen chloride/ethyl acetate solution (2.84 mL) was stirred at room temperature under a dry atmosphere ($CaCl_2$) overnight. The mixture was concentrated in vacuo. A mixture of the residue (244 mg), DIPEA (737 mg) and THE (5 mL) was stirred at room temperature for 30 min. To the suspension was added dropwise 1-chloro-2-methyl-1-oxopropan-2-yl acetate (113 mg) at 0° C. and the mixture was stirred at same temperature for 1 h. To the mixture was added 4M aqueous lithium hydroxide solution (1.14 mL) and the mixture was stirred at room temperature overnight. The mixture was diluted with saturated brine and extracted with ethyl acetate. The organic layer was separated, dried over anhydrous magnesium sulfate and concentrated in vacuo. The residue was purified by preparative HPLC (C18, mobile phase: water/acetonitrile (containing 0.1% TFA)). The desired fraction was neutralized with saturated aqueous sodium hydrogencarbonate solution and extracted with ethyl acetate. The organic layer was separated, dried over anhydrous magnesium sulfate and concentrated in vacuo to give the title compound (20 mg).

$^1H$ NMR (400 MHz, DMSO-$d_6$) δ 0.97-1.27 (6H, m), 1.35-1.64 (4H, m), 2.03-2.29 (2H, m), 2.57-2.70 (1H, m), 2.98-3.09 (1H, m), 3.66-3.96 (2H, m), 3.98-4.09 (1H, m), 4.58-4.76 (1H, m), 4.90-5.06 (1H, m), 7.03-7.18 (1H, m), 7.21-7.33 (2H, m), 7.34-7.41 (1H, m), 7.42-7.48 (2H, m), 7.49-7.57 (2H, m), 8.35 (1H, brs).

Example 480

1-fluoro-N-{(2S,3S)-1-(2-hydroxy-2-methylpropanoyl)-2-[(2,3',5'-trifluoro[1,1'-biphenyl]-3-yl)methyl]pyrrolidin-3-yl}cyclopropane-1-sulfonamide A) tert-butyl (2S,3S)-3-((cyclopropylsulfonyl)amino)-2-((2,3',5'-trifluoro[biphenyl]-3-yl)methyl)pyrrolidine-1-carboxylate A mixture of tert-butyl (2S,3S)-2-(3-bromo-2-fluorobenzyl)-3-((cyclopropylsulfonyl)amino)pyrrolidine-1-carboxylate (500 mg), (3,5-difluorophenyl)boronic acid (248 mg), XPhos Pd G3 (44.3 mg), 1M aqueous tripotassium phosphate solution (3.14 mL) and THE (2 mL) was stirred at 70° C. for 2 hr. The mixture was poured into water at room temperature and extracted with ethyl acetate. The organic layer was separated, washed with saturated brine, dried over anhydrous magnesium sulfate and concentrated in vacuo. The residue was purified by silica gel column chromatography (NH, ethyl acetate/hexane) to give the title compound (488 mg).

MS: $[M-H]^-$ 509.2.

B) 1-fluoro-N-{(2S,3S)-1-(2-hydroxy-2-methylpropanoyl)-2-[(2,3',5'-trifluoro[1,1'-biphenyl]-3-yl)methyl]pyrrolidin-3-yl}cyclopropane-1-sulfonamide To a mixture of tert-butyl (2S,3S)-3-((cyclopropylsulfonyl)amino)-2-((2,3',5'-trifluoro[biphenyl]-3-yl)methyl)pyrrolidine-1-carboxylate (453 mg) and THE (6 mL) was added 2.6M n-butyllithium/hexane solution (1.19 mL) dropwise at −78° C. After being stirred at −78° C. for 30 min, a mixture of N-fluoro-N-(phenylsulfonyl)benzenesulfonamide (699 mg) and THE (12 mL) was added dropwise to the reaction mixture. The mixture was slowly warmed up to room temperature and stirred under nitrogen atmosphere overnight. The mixture was quenched with saturated aqueous ammonium chloride solution and extracted with ethyl acetate. The organic layer was separated, washed with water and saturated brine, dried over anhydrous magnesium sulfate and concentrated in vacuo. The residue was purified by silica gel column chromatography (ethyl acetate/hexane). A mixture of the residue and 4M hydrogen chloride/CPME solution (5 mL) was stirred at room temperature overnight. The mixture was concentrated in vacuo. The residue was triturated with ethyl acetate and the resulting solid was collected by filtration to give a solid. To a mixture of the residue, DIPEA (143 mg) and THE (5 mL) was added dropwise 1-chloro-2-methyl-1-oxopropan-2-yl acetate (43.8 mg) at room temperature and the mixture was stirred at same temperature for 1 hr. To the mixture were added water (2 mL) and 4M aqueous lithium hydroxide solution (0.443 mL) and the mixture was stirred at room temperature overnight. The mixture was diluted with saturated brine and extracted with ethyl acetate. The organic layer was separated, dried over anhydrous magnesium sulfate and concentrated in vacuo. The residue was purified by preparative HPLC (C18, mobile phase: water (containing 10 mM $NH_4HCO_3$)/acetonitrile). The desired fraction was concentrated in vacuo to give the title compound (8.1 mg).

$^1H$ NMR (300 MHz, $CDCl_3$) δ 1.30-1.54 (10H, m), 1.85-2.12 (1H, m), 2.29-2.48 (1H, m), 2.84-3.03 (1H, m), 3.08-3.30 (1H, m), 3.59-3.94 (3H, m), 4.14 (1H, dt, J=11.7, 7.2 Hz), 4.79 (1H, brs), 6.82 (1H, tt, J=9.0, 2.4 Hz), 6.99-7.10 (2H, m), 7.11-7.22 (2H, m), 7.22-7.31 (1H, m), 7.38 (1H, t, J=6.2 Hz).

Example 482

N-((2S,3S)-2-((2,3'-difluorobiphenyl-3-yl)methyl)-1-(2-hydroxy-2-methylpropanoyl)pyrrolidin-3-yl)ethanesulfonamide A) N-((2S,3S)-2-((2,3'-difluorobiphenyl-3-yl)methyl)pyrrolidin-3-yl)ethanesulfonamide hydrochloride To a mixture of tert-butyl (2S,3S)-2-((2,3'-difluorobiphenyl-3-yl)methyl)-3-((ethylsulfonyl)amino)pyrrolidine-1-carboxylate (5.69 g) and MeOH (10 mL) was added 4M hydrogen chloride/ethyl acetate solution (35.5 mL) at room temperature. The mixture was stirred at room temperature overnight. The solvent was removed in vacuo and the resulting solid was triturated with diisopropyl ether. The precipitate was collected by filtration, washed with diisopropyl ether and dried to give the title compound (4.87 g).

MS: $[M+H]^+$ 381.3.

B) N-((2S,3S)-2-((2,3'-difluorobiphenyl-3-yl)methyl)-1-(2-hydroxy-2-methylpropanoyl)pyrrolidin-3-yl)ethanesulfonamide A mixture of N-((2S,3S)-2-((2,3'-difluorobiphenyl-3-yl)methyl)pyrrolidin-3-yl)ethanesulfonamide hydrochloride (4.87 g), DIPEA (7.55 g) and THE (50 mL) was stirred at room temperature for 30 min. To the suspension was added dropwise 1-chloro-2-methyl-1-oxopropan-2-yl acetate (2.31 g) at 0° C. and the mixture was stirred at same temperature for 1 hr. To the mixture were added water (30 mL), 2-propanol (10 mL) and 4M aqueous lithium hydroxide solution (14.6 mL) and the mixture was stirred at room temperature overnight. 4M aqueous lithium hydroxide solution (4.38 mL) was added to the mixture. The mixture was stirred at room temperature for 2 hr. The mixture was diluted with saturated brine and extracted with ethyl acetate. The organic layer was separated, dried over anhydrous magnesium sulfate and concentrated in vacuo. The residue was purified by silica gel column chromatography (ethyl acetate/hexane). The residue was crystallized from ethanol/water to give the title compound (4.75 g) as its hydrate.

$^1H$ NMR (400 MHz, $CDCl_3$) δ 1.22 (3H, t, J=7.2 Hz), 1.33-1.47 (6H, m), 1.80-2.03 (1H, m), 2.27-2.42 (1H, m), 2.78-2.92 (2H, m), 2.96 (1H, dd, J=14.4, 5.5 Hz), 3.13 (1H, dd, J=14.4, 7.6 Hz), 3.66 (2H, brs), 3.90 (1H, brs), 3.94-4.06 (1H, m), 4.55 (1H, brs), 4.73 (1H, brs), 7.04-7.11 (1H, m), 7.16-7.21 (1H, m), 7.21-7.25 (1H, m), 7.27-7.33 (2H, m), 7.35-7.44 (2H, m).

Anal. Calcd for $C_{23}H_{28}F_2N_2O_4S{\cdot}0.3H_2O$: C, 58.53; H, 6.11; N, 5.94.

Found: C, 58.42; H, 6.35; N, 6.00.

Example 483

N-((2S,3S)-1-(2-hydroxy-2-methylpropanoyl)-2-((2,3',5'-trifluorobiphenyl-3-yl)methyl)pyrrolidin-3-yl)methanesulfonamide A mixture of N-((2S,3S)-2-((2,3',5'-trifluorobiphenyl-3-yl)methyl)pyrrolidin-3-yl)methanesulfonamide hydrochloride (8.5 g), DIPEA (13.1 g) and THE (81 mL) was stirred at room temperature for 30 min. To the suspension was added dropwise 1-chloro-2-methyl-1-oxopropan-2-yl acetate (3.99 g) at 0° C. and stirred at same temperature for overnight. To the mixture were added water (53.9 mL) and 4M aqueous lithium hydroxide solution (25.2 mL) and the mixture was stirred at room temperature overnight. The mixture was quenched with saturated aqueous sodium hydrogencarbonate solution, and extracted with ethyl acetate. The extract was washed with saturated brine and passed through a silica gel pad. The solution was purified by silica gel column chromatography (NH, ethyl acetate/hexane). The obtained product was crystallized from ethanol/water to give the title compound (5.27 g) as its hydrate.

$^1H$ NMR (400 MHz, DMSO-$d_6$) δ 1.04-1.19 (6H, m), 1.90-2.07 (1H, m), 2.11-2.23 (1H, m), 2.59-2.70 (1H, m), 2.85-2.95 (3H, m), 2.95-3.10 (1H, m), 3.69-3.99 (3H, m), 4.50-4.68 (1H, m), 5.00 (1H, s), 7.08-7.18 (1H, m), 7.21-7.51 (6H, m).

Anal. Calcd for $C_{24}H_{27}F_3N_2O_5S{\cdot}1.5H_2O$: C, 53.11; H, 5.67; N, 5.63.

Found: C, 53.19; H, 5.65; N, 5.61.

Example 484

N-((2S,3S)-1-(2-hydroxy-2-methylpropanoyl)-2-((2,3',5'-trifluorobiphenyl-3-yl)methyl)pyrrolidin-3-yl)ethanesulfonamide A) N-((2S,3S)-2-((2,3',5'-trifluorobiphenyl-3-yl)methyl)pyrrolidin-3-yl)ethanesulfonamide hydrochloride To a mixture of tert-butyl (2S,3S)-2-(3-bromo-2-fluorobenzyl)-3-((ethylsulfonyl)amino)pyrrolidine-1-carboxylate (10 g), (3,5-difluorophenyl)boronic acid (5.09 g), tripotassium phosphate (13.7 g), THF (50 mL) and water (30 mL) was added XPhos Pd G3 (0.273 g) at room temperature. The mixture was stirred at 70° C. for 1 hr. After concentration in vacuo, the residue was purified by silica gel column chromatography (NH, ethyl acetate/hexane) to give an oil. 4M Hydrogen chloride/ethyl acetate solution (53.7 mL) was added to a stirred mixture of the oil and ethyl acetate (10 mL) at room temperature. After 18 hr, the reaction mixture was concentrated in vacuo, and the resulting solid was collected by filtration to give the title compound (8.81 g).

MS: $[M+H]^+$ 399.3.

B) N-((2S,3S)-1-(2-hydroxy-2-methylpropanoyl)-2-((2,3',5'-trifluorobiphenyl-3-yl)methyl)pyrrolidin-3-yl)ethanesulfonamide A mixture of N-((2S,3S)-2-((2,3',5'-trifluorobiphenyl-3-yl)methyl)pyrrolidin-3-yl)ethanesulfonamide hydrochloride (8.81 g), DIPEA (7.85 g) and THF (100 mL) was stirred at room temperature for 30 min. To the suspension was added dropwise 1-chloro-2-methyl-1-oxopropan-2-yl acetate (4.00 g) at 0° C. After being stirred for 1 hr at room temperature, water (10 mL) and 4M aqueous lithium hydroxide solution (25.3 mL) were added to the reaction mixture. After 48 hr, the mixture was quenched with saturated aqueous sodium hydrogencarbonate solution, diluted with ethyl acetate, washed with saturated brine, dried over anhydrous sodium sulfate, filtrated and concentrated in vacuo. The residue was purified by silica gel column chromatography (ethyl acetate) and crystallized from ethyl acetate/hexane to give the title compound (8.71 g).

$^1H$ NMR (400 MHz, $CDCl_3$) δ 1.24 (3H, t, J=7.3 Hz), 1.39 (3H, s), 1.41 (3H, s), 1.83-2.03 (1H, m), 2.23-2.43 (1H, m), 2.83-2.97 (3H, m), 3.12 (1H, dd, J=14.0, 7.5 Hz), 3.58-3.76 (2H, m), 3.84 (1H, brs), 3.91-4.07 (1H, m), 4.45-4.63 (1H, m), 4.67-4.89 (1H, m), 6.77-6.87 (1H, m), 6.99-7.10 (2H, m), 7.16-7.22 (1H, m), 7.26-7.30 (1H, m), 7.37-7.46 (1H, m).

N-((2S,3S)-1-(2-Hydroxy-2-methylpropanoyl)-2-((2,3',5'-trifluorobiphenyl-3-yl)methyl)pyrrolidin-3-yl)ethanesulfonamide (550 mg) was crystallized from ethyl acetate/hexane to give the title compound (400 mg).

mp 139° C.

Example 485

N-((2S,3S)-1-(azetidin-1-ylcarbonyl)-2-((2,3'-difluorobiphenyl-3-yl)methyl)pyrrolidin-3-yl)methanesulfonamide A) N-((2S,3S)-2-((2,3'-difluorobiphenyl-3-yl)methyl)pyrrolidin-3-yl)methanesulfonamide hydrochloride To a mixture of tert-butyl (2S,3S)-2-((2,3'-difluorobiphenyl-3-yl)methyl)-3-((methylsulfonyl)amino)pyrrolidine-1-carboxylate (1.77 g) and ethyl acetate (20 ml) was added 4M hydrogen chloride/ethyl acetate solution (28.5 mL) at room temperature. The mixture was stirred at room temperature for 2 hr and then at 60° C. for 1 hr. After evaporation, the solid was collected by filtration with diisopropyl ether to give the title compound (1.44 g).

MS: $[M+H]^+$ 367.0.

B) (2S,3S)-2-((2,3'-difluorobiphenyl-3-yl)methyl)-3-((methylsulfonyl)amino)pyrrolidine-1-carbonyl chloride To a mixture of N-((2S,3S)-2-((2,3'-difluorobiphenyl-3-yl)methyl)pyrrolidin-3-yl)methanesulfonamide hydrochloride (492 mg), bis(trichloromethyl) carbonate (217 mg) and THF (6 mL) was added DIPEA (316 mg) at 0° C. After being stirred at room temperature for 30 min, the reaction mixture was concentrated in vacuo. The residue was diluted with ethyl acetate, washed with saturated brine, and purified by silica gel column chromatography (ethyl acetate/hexane) to give the title compound (548 mg).

MS: $[M-H]^-$ 427.2.

C) N-((2S,3S)-1-(azetidin-1-ylcarbonyl)-2-((2,3'-difluorobiphenyl-3-yl)methyl)pyrrolidin-3-yl)methanesulfonamide Azetidine (209 mg) was added to a stirred mixture of (2S,3S)-2-((2,3'-difluorobiphenyl-3-yl)methyl)-3-((methylsulfonyl)amino)pyrrolidine-1-carbonyl chloride (524 mg) and THF (6 mL) at room temperature. After being stirred for 30 min, the reaction mixture was concentrated in vacuo. The residue was diluted with ethyl acetate, washed with saturated brine, dried over anhydrous sodium sulfate, filtrated and concentrated in vacuo. The obtained solid was crystallized from ethyl acetate/EtOH to give the title compound (404 mg).

$^1H$ NMR (400 MHz, $CDCl_3$) δ 1.87-2.00 (1H, m), 2.09-2.32 (3H, m), 2.69 (3H, s), 2.91-2.99 (1H, m), 3.01-3.10 (1H, m), 3.24-3.41 (2H, m), 3.84 (2H, q, J=7.8 Hz), 3.90-4.07 (3H, m), 4.53 (1H, q, J=6.5 Hz), 4.68 (1H, d, J=6.6 Hz), 7.01-7.11 (1H, m), 7.14-7.25 (2H, m), 7.27-7.33 (2H, m), 7.35-7.46 (2H, m).

Example 486

(2S,3S)-2-((2,3'-difluorobiphenyl-3-yl)methyl)-3-((ethylsulfonyl)amino)-N,N-dimethylpyrrolidine-1-carboxamide (2S,3S)-2-((2,3'-Difluorobiphenyl-3-yl)methyl)-3-((ethylsulfonyl)amino)-N,N-dimethylpyrrolidine-1-carboxamide (200 mg) was recrystallized from ethyl acetate/hexane to give the title compound (152 mg).

$^1H$ NMR (300 MHz, $CDCl_3$) δ 1.26 (3H, t, J=7.4 Hz), 1.99-2.26 (2H, m), 2.80 (6H, s), 2.81-2.96 (3H, m), 2.99-3.12 (1H, m), 3.28 (1H, ddd, J=10.4, 8.3, 4.4 Hz), 3.61 (1H, dt, J=10.4, 7.7 Hz), 3.87-3.98 (1H, m), 4.44 (1H, d, J=8.3 Hz), 4.50-4.60 (1H, m), 7.01-7.10 (1H, m), 7.12-7.19 (1H, m), 7.20-7.31 (3H, m), 7.32-7.44 (2H, m).

Example 487

(2S,3S)-3-((ethylsulfonyl)amino)-N,N-dimethyl-2-((2,3',5'-trifluorobiphenyl-3-yl)methyl)pyrrolidine-1-carboxamide (2S,3S)-3-((Ethylsulfonyl)amino)-N,N-dimethyl-2-((2,3',5'-trifluorobiphenyl-3-yl)methyl)pyrrolidine-1-carboxamide (137 mg) was crystallized from ethyl acetate/hexane to give the title compound (115 mg).

$^1H$ NMR (400 MHz, $CDCl_3$) δ 1.29 (3H, t, J=7.4 Hz), 1.99-2.10 (1H, m), 2.11-2.24 (1H, m), 2.79 (6H, s), 2.83-3.10 (4H, m), 3.23-3.34 (1H, m), 3.56-3.66 (1H, m), 3.89-3.98 (1H, m), 4.43 (1H, d, J=8.6 Hz), 4.50-4.59 (1H, m), 6.76-6.85 (1H, m), 7.00-7.09 (2H, m), 7.12-7.21 (1H, m), 7.22-7.25 (1H, m), 7.35-7.43 (1H, m).

Example 488

N-((2S,3S)-2-((2,3'-difluorobiphenyl-3-yl)methyl)-1-(2-hydroxy-2-methylpropanoyl)pyrrolidin-3-yl)ethanesulfonamide A mixture of N-((2S,3S)-2-((2,3'-difluorobiphenyl-3-yl)methyl)-1-(2-hydroxy-2-methylpropanoyl)pyrrolidin-3-yl)ethanesulfonamide (1.00 g) and diisopropyl ether (15 ml) was stirred at room temperature for 6 days. The precipitate was collected by filtration and dried to give the title compound (0.973 g).

$^1H$ NMR (400 MHz, $CDCl_3$) δ 1.22 (3H, t, J=7.2 Hz), 1.36-1.46 (6H, m), 1.80-2.03 (1H, m), 2.28-2.43 (1H, m), 2.76-2.91 (2H, m), 2.96 (1H, dd, J=14.5, 4.6 Hz), 3.13 (1H, dd, J=14.4, 7.2 Hz), 3.66 (2H, brs), 3.89 (1H, brs), 3.94-4.05 (1H, m), 4.54 (1H, brs), 4.73 (1H, brs), 7.04-7.11 (1H, m), 7.16-7.21 (1H, m), 7.21-7.25 (1H, m), 7.27-7.33 (2H, m), 7.35-7.45 (2H, m).

mp 89° C.

The compounds of Examples are shown in the following tables. MS in the tables means actual measured value. The compounds of Examples 2 to 18, 20 to 23, 25, 26, 28 to 63, 65 to 74, 77 to 80, 82 to 87, 90 to 92, 94 to 99, 102 to 115, 118 to 121, 123 to 177, 179 to 205, 207, 208, 211, 212, 215 to 226, 228 to 253, 257, 260, 263 to 265, 267, 268, 270 to 292, 295 to 298, 301, 302, 325 to 327, 329 to 332, 334 to 337, 353 to 361, 363, 365, 367 to 371, 374 to 376, 378 to 386, 388, 390 to 394, 396 to 398, 400, 401, 403, 405, 406, 408 to 416, 418 to 420, 422, 425 to 427, 429, 430, 432 to 434, 436, 438, 440, 442 to 449, 451 to 455, 458, 461, 464, 465, 468-470, 472, 473, 478 and 481 in the following tables were produced according to the methods described in the above-mentioned Examples, or methods analogous thereto.

TABLE 1

| EXAMPLE | IUPACNAME | Structure | ADDITIVE | MS |
|---|---|---|---|---|
| 1 | cis-2-(3-benzylbenzyl-N-ethyl-3-((methylsulfonyl)amino)piperidine-1-carboxamide | 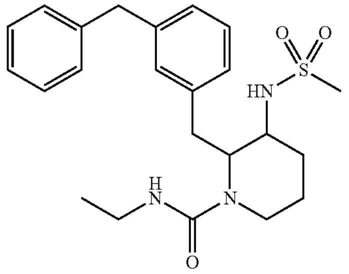 [SMILES: CCNC(=O)N1CCCC(NS(C)(=O)=O)C1Cc1cccc(Cc2ccccc2)c1] | | 430.3 |
| 2 | cis-N-ethyl-2-(3-(3-methylbenzyl)benzyl)-3-((methylsulfonyl)amino)piperidine-1-carboxamide | 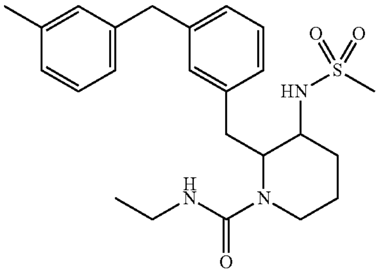 | | 444.2 |
| 3 | cis-2-(biphenyl-3-ylmethyl)-N-ethyl-3-((methylsulfonyl)amino)piperidine-1-carboxamide | 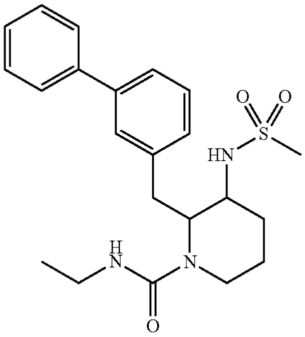 [SMILES: CCNC(=O)N1CCCC(NS(C)(=O)=O)C1Cc1cccc(-c2ccccc2)c1] | | 416.1 |
| 4 | cis-N-ethyl-2-(3-(2-methylbenzyl)benzyl)-3-((methylsulfonyl)amino)piperidine-1-carboxamide | 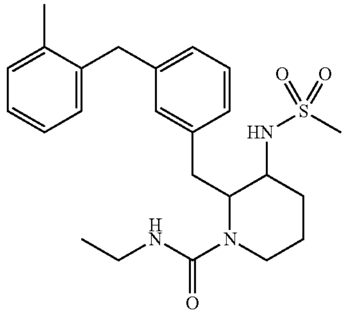 [SMILES: CCNC(=O)N1CCCC(NS(C)(=O)=O)C1Cc1cccc(Cc2ccccc2C)c1] | | 444.2 |
| 5 | trans-N-ethyl-2-(3-(2-methybenzyl)benzyl-3-((methylsulfonyl)amino)piperidine-1-carboxamide | 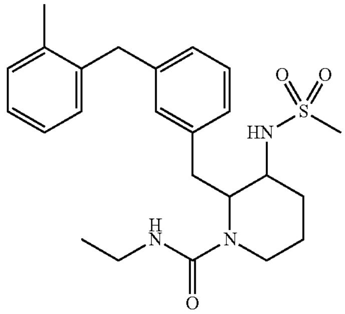 [SMILES: CCNC(=O)N1CCCC(NS(C)(=O)=O)C1Cc1cccc(Cc2ccccc2C)c1] | | 442.2 |

TABLE 1-continued

| EXAMPLE | IUPACNAME | Structure | ADDITIVE | MS |
|---|---|---|---|---|
| 6 | trans-2-(biphenyl-3-ylmethyl)-N-ethyl-3-((methylsulfonyl)amino)piperidine-1-carboxamide | 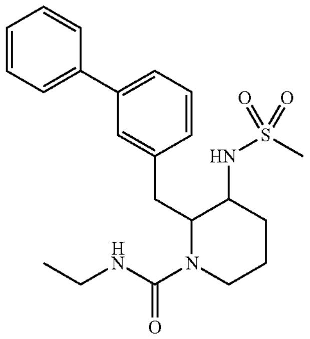 [SMILES: CCNC(=O)N1CCCC(NS(C)(=O)=O)C1Cc1cccc(-c2ccccc2)c1] | | 416.1 |
| 7 | cis-2-(3-(cyclohexyloxy)benzyl)-N-ethyl-3-((methylsulfonyl)amino)piperidine-1-carboxamide | 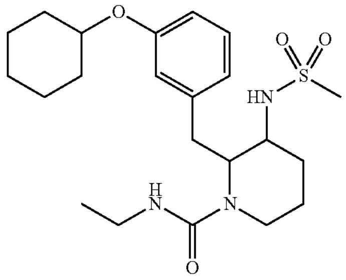 [SMILES: CCNC(=O)N1CCCC(NS(C)(=O)=O)C1Cc1cccc(OC2CCCCC2)c1] | | 438.1 |
| 8 | cis-N-ethyl-2-(3-(4-methylbenzyl)benzyl)-3-((methylsulfonyl)amino)piperidine-1-carboxamide | 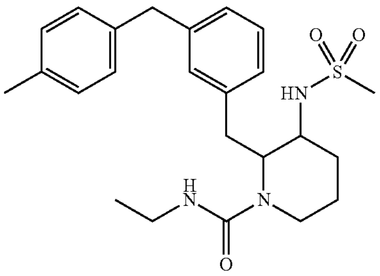 | | 444.2 |
| 9 | (2S,3S)-2-(biphenyl-3-ylmethyl)-N-ethyl-3-((methylsulfonyl)amino)piperidine-1-carboxamide | 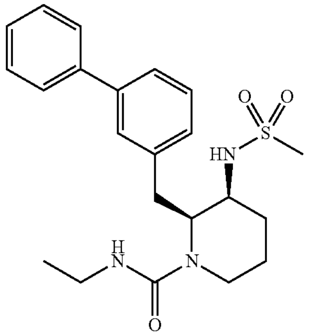 [SMILES: CCNC(=O)N1CCC[C@H](NS(C)(=O)=O)[C@@H]1Cc1cccc(-c2ccccc2)c1] | | 416.1 |
| 10 | cis-N-ethyl-3-((methylsulfonyl)amino)-2-(3-phenoxybenzyl)piperidine-1-carboxamide | 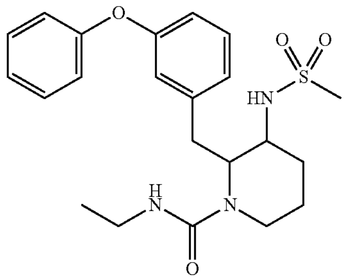 [SMILES: CCNC(=O)N1CCCC(NS(C)(=O)=O)C1Cc1cccc(Oc2ccccc2)c1] | | 430.1 |

TABLE 1-continued

| EXAMPLE | IUPACNAME | Structure | ADDITIVE | MS |
|---|---|---|---|---|
| 11 | methyl cis-2-(biphenyl-3-ylmethyl)-3-((methylsulfonyl)amino)piperidine-1-carboxylate | 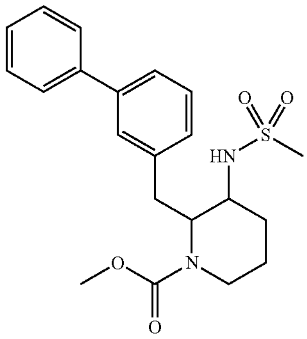 [SMILES: COC(=O)N1CCCC(NS(C)(=O)=O)C1Cc1cccc(-c2ccccc2)c1] | | 403.1 |
| 12 | trans-N-ethyl-2-((3'-fluorobiphenyl-3-yl)methyl)-3-(methylsulfonyl)amino) piperidine-1-carboxamide | 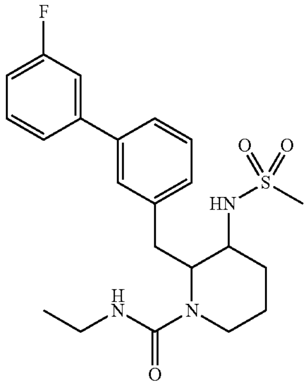 [SMILES: CCNC(=O)N1CCCC(NS(C)(=O)=O)C1Cc1cccc(-c2cccc(F)c2)c1] | | 434.1 |
| 13 | cis-N-ethyl-2-((3'-fluorobiphenyl-3-yl) methyl)-3-((methylsulfonyl)amino) piperidine-1-carboxamide | 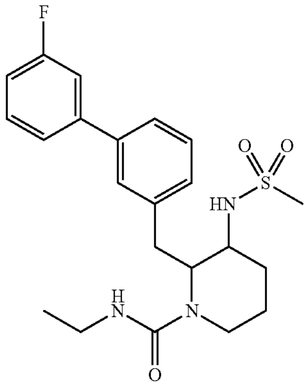 [SMILES: CCNC(=O)N1CCCC(NS(C)(=O)=O)C1Cc1cccc(-c2cccc(F)c2)c1] | | 434.1 |
| 14 | methyl cis-2-((3'-fluorobiphenyl-3-yl)methyl)-3-((methylsulfonyl)amino) piperidine-1-carboxylate | 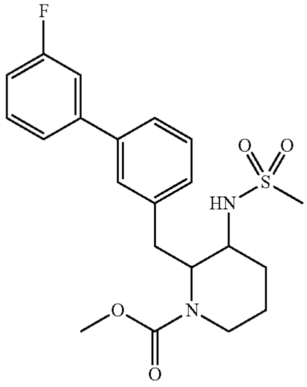 [SMILES: COC(=O)N1CCCC(NS(C)(=O)=O)C1Cc1cccc(-c2cccc(F)c2)c1] | | 421.1 |

TABLE 1-continued

| EXAMPLE | IUPACNAME | Structure | ADDITIVE | MS |
|---|---|---|---|---|
| 15 | cis-N-ethyl-2-((2'-fluorobiphenyl-3-yl)methyl)-3-((methylsulfonyl)amino) piperidine-1-carboxamide | 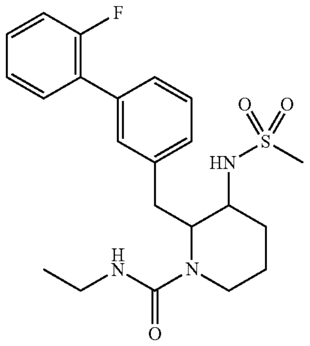 [SMILES: CCNC(=O)N1CCCC(NS(C)(=O)=O)C1Cc1cccc(-c2ccccc2F)c1] | | 434.1 |
| 16 | trans-N-ethyl-2-((2'-fluorobiphenyl-3-yl)methyl)-3-((methylsulfonyl)amino) piperidine-1-carboxamide | 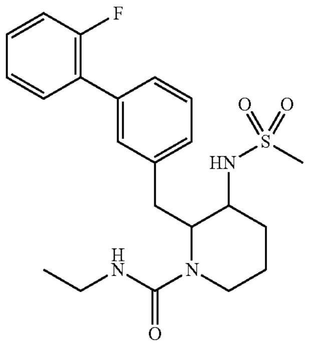 [SMILES: CCNC(=O)N1CCCC(NS(C)(=O)=O)C1Cc1cccc(-c2ccccc2F)c1] | | 434.1 |
| 17 | cis-N-ethyl-3-((methylsulfonyl)amino)-2-(3-((triisopropylsilyl)oxy)benzyl)piperidine-1-carboxamide | 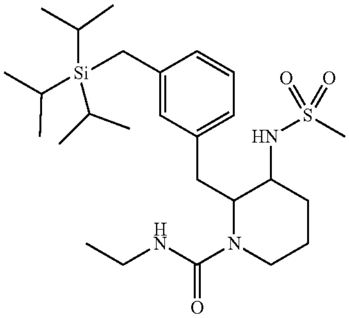 [SMILES: CCNC(=O)N1CCCC(NS(C)(=O)=O)C1Cc1cccc(C[Si](C(C)C)(C(C)C)C(C)C)c1] | | 512.3 |
| 18 | methyl cis-2-((2'-fluorobiphenyl-3-yl) methyl)-3-((methylsulfonyl)amino) piperidine-1-carboxylate | 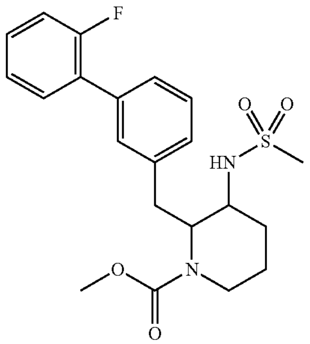 [SMILES: COC(=O)N1CCCC(NS(C)(=O)=O)C1Cc1cccc(-c2ccccc2F)c1] | | 421.1 |

TABLE 1-continued

| EXAMPLE | IUPACNAME | Structure | ADDITIVE | MS |
|---|---|---|---|---|
| 19 | tert-butyl cis-2-(biphenyl-3-ylmethyl)-3-((methylsulfonyl)amino)piperidine-1-carboxylate | 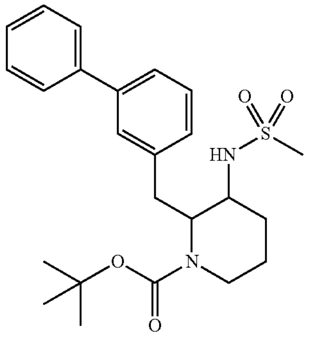 [SMILES: CC(C)(C)OC(=O)N1CCCC(NS(C)(=O)=O)C1Cc1cccc(-c2ccccc2)c1] | | 443.1 |
| 20 | methyl cis-2-((4'-fluorobiphenyl-3-yl)methyl)-3-((methylsulfonyl)amino) piperidine-1-carboxylate | 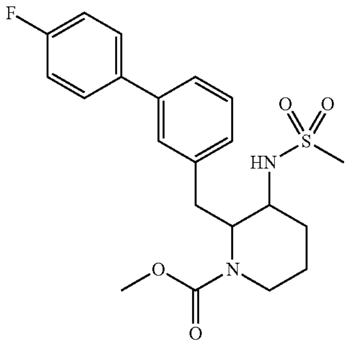 [SMILES: COC(=O)N1CCCC(NS(C)(=O)=O)C1Cc1cccc(-c2ccc(F)cc2)c1] | | 421.1 |
| 21 | methyl cis-2-((2'-methylbiphenyl-3-yl)methyl)-3-((methylsulfonyl)amino) piperidine-1-carboxylate | 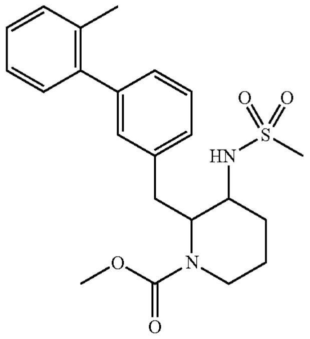 [SMILES: COC(=O)N1CCCC(NS(C)(=O)=O)C1Cc1cccc(-c2ccccc2C)c1] | | 417.1 |
| 22 | N-(cis-1-acetyl-2-(biphenyl-3-ylmethyl) piperidin-3-yl)methanesulfonamide | 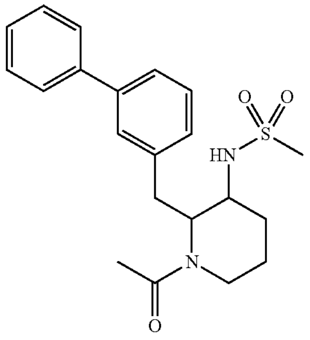 [SMILES: CC(=O)N1CCCC(NS(C)(=O)=O)C1Cc1cccc(-c2ccccc2)c1] | | 387.1 |

TABLE 1-continued

| EXAMPLE | IUPACNAME | Structure | ADDITIVE | MS |
|---|---|---|---|---|
| 23 | methyl cis-2-((3'-methylbiphenyl-3-yl)methyl)-3-((methylsulfonyl)amino) piperidine-1-carboxylate | 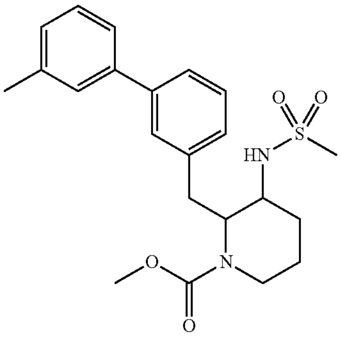 | | 417.1 |
| 24 | methyl cis-2-(3-iodobenzyl)-3-((methylsulfonyl)amino)piperidine-1-carboxylate | 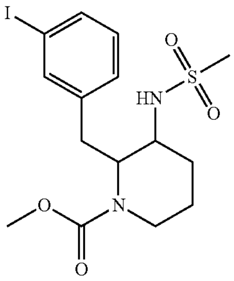 [SMILES: COC(=O)N1CCCC(NS(C)(=O)=O)C1Cc1cccc(I)c1] | | 452.8 |
| 25 | methyl cis-3-((methylsulfonyl)amino)-2-(3-(pyridin-3-yl)benzyl) piperidine-1-carboxylate | 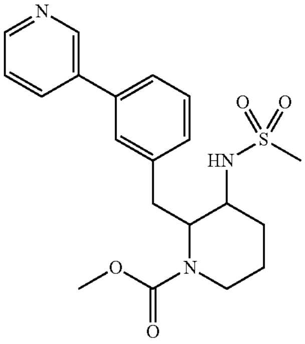 [SMILES: COC(=O)N1CCCC(NS(C)(=O)=O)C1Cc1cccc(-c2cccnc2)c1] | | 404.0 |
| 26 | methyl cis-2-((4'-methoxybiphenyl-3-yl)methyl)-3-((methylsulfonyl)amino) piperidine-1-carboxylate | 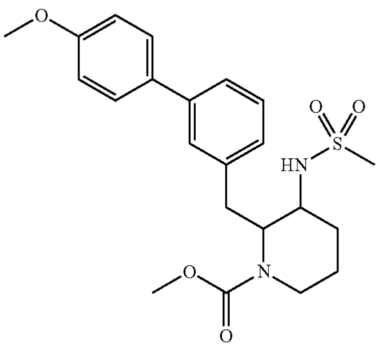 | | 433.0 |

TABLE 1-continued

| EXAMPLE | IUPACNAME | Structure | ADDITIVE | MS |
|---|---|---|---|---|
| 27 | methyl cis-3-((methylsulfonyl)amino)-2-(3-(pyrrolidin-1-yl)benzyl) piperidine-1-carboxylate | 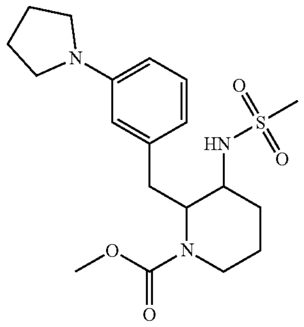 [SMILES: COC(=O)N1CCCC(NS(C)(=O)=O)C1Cc1cccc(N2CCCC2)c1] | | 396.2 |
| 28 | methyl cis-3-((methylsulfonyl)amino)-2-(3-(pyridin-2-yl)benzyl) piperidine-1-carboxylate | 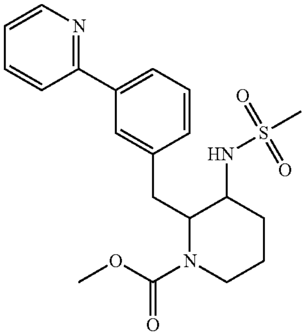 [SMILES: COC(=O)N1CCCC(NS(C)(=O)=O)C1Cc1cccc(-c2ccccn2)c1] | | 404.1 |
| 29 | ethyl cis-2-(biphenyl-3-ylmethyl)-3-((methylsulfonyl)amino)piperidine-1-carboxylate | 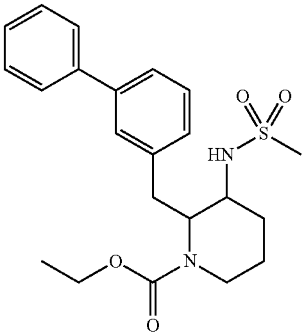 [SMILES: CCOC(=O)N1CCCC(NS(C)(=O)=O)C1Cc1cccc(-c2ccccc2)c1] | | 417.1 |
| 30 | cis-N-ethyl-2-((4'-fluorobiphenyl-3-yl)methyl)-3-((methylsulfonyl)amino) piperidine-1-carboxamide | 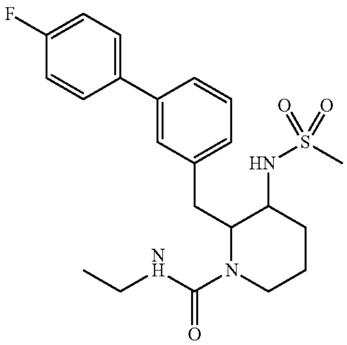 [SMILES: CCNC(=O)N1CCCC(NS(C)(=O)=O)C1Cc1cccc(-c2ccc(F)cc2)c1] | | 434.1 |

TABLE 1-continued

| EXAMPLE | IUPACNAME | Structure | ADDITIVE | MS |
|---|---|---|---|---|
| 31 | methyl cis-2-((2'-methoxybiphenyl-3-yl)methyl)-3-((methylsulfonylamino) piperidine-1-carboxylate | 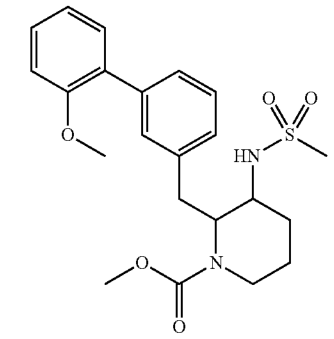 [SMILES: COC(=O)N1CCCC(NS(C)(=O)=O)C1Cc1cccc(-c2ccccc2OC)c1] | | 433.0 |
| 32 | methyl cis-2-((3'-methoxybiphenyl-3-yl)methyl)-3-((methylsulfonyl)amino) piperidine-1-carboxylate | 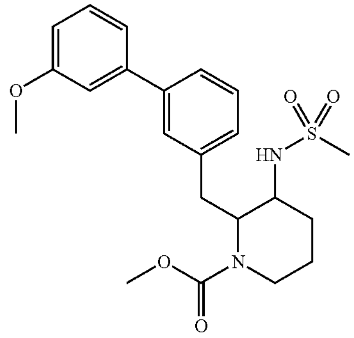 [SMILES: COC(=O)N1CCCC(NS(C)(=O)=O)C1Cc1cccc(-c2cccc(OC)c2)c1] | | 433.0 |
| 33 | cis-N-ethyl-2-((2'-methoxybiphenyl-3-yl)methyl)-3-((methylsulfonylamino) piperidine-1-carboxamide | 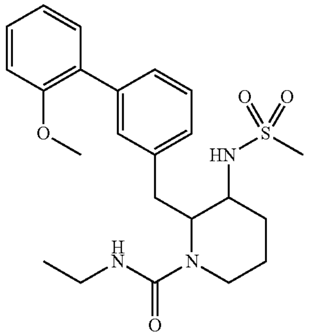 [SMILES: CCNC(=O)N1CCCC(NS(C)(=O)=O)C1Cc1cccc(-c2ccccc2OC)c1] | | 446.1 |
| 34 | cis-N-ethyl-2-((3'-methoxybiphenyl-3-yl)methyl)-3-((methylsulfonyl)amino) piperidine-1-carboxamide | 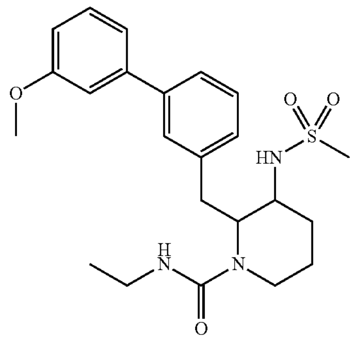 [SMILES: CCNC(=O)N1CCCC(NS(C)(=O)=O)C1Cc1cccc(-c2cccc(OC)c2)c1] | | 446.1 |

TABLE 1-continued

| EXAMPLE | IUPACNAME | Structure | ADDITIVE | MS |
|---|---|---|---|---|
| 35 | cis-N-ethyl-3-((methylsulfonyl)amino)-2-((4'-(trifluoromethyl)biphenyl-3-yl)methyl)piperidine-1-carboxamide | 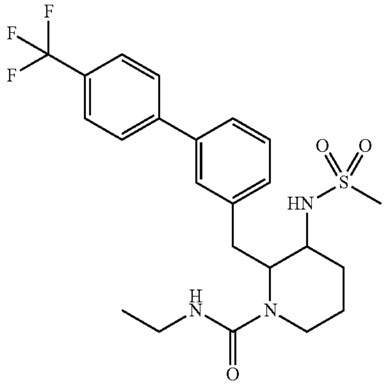 [SMILES: CCNC(=O)N1CCCC(NS(C)(=O)=O)C1Cc1cccc(-c2ccc(C(F)(F)F)cc2)c1] | | 484.0 |
| 36 | cis-N-ethyl-2-((2'-methylbiphenyl-3-ylmethyl)-3-((methylsulfonyl)amino) piperidine-1-carboxamide | 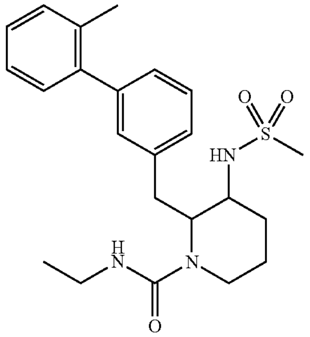 [SMILES: CCNC(=O)N1CCCC(NS(C)(=O)=O)C1Cc1cccc(-c2ccccc2C)c1] | | 430.1 |
| 37 | methyl cis-3-((methylsulfonyl)amino)-2-((6-phenylpyridin-2-yl)methyl) piperidine-1-carboxylate | 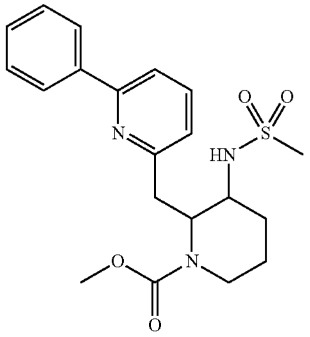 [SMILES: COC(=O)N1CCCC(NS(C)(=O)=O)C1Cc1cccc(-c2ccccc2)n1] | | 404.1 |
| 38 | ethyl cis-3-((methylsulfonyl)amino)-2-((6-phenylpyridin-2-yl)methyl) piperidine-1-carboxylate | 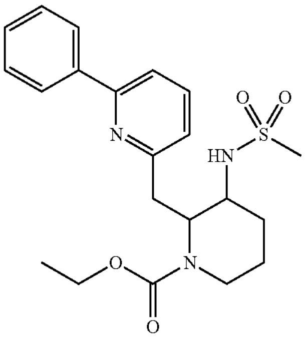 | | 418.1 |

TABLE 1-continued

| EXAMPLE | IUPACNAME | Structure | ADDITIVE | MS |
|---|---|---|---|---|
| 39 | cis-N-ethyl-3-((methylsulfonyl)amino)-2-((6-phenylpyridin-2-yl)methyl) piperidine-1-carboxamide | 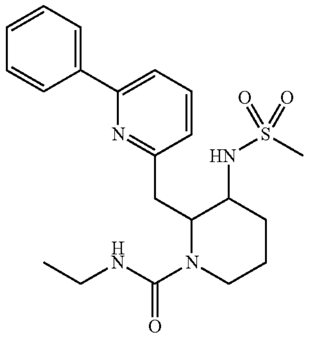 [SMILES: CCNC(=O)N1CCCC(NS(C)(=O)=O)C1Cc1cccc(-c2ccccc2)n1] | | 417.1 |
| 40 | methyl cis-2-((4-fluorobiphenyl-3-yl)methyl)-3-(methylsulfonyl)amino) piperidine-1-carboxylate | 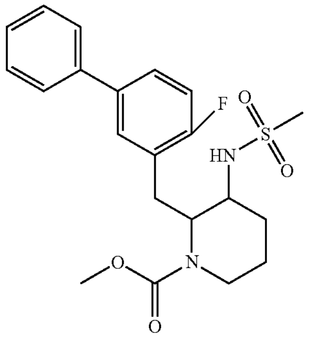 [SMILES: COC(=O)N1CCCC(NS(C)(=O)=O)C1Cc1cc(-c2ccccc2)ccc1F] | | 421.1 |
| 41 | methyl cis-2-((6-fluorobiphenyl-3-yl)methyl)-3-((methylsulfonyl)amino) piperidine-1-carboxylate | 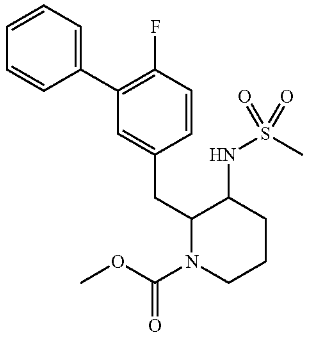 [SMILES: COC(=O)N1CCCC(NS(C)(=O)=O)C1Cc1ccc(F)c(-c2ccccc2)c1] | | 421.1 |
| 42 | ethyl cis-2-((6-fluorobiphenyl-3-yl)methyl)-3-((methylsulfonyl)amino) piperidine-1-carboxylate | 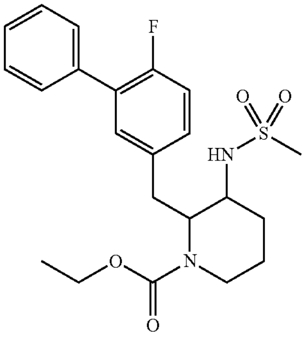 [SMILES: CCOC(=O)N1CCCC(NS(C)(=O)=O)C1Cc1ccc(F)c(-c2ccccc2)c1] | | 435.1 |
| 43 | N-(cis-2-(biphenyl-2-ylmethyl)piperidin-3-yl)methanesulfonamide | 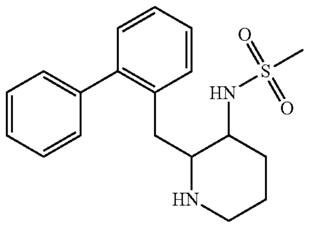 [SMILES: CS(=O)(=O)NC1CCCNC1Cc1ccccc1-c1ccccc1] | HCl | 345.0 |

TABLE 1-continued

| EXAMPLE | IUPACNAME | Structure | ADDITIVE | MS |
|---|---|---|---|---|
| 44 | methyl cis-3-((methylsulfonyl)amino)-2-(3-(trifluoromethyl)benzyl)piperidine-1-carboxylate | 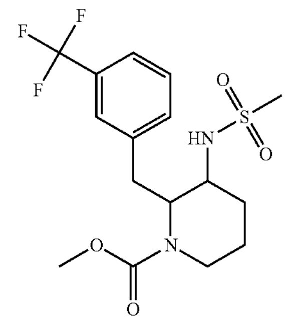 [SMILES: COC(=O)N1CCCC(NS(C)(=O)=O)C1Cc1cccc(C(F)(F)F)c1] | | 395.1 |
| 45 | propyl cis-2-(biphenyl-3-ylmethyl)-3-((methylsulfonyl)amino)piperidine-1-carboxylate | 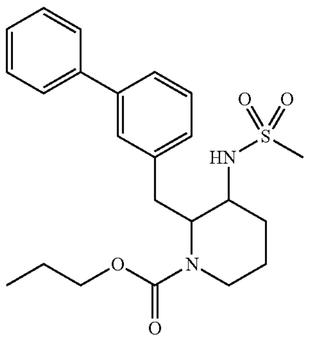 [SMILES: CCCOC(=O)N1CCCC(NS(C)(=O)=O)C1Cc1cccc(-c2ccccc2)c1] | | 431.1 |
| 46 | butyl cis-2-(biphenyl-3-ylmethyl)-3-((methylsulfonyl)amino)piperidine-1-carboxylate | 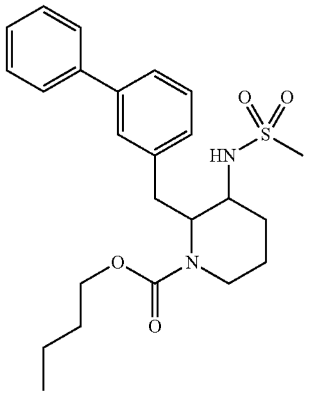 [SMILES: CCCCOC(=O)N1CCCC(NS(C)(=O)=O)C1Cc1cccc(-c2ccccc2)c1] | | 445.1 |
| 47 | 2-methoxyethyl cis-2-(biphenyl-3-ylmethyl)-3-((methylsulfonyl)amino) piperidine-1-carboxylate | 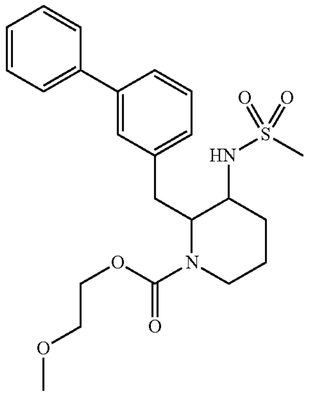 [SMILES: COCCOC(=O)N1CCCC(NS(C)(=O)=O)C1Cc1cccc(-c2ccccc2)c1] | | 447.0 |

TABLE 1-continued

| EXAMPLE | IUPACNAME | Structure | ADDITIVE | MS |
|---|---|---|---|---|
| 48 | 2,2-difluoroethyl cis-2-(biphenyl-3-ylmethyl)-3-((methylsulfonyl)amino) piperidine-1-carboxylate | 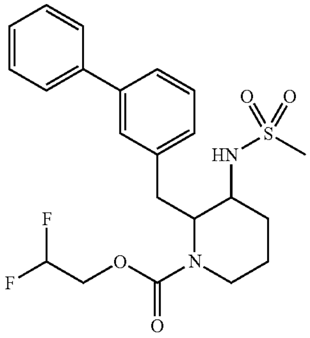 [SMILES: CS(=O)(=O)NC1CCCN(C(=O)OCC(F)F)C1Cc1cccc(-c2ccccc2)c1] | | 451.1 |
| 49 | 2,2,2-trifluoroethyl cis-2-(biphenyl-3-ylmethyl)-3-((methylsulfonyl)amino) piperidine-1-carboxylate | 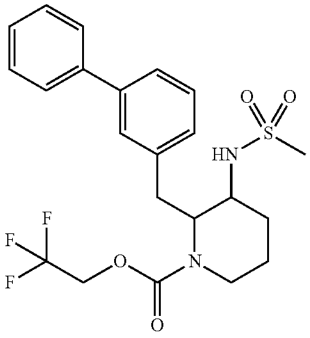 [SMILES: CS(=O)(=O)NC1CCCN(C(=O)OCC(F)(F)F)C1Cc1cccc(-c2ccccc2)c1] | | 469.0 |
| 50 | isopropyl cis-2-(biphenyl-3-ylmethyl)-3-((methylsulfonyl)amino)piperidine-1-carboxylate | 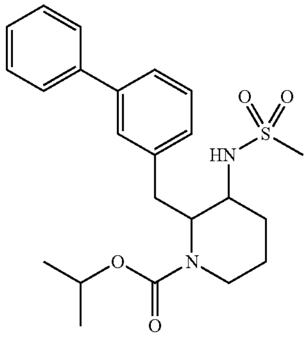 [SMILES: CC(C)OC(=O)N1CCCC(NS(C)(=O)=O)C1Cc1cccc(-c2ccccc2)c1] | | 431.1 |
| 51 | 1,1,1-trifluoropropan-2-yl cis-2-(biphenyl-3-ylmethyl)-3-((methylsulfonyl)amino) piperidine-1-carboxylate | 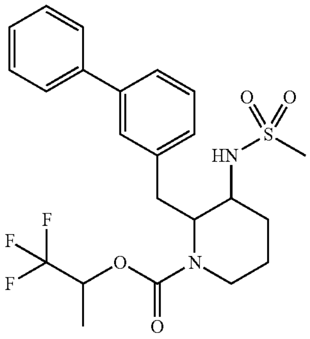 [SMILES: CC(OC(=O)N1CCCC(NS(C)(=O)=O)C1Cc1cccc(-c2ccccc2)c1)C(F)(F)F] | | 483.0 |

TABLE 1-continued

| EXAM-PLE | IUPACNAME | Structure | ADDITIVE | MS |
|---|---|---|---|---|
| 52 | methyl cis-2-((4'-(difluoromethyl)biphenyl-3-yl)methyl)-3-(methylsulfonyl)amino) piperidine-1-carboxylate | 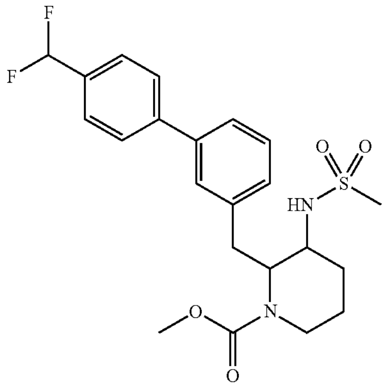 [SMILES: COC(=O)N1CCCC(NS(C)(=O)=O)C1Cc1cccc(-c2ccc(C(F)F)cc2)c1] | | 453.0 |
| 53 | methyl cis-2-(3-(1-methyl-1H-indazol-5-yl)benzyl)-3-((methylsulfonyl)amino) piperidine-1-carboxylate | 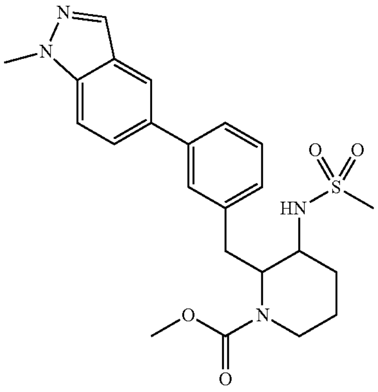 | | 457.1 |
| 54 | methyl cis-3-((methylsulfonyl)amino)-2-(3-vinylbenzyl)piperidine-1-carboxylate | 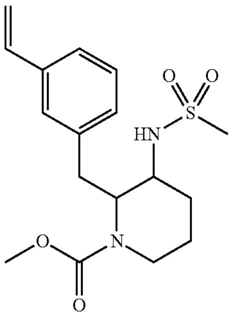 [SMILES: C=Cc1cccc(CC2C(NS(C)(=O)=O)CCCN2C(=O)OC)c1] | | 353.0 |
| 55 | methyl cis-3-((methylsulfonyl)amino)-2-(3-(prop-1-en-2-yl)benzyl)piperidine-1-carboxylate | 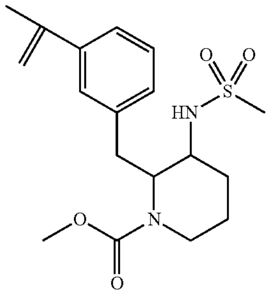 [SMILES: C=C(C)c1cccc(CC2C(NS(C)(=O)=O)CCCN2C(=O)OC)c1] | | 367.1 |

TABLE 1-continued

| EXAMPLE | IUPACNAME | Structure | ADDITIVE | MS |
|---|---|---|---|---|
| 56 | methyl cis-2-(3-(cyclopent-1-en-1-yl)benzyl)-3-((methylsulfonyl)amino) piperidine-1-carboxylate | 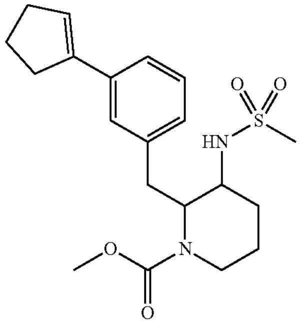 [SMILES: COC(=O)N1CCCC(NS(C)(=O)=O)C1Cc1cccc(C2=CCCC2)c1] | | 393.1 |
| 57 | methyl cis-2-(3-(cyclohex-1-en-1-yl) benzyl)-3-((methylsulfonyl)amino) piperidine-1-carboxylate | 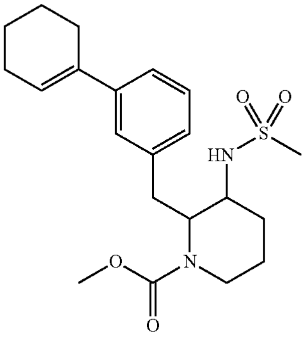 [SMILES: COC(=O)N1CCCC(NS(C)(=O)=O)C1Cc1cccc(C2=CCCCC2)c1] | | 407.1 |
| 58 | methyl cis-2-((2-fluorobiphenyl-3-yl)methyl)-3-((methylsulfonyl)amino) piperidine-1-carboxylate | 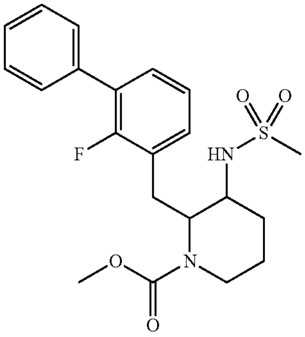 [SMILES: COC(=O)N1CCCC(NS(C)(=O)=O)C1Cc1cccc(-c2ccccc2)c1F] | | 421.0 |
| 59 | ethyl cis-2-((2-fluorobiphenyl-3-yl) methyl)-3-((methylsulfonyl)amino) piperidine-1-carboxylate | 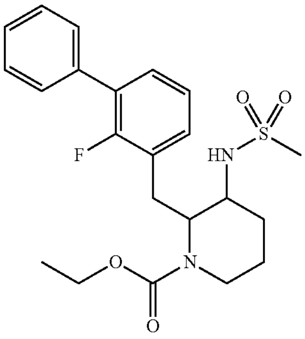 [SMILES: CCOC(=O)N1CCCC(NS(C)(=O)=O)C1Cc1cccc(-c2ccccc2)c1F] | | 435.1 |

TABLE 1-continued

| EXAM-PLE | IUPACNAME | Structure | ADDITIVE | MS |
|---|---|---|---|---|
| 60 | methyl cis-2-(3-cyclobutylbenzyl)-3-((methylsulfonyl)amino)piperidine-1-carboxylate | 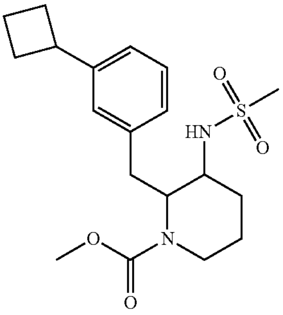 [SMILES: COC(=O)N1CCCC(NS(C)(=O)=O)C1Cc1cccc(C2CCC2)c1] | | 381.1 |
| 61 | methyl cis-2-(biphenyl-3-yimethyl)-3-((methylsulfonyl)amino)pyrrolidine-1-carboxylate | 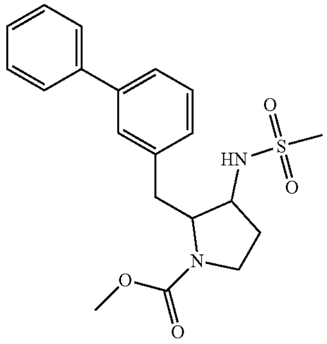 [SMILES: COC(=O)N1CCC(NS(C)(=O)=O)C1Cc1cccc(-c2ccccc2)c1] | | 389.1 |
| 62 | cis-N-ethyl-3-((methylsulfonyl)amino)-2-(2-phenoxybenzyl)piperidine-1-carboxamide | 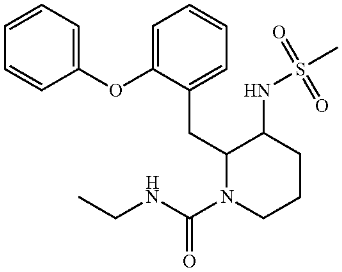 [SMILES: CCNC(=O)N1CCCC(NS(C)(=O)=O)C1Cc1ccccc1Oc1ccccc1] | | 432.1 |
| 63 | cis-N-ethyl-3-((methylsulfonyl)amino)-2-(4-phenoxybenzyl)piperidine-1-carboxamide | 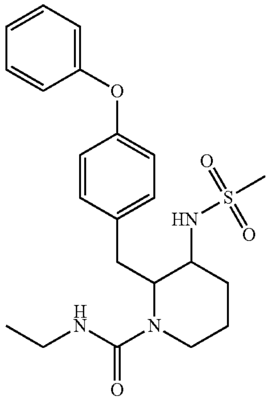 [SMILES: CCNC(=O)N1CCCC(NS(C)(=O)=O)C1Cc1ccc(Oc2ccccc2)cc1] | | 432.0 |

TABLE 1-continued

| EXAMPLE | IUPACNAME | Structure | ADDITIVE | MS |
|---|---|---|---|---|
| 64 | isopropyl cis-3-((methylsulfonyl)amino)-2-((6-phenylpyridin-2-yl)methyl) piperidine-1-carboxylate | 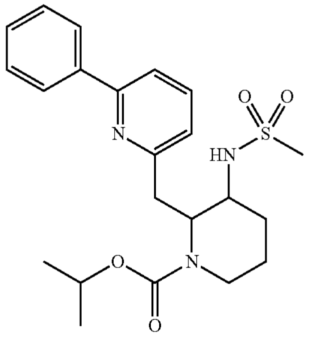 [SMILES: CC(C)OC(=O)N1CCCC(NS(C)(=O)=O)C1Cc1cccc(-c2ccccc2)n1] | | 432.1 |
| 65 | ethyl cis-3-((methylsulfonyl)amino)-2-((5-phenylpyridin-3-yl) methylpiperidine-1-carboxylate | 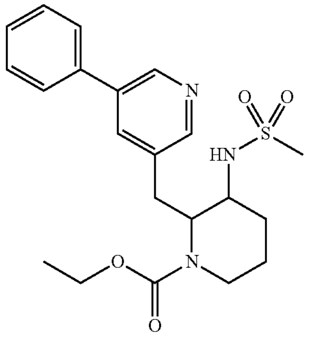 [SMILES: CCOC(=O)N1CCCC(NS(C)(=O)=O)C1Cc1cncc(-c2ccccc2)c1] | | 418.1 |
| 66 | isopropyl cis-3-((methylsulfonyl)amino)-2-((5-phenylpyridin-3-yl)methyl)piperidine-1-carboxylate | 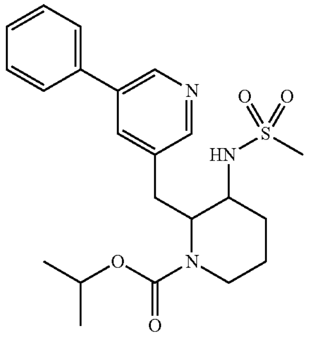 [SMILES: CC(C)OC(=O)N1CCCC(NS(C)(=O)=O)C1Cc1cncc(-c2ccccc2)c1] | | 432.1 |
| 67 | ethyl cis-2-(3-chloro-2-fluorobenzyl)-3-((methylsulfonyl)amino)piperidine-1-carboxylate | 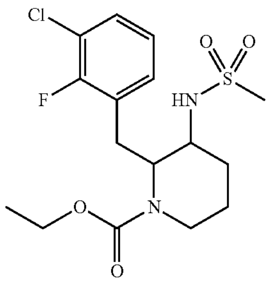 [SMILES: CCOC(=O)N1CCCC(NS(C)(=O)=O)C1Cc1cccc(Cl)c1F] | | 393.0 |

TABLE 1-continued

| EXAMPLE | IUPACNAME | Structure | ADDITIVE | MS |
|---|---|---|---|---|
| 68 | methyl cis-2-((6-methylbiphenyl-3-yl) methyl)-3-((methylsulfonyl)amino) piperidine-1-carboxylate | 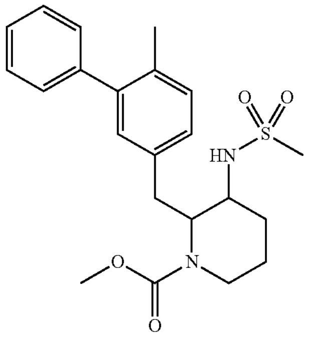 [SMILES: COC(=O)N1CCCC(NS(C)(=O)=O)C1Cc1ccc(C)c(-c2ccccc2)c1] | | 417.2 |
| 69 | methyl cis-2-((5-methylbiphenyl-3-yl) methyl)-3-((methylsulfonyl)amino) piperidine-1-carboxylate | 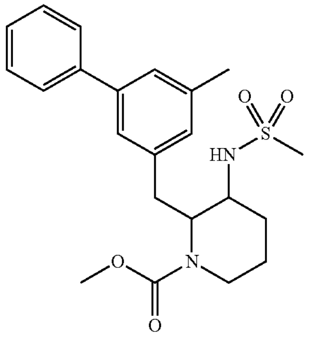 [SMILES: COC(=O)N1CCCC(NS(C)(=O)=O)C1Cc1cc(C)cc(-c2ccccc2)c1] | | 417.2 |
| 70 | ethyl cis-3-((methylsulfonyl)amino)-2-((2-phenylpyridin-4-yl)methyl)piperidine-1-carboxylate | 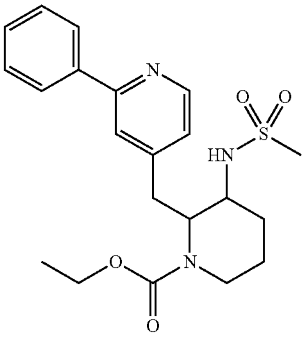 [SMILES: CCOC(=O)N1CCCC(NS(C)(=O)=O)C1Cc1ccnc(-c2ccccc2)c1] | | 418.1 |
| 71 | isopropyl cis-3-((methylsulfonyl)amino)-2-((2-phenylpyridin-4-yl)methyl) piperidine-1-carboxylate | 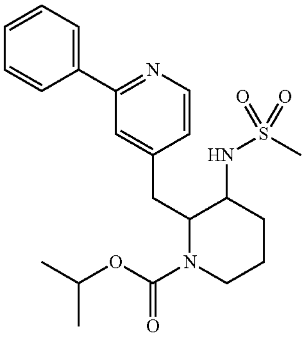 [SMILES: CC(C)OC(=O)N1CCCC(NS(C)(=O)=O)C1Cc1ccnc(-c2ccccc2)c1] | | 432.1 |

TABLE 1-continued

| EXAMPLE | IUPACNAME | Structure | ADDITIVE | MS |
|---|---|---|---|---|
| 72 | cis-N-ethyl-3-((methylsulfonyl)amino)-2-((2-phenylpyridin-4-yl)methyl) piperidine-1-carboxamide | 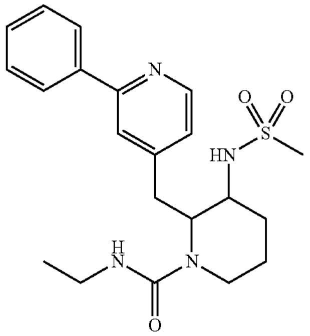 [SMILES: CCNC(=O)N1CCCC(NS(C)(=O)=O)C1Cc1ccnc(-c2ccccc2)c1] | | 417.2 |
| 73 | isopropyl cis-3-((methylsulfonyl)amino)-2-(2-phenoxybenzyl)piperidine-1-carboxylate | 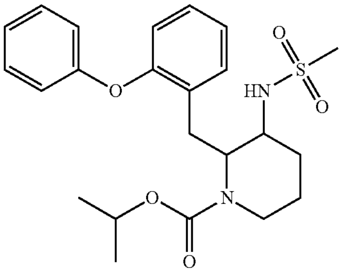 [SMILES: CC(C)OC(=O)N1CCCC(NS(C)(=O)=O)C1Cc1ccccc1Oc1ccccc1] | | 445.2 |
| 74 | isopropyl cis-2-(biphenyl-3-ylmethyl)-3-((methylsulfonyl)amino) pyrrolidine-1-carboxylate | 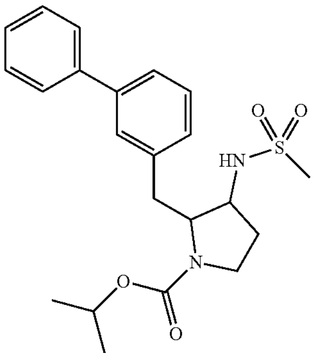 [SMILES: CC(C)OC(=O)N1CCC(NS(C)(=O)=O)C1Cc1cccc(-c2ccccc2)c1] | | 417.1 |
| 75 | ethyl cis-2-(biphenyl-3-ylmethyl)-3-((methylsulfonyl)amino)pyrrolidine-1-carboxylate | 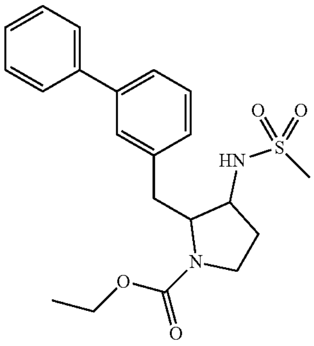 [SMILES: CCOC(=O)N1CCC(NS(C)(=O)=O)C1Cc1cccc(-c2ccccc2)c1] | | 403.1 |

TABLE 1-continued

| EXAMPLE | IUPACNAME | Structure | ADDITIVE | MS |
|---|---|---|---|---|
| 76 | isopropyl cis-3-((methylsulfonyl)amino)-2-((6-phenylpyridin-2-yl)methyl) piperidine-1-carboxylate(optical isomer) | 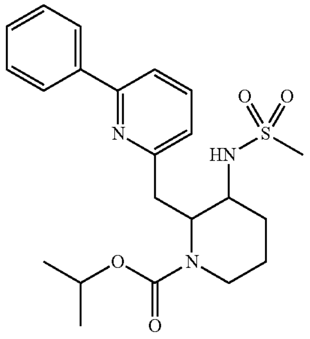 [SMILES: CC(C)OC(=O)N1CCCC(NS(C)(=O)=O)C1Cc1cccc(-c2ccccc2)n1] | | 432.1 |
| 77 | methyl cis-2-(3-cyclopropylbenzyl)-3-((methylsulfonyl)amino)piperidine-1-carboxylate | 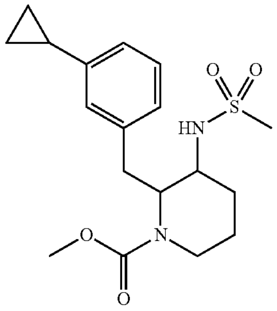 [SMILES: COC(=O)N1CCCC(NS(C)(=O)=O)C1Cc1cccc(C2CC2)c1] | | 367.1 |
| 78 | isopropyl cis-2-(dibenzo[b,d]furan-4-ylmethyl)-3-((methylsulfonyl)amino) piperidine-1-carboxylate | 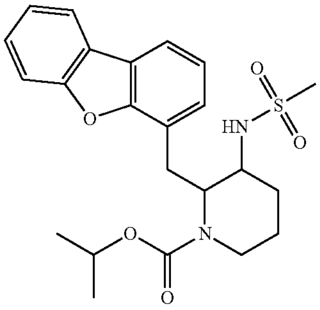 [SMILES: CC(C)OC(=O)N1CCCC(NS(C)(=O)=O)C1Cc1cccc2c1oc1ccccc12] | | 443.2 |
| 79 | propyl cis-2-(biphenyl-3-ylmethyl)-3-((methylsulfonyl)amino) pyrrolidine-1-carboxylate | 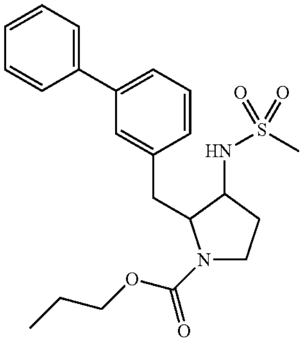 [SMILES: CCCOC(=O)N1CCC(NS(C)(=O)=O)C1Cc1cccc(-c2ccccc2)c1] | | 417.2 |

TABLE 1-continued

| EXAMPLE | IUPACNAME | Structure | ADDITIVE | MS |
|---|---|---|---|---|
| 80 | trans-2-(biphenyl-3-ylmethyl)-N-ethyl-3-((methylsulfonyl)amino)pyrrolidine-1-carboxamide | 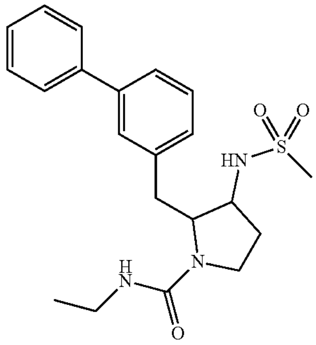 [SMILES: CCNC(=O)N1CCC(NS(C)(=O)=O)C1Cc1cccc(-c2ccccc2)c1] | | 402.0 |
| 81 | N-(cis-2-(biphenyl-3-ylmethyl)pyrrolidin-3-yl)methanesulfonamide | 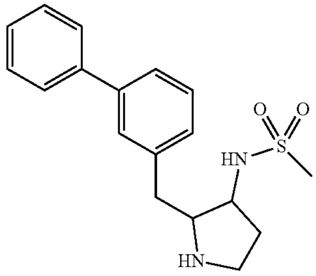 [SMILES: CS(=O)(=O)NC1CCNC1Cc1cccc(-c2ccccc2)c1] | | 331.0 |
| 82 | isopropyl cis-3-((methylsulfonyl)amino)-2-((6-(prop-1-en-2-yl)pyridin-2-yl)methyl)piperidine-1-carboxylate | 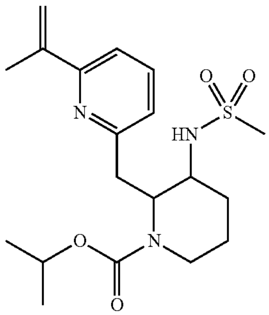 [SMILES: C=C(C)c1cccc(CC2C(NS(C)(=O)=O)CCCN2C(=O)OC(C)C)n1] | | 396.2 |
| 83 | isopropyl cis-2-((6-isopropylpyridin-2-yl)methyl)-3-((methylsulfonyl)amino) piperidine-1-carboxylate | 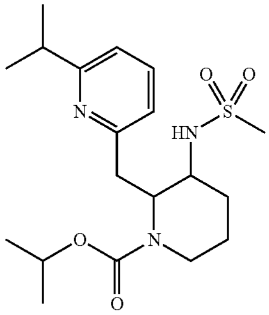 [SMILES: CC(C)OC(=O)N1CCCC(NS(C)(=O)=O)C1Cc1cccc(C(C)C)n1] | | 398.1 |

TABLE 1-continued

| EXAMPLE | IUPACNAME | Structure | ADDITIVE | MS |
|---|---|---|---|---|
| 84 | isopropyl cis-3-((methylsulfonyl)amino)-2-((4-phenyl-1H-pyrazol-1-yl)methyl) piperidine-1-carboxylate | 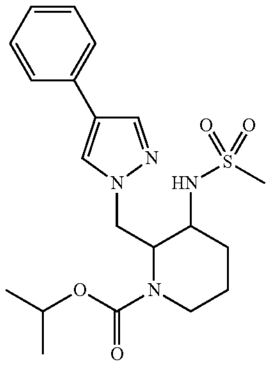 [SMILES: CC(C)OC(=O)N1CCCC(NS(C)(=O)=O)C1Cn1cc(-c2ccccc2)cn1] | | 421.1 |
| 85 | methyl cis-2-(dibenzo[b,d]furan-4-ylmethyl)-3-((methylsulfonyl)amino) piperidine-1-carboxylate | 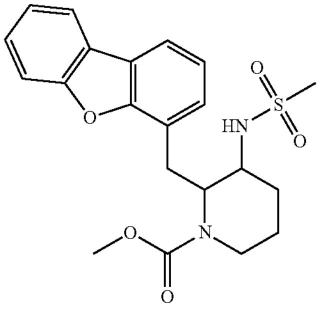 [SMILES: COC(=O)N1CCCC(NS(C)(=O)=O)C1Cc1cccc2c1oc1ccccc12] | | 417.0 |
| 86 | methyl cis-3-((methylsulfonyl)amino)-2-(1-naphthylmethyl)piperidine-1-carboxylate | 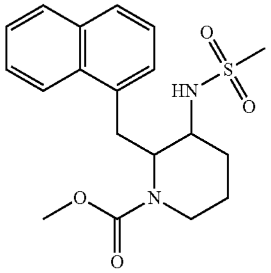 [SMILES: COC(=O)N1CCCC(NS(C)(=O)=O)C1Cc1cccc2ccccc12] | | 377.0 |
| 87 | isopropyl cis-2-(3-isopropylbenzyl)-3-((methylsulfonyl)amino)piperidine-1-carboxylate | 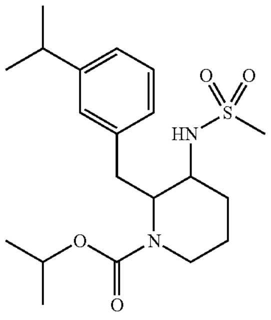 [SMILES: CC(C)OC(=O)N1CCCC(NS(C)(=O)=O)C1Cc1cccc(C(C)C)c1] | | 395.1 |

TABLE 1-continued

| EXAM-PLE | IUPACNAME | Structure | ADDITIVE | MS |
|---|---|---|---|---|
| 88 | tert-butyl cis-3-((methylsulfonyl)amino)-2-((2-phenyl-1,3-thiazol-4-yl)methyl) piperidine-1-carboxylate | 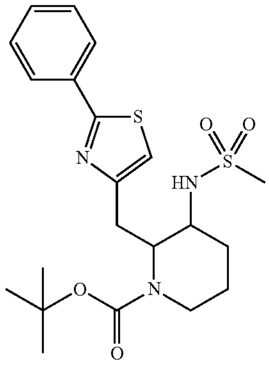 [SMILES: CC(C)(C)OC(=O)N1CCCC(NS(C)(=O)=O)C1Cc1csc(-c2ccccc2)n1] | | 452.0 |
| 89 | isopropyl cis-3-((methylsulfonyl)amino)-2-((2-phenyl-1,3-thiazol-4-yl)methyl) piperidine-1-carboxylate | 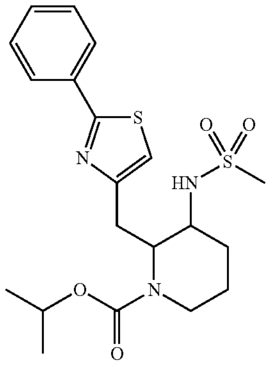 | | 438.1 |
| 90 | ethyl cis-3-((methylsulfonyl)amino)-2-((2-phenyl-1,3-thiazol-4-yl)methyl) piperidine-1-carboxylate | 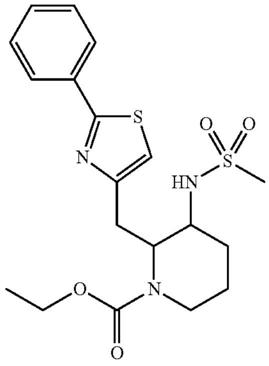 | | 424.0 |
| 91 | methyl cis-2-((4-methylbiphenyl-3-yl) methyl)-3-((methylsulfonyl)amino) piperidine-1-carboxylate | 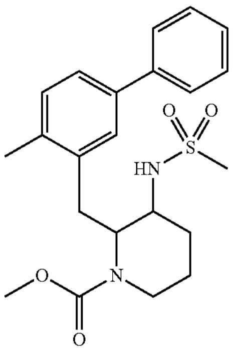 [SMILES: COC(=O)N1CCCC(NS(C)(=O)=O)C1Cc1cc(-c2ccccc2)ccc1C] | | 417.0 |

TABLE 1-continued
| EXAM-PLE | IUPACNAME | Structure | ADDITIVE | MS |
|---|---|---|---|---|
| 92 | N-(cis-2-(bipheny-3-ylmethyl)-1-propionylpiperidin-3-yl) methanesulfonamide | 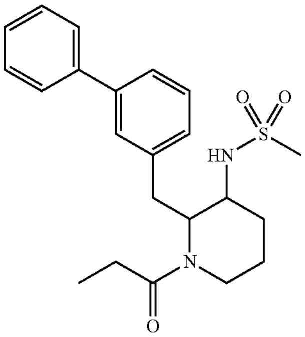 [SMILES: CCC(=O)N1CCCC(NS(C)(=O)=O)C1Cc1cccc(-c2ccccc2)c1] | | 401.1 |
| 93 | N-(cis-2-(biphenyl-3-ylmethyl)-1-(cyclopropylcarbonyl)piperidin-3-ylmethanesulfonamide | 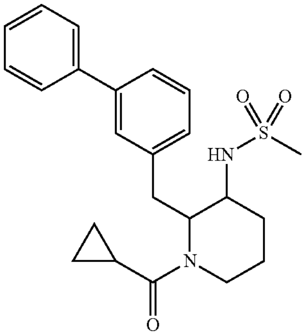 [SMILES: CS(=O)(=O)NC1CCCN(C(=O)C2CC2)C1Cc1cccc(-c2ccccc2)c1] | | 413.2 |
| 94 | N-(cis-2-(bipheny-3-ylmethyl)-1-(2,2-difluoropropanoyl)piperidin-3-yl) methanesulfonamide | 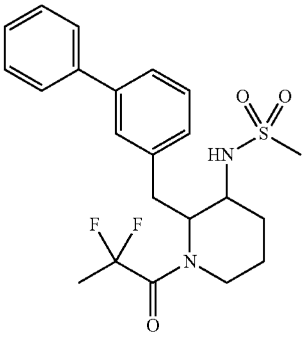 [SMILES: CC(F)(F)C(=O)N1CCCC(NS(C)(=O)=O)C1Cc1cccc(-c2ccccc2)c1] | | 437.1 |
| 95 | N-(cis-2-(biphenyl-3-ylmethyl-1-isobutyrylpiperidin-3-yl) methanesulfonamide | 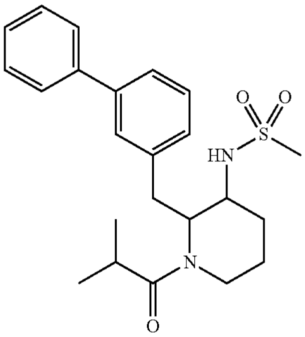 [SMILES: CC(C)C(=O)N1CCCC(NS(C)(=O)=O)C1Cc1cccc(-c2ccccc2)c1] | | 415.1 |

TABLE 1-continued

| EXAMPLE | IUPACNAME | Structure | ADDITIVE | MS |
|---|---|---|---|---|
| 96 | isopropyl cis-2-((6-(3-fluorophenyl) pyridin-2-yl)methyl)-3-((nnethylsulfonyl) amino)piperidine-1-carboxylate | 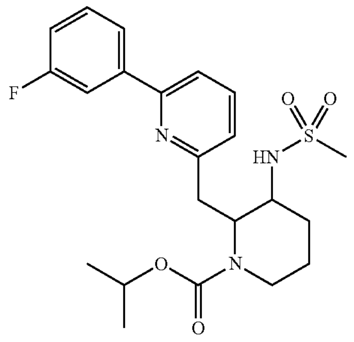 [SMILES: CC(C)OC(=O)N1CCCC(NS(C)(=O)=O)C1Cc1cccc(-c2cccc(F)c2)n1] | | 450.1 |
| 97 | isopropyl cis-2-((6-(2-fluorophenyl)pyridin-2-yl)methyl)-3-((methylsulfonyl) amino)piperidine-1-carboxylate | 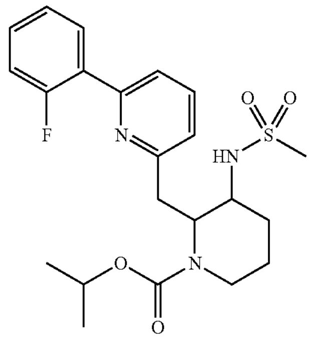 [SMILES: CC(C)OC(=O)N1CCCC(NS(C)(=O)=O)C1Cc1cccc(-c2ccccc2F)n1] | | 450.1 |
| 98 | isopropyl cis-2-((6-(2,3-difluorophenyl) pyridin-2-yl)methyl)-3-((methylsulfonyl) amino)piperidine-1-carboxylate | 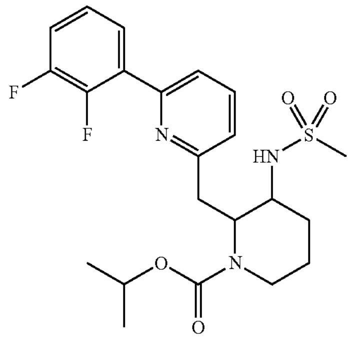 [SMILES: CC(C)OC(=O)N1CCCC(NS(C)(=O)=O)C1Cc1cccc(-c2cccc(F)c2F)n1] | | 468.1 |
| 99 | isopropyl cis-2-((6-(3,5-difluorophenyl) pyridin-2-yl)methyl)-3-((methylsulfonyl) amino)piperidine-1-carboxylate | 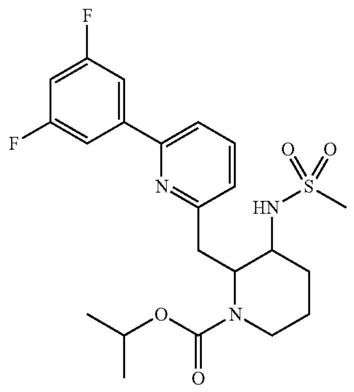 [SMILES: CC(C)OC(=O)N1CCCC(NS(C)(=O)=O)C1Cc1cccc(-c2cc(F)cc(F)c2)n1] | | 468.2 |

TABLE 1-continued

| EXAMPLE | IUPACNAME | Structure | ADDITIVE | MS |
|---|---|---|---|---|
| 100 | isopropyl cis-2-((6-(2,5-difluorophenyl) pyridin-2-yl)methyl)-3-((methylsulfonyl) amino)piperidine-1-carboxylate | 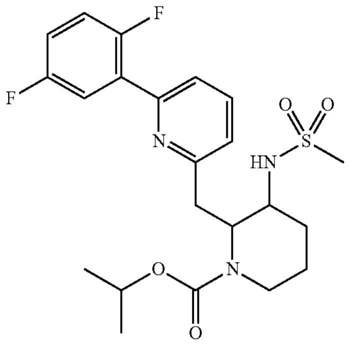 [SMILES: CC(C)OC(=O)N1CCCC(NS(C)(=O)=O)C1Cc1cccc(-c2cc(F)ccc2F)n1] | | 468.2 |
| 101 | ethyl (2S,3S)-2-(biphenyl-3-ylmethyl)-3-((methylsulfonyl)amino)pyrrolidine-1-carboxylate (optical isomer) | 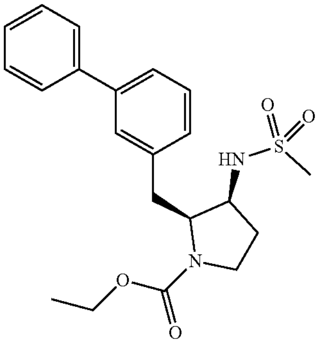 [SMILES: CCOC(=O)N1CC[C@H](NS(C)(=O)=O)[C@@H]1Cc1cccc(-c2ccccc2)c1] | | 403.1 |
| 102 | butyl cis-2-(biphenyl-3-ylmethyl)-3-((methylsulfonyl)amino)pyrrolidine-1-carboxylate | 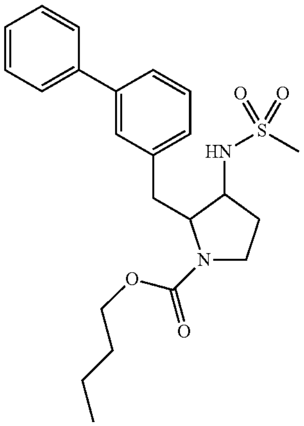 [SMILES: CCCCOC(=O)N1CCC(NS(C)(=O)=O)C1Cc1cccc(-c2ccccc2)c1] | | 431.0 |
| 103 | 2-methoxyethyl cis-2-(biphenyl-3-ylmethyl)-3-((methylsulfonyl)amino) pyrrolidine-1-carboxylate | 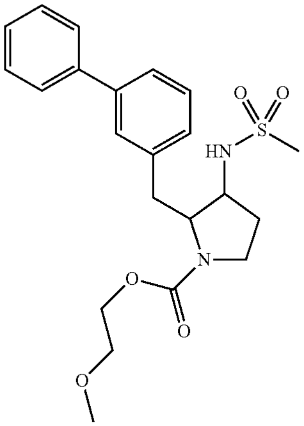 [SMILES: COCCOC(=O)N1CCC(NS(C)(=O)=O)C1Cc1cccc(-c2ccccc2)c1] | | 433.0 |

TABLE 1-continued

| EXAM-PLE | IUPACNAME | Structure | ADDITIVE | MS |
|---|---|---|---|---|
| 104 | 2,2-difluoroethyl cis-2-(biphenyl-3-ylmethyl)-3-((methylsulfonyl)amino) pyrrolidine-1-carboxylate | 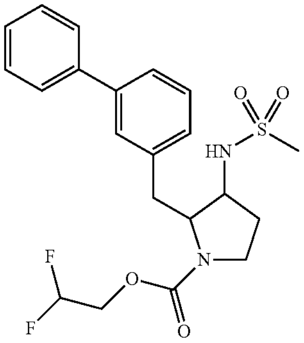 [SMILES: CS(=O)(=O)NC1CCN(C(=O)OCC(F)F)C1Cc1cccc(-c2ccccc2)c1] | | 437.0 |
| 105 | 2,2,2-trifluoroethyl cis-2-(biphenyl-3-ylmethyl)-3-((methylsulfonyl)amino) pyrrolidine-1-carboxylate | 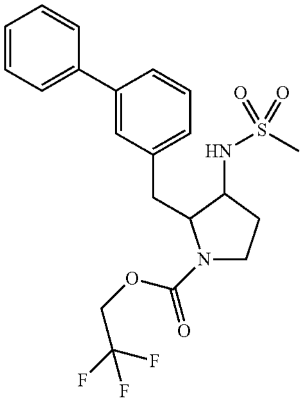 [SMILES: CS(=O)(=O)NC1CCN(C(=O)OCC(F)(F)F)C1Cc1cccc(-c2ccccc2)c1] | | 455.0 |
| 106 | sec-butyl cis-2-(biphenyl-3-ylmethyl)-3-((methylsulfonyl)amino)pyrrolidine-1-carboxylate | 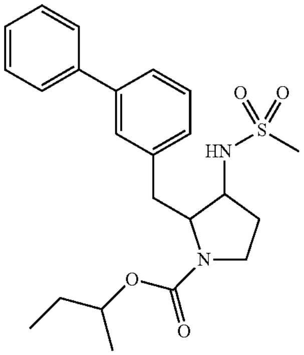 [SMILES: CCC(C)OC(=O)N1CCC(NS(C)(=O)=O)C1Cc1cccc(-c2ccccc2)c1] | | 429.1 |
| 107 | isobutyl cis-2-(biphenyl-3-ylmethyl)-3-((methylsulfonylamino)pyrrolidine-1-carboxylate | 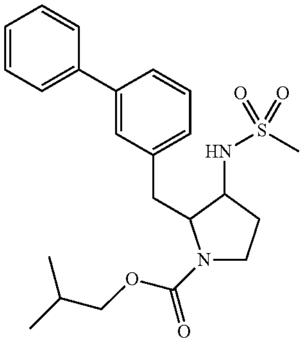 [SMILES: CC(C)COC(=O)N1CCC(NS(C)(=O)=O)C1Cc1cccc(-c2ccccc2)c1] | | 431.0 |

TABLE 1-continued

| EXAM-PLE | IUPACNAME | Structure | ADDITIVE | MS |
| --- | --- | --- | --- | --- |
| 108 | cyclopropyl cis-2-(biphenyl-3-ylmethyl)-3-((methylsulfonyl)amino)pyrrolidine-1-carboxylate | 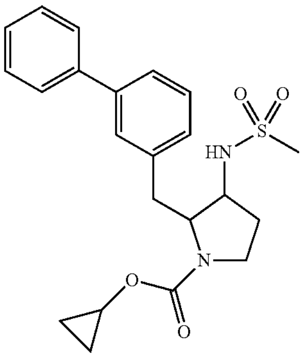 [SMILES: CS(=O)(=O)NC1CCN(C(=O)OC2CC2)C1Cc1cccc(-c2ccccc2)c1] | | 415.0 |
| 109 | cyclobutyl cis-2-(biphenyl-3-ylmethyl)-3-((methylsulfonyl)amino)pyrrolidine-1-carboxylate | 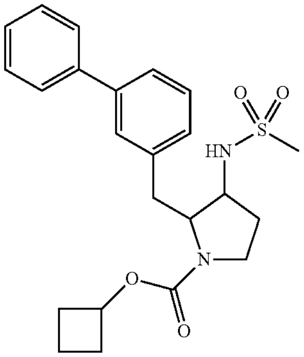 [SMILES: CS(=O)(=O)NC1CCN(C(=O)OC2CCC2)C1Cc1cccc(-c2ccccc2)c1] | | 429.0 |
| 110 | 3,3-difluorocyclobutyl cis-2-(biphenyl-3-ylmethyl)-3-((methylsulfonyl)amino) pyrrolidine-1-carboxylate | 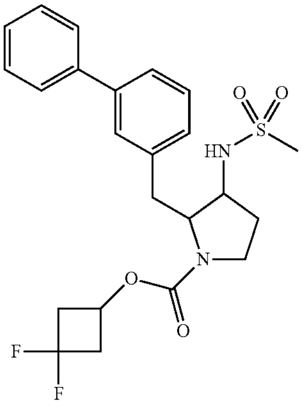 [SMILES: CS(=O)(=O)NC1CCN(C(=O)OC2CC(F)(F)C2)C1Cc1cccc(-c2ccccc2)c1] | | 465.0 |
| 111 | cyclopentyl cis-2-(biphenyl-3-ylmethyl)-3-((methylsulfonyl)amino)pyrrolidine-1-carboxylate | 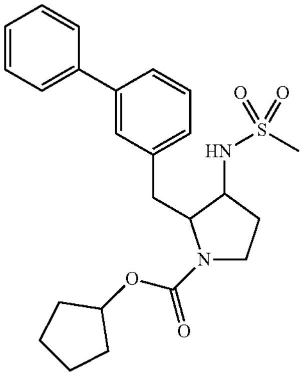 [SMILES: CS(=O)(=O)NC1CCN(C(=O)OC2CCCC2)C1Cc1cccc(-c2ccccc2)c1] | | 441.0 |

TABLE 1-continued

| EXAMPLE | IUPACNAME | Structure | ADDITIVE | MS |
|---|---|---|---|---|
| 112 | cyclopropylmethyl cis-2-(biphenyl-3-ylmethyl)-3-((methylsulfonyl)amino) pyrrolidine-1-carboxylate | 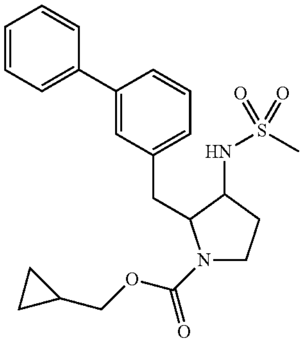 [SMILES: CS(=O)(=O)NC1CCN(C(=O)OCC2CC2)C1Cc1cccc(-c2ccccc2)c1] | | 429.0 |
| 113 | (1-methylcyclopropyl)methyl cis-2-(biphenyl-3-ylmethyl)-3-((methylsulfonyl) amino)pyrrolidine-1-carboxylate | 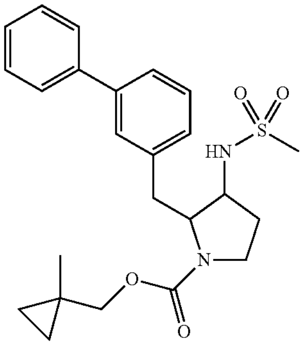 [SMILES: CC1(COC(=O)N2CCC(NS(C)(=O)=O)C2Cc2cccc(-c3ccccc3)c2)CC1] | | 441.0 |
| 114 | (1-fluorocyclopropyl)methyl cis-2-(biphenyl-3-ylmethyl)-3-((methylsulfonyl) amino)pyrrolidine-1-carboxylate | 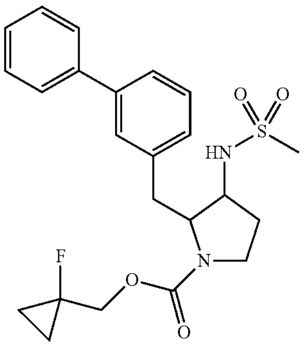 | | 445.2 |
| 115 | cyclobutylmethyl cis-2-(biphenyl-3-ylmethyl)-3-((methylsulfonyl)amino) pyrrolidine-1-carboxylate | 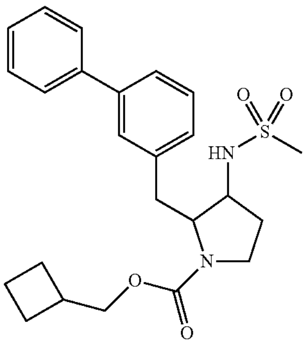 [SMILES: CS(=O)(=O)NC1CCN(C(=O)OCC2CCC2)C1Cc1cccc(-c2ccccc2)c1] | | 441.0 |

TABLE 1-continued

| EXAMPLE | IUPACNAME | Structure | ADDITIVE | MS |
| --- | --- | --- | --- | --- |
| 116 | isopropyl cis-2-((2',3'-difluorobiphenyl-3-yl)methyl)-3-(methylsulfonyl)amino) piperidine-1-carboxylate | 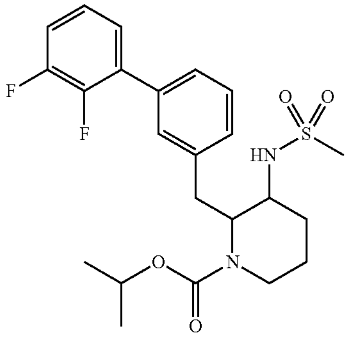 [SMILES: CC(C)OC(=O)N1CCCC(NS(C)(=O)=O)C1Cc1cccc(-c2cccc(F)c2F)c1] | | 467.2 |
| 117 | isopropyl cis-2-(3-iodobenzyl)-3-((methylsulfonyl)amino) piperidine-1-carboxylate | 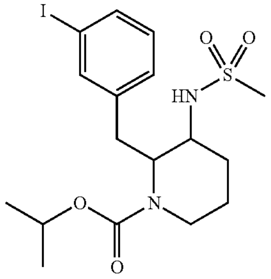 [SMILES: CC(C)OC(=O)N1CCCC(NS(C)(=O)=O)C1Cc1cccc(I)c1] | | 478.9 |
| 118 | N-(cis-2-(biphenyl-3-ylmethyl)-1-(difluoroacetyl)piperidin-3-yl) methanesulfonamide | 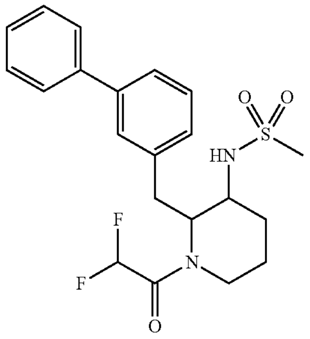 | | 423.1 |
| 119 | isopropyl cis-2-(3-(dimethylamino) benzyl)-3-((methylsulfonyl)amino) piperidine-1-carboxylate | 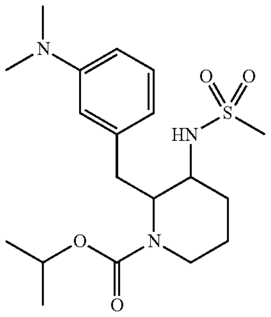 | | 398.1 |

TABLE 1-continued

| EXAMPLE | IUPACNAME | Structure | ADDITIVE | MS |
|---|---|---|---|---|
| 120 | N-(cis-2-(biphenyl-3-ylmethyl)-1-((1-fluorocyclopropyl)carbonyl)piperidin-3-yl)methanesulfonamide | 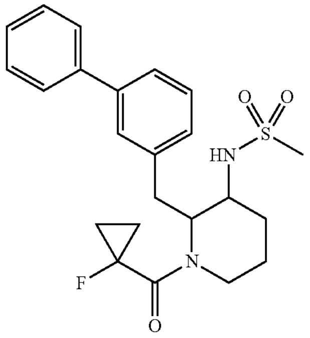 [SMILES: CS(=O)(=O)NC1CCCN(C(=O)C2(F)CC2)C1Cc1cccc(-c2ccccc2)c1] | | 431.1 |
| 121 | isopropyl cis-3-((methylsulfonyl)amino)-2-(2-naphthylmethyl)piperidine-1-carboxylate | 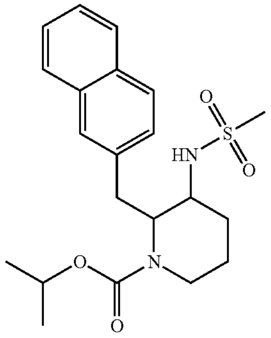 [SMILES: CC(C)OC(=O)N1CCCC(NS(C)(=O)=O)C1Cc1ccc2ccccc2c1] | | 403.1 |
| 122 | isopropyl cis-3-((methylsulfonyl)amino)-2-((3-phenyl-1H-pyrazol-1-yl)methyl)piperidine-1-carboxylate | 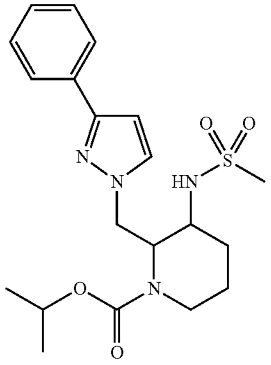 [SMILES: CC(C)OC(=O)N1CCCC(NS(C)(=O)=O)C1Cn1ccc(-c2ccccc2)n1] | | 421.1 |
| 123 | sec-butyl cis-2-(biphenyl-3-ylmethyl)-3-((methylsulfonyl)amino)piperidine-1-carboxylate | 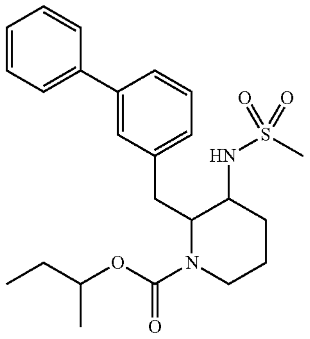 [SMILES: CCC(C)OC(=O)N1CCCC(NS(C)(=O)=O)C1Cc1cccc(-c2ccccc2)c1] | | 443.1 |

TABLE 1-continued

| EXAMPLE | IUPACNAME | Structure | ADDITIVE | MS |
|---|---|---|---|---|
| 124 | 3-methylbutan-2-yl cis-2-(biphenyl-3-ylmethyl)-3-((methylsulfonyl)amino) piperidine-1-carboxylate | 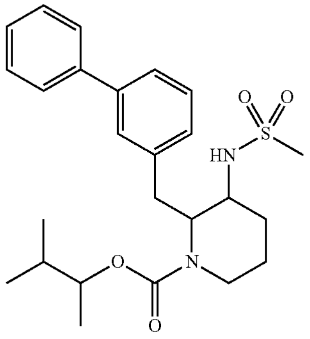 [SMILES: CC(C)C(C)OC(=O)N1CCCC(NS(C)(=O)=O)C1Cc1cccc(-c2ccccc2)c1] | | 457.1 |
| 125 | isobutyl cis-2-(biphenyl-3-ylmethyl)-3-((methylsulfonyl)amino)piperidine-1-carboxylate | 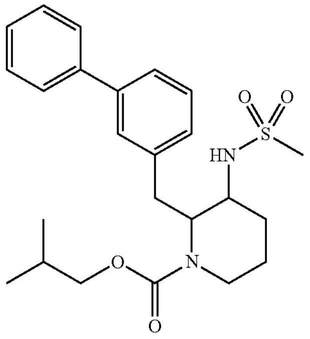 [SMILES: CC(C)COC(=O)N1CCCC(NS(C)(=O)=O)C1Cc1cccc(-c2ccccc2)c1] | | 445.0 |
| 126 | cyclopropyl cis-2-(biphenyl-3-ylmethyl)-3-((methylsulfonyl)amino)piperidine-1-carboxylate | 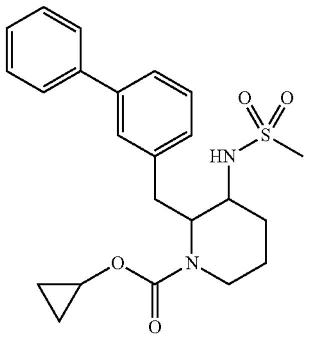 [SMILES: CS(=O)(=O)NC1CCCN(C(=O)OC2CC2)C1Cc1cccc(-c2ccccc2)c1] | | 429.1 |
| 127 | cyclobutyl cis-2-(biphenyl-3-ylmethyl)-3-((methylsulfonyl)amino)piperidine-1-carboxylate | 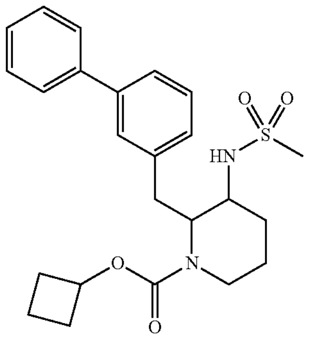 [SMILES: CS(=O)(=O)NC1CCCN(C(=O)OC2CCC2)C1Cc1cccc(-c2ccccc2)c1] | | 443.0 |

TABLE 1-continued

| EXAMPLE | IUPACNAME | Structure | ADDITIVE | MS |
|---|---|---|---|---|
| 128 | 3,3-difluorocyclobutyl cis-2-(biphenyl-3-ylmethyl)-3-((methylsulfonyl)amino) piperidine-1-carboxylate | 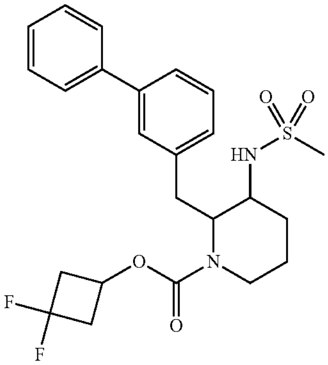 [SMILES: CS(=O)(=O)NC1CCCN(C(=O)OC2CC(F)(F)C2)C1Cc1cccc(-c2ccccc2)c1] | | 477.0 |
| 129 | cyclopentyl cis-2-(biphenyl-3-ylmethyl)-3-((methylsulfonyl)amino)piperidine-1-carboxylate | 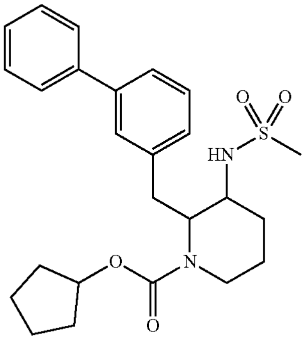 [SMILES: CS(=O)(=O)NC1CCCN(C(=O)OC2CCCC2)C1Cc1cccc(-c2ccccc2)c1] | | 455.0 |
| 130 | cyclohexyl cis-2-(biphenyl-3-ylmethyl)-3-((methylsulfonyl)amino)piperidine-1-carboxylate | 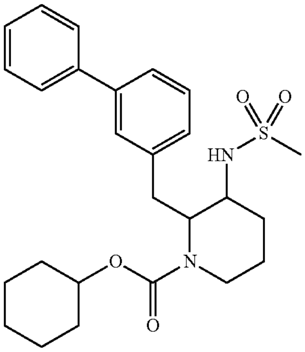 [SMILES: CS(=O)(=O)NC1CCCN(C(=O)OC2CCCCC2)C1Cc1cccc(-c2ccccc2)c1] | | 469.0 |
| 131 | 1-methylcyclopropy cis-2-(biphenyl-3-ylmethyl)-3-(methylsulfonyl)amino) piperidine-1-carboxylate | 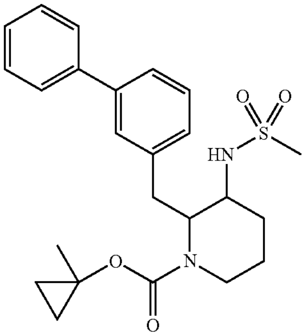 [SMILES: CC1(OC(=O)N2CCCC(NS(C)(=O)=O)C2Cc2cccc(-c3ccccc3)c2)CC1] | | 441.0 |

TABLE 1-continued

| EXAMPLE | IUPACNAME | Structure | ADDITIVE | MS |
|---|---|---|---|---|
| 132 | oxetan-3-yl cis-2-(biphenyl-3-ylmethyl)-3-((methylsulfonyl)amino)piperidine-1-carboxylate | 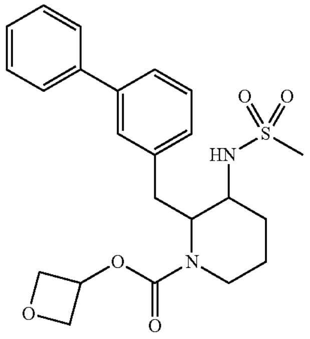 [SMILES: CS(=O)(=O)NC1CCCN(C(=O)OC2COC2)C1Cc1cccc(-c2ccccc2)c1] | | 445.0 |
| 133 | tetrahydrofuran-3-yl cis-2-(biphenyl-3-ylmethyl)-3-((methylsulfonyl)amino)piperidine-1-carboxylate | 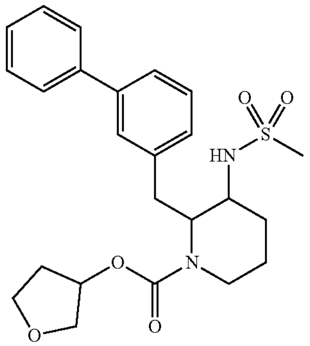 [SMILES: CS(=O)(=O)NC1CCCN(C(=O)OC2CCOC2)C1Cc1cccc(-c2ccccc2)c1] | | 459.0 |
| 134 | tetrahydro-2H-pyran-4-yl cis-2-(biphenyl-3-ylmethyl)-3-((methylsulfonyl)amino)piperidine-1-carboxylate | 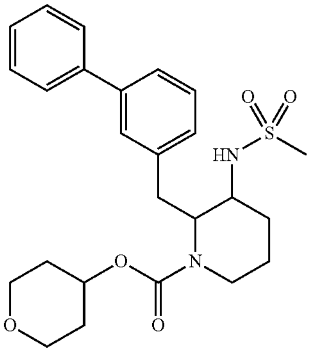 [SMILES: CS(=O)(=O)NC1CCCN(C(=O)OC2CCOCC2)C1Cc1cccc(-c2ccccc2)c1] | | 471.0 |
| 135 | tetrahydro-2H-pyran-3-yl cis-2-(biphenyl-3-ylmethyl)-3-((methylsulfonyl)amino)piperidine-1-carboxylate | 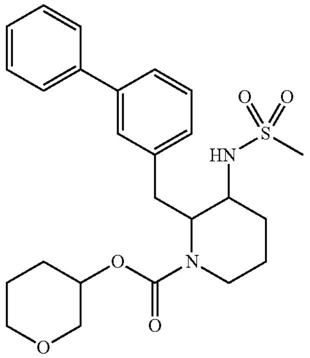 [SMILES: CS(=O)(=O)NC1CCCN(C(=O)OC2CCCOC2)C1Cc1cccc(-c2ccccc2)c1] | | 473.0 |

TABLE 1-continued

| EXAMPLE | IUPACNAME | Structure | ADDITIVE | MS |
|---|---|---|---|---|
| 136 | cyclopropylmethyl cis-2-(biphenyl-3-ylmethyl)-3-((methylsulfonyl)amino) piperidine-1-carboxylate | 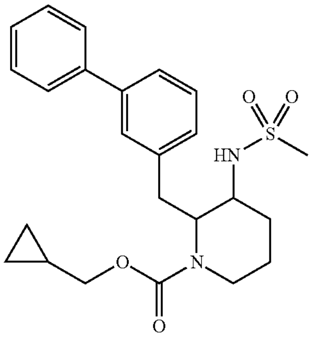 [SMILES: CS(=O)(=O)NC1CCCN(C(=O)OCC2CC2)C1Cc1cccc(-c2ccccc2)c1] | | 443.0 |
| 137 | (1-methylcyclopropyl)methyl cis-2-(biphenyl-3-ylmethyl)-3-((methylsulfonyl) amino)piperidine-1-carboxylate | 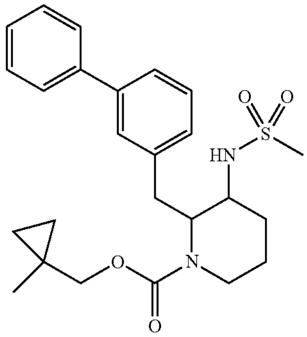 [SMILES: CC1(COC(=O)N2CCCC(NS(C)(=O)=O)C2Cc2cccc(-c3ccccc3)c2)CC1] | | 457.0 |
| 138 | (1-fluorocyclopropylmethyl cis-2-(biphenyl-3-ylmethyl)-3-((methylsulfonyl) amino)piperidine-1-carboxylate | 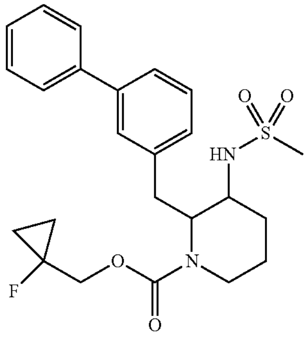 [SMILES: CS(=O)(=O)NC1CCCN(C(=O)OCC2(F)CC2)C1Cc1cccc(-c2ccccc2)c1] | | 459.0 |
| 139 | (2,2-difluorocyclopropyl)methyl cis-2-(biphenyl-3-ylmethyl)-3-((methylsulfonyl) amino)piperidine-1-carboxylate | 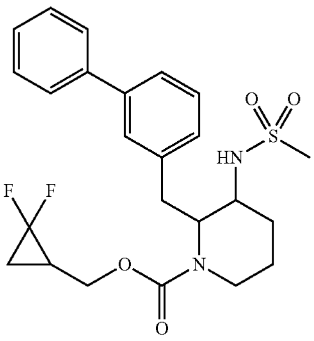 [SMILES: CS(=O)(=O)NC1CCCN(C(=O)OCC2CC2(F)F)C1Cc1cccc(-c2ccccc2)c1] | | 477.0 |

TABLE 1-continued

| EXAMPLE | IUPACNAME | Structure | ADDITIVE | MS |
| --- | --- | --- | --- | --- |
| 140 | cyclobutylmethyl cis-2-(biphenyl-3-ylmethyl)-3-((methylsulfonyl)amino) piperidine-1-carboxylate | 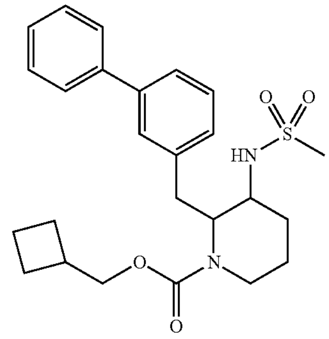 [SMILES: CS(=O)(=O)NC1CCCN(C(=O)OCC2CCC2)C1Cc1cccc(-c2ccccc2)c1] | | 455.0 |
| 141 | cyclopentylmethyl cis-2-(biphenyl-3-ylmethyl)-3-((methylsulfonyl)amino) piperidine-1-carboxylate | 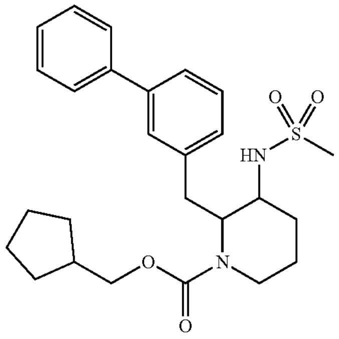 [SMILES: CS(=O)(=O)NC1CCCN(C(=O)OCC2CCCC2)C1Cc1cccc(-c2ccccc2)c1] | | 469.0 |
| 142 | oxetan-2-ylmethyl cis-2-(biphenyl-3-ylmethyl)-3-((methylsulfonyl)amino) piperidine-1-carboxylate | 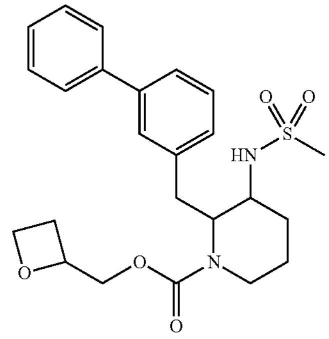 [SMILES: CS(=O)(=O)NC1CCCN(C(=O)OCC2CCO2)C1Cc1cccc(-c2ccccc2)c1] | | 458.9 |
| 143 | oxetan-3-ylmethyl cis-2-(biphenyl-3-ylmethyl)-3-((methylsulfonyl)amino) piperidine-1-carboxylate | 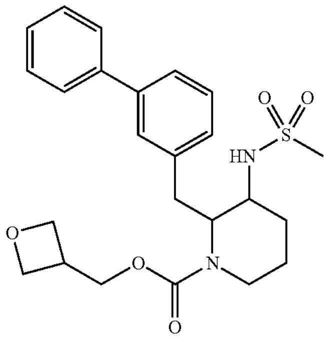 [SMILES: CS(=O)(=O)NC1CCCN(C(=O)OCC2COC2)C1Cc1cccc(-c2ccccc2)c1] | | 459.0 |

TABLE 1-continued

| EXAMPLE | IUPACNAME | Structure | ADDITIVE | MS |
|---|---|---|---|---|
| 144 | tetrahydrofuran-2-ylmethyl cis-2-(biphenyl-3-ylmethyl)-3-((methylsulfonyl)amino)piperidine-1-carboxylate | 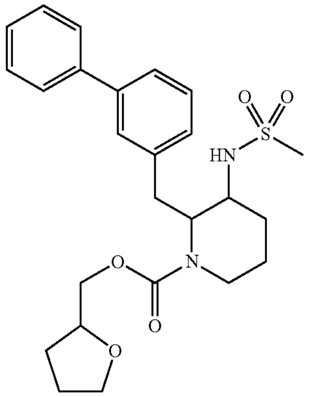 [SMILES: CS(=O)(=O)NC1CCCN(C(=O)OCC2CCCO2)C1Cc1cccc(-c2ccccc2)c1] | | 473.0 |
| 145 | phenyl cis-2-(biphenyl-3-ylmethyl)-3-((methylsulfonyl)amino)piperidine-1-carboxylate | 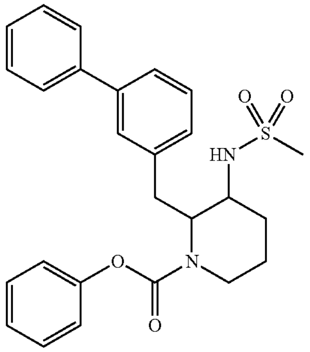 [SMILES: CS(=O)(=O)NC1CCCN(C(=O)Oc2ccccc2)C1Cc1cccc(-c2ccccc2)c1] | | 465.0 |
| 146 | benzyl cis-2-(biphenyl-3-ylmethyl)-3-((methylsulfonyl)amino)piperidine-1-carboxylate | 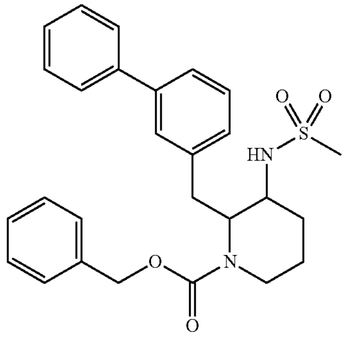 [SMILES: CS(=O)(=O)NC1CCCN(C(=O)OCc2ccccc2)C1Cc1cccc(-c2ccccc2)c1] | | 477.0 |
| 147 | ethyl cis-2-((4-fluorobiphenyl-3-yl)methyl)-3-((methylsulfonyl)amino)piperidine-1-carboxylate | 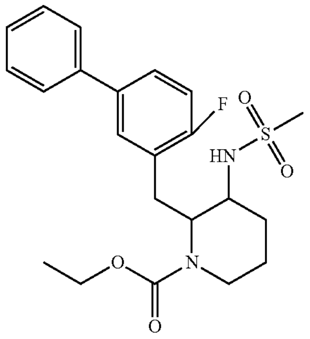 [SMILES: CCOC(=O)N1CCCC(NS(C)(=O)=O)C1Cc1cc(-c2ccccc2)ccc1F] | | 435.1 |

TABLE 1-continued

| EXAMPLE | IUPACNAME | Structure | ADDITIVE | MS |
|---|---|---|---|---|
| 148 | ethyl cis-2-(3-bromo-4-fluorobenzyl)-3-((methylsulfonyl)amino)piperidine-1-carboxylate | 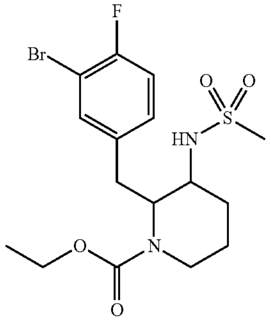 [SMILES: CCOC(=O)N1CCCC(NS(C)(=O)=O)C1Cc1ccc(F)c(Br)c1] | | 436.9 |
| 149 | methyl cis-2-((5-fluorobiphenyl-3-yl)methyl)-3-((methylsulfonyl)amino)piperidine-1-carboxylate | 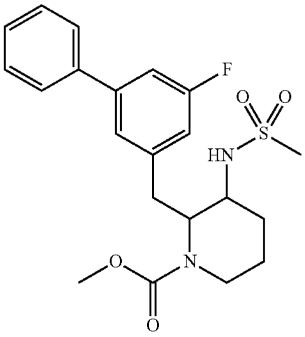 [SMILES: COC(=O)N1CCCC(NS(C)(=O)=O)C1Cc1cc(F)cc(-c2ccccc2)c1] | | 421.1 |
| 150 | N-(cis-2-((6-fluorobiphenyl-3-yl)methyl)piperidin-3-yl)methanesulfonamide hydrochloride | 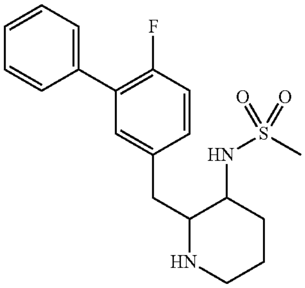 [SMILES: CS(=O)(=O)NC1CCCNC1Cc1ccc(F)c(-c2ccccc2)c1] | HCl | 363.0 |
| 151 | cis-N-ethyl-2-((3'-methylbiphenyl-3-yl)methyl)-3-((methylsulfonyl)amino)piperidine-1-carboxamide | 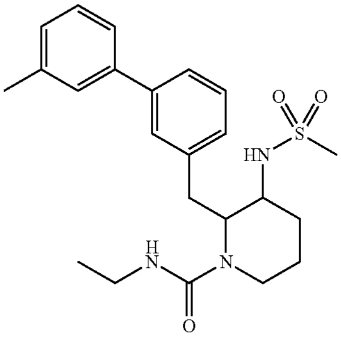 | | 430.1 |

TABLE 1-continued

| EXAMPLE | IUPACNAME | Structure | ADDITIVE | MS |
|---|---|---|---|---|
| 152 | methyl cis-3-(methylsulfonyl)amino)-2-((4-phenylpyridin-2-yl)methyl)piperidine-1-carboxylate | 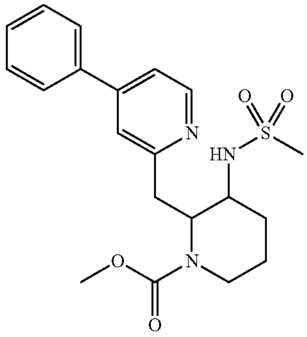 [SMILES: COC(=O)N1CCCC(NS(C)(=O)=O)C1Cc1cc(-c2ccccc2)ccn1] | | 404.1 |
| 153 | ethyl cis-3-((methylsulfonyl)amino)-2-((4-phenylpyridin-2-yl)methyl)piperidine-1-carboxylate | 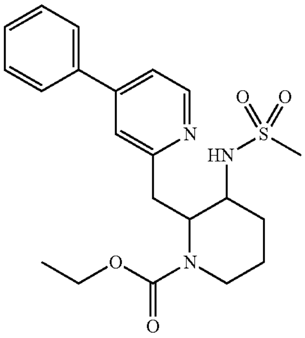 [SMILES: CCOC(=O)N1CCCC(NS(C)(=O)=O)C1Cc1cc(-c2ccccc2)ccn1] | | 418.1 |
| 154 | cis-N-ethyl-3-((methylsulfonyl)amino)-2-((4-phenylpyridin-2-yl)methyl)piperidine-1-carboxamide | 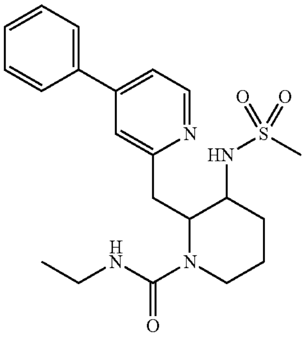 [SMILES: CCNC(=O)N1CCCC(NS(C)(=O)=O)C1Cc1cc(-c2ccccc2)ccn1] | | 417.1 |
| 155 | methyl cis-2-((4'-methylbiphenyl-3-yl)methyl)-3-((methylsulfonyl)amino)piperidine-1-carboxylate | 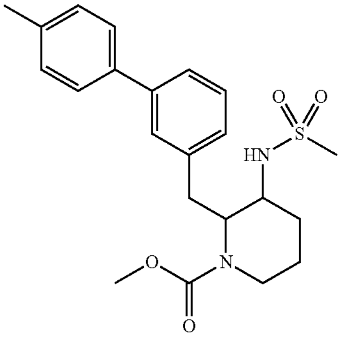 | | 417.1 |

TABLE 1-continued

| EXAMPLE | IUPACNAME | Structure | ADDITIVE | MS |
|---|---|---|---|---|
| 156 | methyl cis-3-((methylsulfonyl)amino)-2-((2'-(trifluoromethyl)biphenyl-3-yl)methyl) piperidine-1-carboxylate | 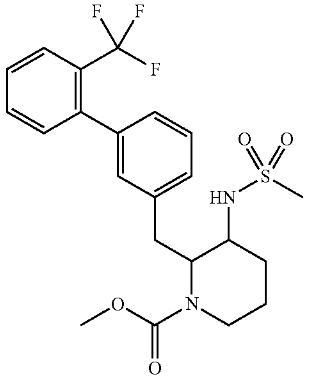 [SMILES: COC(=O)N1CCCC(NS(C)(=O)=O)C1Cc1cccc(-c2ccccc2C(F)(F)F)c1] | | 471.0 |
| 157 | methyl cis-3-((methylsulfonyl)amino)-2-((3'-(trifluoromethyl)biphenyl-3-yl) methyl)piperidine-1-carboxylate | 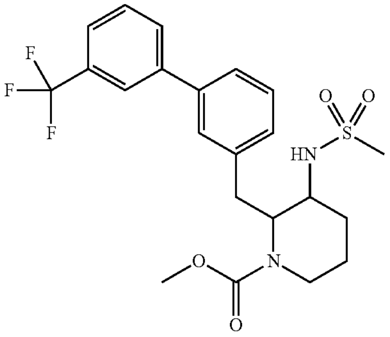 [SMILES: COC(=O)N1CCCC(NS(C)(=O)=O)C1Cc1cccc(-c2cccc(C(F)(F)F)c2)c1] | | 470.9 |
| 158 | methyl cis-3-((methylsulfonyl)amino)-2-(3-(pyridin-4-y)benzyl)piperidine-1-carboxylate | 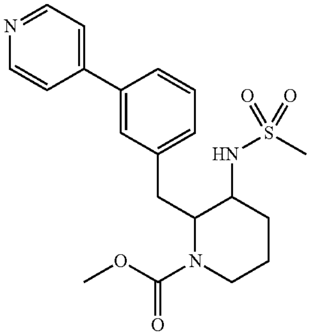 [SMILES: COC(=O)N1CCCC(NS(C)(=O)=O)C1Cc1cccc(-c2ccncc2)c1] | | 404.0 |
| 159 | methyl cis-3-((methylsulfonyl)amino)-2-(3-(3-thienyl)benzyl)piperidine-1-carboxylate | 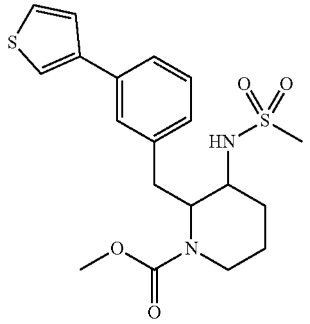 [SMILES: COC(=O)N1CCCC(NS(C)(=O)=O)C1Cc1cccc(-c2ccsc2)c1] | | 407.0 |

TABLE 1-continued

| EXAMPLE | IUPACNAME | Structure | ADDITIVE | MS |
|---|---|---|---|---|
| 160 | methyl cis-3-((methylsulfonyl)amino)-2-(3-(2-thienyl)benzyl)piperidine-1-carboxylate | 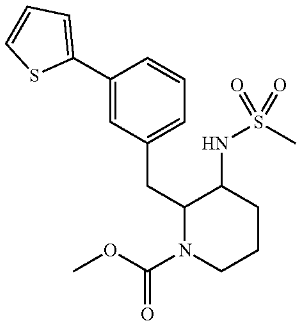 [SMILES: COC(=O)N1CCCC(NS(C)(=O)=O)C1Cc1cccc(-c2cccs2)c1] | | 409.1 |
| 161 | methyl cis-2-(3-(1-methyl-1H-pyrazol-3-yl)benzyl-3-(methylsulfonyl)amino) piperidine-1-carboxylate | 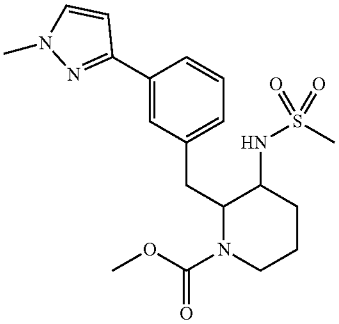 | | 407.0 |
| 162 | methyl cis-2-(3-(1-methyl-1H-pyrazol-4-yl)benzyl)-3-((methylsulfonyl)amino) piperidine-1-carboxylate | 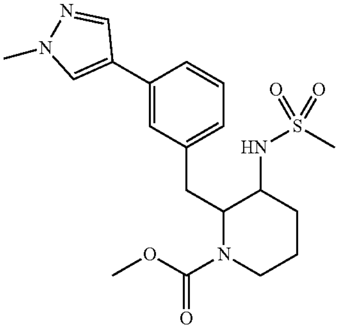 | | 407.1 |
| 163 | methyl cis-2-(3-(1-methyl-1H-pyrazol-5-yl)benzyl)-3-((methylsulfonyl)amino) piperidine-1-carboxylate | 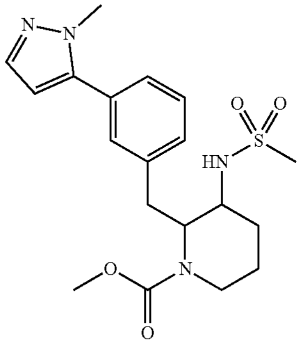 [SMILES: COC(=O)N1CCCC(NS(C)(=O)=O)C1Cc1cccc(-c2ccnn2C)c1] | | 407.1 |

TABLE 1-continued

| EXAM-PLE | IUPACNAME | Structure | ADDITIVE | MS |
|---|---|---|---|---|
| 164 | methyl cis-2-(3-methylbenzyl)-3-((methylsulfonyl)amino)piperidine-1-carboxylate | 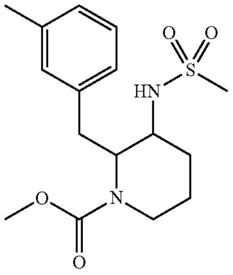 | | 340.9 |
| 165 | methyl cis-2-((3',4'-difluorobiphenyl-3-yl)methyl)-3-((methylsulfonyl)amino) piperidine-1-carboxylate | 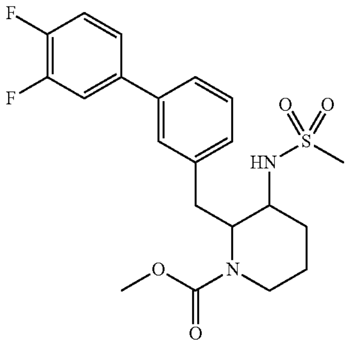 [SMILES: COC(=O)N1CCCC(NS(C)(=O)=O)C1Cc1cccc(-c2ccc(F)c(F)c2)c1] | | 437.1 |
| 166 | methyl cis-2-((2',4'-difluorobiphenyl-3-yl)methyl)-3-((methylsulfonyl)amino) piperidine-1-carboxylate | 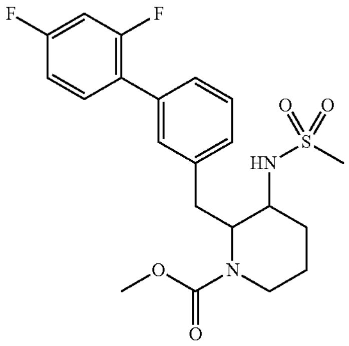 [SMILES: COC(=O)N1CCCC(NS(C)(=O)=O)C1Cc1cccc(-c2ccc(F)cc2F)c1] | | 439.0 |
| 167 | methyl cis-2-((2',3'-difluorobiphenyl-3-yl)methyl)-3-((methylsulfonyl)amino) piperidine-1-carboxylate | 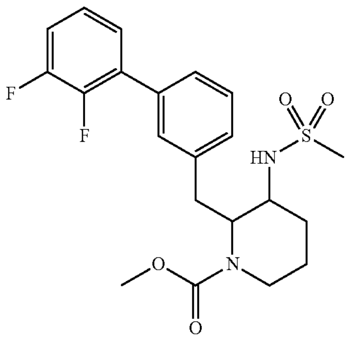 [SMILES: COC(=O)N1CCCC(NS(C)(=O)=O)C1Cc1cccc(-c2cccc(F)c2F)c1] | | 439.1 |

TABLE 1-continued

| EXAMPLE | IUPACNAME | Structure | ADDITIVE | MS |
|---|---|---|---|---|
| 168 | methyl cis-2-((2',6'-difluorobiphenyl-3-yl)methyl)-3-((methylsulfonyl)amino) piperidine-1-carboxylate | 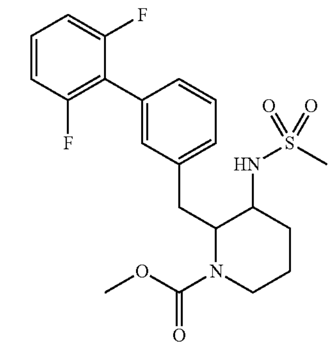 [SMILES: COC(=O)N1CCCC(NS(C)(=O)=O)C1Cc1cccc(-c2c(F)cccc2F)c1] | | 439.0 |
| 169 | methyl cis-2-((3',5'-difluorobiphenyl-3-yl) methyl)-3-((methylsulfonyl)amino) piperidine-1-carboxylate | 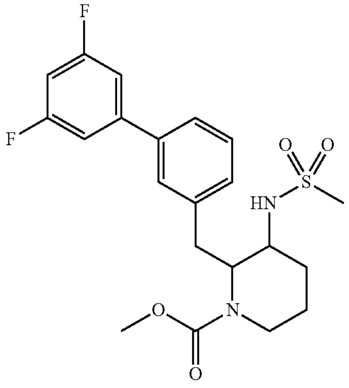 [SMILES: COC(=O)N1CCCC(NS(C)(=O)=O)C1Cc1cccc(-c2cc(F)cc(F)c2)c1] | | 439.1 |
| 170 | methyl cis-2-((2',5'-difluorobiphenyl-3-yl) methyl)-3-((methylsulfonyl)amino) piperidine-1-carboxylate | 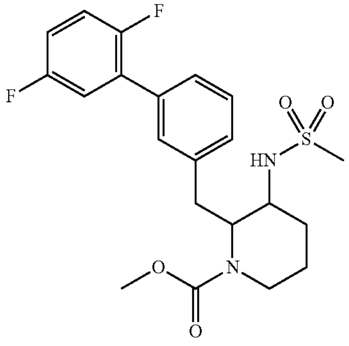 [SMILES: COC(=O)N1CCCC(NS(C)(=O)=O)C1Cc1cccc(-c2cc(F)ccc2F)c1] | | 439.1 |
| 171 | methyl cis-2-((3'-(difluoromethyl)biphenyl-3-yl)methyl)-3-((methylsulfonyl)amino) piperidine-1-carboxylate | 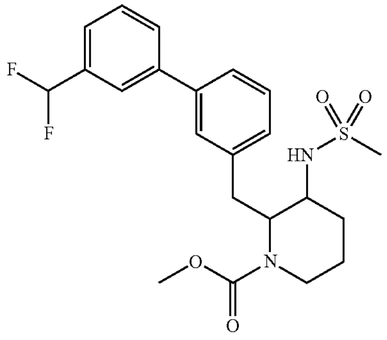 [SMILES: COC(=O)N1CCCC(NS(C)(=O)=O)C1Cc1cccc(-c2cccc(C(F)F)c2)c1] | | 453.0 |

TABLE 1-continued

| EXAMPLE | IUPACNAME | Structure | ADDITIVE | MS |
|---|---|---|---|---|
| 172 | isopropyl cis-3-((ethylsulfonyl)amino)-2-((6-phenylpyridin-2-yl)methyl) piperidine-1-carboxylate | 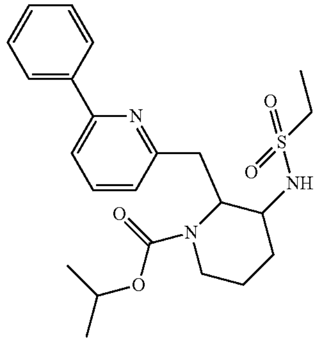 [SMILES: CCS(=O)(=O)NC1CCCN(C(=O)OC(C)C)C1Cc1cccc(-c2ccccc2)n1] | | 446.2 |
| 173 | isopropyl cis-2-((6-phenylpyridin-2-yl) methyl)-3-((propylsulfonyl)amino) piperidine-1-carboxylate | 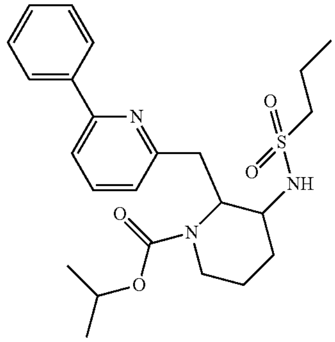 [SMILES: CCCS(=O)(=O)NC1CCCN(C(=O)OC(C)C)C1Cc1cccc(-c2ccccc2)n1] | | 460.0 |
| 174 | isopropyl cis-3-((butylsulfonyl)amino)-2-((6-phenylpyridin-2-yl)methyl) piperidine-1-carboxylate | 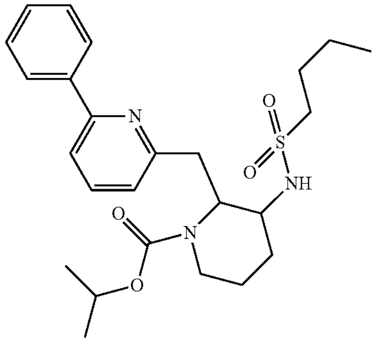 [SMILES: CCCCS(=O)(=O)NC1CCCN(C(=O)OC(C)C)C1Cc1cccc(-c2ccccc2)n1] | | 474.0 |
| 175 | isopropyl cis-3-((isobutylsulfonyl)amino)-2-((6-phenylpyridin-2-yl)methyl) piperidine-1-carboxylate | 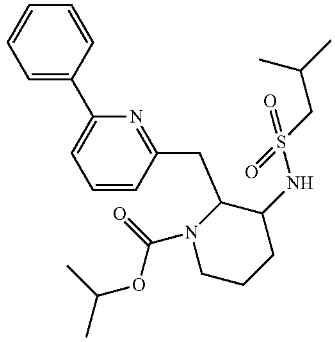 [SMILES: CC(C)CS(=O)(=O)NC1CCCN(C(=O)OC(C)C)C1Cc1cccc(-c2ccccc2)n1] | | 474.0 |

TABLE 1-continued

| EXAMPLE | IUPACNAME | Structure | ADDITIVE | MS |
|---|---|---|---|---|
| 176 | isopropyl cis-2-((6-phenylpyridin-2-yl) methyl)-3-((vinylsulfonyl)amino) piperidine-1-carboxylate | 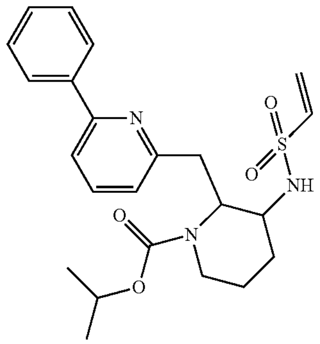 [SMILES: C=CS(=O)(=O)NC1CCCN(C(=O)OC(C)C)C1Cc1cccc(-c2ccccc2)n1] | | 444.2 |
| 177 | isopropyl cis-3-((allylsulfonyl)amino)-2-((6-phenylpyridin-2-yl)methyl) piperidine-1-carboxylate | 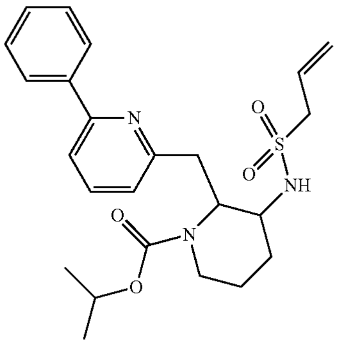 [SMILES: C=CCS(=O)(=O)NC1CCCN(C(=O)OC(C)C)C1Cc1cccc(-c2ccccc2)n1] | | 458.0 |
| 178 | isopropyl cis-3-((cyclopropylsulfonyl) amino)-2-((6-phenylpyridin-2-yl) methyl)piperidine-1-carboxylate | 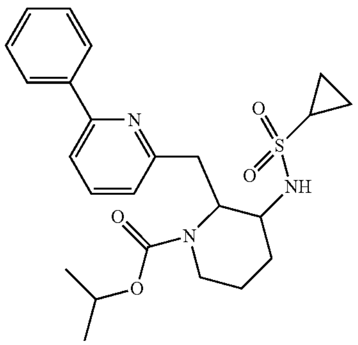 [SMILES: CC(C)OC(=O)N1CCCC(NS(=O)(=O)C2CC2)C1Cc1cccc(-c2ccccc2)n1] | | 458.1 |
| 179 | isopropyl cis-3-((oxetan-3-ylsulfonyl) amino)-2-((6-phenylpyridin-2-yl)methyl) piperidine-1-carboxylate | 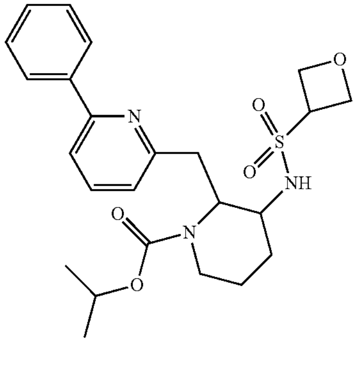 [SMILES: CC(C)OC(=O)N1CCCC(NS(=O)(=O)C2COC2)C1Cc1cccc(-c2ccccc2)n1] | | 474.1 |

TABLE 1-continued

| EXAMPLE | IUPACNAME | Structure | ADDITIVE | MS |
| --- | --- | --- | --- | --- |
| 180 | isopropyl cis-2-((6-phenylpyridin-2-yl) methyl)-3-(((2,2,2-trifluoroethyl)sulfonyl) amino)piperidine-1-carboxylate | 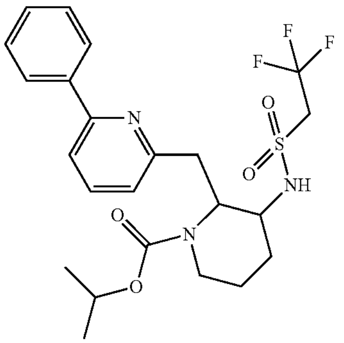 [SMILES: CC(C)OC(=O)N1CCCC(NS(=O)(=O)CC(F)(F)F)C1Cc1cccc(-c2ccccc2)n1] | | 500.1 |
| 181 | isopropyl cis-3-(((chloromethyl)sulfonyl) amino)-2-((6-phenylpyridin-2-yl)methyl) piperidine-1-carboxylate | 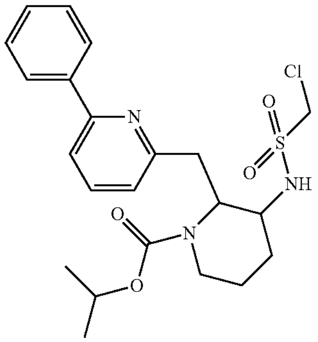 [SMILES: CC(C)OC(=O)N1CCCC(NS(=O)(=O)CCl)C1Cc1cccc(-c2ccccc2)n1] | | 466.1 |
| 182 | isopropyl cis-3-(((2-hydroxyethyl)sulfonyl) amino)-2-((6-phenylpyridin-2-yl)methyl) piperidine-1-carboxylate trifluoroacetic acid salt | 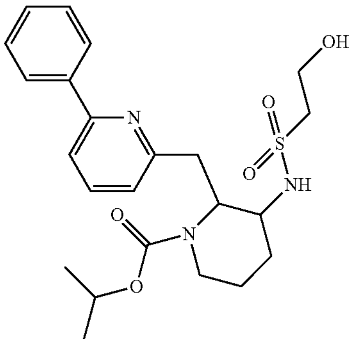 [SMILES: CC(C)OC(=O)N1CCCC(NS(=O)(=O)CCO)C1Cc1cccc(-c2ccccc2)n1] | CF3COOH | 461.9 |
| 183 | isopropyl cis-3-(((2-methoxyethyl)sulfonyl) amino)-2-((6-phenylpyridin-2-yl)methyl) piperidine-1-carboxylate | 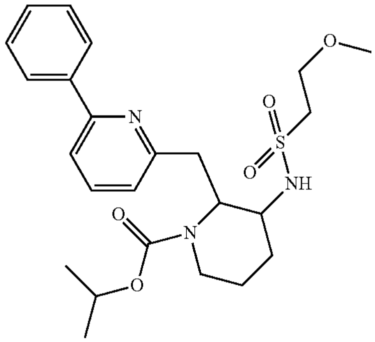 | | 476.1 |

TABLE 1-continued

| EXAMPLE | IUPACNAME | Structure | ADDITIVE | MS |
|---|---|---|---|---|
| 184 | isopropyl cis-3-(((cyanomethyl)sulfonyl) amino)-2-((6-phenylpyridin-2-yl)methyl) piperidine-1-carboxylate | 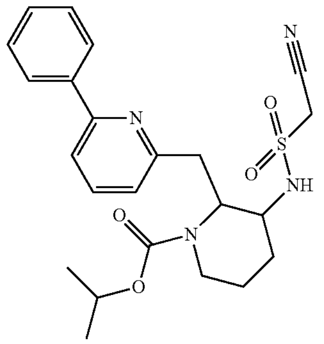 [SMILES: CC(C)OC(=O)N1CCCC(NS(=O)(=O)CC#N)C1Cc1cccc(-c2ccccc2)n1] | | 457.0 |
| 185 | isopropyl cis-3-((dimethylsulfamoyl)amino)-2-((6-phenylpyridin-2-yl)methyl) piperidine-1-carboxylate | 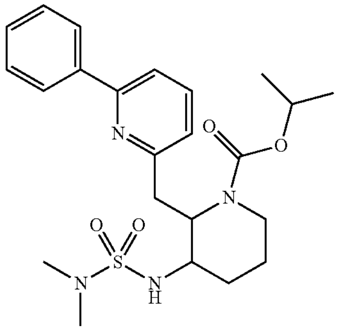 [SMILES: CC(C)OC(=O)N1CCCC(NS(=O)(=O)N(C)C)C1Cc1cccc(-c2ccccc2)n1] | | 461.2 |
| 186 | isopropyl cis-3-((ethylsulfonyl)amino)-2-((6-(prop-1-en-2-yl)pyridin-2-yl)methyl) piperidine-1-carboxylate | 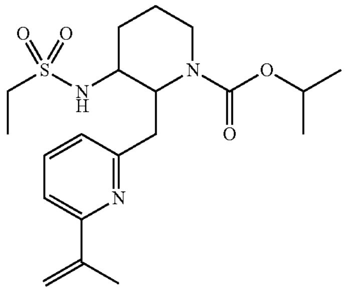 [SMILES: C=C(C)c1cccc(CC2C(NS(=O)(=O)CC)CCCN2C(=O)OC(C)C)n1] | | 410.0 |
| 187 | isopropyl cis-2-((6-(prop-1-en-2-yl)pyridin-2-yl)methyl)-3-((propylsulfonyl)amino) piperidine-1-carboxylate | 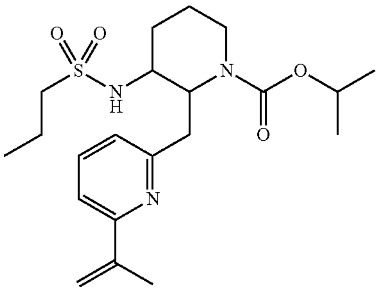 [SMILES: C=C(C)c1cccc(CC2C(NS(=O)(=O)CCC)CCCN2C(=O)OC(C)C)n1] | | 424.1 |
| 188 | isopropyl cis-3-((butylsulfonyl)amino)-2-((6-(prop-1-en-2-yl)pyridin-2-yl)methyl) piperidine-1-carboxylate | 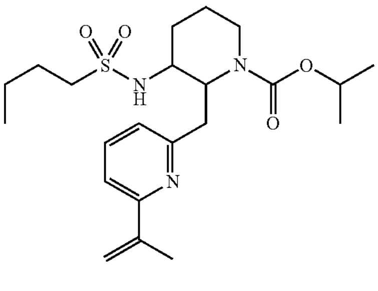 [SMILES: C=C(C)c1cccc(CC2C(NS(=O)(=O)CCCC)CCCN2C(=O)OC(C)C)n1] | | 438.0 |

TABLE 1-continued

| EXAMPLE | IUPACNAME | Structure | ADDITIVE | MS |
|---|---|---|---|---|
| 189 | isopropyl cis-2-((6-(prop-1-en-2-yl)pyridin-2-yl)methyl)-3-((vinylsulfonyl)amino) piperidine-1-carboxylate | 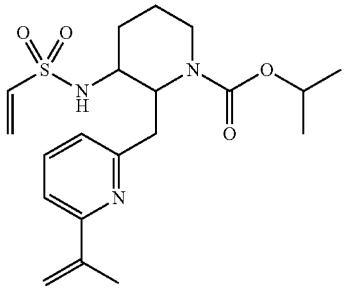 [SMILES: C=CS(=O)(=O)NC1CCCN(C(=O)OC(C)C)C1Cc1cccc(C(=C)C)n1] | | 408.0 |
| 190 | isopropyl cis-3-((allylsulfonyl)amino)-2-((6-(prop-1-en-2-yl)pyridin-2-yl)methyl) piperidine-1-carboxylate | 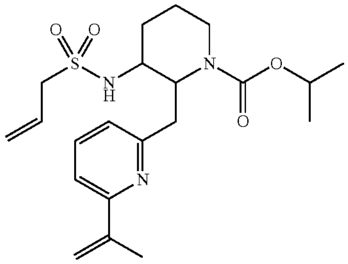 [SMILES: C=CCS(=O)(=O)NC1CCCN(C(=O)OC(C)C)C1Cc1cccc(C(=C)C)n1] | | 422.0 |
| 191 | isopropyl cis-3-((cyclopropylsulfonyl) amino)-2-((6-(prop-1-en-2-yl)pyridin-2-yl)methyl)piperidine-1-carboxylate | 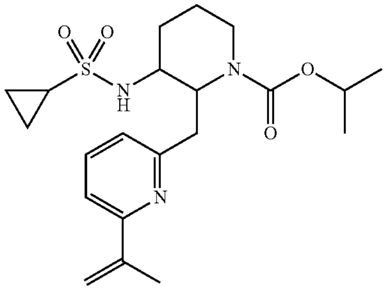 [SMILES: C=C(C)c1cccc(CC2C(NS(=O)(=O)C3CC3)CCCN2C(=O)OC(C)C)n1] | | 422.0 |
| 192 | isopropyl cis-3-((oxetan-3-ylsulfonyl) amino)-2-((6-(prop-1-en-2-yl)pyridin-2-yl) methyl)piperidine-1-carboxylate | 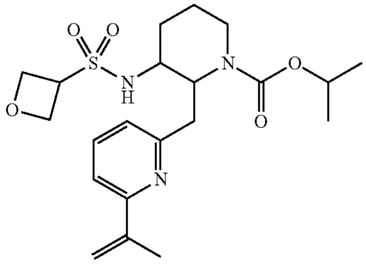 [SMILES: C=C(C)c1cccc(CC2C(NS(=O)(=O)C3COC3)CCCN2C(=O)OC(C)C)n1] | | 438.0 |
| 193 | isopropyl cis-2-((6-(prop-1-en-2-yl)pyridin-2-yl)methyl)-3-(((2,2,2-trifluoroethyl)sulfonyl)amino) piperidine-1-carboxylate | 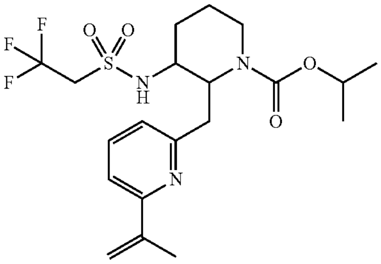 [SMILES: C=C(C)c1cccc(CC2C(NS(=O)(=O)CC(F)(F)F)CCCN2C(=O)OC(C)C)n1] | | 464.0 |

TABLE 1-continued

| EXAMPLE | IUPACNAME | Structure | ADDITIVE | MS |
|---|---|---|---|---|
| 194 | isopropyl cis-3-(((chloromethyl)sulfonyl)amino)-2-((6-(prop-1-en-2-yl)pyridin-2-yl)methyl)piperidine-1-carboxylate | 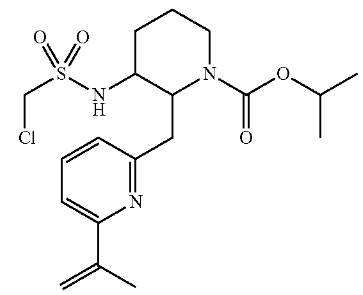 [SMILES: C=C(C)c1cccc(CC2C(NS(=O)(=O)CCl)CCCN2C(=O)OC(C)C)n1] | | 430.0 |
| 195 | isopropyl cis-3-(((2-methoxyethyl)sulfonyl)amino)-2-((6-(prop-1-en-2-yl)pyridin-2-yl)methyl)piperidine-1-carboxylate | 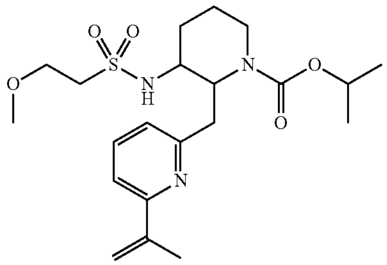 [SMILES: C=C(C)c1cccc(CC2C(NS(=O)(=O)CCOC)CCCN2C(=O)OC(C)C)n1] | | 440.0 |
| 196 | isopropyl cis-3-(((cyanomethyl)sulfonyl)amino)-2-((6-(prop-1-en-2-yl)pyridin-2-yl)methyl)piperidine-1-carboxylate | 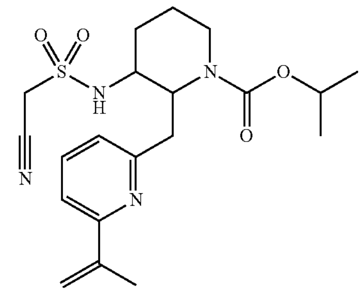 [SMILES: C=C(C)c1cccc(CC2C(NS(=O)(=O)CC#N)CCCN2C(=O)OC(C)C)n1] | | 421.0 |
| 197 | isopropyl cis-3-((dimethylsulfamoyl)amino)-2-((6-(prop-1-en-2-yl)pyridin-2-yl)methyl)piperidine-1-carboxylate | 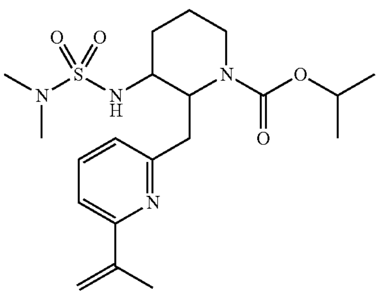 [SMILES: C=C(C)c1cccc(CC2C(NS(=O)(=O)N(C)C)CCCN2C(=O)OC(C)C)n1] | | 425.1 |
| 198 | isopropyl 3-((methylsulfonyl)amino)-2-((1-phenylpyrrolidin-3-yl)methyl)piperidine-1-carboxylate | 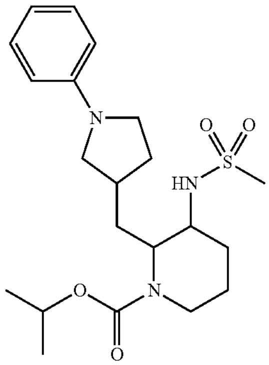 [SMILES: CC(C)OC(=O)N1CCCC(NS(C)(=O)=O)C1CC1CCN(c2ccccc2)C1] | | 424.1 |

TABLE 1-continued

| EXAMPLE | IUPACNAME | Structure | ADDITIVE | MS |
|---|---|---|---|---|
| 199 | methyl cis-2-(biphenyl-3-ylmethyl)-3-((cyclopropylsulfonyl)amino) piperidine-1-carboxylate | 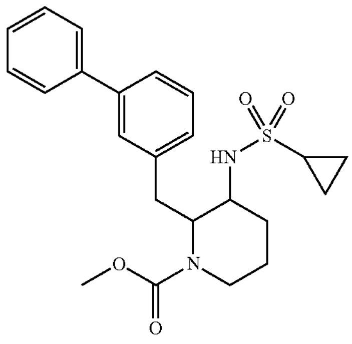 [SMILES: COC(=O)N1CCCC(NS(=O)(=O)C2CC2)C1Cc1cccc(-c2ccccc2)c1] | | 429.1 |
| 200 | methyl cis-2-(biphenyl-3-ylmethyl)-3-((dimethylsulfamoyl)amino) piperidine-1-carboxylate | 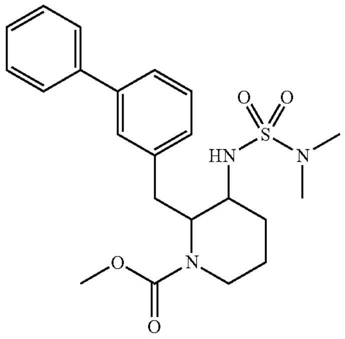 [SMILES: COC(=O)N1CCCC(NS(=O)(=O)N(C)C)C1Cc1cccc(-c2ccccc2)c1] | | 432.1 |
| 201 | ethyl cis-3-((methylsulfonyl)amino)-2-((2-phenyl-1,3-oxazol-4-yl)methyl) piperidine-1-carboxylate | 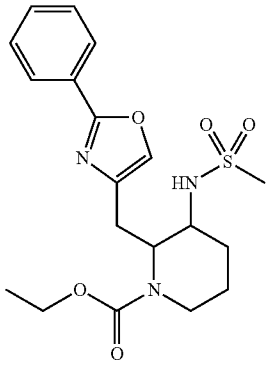 [SMILES: CCOC(=O)N1CCCC(NS(C)(=O)=O)C1Cc1coc(-c2ccccc2)n1] | | 408.1 |
| 202 | isopropyl cis-3-(methylsulfonyl)amino)-2-((2-phenyl-1,3-oxazol-4-y)methyl) piperidine-1-carboxylate | 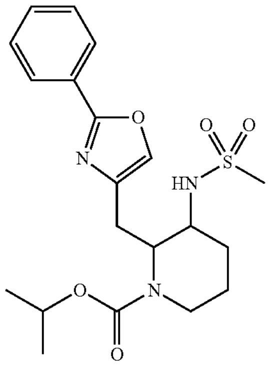 [SMILES: CC(C)OC(=O)N1CCCC(NS(C)(=O)=O)C1Cc1coc(-c2ccccc2)n1] | | 422.1 |

TABLE 1-continued

| EXAMPLE | IUPACNAME | Structure | ADDITIVE | MS |
|---|---|---|---|---|
| 203 | isopropyl cis-2-(3-(1-methyl-1H-indazol-5-yl)benzyl)-3-((methylsulfonyl)amino) piperidine-1-carboxylate | 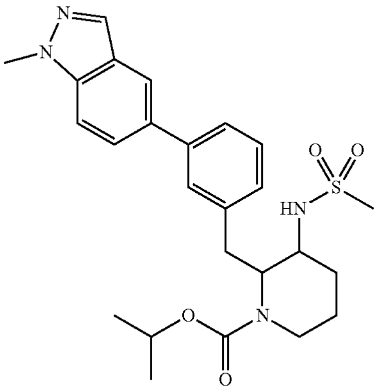 | | 485.2 |
| 204 | cis-2-(biphenyl-3-ylmethyl)-N,N-dimethyl-3-((methylsulfonyl)amino) piperidine-1-carboxamide | 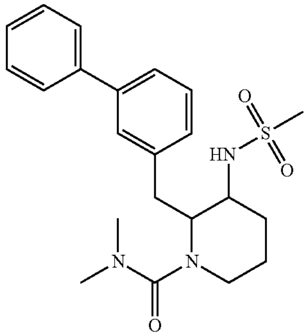 [SMILES: CN(C)C(=O)N1CCCC(NS(C)(=O)=O)C1Cc1cccc(-c2ccccc2)c1] | | 416.1 |
| 205 | N-(cis-2-(biphenyl-3-ylmethyl)-1-propionylpyrrolidin-3-yl) methanesulfonamide | 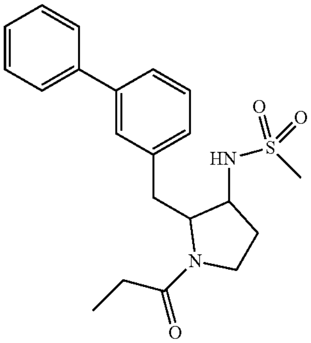 [SMILES: CCC(=O)N1CCC(NS(C)(=O)=O)C1Cc1cccc(-c2ccccc2)c1] | | 387.1 |
| 206 | N-(cis-2-(biphenyl-3-ylmethyl)-1-(cyclopropylcarbonyl)pyrrolidin-3-yl)methanesulfonamide | 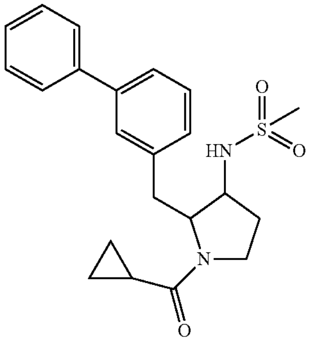 [SMILES: CS(=O)(=O)NC1CCN(C(=O)C2CC2)C1Cc1cccc(-c2ccccc2)c1] | | 399.1 |

TABLE 1-continued

| EXAM-PLE | IUPACNAME | Structure | ADDITIVE | MS |
|---|---|---|---|---|
| 207 | N-(cis-1-acetyl-2-(biphenyl-3-ylmethyl) pyrrolidin-3-yl)methanesulfonamide | 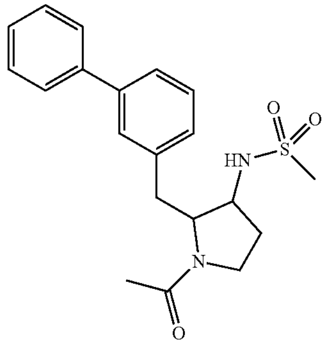 [SMILES: CC(=O)N1CCC(NS(C)(=O)=O)C1Cc1cccc(-c2ccccc2)c1] | | 373.1 |
| 208 | cis-2-(biphenyl-3-ylmethyl)-N-ethyl-N-methyl-3-((methylsulfonyl)amino) piperidine-1-carboxamide | 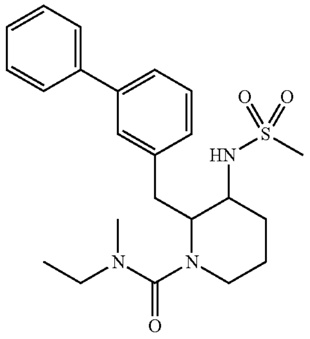 [SMILES: CCN(C)C(=O)N1CCCC(NS(C)(=O)=O)C1Cc1cccc(-c2ccccc2)c1] | | 430.1 |
| 209 | N-(cis-2-(biphenyl-3-ylmethyl)-1-isobutyrylpyrrolidin-3-yl) methanesulfonamide | 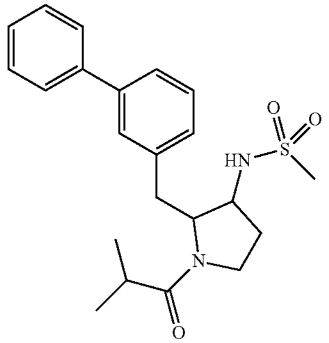 [SMILES: CC(C)C(=O)N1CCC(NS(C)(=O)=O)C1Cc1cccc(-c2ccccc2)c1] | | 401.1 |
| 210 | isopropyl cis-3-((methylsulfonyl)amino)-2-((2-phenyl-1,3-thiazol-4-yl)methyl) piperidine-1-carboxylate (optical isomer) | 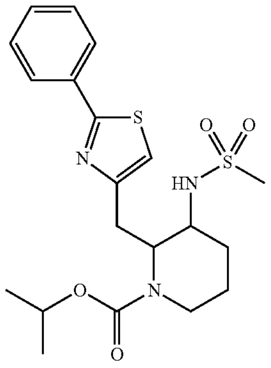 [SMILES: CC(C)OC(=O)N1CCCC(NS(C)(=O)=O)C1Cc1csc(-c2ccccc2)n1] | | 438.1 |

TABLE 1-continued

| EXAMPLE | IUPACNAME | Structure | ADDITIVE | MS |
|---|---|---|---|---|
| 211 | ethyl cis-3-((methylsulfonyl)amino)-2-((4-phenyl-1,3-thiazol-2-yl)methyl) piperidine-1-carboxylate | 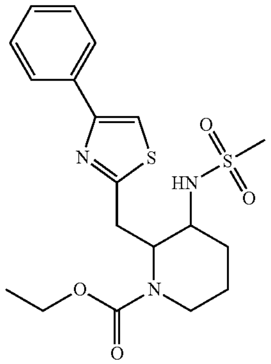 [SMILES: CCOC(=O)N1CCCC(NS(C)(=O)=O)C1Cc1nc(-c2ccccc2)cs1] | | 424.0 |
| 212 | isopropyl cis-3-((methylsulfonyl)amino)-2-((4-phenyl-1,3-thiazol-2-yl)methyl) piperidine-1-carboxylate | 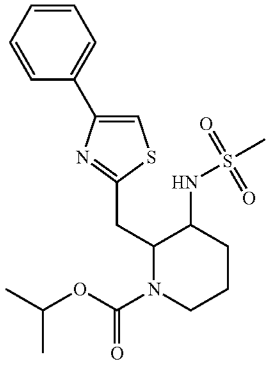 [SMILES: CC(C)OC(=O)N1CCCC(NS(C)(=O)=O)C1Cc1nc(-c2ccccc2)cs1] | | 438.1 |
| 213 | isopropyl cis-3-((methylsulfonyl)amino)-2-(pyridin-3-ylmethyl)piperidine-1-carboxylate | 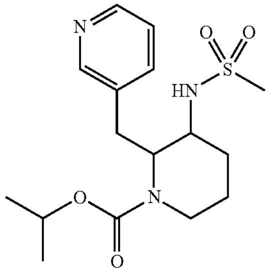 [SMILES: CC(C)OC(=O)N1CCCC(NS(C)(=O)=O)C1Cc1cccnc1] | | 356.0 |
| 214 | isopropyl cis-3-((methylsulfonyl)amino)-2-((1-phenylpiperidin-3-yl)methyl)piperidine-1-carboxylate | 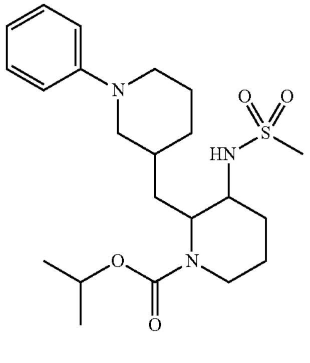 [SMILES: CC(C)OC(=O)N1CCCC(NS(C)(=O)=O)C1CC1CCCN(c2ccccc2)C1] | | 438.1 |

TABLE 1-continued

| EXAMPLE | IUPACNAME | Structure | ADDITIVE | MS |
|---|---|---|---|---|
| 215 | isopropyl cis-3-((methylsulfonyl)amino)-2-(3-(pyrimidin-2-yl)benzyl) piperidine-1-carboxylate | 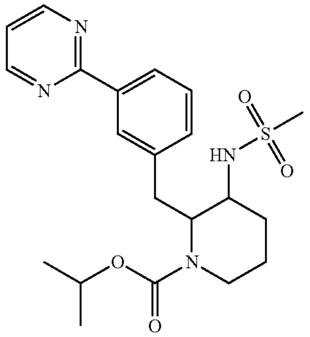 [SMILES: CC(C)OC(=O)N1CCCC(NS(C)(=O)=O)C1Cc1cccc(-c2ncccn2)c1] | | 433.2 |
| 216 | isopropyl cis-3-((methylsulfonyl)amino)-2-((1-phenyl-1H-pyrazol-3-yl)methyl) piperidine-1-carboxylate | 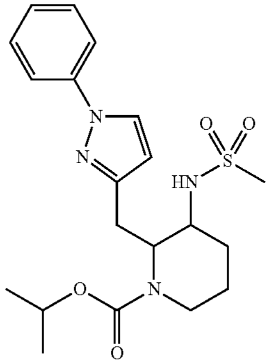 [SMILES: CC(C)OC(=O)N1CCCC(NS(C)(=O)=O)C1Cc1ccn(-c2ccccc2)n1] | | 421.2 |
| 217 | methyl cis-3-((methylsulfonyl)amino)-2-((1-phenylpiperidin-3-yl)methyl) piperidine-1-carboxylate | 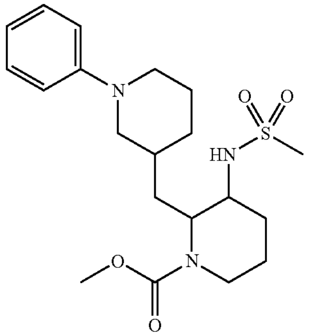 [SMILES: COC(=O)N1CCCC(NS(C)(=O)=O)C1CC1CCCN(c2ccccc2)C1] | | 410.3 |
| 218 | isopropyl cis-3-((methylsulfonyl)amino)-2-((1-(pyrimidin-2-yl)piperidin-3-yl)methyl) piperidine-1-carboxylate | 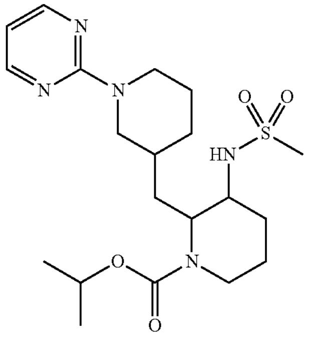 [SMILES: CC(C)OC(=O)N1CCCC(NS(C)(=O)=O)C1CC1CCCN(c2ncccn2)C1] | | 440.2 |

TABLE 1-continued

| EXAMPLE | IUPACNAME | Structure | ADDITIVE | MS |
|---|---|---|---|---|
| 219 | isopropyl cis-3-((methylsulfonyl)amino)-2-((2-phenyl-1,3-thiazol-4-yl)methyl) pyrrolidine-1-carboxylate | 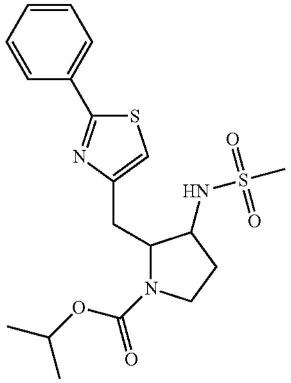 [SMILES: CC(C)OC(=O)N1CCC(NS(C)(=O)=O)C1Cc1csc(-c2ccccc2)n1] | | 424.0 |
| 220 | N-(cis-2-((2-(2,3-difluorophenyl)-1,3-thiazol-4-yl)methyl)-1-isobutyrylpyrrolidin-3-yl)methanesulfonamide | 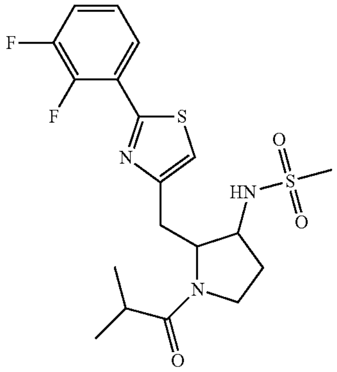 [SMILES: CC(C)C(=O)N1CCC(NS(C)(=O)=O)C1Cc1csc(-c2cccc(F)c2F)n1] | | 444.1 |
| 221 | N-(cis-2-(biphenyl-3-ylmethyl)-1-(cyclobutylcarbonyl)pyrrolidin-3-yl)methanesulfonamide | 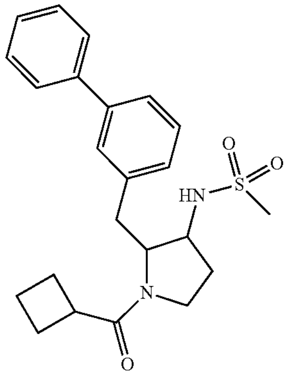 [SMILES: CS(=O)(=O)NC1CCN(C(=O)C2CCC2)C1Cc1cccc(-c2ccccc2)c1] | | 413.2 |
| 222 | N-(cis-2-(biphenyl-3-ylmethyl)-1-(cyclopropylacetyl)pyrrolidin-3-yl)methanesulfonamide | 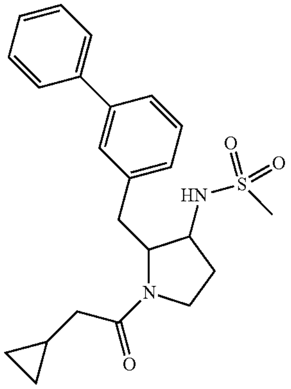 [SMILES: CS(=O)(=O)NC1CCN(C(=O)CC2CC2)C1Cc1cccc(-c2ccccc2)c1] | | 413.2 |

TABLE 1-continued

| EXAMPLE | IUPACNAME | Structure | ADDITIVE | MS |
|---|---|---|---|---|
| 223 | N-(cis-2-(biphenyl-3-ylmethyl)-1-butyrylpyrrolidin-3-yl) methanesulfonamide | 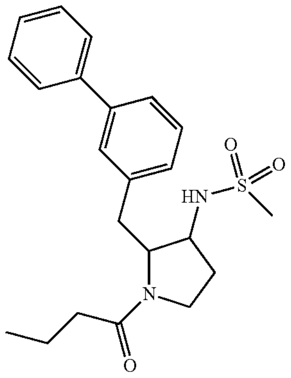 [SMILES: CCCC(=O)N1CCC(NS(C)(=O)=O)C1Cc1cccc(-c2ccccc2)c1] | | 401.1 |
| 224 | N-(cis-2-(biphenyl-3-ylmethyl)-1-(3-methylbutanoyl)pyrrolidin-3-yl) methanesulfonamide | 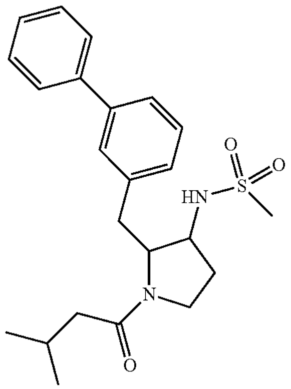 [SMILES: CC(C)CC(=O)N1CCC(NS(C)(=O)=O)C1Cc1cccc(-c2ccccc2)c1] | | 415.1 |
| 225 | N-(cis-2-(biphenyl-3-ylmethyl)-1-(cyclopentylcarbonyl)pyrrolidin-3-yl)methanesulfonamide | 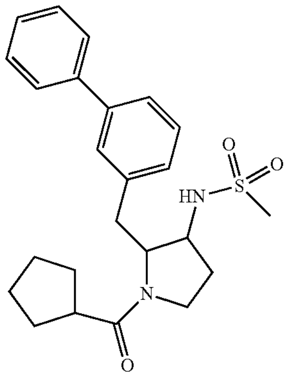 [SMILES: CS(=O)(=O)NC1CCN(C(=O)C2CCCC2)C1Cc1cccc(-c2ccccc2)c1] | | 427.1 |
| 226 | N-(cis-2-(biphenyl-3-ylmethyl)-1-(2-methylbutanoyl)pyrrolidin-3-yl) methanesulfonamide | 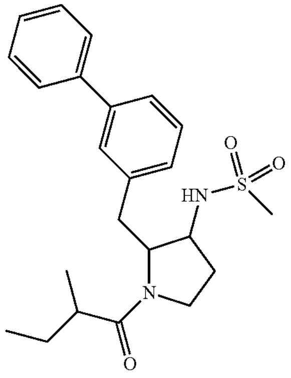 [SMILES: CCC(C)C(=O)N1CCC(NS(C)(=O)=O)C1Cc1cccc(-c2ccccc2)c1] | | 415.1 |

TABLE 1-continued

| EXAMPLE | IUPACNAME | Structure | ADDITIVE | MS |
| --- | --- | --- | --- | --- |
| 227 | N-(cis-2-(biphenyl-3-ylmethyl)-1-(2,2-dimethylpropanoyl)pyrrolidin-3-yl)methanesulfonamide | 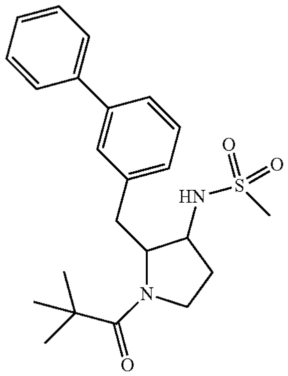 [SMILES: CC(C)(C)C(=O)N1CCC(NS(C)(=O)=O)C1Cc1cccc(-c2ccccc2)c1] | | 415.2 |
| 228 | N-(cis-2-(biphenyl-3-ylmethyl)-1-((2S)-2-methylbutanoyl)pyrrolidin-3-yl) methanesulfonamide | 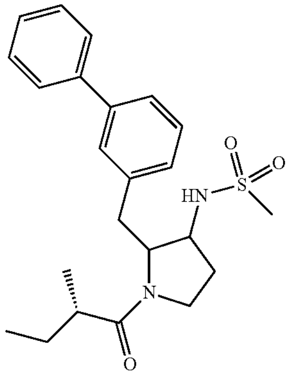 [SMILES: CC[C@H](C)C(=O)N1CCC(NS(C)(=O)=O)C1Cc1cccc(-c2ccccc2)c1] | | 415.1 |
| 229 | N-(cis-2-(biphenyl-3-ylmethyl)-1-isobutyrylpyrrolidin-3-yl) cyclopropanesulfonamide | 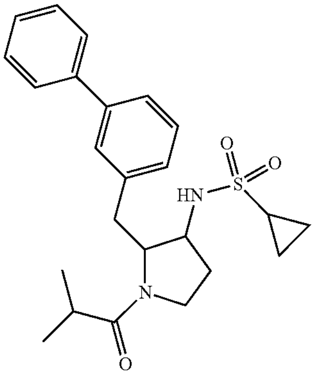 [SMILES: CC(C)C(=O)N1CCC(NS(=O)(=O)C2CC2)C1Cc1cccc(-c2ccccc2)c1] | | 427.3 |
| 230 | N-(cis-2-(biphenyl-3-ylmethyl)-1-(cyclopropylcarbonyl)pyrrolidin-3-yl)-1-methoxymethanesulfonamide | 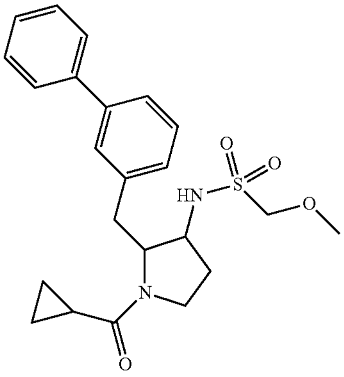 [SMILES: COCS(=O)(=O)NC1CCN(C(=O)C2CC2)C1Cc1cccc(-c2ccccc2)c1] | | 429.1 |

TABLE 1-continued

| EXAMPLE | IUPACNAME | Structure | ADDITIVE | MS |
|---|---|---|---|---|
| 231 | N-(cis-2-(bipheny-3-ylmethyl)-1-isobutyrylpyrrolidin-3-yl)-1-chloromethanesulfonamide | 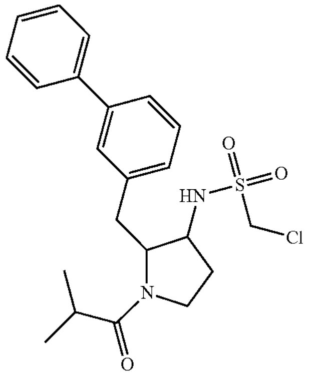 [SMILES: CC(C)C(=O)N1CCC(NS(=O)(=O)CCl)C1Cc1cccc(-c2ccccc2)c1] | | 435.1 |
| 232 | N-(cis-2-(biphenyl-3-ylmethyl)-1-isobutyrylpyrrolidin-3-yl)-1-fluoromethanesulfonamide | 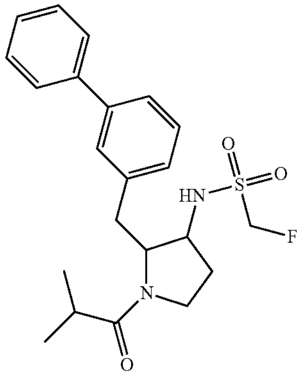 [SMILES: CC(C)C(=O)N1CCC(NS(=O)(=O)CF)C1Cc1cccc(-c2ccccc2)c1] | | 419.1 |
| 233 | N-(cis-2-(biphenyl-3-ylmethyl)-1-isobutyrylpyrrolidin-3-yl)-1,1-difluoromethanesulfonamide | 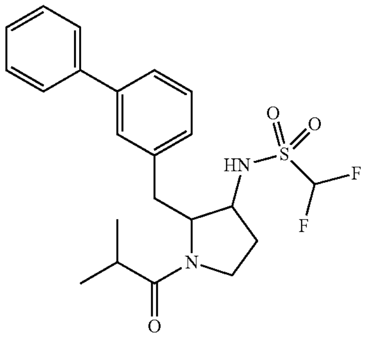 [SMILES: CC(C)C(=O)N1CCC(NS(=O)(=O)C(F)F)C1Cc1cccc(-c2ccccc2)c1] | | 437.1 |
| 234 | N-(cis-2-((3',5'-difluorobiphenyl-3-yl)methyl)-1-isobutyrylpyrrolidin-3-yl)methanesulfonamide | 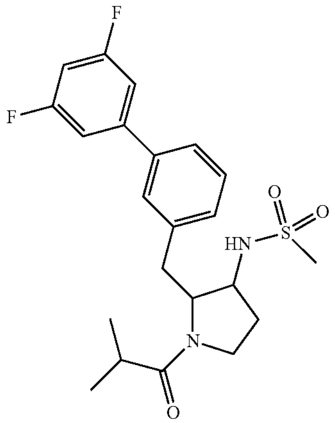 [SMILES: CC(C)C(=O)N1CCC(NS(C)(=O)=O)C1Cc1cccc(-c2cc(F)cc(F)c2)c1] | | 437.1 |

TABLE 1-continued

| EXAMPLE | IUPACNAME | Structure | ADDITIVE | MS |
|---|---|---|---|---|
| 235 | N-(cis-2-((2',5'-difluorobiphenyl-3-yl)methyl)-1-isobutyrylpyrrolidn-3-yl)methanesulfonamide | 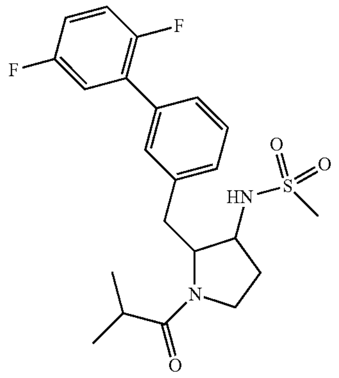 [SMILES: CC(C)C(=O)N1CCC(NS(C)(=O)=O)C1Cc1cccc(-c2cc(F)ccc2F)c1] | | 437.1 |
| 236 | N-(cis-1-isobutyryl-2-((2'-(trifluoromethyl)biphenyl-3-yl)methyl)pyrrolidin-3-yl)methanesulfonamide | 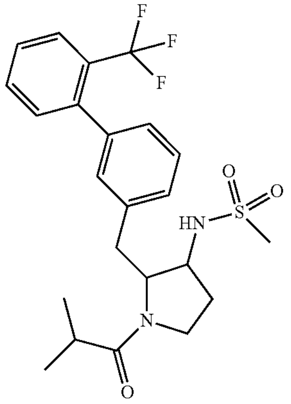 [SMILES: CC(C)C(=O)N1CCC(NS(C)(=O)=O)C1Cc1cccc(-c2ccccc2C(F)(F)F)c1] | | 469.0 |
| 237 | N-(cis-2-((2'-chlorobiphenyl-3-yl)methyl)-1-isobutyrylpyrrolidin-3-yl)methanesulfonamide | 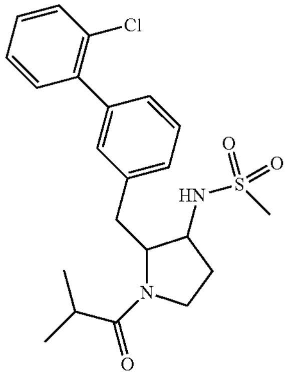 [SMILES: CC(C)C(=O)N1CCC(NS(C)(=O)=O)C1Cc1cccc(-c2ccccc2Cl)c1] | | 435.1 |
| 238 | N-(cis-2-((2',3'-difluorobiphenyl-3-yl)methyl)-1-isobutyrylpyrrolidin-3-yl)methanesulfonamide | 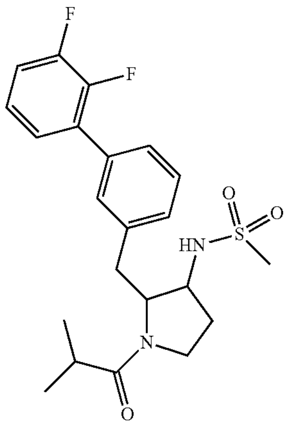 [SMILES: CC(C)C(=O)N1CCC(NS(C)(=O)=O)C1Cc1cccc(-c2cccc(F)c2F)c1] | | 437.1 |

TABLE 1-continued

| EXAMPLE | IUPACNAME | Structure | ADDITIVE | MS |
|---|---|---|---|---|
| 239 | N-(cis-2-((2',6'-difluorobiphenyl-3-yl) methyl)-1-isobutyrylpyrrolidin-3-yl) methanesulfonamide | 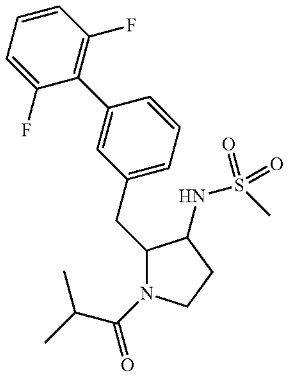 [SMILES: CC(C)C(=O)N1CCC(NS(C)(=O)=O)C1Cc1cccc(-c2c(F)cccc2F)c1] | | 437.1 |
| 240 | N-(cis-2-((2'-fluorobiphenyl-3-yl) methyl)-1-isobutyrylpyrrolidin-3-yl) methanesulfonamide | 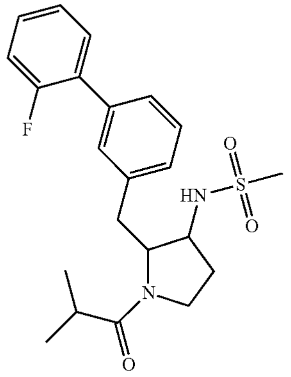 [SMILES: CC(C)C(=O)N1CCC(NS(C)(=O)=O)C1Cc1cccc(-c2ccccc2F)c1] | | 419.1 |
| 241 | N-(cis-2-((3'-fluorobiphenyl-3-yl)methyl)-1-isobutyrylpyrrolidin-3-yl) methanesulfonamide | 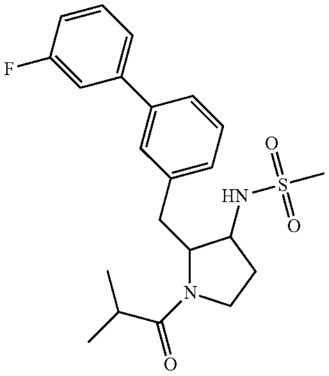 [SMILES: CC(C)C(=O)N1CCC(NS(C)(=O)=O)C1Cc1cccc(-c2cccc(F)c2)c1] | | 419.1 |
| 242 | N-(cis-1-isobutyryl-2-((2',3',5'-trifluorobiphenyl-3-yl)methylpyrrolidin-3-yl)methanesulfonamide | 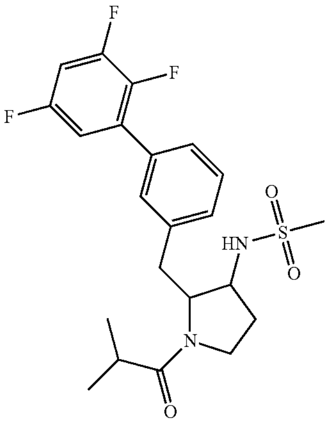 [SMILES: CC(C)C(=O)N1CCC(NS(C)(=O)=O)C1Cc1cccc(-c2cc(F)cc(F)c2F)c1] | | 455.1 |

TABLE 1-continued

| EXAMPLE | IUPACNAME | Structure | ADDITIVE | MS |
|---|---|---|---|---|
| 243 | N-(cis-1-isobutyryl-2-((2',3',5',6'-tetrafluorobiphenyl-3-yl)methyl)pyrrolidin-3-yl)methanesulfonamide | 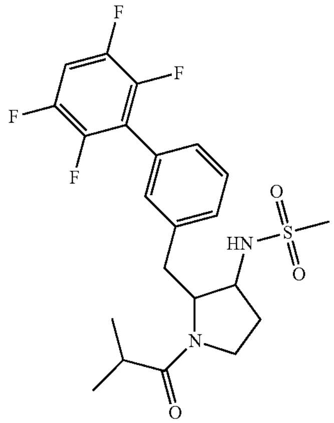 [SMILES: CC(C)C(=O)N1CCC(NS(C)(=O)=O)C1Cc1cccc(-c2c(F)c(F)cc(F)c2F)c1] | | 473.1 |
| 244 | N-(cis-1-isobutyryl-2-(3-(pyrrolidin-1-yl)benzyl)pyrrolidin-3-yl)methanesulfonamide | 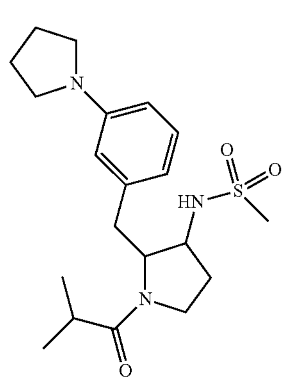 [SMILES: CC(C)C(=O)N1CCC(NS(C)(=O)=O)C1Cc1cccc(N2CCCC2)c1] | | 394.2 |
| 245 | N-(cis-2-(3-(2,3-dihydro-1H-indol-1-yl)benzyl)-1-isobutyrylpyrrolidin-3-yl)methanesulfonamide | 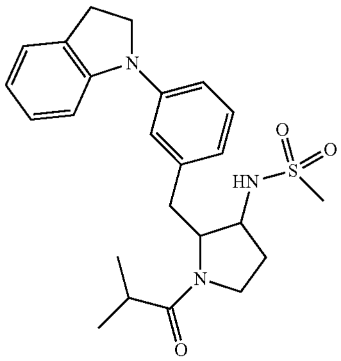 [SMILES: CC(C)C(=O)N1CCC(NS(C)(=O)=O)C1Cc1cccc(N2CCc3ccccc32)c1] | | 442.0 |
| 246 | N-(cis-1-isobutyryl-2-((2-phenyl-1,3-thiazol-4-yl)methyl)pyrrolidin-3-yl)methanesulfonamide | 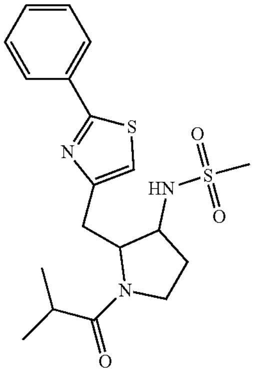 [SMILES: CC(C)C(=O)N1CCC(NS(C)(=O)=O)C1Cc1csc(-c2ccccc2)n1] | | 408.1 |

TABLE 1-continued

| EXAMPLE | IUPACNAME | Structure | ADDITIVE | MS |
|---|---|---|---|---|
| 247 | N-(cis-1-(cyclopropylcarbonyl)-2-((6-phenylpyridin-2-yl)methyl)pyrrolidin-3-yl)methanesulfonamide | 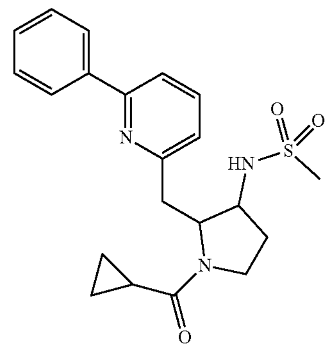 [SMILES: CS(=O)(=O)NC1CCN(C(=O)C2CC2)C1Cc1cccc(-c2ccccc2)n1] | | 400.1 |
| 248 | ethyl cis-3-((methylsulfonyl)amino)-2-((6-phenylpyridin-2-yl)methyl) pyrrolidine-1-carboxylate | 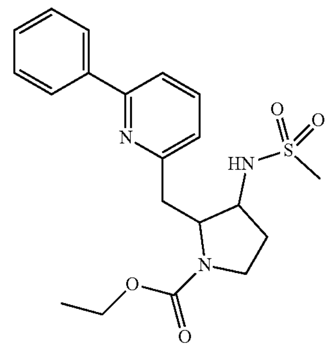 [SMILES: CCOC(=O)N1CCC(NS(C)(=O)=O)C1Cc1cccc(-c2ccccc2)n1] | | 404.0 |
| 249 | methyl cis-2-(biphenyl-3-ylmethyl)-3-((ethylsulfonyl)amino)piperidine-1-carboxylate | 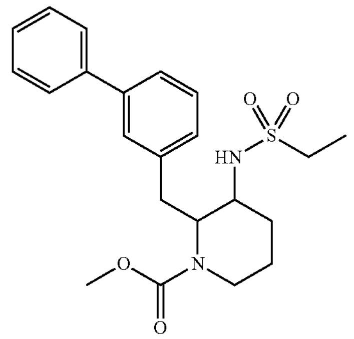 [SMILES: CCS(=O)(=O)NC1CCCN(C(=O)OC)C1Cc1cccc(-c2ccccc2)c1] | | 417.0 |
| 250 | methyl cis-2-(biphenyl-3-ylmethyl)-3-((isopropylsulfonyl)amino) piperidine-1-carboxylate | 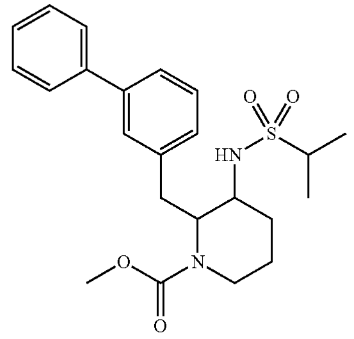 | | 431.0 |

TABLE 1-continued

| EXAMPLE | IUPACNAME | Structure | ADDITIVE | MS |
|---|---|---|---|---|
| 251 | cis-2-(biphenyl-3-ylmethyl)-N-ethyl-3-((methylsulfonyl)amino) azetidine-1-carboxamide | 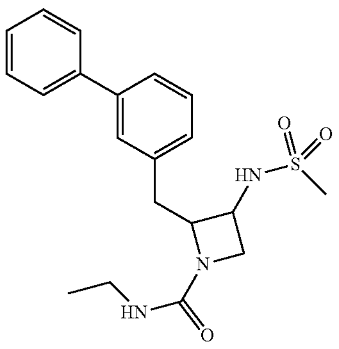 [SMILES: CCNC(=O)N1CC(NS(C)(=O)=O)C1Cc1cccc(-c2ccccc2)c1] | | 388.0 |
| 252 | N-(cis-1-(2,2-dimethylpropanoyl)-2-((2-phenyl-1,3-thiazol-4-yl)methyl)pyrrolidin-3-yl)methanesulfonamide | 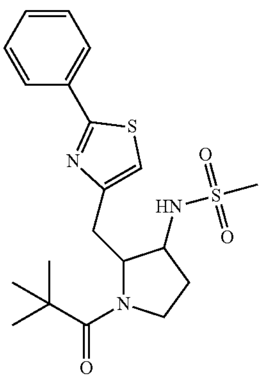 [SMILES: CC(C)(C)C(=O)N1CCC(NS(C)(=O)=O)C1Cc1csc(-c2ccccc2)n1] | | 422.2 |
| 253 | 1-fluoro-N-(cis-1-isobutyryl-2-((2-phenyl-1,3-thiazol-4-yl)methyl)pyrrolidin-3-yl)methanesulfonamide | 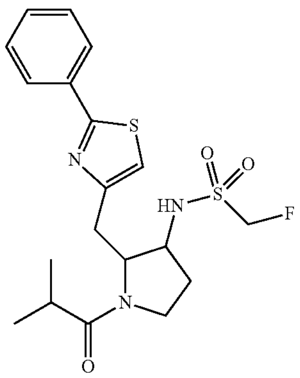 [SMILES: CC(C)C(=O)N1CCC(NS(=O)(=O)CF)C1Cc1csc(-c2ccccc2)n1] | | 426.2 |
| 254 | N-(cis-1-(cyclobutylcarbonyl)-2-((2-(3-fluorophenyl)-1,3-thiazol-4-yl)methyl) pyrrolidin-3-yl)methanesulfonamide | 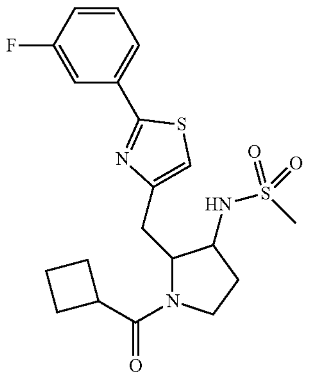 [SMILES: CS(=O)(=O)NC1CCN(C(=O)C2CCC2)C1Cc1csc(-c2cccc(F)c2)n1] | | 438.1 |

TABLE 1-continued
| EXAMPLE | IUPACNAME | Structure | ADDITIVE | MS |
|---|---|---|---|---|
| 255 | N-(cis-1-(cyclobutylcarbonyl)-2-((2-(2-fluorophenyl)-1,3-thiazol-4-yl)methyl) pyrrolidin-3-yl)methanesulfonamide | 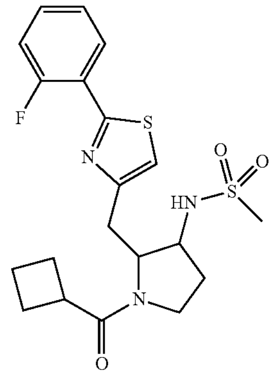 [SMILES: CS(=O)(=O)NC1CCN(C(=O)C2CCC2)C1Cc1csc(-c2ccccc2F)n1] | | 438.2 |
| 256 | N-(cis-1-(cyclobutylcarbonyl)-2-((2-(2,3-difluorophenyl)-1,3-thiazol-4-yl)methyl) pyrrolidin-3-yl)methanesulfonamide | 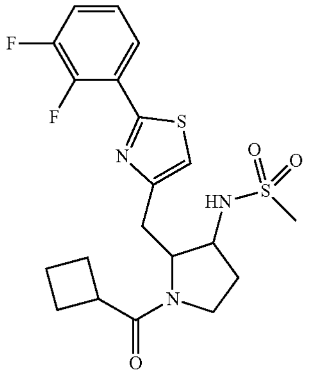 [SMILES: CS(=O)(=O)NC1CCN(C(=O)C2CCC2)C1Cc1csc(-c2cccc(F)c2F)n1] | | 456.1 |
| 257 | N-(cis-1-(cyclobutylcarbonyl)-2-((2-(4-fluorophenyl)-1,3-thiazol-4-yl)methyl) pyrrolidin-3-yl)methanesulfonamide | 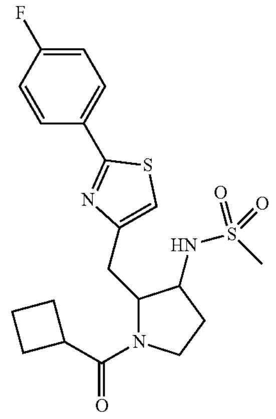 [SMILES: CS(=O)(=O)NC1CCN(C(=O)C2CCC2)C1Cc1csc(-c2ccc(F)cc2)n1] | | 438.1 |

TABLE 1-continued

| EXAM-PLE | IUPACNAME | Structure | ADDITIVE | MS |
|---|---|---|---|---|
| 258 | N-(cis-1-(cyclobutylcarbonyl)-2-((2-(3,5-difluorophenyl)-1,3-thiazol-4-yl)methyl)pyrrolidin-3-yl)methanesulfonamide | 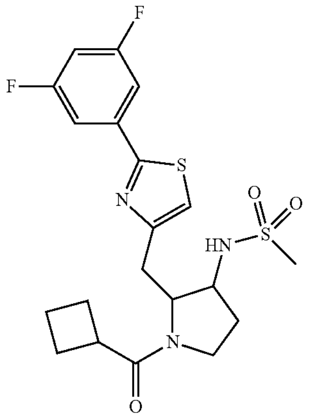 [SMILES: CS(=O)(=O)NC1CCN(C(=O)C2CCC2)C1Cc1csc(-c2cc(F)cc(F)c2)n1] | | 456.1 |
| 259 | N-(cis-1-(cyclobutylcarbonyl)-2-((2-phenyl-1,3-thiazol-4-yl)methyl)pyrrolidin-3-yl)cyclopropanesulfonamide | 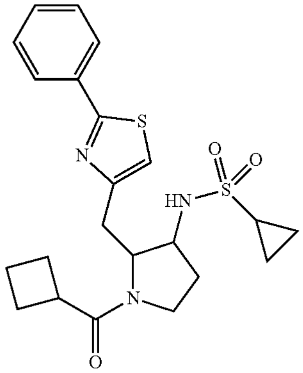 [SMILES: O=C(C1CCC1)N1CCC(NS(=O)(=O)C2CC2)C1Cc1csc(-c2ccccc2)n1] | | 446.2 |
| 260 | N-(cis-1-isobutyryl-2-((2-phenyl-1,3-thiazol-4-yl)methyl)pyrrolidin-3-yl)cyclopropanesulfonamide | 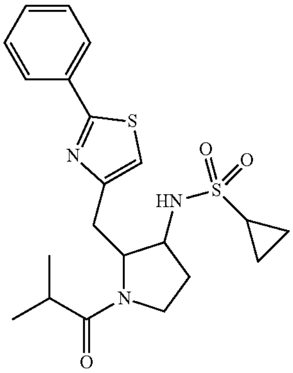 [SMILES: CC(C)C(=O)N1CCC(NS(=O)(=O)C2CC2)C1Cc1csc(-c2ccccc2)n1] | | 434.2 |
| 261 | N-((2S,3S)-2-(biphenyl-3-ylmethyl)-1-(cyclobutylcarbonyl)pyrrolidin-3-yl)methanesulfonamide | 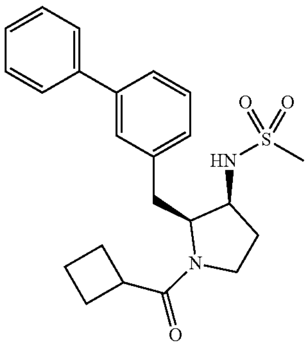 [SMILES: CS(=O)(=O)N[C@H]1CCN(C(=O)C2CCC2)[C@H]1Cc1cccc(-c2ccccc2)c1] | | 413.3 |

TABLE 1-continued

| EXAMPLE | IUPACNAME | Structure | ADDITIVE | MS |
|---|---|---|---|---|
| 262 | N-((2S,3S)-1-(cyclobutylcarbonyl)-2-((3'-fluorobiphenyl-3-yl)methyl)pyrrolidin-3-yl)methanesulfonamide | 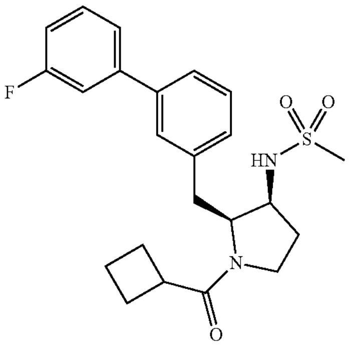 [SMILES: CS(=O)(=O)N[C@H]1CCN(C(=O)C2CCC2)[C@H]1Cc1cccc(-c2cccc(F)c2)c1] | | 431.2 |
| 263 | N-((2S,3S)-2-(biphenyl-3-ylmethyl)-1-((3,3-difluorocyclobutyl)carbonyl) pyrrolidin-3-yl)methanesulfonamide | 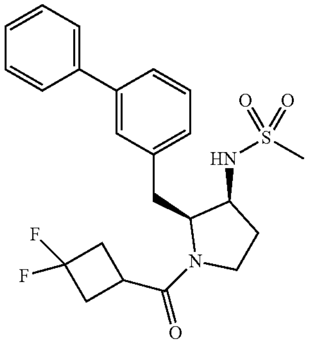 [SMILES: CS(=O)(=O)N[C@H]1CCN(C(=O)C2CC(F)(F)C2)[C@H]1Cc1cccc(-c2ccccc2)c1] | | 447.1 |
| 264 | N-((2S,3S)-1-((3,3-difluorocyclobutyl) carbonyl)-2-((3'-fluorobiphenyl-3-yl) methyl)pyrrolidin-3-yl) methanesulfonamide | 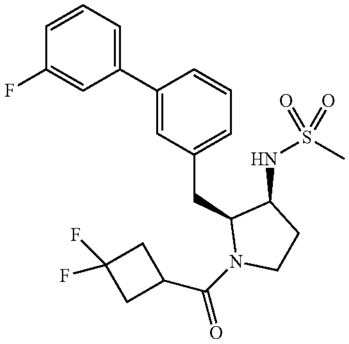 [SMILES: CS(=O)(=O)N[C@H]1CCN(C(=O)C2CC(F)(F)C2)[C@H]1Cc1cccc(-c2cccc(F)c2)c1] | | 465.0 |
| 265 | N-((2S,3S)-2-(biphenyl-3-ylmethyl)-1-((1-fluorocyclobutyl)carbonyl)pyrrolidin-3-yl)methanesulfonamide | 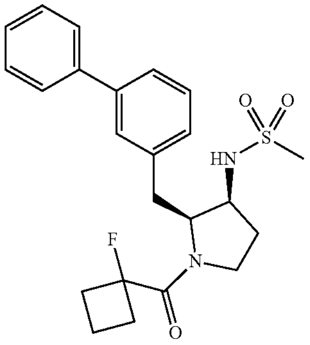 [SMILES: CS(=O)(=O)N[C@H]1CCN(C(=O)C2(F)CCC2)[C@H]1Cc1cccc(-c2ccccc2)c1] | | 431.2 |

TABLE 1-continued

| EXAMPLE | IUPACNAME | Structure | ADDITIVE | MS |
|---|---|---|---|---|
| 266 | N-((2S,3S)-2-((3'-fluorobiphenyl-3-yl) methyl)-1-((1-fluorocyclobutyl)carbonyl) pyrrolidin-3-yl)methanesulfonamide | 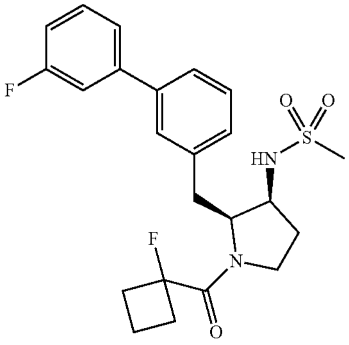 [SMILES: CS(=O)(=O)N[C@H]1CCN(C(=O)C2(F)CCC2)[C@H]1Cc1cccc(-c2cccc(F)c2)c1] | | 447.1 |
| 267 | N-((2S,3S)-2-(biphenyl-3-ylmethyl)-1-(cyclobutylcarbonyl)pyrrolidin-3-yl)-1-fluoromethanesulfonamide | 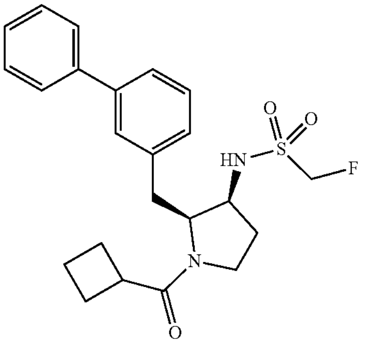 [SMILES: O=C(C1CCC1)N1CC[C@H](NS(=O)(=O)CF)[C@@H]1Cc1cccc(-c2ccccc2)c1] | | 431.2 |
| 268 | N-((2S,3S)-1-(cyclobutylcarbonyl)-2-((3'-fluorobiphenyl-3-yl)methyl)pyrrolidin-3-yl)-1-fluoromethanesulfonamide | 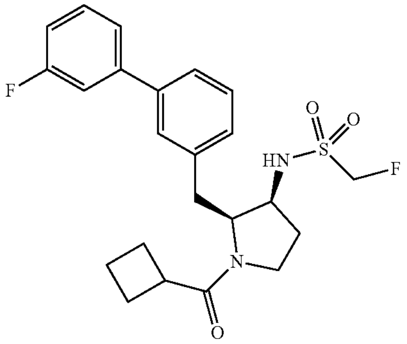 [SMILES: O=C(C1CCC1)N1CC[C@H](NS(=O)(=O)CF)[C@@H]1Cc1cccc(-c2cccc(F)c2)c1] | | 449.1 |
| 269 | N-(cis-1-(cyclobutylcarbonyl)-2-((2-phenyl-1,3-thiazol-4-yl)methyl)pyrrolidin-3-yl)-1-fluoromethanesulfonamide | 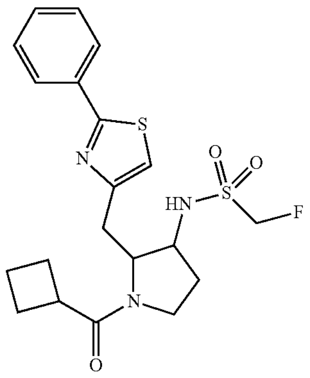 [SMILES: O=C(C1CCC1)N1CCC(NS(=O)(=O)CF)C1Cc1csc(-c2ccccc2)n1] | | 438.0 |

TABLE 1-continued

| EXAM-PLE | IUPACNAME | Structure | ADDITIVE | MS |
|---|---|---|---|---|
| 270 | N-(cis-1-isobutyryl-2-((3'-methylbiphenyl-3-yl)methyl)pyrrolidin-3-yl) methanesulfonamide | 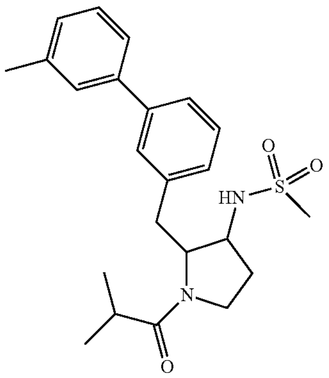 [SMILES: Cc1cccc(-c2cccc(CC3C(NS(C)(=O)=O)CCN3C(=O)C(C)C)c2)c1] | | 415.2 |
| 271 | N-(cis-2-((3'-chlorobiphenyl-3-yl) methyl)-1-isobutyrylpyrrolidin-3-yl) methanesulfonamide | 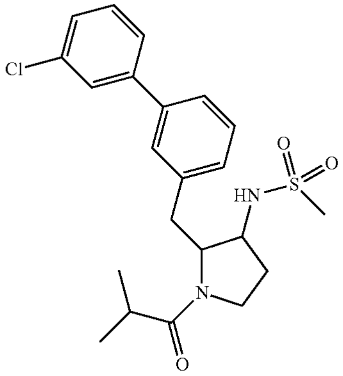 [SMILES: CC(C)C(=O)N1CCC(NS(C)(=O)=O)C1Cc1cccc(-c2cccc(Cl)c2)c1] | | 435.2 |
| 272 | N-(cis-1-isobutyryl-2-((3'-methoxybiphenyl-3-yl)methyl)pyrrolidin-3-yl)methanesulfonamide | 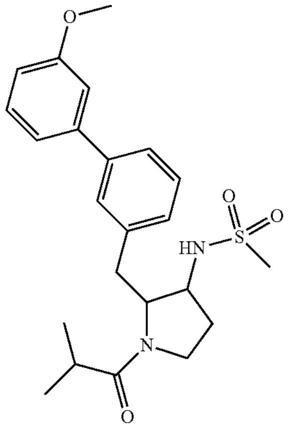 [SMILES: COc1cccc(-c2cccc(CC3C(NS(C)(=O)=O)CCN3C(=O)C(C)C)c2)c1] | | 431.0 |
| 273 | N-(cis-2-((3'-(difluoromethyl)biphenyl-3-yl)methyl)-1-isobutyrylpyrrolidin-3-yl)methanesulfonamide | 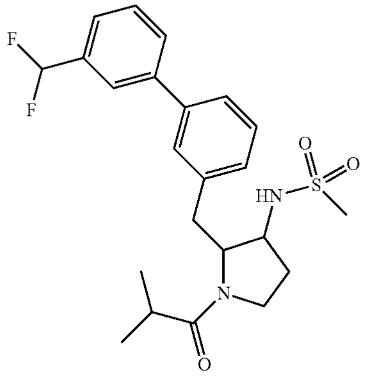 [SMILES: CC(C)C(=O)N1CCC(NS(C)(=O)=O)C1Cc1cccc(-c2cccc(C(F)F)c2)c1] | | 451.2 |

TABLE 1-continued

| EXAMPLE | IUPACNAME | Structure | ADDITIVE | MS |
|---|---|---|---|---|
| 274 | N-(cis-2-(biphenyl-3-ylmethyl)-1-((1-methylcyclopropyl)carbonyl)pyrrolidin-3-yl)methanesulfonamide | 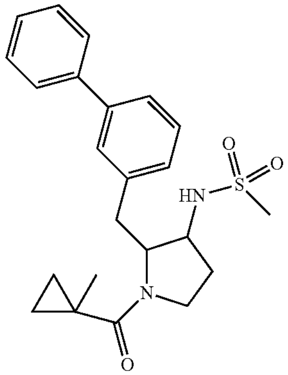 [SMILES: CC1(C(=O)N2CCC(NS(C)(=O)=O)C2Cc2cccc(-c3ccccc3)c2)CC1] | | 413.3 |
| 275 | N-(cis-2-(biphenyl-3-ylmethyl)-1-((2,2-dimethylcyclopropyl)carbonyl)pyrrolidin-3-yl)methanesulfonamide | 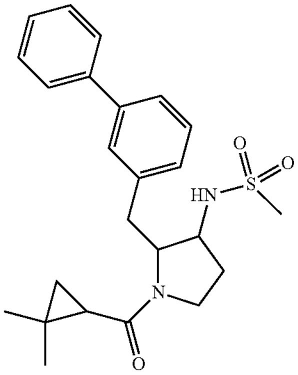 [SMILES: CC1(C)CC1C(=O)N1CCC(NS(C)(=O)=O)C1Cc1cccc(-c2ccccc2)c1] | | 427.0 |
| 276 | N-(cis-1-(bicyclo[1.1.1]pent-1-ylcarbonyl)-2-(biphenyl-3-ylmethyl)pyrrolidin-3-yl)methanesulfonamide | 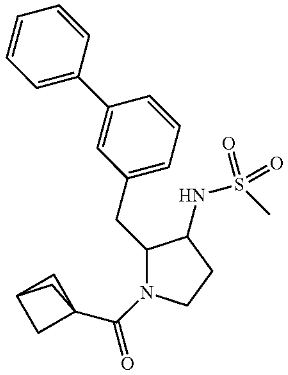 [SMILES: CS(=O)(=O)NC1CCN(C(=O)C23CC(C2)C3)C1Cc1cccc(-c2ccccc2)c1] | | 425.0 |
| 277 | N-(cis-2-(biphenyl-3-ylmethyl)-1-(2,2-difluoropropanoyl)pyrrolidin-3-yl)methanesulfonamide | 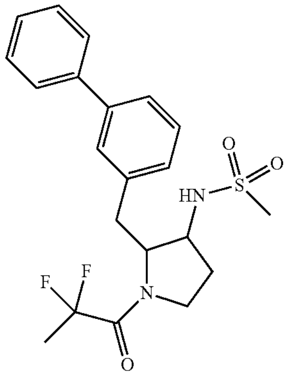 [SMILES: CC(F)(F)C(=O)N1CCC(NS(C)(=O)=O)C1Cc1cccc(-c2ccccc2)c1] | | 423.0 |

TABLE 1-continued

| EXAMPLE | IUPACNAME | Structure | ADDITIVE | MS |
|---|---|---|---|---|
| 278 | N-(cis-2-(biphenyl-3-ylmethyl)-1-(2-fluoro-2-methylpropanoyl)pyrrolidin-3-yl)methanesulfonamide | 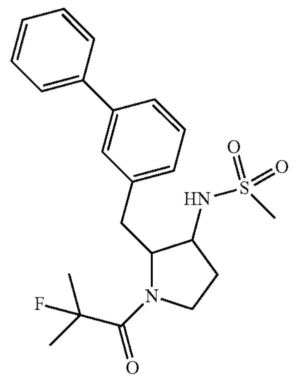 [SMILES: CC(C)(F)C(=O)N1CCC(NS(C)(=O)=O)C1Cc1cccc(-c2ccccc2)c1] | | 417.2 |
| 279 | N-(cis-2-(biphenyl-3-ylmethyl)-1-(3,3,3-trifluoro-2-methylpropanoyl)pyrrolidin-3-yl)methanesulfonamide | 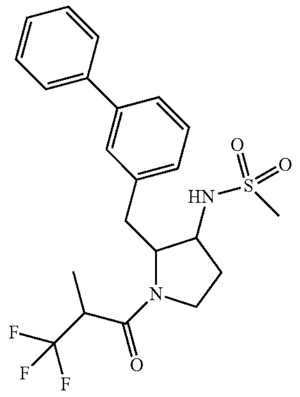 [SMILES: CC(C(=O)N1CCC(NS(C)(=O)=O)C1Cc1cccc(-c2ccccc2)c1)C(F)(F)F] | | 454. 9 |
| 280 | N-(cis-2-(biphenyl-3-ylmethyl)-1-((1-fluorocyclopropyl)carbonyl)pyrrolidin-3-yl)methanesulfonamide | 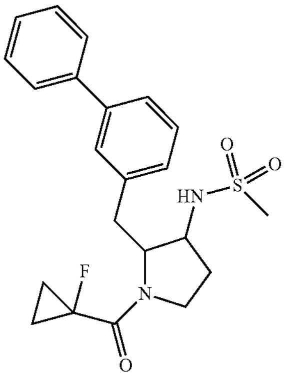 [SMILES: CS(=O)(=O)NC1CCN(C(=O)C2(F)CC2)C1Cc1cccc(-c2ccccc2)c1] | | 417.0 |
| 281 | N-(cis-2-(biphenyl-3-ylmethyl)-1-((trans-2-fluorocyclopropyl)carbonyl)pyrrolidin-3-yl)methanesulfonamide | 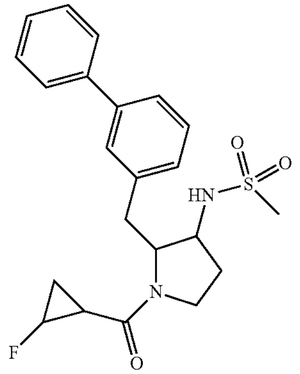 [SMILES: CS(=O)(=O)NC1CCN(C(=O)C2CC2F)C1Cc1cccc(-c2ccccc2)c1] | | 417.0 |

TABLE 1-continued

| EXAMPLE | IUPACNAME | Structure | ADDITIVE | MS |
|---|---|---|---|---|
| 282 | N-(cis-2-(biphenyl-3-ylmethyl)-1-((cis-2-fluorocyclopropyl)carbonyl)pyrrolidin-3-yl)methanesulfonamide | 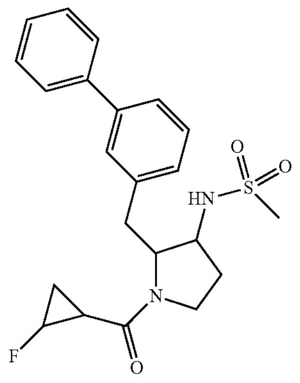 [SMILES: CS(=O)(=O)NC1CCN(C(=O)C2CC2F)C1Cc1cccc(-c2ccccc2)c1] | | 417.0 |
| 283 | N-(cis-2-(biphenyl-3-ylmethyl)-1-((2,2-difluorocyclopropyl)carbonyl)pyrrolidin-3-yl)methanesulfonamide | 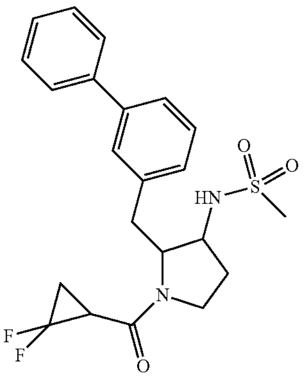 [SMILES: CS(=O)(=O)NC1CCN(C(=O)C2CC2(F)F)C1Cc1cccc(-c2ccccc2)c1] | | 435. 0 |
| 284 | N-(cis-2-(biphenyl-3-ylmethyl)-1-(oxetan-3-ylcarbonyl)pyrrolidin-3-yl) methanesulfonamide | 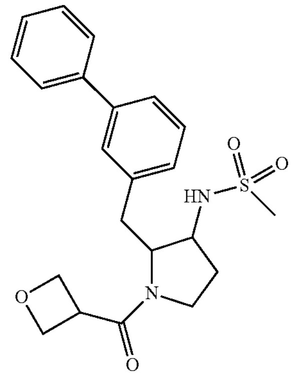 [SMILES: CS(=O)(=O)NC1CCN(C(=O)C2COC2)C1Cc1cccc(-c2ccccc2)c1] | | 415.0 |
| 285 | N-(cis-1-(cyclopropylcarbonyl)-2-((2-phenyl-1,3-thiazol-4-yl)methyl) pyrrolidin-3-yl)methanesulfonamide | 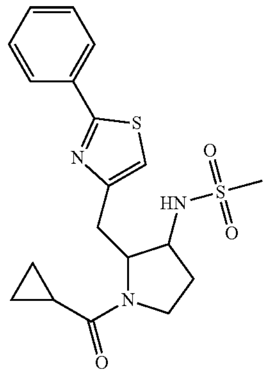 [SMILES: CS(=O)(=O)NC1CCN(C(=O)C2CC2)C1Cc1csc(-c2ccccc2)n1] | | 406.0 |

TABLE 1-continued

| EXAMPLE | IUPACNAME | Structure | ADDITIVE | MS |
|---|---|---|---|---|
| 286 | ethyl cis-3-((methylsulfonyl)amino)-2-((2-phenyl-1,3-thiazol-4-yl)methyl) pyrrolidine-1-carboxylate | 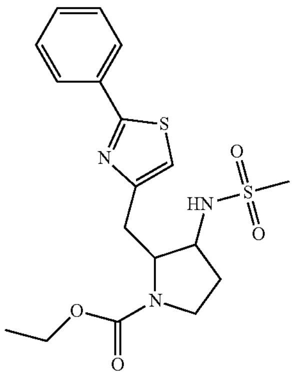 [SMILES: CCOC(=O)N1CCC(NS(C)(=O)=O)C1Cc1csc(-c2ccccc2)n1] | | 410.1 |
| 287 | isopropyl cis-2-(biphenyl-3-yl(difluoro) methyl)-3-((methylsulfonyl)amino) piperidine-1-carboxylate | 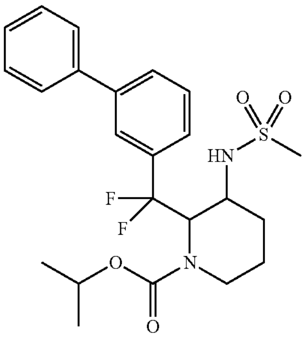 [SMILES: CC(C)OC(=O)N1CCCC(NS(C)(=O)=O)C1C(F)(F)c1cccc(-c2ccccc2)c1] | | 465.1 |
| 288 | N-(cis-2-(biphenyl-3-yl(difluoro)methyl)-1-(cyclopropylcarbonyl)piperidin-3-yl)methanesulfonamide | 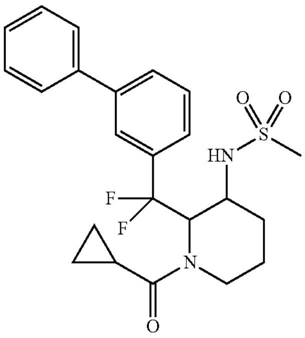 [SMILES: CS(=O)(=O)NC1CCCN(C(=O)C2CC2)C1C(F)(F)c1cccc(-c2ccccc2)c1] | | 449.2 |
| 289 | N-(cis-1-aoetyl-2-(biphenyl-3-yl(difluoro)methyl)piperidin-3-yl)methanesulfonamide | 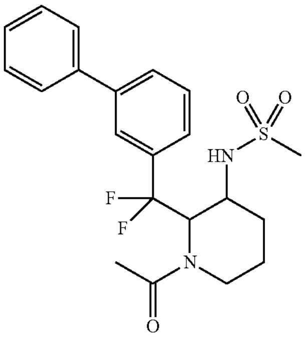 [SMILES: CC(=O)N1CCCC(NS(C)(=O)=O)C1C(F)(F)c1cccc(-c2ccccc2)c1] | | 423.0 |

TABLE 1-continued

| EXAMPLE | IUPACNAME | Structure | ADDITIVE | MS |
|---|---|---|---|---|
| 290 | ethyl cis-2-(biphenyl-3-yl(difluoro) methyl)-3-((methylsulfonyl)amino) piperidine-1-carboxylate | 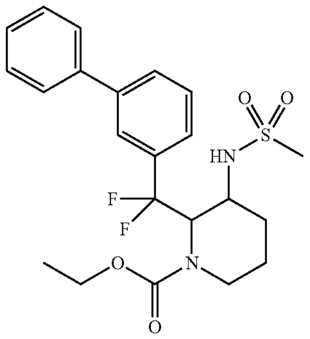 [SMILES: CCOC(=O)N1CCCC(NS(C)(=O)=O)C1C(F)(F)c1cccc(-c2ccccc2)c1] | | 451.0 |
| 291 | ethyl cis-2-((2-fluorobiphenyl-3-yl) methyl)-3-((methylsulfonyl)amino) pyrrolidine-1-carboxylate | 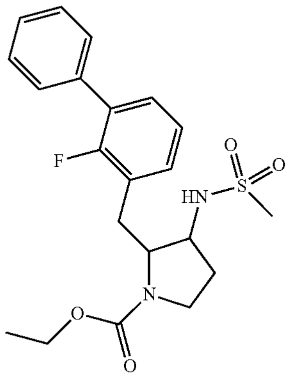 [SMILES: CCOC(=O)N1CCC(NS(C)(=O)=O)C1Cc1cccc(-c2ccccc2)c1F] | | 421.0 |
| 292 | ethyl cis-2-((2,3'-difluorobiphenyl-3-yl) methyl)-3-((methylsulfonyl)amino) pyrrolidine-1-carboxylate | 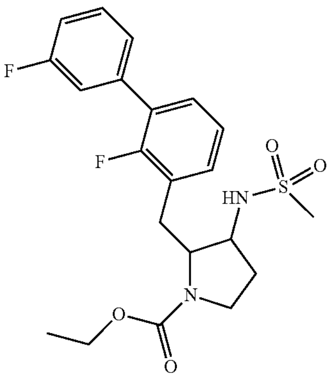 [SMILES: CCOC(=O)N1CCC(NS(C)(=O)=O)C1Cc1cccc(-c2cccc(F)c2)c1F] | | 439.2 |
| 293 | N-(cis-2-((2-fluorobiphenyl-3-yl) methyl)-1-isobutyrylpyrrolidin-3-yl) methanesulfonamide | 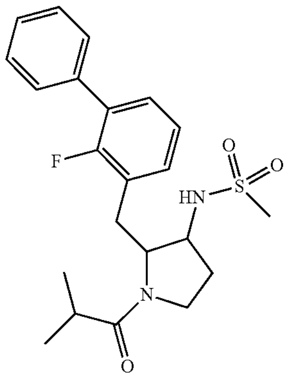 [SMILES: CC(C)C(=O)N1CCC(NS(C)(=O)=O)C1Cc1cccc(-c2ccccc2)c1F] | | 419.2 |

TABLE 1-continued

| EXAMPLE | IUPACNAME | Structure | ADDITIVE | MS |
|---|---|---|---|---|
| 294 | N-(cis-2-((2,3'-difluorobiphenyl-3-yl)methyl)-1-isobutyrylpyrrolidin-3-yl)methanesulfonamide | 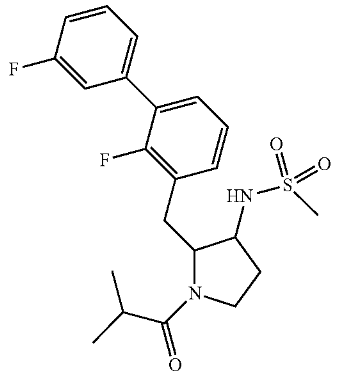 [SMILES: CC(C)C(=O)N1CCC(NS(C)(=O)=O)C1Cc1cccc(-c2cccc(F)c2)c1F] | | 437.2 |
| 295 | ethyl cis-2-((5-fluorobiphenyl-3-yl)methyl)-3-((methylsulfonyl)amino)pyrrolidine-1-carboxylate | 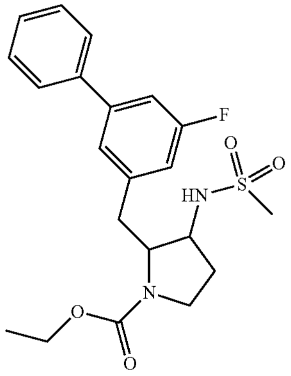 [SMILES: CCOC(=O)N1CCC(NS(C)(=O)=O)C1Cc1cc(F)cc(-c2ccccc2)c1] | | 421.0 |
| 296 | ethyl cis-2-((3',5-difluorobiphenyl-3-yl)methyl)-3-((methylsulfonyl)amino)pyrrolidine-1-carboxylate | 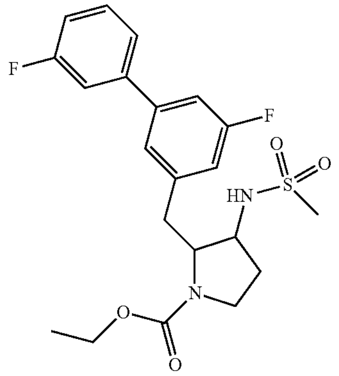 [SMILES: CCOC(=O)N1CCC(NS(C)(=O)=O)C1Cc1cc(F)cc(-c2cccc(F)c2)c1] | | 438.9 |
| 297 | N-(cis-2-((5-fluorobiphenyl-3-yl)methyl)-1-isobutyrylpyrrolidin-3-yl)methanesulfonamide | 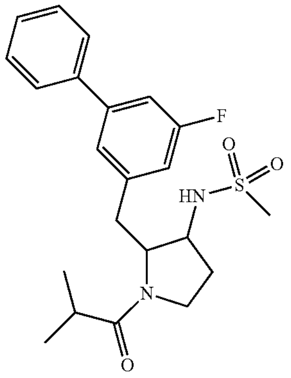 [SMILES: CC(C)C(=O)N1CCC(NS(C)(=O)=O)C1Cc1cc(F)cc(-c2ccccc2)c1] | | 419.2 |

TABLE 1-continued

| EXAMPLE | IUPACNAME | Structure | ADDITIVE | MS |
|---|---|---|---|---|
| 298 | N-(cis-2-((3',5-difluorobiphenyl-3-yl)methyl)-1-isobutyrylpyrrolidin-3-yl)methanesulfonamide | 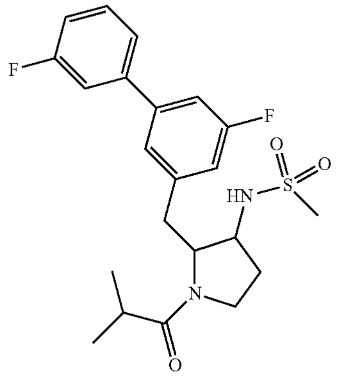 [SMILES: CC(C)C(=O)N1CCC(NS(C)(=O)=O)C1Cc1cc(F)cc(-c2cccc(F)c2)c1] | | 437.2 |
| 299 | N-(cis-1-(cyclobutylcarbonyl)-2-(5-fluorobiphenyl-3-yl)methyl)pyrrolidin-3-yl)methanesulfonamide | 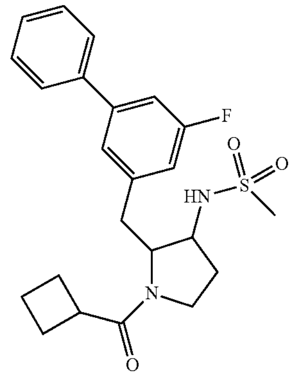 [SMILES: CS(=O)(=O)NC1CCN(C(=O)C2CCC2)C1Cc1cc(F)cc(-c2ccccc2)c1] | | 431.2 |
| 300 | N-(cis-1-(cyclobutylcarbonyl)-2-((3',5-difluorobiphenyl-3-yl)methyl)pyrrolidin-3-yl)methanesulfonamide | 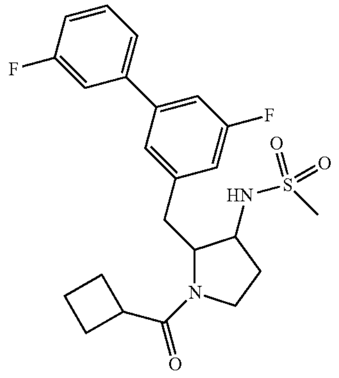 [SMILES: CS(=O)(=O)NC1CCN(C(=O)C2CCC2)C1Cc1cc(F)cc(-c2cccc(F)c2)c1] | | 449.2 |
| 301 | ethyl cis-2-((6-fluorobiphenyl-3-yl)methyl)-3-((methylsulfonyl)amino)pyrrolidine-1-carboxylate | 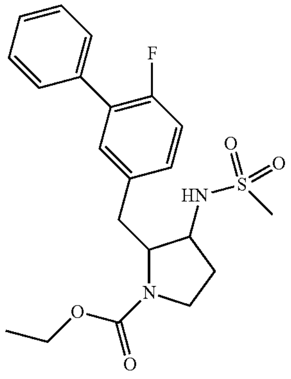 [SMILES: CCOC(=O)N1CCC(NS(C)(=O)=O)C1Cc1ccc(F)c(-c2ccccc2)c1] | | 421.0 |

TABLE 1-continued

| EXAMPLE | IUPACNAME | Structure | ADDITIVE | MS |
|---|---|---|---|---|
| 302 | ethyl cis-2-((3',6-difluorobiphenyl-3-yl)methyl)-3-((methylsulfonyl)amino)pyrrolidine-1-carboxylate | 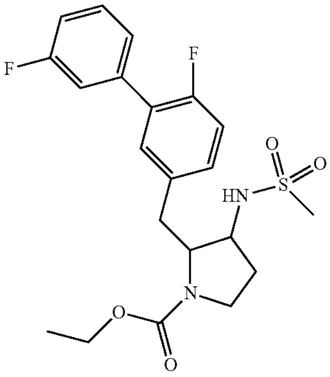 [SMILES: CCOC(=O)N1CCC(NS(C)(=O)=O)C1Cc1ccc(F)c(-c2cccc(F)c2)c1] | | 439.0 |
| 303 | N-(cis-1-(cyclobutylcarbonyl)-2-((6-fluorobiphenyl-3-yl)methyl)pyrrolidin-3-yl)methanesulfonamide | 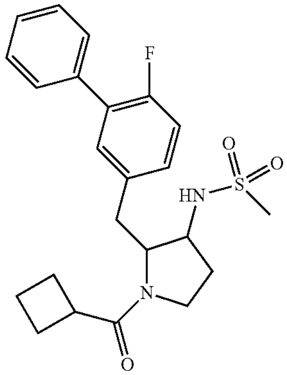 [SMILES: CS(=O)(=O)NC1CCN(C(=O)C2CCC2)C1Cc1ccc(F)c(-c2ccccc2)c1] | | 431.2 |
| 304 | N-(cis-1-(cyclobutylcarbony)-2-((3',6-difluorobiphenyl-3-yl)methyl)pyrrolidin-3-yl)methanesulfonamide | 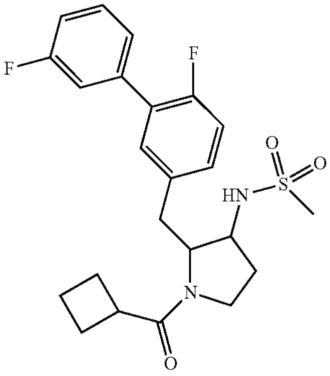 [SMILES: CS(=O)(=O)NC1CCN(C(=O)C2CCC2)C1Cc1ccc(F)c(-c2cccc(F)c2)c1] | | 449.2 |
| 305 | N-((2S,3S)-2-((3'-fluorobiphenyl-3-yl)methyl)-1-((1-methylcyclobutyl)carbonyl)pyrrolidin-3-yl)methanesulfonamide | 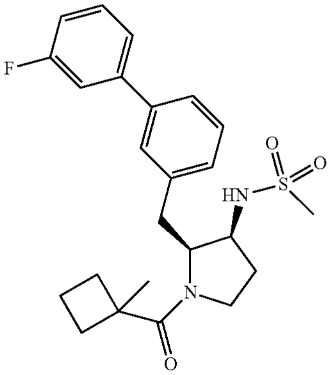 [SMILES: CC1(C(=O)N2CC[C@H](NS(C)(=O)=O)[C@@H]2Cc2cccc(-c3cccc(F)c3)c2)CCC1] | | 445.3 |

TABLE 1-continued

| EXAMPLE | IUPACNAME | Structure | ADDITIVE | MS |
|---|---|---|---|---|
| 306 | N-((2S,3S)-1-(bicyclo[1.1.1]pent-1-ylcarbonyl)-2-((3'-fluorobiphenyl-3-yl)methyl)pyrrolidin-3-yl)methanesulfonamide | 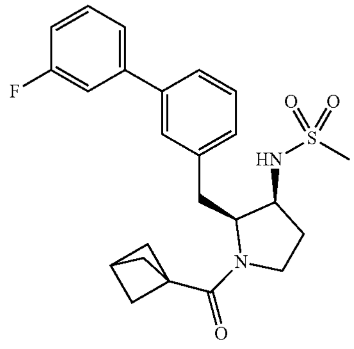 [SMILES: CS(=O)(=O)N[C@H]1CCN(C(=O)C23CC(C2)C3)[C@H]1Cc1cccc(-c2cccc(F)c2)c1] | | 443.3 |
| 307 | N-((2S,3S)-1-(bicyclo[1.1.1]pent-1-ylcarbonyl)-2-((3',5'-difluorobiphenyl-3-yl)methyl)pyrrolidin-3-yl)methanesulfonamide | 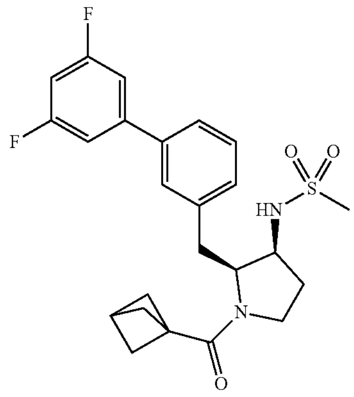 [SMILES: CS(=O)(=O)N[C@H]1CCN(C(=O)C23CC(C2)C3)[C@H]1Cc1cccc(-c2cc(F)cc(F)c2)c1] | | 460.9 |
| 308 | N-((2S,3S)-2-((3'-fluorobiphenyl-3-yl)methyl)-1-((1-hydroxycyclobutyl)carbonyl)pyrrolidin-3-yl)methanesulfonamide | 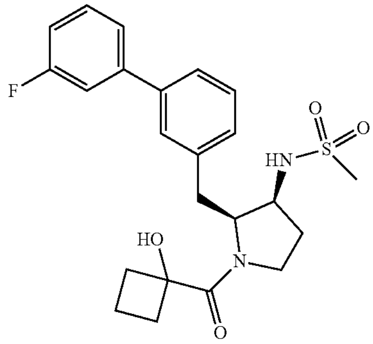 [SMILES: CS(=O)(=O)N[C@H]1CCN(C(=O)C2(O)CCC2)[C@H]1Cc1cccc(-c2cccc(F)c2)c1] | | 447.0 |
| 309 | N-((2S,3S)-2-((3'-fluorobiphenyl-3-yl)methyl)-1-((1-(trifluoromethyl)cyclobutyl)carbonyl)pyrrolidin-3-yl)methanesulfonamide | 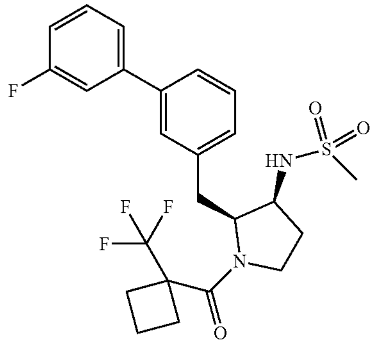 [SMILES: CS(=O)(=O)N[C@H]1CCN(C(=O)C2(C(F)(F)F)CCC2)[C@H]1Cc1cccc(-c2cccc(F)c2)c1] | | 498. 9 |

TABLE 1-continued

| EXAM-PLE | IUPACNAME | Structure | ADDITIVE | MS |
|---|---|---|---|---|
| 310 | N-((2S,3S)-1-(cyclobutylcarbonyl)-2-((3',5'-difluorobiphenyl-3-yl)methyl)pyrrolidin-3-yl)methanesulfonamide | 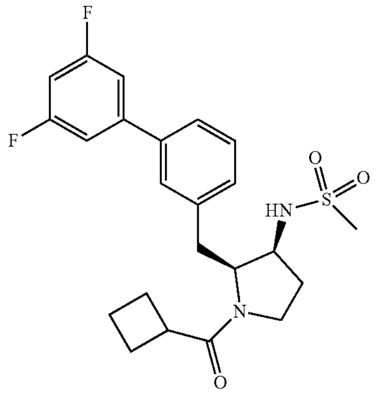 [SMILES: CS(=O)(=O)N[C@H]1CCN(C(=O)C2CCC2)[C@H]1Cc1cccc(-c2cc(F)cc(F)c2)c1] | | 448. 9 |
| 311 | N-((2S,3S)-1-(cyclobutylcarbanyl)-2-((3'-methylbiphenyl-3-yl)methyl)pyrrolidin-3-yl)methanesulfonamide | 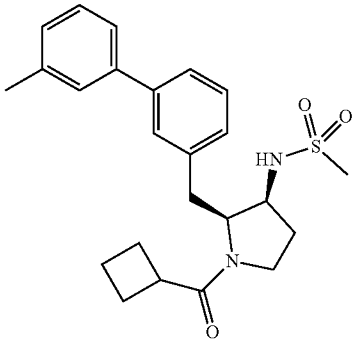 | | 427.0 |
| 312 | N-((2S,3S)-1-(cyclobutylcarbonyl)-2-((3'-fluorobiphenyl-3-yl)methyl)pyrrolidin-3-yl)-1-methoxymethanesulfonamide | 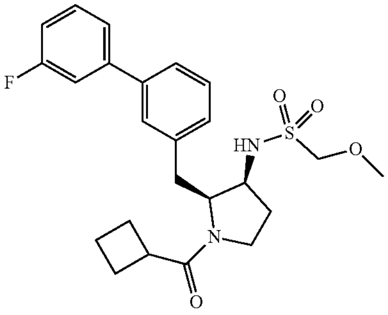 [SMILES: COCS(=O)(=O)N[C@H]1CCN(C(=O)C2CCC2)[C@H]1Cc1cccc(-c2cccc(F)c2)c1] | | 461.0 |
| 313 | N-((2S,3S)-1-(azetidin-1-ylcarbonyl)-2-((3'-fluorobiphenyl-3-yl)methyl) pyrrolidin-3-yl)methanesulfonamide | 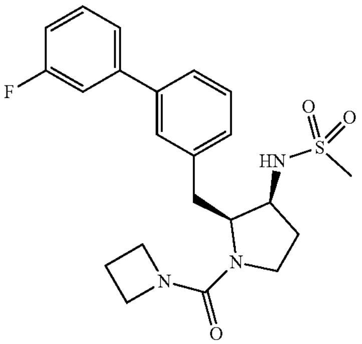 [SMILES: CS(=O)(=O)N[C@H]1CCN(C(=O)N2CCC2)[C@H]1Cc1cccc(-c2cccc(F)c2)c1] | | 432.2 |

TABLE 1-continued
| EXAMPLE | IUPACNAME | Structure | ADDITIVE | MS |
|---|---|---|---|---|
| 314 | N-((2S,3S)-2-((3'-fluorobiphenyl-3-yl) methyl)-1-((1-methoxycyclobutyl) carbonyl)pyrrolidin-3-yl)methanesulfonamide | 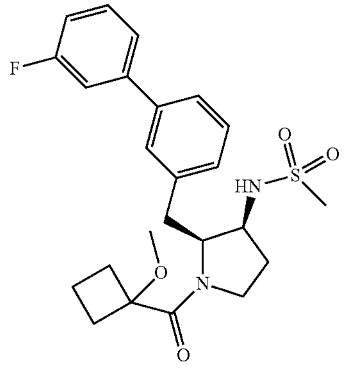 [SMILES: COC1(C(=O)N2CC[C@H](NS(C)(=O)=O)[C@@H]2Cc2cccc(-c3cccc(F)c3)c2)CCC1] | | 461.1 |
| 315 | N-(cis-1-(cyclobutylcarbonyl)-2-((2-(3,5-difluorophenyl)-1,3-thiazol-4-yl)methyl) pyrrolidin-3-yl)ethanesulfonamide | 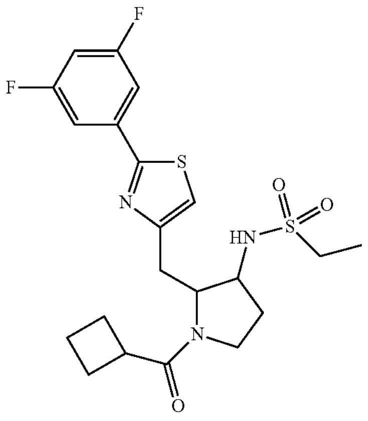 [SMILES: CCS(=O)(=O)NC1CCN(C(=O)C2CCC2)C1Cc1csc(-c2cc(F)cc(F)c2)n1] | | 470.1 |
| 316 | N-(cis-2-((2-(3,5-difluorophenyl)-1,3-thiazol-4-yl)methyl-1-((1-methylcyclobutyl)carbonyl)pyrrolidin-3-yl)ethanesulfonamide | 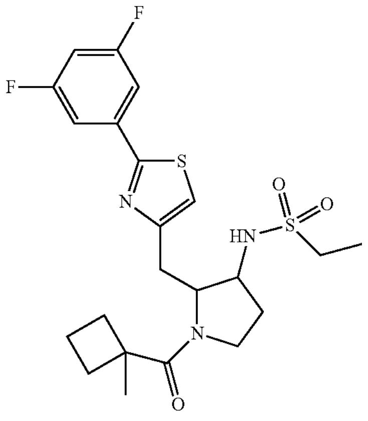 [SMILES: CCS(=O)(=O)NC1CCN(C(=O)C2(C)CCC2)C1Cc1csc(-c2cc(F)cc(F)c2)n1] | | 484.1 |

TABLE 1-continued

| EXAMPLE | IUPACNAME | Structure | ADDITIVE | MS |
|---|---|---|---|---|
| 317 | N-(cis-2-((2-(3,5-difluorophenyl)-1,3-thiazol-4-yl)methyl)-1-((1-hydroxycyclobutyl)carbonyl)pyrrolidin-3-yl)ethanesulfonamide | 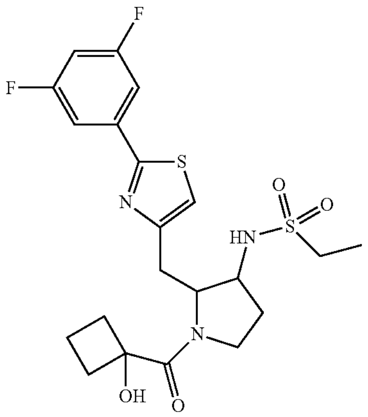 [SMILES: CCS(=O)(=O)NC1CCN(C(=O)C2(O)CCC2)C1Cc1csc(-c2cc(F)cc(F)c2)n1] | | 486.1 |
| 318 | N-(cis-1-(bicyclo[1.1.1]pent-1-ylcarbonyl)-2-((2-(3,5-difluorophenyl)-1,3-thiazol-4-yl)methyl)pyrrolidin-3-yl) ethanesulfonamide | 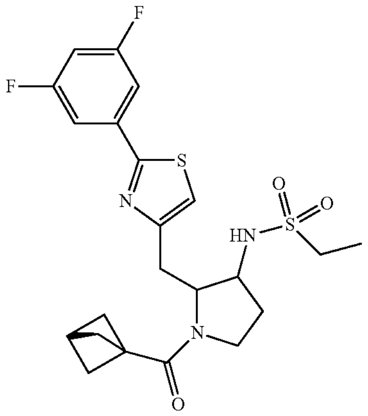 | | 482.1 |
| 319 | N-(cis-1-(cyclobutylcarbonyl)-2-((2-phenyl-1,3-thiazol-4-yl)methyl) pyrrolidin-3-yl)methanesulfonamide | 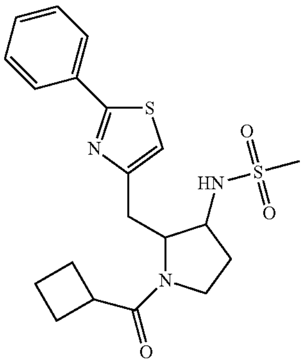 [SMILES: CS(=O)(=O)NC1CCN(C(=O)C2CCC2)C1Cc1csc(-c2ccccc2)n1] | | 420.2 |
| 320 | N-((2S,3S)-1-(cyclobutylcarbonyl)-2-((2-(3-fluorophenyl)-1,3-thiazol-4-yl) methyl)pyrrolidin-3-yl) methanesulfonamide | 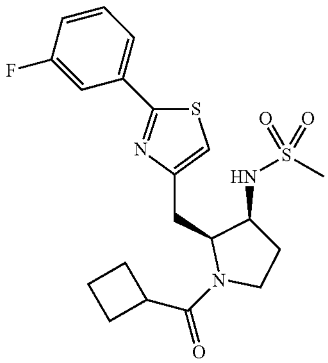 [SMILES: CS(=O)(=O)N[C@H]1CCN(C(=O)C2CCC2)[C@H]1Cc1csc(-c2cccc(F)c2)n1] | | 438.2 |

TABLE 1-continued

| EXAMPLE | IUPACNAME | Structure | ADDITIVE | MS |
|---|---|---|---|---|
| 321 | N-((2S,3S)-1-(cyclobutylcarbonyl)-2-((2-phenyl-1,3-thiazol-4-yl)methyl)pyrrolidin-3-yl)cyclopropanesulfonamide (optical isomer) | 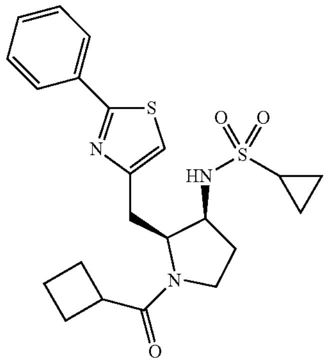 [SMILES: O=C(C1CCC1)N1CC[C@H](NS(=O)(=O)C2CC2)[C@@H]1Cc1csc(-c2ccccc2)n1] | | 446.1 |
| 322 | N-(cis-2-((2-(3,5-difluorophenyl)-1,3-thiazol-4-yl)methyl)-1-((1-methylcyclobutyl)carbonyl)pyrrolidin-3-yl)methanesulfonamide | 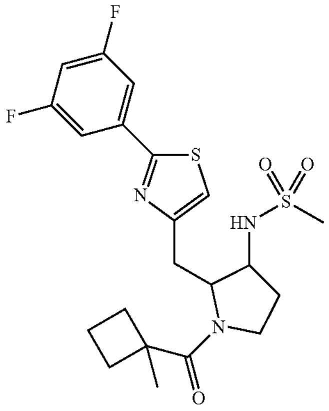 [SMILES: CC1(C(=O)N2CCC(NS(C)(=O)=O)C2Cc2csc(-c3cc(F)cc(F)c3)n2)CCC1] | | 468.0 |
| 323 | N-(cis-2-((2-(3,5-difluorophenyl)-1,3-thiazol-4-yl)methyl)-1-((1-hydroxycyclobutyl)carbonyl)pyrrolidin-3-yl)methanesulfonamide | 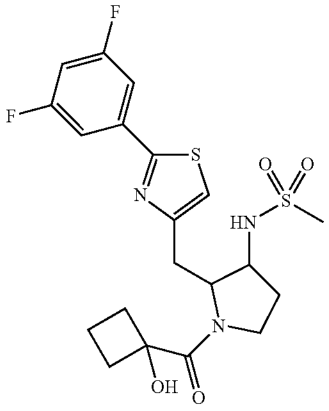 [SMILES: CS(=O)(=O)NC1CCN(C(=O)C2(O)CCC2)C1Cc1csc(-c2cc(F)cc(F)c2)n1] | | 469.9 |
| 324 | N-((2S,3S)-2-(biphenyl-3-ylmethyl)-1-(cyclobutylcarbonyl)pyrrolidin-3-yl)-1-methoxymethanesulfonamide | 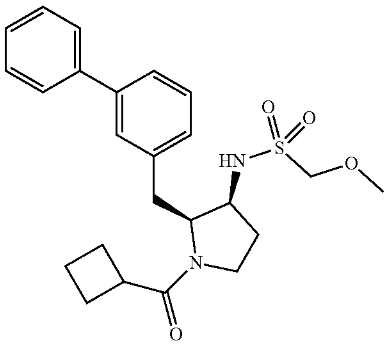 [SMILES: COCS(=O)(=O)N[C@H]1CCN(C(=O)C2CCC2)[C@H]1Cc1cccc(-c2ccccc2)c1] | | 443.1 |

TABLE 1-continued

| EXAMPLE | IUPACNAME | Structure | ADDITIVE | MS |
|---|---|---|---|---|
| 325 | N-(cis-1-(cyclobutylcarbonyl)-2-((5-methyl-2-phenyl-1,3-thiazol-4-yl)methyl) pyrrolidin-3-yl)methanesulfonamide | 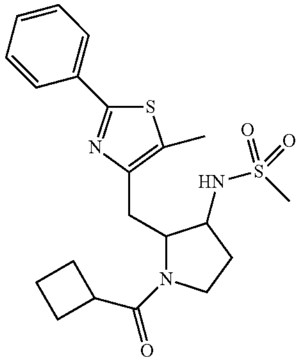 [SMILES: Cc1sc(-c2ccccc2)nc1CC1C(NS(C)(=O)=O)CCN1C(=O)C1CCC1] | | 434.1 |
| 326 | N-(cis-1-((1-hydroxycyclobutyl)carbonyl)-2-((5-methyl-2-phenyl-1,3-thiazol-4-yl)methyl)pyrrolidin-3-yl) methanesulfonamide | 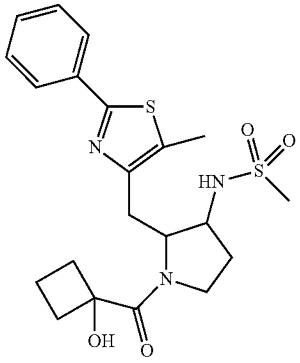 [SMILES: Cc1sc(-c2ccccc2)nc1CC1C(NS(C)(=O)=O)CCN1C(=O)C1(O)CCC1] | | 450.1 |
| 327 | N-(cis-1-(azetidin-1-ylcarbonyl)-2-((5-methyl-2-phenyl-1,3-thiazol-4-yl)methyl) pyrrolidin-3-yl)methanesulfonamide | 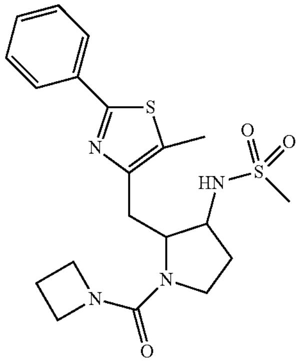 [SMILES: Cc1sc(-c2ccccc2)nc1CC1C(NS(C)(=O)=O)CCN1C(=O)N1CCC1] | | 435.2 |
| 328 | N-((2S,3S)-2-((3'-fluorobiphenyl-3-yl) methyl)-1-(oxetan-2-ylcarbonyl) pyrrolidin-3-yl)methanesulfonamide | 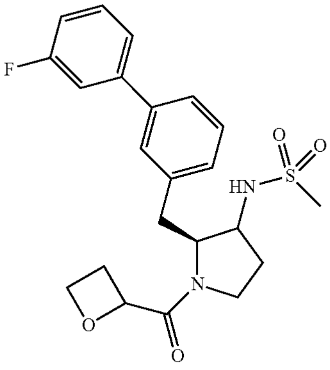 [SMILES: CS(=O)(=O)NC1CCN(C(=O)C2CCO2)[C@H]1Cc1cccc(-c2cccc(F)c2)c1] | | 433.1 |

TABLE 1-continued

| EXAMPLE | IUPACNAME | Structure | ADDITIVE | MS |
| --- | --- | --- | --- | --- |
| 329 | N-(cis-2-((6-(3-fluorophenyl)pyridin-2-yl)methyl)-1-isobutyrylpyrrolidin-3-yl) methanesulfonamide | 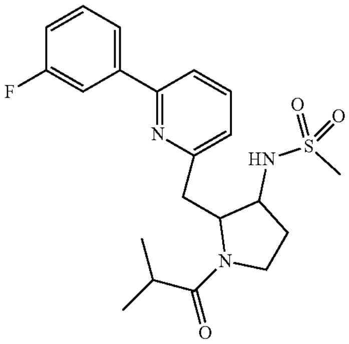 [SMILES: CC(C)C(=O)N1CCC(NS(C)(=O)=O)C1Cc1cccc(-c2cccc(F)c2)n1] | | 420.2 |
| 330 | N-(cis-1-(2,2-dimethylpropanoyl)-2-((6-(3-fluorophenyl)pyridin-2-yl)methyl) pyrrolidin-3-yl)methanesulfonamide | 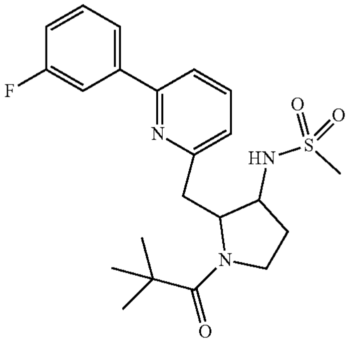 [SMILES: CC(C)(C)C(=O)N1CCC(NS(C)(=O)=O)C1Cc1cccc(-c2cccc(F)c2)n1] | | 434.2 |
| 331 | N-(cis-1-(cyclopentylcarbonyl)-2-((6-(3-fluorophenyl)pyridin-2-yl)methyl) pyrrolidin-3-yl)methanesulfonamide | 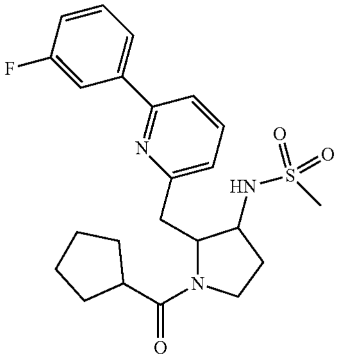 [SMILES: CS(=O)(=O)NC1CCN(C(=O)C2CCCC2)C1Cc1cccc(-c2cccc(F)c2)n1] | | 446.2 |
| 332 | N-(cis-1-(cyclopropylcarbonyl)-2-((6-(3-fluorophenyl)pyridin-2-yl)methyl) pyrrolidin-3-yl)methanesulfonamide | 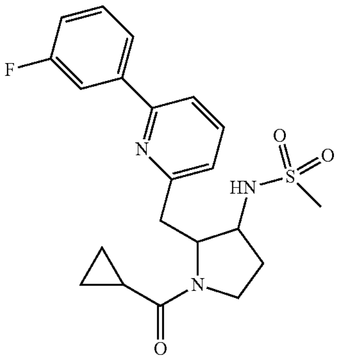 [SMILES: CS(=O)(=O)NC1CCN(C(=O)C2CC2)C1Cc1cccc(-c2cccc(F)c2)n1] | | 418.2 |

TABLE 1-continued

| EXAMPLE | IUPACNAME | Structure | ADDITIVE | MS |
|---|---|---|---|---|
| 333 | N-(cis-1-(azetidin-1-ylcarbonyl)-2-((6-(3-fluorophenyl)pyridin-2-yl)methyl) pyrrolidin-3-yl)methanesulfonamide | 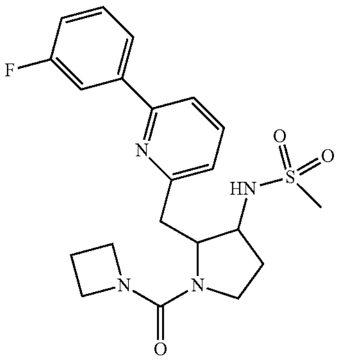 [SMILES: CS(=O)(=O)NC1CCN(C(=O)C2CCC2)C1Cc1cccc(-c2cccc(F)c2)n1] | | 433.2 |
| 334 | N-(cis-1-(cyclobutylcarbonyl)-2-((6-(3-fluorophenyl)pyridin-2-yl)methyl) pyrrolidin-3-yl)methanesulfonamide | 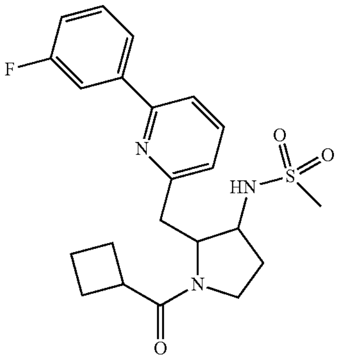 | | 432.2 |
| 335 | N-(cis-2-((6-(3-fluorophenyl)pyridin-2-yl) methyl)-1-((1-methylcyclobutyl)carbonyl) pyrrolidin-3-yl)methanesulfonamide | 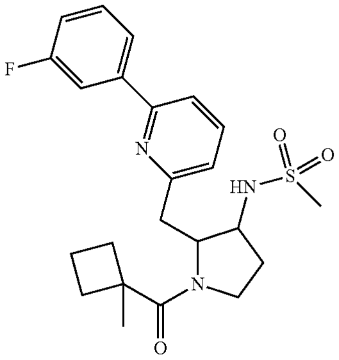 [SMILES: CC1(C(=O)N2CCC(NS(C)(=O)=O)C2Cc2cccc(-c3cccc(F)c3)n2)CCC1] | | 446.2 |
| 336 | N-(cis-1-(bicyclo[1.1.1]pent-1-ylcarbonyl)-2-((6-(3-fluorophenyl)pyridin-2-yl)methyl)pyrrolidin-3-yl)methanesulfonamide | 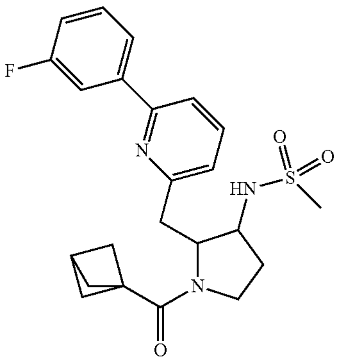 [SMILES: CS(=O)(=O)NC1CCN(C(=O)C23CC(C2)C3)C1Cc1cccc(-c2cccc(F)c2)n1] | | 444.2 |

TABLE 1-continued

| EXAM-PLE | IUPACNAME | Structure | ADDITIVE | MS |
| --- | --- | --- | --- | --- |
| 337 | N-(cis-2-((6-(3-fluorophenyl)pyridin-2-yl) methyl)-1-((1-methylcyclopropyl)carbonyl) pyrrolidin-3-yl)methanesulfonamide | 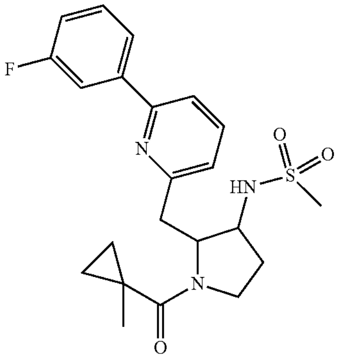 [SMILES: CC1(C(=O)N2CCC(NS(C)(=O)=O)C2Cc2cccc(-c3cccc(F)c3)n2)CC1] | | 432.2 |
| 338 | N-(cis-2-((6-(3-fluorophenyl)pyridin-2-yl) methyl)-1-((1-hydroxycyclobutyl)carbonyl) pyrrolidin-3-yl)methanesulfonamide | 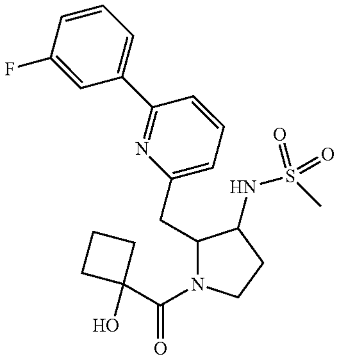 [SMILES: CS(=O)(=O)NC1CCN(C(=O)C2(O)CCC2)C1Cc1cccc(-c2cccc(F)c2)n1] | | 448.2 |
| 339 | N-((2S,3S)-2-((2-(3,5-difluorophenyl)-1,3-thiazol-4-yl)methyl-1-((1-hydroxycyclobutyl)carbonyl)pyrrolidin-3-yl)methanesulfonamide | 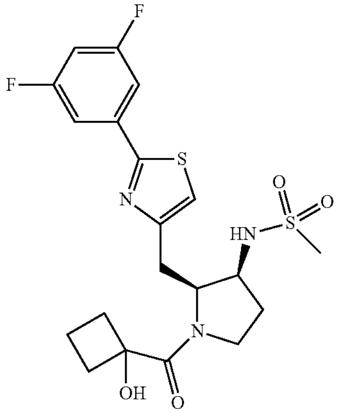 [SMILES: CS(=O)(=O)N[C@H]1CCN(C(=O)C2(O)CCC2)[C@H]1Cc1csc(-c2cc(F)cc(F)c2)n1] | | 469.9 |
| 340 | N-((2S,3S)-1-(azetidin-1-ylcarbonyl)-2-((2-(3,5-difluorophenyl)-1,3-thiazol-4-yl) methyl)pyrrolidin-3-yl)methanesulfonamide | 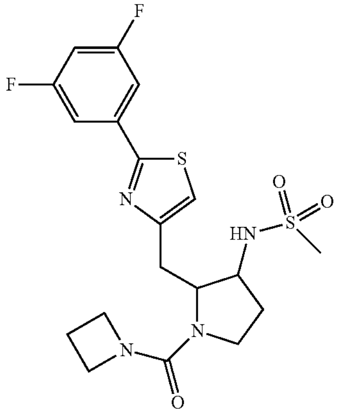 [SMILES: CS(=O)(=O)NC1CCN(C(=O)N2CCC2)C1Cc1csc(-c2cc(F)cc(F)c2)n1] | | 454.9 |

TABLE 1-continued

| EXAMPLE | IUPACNAME | Structure | ADDITIVE | MS |
|---|---|---|---|---|
| 341 | N-((2S,3S)-1-((3-fluoroazetidin-1-yl)carbonyl)-2-((3'-fluorobiphenyl-3-yl)methyl)pyrrolidin-3-yl)methanesulfonamide | 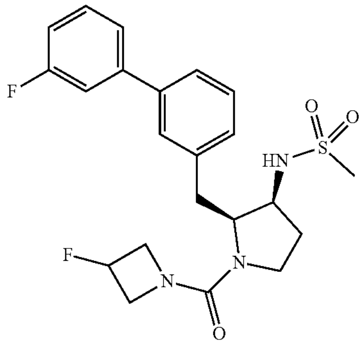 [SMILES: CS(=O)(=O)N[C@H]1CCN(C(=O)N2CC(F)C2)[C@H]1Cc1cccc(-c2cccc(F)c2)c1] | | 450.2 |
| 342 | N-((2S,3S)-1-((3,3-difluoroazetidin-1-yl)carbonyl)-2-((3'-fluorobiphenyl-3-yl)methyl)pyrrolidin-3-yl)methanesulfonamide | 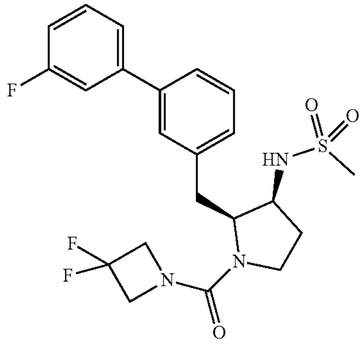 [SMILES: CS(=O)(=O)N[C@H]1CCN(C(=O)N2CC(F)(F)C2)[C@H]1Cc1cccc(-c2cccc(F)c2)c1] | | 468.1 |
| 343 | N-((2S,3S)-2-((3'-fluorobiphenyl-3-yl)methyl)-1-((2-methylazetidin-1-yl)carbonyl)pyrrolidin-3-yl)methanesulfonamide | 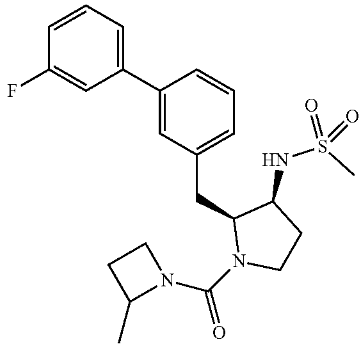 [SMILES: CC1CCN1C(=O)N1CC[C@H](NS(C)(=O)=O)[C@@H]1Cc1cccc(-c2cccc(F)c2)c1] | | 446.2 |
| 344 | N-((2S,3S)-2-((3',5'-difluorobiphenyl-3-yl)methyl)-1-((1-hydroxycyclobutyl)carbonyl)pyrrolidin-3-yl)methanesulfonamide | 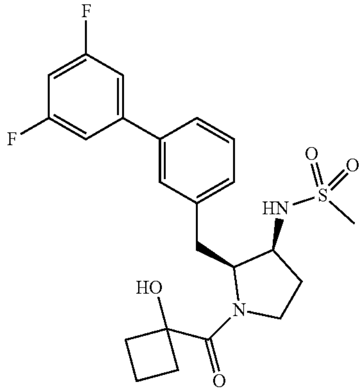 [SMILES: CS(=O)(=O)N[C@H]1CCN(C(=O)C2(O)CCC2)[C@H]1Cc1cccc(-c2cc(F)cc(F)c2)c1] | | 465.1 |

TABLE 1-continued

| EXAMPLE | IUPACNAME | Structure | ADDITIVE | MS |
| --- | --- | --- | --- | --- |
| 345 | N-((2S,3S)-1-(azetidin-1-ylcarbonyl)-2-((3',5'-difluorobiphenyl-3-yl)methyl) pyrrolidin-3-yl)methanesulfonamide | 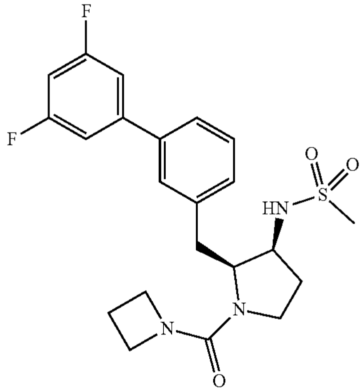 [SMILES: CS(=O)(=O)N[C@H]1CCN(C(=O)N2CCC2)[C@H]1Cc1cccc(-c2cc(F)cc(F)c2)c1] | | 450.2 |
| 346 | N-((2S,3S)-1-((1-cyanocyclobutyl) carbonyl)-2-((3'-fluorobiphenyl-3-yl) methyl)pyrrolidin-3-yl)methanesulfonamide | 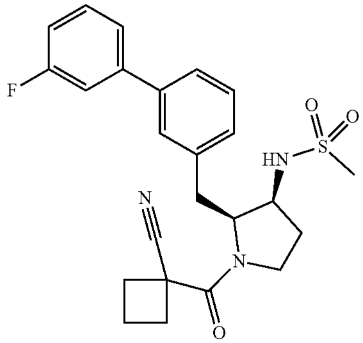 [SMILES: CS(=O)(=O)N[C@H]1CCN(C(=O)C2(C#N)CCC2)[C@H]1Cc1cccc(-c2cccc(F)c2)c1] | | 456.3 |
| 347 | N-((2S,3S)-1-(5-azaspiro[2.3]hex-5-ylcarbonyl)-2-((3'-fluorobiphenyl-3-yl) methyl)pyrrolidin-3-yl) methanesulfonamide | 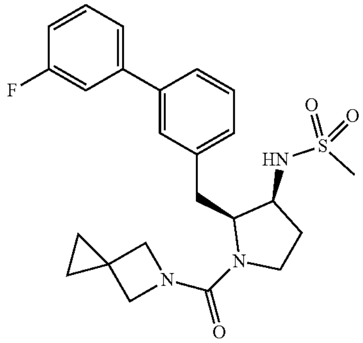 [SMILES: CS(=O)(=O)N[C@H]1CCN(C(=O)N2CC3(CC3)C2)[C@H]1Cc1cccc(-c2cccc(F)c2)c1] | | 458.3 |
| 348 | N-((2S,3S)-1-(azetidin-1-ylcarbonyl)-2-((2-(3,5-difluorophenyl)-1,3-thiazol-4-yl) methyl)pyrrolidin-3-yl)ethanesulfonamide | 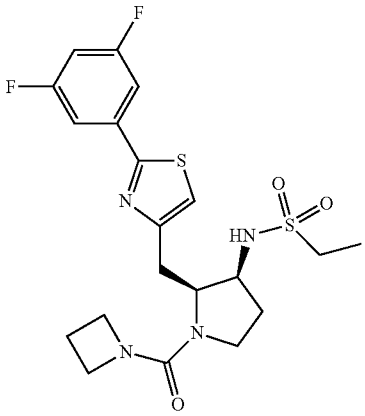 [SMILES: CCS(=O)(=O)N[C@H]1CCN(C(=O)N2CCC2)[C@H]1Cc1csc(-c2cc(F)cc(F)c2)n1] | | 471.2 |

TABLE 1-continued

| EXAMPLE | IUPACNAME | Structure | ADDITIVE | MS |
|---|---|---|---|---|
| 349 | N-((2S,3S)-2-((2,3'-difluorobiphenyl-3-yl)methyl)-1-(2,2-dimethylpropanoyl)pyrrolidin-3-yl)methanesulfonamide | 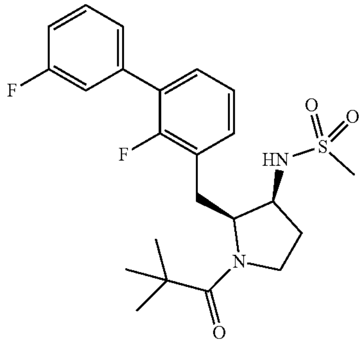 [SMILES: CC(C)(C)C(=O)N1CC[C@H](NS(C)(=O)=O)[C@@H]1Cc1cccc(-c2cccc(F)c2)c1F] | | 451.1 |
| 350 | N-((2S,3S)-1-(cyclobutylcarbonyl)-2-((2,3'-difluorobiphenyl-3-yl)methyl)pyrrolidin-3-yl)methanesulfonamide | 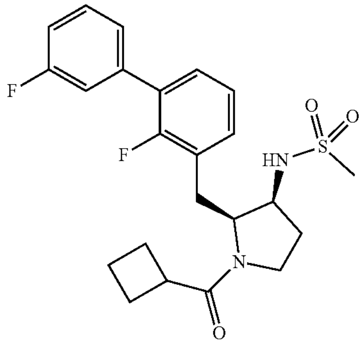 [SMILES: CS(=O)(=O)N[C@H]1CCN(C(=O)C2CCC2)[C@H]1Cc1cccc(-c2cccc(F)c2)c1F] | | 449.1 |
| 351 | N-((2S,3S)-2-((2,3'-difluorobiphenyl-3-yl)methyl)-1-((1-methylcyclopropyl)carbonyl)pyrrolidin-3-yl)methanesulfonamide | 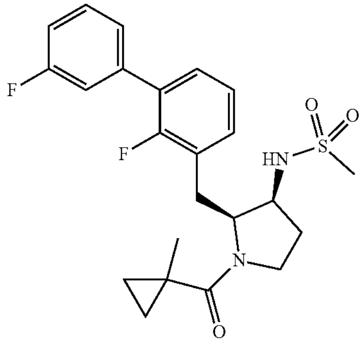 [SMILES: CC1(C(=O)N2CC[C@H](NS(C)(=O)=O)[C@@H]2Cc2cccc(-c3cccc(F)c3)c2F)CC1] | | 449.1 |
| 352 | N-((2S,3S)-1-(azetidin-1-ylcarbonyl)-2-((2,3'-difluorobiphenyl-3-yl)methyl)pyrrolidin-3-yl)methanesulfonamide | 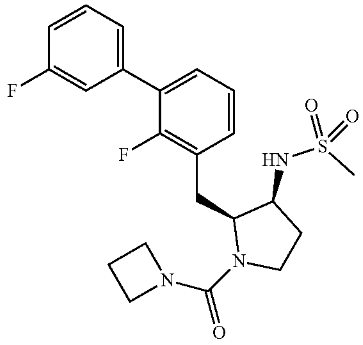 [SMILES: CS(=O)(=O)N[C@H]1CCN(C(=O)N2CCC2)[C@H]1Cc1cccc(-c2cccc(F)c2)c1F] | | 450.1 |

TABLE 1-continued

| EXAMPLE | IUPACNAME | Structure | ADDITIVE | MS |
|---|---|---|---|---|
| 353 | N-((2S,3S)-1-(azetidin-1-ylcarbonyl)-2-(biphenyl-3-ylmethyl)pyrrolidin-3-yl) methanesulfonamide | 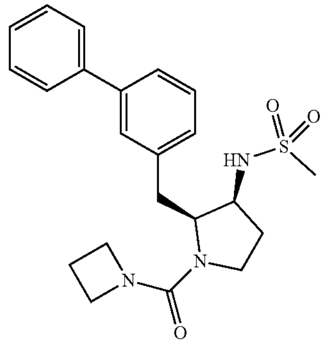 [SMILES: CS(=O)(=O)N[C@H]1CCN(C(=O)N2CCC2)[C@H]1Cc1cccc(-c2ccccc2)c1] | | 414.2 |
| 354 | (2S,3S)-2-((3'-fluorobiphenyl-3-yl) methyl)-N,N-dimethyl-3-((methylsulfonyl) amino)pyrrolidine-1-carboxamide | 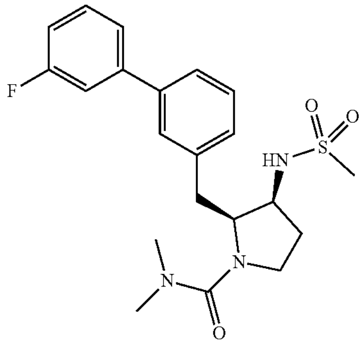 [SMILES: CN(C)C(=O)N1CC[C@H](NS(C)(=O)=O)[C@@H]1Cc1cccc(-c2cccc(F)c2)c1] | | 420.2 |
| 355 | N-((2S,3S)-1-(cyclobutylcarbonyl)-2-((2,3',5-trifluorobiphenyl-3-yl)methyl) pyrrolidin-3-yl)methanesulfonamide | 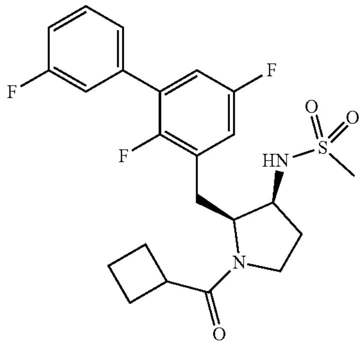 [SMILES: CS(=O)(=O)N[C@H]1CCN(C(=O)C2CCC2)[C@H]1Cc1cc(F)cc(-c2cccc(F)c2)c1F] | | 467.2 |
| 356 | N-((2S,3S)-1-(azetidin-1-ylcarbonyl)-2-((2,3',5-trifluorobiphenyl-3-yl)methyl) pyrrolidin-3-yl)methanesulfonamide | 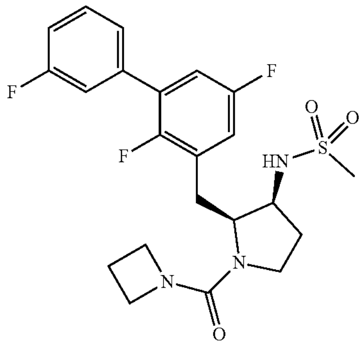 [SMILES: CS(=O)(=O)N[C@H]1CCN(C(=O)N2CCC2)[C@H]1Cc1cc(F)cc(-c2cccc(F)c2)c1F] | | 468.2 |

TABLE 1-continued

| EXAMPLE | IUPACNAME | Structure | ADDITIVE | MS |
|---|---|---|---|---|
| 357 | N-((2S,3S)-1-(cyclobutylcarbonyl)-2-((2,3',5-trifluorobiphenyl-3-yl)methyl)pyrrolidin-3-yl)ethanesulfonamide | 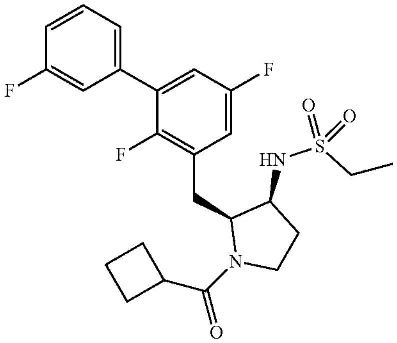 [SMILES: CCS(=O)(=O)N[C@H]1CCN(C(=O)C2CCC2)[C@H]1Cc1cc(F)cc(-c2cccc(F)c2)c1F] | | 481.2 |
| 358 | N-((2S,3S)-1-(azetidin-1-ylcarbonyl)-2-((2,3',5-trifluorobiphenyl-3-yl)methyl)pyrrolidin-3-yl)ethanesulfonamide | 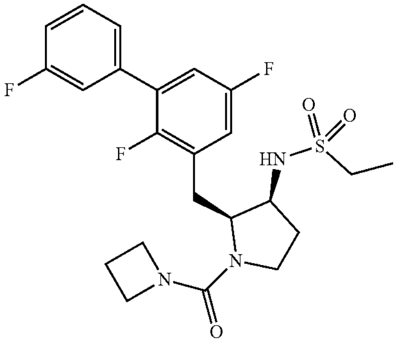 [SMILES: CCS(=O)(=O)N[C@H]1CCN(C(=O)N2CCC2)[C@H]1Cc1cc(F)cc(-c2cccc(F)c2)c1F] | | 482.2 |
| 359 | N'-((2S,3S)-1-(cyclobutylcarbonyl)-2-((2,3',5-trifluorobiphenyl-3-yl)methyl)pyrrolidin-3-yl)-N,N-dimethylsulfuric diamide | 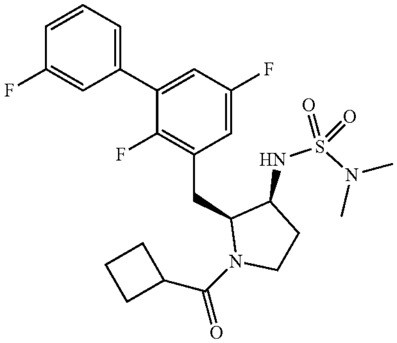 [SMILES: CN(C)S(=O)(=O)N[C@H]1CCN(C(=O)C2CCC2)[C@H]1Cc1cc(F)cc(-c2cccc(F)c2)c1F] | | 496.2 |
| 360 | N'-((2S,3S)-1-(azetidin-1-ylcarbonyl)-2-((2,3',5-trifluorobiphenyl-3-yl)methyl)pyrrolidin-3-yl)-N,N-dimethylsulfuric diamide | 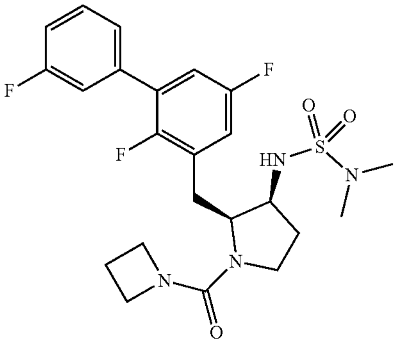 | | 497.1 |

TABLE 1-continued

| EXAMPLE | IUPACNAME | Structure | ADDITIVE | MS |
| --- | --- | --- | --- | --- |
| 361 | (2S,3S)-N-ethyl-2-((3'-fluorobiphenyl-3-yl)methyl)-N-methyl-3-((methylsulfonyl)amino)pyrrolidine-1-carboxamide | 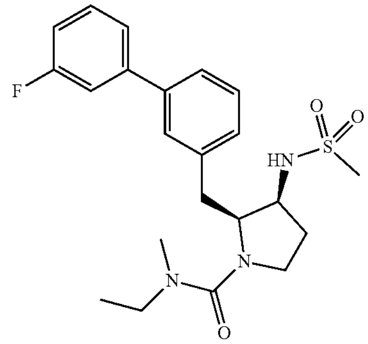 [SMILES: CCN(C)C(=O)N1CC[C@H](NS(C)(=O)=O)[C@@H]1Cc1cccc(-c2cccc(F)c2)c1] | | 434.2 |
| 362 | N-((2S,3S)-1-(azetidin-1-ylcarbonyl)-2-((3',5'-difluorobiphenyl-3-yl)methyl)pyrrolidin-3-yl)ethanesulfonamide | 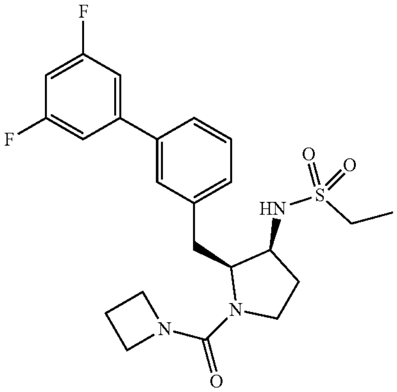 [SMILES: CCS(=O)(=O)N[C@H]1CCN(C(=O)N2CCC2)[C@H]1Cc1cccc(-c2cc(F)cc(F)c2)c1] | | 464.2 |
| 363 | N-((2S,3S)-1-(azetidin-1-ylcarbonyl)-2-((3'-fluorobiphenyl-3-yl)methyl)pyrrolidin-3-yl)ethanesulfonamide | 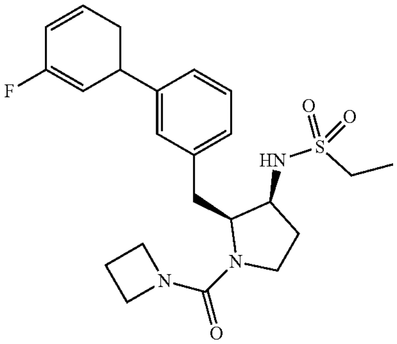 [SMILES: CCS(=O)(=O)N[C@H]1CCN(C(=O)N2CCC2)[C@H]1Cc1cccc(C2C=C(F)C=CC2)c1] | | 446.2 |
| 364 | N-((2S,3S)-1-(azetidin-1-ylcarbonyl)-2-(biphenyl-3-ylmethyl)pyrrolidin-3-yl)ethanesulfonamide | 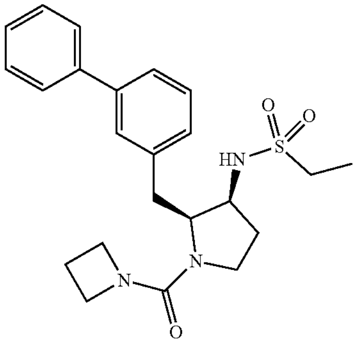 [SMILES: CCS(=O)(=O)N[C@H]1CCN(C(=O)N2CCC2)[C@H]1Cc1cccc(-c2ccccc2)c1] | | 428.3 |

TABLE 1-continued

| EXAMPLE | IUPACNAME | Structure | ADDITIVE | MS |
|---|---|---|---|---|
| 365 | (2S,3S)-3-((ethylsulfonyl)amino)-2-((3'-fluorobiphenyl-3-yl)methyl)-N,N-dimethylpyrrolidine-1-carboxamide | 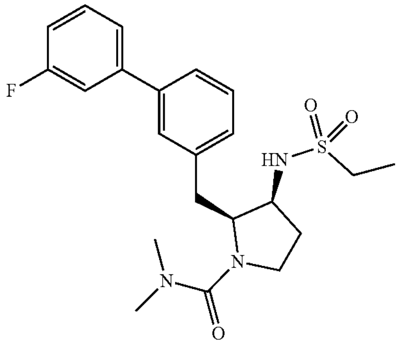 [SMILES: CCS(=O)(=O)N[C@H]1CCN(C(=O)N(C)C)[C@H]1Cc1cccc(-c2cccc(F)c2)c1] | | 434.2 |
| 366 | (2S,3S)-2-((3',5'-difluorobiphenyl-3-yl)methyl)-N,N-dimethyl-3-((methylsulfonyl)amino)pyrrolidine-1-carboxamide | 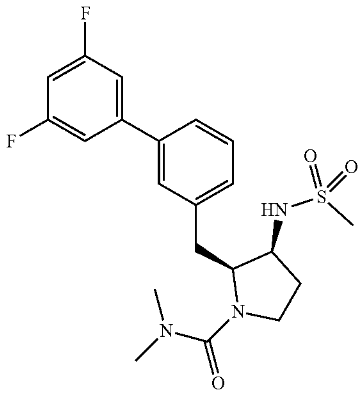 [SMILES: CN(C)C(=O)N1CC[C@H](NS(C)(=O)=O)[C@@H]1Cc1cccc(-c2cc(F)cc(F)c2)c1] | | 438.2 |
| 367 | (2S,3S)-2-((3',5'-difluorobiphenyl-3-yl)methyl)-3-((ethylsulfonyl)amino)-N,N-dimethylpyrrolidine-1-carboxamide | 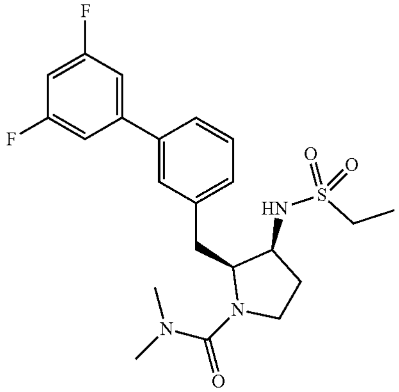 [SMILES: CCS(=O)(=O)N[C@H]1CCN(C(=O)N(C)C)[C@H]1Cc1cccc(-c2cc(F)cc(F)c2)c1] | | 452.1 |
| 368 | (2S,3S)-2-((3'-fluorobiphenyl-3-yl)methyl)-N-isopropyl-N-methyl-3-((methylsulfonyl)amino)pyrrolidine-1-carboxamide | 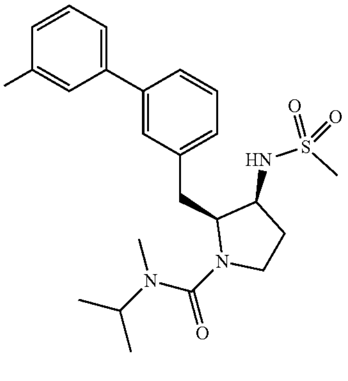 | | 448.2 |

TABLE 1-continued

| EXAMPLE | IUPACNAME | Structure | ADDITIVE | MS |
|---|---|---|---|---|
| 369 | (2S,3S)-2-((3',5'-difluorobiphenyl-3-yl) methyl)-N-ethyl-3-((ethylsulfonyl) amino)-N-methylpyrrolidine-1-carboxamide | 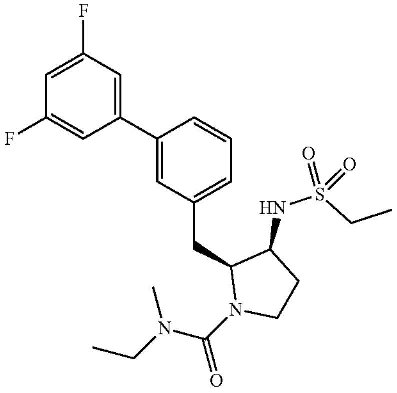 | | 466.2 |
| 370 | (2S,3S)-2-((2,3'-difluorobiphenyl-3-yl) methyl)-N,N-dimethyl-3-((methylsulfonyl) amino)pyrrolidine-1-carboxamide | 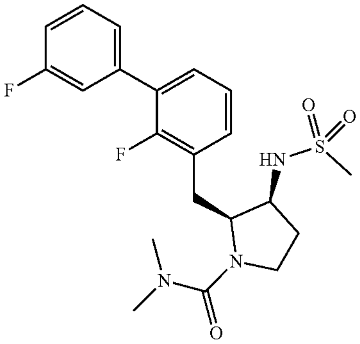 [SMILES: CN(C)C(=O)N1CC[C@H](NS(C)(=O)=O)[C@@H]1Cc1cccc(-c2cccc(F)c2)c1F] | | 438.2 |
| 371 | (2S,3S)-2-((2,3'-difluorobiphenyl-3-yl) methyl)-N-ethyl-N-methyl-3-((methylsulfonyl)amino) pyrrolidine-1-carboxamide | 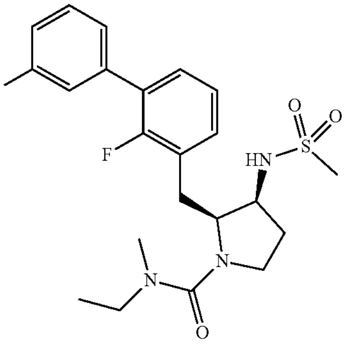 | | 452.2 |
| 372 | N-((2S,3S)-1-(azetidin-1-ylcarbonyl)-2-((2,3'-difluorobiphenyl-3-yl)methyl) pyrrolidin-3-yl)ethanesulfonamide | 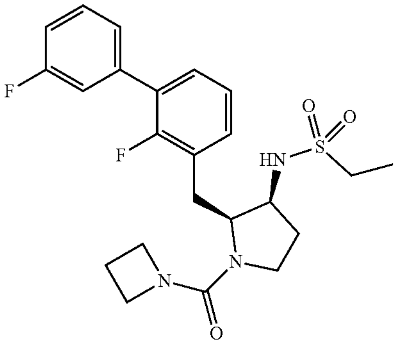 [SMILES: CCS(=O)(=O)N[C@H]1CCN(C(=O)N2CCC2)[C@H]1Cc1cccc(-c2cccc(F)c2)c1F] | | 464.2 |

TABLE 1-continued

| EXAMPLE | IUPACNAME | Structure | ADDITIVE | MS |
|---|---|---|---|---|
| 373 | (2S,3S)-2-((2,3'-difluorobiphenyl-3-yl) methyl)-3-((ethylsulfonyl)amino)-N,N-dimethylpyrrolidine-1-carboxamide | 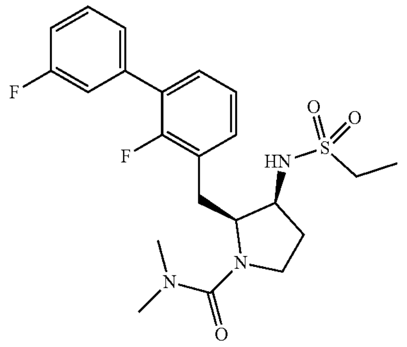 [SMILES: CCS(=O)(=O)N[C@H]1CCN(C(=O)N(C)C)[C@H]1Cc1cccc(-c2cccc(F)c2)c1F] | | 452.2 |
| 374 | N-((2S,3S)-1-(azetidin-1-ylcarbonyl)-2-((2,3'-difluorobiphenyl-3-yl)methyl) pyrrolidin-3-yl)cyclopropanesulfonamide | 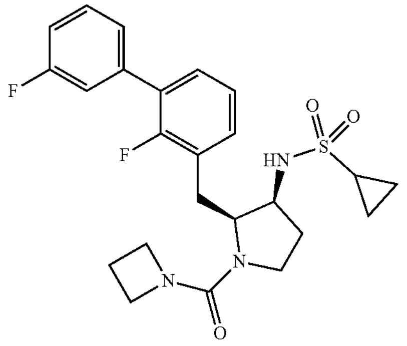 [SMILES: O=C(N1CCC1)N1CC[C@H](NS(=O)(=O)C2CC2)[C@@H]1Cc1cccc(-c2cccc(F)c2)c1F] | | 476.1 |
| 375 | (2S,3S)-3-((cyclopropylsulfonyl)amino)-2-((2,3'-difluorobiphenyl-3-yl)methyl)-N,N-dimethylpyrrolidine-1-carboxamide | 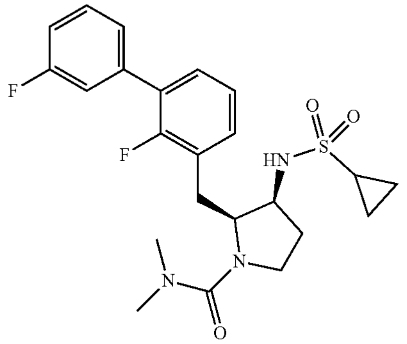 [SMILES: CN(C)C(=O)N1CC[C@H](NS(=O)(=O)C2CC2)[C@@H]1Cc1cccc(-c2cccc(F)c2)c1F] | | 464.2 |
| 376 | N'-((2S,3S)-1-(azetidin-1-ylcarbonyl)-2-((2,3'-difluorobiphenyl-3-yl)methyl) pyrrolidin-3-yl)-N,N-dimethylsulfuric diamide | 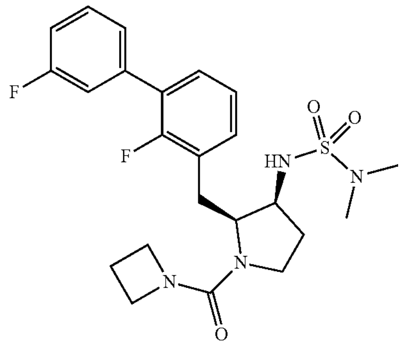 [SMILES: CN(C)S(=O)(=O)N[C@H]1CCN(C(=O)N2CCC2)[C@H]1Cc1cccc(-c2cccc(F)c2)c1F] | | 479.2 |

TABLE 1-continued

| EXAMPLE | IUPACNAME | Structure | ADDITIVE | MS |
|---|---|---|---|---|
| 377 | (2S,3S)-2-((2,3'-difluorobiphenyl-3-yl) methyl)-3-((dimethylsulfamoyl)amino)-N,N-dimethylpyrrolidine-1-carboxamide | 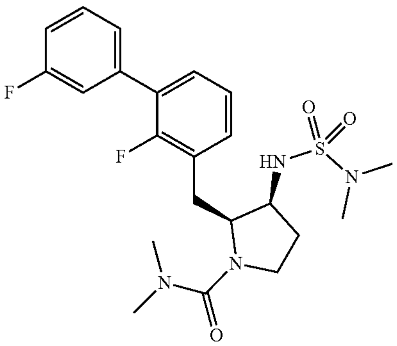 [SMILES: CN(C)C(=O)N1CC[C@H](NS(=O)(=O)N(C)C)[C@@H]1Cc1cccc(-c2cccc(F)c2)c1F] | | 467.2 |
| 378 | N-((2S,3S)-1-(azetidin-1-ylcarbonyl)-2-((2,3',5'-trifluorobiphenyl-3-yl)methyl) pyrrolidin-3-yl)methanesulfonamide | 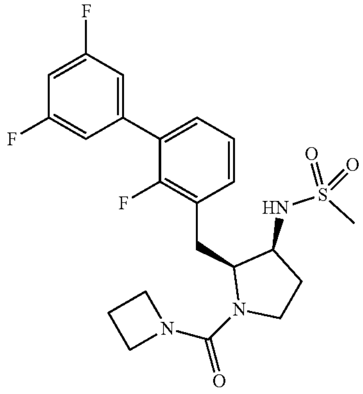 [SMILES: CS(=O)(=O)N[C@H]1CCN(C(=O)N2CCC2)[C@H]1Cc1cccc(-c2cc(F)cc(F)c2)c1F] | | 468.2 |
| 379 | (2S,3S)-N,N-dimethyl-3-((methylsulfonyl) amino)-2-((2,3',5'-trifluorobiphenyl-3-yl) methyl)pyrrolidine-1-carboxamide | 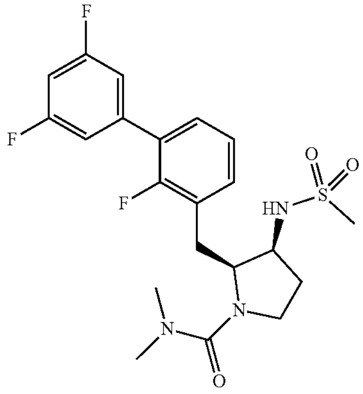 [SMILES: CN(C)C(=O)N1CC[C@H](NS(C)(=O)=O)[C@@H]1Cc1cccc(-c2cc(F)cc(F)c2)c1F] | | 456.2 |
| 380 | N-((2S,3S)-1-(azetidin-1-ylcarbonyl)-2-((3'-chloro-2-fluorobiphenyl-3-yl)methyl) pyrrolidin-3-yl)methanesulfonamide | 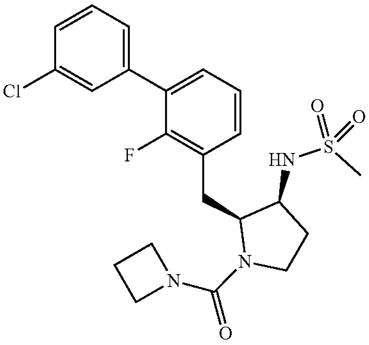 [SMILES: CS(=O)(=O)N[C@H]1CCN(C(=O)N2CCC2)[C@H]1Cc1cccc(-c2cccc(Cl)c2)c1F] | | 466.1 |

TABLE 1-continued

| EXAMPLE | IUPACNAME | Structure | ADDITIVE | MS |
|---|---|---|---|---|
| 381 | (2S,3S)-2-((3'-chloro-2-fluorobiphenyl-3-yl)methyl)-N,N-dimethyl-3-((methylsulfonyl)amino)pyrrolidine-1-carboxamide | 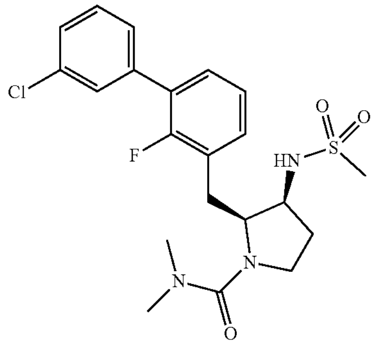 [SMILES: CN(C)C(=O)N1CC[C@H](NS(C)(=O)=O)[C@@H]1Cc1cccc(-c2cccc(Cl)c2)c1F] | | 454.1 |
| 382 | (2S,3S)-2-((3',5'-difluorobiphenyl-3-yl)methyl)-N-methoxy-N-methyl-3-((methylsulfonyl)amino)pyrrolidine-1-carboxamide | 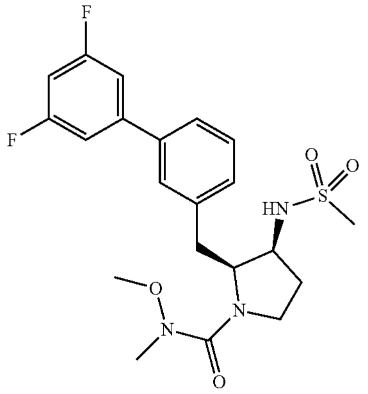 [SMILES: CON(C)C(=O)N1CC[C@H](NS(C)(=O)=O)[C@@H]1Cc1cccc(-c2cc(F)cc(F)c2)c1] | | 454.2 |
| 383 | (2S,3S)-2-((2-fluorobiphenyl-3-yl)methyl)-N,N-dimethyl-3-(methylsulfonyl)amino)pyrrolidine-1-carboxamide | 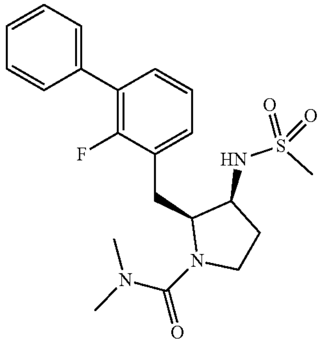 [SMILES: CN(C)C(=O)N1CC[C@H](NS(C)(=O)=O)[C@@H]1Cc1cccc(-c2ccccc2)c1F] | | 420.2 |
| 384 | N-((2S,3S)-1-(azetidin-1-ylcarbonyl)-2-((2-fluorobiphenyl-3-yl)methyl)pyrrolidin-3-yl)methanesulfonamide | 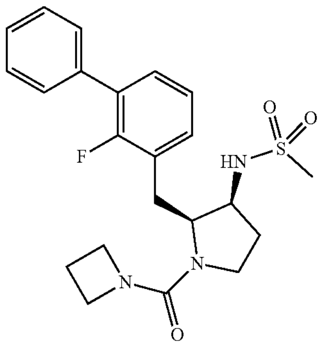 [SMILES: CS(=O)(=O)N[C@H]1CCN(C(=O)N2CCC2)[C@H]1Cc1cccc(-c2ccccc2)c1F] | | 432.1 |

TABLE 1-continued

| EXAMPLE | IUPACNAME | Structure | ADDITIVE | MS |
|---|---|---|---|---|
| 385 | (2S,3S)-2-(biphenyl-3-ylmethyl)-3-((ethylsulfonyl)amino)-N,N-dimethylpyrrolidine-1-carboxamide | 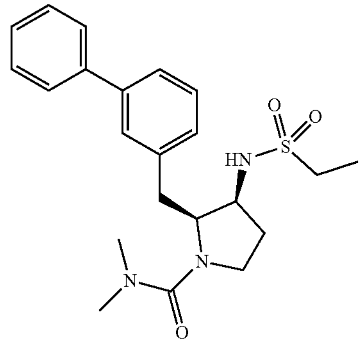 [SMILES: CCS(=O)(=O)N[C@H]1CCN(C(=O)N(C)C)[C@H]1Cc1cccc(-c2ccccc2)c1] | | 416.2 |
| 386 | N-((2S,3S)-2-((2,3'-difluorobiphenyl-3-yl)methyl)-1-((1-hydroxycyclobutyl) carbonyl)pyrrolidin-3-yl) methanesulfonamide | 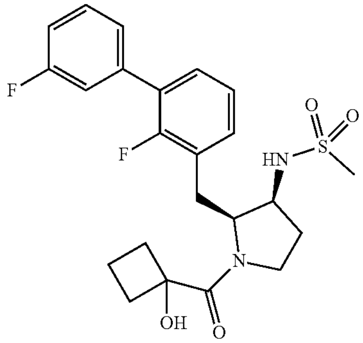 [SMILES: CS(=O)(=O)N[C@H]1CCN(C(=O)C2(O)CCC2)[C@H]1Cc1cccc(-c2cccc(F)c2)c1F] | | 465.2 |
| 387 | N-((2S,3S)-2-((2,3'-difluorobiphenyl-3-yl)methyl)-1-(2-hydroxy-2-methylpropanoyl) pyrrolidin-3-yl)methanesulfonamide | 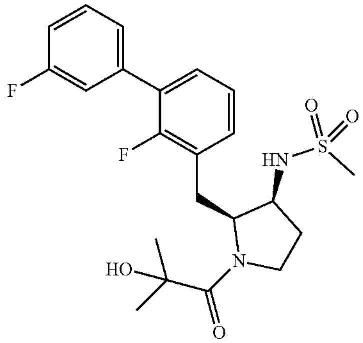 [SMILES: CC(C)(O)C(=O)N1CC[C@H](NS(C)(=O)=O)[C@@H]1Cc1cccc(-c2cccc(F)c2)c1F] | | 453.2 |
| 388 | N-((2S,3S)-2-((2,3'-difluorobiphenyl-3-yl)methyl)-1-((1-hydroxycyclobutyl) carbonyl)pyrrolidin-3-yl)ethanesulfonamide | 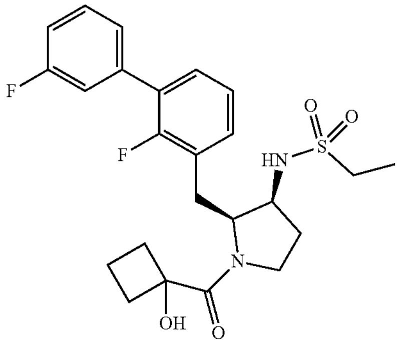 [SMILES: CCS(=O)(=O)N[C@H]1CCN(C(=O)C2(O)CCC2)[C@H]1Cc1cccc(-c2cccc(F)c2)c1F] | | 479.2 |

TABLE 1-continued

| EXAMPLE | IUPACNAME | Structure | ADDITIVE | MS |
|---|---|---|---|---|
| 389 | N-((2S,3S)-2-((2,3'-difluorobiphenyl-3-yl)methyl)-1-(2-hydroxy-2-methylpropanoyl)pyrrolidin-3-yl)ethanesulfonamide | 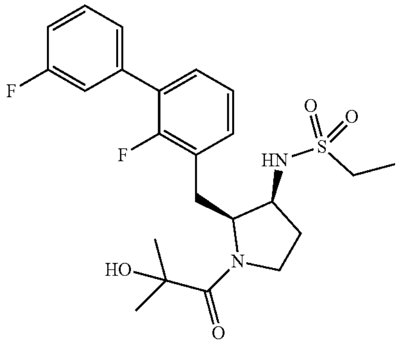 [SMILES: CCS(=O)(=O)N[C@H]1CCN(C(=O)C(C)(C)O)[C@H]1Cc1cccc(-c2cccc(F)c2)c1F] | | 465.1 |
| 390 | N-((2S,3S)-2-((2,3'-difluorobiphenyl-3-yl)methyl)-1-((1-hydroxycyclobutyl)carbonyl)pyrrolidin-3-yl)cyclopropanesulfonamide | 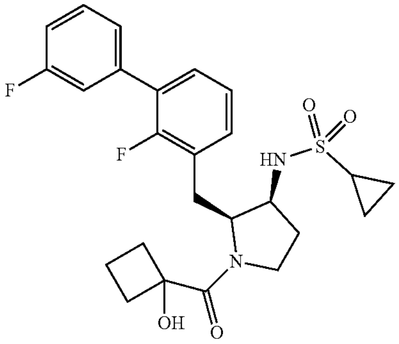 [SMILES: O=C(N1CC[C@H](NS(=O)(=O)C2CC2)[C@@H]1Cc1cccc(-c2cccc(F)c2)c1F)C1(O)CCC1] | | 491.2 |
| 391 | N-((2S,3S)-2-((2,3'-difluorobiphenyl-3-yl)methyl)-1-(2-hydroxy-2-methylpropanoyl)pyrrolidin-3-yl)cyclopropanesulfonamide | 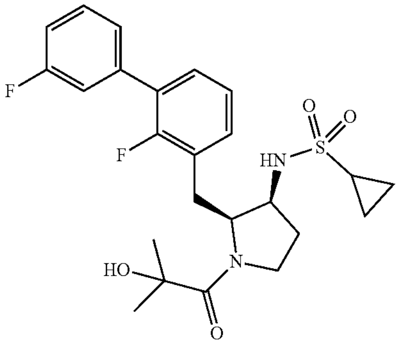 [SMILES: CC(C)(O)C(=O)N1CC[C@H](NS(=O)(=O)C2CC2)[C@@H]1Cc1cccc(-c2cccc(F)c2)c1F] | | 477.2 |
| 392 | N'-((2S,3S)-2-((2,3'-difluorobiphenyl-3-yl)methyl)-1-((1-hydroxycyclobutyl)carbonyl)pyrrolidin-3-yl)-N,N-dimethylsulfuric diamide | 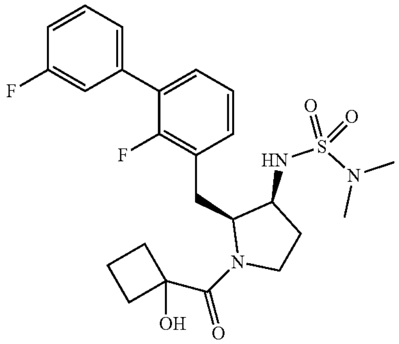 [SMILES: CN(C)S(=O)(=O)N[C@H]1CCN(C(=O)C2(O)CCC2)[C@H]1Cc1cccc(-c2cccc(F)c2)c1F] | | 494.2 |

TABLE 1-continued

| EXAMPLE | IUPACNAME | Structure | ADDITIVE | MS |
|---|---|---|---|---|
| 393 | N'-((2S,3S)-2-((2,3'-difluorobiphenyl-3-yl) methyl)-1-(2-hydroxy-2-methylpropanoyl) pyrrolidin-3-yl)-N,N-dimethylsulfuric diamide | 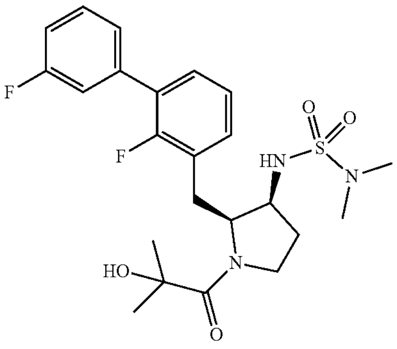 [SMILES: CN(C)S(=O)(=O)N[C@H]1CCN(C(=O)C(C)(C)O)[C@H]1Cc1cccc(-c2cccc(F)c2)c1F] | | 482.2 |
| 394 | N-((2S,3S)-1-((1-hydroxycyclobutyl) carbonyl)-2-((2,3',5'-trifluorobiphenyl-3-yl)methyl)pyrrolidin-3-yl)methanesulfonamide | 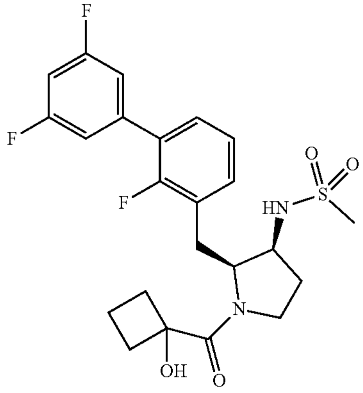 [SMILES: CS(=O)(=O)N[C@H]1CCN(C(=O)C2(O)CCC2)[C@H]1Cc1cccc(-c2cc(F)cc(F)c2)c1F] | | 481.1 |
| 395 | N-((2S,3S)-1-(2-hydroxy-2-methyl-propanoyl)-2-((2,3',5'-trifluorobiphenyl-3-yl)methyl)pyrrolidin-3-yl)methanesulfonamide | 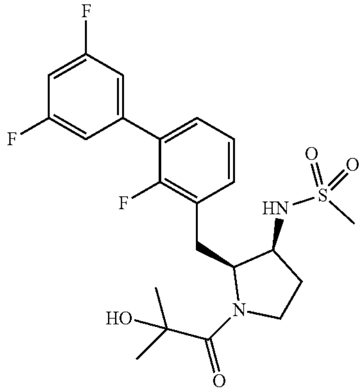 [SMILES: CC(C)(O)C(=O)N1CC[C@H](NS(C)(=O)=O)[C@@H]1Cc1cccc(-c2cc(F)cc(F)c2)c1F] | | 469.1 |
| 396 | N-((2S,3S)-2-((3'-chloro-2-fluorobiphenyl-3-yl)methyl)-1-((1-hydroxycyclobutyl)carbonyl)pyrrolidin-3-yl)methanesulfonamide | 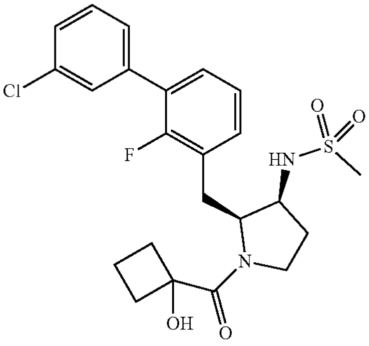 [SMILES: CS(=O)(=O)N[C@H]1CCN(C(=O)C2(O)CCC2)[C@H]1Cc1cccc(-c2cccc(Cl)c2)c1F] | | 481.1 |

TABLE 1-continued

| EXAMPLE | IUPACNAME | Structure | ADDITIVE | MS |
|---|---|---|---|---|
| 397 | N-((2S,3S)-2-((3'-chloro-2-fluorobiphenyl-3-yl)methyl)-1-(2-hydroxy-2-methylpropanoyl)pyrrolidin-3-yl) methanesulfonamide | 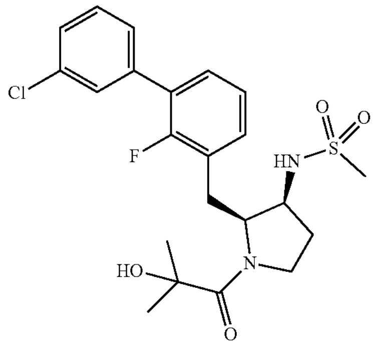 [SMILES: CC(C)(O)C(=O)N1CC[C@H](NS(C)(=O)=O)[C@@H]1Cc1cccc(-c2cccc(Cl)c2)c1F] | | 469.2 |
| 398 | (2S,3S)-3-((ethylsulfonyl)amino)-2-((2-fluorobiphenyl-3-yl)methyl)-N,N-dimethylpyrrolidine-1-carboxamide | 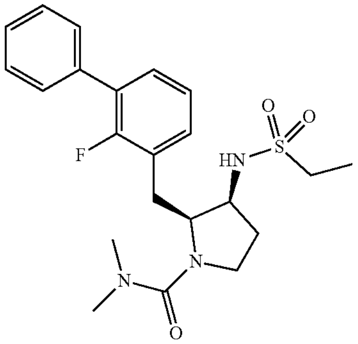 [SMILES: CCS(=O)(=O)N[C@H]1CCN(C(=O)N(C)C)[C@H]1Cc1cccc(-c2ccccc2)c1F] | | 434.2 |
| 399 | (2S,3S)-3-((ethylsulfonyl)amino)-N,N-dimethyl-2-((2,3',5'-trifluorobiphenyl-3-yl)methyl)pyrrolidine-1-carboxamide | 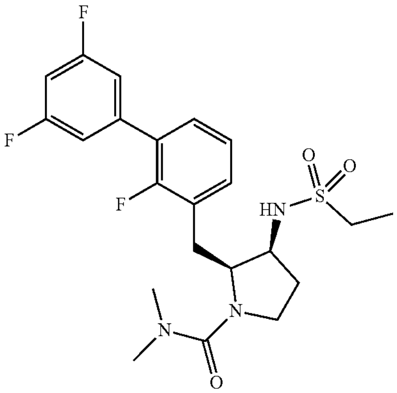 [SMILES: CCS(=O)(=O)N[C@H]1CCN(C(=O)N(C)C)[C@H]1Cc1cccc(-c2cc(F)cc(F)c2)c1F] | | 470.2 |
| 400 | (2S,3S)-2-(biphenyl-3-ylmethyl)-N,N-dimethyl-3-((methylsulfonyl)amino) pyrrolidine-1-carboxamide | 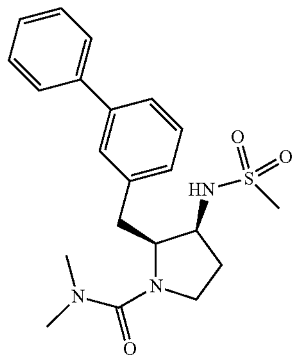 [SMILES: CN(C)C(=O)N1CC[C@H](NS(C)(=O)=O)[C@@H]1Cc1cccc(-c2ccccc2)c1] | | 402.2 |

TABLE 1-continued

| EXAMPLE | IUPACNAME | Structure | ADDITIVE | MS |
|---|---|---|---|---|
| 401 | (2S,3S)-2-((2,3'-difluorobiphenyl-3-yl) methyl)-3-((ethylsulfonyl)amino)-N-methoxy-N-methylpyrrolidine-1-carboxamide | 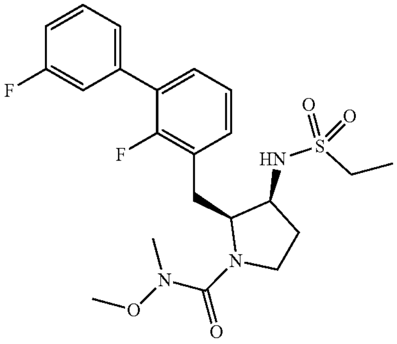 [SMILES: CCS(=O)(=O)N[C@H]1CCN(C(=O)N(C)OC)[C@H]1Cc1cccc(-c2cccc(F)c2)c1F] | | 468.1 |
| 402 | N-((2S,3S)-1-isobutyryl-2-((2,3',5'-trifluorobiphenyl-3-yl)methyl) pyrrolidin-3-yl)methanesulfonamide | 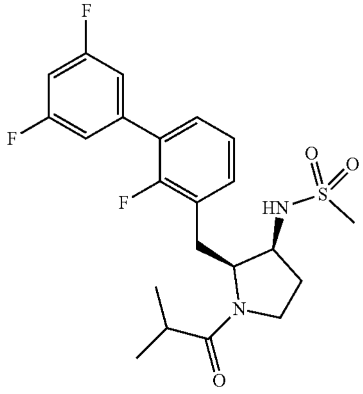 [SMILES: CC(C)C(=O)N1CC[C@H](NS(C)(=O)=O)[C@@H]1Cc1cccc(-c2cc(F)cc(F)c2)c1F] | | 455.2 |
| 403 | (2S,3S)-N-methoxy-N-methyl-3-((methylsulfonyl)amino)-2-((2,3',5'-trifluorobiphenyl-3-yl)methyl)pyrrolidine-1-carboxamide | 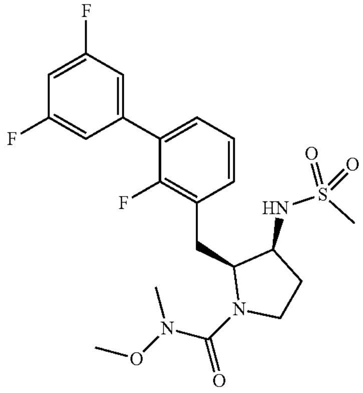 [SMILES: CON(C)C(=O)N1CC[C@H](NS(C)(=O)=O)[C@@H]1Cc1cccc(-c2cc(F)cc(F)c2)c1F] | | 472.2 |
| 404 | N-((2S,3S)-2-((3',5'-difluorobiphenyl-3-yl)methyl)-1-(2-hydroxy-2-methylpropanoyl) pyrrolidin-3-yl)ethanesulfonamide | 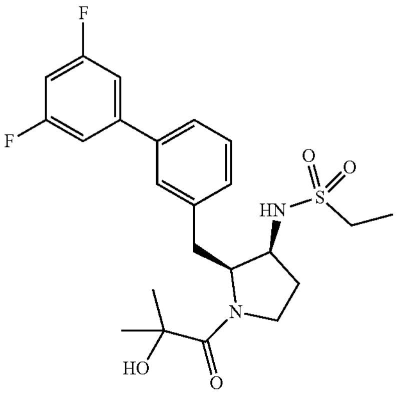 [SMILES: CCS(=O)(=O)N[C@H]1CCN(C(=O)C(C)(C)O)[C@H]1Cc1cccc(-c2cc(F)cc(F)c2)c1] | | 465.1 |

TABLE 1-continued

| EXAMPLE | IUPACNAME | Structure | ADDITIVE | MS |
|---|---|---|---|---|
| 405 | N-((2S,3S)-2-((3',5'-difluorobiphenyl-3-yl)methyl)-1-(oxetan-2-ylcarbonyl) pyrrolidin-3-yl)ethanesulfonamide | 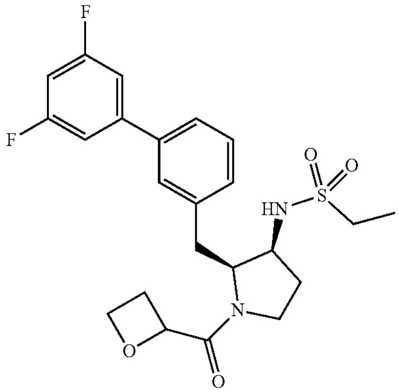 [SMILES: CCS(=O)(=O)N[C@H]1CCN(C(=O)C2CCO2)[C@H]1Cc1cccc(-c2cc(F)cc(F)c2)c1] | | 463.1 |
| 406 | (2S,3S)-2-((3'-fluorobiphenyl-3-yl) methyl)-N-methoxy-N-methyl-3-((methylsulfonyl)amino)pyrrolidine-1-carboxamide | 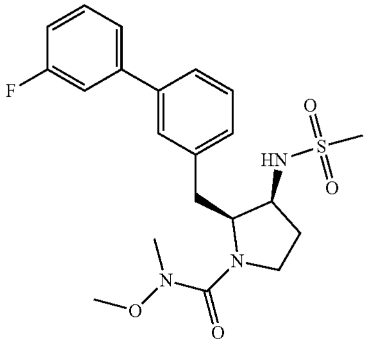 [SMILES: CON(C)C(=O)N1CC[C@H](NS(C)(=O)=O)[C@@H]1Cc1cccc(-c2cccc(F)c2)c1] | | 436.2 |
| 407 | (2S,3S)-2-(biphenyl-3-ylmethyl)-3-((ethylsulfonyl)amino)-N-methoxy-N-methylpyrrolidine-1-carboxamide | 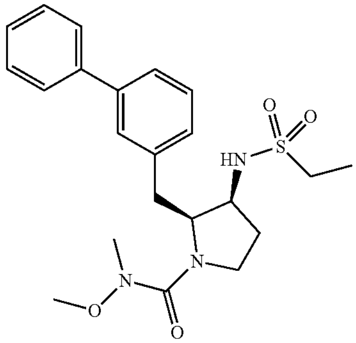 [SMILES: CCS(=O)(=O)N[C@H]1CCN(C(=O)N(C)OC)[C@H]1Cc1cccc(-c2ccccc2)c1] | | 432.2 |
| 408 | (2S,3S)-2-((2-fluorobiphenyl-3-yl)methyl)-N-methoxy-N-methyl-3-((methylsulfonyl)amino) pyrrolidine-1-carboxamide | 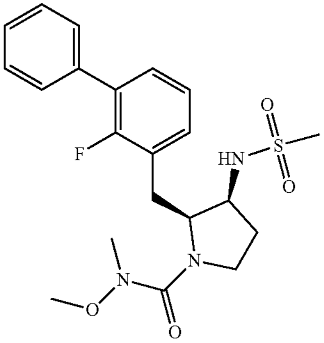 [SMILES: CON(C)C(=O)N1CC[C@H](NS(C)(=O)=O)[C@@H]1Cc1cccc(-c2ccccc2)c1F] | | 436.2 |

TABLE 1-continued

| EXAMPLE | IUPACNAME | Structure | ADDITIVE | MS |
| --- | --- | --- | --- | --- |
| 409 | (2S,3S)-2-(biphenyl-3-ylmethyl)-N-methoxy-N-methyl-3-((methylsulfonyl)amino) pyrrolidine-1-carboxamide | 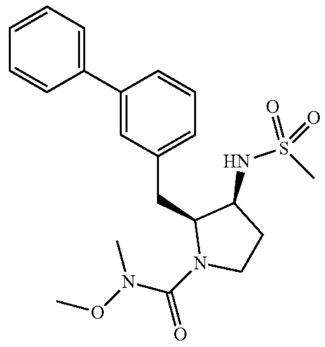 [SMILES: CON(C)C(=O)N1CC[C@H](NS(C)(=O)=O)[C@@H]1Cc1cccc(-c2ccccc2)c1] | | 418.2 |
| 410 | N-((2S,3S)-2-((2-fluoro-3'-methylbiphenyl-3-yl)methyl)-1-(2-hydroxy-2-methylpropanoyl)pyrrolidin-3-yl)methanesulfonamide | 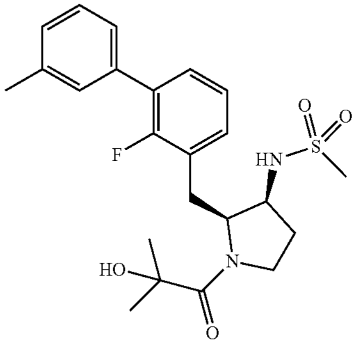 [SMILES: Cc1cccc(-c2cccc(C[C@H]3[C@@H](NS(C)(=O)=O)CCN3C(=O)C(C)(C)O)c2F)c1] | | 449.2 |
| 411 | N-((2S,3S)-2-((2,3'-difluoro-5'-methylbiphenyl-3-yl)methyl)-1-(2-hydroxy-2-methylpropanoyl) pyrrolidin-3-yl)methanesulfonamide | 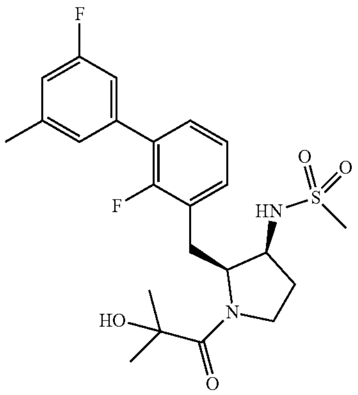 [SMILES: Cc1cc(F)cc(-c2cccc(C[C@H]3[C@@H](NS(C)(=O)=O)CCN3C(=O)C(C)(C)O)c2F)c1] | | 467.2 |
| 412 | N-((2S,3S)-2-((3'-fluorobiphenyl-3-yl) methyl)-1-(2-methoxy-2-methylpropanoyl) pyrrolidin-3-yl)methanesulfonamide | 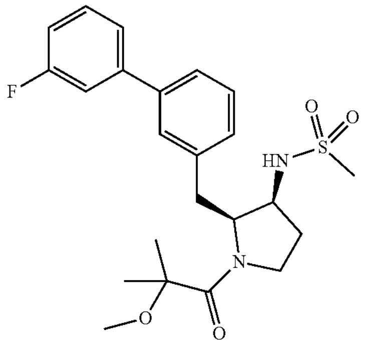 [SMILES: COC(C)(C)C(=O)N1CC[C@H](NS(C)(=O)=O)[C@@H]1Cc1cccc(-c2cccc(F)c2)c1] | | 449.2 |

TABLE 1-continued

| EXAMPLE | IUPACNAME | Structure | ADDITIVE | MS |
|---|---|---|---|---|
| 413 | N-((2S,3S)-1-(2-hydroxy-2-methyl-propanoyl)-2-((2,2',3'-trifluorobiphenyl-3-yl)methyl)pyrrolidin-3-yl)methanesulfonamide | 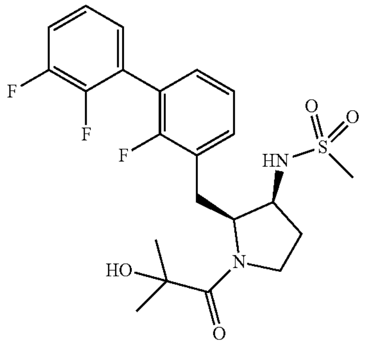 [SMILES: CC(C)(O)C(=O)N1CC[C@H](NS(C)(=O)=O)[C@@H]1Cc1cccc(-c2cccc(F)c2F)c1F] | | 471.2 |
| 414 | N-((2S,3S)-2-((2,2'-difluorobiphenyl-3-yl)methyl)-1-(2-hydroxy-2-methylpropanoyl)pyrrolidin-3-yl)methanesulfonamide | 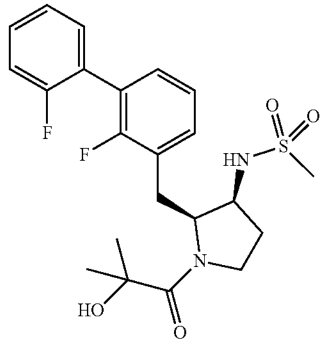 [SMILES: CC(C)(O)C(=O)N1CC[C@H](NS(C)(=O)=O)[C@@H]1Cc1cccc(-c2ccccc2F)c1F] | | 453.2 |
| 415 | 1-fluoro-N-((2S,3S)-2-((3'-fluorobiphenyl-3-yl)methyl)-1-(2-hydroxy-2-methylpropanoyl)pyrrolidin-3-yl)methanesulfonamide | 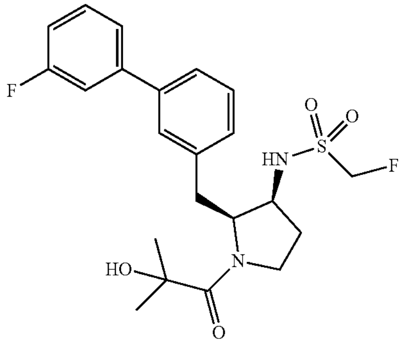 [SMILES: CC(C)(O)C(=O)N1CC[C@H](NS(=O)(=O)CF)[C@@H]1Cc1cccc(-c2cccc(F)c2)c1] | | 451.0 |
| 416 | 1,1-difluoro-N-((2S,3S)-2-((3'-fluorobiphenyl-3-yl)methyl)-1-(2-hydroxy-2-methylpropanoyl)pyrrolidin-3-yl)methanesulfonamide | 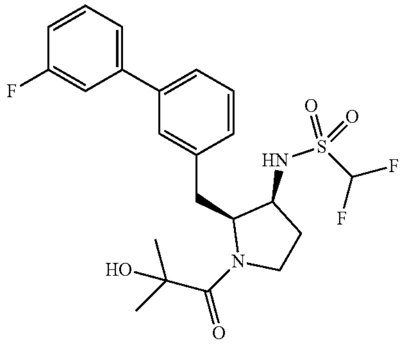 [SMILES: CC(C)(O)C(=O)N1CC[C@H](NS(=O)(=O)C(F)F)[C@@H]1Cc1cccc(-c2cccc(F)c2)c1] | | 468.9 |

TABLE 1-continued

| EXAMPLE | IUPACNAME | Structure | ADDITIVE | MS |
| --- | --- | --- | --- | --- |
| 417 | N-((2S,3S)-2-((2,3'-difluorobiphenyl-3-yl)methyl)-1-(2-hydroxy-2-methylpropanoyl)pyrrolidin-3-yl)-1-fluoromethanesulfonamide | 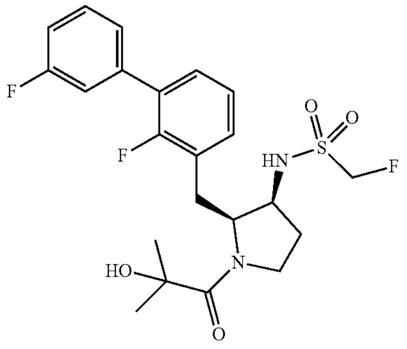 [SMILES: CC(C)(O)C(=O)N1CC[C@H](NS(=O)(=O)CF)[C@@H]1Cc1cccc(-c2cccc(F)c2)c1F] | | 469.1 |
| 418 | N-((2S,3S)-2-((2,3'-difluorobiphenyl-3-yl)methyl)-1-(2-hydroxy-2-methylpropanoyl)pyrrolidin-3-yl)-1,1-difluoromethanesulfonamide | 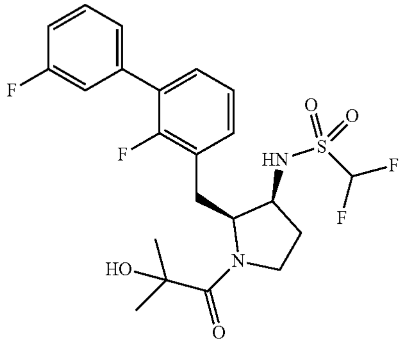 [SMILES: CC(C)(O)C(=O)N1CC[C@H](NS(=O)(=O)C(F)F)[C@@H]1Cc1cccc(-c2cccc(F)c2)c1F] | | 487.0 |
| 419 | N-((2S,3S)-2-((2,3'-difluorobiphenyl-3-yl)methyl)-1-(2-hydroxy-2-methylpropanoyl)pyrrolidin-3-yl)-1-methoxymethanesulfonamide | 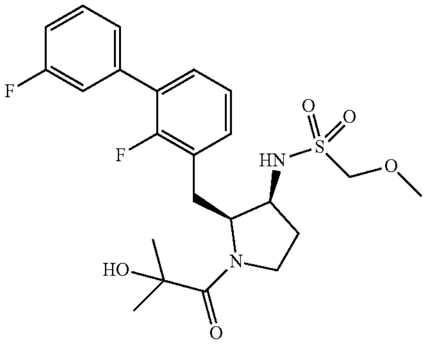 [SMILES: COCS(=O)(=O)N[C@H]1CCN(C(=O)C(C)(C)O)[C@H]1Cc1cccc(-c2cccc(F)c2)c1F] | | 483.2 |
| 420 | N-((2S,3S)-1-(2-hydroxy-2-methyl-propanoyl)-2-((2,3',5'-trifluorobiphenyl-3-yl)methyl)pyrrolidin-3-yl)-1-methoxymethanesulfonamide | 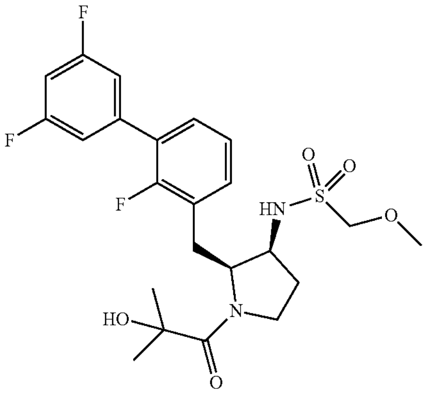 [SMILES: COCS(=O)(=O)N[C@H]1CCN(C(=O)C(C)(C)O)[C@H]1Cc1cccc(-c2cc(F)cc(F)c2)c1F] | | 499.1 |

TABLE 1-continued

| EXAMPLE | IUPACNAME | Structure | ADDITIVE | MS |
| --- | --- | --- | --- | --- |
| 421 | N-((2S,3S)-2-((3',5'-difluorobiphenyl-3-yl)methyl)-1-(2-hydroxy-2-methylpropanoyl)pyrrolidin-3-yl)-1-fluoromethanesulfonamide | 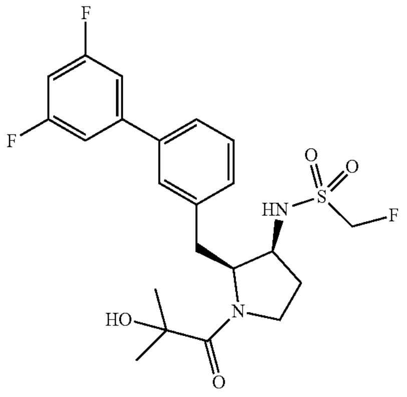 [SMILES: CC(C)(O)C(=O)N1CC[C@H](NS(=O)(=O)CF)[C@@H]1Cc1cccc(-c2cc(F)cc(F)c2)c1] | | 469.1 |
| 422 | N-((2S,3S)-2-((3',5'-difluorobiphenyl-3-yl)methyl)-1-(2-hydroxy-2-methylpropanoyl)pyrrolidin-3-yl)-1,1-difluoromethanesulfonamide | 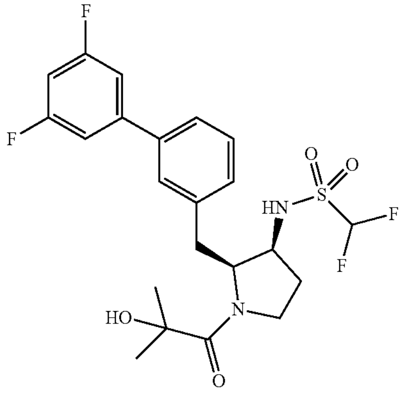 [SMILES: CC(C)(O)C(=O)N1CC[C@H](NS(=O)(=O)C(F)F)[C@@H]1Cc1cccc(-c2cc(F)cc(F)c2)c1] | | 487.0 |
| 423 | 1-fluoro-N-((2S,3S)-1-(2-hydroxy-2-methylpropanoyl)-2-((2,3',5'-trifluorobiphenyl-3-yl)methyl) pyrrolidin-3-yl)methanesulfonamide | 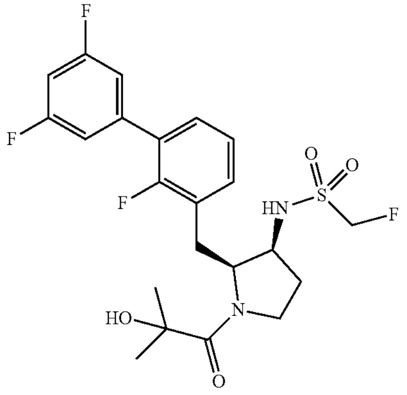 [SMILES: CC(C)(O)C(=O)N1CC[C@H](NS(=O)(=O)CF)[C@@H]1Cc1cccc(-c2cc(F)cc(F)c2)c1F] | | 487.1 |
| 424 | 1,1-difluoro-N-((2S,3S)-1-(2-hydroxy-2-methylpropanoyl)-2-((2,3',5'-trifluorobiphenyl-3-yl)methyl) pyrrolidin-3-yl)methanesulfonamide | 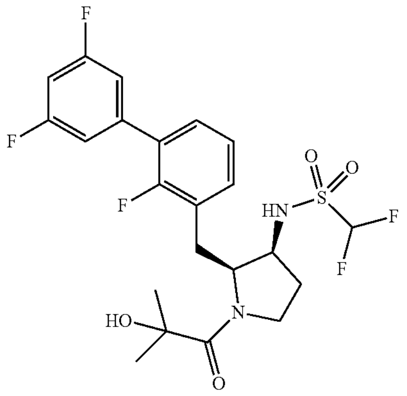 [SMILES: CC(C)(O)C(=O)N1CC[C@H](NS(=O)(=O)C(F)F)[C@@H]1Cc1cccc(-c2cc(F)cc(F)c2)c1F] | | 505.1 |

TABLE 1-continued

| EXAMPLE | IUPACNAME | Structure | ADDITIVE | MS |
|---|---|---|---|---|
| 425 | N-((2S,3S)-2-((2',3'-difluorobiphenyl-3-yl) methyl)-1-(2-hydroxy-2-methylpropanoyl) pyrrolidin-3-yl)ethanesulfonamide | 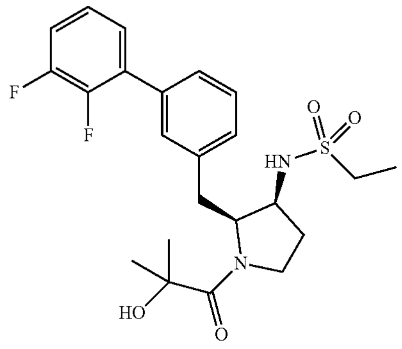 [SMILES: CCS(=O)(=O)N[C@H]1CCN(C(=O)C(C)(C)O)[C@H]1Cc1cccc(-c2cccc(F)c2F)c1] | | 467.2 |
| 426 | N-((2S,3S)-2-((3'-chlorobiphenyl-3-yl) methyl)-1-(2-hydroxy-2-methylpropanoyl) pyrrolidin-3-yl)ethanesulfonamide | 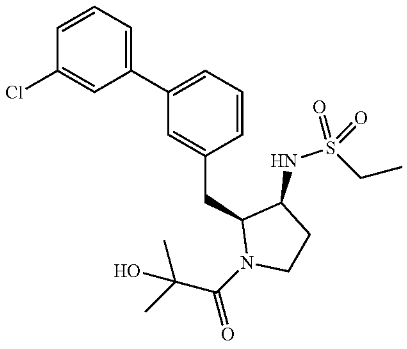 [SMILES: CCS(=O)(=O)N[C@H]1CCN(C(=O)C(C)(C)O)[C@H]1Cc1cccc(-c2cccc(Cl)c2)c1] | | 465.2 |
| 427 | N-((2S,3S)-1-(2-hydroxy-2-methyl-propanoyl)-2-((2,2',5'-trifluorobiphenyl-3-yl)methyl)pyrrolidin-3-yl) methanesulfonamide | 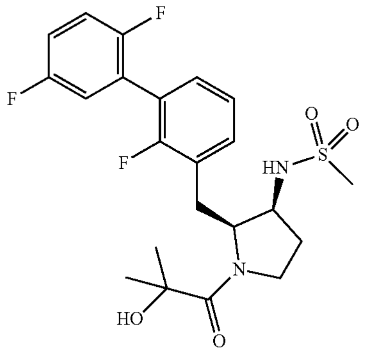 [SMILES: CC(C)(O)C(=O)N1CC[C@H](NS(C)(=O)=O)[C@@H]1Cc1cccc(-c2cc(F)ccc2F)c1F] | | 471.2 |
| 428 | N-((2S,3S)-2-((3'-chloro-2,5'-difluorobiphenyl-3-yl)methyl)-1-(2-hydroxy-2-methylpropanoyl)pyrrolidin-3-yl) methanesulfonamide | 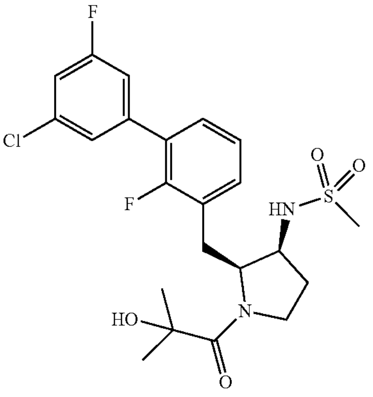 [SMILES: CC(C)(O)C(=O)N1CC[C@H](NS(C)(=O)=O)[C@@H]1Cc1cccc(-c2cc(F)cc(Cl)c2)c1F] | | 484.9 |

TABLE 1-continued

| EXAMPLE | IUPACNAME | Structure | ADDITIVE | MS |
| --- | --- | --- | --- | --- |
| 429 | N-((2S,3S)-2-((3'-fluorobiphenyl-3-yl)methyl)-1-(2-hydroxy-2-methylpropanoyl)pyrrolidin-3-yl)ethanesulfonamide | 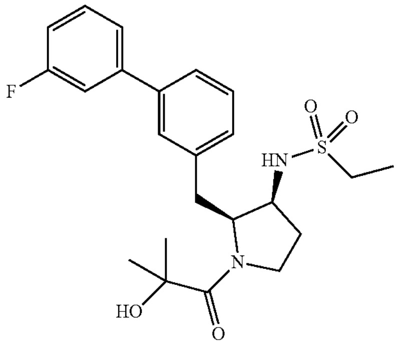 [SMILES: CCS(=O)(=O)N[C@H]1CCN(C(=O)C(C)(C)O)[C@H]1Cc1cccc(-c2cccc(F)c2)c1] | | 447.0 |
| 430 | N-((2S,3S)-2-((2-fluorobiphenyl-3-yl)methyl)-1-(2-hydroxy-2-methylpropanoyl)pyrrolidin-3-yl)ethanesulfonamide | 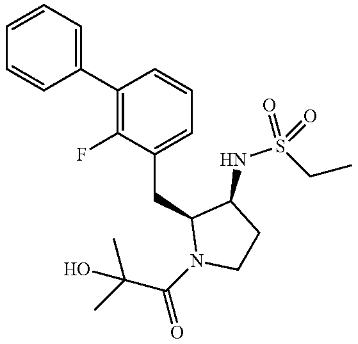 [SMILES: CCS(=O)(=O)N[C@H]1CCN(C(=O)C(C)(C)O)[C@H]1Cc1cccc(-c2ccccc2)c1F] | | 449.2 |
| 431 | N-((2S,3S)-2-((3'-chloro-2-fluorobiphenyl-3-yl)methyl)-1-(2-hydroxy-2-methylpropanoyl)pyrrolidin-3-yl)ethanesulfonamide | 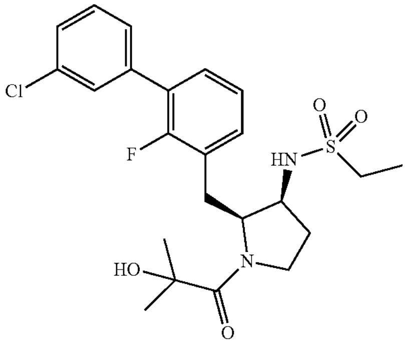 [SMILES: CCS(=O)(=O)N[C@H]1CCN(C(=O)C(C)(C)O)[C@H]1Cc1cccc(-c2cccc(Cl)c2)c1F] | | 483.1 |
| 432 | N-((2S,3S)-2-((2-fluoro-3'-methylbiphenyl-3-yl)methyl)-1-(2-hydroxy-2-methylpropanoyl)pyrrolidin-3-yl)ethanesulfonamide | 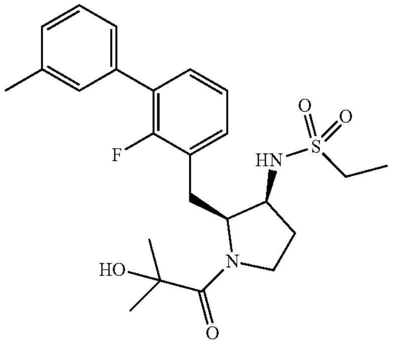 [SMILES: CCS(=O)(=O)N[C@H]1CCN(C(=O)C(C)(C)O)[C@H]1Cc1cccc(-c2cccc(C)c2)c1F] | | 463.2 |

TABLE 1-continued

| EXAM-PLE | IUPACNAME | Structure | ADDITIVE | MS |
|---|---|---|---|---|
| 433 | N-((2S,3S)-2-((2-fluorobiphenyl-3-yl) methyl)-1-(2-hydroxy-2-methylpropanoyl) pyrrolidin-3-yl)methanesulfonamide | 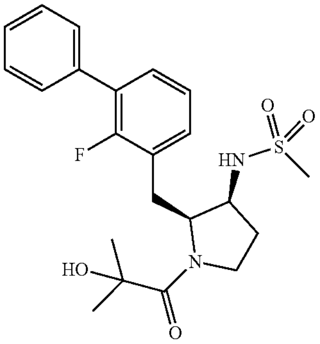 [SMILES: CC(C)(O)C(=O)N1CC[C@H](NS(C)(=O)=O)[C@@H]1Cc1cccc(-c2ccccc2)c1F] | | 435.2 |
| 434 | N-((2S,3S)-1-(2-hydroxy-2-methyl-propanoyl)-2-((2,2',5'-trifluorobiphenyl-3-yl) methyl)pyrrolidin-3-yl)ethanesulfonamide | 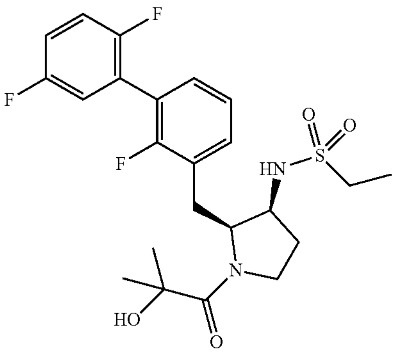 [SMILES: CCS(=O)(=O)N[C@H]1CCN(C(=O)C(C)(C)O)[C@H]1Cc1cccc(-c2cc(F)ccc2F)c1F] | | 485.2 |
| 435 | N-((2S,3S)-1-(2-hydroxy-2-methyl-propanoyl)-2-((2,3',5'-trifluorobiphenyl-3-yl)methyl)pyrrolidin-3-yl)ethanesulfonamide | 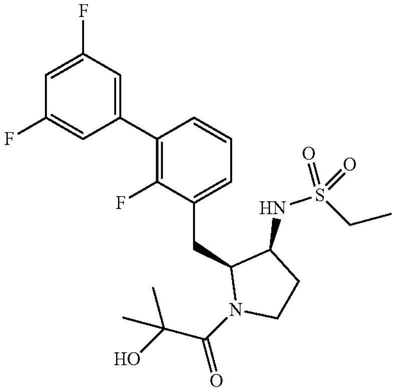 [SMILES: CCS(=O)(=O)N[C@H]1CCN(C(=O)C(C)(C)O)[C@H]1Cc1cccc(-c2cc(F)cc(F)c2)c1F] | | 483.1 |
| 436 | N-((2S,3S)-1-(2-hydroxy-2-methylpropanoyl)-2-((2,2',3'-trifluorobiphenyl-3-yl) methyl)pyrrolidin-3-yl)ethanesulfonamide | 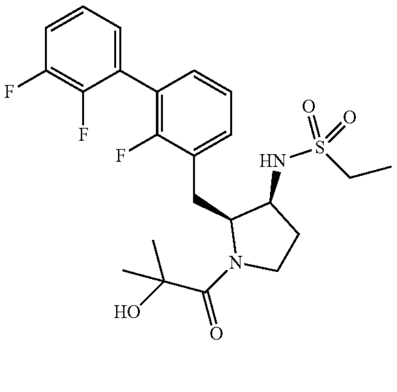 [SMILES: CCS(=O)(=O)N[C@H]1CCN(C(=O)C(C)(C)O)[C@H]1Cc1cccc(-c2cccc(F)c2F)c1F] | | 485.2 |

TABLE 1-continued

| EXAMPLE | IUPACNAME | Structure | ADDITIVE | MS |
|---|---|---|---|---|
| 437 | N-((2S,3S)-2-((3'-chloro-2,5'-difluorobiphenyl-3-yl)methyl)-1-(2-hydroxy-2-methylpropanoyl)pyrrolidin-3-yl) ethanesulfonamide | 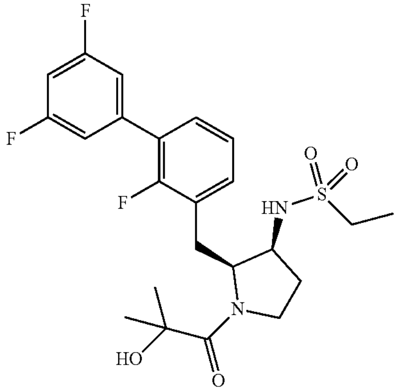 [SMILES: CCS(=O)(=O)N[C@H]1CCN(C(=O)C(C)(C)O)[C@H]1Cc1cccc(-c2cc(F)cc(F)c2)c1F] | | 499.0 |
| 438 | N-((2S,3S)-2-((2,3'-difluoro-5'-methyl-biphenyl-3-yl)methyl)-1-(2-hydroxy-2-methylpropanoyl)pyrrolidin-3-yl) ethanesulfonamide | 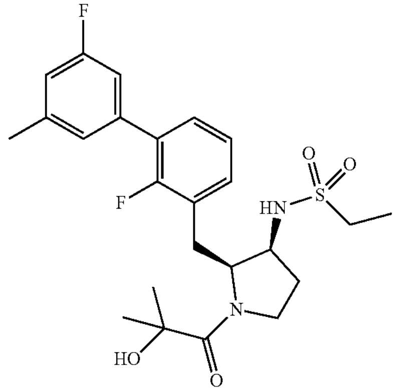 [SMILES: CCS(=O)(=O)N[C@H]1CCN(C(=O)C(C)(C)O)[C@H]1Cc1cccc(-c2cc(C)cc(F)c2)c1F] | | 481.2 |
| 439 | N-((2S,3S)-1-(2-hydroxy-2-methyl-propanoyl)-2-((2,3',5'-trifluorobiphenyl-3-yl)methyl)pyrrolidin-3-yl)cyclopropanesulfonamide | 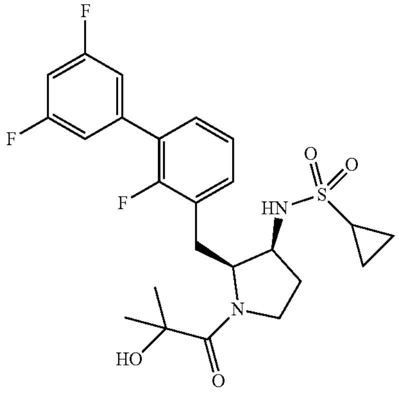 [SMILES: CC(C)(O)C(=O)N1CC[C@H](NS(=O)(=O)C2CC2)[C@@H]1Cc1cccc(-c2cc(F)cc(F)c2)c1F] | | 495.1 |
| 440 | N-((2S,3S)-2-((2-fluorobiphenyl-3-yl)methyl)-1-(2-hydroxy-2-methylpropanoyl)pyrrolidin-3-yl)cyclopropanesulfonamide | 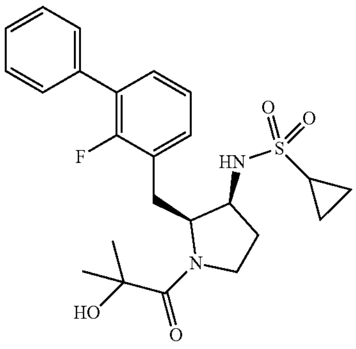 [SMILES: CC(C)(O)C(=O)N1CC[C@H](NS(=O)(=O)C2CC2)[C@@H]1Cc1cccc(-c2ccccc2)c1F] | | 461.2 |

TABLE 1-continued

| EXAMPLE | IUPACNAME | Structure | ADDITIVE | MS |
|---|---|---|---|---|
| 441 | N-{(2S,3S)-1-(oxetane-2-carbonyl)-2-[(2,3',5'-trifluoro[1,1'-bipheny]-3-yl)methy] pyrrolidin-3-yl}methanesulfonamide | 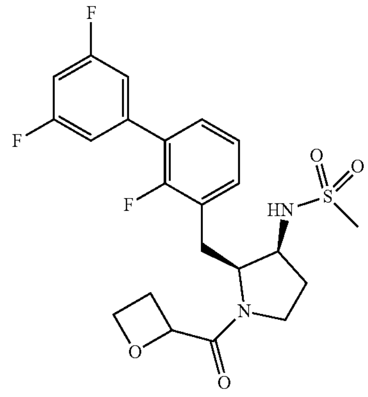 [SMILES: CS(=O)(=O)N[C@H]1CCN(C(=O)C2CCO2)[C@H]1Cc1cccc(-c2cc(F)cc(F)c2)c1F] | | 469.1 |
| 442 | N-[(2S,3S)-2-[(2-fluoro[1,1'-biphenyl-3-yl)methy]-1-(oxetane-2-carbonyl)pyrrolidin-3-yl]methanesulfonamide | 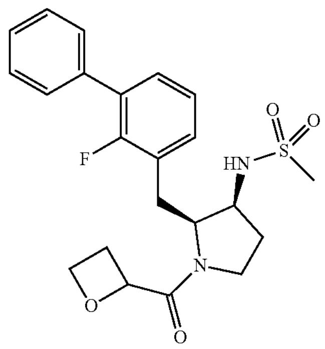 [SMILES: CS(=O)(=O)N[C@H]1CCN(C(=O)C2CCO2)[C@H]1Cc1cccc(-c2ccccc2)c1F] | | 433.2 |
| 443 | N-{(2S,3S)-1-(azetidine-1-carbonyl)-2-[(3-benzylphenyl)methyl]pyrrolidin-3-yl}ethanesulfonamide | 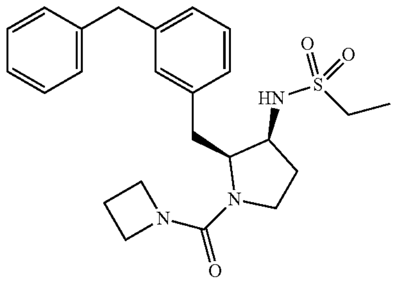 [SMILES: CCS(=O)(=O)N[C@H]1CCN(C(=O)N2CCC2)[C@H]1Cc1cccc(Cc2ccccc2)c1] | | 442.3 |
| 444 | N-{cis-1-(azetidine-1-carbonyl)-2-[(dibenzo[b,d]furan-2-yl)methyl] pyrrolidin-3-yl}methanesulfonamide | 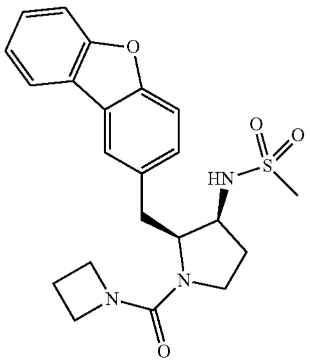 [SMILES: CS(=O)(=O)N[C@H]1CCN(C(=O)N2CCC2)[C@H]1Cc1ccc2oc3ccccc3c2c1] | | 428.3 |

TABLE 1-continued

| EXAMPLE | IUPACNAME | Structure | ADDITIVE | MS |
| --- | --- | --- | --- | --- |
| 445 | N-{cis-1-(azetidine-1-carbonyl)-2-[(3-phenoxyphenyl)methyl]pyrrolidin-3-yl]ethanesulfonamide | 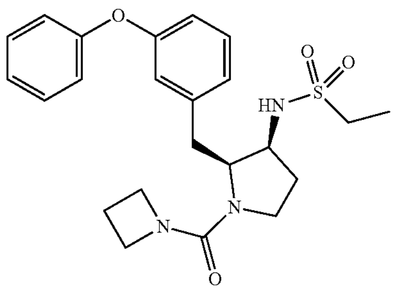 [SMILES: CCS(=O)(=O)N[C@H]1CCN(C(=O)N2CCC2)[C@H]1Cc1cccc(Oc2ccccc2)c1] | | 444.2 |
| 446 | N-{cis-1-(cyclobutanecarbonyl)-2-[(3-phenoxyphenyl)methyl]pyrrolidin-3-yl]ethanesulfonamide | 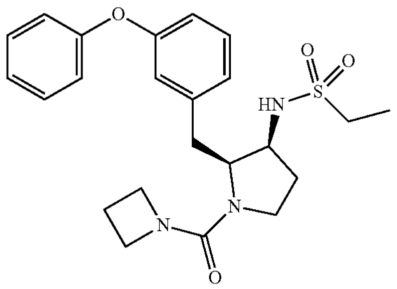 [SMILES: CCS(=O)(=O)N[C@H]1CCN(C(=O)N2CCC2)[C@H]1Cc1cccc(Oc2ccccc2)c1] | | 443.2 |
| 447 | N-[cis-1-(azetidine-1-carbonyl)-2-{[3-(propan-2-yl)-1-benzofuran-5-yl]methyl}pyrrolidin-3-yl]methanesulfonamide | 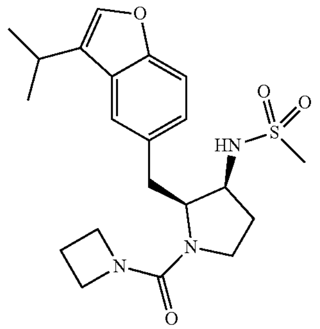 [SMILES: CC(C)c1coc2ccc(C[C@H]3[C@@H](NS(C)(=O)=O)CCN3C(=O)N3CCC3)cc12] | | 420.2 |
| 448 | N-{cis-1-(azetidine-1-carbonyl)-2-[(4-phenoxyphenyl)methyl]pyrrolidin-3-yl}methanesulfonamide | 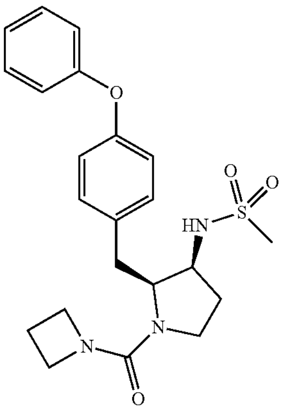 [SMILES: CS(=O)(=O)N[C@H]1CCN(C(=O)N2CCC2)[C@H]1Cc1ccc(Oc2ccccc2)cc1] | | 430.2 |

TABLE 1-continued

| EXAMPLE | IUPACNAME | Structure | ADDITIVE | MS |
|---|---|---|---|---|
| 449 | 1,1,1-trifluoro-N-{(2S,3S)-1-(2-hydroxy-2-methylpropanoyl)-2-[(2,3',5'-trifluoro[1,1'-biphenyl]-3-yl)methyl]pyrrolidin-3-yl}methanesulfonamide | 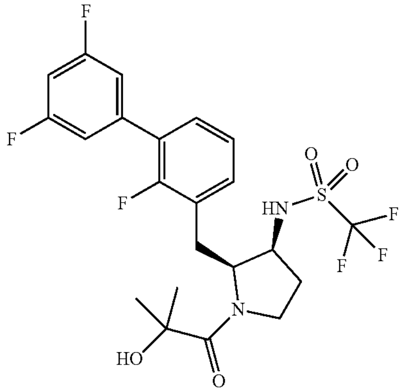 [SMILES: CC(C)(O)C(=O)N1CC[C@H](NS(=O)(=O)C(F)(F)F)[C@@H]1Cc1cccc(-c2cc(F)cc(F)c2)c1F] | | 523.0 |
| 450 | N-[(2S,3S)-2-[(2,3'-difluoro[1,1'-biphenyl]-3-yl)methyl]-1-(2-hydroxy-2-methylpropanoyl)pyrrolidin-3-yl]-1-fluorocyclopropane-1-sulfonamide | 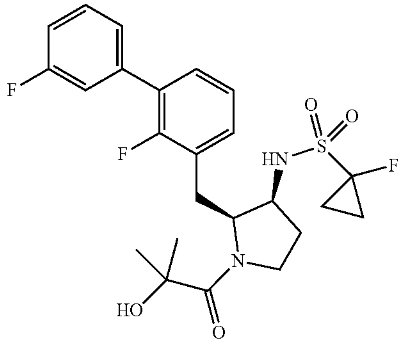 [SMILES: CC(C)(O)C(=O)N1CC[C@H](NS(=O)(=O)C2(F)CC2)[C@@H]1Cc1cccc(-c2cccc(F)c2)c1F] | | 497.2 |
| 451 | (2S,3S)-N-ethyl-2-[(3'-fluoro[1,1'-biphenyl-3-yl)methyl]-3-[(methanesulfonyl)amino] pyrrolidine-1-carboxamide | 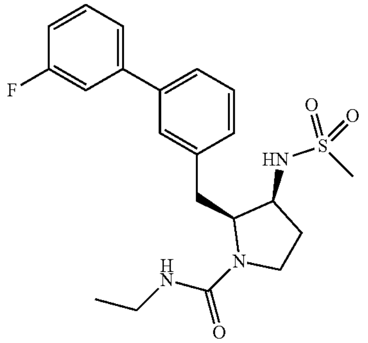 [SMILES: CCNC(=O)N1CC[C@H](NS(C)(=O)=O)[C@@H]1Cc1cccc(-c2cccc(F)c2)c1] | | 420.1 |
| 452 | N-[(2S,3S)-2-[(2,3'-difluoro[1,1'-biphenyl]-3-yl)methyl]-1-(2-hydroxy-2-methylpropanoyl)pyrrolidin-3-yl]-1-fluoroethane-1-sulfonamide | 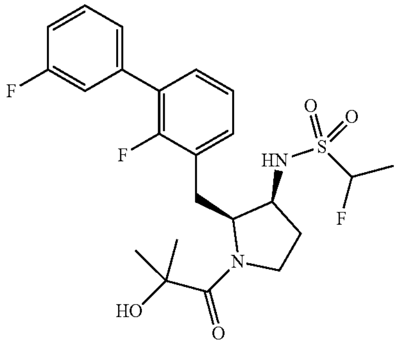 [SMILES: CC(F)S(=O)(=O)N[C@H]1CCN(C(=O)C(C)(C)O)[C@H]1Cc1cccc(-c2cccc(F)c2)c1F] | | 485.2 |

TABLE 1-continued

| EXAMPLE | IUPACNAME | Structure | ADDITIVE | MS |
|---|---|---|---|---|
| 453 | N'-{(2S,3S)-1-(azetidine-1-carbonyl)-2-[(3-bromo-2-fluorophenyl)methyl] pyrrolidin-3-yl}-N,N-dimethylsulfuric diamide | 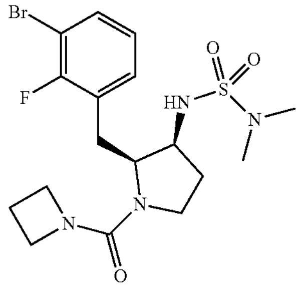 [SMILES: CN(C)S(=O)(=O)N[C@H]1CCN(C(=O)N2CCC2)[C@H]1Cc1cccc(Br)c1F] | | 463.1 |
| 454 | N-[(2S,3S)-2-[(3',5'-difluoro[1,1'-biphenyl]-3-yl)methyl]-1-(1-methyl-1H-pyrazole-3-carbonyl)pyrrolidin-3-yl] ethanesulfonamide | 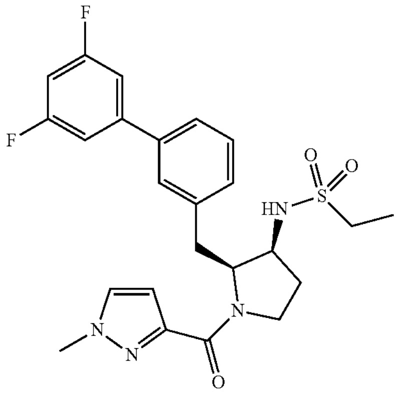 [SMILES: CCS(=O)(=O)N[C@H]1CCN(C(=O)c2ccn(C)n2)[C@H]1Cc1cccc(-c2cc(F)cc(F)c2)c1] | | 489.2 |
| 455 | N-[(2S,3S)-2-[(3',5'-difluoro[1,1'-biphenyl]-3-yl)methyl]-1-(furan-2-carbonyl)pyrrolidin-3-yl]ethanesulfonamide | 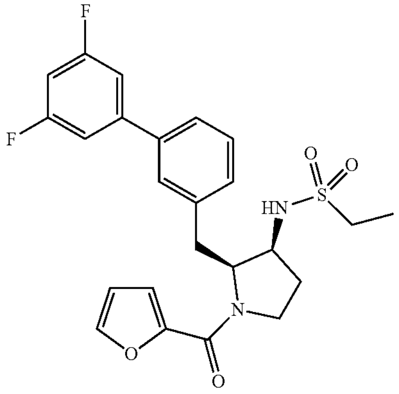 [SMILES: CCS(=O)(=O)N[C@H]1CCN(C(=O)c2ccco2)[C@H]1Cc1cccc(-c2cc(F)cc(F)c2)c1] | | 475.2 |
| 456 | N{(2S,3S)-1-(azetidine-1-carbonyl)-2-[(2-fluoro[1,1'-biphenyl]-3-yl)methyl]pyrrolidin-3-yl]ethanesulfonamide | 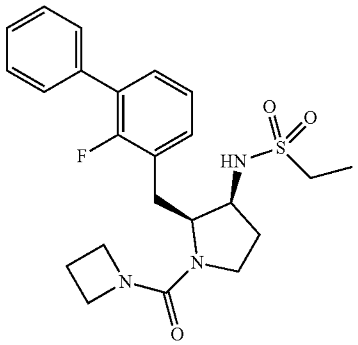 [SMILES: CCS(=O)(=O)N[C@H]1CCN(C(=O)N2CCC2)[C@H]1Cc1cccc(-c2ccccc2)c1F] | | 446.0 |

TABLE 1-continued

| EXAMPLE | IUPACNAME | Structure | ADDITIVE | MS |
|---|---|---|---|---|
| 457 | N-{(2S,3S)-1-(3-hydroxy-2,2-dimethylpropanoyl)-2-[(2,3',5'-trifluoro[1,1'-biphenyl]-3-yl)methyl]pyrrolidin-3-yl} methanesulfonamide | 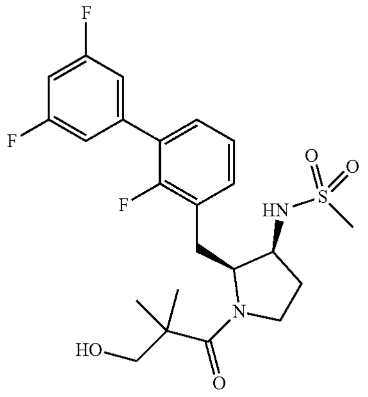 [SMILES: CC(C)(CO)C(=O)N1CC[C@H](NS(C)(=O)=O)[C@@H]1Cc1cccc(-c2cc(F)cc(F)c2)c1F] | | 484.9 |
| 458 | N-[(2S,3S)-2-[(3',5'-difluoro[1,1'-biphenyl]-3-yl)methyl]-1-(1H-imidazol-2-yl)pyrrolidin-3-yl]ethanesulfonamide | 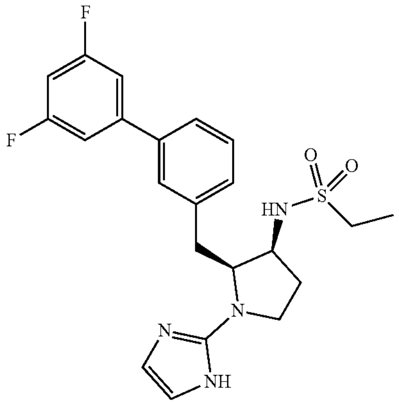 [SMILES: CCS(=O)(=O)N[C@H]1CCN(c2ncc[nH]2)[C@H]1Cc1cccc(-c2cc(F)cc(F)c2)c1] | | 447.2 |
| 459 | N-{(2S,3S)-1-(azetidine-1-carbonyl)-2-[(3'-fluoro[1,1'-biphenyl]-3-yl)methyl] pyrrolidin-3-yl}-1-fluoromethanesulfonamide | 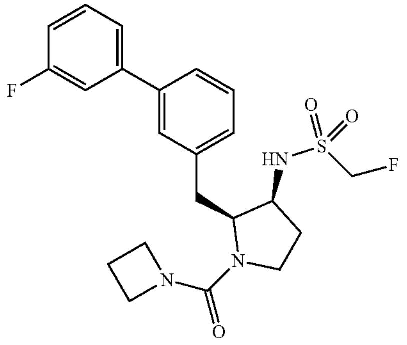 [SMILES: O=C(N1CCC1)N1CC[C@H](NS(=O)(=O)CF)[C@@H]1Cc1cccc(-c2cccc(F)c2)c1] | | 450.2 |
| 460 | N-{(2S,3S)-1-(azetidine-1-carbonyl)-2-[([1,1'-biphenyl]-3-yl)methyl]pyrrolidin-3-yl}-1-fluoromethanesulfonamide | 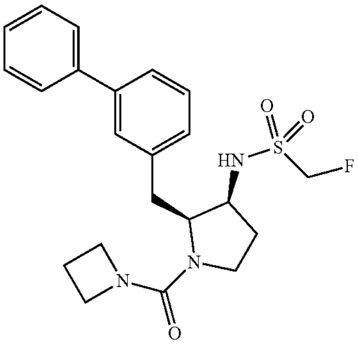 [SMILES: O=C(N1CCC1)N1CC[C@H](NS(=O)(=O)CF)[C@@H]1Cc1cccc(-c2ccccc2)c1] | | 432.2 |

TABLE 1-continued

| EXAMPLE | IUPACNAME | Structure | ADDITIVE | MS |
|---|---|---|---|---|
| 461 | N-[(2S,3S)-2-[(3',5'-difluoro[1,1'-biphenyl]-3-yl)methyl]-1-(1-methyl-1H-imidazol-2-yl)pyrrolidin-3-yl]ethanesulfonamide | 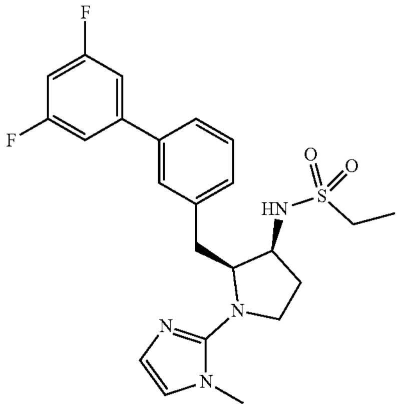 [SMILES: CCS(=O)(=O)N[C@H]1CCN(c2nccn2C)[C@H]1Cc1cccc(-c2cc(F)cc(F)c2)c1] | | 461.2 |
| 462 | N-{(2S,3S)-1-(azetidine-1-carbonyl)-2-[(3'-fluoro[1,1'-biphenyl]-3-yl)methyl]pyrrolidin-3-yl}cyclopropanesulfonamide | 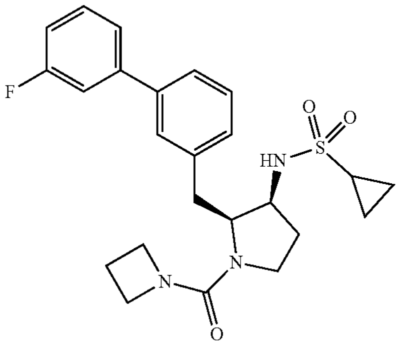 [SMILES: O=C(N1CCC1)N1CC[C@H](NS(=O)(=O)C2CC2)[C@@H]1Cc1cccc(-c2cccc(F)c2)c1] | | 458.2 |
| 463 | N-[(2S,3S)-1-(azetidine-1-carbonyl)-2-[([1,1'-biphenyl]-3-yl)methyl]pyrrolidin-3-yl}cyclopropanesulfonamide | 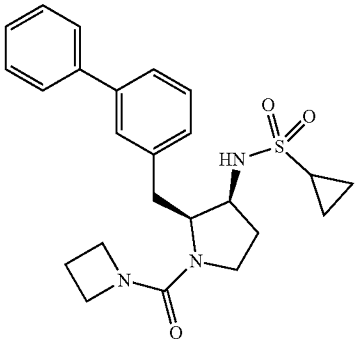 [SMILES: O=C(N1CCC1)N1CC[C@H](NS(=O)(=O)C2CC2)[C@@H]1Cc1cccc(-c2ccccc2)c1] | | 440.2 |
| 464 | N-{(2S,3S)-1-[1-(hydroxymethyl)cyclopropane-1-carbonyl]-2-[(2,3',5'-trifluoro[1,1'-biphenyl]-3-yl)methyl]pyrrolidin-3-yl}methanesulfonamide | 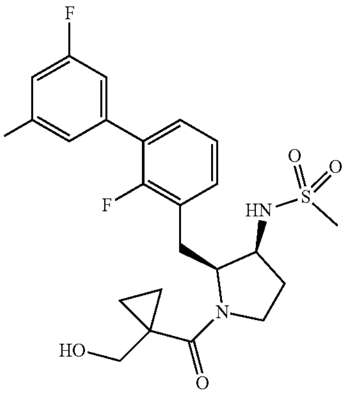 | | 483.1 |

TABLE 1-continued

| EXAM-PLE | IUPACNAME | Structure | ADDITIVE | MS |
|---|---|---|---|---|
| 465 | N-{(2S,3S)-1-(1H-imidazol-2-yl)-2-[(2,3',5'-trifluoro[1,1'-biphenyl]-3-yl)methyl]pyrrolidin-3-yl}ethanesulfonamide | 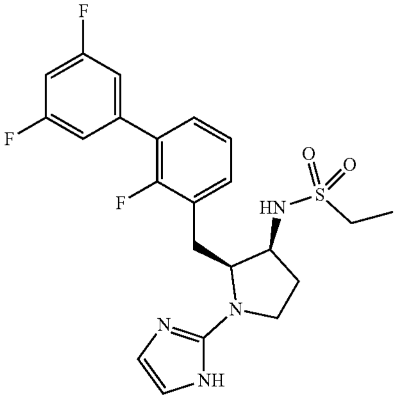 [SMILES: CCS(=O)(=O)N[C@H]1CCN(c2ncc[nH]2)[C@H]1Cc1cccc(-c2cc(F)cc(F)c2)c1F] | | 465.2 |
| 466 | N-{(2S,3S)-1-(azetidine-1-carbonyl)-2-[(2-fluoro[1,1'-biphenyl]-3-yl)methyl]pyrrolidin-3-yl}-1-fluoromethanesulfonamide | 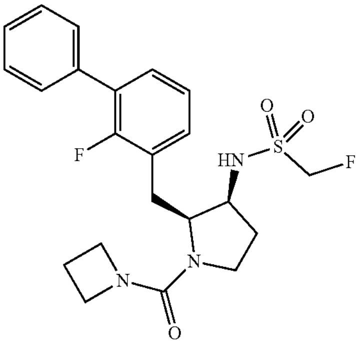 [SMILES: O=C(N1CCC1)N1CC[C@H](NS(=O)(=O)CF)[C@@H]1Cc1cccc(-c2ccccc2)c1F] | | 450.2 |
| 467 | N-{(2S,3S)-1-(azetidine-1-carbonyl)-2-[(2,3'-difluoro[1,1'-biphenyl]-3-yl)methyl]pyrrolidin-3-yl}-1-fluoromethanesulfonamide | 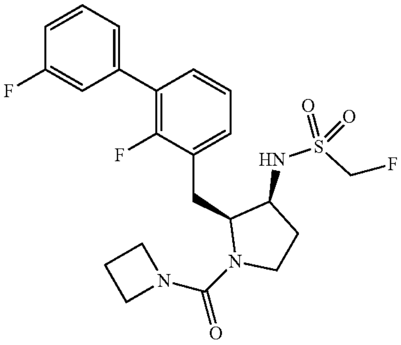 [SMILES: O=C(N1CCC1)N1CC[C@H](NS(=O)(=O)CF)[C@@H]1Cc1cccc(-c2cccc(F)c2)c1F] | | 468.2 |
| 468 | N-[(2S,3S)-2-[(3',5'-difluoro[1,1'-biphenyl]-3-yl)methyl]-1-(1-ethyl-1H-imidazol-2-yl)pyrrolidin-3-yl]ethanesulfonamide | 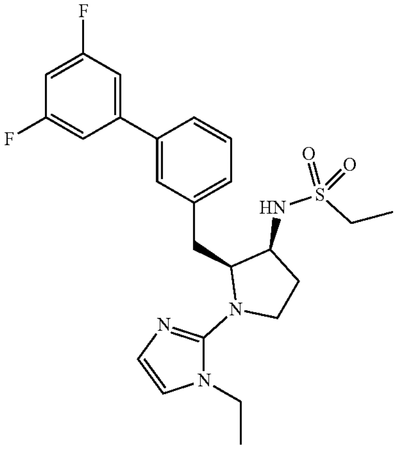 [SMILES: CCn1ccnc1N1CC[C@H](NS(=O)(=O)CC)[C@@H]1Cc1cccc(-c2cc(F)cc(F)c2)c1] | | 475.3 |

TABLE 1-continued
| EXAMPLE | IUPACNAME | Structure | ADDITIVE | MS |
|---|---|---|---|---|
| 469 | N-{(2S,3S)-1-[1-(hydroxymethyl) cyclobutane-1-carbonyl]-2-[(2,3',5'-trifluoro[1,1'-biphenyl]-3-yl)methyl]pyrrolidin-3-yl] methanesulfonamide | 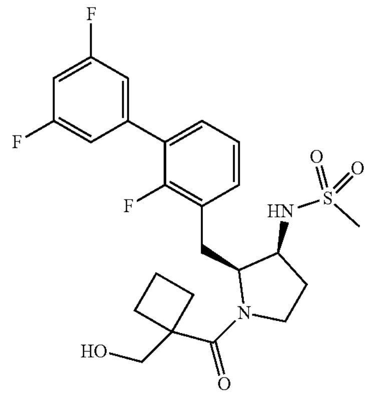 [SMILES: CS(=O)(=O)N[C@H]1CCN(C(=O)C2(CO)CCC2)[C@H]1Cc1cccc(-c2cc(F)cc(F)c2)c1F] | | 497.2 |
| 470 | N-{(2S,3S)-1-(6-chloropyridazin-3-yl)-2-[(3',5'-difluoro[1,1'-biphenyl]-3-yl) methyl]pyrrolidin-3-yl}ethanesulfonamide | 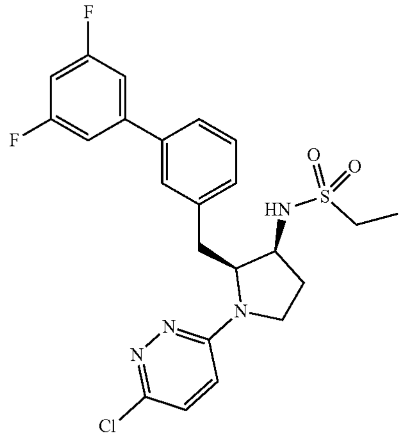 [SMILES: CCS(=O)(=O)N[C@H]1CCN(c2ccc(Cl)nn2)[C@H]1Cc1cccc(-c2cc(F)cc(F)c2)c1] | | 493.1 |
| 471 | N-[(2S,3S)-2-[([1,1'-biphenyl]-3-yl) methyl]-1-(cyclobutanecarbonyl) pyrrolidin-3-yl]ethanesulfonamide | 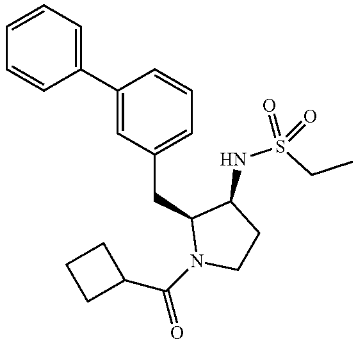 [SMILES: CCS(=O)(=O)N[C@H]1CCN(C(=O)C2CCC2)[C@H]1Cc1cccc(-c2ccccc2)c1] | | 427.3 |

TABLE 1-continued

| EXAMPLE | IUPACNAME | Structure | ADDITIVE | MS |
|---|---|---|---|---|
| 472 | N-[(2S,3S)-2-[(3',5'-difluoro[1,1'-biphenyl]-3-yl)methyl]-1-(6-methylpyridazin-3-yl)pyrrolidin-3-yl]ethanesulfonamide | 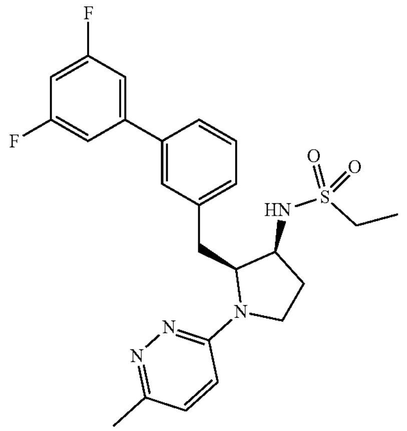 [SMILES: CCS(=O)(=O)N[C@H]1CCN(c2ccc(C)nn2)[C@H]1Cc1cccc(-c2cc(F)cc(F)c2)c1] | | 473.2 |
| 473 | N-[(2S,3S)-2-[(3',5'-difluoro[1,1'-biphenyl]-3-yl)methyl]-1-(pyridazin-3-yl)pyrrolidin-3-yl]ethanesulfonamide | 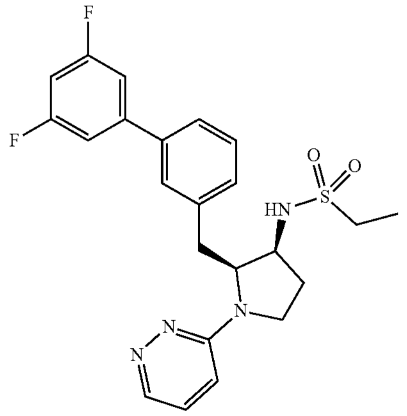 [SMILES: CCS(=O)(=O)N[C@H]1CCN(c2cccnn2)[C@H]1Cc1cccc(-c2cc(F)cc(F)c2)c1] | | 459.1 |
| 474 | (2S,3S)-3-[(ethanesulfonyl)amino]-2-[(3'-fluoro[1,1'-biphenyl]-3-yl)methyl]-N-methoxy-N-methylpyrrolidine-1-carboxamide | 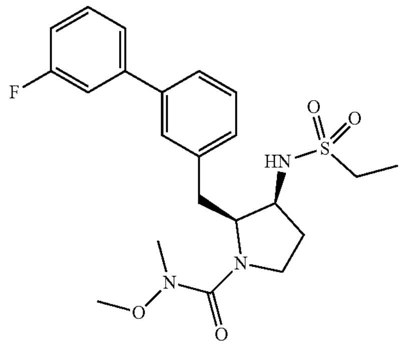 [SMILES: CCS(=O)(=O)N[C@H]1CCN(C(=O)N(C)OC)[C@H]1Cc1cccc(-c2cccc(F)c2)c1] | | 450.2 |
| 475 | (2S,3S)-3-[(dimethylsulfamoyl)amino]-2-[(2-fluoro[1,1'-biphenyl]-3-yl)methyl]-N,N-dimethylpyrrolidine-1-carboxamide | 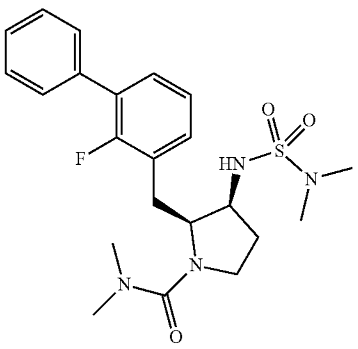 [SMILES: CN(C)C(=O)N1CC[C@H](NS(=O)(=O)N(C)C)[C@@H]1Cc1cccc(-c2ccccc2)c1F] | | 449.2 |

TABLE 1-continued

| EXAMPLE | IUPACNAME | Structure | ADDITIVE | MS |
|---|---|---|---|---|
| 476 | (2S,3S)-3-[(dimethylsulfamoyl)amino]-N,N-dimethyl-2-[(2,3',5'-trifluoro[1,1'-biphenyl]-3-yl)methyl] pyrrolidine-1-carboxamide | 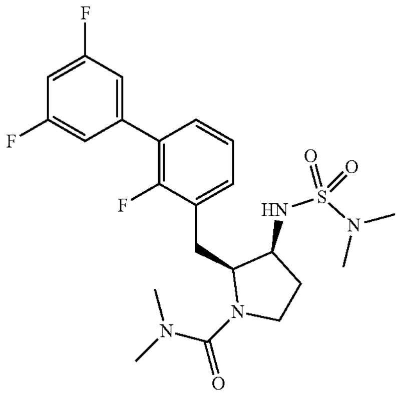 [SMILES: CN(C)C(=O)N1CC[C@H](NS(=O)(=O)N(C)C)[C@@H]1Cc1cccc(-c2cc(F)cc(F)c2)c1F] | | 485.2 |
| 477 | (2S,3S)-2-[(3',5'-difluoro[1,1'-biphenyl]-3-yl)methyl]-3-[(ethanesulfonyl)amino]-N-methoxy-N-methylpyrrolidine-1-carboxamide | 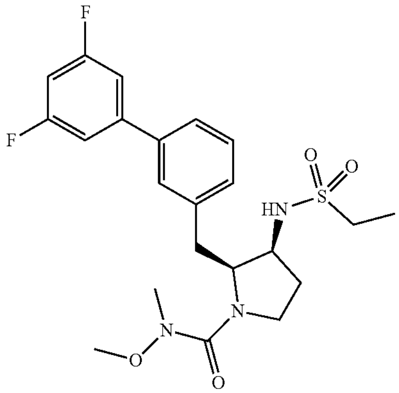 [SMILES: CCS(=O)(=O)N[C@H]1CCN(C(=O)N(C)OC)[C@H]1Cc1cccc(-c2cc(F)cc(F)c2)c1] | | 468.1 |
| 478 | N-[(2S,3S)-2-[(3',5'-difluoro[1,1'-biphenyl]-3-yl)methyl]-1-(1,2-oxazolidine-2-carbonyl)pyrrolidin-3-yl]ethanesulfonamide | 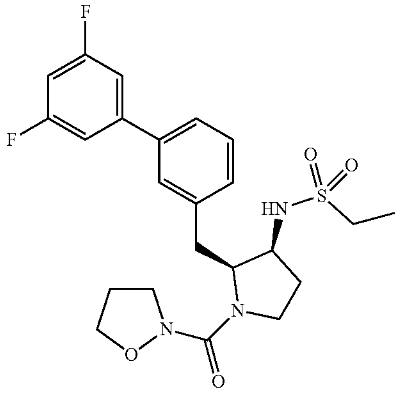 [SMILES: CCS(=O)(=O)N[C@H]1CCN(C(=O)N2CCCO2)[C@H]1Cc1cccc(-c2cc(F)cc(F)c2)c1] | | 480.2 |
| 479 | 1-fluoro-N-[(2S,3S)-2-[(2-fluoro[1,1'-biphenyl]-3-yl)methyl]-1-(2-hydroxy-2-methylpropanoyl)pyrrolidin-3-yl] cyclopropane-1-sulfonamide | 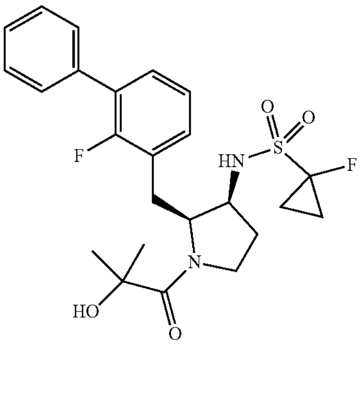 [SMILES: CC(C)(O)C(=O)N1CC[C@H](NS(=O)(=O)C2(F)CC2)[C@@H]1Cc1cccc(-c2ccccc2)c1F] | | 479.2 |

TABLE 1-continued

| EXAMPLE | IUPACNAME | Structure | ADDITIVE | MS |
|---|---|---|---|---|
| 480 | 1-fluoro-N-{(2S,3S)-1-(2-hydroxy-2-methylpropanoyl)-2-[(2,3',5'-trifluoro[1,1'-biphenyl]-3-yl)methyl]pyrrolidin-3-yl}cyclopropane-1-sulfonamide | 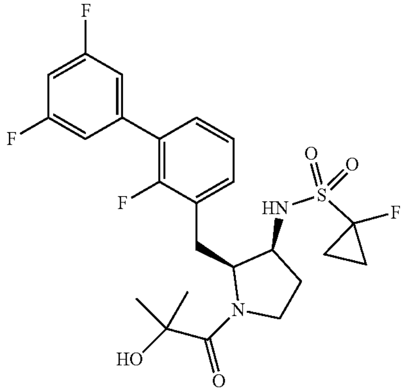 [SMILES: CC(C)(O)C(=O)N1CC[C@H](NS(=O)(=O)C2(F)CC2)[C@@H]1Cc1cccc(-c2cc(F)cc(F)c2)c1F] | | 515.1 |
| 481 | N-[(2S,3S)-2-[(3',5'-difluoro[1,1-biphenyl]-3-yl)methyl]-1-(trimethylhydrazine-carbonyl)pyrrolidin-3-yl]ethanesulfonamide | 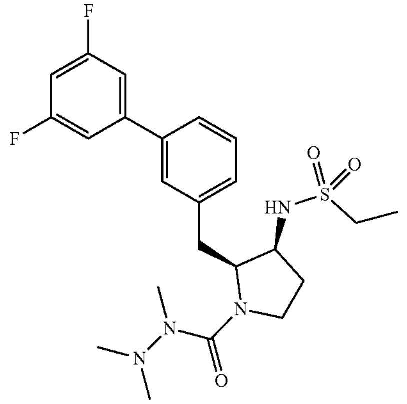 [SMILES: CCS(=O)(=O)N[C@H]1CCN(C(=O)N(C)N(C)C)[C@H]1Cc1cccc(-c2cc(F)cc(F)c2)c1] | | 481.2 |
| 482 | N-((2S,3S)-2-((2,3'-difluorobiphenyl-3-yl)methyl)-1-(2-hydroxy-2-methylpropanoyl)pyrrolidin-3-yl)ethanesulfonamide | 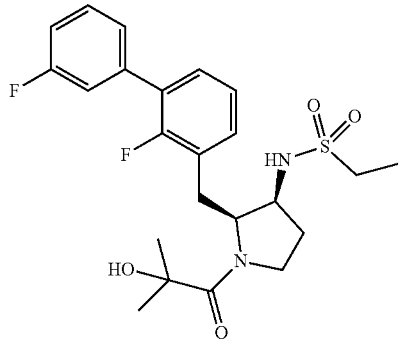 [SMILES: CCS(=O)(=O)N[C@H]1CCN(C(=O)C(C)(C)O)[C@H]1Cc1cccc(-c2cccc(F)c2)c1F] | | 467.1 |
| 483 | N-((2S,3S)-1-(2-hydroxy-2-methyl-propanoyl)-2-((2,3',5'-trifluorobiphenyl-3-yl)methyl)pyrrolidin-3-yl)methanesulfonamide | 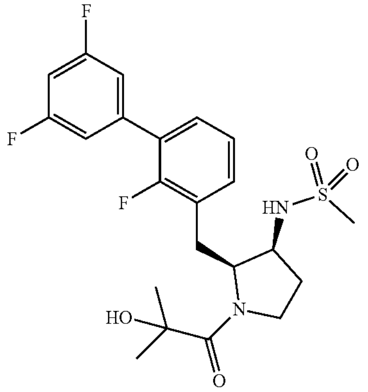 [SMILES: CC(C)(O)C(=O)N1CC[C@H](NS(C)(=O)=O)[C@@H]1Cc1cccc(-c2cc(F)cc(F)c2)c1F] | | 469.1 |

TABLE 1-continued

| EXAMPLE | IUPACNAME | Structure | ADDITIVE | MS |
|---|---|---|---|---|
| 484 | N-((2S,3S)-1-(2-hydroxy-2-methyl-propanoyl)-2-((2,3',5'-trifluoro-biphenyl-3-yl)methyl) pyrrolidin-3-yl)ethanesulfonamide | 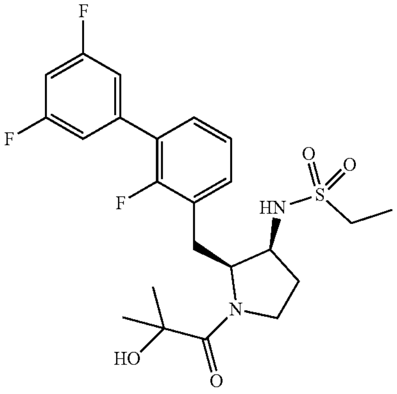 [SMILES: CCS(=O)(=O)N[C@H]1CCN(C(=O)C(C)(C)O)[C@H]1Cc1cccc(-c2cc(F)cc(F)c2)c1F] | | 485.2 |
| 485 | N-((2S,3S)-1-(azetidin-1-ylcarbonyl)-2-((2,3'-difluorobiphenyl-3-yl)methyl) pyrrolidin-3-yl)methanesulfonamide | 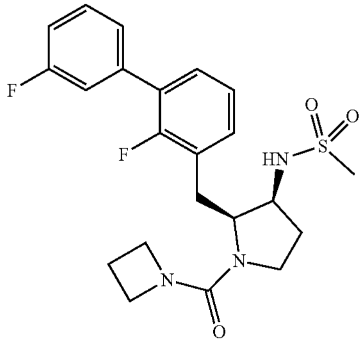 [SMILES: CS(=O)(=O)N[C@H]1CCN(C(=O)N2CCC2)[C@H]1Cc1cccc(-c2cccc(F)c2)c1F] | | 450.1 |
| 486 | (2S,3S)-2-((2,3'-difluorobiphenyl-3-yl)methyl)-3-((ethylsulfonyl) amino)-N,N-dimethylpyrrolidine-1-carboxamide | 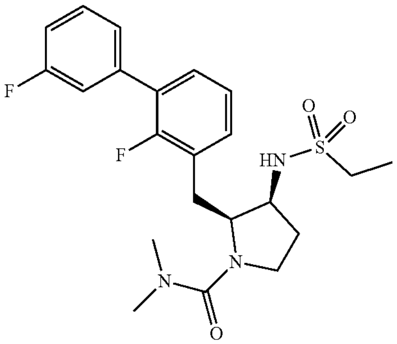 [SMILES: CCS(=O)(=O)N[C@H]1CCN(C(=O)N(C)C)[C@H]1Cc1cccc(-c2cccc(F)c2)c1F] | | 452.1 |
| 487 | (2S,3S)-3-((ethylsulfonyl)amino)-N,N-dimethyl-2-((2,3',5'-trifluorobiphenyl-3-yl)methyl)pyrrolidine-1-carboxamide | 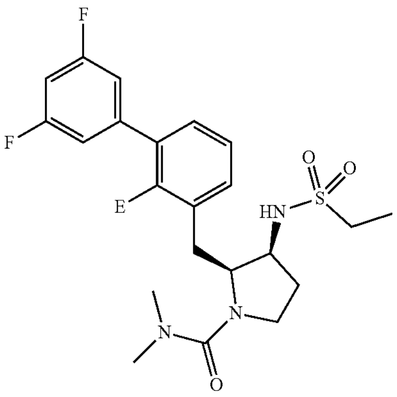 | | 470.2 |

TABLE 1-continued

| EXAMPLE | IUPACNAME | Structure | ADDITIVE | MS |
|---|---|---|---|---|
| 488 | N-((2S,3S)-2-((2,3'-difluorobiphenyl-3-yl)methyl)-1-(2-hydroxy-2-methylpropanoyl)pyrrolidin-3-yl)ethanesulfonamide | 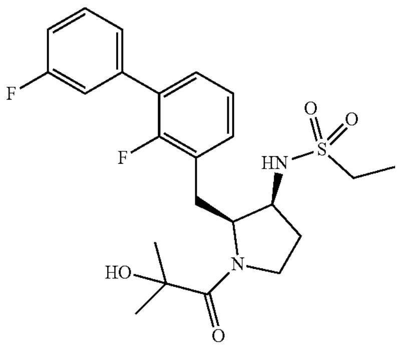 [SMILES: CCS(=O)(=O)N[C@H]1CCN(C(=O)C(C)(C)O)[C@H]1Cc1cccc(-c2cccc(F)c2)c1F] | | 467.2 |

Experimental Example 1: Obtainment of Cell Stably Expressing Human Orexin Type 2 Receptor (hOX2R)

To obtain a cell clone stably expressing human orexin type 2 receptor, human orexin type 2 receptor cDNA was inserted into pcDNA3.1(+) plasmid vector (Invitrogen), and a plasmid DNA for expression of human orexin type 2 receptor (pcDNA3.1(+)/hOX2R) was cloned. The plasmid DNA was introduced into CHO-dhfr cell by an electroporation method, and human orexin type 2 receptor expressing clone cells were obtained by limiting dilution method by using G418 drug resistance as a selection marker.

Experimental Example 2: Measurement of Orexin Type 2 Receptor Agonist Activity CHO cells forcibly expressing human OX2 receptor were seeded in each well of 384 well black transparent bottom plate (BD Falcon) at 7,500 cells/well, and cultured for one day in a 5% $CO_2$ incubator at 37° C. After removal of the medium in the cell plate, assay buffer A containing a calcium indicator (HBSS (Thermo Fisher Scientific), 20 mM HEPES (Thermo Fisher Scientific), 0.1% BSA (Wako Pure Chemical Industries, Ltd. or Sigma-Aldrich), 2.5 μg/mL Fluo-4 AM (DOJINDO Chemical), 0.08% Pluronic F127 (DOJINDO Chemical), 1.25 mM probenecid (DOJINDO Chemical)) was added at 30 μL/well. The plate was stood for 30 min in a 5% $CO_2$ incubator at 37° C., and further stood at room temperature for 30 min. A test compound prepared by diluting with assay buffer B (HBSS, 20 mM HEPES, 0.1% BSA) was added at 10 μL/well, and the fluorescence value was measured by FDSSμCELL (Hamamatsu Photonics K.K.) every one sec for 1 min, and thereafter every two sec for 1 min 40 sec. The activity (%) of the test compound was calculated assuming that variation in the fluorescence value when DMSO was added instead of the test compound was 0%, and variation in the fluorescence value when orexin A (human) (PEPTIDE INSTITUTE, INC.) was added at the final concentration of 10 nM was 100%. The activity of each compound at the concentration of 3 μM was shown in Table 2. As is clear from the results, the compound of the present invention was shown to have an agonist activity on human orexin type 2 receptor.

TABLE 2

| Example No. | OX2R agonist activity (3 μM, %) |
|---|---|
| 1 | 81 |
| 2 | 90 |
| 3 | 101 |
| 7 | 62 |
| 10 | 91 |
| 11 | 80 |
| 14 | 82 |
| 17 | 29 |
| 22 | 60 |
| 27 | 66 |
| 29 | 98 |
| 35 | 41 |
| 38 | 75 |
| 41 | 67 |
| 50 | 97 |
| 53 | 72 |
| 55 | 84 |
| 60 | 26 |
| 61 | 74 |
| 62 | 93 |
| 63 | 24 |
| 64 | 96 |
| 74 | 104 |
| 76 | 106 |
| 78 | 35 |
| 89 | 96 |
| 93 | 101 |
| 95 | 97 |
| 100 | 107 |
| 101 | 96 |
| 108 | 69 |
| 116 | 106 |
| 122 | 82 |
| 126 | 90 |
| 145 | 24 |
| 159 | 65 |
| 173 | 68 |
| 178 | 99 |
| 181 | 100 |
| 185 | 99 |
| 191 | 79 |
| 204 | 95 |
| 206 | 94 |
| 209 | 106 |
| 210 | 102 |
| 214 | 70 |
| 227 | 99 |
| 254 | 101 |
| 255 | 101 |
| 256 | 97 |
| 258 | 95 |
| 259 | 95 |

TABLE 2-continued

| Example No. | OX2R agonist activity (3 μM, %) |
|---|---|
| 261 | 97 |
| 262 | 101 |
| 266 | 107 |
| 269 | 111 |
| 293 | 102 |
| 294 | 104 |
| 299 | 100 |
| 300 | 99 |
| 303 | 95 |
| 304 | 94 |
| 305 | 105 |
| 306 | 100 |
| 307 | 102 |
| 308 | 107 |
| 309 | 101 |
| 310 | 102 |
| 311 | 103 |
| 312 | 103 |
| 313 | 100 |
| 314 | 107 |
| 315 | 105 |
| 316 | 104 |
| 317 | 103 |
| 318 | 102 |
| 319 | 101 |
| 320 | 103 |
| 321 | 104 |
| 322 | 104 |
| 323 | 109 |
| 324 | 103 |
| 328 | 104 |
| 333 | 101 |
| 338 | 103 |
| 339 | 102 |
| 340 | 103 |
| 341 | 98 |
| 342 | 109 |
| 343 | 107 |
| 344 | 99 |
| 345 | 93 |
| 346 | 107 |
| 347 | 87 |
| 348 | 109 |
| 349 | 99 |
| 350 | 99 |
| 351 | 106 |
| 352 | 102 |
| 364 | 104 |
| 366 | 100 |
| 373 | 96 |
| 387 | 106 |
| 389 | 102 |
| 395 | 104 |
| 399 | 107 |
| 402 | 107 |
| 404 | 100 |
| 417 | 110 |
| 421 | 106 |
| 423 | 109 |
| 424 | 101 |
| 428 | 102 |
| 431 | 101 |
| 435 | 107 |
| 437 | 99 |
| 439 | 98 |
| 362 | 103 |
| 372 | 98 |
| 377 | 103 |
| 407 | 107 |
| 441 | 99 |
| 450 | 107 |
| 456 | 104 |
| 457 | 103 |
| 459 | 93 |
| 460 | 92 |
| 462 | 112 |
| 463 | 105 |

TABLE 2-continued

| Example No. | OX2R agonist activity (3 μM, %) |
|---|---|
| 466 | 108 |
| 467 | 101 |
| 471 | 116 |
| 474 | 109 |
| 475 | 104 |
| 476 | 103 |
| 477 | 106 |
| 479 | 103 |
| 480 | 113 |
| 482 | 110 |
| 483 | 103 |
| 484 | 112 |
| 485 | 104 |
| 486 | 102 |
| 487 | 104 |
| 488 | 101 |

Experimental Example 3: Evaluation of Microsome Stability in Human

Human liver microsomes were purchased from Xenotech, LLC (Lenexa, KS). An incubation mixture consisted of microsomes in 50 mmol/L $KH_2PO_4$—$K_2HPO_4$ phosphate buffer (pH 7.4) and 1 μmol/L test compound. The concentration of microsomal protein was 0.2 mg/mL. An NADPH-generating system (5 mmol/L $MgCl_2$, 5 mmol/L glucose-6-phosphate, 0.5 mmol/L beta-NADP+ and 1.5 unit/mL glucose-6-phosphate dehydrogenase) was added to the incubation mixture with a half volume of the reaction mixture to initiate the enzyme reaction. The reaction was terminated 15 and 30 minutes after the initiation of the reaction by mixing the reaction mixture with acetonitrile, followed by centrifugation at 2500 rpm for 10 min. The supernatant was subjected to LC/MS/MS analysis. The metabolic velocity was calculated as the slope of the concentration-time plot. The in vitro intrinsic metabolic clearance was calculated by dividing initial metabolic velocity by the test compound concentration in the incubation mixture. The results were shown in Table 3.

TABLE 3

| Test compound | Clearance (μL/min/mg) |
|---|---|
| Example 450 | 78 |
| Example 482 | 26 |
| Example 483 | 6 |
| Example 484 | 23 |

As is clear from the results, in vitro intrinsic metabolic clearance of the test compounds of the present invention was low. That is, these compounds were shown to have good metabolic stabilities.

Experimental Example 4: Evaluation of Wake-Promoting Effects in Cynomolgus Monkeys The wake-promoting effects were evaluated by measuring the electroencephalogram (EEG), electromyogram (EMG) and electrooculogram (EOG) in cynomolgus monkeys. Under isoflurane anesthesia (1-5%, Pfizer Japan Inc., Tokyo, Japan), male cynomolgus monkeys (3-5 years old, Hamri Co., Ltd., Ibaraki, Japan) were surgically implanted with radio-telemetry transmitters (TL10M3-D70-EEE, Data Sciences International Inc., MN, USA). EEG leads were stereotaxically positioned at the parietal area and secured to the cranium with stainless-steel screws in contact with the dura. Unilateral EOG leads were positioned at superior orbital margin of one eye and secured with stainless-steel screws. Bilateral EMG leads were implanted into the back cervical muscles. After the surgery, each monkey was given penicillin (100,000 units/head, i.m., Meiji Seika Pharma Co., Ltd., Tokyo, Japan), buprenorphine (0.02 mg/kg, i.m., Otsuka Pharmaceutical Co., Ltd., Tokyo, Japan) and prednisolone (1 mg/kg, s.c., Kyoritsu Seiyaku Co., Ltd., Tokyo, Japan) daily for one week. After at least a 1-month recovery period in home cages, the monkeys were habituated to the recording chamber (an acrylic cage 60W×55D×75H (cm)) located in a soundproof, electrically shielded room. After we confirmed that monkeys slept sufficiently in the experimental room, cortical EEG, EMG and EOG signals were recorded using Dataquest ART software (Data Sciences International Inc., MN, USA). The signals were semi automatically scored in 20 sec epochs by a sleep scoring system (SleepSign, Kissei Comtec Co., Ltd., Nagano, Japan). This preliminary scoring was visually inspected and corrected if necessary. Test compound (10 mg/kg, Table 4-1) suspended in 0.5% methylcellulose aqueous solution, or vehicle (i.e., 0.5% methylcellulose aqueous solution) was administered orally (p.o.) to monkeys at zeitgeber time 12 (ZT12) in a volume of 5 mL/kg body weight in a cross-over design. EEG, EMG and EOG recordings were performed for 4 h after the compound administration/treatments. The time spent in wakefulness for 4 h after administration (% of vehicle treatment) was calculated by using SleepSign. Test compound (1 mg/kg, Table 4-2) dissolved in a mixed solution comprising 5% DMSO, 5% Cremophor EL, 20% PEG400 and 70% soluplus (1% (w/v)), or vehicle (i.e., a mixed solution comprising 5% DMSO, 5% Cremophor EL, 20% PEG400 and 70% soluplus (1% (w/v))) was administered subcutaneously (s.c.) to monkeys at ZT12 in a volume of 0.5 mL/kg body weight in a pre-post design. EEG, EMG and EOG recordings were performed for 4 h after the compound administration/treatments. The time spent in wakefulness for 4 h after administration (% of vehicle treatment) was calculated by using SleepSign. The results were shown in Table 4.

TABLE 4

| Test compound (10 mg/kg, p. o.) | Wakefulness time (% of vehicle treatment) (Mean, n = 4-8) |
|---|---|
| Example 482 | 280.82 |
| Example 483 | 359.35 |
| Example 484 | 492.32 |

| Test compound (1 mg/kg, s. c.) | Wakefulness time (% of vehicle treatment) (Mean, n = 1-2) |
|---|---|
| Example 362 | 270.87 |
| Example 364 | 375.40 |
| Example 372 | 327.78 |
| Example 377 | 343.49 |
| Example 407 | 391.30 |
| Example 450 | 242.72 |
| Example 456 | 445.67 |
| Example 474 | 329.00 |
| Example 475 | 410.04 |
| Example 476 | 392.22 |
| Example 477 | 382.61 |
| Example 485 | 449.21 |

TABLE 4-continued

| | |
|---|---|
| Example 486 | 328.47 |
| Example 487 | 354.86 |

As is clear from the results, the test compounds of the present invention increased the wakefulness time as compared with the vehicle treatment group in cynomolgus monkeys. That is, these compounds were shown to be effective for the treatment of narcolepsy.

| Formulation Example 1 (production of capsule) | |
|---|---|
| 1) compound of Example 1 | 30 mg |
| 2) crystalline cellulose | 10 mg |
| 3) lactose | 19 mg |
| 4) magnesium stearate | 1 mg |
| total | 60 mg |

1), 2), 3) and 4) are mixed and filled in a gelatin capsule.

| Formulation Example 2 (production of tablet) | |
|---|---|
| 1) compound of Example 1 | 30 g |
| 2) lactose | 50 g |
| 3) cornstarch | 15 g |
| 4) calcium carboxymethylcellulose | 44 g |
| 5) magnesium stearate | 1 g |
| 1000 tablets | 140 g in total |

The total amount of 1), 2), 3) and 30 g of 4) are kneaded with water, vacuum dried and sieved. The sieved powder is mixed with 14 g of 4) and 1 g of 5), and the mixture is punched by a tableting machine. In this way, 1000 tablets containing 30 mg of the compound of Example 1 per tablet are obtained.

INDUSTRIAL APPLICABILITY

The compound of the present invention has an orexin type 2 receptor agonist activity, and is useful as an agent for the prophylaxis or treatment of narcolepsy.

This application is based on patent applications No. 2017-150685 filed on Aug. 3, 2017 and No. 2017-248495 filed on Dec. 25, 2017 in Japan, the contents of which are encompassed in full herein.

The invention claimed is:

1. A method of activating an orexin type 2 receptor in a mammal, which comprises administering an effective amount of a compound selected from N-((2S,3S)-1-(2-hydroxy-2-methylpropanoyl)-2-((2,3',5'-trifluorobiphenyl-3-yl)methyl)pyrrolidin-3-yl)methanesulfonamide;

N-((2S,3S)-2-((2,3'-difluorobiphenyl-3-yl)methyl)-1-(2-hydroxy-2-methylpropanoyl)pyrrolidin-3-yl)ethanesulfonamide; and N-((2S,3S)-1-(2-hydroxy-2-methylpropanoyl)-2-((2,3',5'-trifluorobiphenyl-3-yl)methyl)pyrrolidin-3-yl)ethanesulfonamide;

or a salt thereof, to the mammal.

2. The method of claim 1, wherein the compound is N-((2S,3S)-1-(2-hydroxy-2-methylpropanoyl)-2-((2,3',5'-trifluorobiphenyl-3-yl)methyl)pyrrolidin-3-yl)methanesulfonamide, or a salt thereof.

3. The method of claim 1, wherein the compound is N-((2S,3S)-2-((2,3'-difluorobiphenyl-3-yl)methyl)-1-(2-hydroxy-2-methylpropanoyl)pyrrolidin-3-yl)ethanesulfonamide, or a salt thereof.

4. The method of claim 1, wherein the compound is N-((2S,3S)-1-(2-hydroxy-2-methylpropanoyl)-2-((2,3',5'-trifluorobiphenyl-3-yl)methyl)pyrrolidin-3-yl)ethanesulfonamide, or a salt thereof.

5. A method for the prophylaxis or treatment of narcolepsy in a mammal, which comprises administering an effective amount of a compound selected from:

N-((2S,3S)-1-(2-hydroxy-2-methylpropanoyl)-2-((2,3',5'-trifluorobiphenyl-3-yl)methyl)pyrrolidin-3-yl)methanesulfonamide;

N-((2S,3S)-2-((2,3'-difluorobiphenyl-3-yl)methyl)-1-(2-hydroxy-2-methylpropanoyl)pyrrolidin-3-yl)ethanesulfonamide; and N-((2S,3S)-1-(2-hydroxy-2-methylpropanoyl)-2-((2,3',5'-trifluorobiphenyl-3-yl)methyl)pyrrolidin-3-yl)ethanesulfonamide;

or a salt thereof, to the mammal.

6. The method of claim 5, wherein the compound is N-((2S,3S)-1-(2-hydroxy-2-methylpropanoyl)-2-((2,3',5'-trifluorobiphenyl-3-yl)methyl)pyrrolidin-3-yl)methanesulfonamide, or a salt thereof.

7. The method of claim 5, wherein the compound is N-((2S,3S)-2-((2,3'-difluorobiphenyl-3-yl)methyl)-1-(2-hydroxy-2-methylpropanoyl)pyrrolidin-3-yl)ethanesulfonamide, or a salt thereof.

8. The method of claim 5, wherein the compound is N-((2S,3S)-1-(2-hydroxy-2-methylpropanoyl)-2-((2,3',5'-trifluorobiphenyl-3-yl)methyl)pyrrolidin-3-yl)ethanesulfonamide, or a salt thereof.

* * * * *